United States Patent
Zhang et al.

(10) Patent No.: US 11,352,352 B2
(45) Date of Patent: Jun. 7, 2022

(54) AMINOPYRIMIDINE COMPOUND, PREPARATION METHOD THEREFOR AND USE THEREOF

(71) Applicant: BEIJING ADAMADLE BIOTECHNOLOGY LIMITED LIABILITY COMPANY, Beijing (CN)

(72) Inventors: Peilong Zhang, Beijing (CN); Hepeng Shi, Beijing (CN); Wenli Lan, Beijing (CN); Zhitao Song, Beijing (CN)

(73) Assignee: BEIJING ADAMADLE BIOTECHNOLOGY LIMITED LIABILITY COMPANY, Beijing (CN)

( * ) Notice: Subject to any disclaimer, the term of this patent is extended or adjusted under 35 U.S.C. 154(b) by 112 days.

(21) Appl. No.: 16/617,387

(22) PCT Filed: Jun. 13, 2018

(86) PCT No.: PCT/CN2018/091114
§ 371 (c)(1),
(2) Date: Nov. 26, 2019

(87) PCT Pub. No.: WO2018/228446
PCT Pub. Date: Dec. 20, 2018

(65) Prior Publication Data
US 2020/0087296 A1    Mar. 19, 2020

(30) Foreign Application Priority Data
Jun. 13, 2017 (CN) .......................... 201710445095.1

(51) Int. Cl.
| | | |
|---|---|---|
| C07D 417/14 | (2006.01) | |
| A61P 35/00 | (2006.01) | |
| C07D 403/10 | (2006.01) | |
| C07D 403/14 | (2006.01) | |
| C07D 405/14 | (2006.01) | |
| C07D 413/14 | (2006.01) | |
| C07D 417/10 | (2006.01) | |
| C07D 487/08 | (2006.01) | |
| C07D 491/107 | (2006.01) | |

(52) U.S. Cl.
CPC ............ *C07D 417/14* (2013.01); *A61P 35/00* (2018.01); *C07D 403/10* (2013.01); *C07D 403/14* (2013.01); *C07D 405/14* (2013.01); *C07D 413/14* (2013.01); *C07D 417/10* (2013.01); *C07D 487/08* (2013.01); *C07D 491/107* (2013.01)

(58) Field of Classification Search
CPC combination set(s) only.
See application file for complete search history.

(56) References Cited

U.S. PATENT DOCUMENTS

2017/0008889 A1*    1/2017   Lan .......................... A61P 9/00

OTHER PUBLICATIONS

Mellinghoff (Moelcular Determinants of the Response of Gioblastomas to EGFR Kinase Inhibitors, n engl j med 353;19 www.nejm.org Nov. 10, 2005).*
Thornber (Isosterism and Molecular Modification in Drug Design (Progress in Drug Research 1979, 37, 563-580).*

* cited by examiner

*Primary Examiner* — Kathrien A Cruz
(74) *Attorney, Agent, or Firm* — Lewis Roca Rothgerber Christie LLP

(57) ABSTRACT

The present invention relates to an aminopyrimidine compound, a preparation method therefor and use thereof. The aminopyrimidine compound has the structure as shown in formula I:

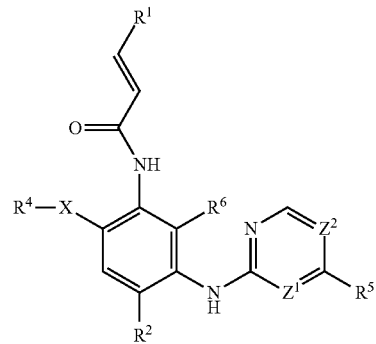

the compound is an inhibitor of an epidermal growth factor receptor (EGFR) kinase. The present invention also relates to a pharmaceutical composition containing the compounds, a method for preparing same and the use of same in preparation of anti-tumor drugs.

17 Claims, No Drawings

AMINOPYRIMIDINE COMPOUND, PREPARATION METHOD THEREFOR AND USE THEREOF

CROSS-REFERENCE TO RELATED APPLICATION(S)

This application is a National Phase Patent Application of International Patent Application Number PCT/CN2018/091114, filed on Jun. 13, 2018, which claims priority of Chinese Patent Application No. 201710445095.1, filed Jun. 13, 2017. The entire contents of both of which are incorporated herein by reference.

TECHNICAL FIELD

The present invention relates to aminopyrimidine compounds, preparation method therefor and use thereof, specifically relates to compounds for inhibiting, regulating and/or modulating EGFR kinase signal transduction, method for preparing the same, pharmaceutical composition containing the same and use thereof.

BACKGROUND ART

Protein kinases are enzymatic components of the signal transduction pathways, which catalyze the transfer of the terminal phosphate from ATP to the hydroxyl group of tyrosine, serine and/or threonine residues of proteins. Thus, compounds which inhibit protein kinase functions are valuable tools for assessing the physiological consequences of protein kinase activation. The overexpression or inappropriate expression of normal or mutant protein kinases in mammals has been extensive studied and demonstrated to play a significant role in the development of many diseases, including diabetes, angiogenesis, psoriasis, restenosis, ocular disease, schizophrenia, rheumatoid arthritis, atherosclerosis, cardiovascular disease and cancer. Inhibitors of protein kinases have particular utility in the treatment of human and animal disease.

One of the principal mechanisms by which cellular regulation is achieved is through the transduction of extracellular signal across the membrane that in turn modulates biochemical pathways within the cell. Protein phosphorylation represents one course by which intracellular signals propagated from molecule to molecule resulting eventually in a cellular response. Phosphorylation of proteins occurs predominantly at serine, threonine or tyrosine residues and protein kinases have therefore been classified by their specificity of phosphorylation sites, i.e. serine/threonine kinases and tyrosine kinases. Because phosphorylation is such a ubiquitous process within cells, and because cellular phenotypes are largely influenced by the activity of these pathways, it is currently believed that a number of diseases states and/or disorders are a result of either aberrant activation or functional mutations in the molecular components of kinase cascades.

EGFR is a member of receptor tyrosine kinases of ErbB receptor family. Overexpression (upregulation) or over-activity of EGFR has been related with many kinds of cancers, including head and neck cancer, ovarian cancer, cervical cancer, bladder cancer, esophageal cancer, gastric cancer, breast cancer, endometrial cancer, colorectal cancer, non-small cell lung cancer, and glioblastoma.

EGFR, as a oncogene, provided an anti-cancer therapy by small molecule inhibitors targeting EGFR, for example, gefitinib (Iressa) and erlotinib (Tarceva) for non-small cell lung cancer (NSCLC). However, many patients have developed drug resistances after a period of treatment, one of the main reasons is T790M mutation. T790M increases the affinity of EGFR to ATP, which is the most common mechanism of acquired resistance to reversible tyrosine kinases inhibitors. Irreversible EGFR inhibitors can covalently alkylate cysteine residue (Cys797) located in the active center and accordingly overcome such acquired resistance to the reversible inhibitors.

EGFR is overexpressed in 50%-80% of NSCLC patients, thereby causing cancer. The first generation of EGFR inhibitors which have been used clinically, such as Iressa and Tarceva, have achieved great success in the treatment of NSCLC. However, obvious side effects such as rash and diarrhea have been observed in clinic, furthermore patients develop drug resistance after one-year treatment. Clinical data indicated that about 50% of patients develop drug resistance due to the T790M mutation. The second-generation inhibitors, such as afatinib, have stronger affinity to EGFR and poor selectivity to T790M mutant, therefore, the drugs cannot reach their effective concentration in vivo.

In order to better solve the problems of drug resistance of the first generation inhibitors and the selectivity of the second generation inhibitors, it is of great significance to develop the third generation inhibitors capable of selectively inhibiting T790M.

SUMMARY OF THE INVENTION

The present invention provides a novel aminopyrimidine compound with high selective inhibition of EGFR T790M, wherein the aminopyrimidine compound has the structure represented by the following Formula I,

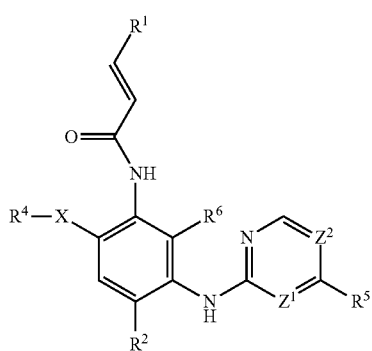

wherein
$R^1$ is hydrogen or

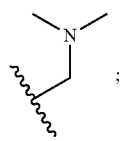

$R^2$ is $C_{1-6}$ alkyl or $OR^8$, $R^8$ is hydrogen, $C_{1-8}$ alkyl, halogenated $C_{1-8}$ alkyl, $C_{3-8}$ cycloalkyl, halogenated $C_{3-8}$ cycloalkyl, $C_{3-7}$ cycloalkyl-$C_{1-6}$ alkyl, substituted or unsubstituted 4-7 membered heterocyclyl containing 1-2 heteroatoms selected from N, O and S, or substituted or unsubstituted 4-7 membered heterocyclyl-$C_{1-8}$ alkyl containing 1-2 heteroatoms selected from N, O and S;

X is a chemical bond, O, S, CO, $NR^3$ or $CR^3$, wherein $R^3$ is hydrogen, $C_{1-6}$ alkyl, halogenated $C_{1-6}$ alkyl, $C_{3-8}$ cycloalkyl, halogenated $C_{3-8}$ cycloalkyl, $C_{1-6}$ alkoxy-$C_{1-6}$ alkyl, $C_{1-8}$ alkyl-CO or 4-6 membered heterocyclyl;

$R^4$ is $C_{1-6}$ alkyl, $C_{3-6}$ cycloalkyl, 4-7 membered heterocyclyl or 4-7 membered bicyclo-bridged heterocyclyl, which can be optionally substituted by 1-3 substituents independently selected from the group consisting of: $C_{1-6}$ alkyl, halogenated $C_{1-6}$ alkyl, $C_{1-6}$ alkoxy, halogenated $C_{1-6}$ alkoxy, $C_{3-6}$ cycloalkyl, halogenated $C_{3-6}$ cycloalkyl, $C_{3-6}$ cycloalkoxy, halogenated $C_{3-6}$ cycloalkoxy, $C_{1-6}$ alkoxy-$C_{1-6}$ alkyl, hydroxy-$C_{1-6}$ alkyl, amino-$C_{1-6}$ alkyl, $C_{1-6}$ alkyl-amino-$C_{1-6}$ alkyl, halogen, hydroxy, cyano, cyano-$C_{1-8}$ alkyl, amino, $C_{1-6}$ alkyl-amino, di($C_{1-6}$ alkyl)-amino, $C_{3-6}$ cycloalkyl-amino, $C_{1-6}$ alkylcarbonyl, $C_{1-6}$ alkyl-amino-acyl, di($C_{1-6}$ alkyl)-amino-acyl, $C_{3-6}$ cycloalkyl-amino-acyl, $C_{1-6}$ acyl-amino, substituted or unsubstituted heterocyclyl, and substituted or unsubstituted heterocyclyl-alkyl, wherein the substituent can optionally form a ring together with the carbon atom to which they are linked;

$R^5$ is a fused ring formed by two rings and selected from

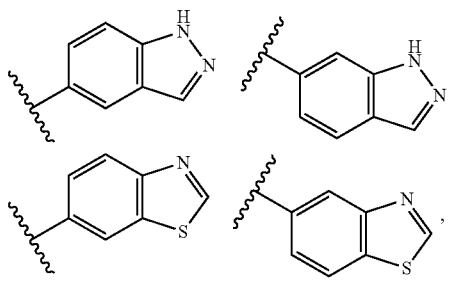

the fused ring is unnecessarily substituted by 1-3 substituents independently selected from the group consisting of: $C_{1-6}$ alkyl, halogenated $C_{1-6}$ alkyl, $C_{1-6}$ alkoxy, halogenated $C_{1-6}$ alkoxy, $C_{3-6}$ cycloalkyl, halogenated $C_{3-6}$ cycloalkyl, $C_{3-6}$ cycloalkoxy, halogenated $C_{3-6}$ cycloalkoxy, $C_{1-6}$ alkoxy-$C_{1-6}$ alkyl, hydroxy-$C_{1-6}$ alkyl, amino-$C_{1-6}$ alkyl, $C_{1-6}$ alkyl-amino-$C_{1-6}$ alkyl, halogen, hydroxyl, cyano, cyano-$C_{1-8}$ alkyl, amino, $C_{1-6}$ alkyl-amino, di($C_{1-6}$ alkyl)-amino, $C_{3-6}$ cycloalkyl-amino, $C_{1-6}$ alkyl-amino-acyl, di($C_{1-6}$ alkyl)-amino-acyl, $C_{3-6}$ cycloalkyl-amino-acyl, $C_{1-6}$ acyl-amino, substituted or unsubstituted heterocyclyl, and substituted or unsubstituted heterocyclyl-alkyl, wherein the substituent can optionally form a ring together with the carbon atom to which they are linked;

$R^6$ is hydrogen, halogen, hydroxyl, cyano, $C_{1-3}$ alkyl, halogenated $C_{1-3}$ alkyl, $C_{3-6}$ cycloalkyl, halogenated $C_{3-6}$ cycloalkyl, $C_{1-3}$ alkoxy, halogenated $C_{1-3}$ alkoxy, $C_{3-6}$ cycloalkoxy, or halogenated $C_{3-6}$ cycloalkoxy;

$Z^1$ is C—$R^7$, $Z^2$ is N, or $Z^1$ is N, $Z^2$ is C—$R^7$ (i.e. $Z^1$ and $Z^2$ cannot be N simultaneously), wherein $R^7$ is hydrogen, halogen, cyano, $C_{1-3}$ alkyl, halogenated $C_{1-3}$ alkyl, $C_{3-6}$ cycloalkyl, or halogenated $C_{3-6}$ cycloalkyl.

In some embodiments, $R^2$ is $OR^8$, $R^8$ is $C_{1-5}$ alkyl, halogenated $C_{1-5}$ alkyl, $C_{3-7}$ cycloalkyl, halogenated $C_{3-7}$ cycloalkyl or $C_{3-7}$ cycloalkyl-methyl; preferably, $R^2$ is $OR^8$, $R^8$ is methyl, ethyl, n-propyl, isopropyl, cyclopropyl, difluoromethyl, trifluoromethyl, cyclobutyl, or cyclopropylmethyl;

in some embodiments, X is a chemical bond or $NR^3$, wherein $R^3$ is hydrogen, methyl, ethyl, and methoxyethyl;

in some embodiments, $R^4$ is $C_{1-3}$ alkyl, $C_{3-6}$ cycloalkyl, 4-7 membered heterocyclyl or 4-7 membered bicyclo-bridged heterocyclyl containing 1-2 heteroatoms selected from the group consisting of: N, O and S, which can be optionally substituted by 1-3 substituents independently selected from the group consisting of: $C_{1-6}$ alkyl, halogenated $C_{1-6}$ alkyl, $C_{1-6}$ alkoxy, halogenated $C_{1-6}$ alkoxy, $C_{3-6}$ cycloalkyl, halogenated $C_{3-6}$ cycloalkyl, $C_{3-6}$ cycloalkoxy, halogenated $C_{3-6}$ cycloalkoxy, $C_{1-6}$ alkoxy-$C_{1-6}$ alkyl, hydroxyl-$C_{1-6}$ alkyl, amino-$C_{1-6}$ alkyl, $C_{1-6}$ alkyl-amino-$C_{1-6}$ alkyl, halogen, hydroxyl, cyano, cyano-$C_{1-8}$ alkyl, amino, $C_{1-6}$ alkyl-amino, di($C_{1-6}$ alkyl)-amino, $C_{3-6}$ cycloalkyl-amino, $C_{1-6}$ alkylcarbonyl, $C_{1-6}$ alkyl-amino-acyl, di($C_{1-6}$ alkyl)-amino-acyl, $C_{3-6}$ cycloalkyl-amino-acyl, $C_{1-6}$ acyl-amino, and substituted or unsubstituted 4-7 membered heterocyclyl;

preferably, $R^4$ is selected from the group consisting of:

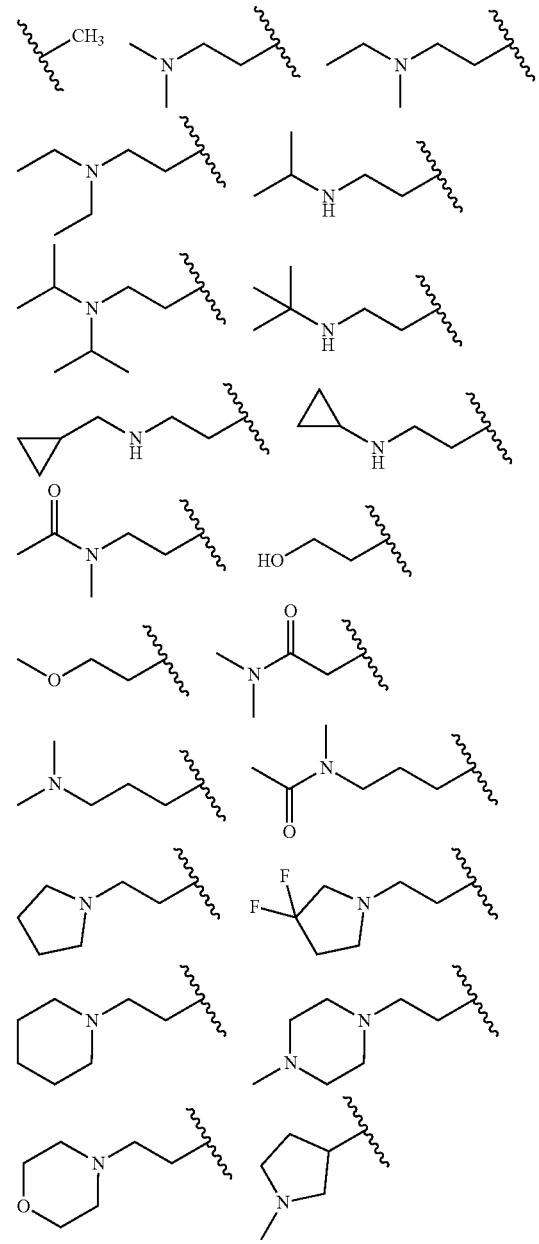

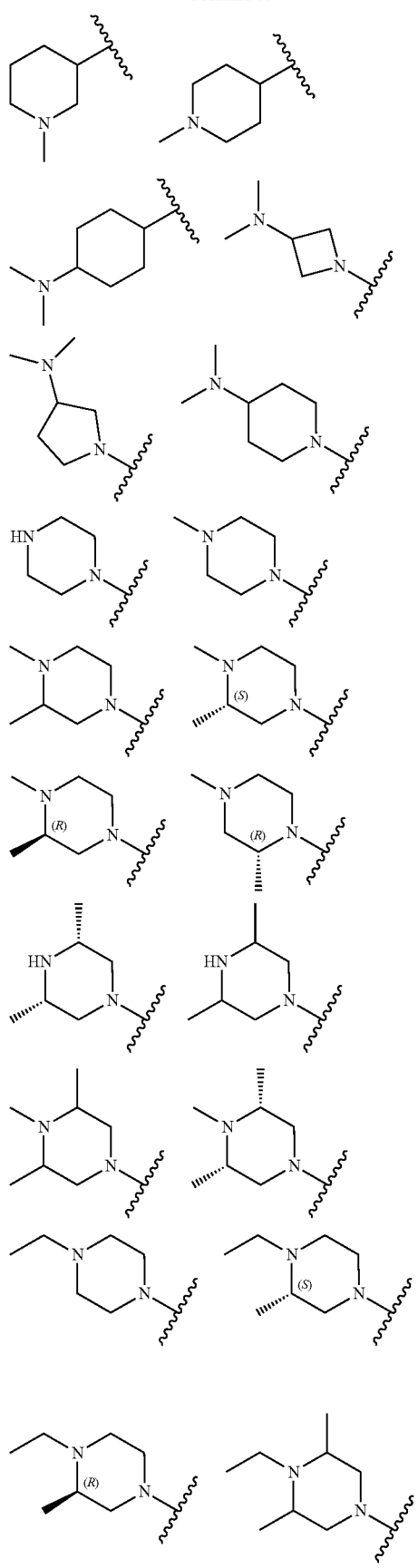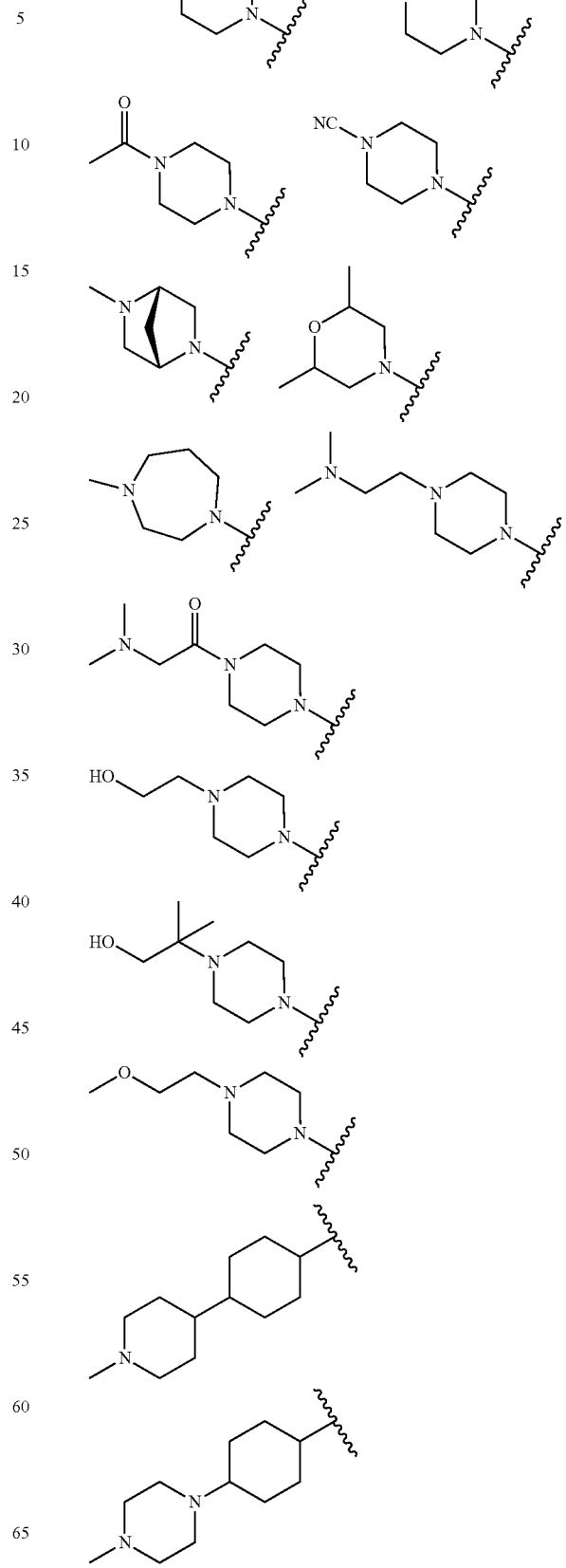

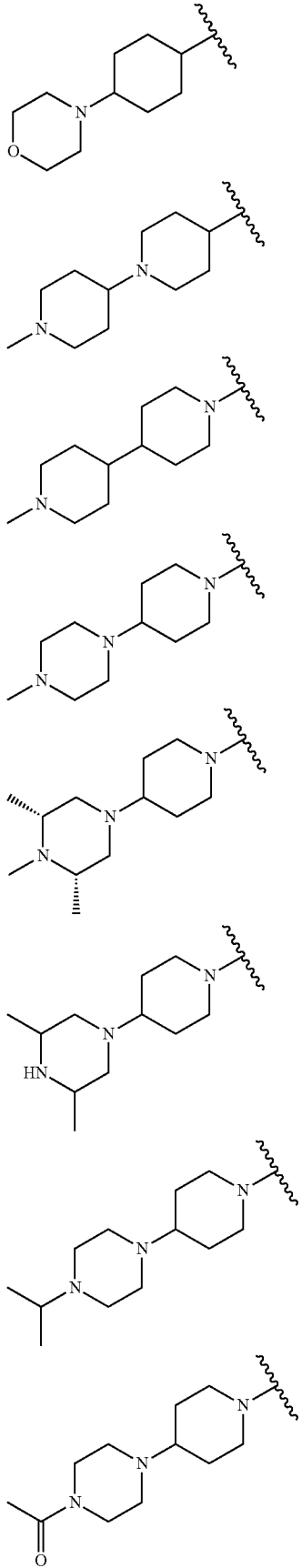
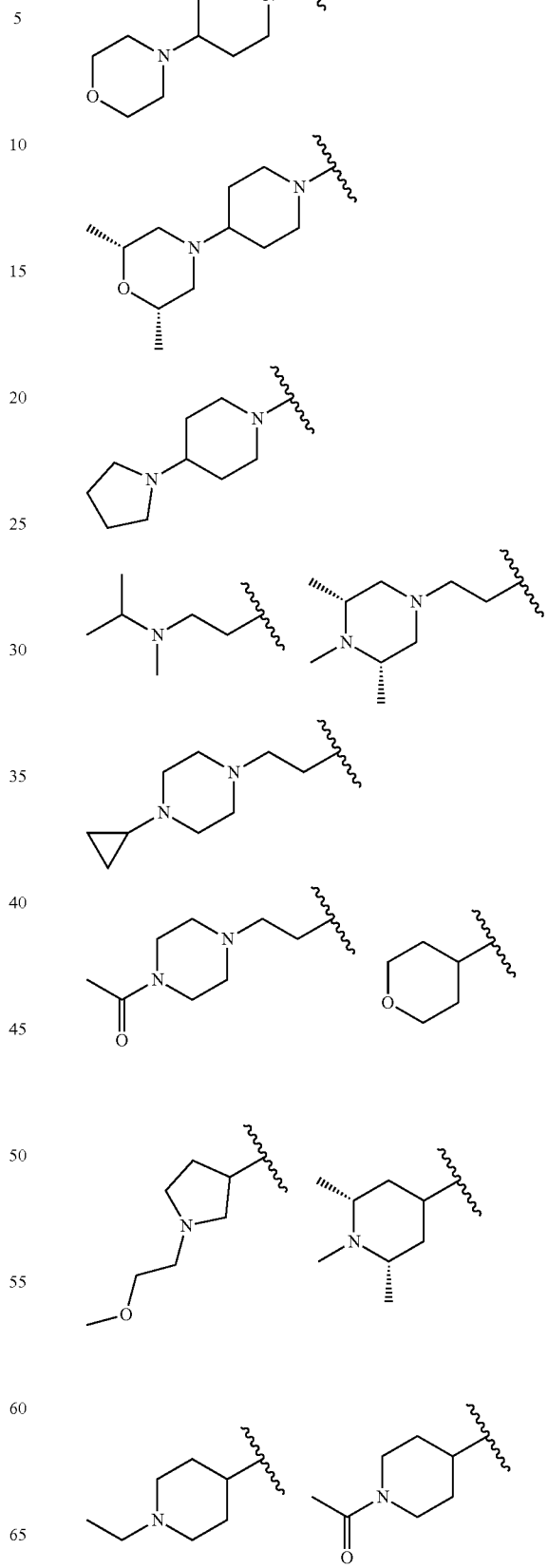

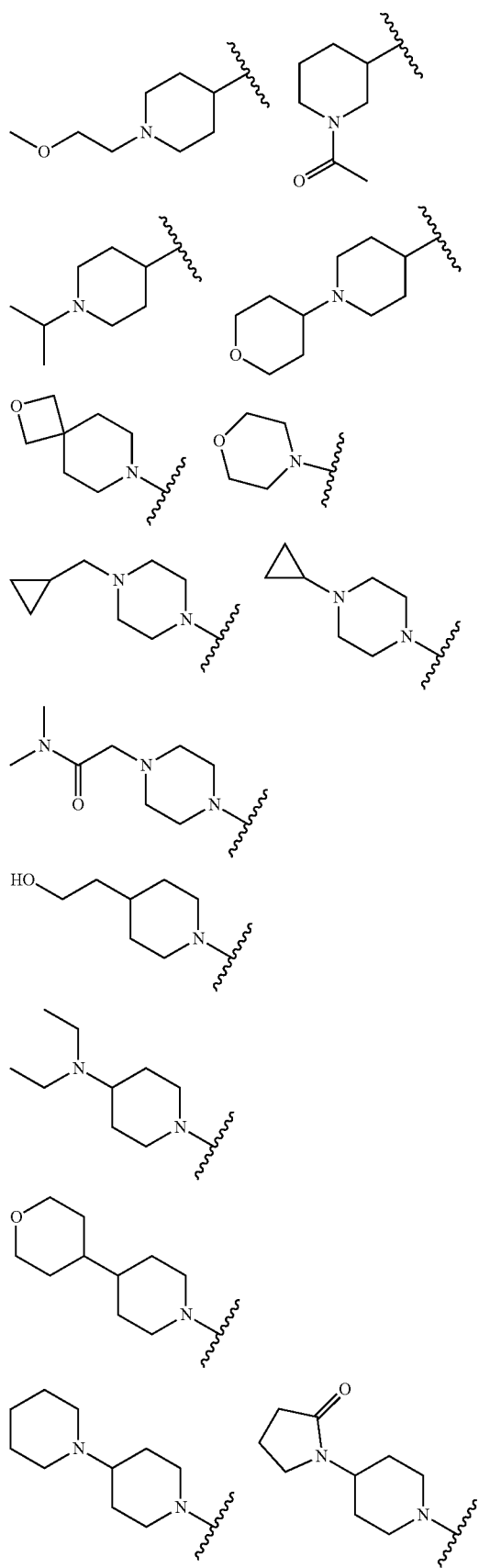
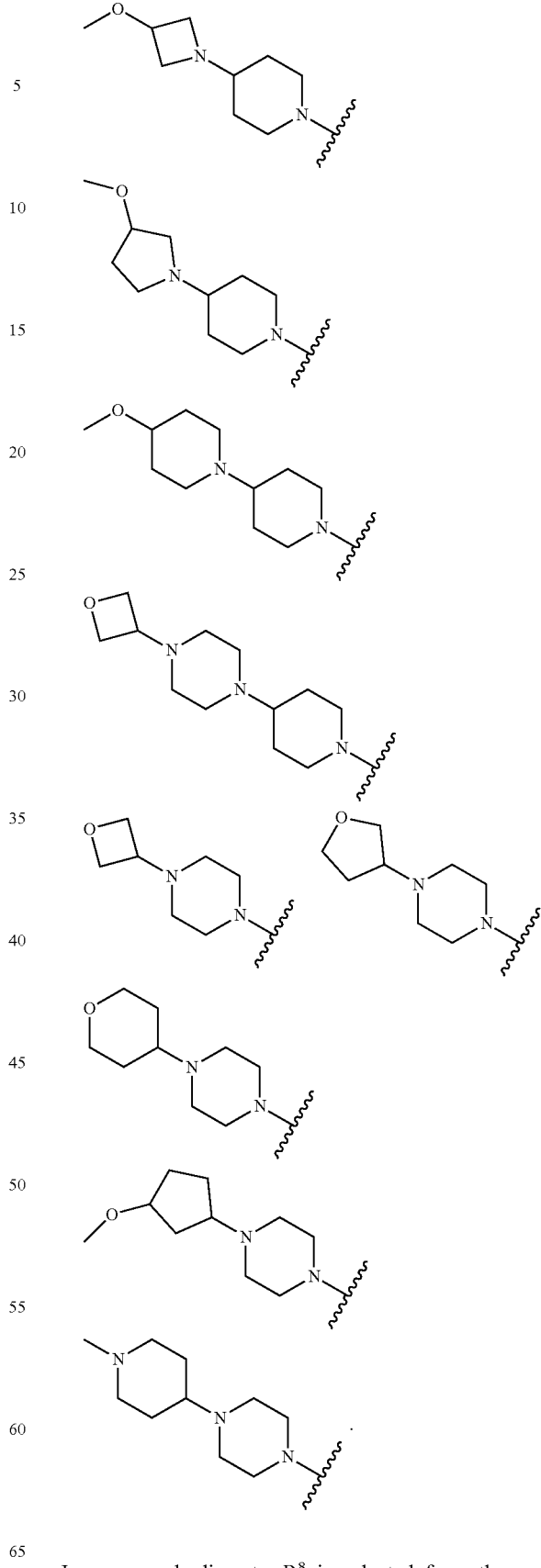
In some embodiments, R[8] is selected from the group consisting of:

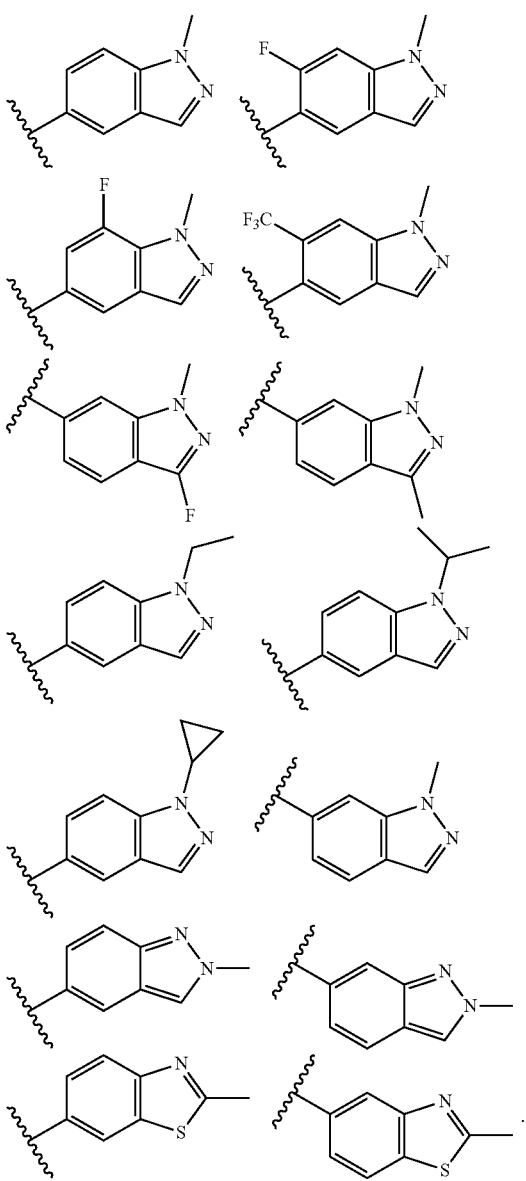

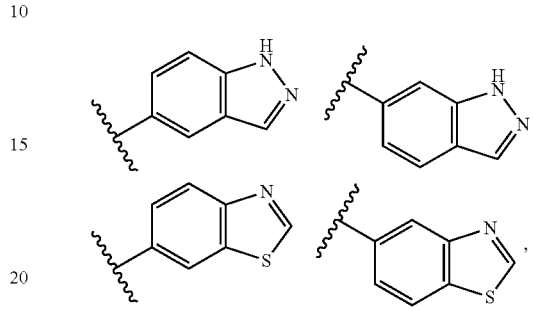

In some embodiments, $R^6$ is hydrogen, halogen, hydroxyl, cyano, $C_{1-3}$ alkyl, halogenated $C_{1-3}$ alkyl, $C_{1-3}$ alkoxy, and halogenated $C_{1-3}$ alkoxy.

In some embodiments, $Z^1$ is C—$R^7$, $Z^2$ is N, or $Z^1$ is N, $Z^2$ is C—$R^7$, wherein $R^7$ is hydrogen.

In some specific embodiments, in Formula I:
$R^1$ is hydrogen;
$R^2$ is $OR^8$, wherein $R^8$ is $C_{1-5}$ alkyl, halogenated $C_{1-5}$ alkyl, $C_{3-7}$ cycloalkyl, halogenated $C_{3-7}$ cycloalkyl or $C_{3-7}$ cycloalkyl-methyl;
X is a chemical bond or $NR^3$, wherein $R^3$ is hydrogen, $C_{1-6}$ alkyl (for example methyl and ethyl), and methoxyethyl;
$R^4$ is $C_{1-3}$ alkyl, $C_{3-6}$ cycloalkyl, 4-7 membered heterocyclyl or 4-7 membered bicyclo-bridged heterocyclyl containing 1-2 heteroatoms selected from the group consisting of: N, O and S, which can be optionally substituted by 1-3 substituents independently selected from the group consisting of: $C_{1-6}$ alkyl, halogenated $C_{1-6}$ alkyl, $C_{1-6}$ alkoxy, halogenated $C_{1-6}$ alkoxy, $C_{3-6}$ cycloalkyl, halogenated $C_{3-6}$ cycloalkyl, $C_{3-6}$ cycloalkoxy, halogenated $C_{3-6}$ cycloalkoxy, $C_{1-6}$ alkoxy-$C_{1-6}$ alkyl, hydroxy-$C_{1-6}$ alkyl, amino-$C_{1-6}$ alkyl, $C_{1-6}$ alkyl-amino-$C_{1-6}$ alkyl, halogen, hydroxyl, cyano, cyano-$C_{1-8}$ alkyl, amino, $C_{1-6}$ alkyl-amino, di($C_{1-6}$ alkyl)-amino, $C_{3-6}$ cycloalkyl-amino, $C_{1-6}$ alkylcarbonyl, $C_{1-6}$ alkyl-amino-acyl, di($C_{1-6}$ alkyl)-amino-acyl, $C_{3-6}$ cycloalkyl-amino-acyl, $C_{1-6}$ acyl-amino, and substituted or unsubstituted 4-7 membered heterocyclyl;

$R^5$ is a fused ring formed by two rings and selected from:

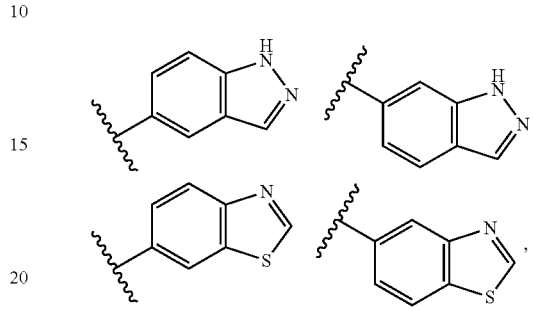

where the fused ring is unnecessarily substituted by 1-3 substituents selected from the group consisting of: $C_{1-6}$ alkyl, halogenated $C_{1-6}$ alkyl, $C_{1-6}$ alkoxy, halogenated $C_{1-6}$ alkoxy, $C_{3-6}$ cycloalkyl, halogenated $C_{3-6}$ cycloalkyl, $C_{3-6}$ cycloalkoxy, halogenated $C_{3-6}$ cycloalkoxy, $C_{1-6}$ alkoxy-$C_{1-6}$ alkyl, hydroxy-$C_{1-6}$ alkyl, amino-$C_{1-6}$ alkyl, $C_{1-6}$ alkyl-amino-$C_{1-6}$ alkyl, halogen, hydroxyl, cyano, cyano-$C_{1-8}$ alkyl, amino, $C_{1-6}$ alkyl-amino, di($C_{1-6}$ alkyl)-amino, $C_{3-6}$ cycloalkyl-amino, $C_{1-6}$ alkyl-amino-acyl, di($C_{1-6}$ alkyl)-amino-acyl, $C_{3-6}$ cycloalkyl-amino-acyl, $C_{1-6}$ acyl-amino, substituted or unsubstituted heterocyclyl, and substituted or unsubstituted heterocyclyl-alkyl, wherein the substituent can optionally form a ring together with the carbon atom to which they are linked;

$R^6$ is hydrogen, halogen, hydroxyl, cyano, $C_{1-3}$ alkyl, halogenated $C_{1-3}$ alkyl, $C_{1-3}$ alkoxy, and halogenated $C_{1-3}$ alkoxy;

$Z^1$ is C—$R^7$, $Z^2$ is N, or $Z^1$ is N, $Z^2$ is C—$R^7$, wherein $R^7$ is hydrogen.

In other specific embodiments, in Formula I:
$R^1$ is hydrogen;
$R^2$ is $OR^8$, $R^8$ is methyl, ethyl, n-propyl, isopropyl, cyclopropyl, difluoromethyl, trifluoromethyl, cyclobutyl, and cyclopropylmethyl;
X is a chemical bond or $NR^3$, wherein $R^3$ is hydrogen, $C_{1-6}$ alkyl (for example methyl and ethyl), and methoxyethyl;
$R^4$ is selected from the group consisting of:

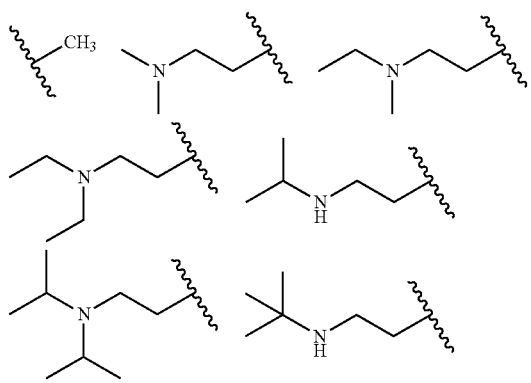

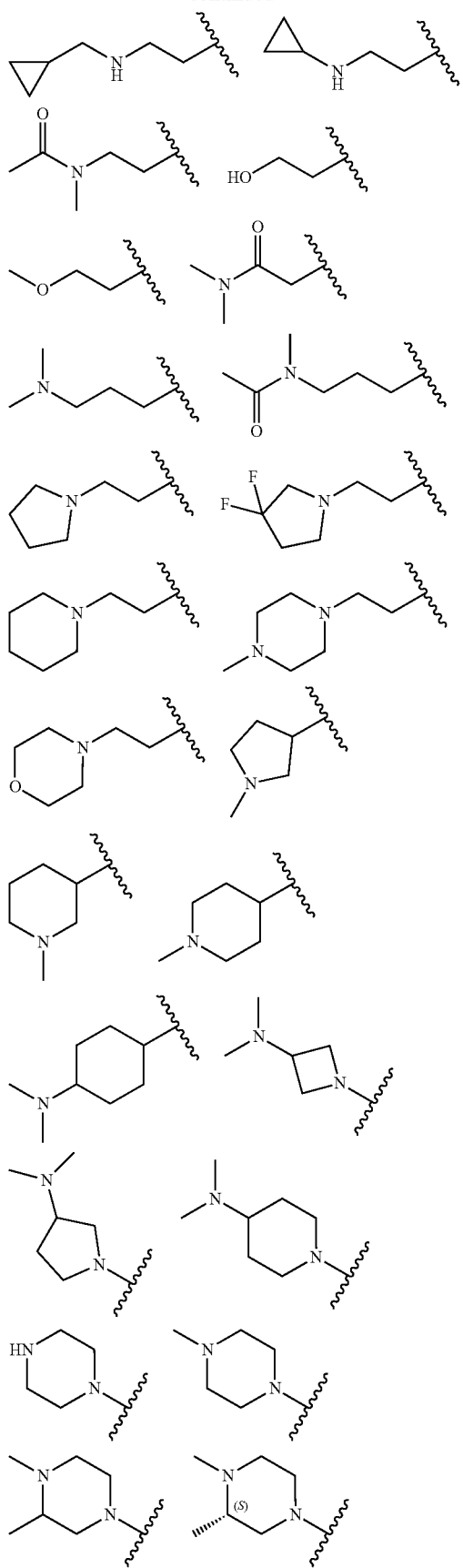
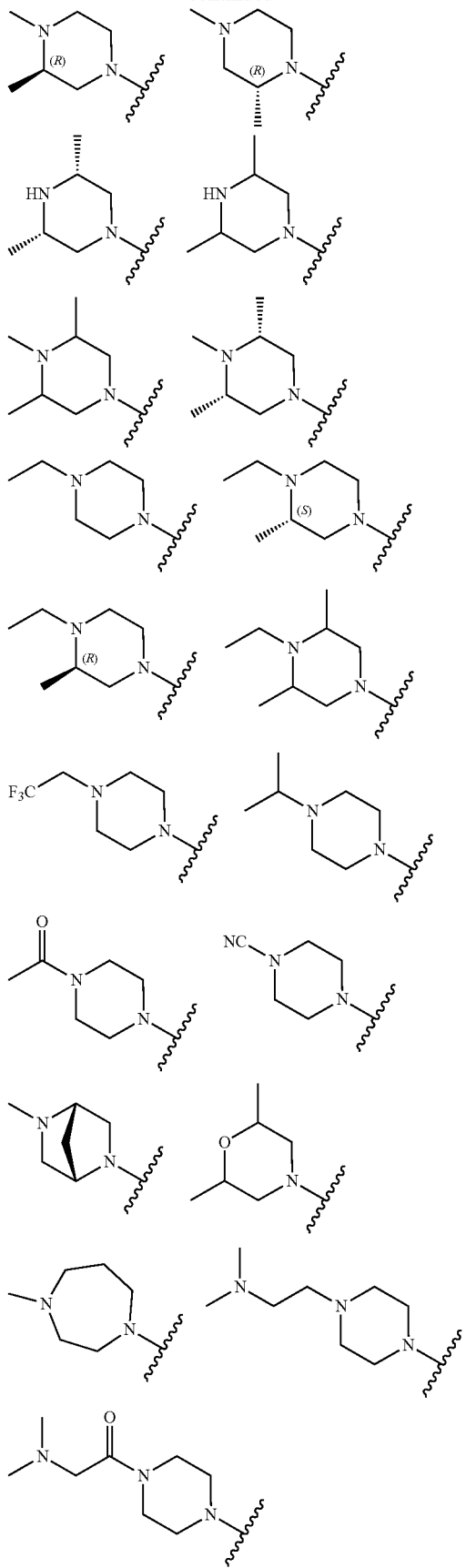

-continued
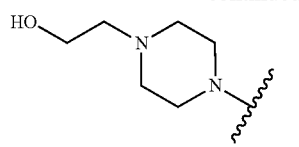
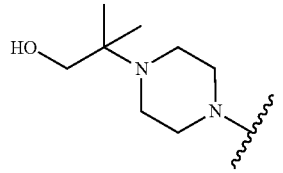
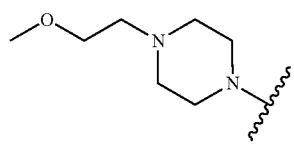
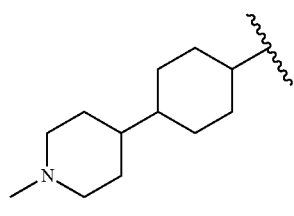
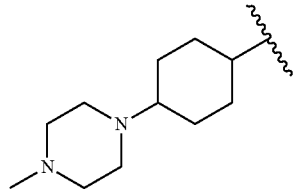
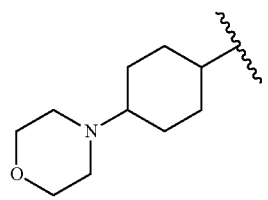
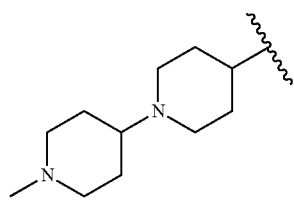
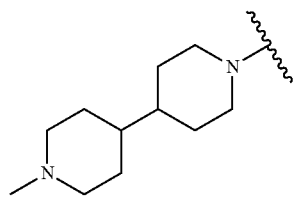
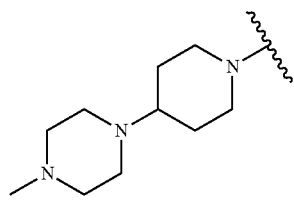
-continued
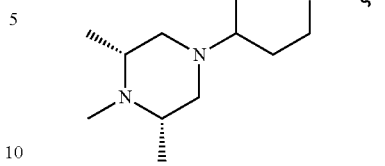
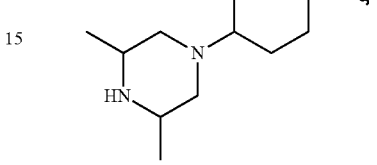
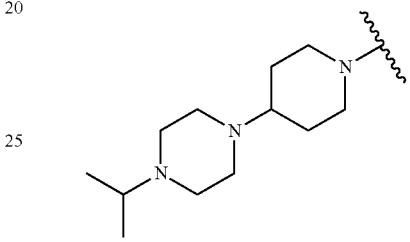
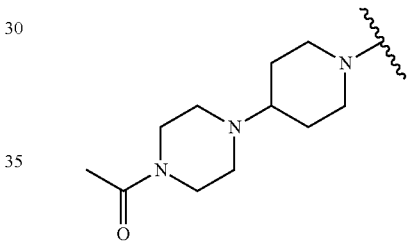
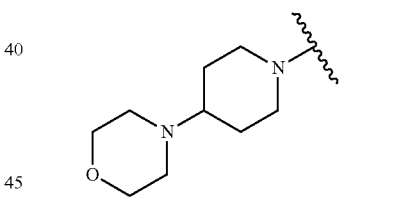
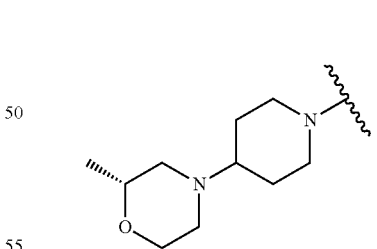
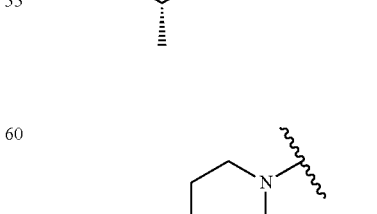
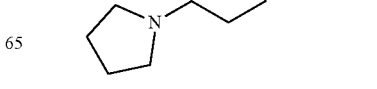

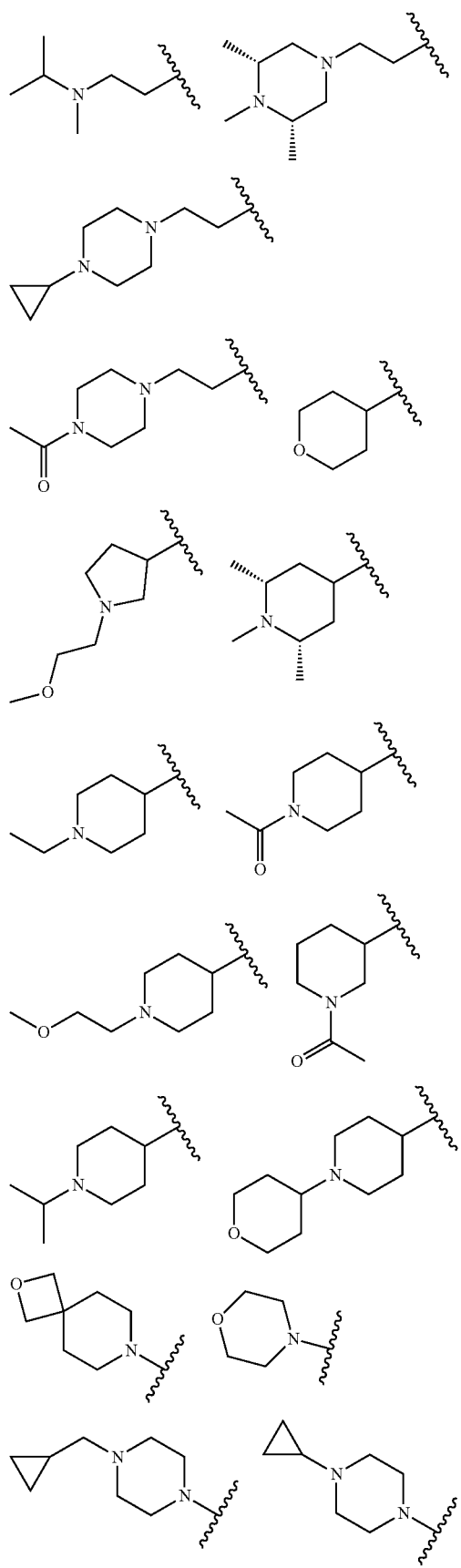
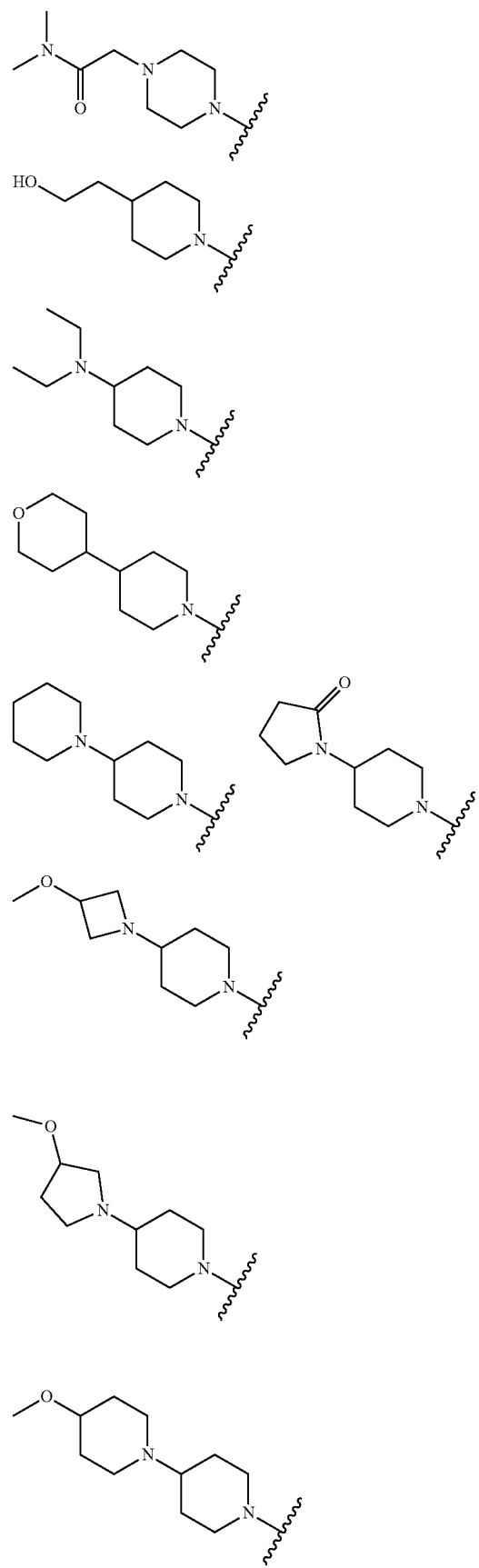

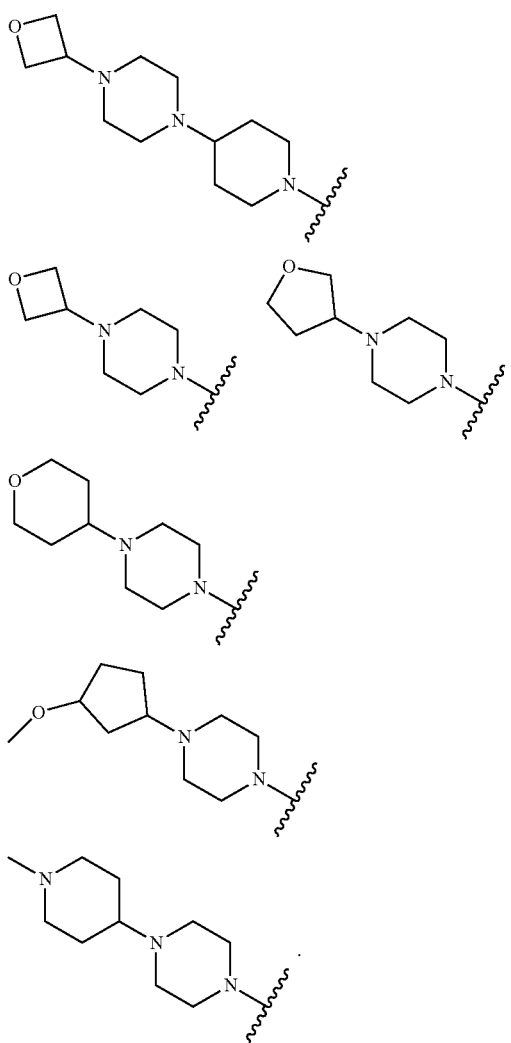

R⁵ is selected from the group consisting of:

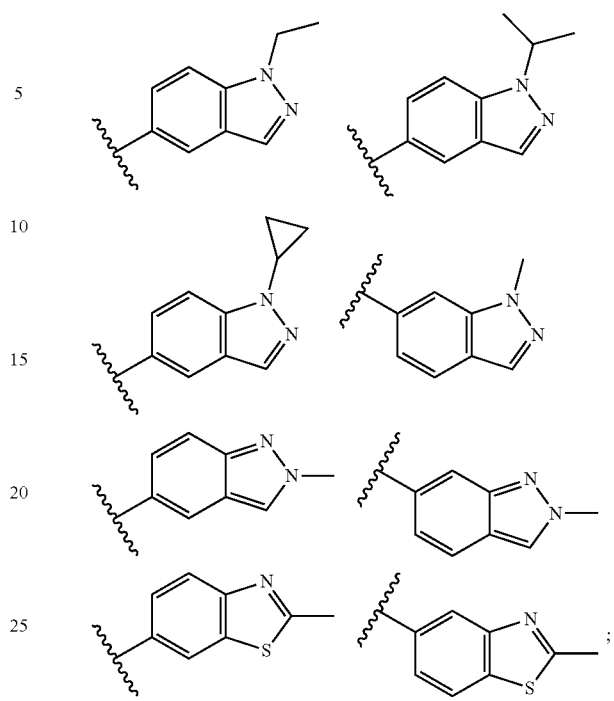

R⁶ is hydrogen or halogen;

Z¹ is C—R⁷, Z² is N, or Z¹ is N, Z² is C—R, wherein R⁷ is hydrogen.

In still other specific embodiments, in Formula I:

R¹ is hydrogen;

R² is OR⁸, R⁸ is methyl, ethyl or difluoromethyl;

X is a chemical bond or NR³, wherein R³ is hydrogen, C₁₋₆ alkyl (for example methyl and ethyl);

R⁴ s selected from the group consisting of:

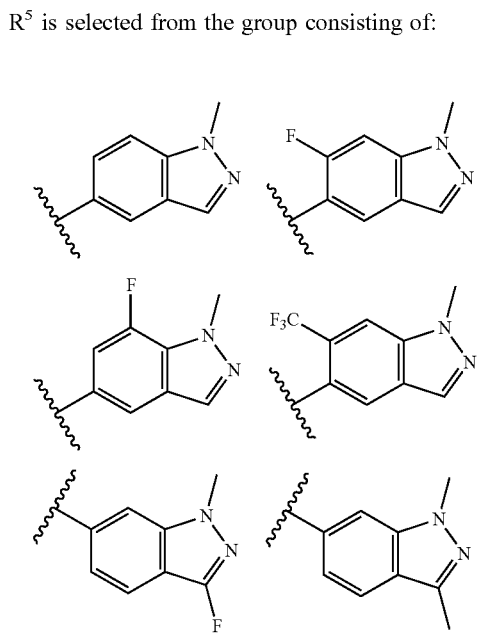

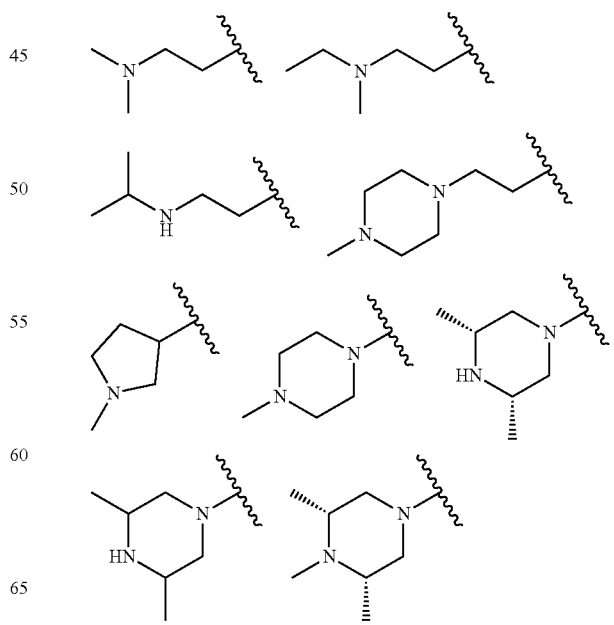

-continued

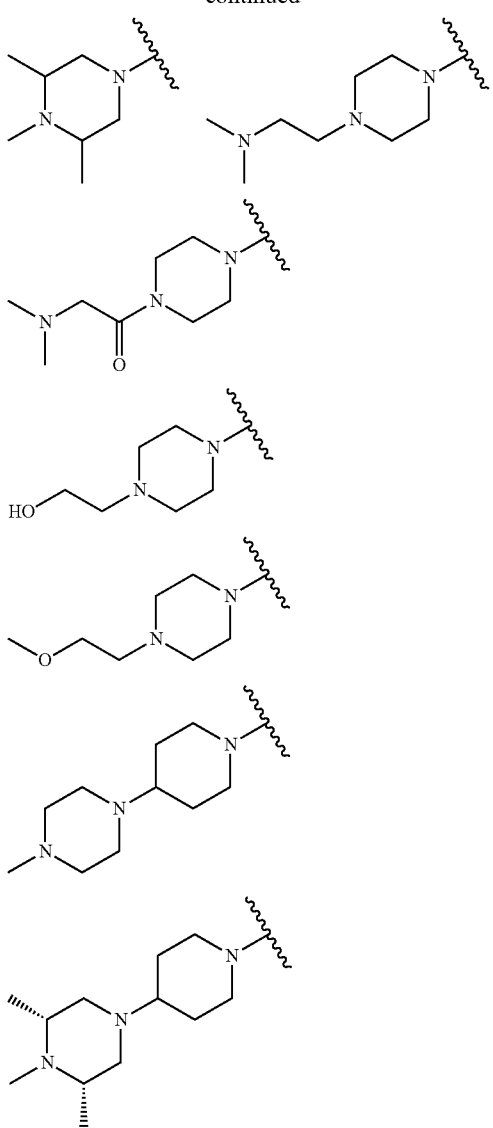

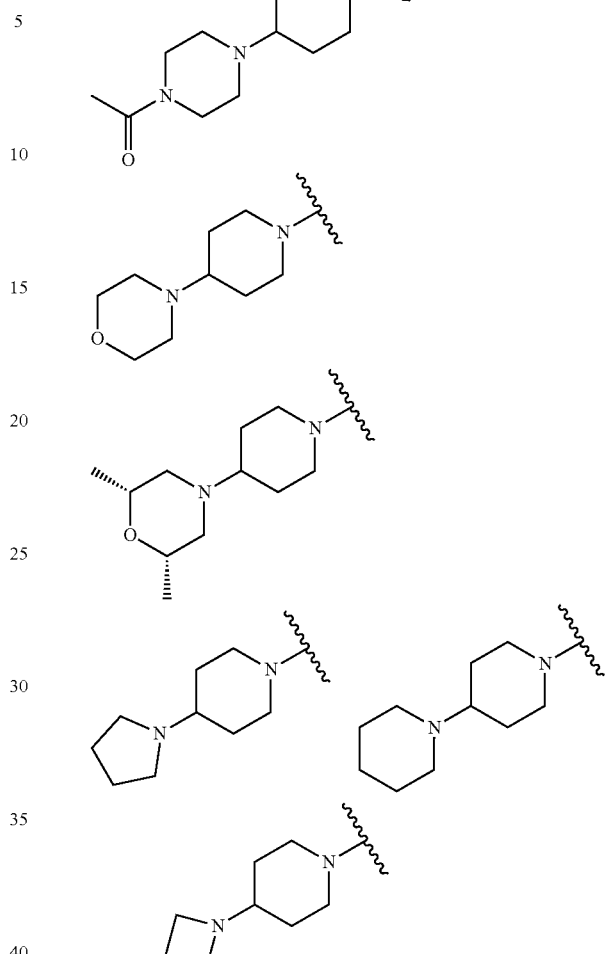

$R^5$ is selected from the group consisting of:

$R^6$ is hydrogen or halogen;

$Z^1$ is C—$R^7$, $Z^2$ is N, or $Z^1$ is N, $Z^2$ is C—$R^7$, wherein $R^7$ is hydrogen.

In some embodiments, the present application provides a pharmaceutical composition comprising the above-mentioned compound and pharmaceutically acceptable carriers or excipients. In some embodiments, the pharmaceutical composition is tablet, capsule, pill, granule, powder, suppository, injection, solution, suspension, plaster, patch, lotion, drop, liniment and spray.

In some embodiments, the present application provides a use of the above-mentioned compound and/or the pharmaceutical composition in the preparation of antitumor drugs. In some embodiments, the antitumor drugs are applied for the following conditions: head and neck cancer, melanoma, bladder cancer, esophageal cancer, anaplastic large cell lymphoma, renal cell cancer, breast cancer, colorectal cancer, ovarian cancer, cervical cancer, pancreatic cancer, glioma, glioblastoma, prostate cancer, leukemia, lymphoma, non-Hodgkin's lymphoma, stomach cancer, lung cancer, hepatocellular cancer, gastrointestinal stromal tumors, thyroid cancer, cholangiocarcinoma, uterus endometrial cancer, multiple myeloma and mesothelioma.

In some embodiments, the present application provides a method for treating tumors in a subject comprising administering to the subject a therapeutically effective amount of the above-mentioned compound or the pharmaceutical composition, wherein the subject is preferably a mammal, and the mammal is preferably a human being.

In some embodiments, the administration approach includes oral, mucosal, sublingual, ophthalmic, topical, parenteral, rectal, cisterna, vaginal, peritoneal, bladder and nasal administration.

In some embodiments, the tumor includes: head and neck cancer, melanoma, bladder cancer, esophageal cancer, anaplastic large cell lymphoma, renal cell cancer, breast cancer, colorectal cancer, ovarian cancer, cervical cancer, pancreatic cancer, glioma, glioblastoma, prostate cancer, leukemia, lymphoma, non-Hodgkin's lymphoma, stomach cancer, lung cancer, hepatocellular cancer, gastrointestinal stromal tumors, thyroid cancer, cholangiocarcinoma, uterus endometrial cancer, multiple myeloma and mesothelioma In some embodiments, the present invention provides a method for preparing the compound as shown in Formula I, comprising the following steps: reacting compound 1 with compound M to form compound 2 in the presence of base, after that reacting the compound 2 with compound 3 to give the compound as shown in Formula I in the presence of acid;

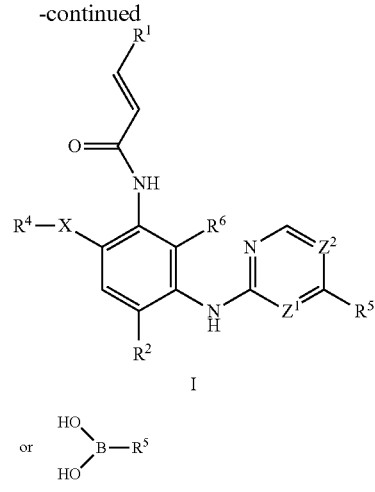

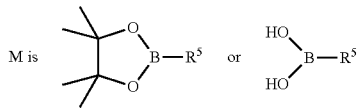

wherein $R^1$, $R^2$, $R^4$, $R^5$, $R^6$, X, $Z^1$ and $Z^2$ are as defined above, preferably, the base is sodium carbonate or sodium bicarbonate;

preferably, the acid is methylsulfonic acid or p-toluenesulfonic acid;

in some embodiments, the method for preparing the compound as shown in Formula I comprising the following steps:

(1) reacting compound 1 with compound M to supply compound 2 in the presence of base;

(2) reacting the compound 2 with compound 4 to form compound 5 in the presence of acid;

(3) reacting the compound 5 with $R^4$—X—H to give compound 6 in the presence of base;

(4) reducing the compound 6 to provide compound 7; (5) reacting the compound 7 with compound 8 to form the compound as shown in Formula I;

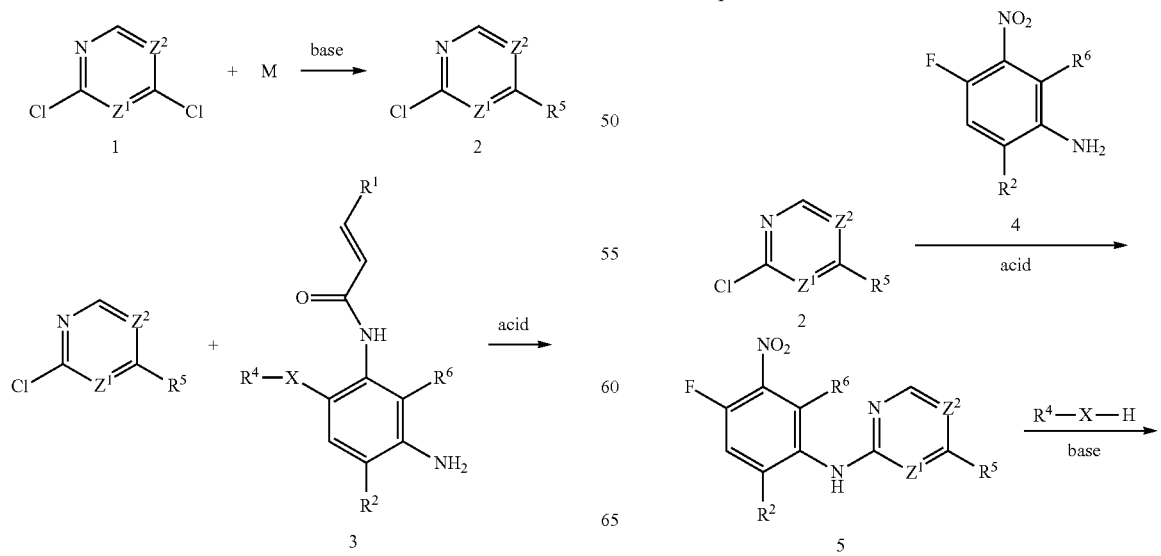

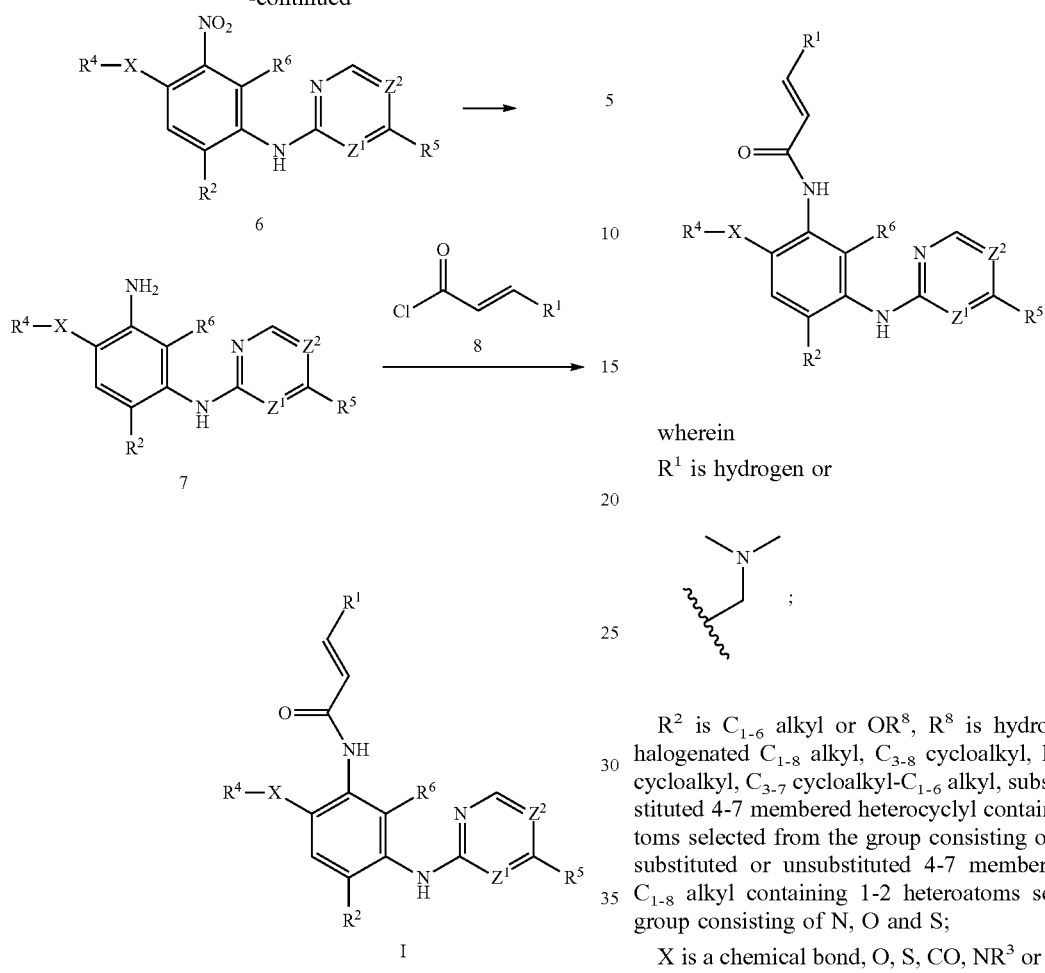

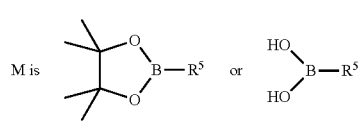

Wherein $R^1$, $R^2$, $R^4$, $R^5$, $R^6$, X, $Z^1$ and $Z^2$ are as defined above.

Preferably, in step (1), the base is sodium carbonate or sodium bicarbonate;

preferably, in step (2), the acid is methylsulfonic acid or p-toluene sulfonic acid;

preferably, in step (3), the base is selected from diisopropylethylamine, sodium carbonate and triethylamine.

Other features and advantages of the present invention are described in details as follows. The following examples and specific embodiments are aimed at describing the technical solutions of the present invention and technical effects and advantages thereof, rather than limiting the scope the present invention.

Structure of Compound as EGFR Kinase Inhibitors

The present invention relates to a compound of Formula I or pharmaceutically acceptable salt, stereoisomer, prodrug or solvate thereof wherein
$R^1$ is hydrogen or $R^2$ is $C_{1-6}$ alkyl or $OR^8$, $R^8$ is hydrogen, $C_{1-8}$ alkyl, halogenated $C_{1-8}$ alkyl, $C_{3-8}$ cycloalkyl, halogenated $C_{3-8}$ cycloalkyl, $C_{3-7}$ cycloalkyl-$C_{1-6}$ alkyl, substituted or unsubstituted 4-7 membered heterocyclyl containing 1-2 heteroatoms selected from the group consisting of N, O and S, or substituted or unsubstituted 4-7 membered heterocyclyl-$C_{1-8}$ alkyl containing 1-2 heteroatoms selected from the group consisting of N, O and S;

X is a chemical bond, O, S, CO, $NR^3$ or $CR^3$, wherein $R^3$ is hydrogen, $C_{1-6}$ alkyl, halogenated $C_{1-6}$ alkyl, $C_{3-8}$ cycloalkyl, halogenated $C_{3-8}$ cycloalkyl, $C_{1-6}$ alkoxy-$C_{1-6}$ alkyl, $C_{1-8}$ alkyl-CO or 4-6 membered heterocyclyl;

$R^4$ is $C_{1-6}$ alkyl, $C_{3-6}$ cycloalkyl, 4-7 membered heterocyclyl or 4-7 membered bicyclo-bridged heterocyclyl, which can be optionally substituted by 1-3 substituents independently selected from the group consisting of: $C_{1-6}$ alkyl, halogenated $C_{1-6}$ alkyl, $C_{1-6}$ alkoxy, halogenated $C_{1-6}$ alkoxy, $C_{3-6}$ cycloalkyl, halogenated $C_{3-6}$ cycloalkyl, $C_{3-6}$ cycloalkoxy, halogenated $C_{3-6}$ cycloalkoxy, $C_{1-6}$ alkoxy-$C_{1-6}$ alkyl, hydroxy-$C_{1-6}$ alkyl, amino-$C_{1-6}$ alkyl, $C_{1-6}$ alkyl-amino-$C_{1-6}$ alkyl, halogen, hydroxy, cyano, cyano-$C_{1-8}$ alkyl, amino, $C_{1-6}$ alkyl-amino, di($C_{1-6}$ alkyl)-amino, $C_{3-6}$ cycloalkyl-amino, $C_{1-6}$ alkylcarbonyl, $C_{1-6}$ alkyl-amino-acyl, di($C_{1-6}$ alkyl)-amino-acyl, $C_{3-6}$ cycloalkyl-amino-acyl, $C_{1-6}$ acyl-amino, substituted or unsubstituted heterocyclyl, and substituted or unsubstituted heterocyclyl-alkyl, wherein the substituent can optionally form a ring together with the carbon atom to which they are linked;

$R^5$ is a fused ring formed by two rings and selected from

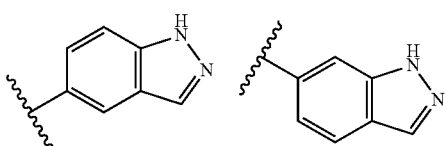

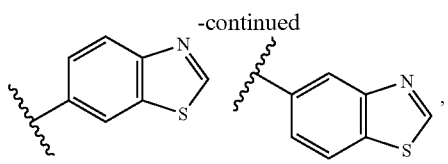

the fused ring is unnecessarily substituted by 1-3 substituents independently selected from the group consisting of: $C_{1-6}$ alkyl, halogenated $C_{1-6}$ alkyl, $C_{1-6}$ alkoxy, halogenated $C_{1-6}$ alkoxy, $C_{3-6}$ cycloalkyl, halogenated $C_{3-6}$ cycloalkyl, $C_{3-6}$ cycloalkoxy, halogenated $C_{3-6}$ cycloalkoxy, $C_{1-6}$ alkoxy-$C_{1-6}$ alkyl, hydroxy-$C_{1-6}$ alkyl, amino-$C_{1-6}$ alkyl, $C_{1-6}$ alkyl-amino-$C_{1-6}$ alkyl, halogen, hydroxyl, cyano, cyano-$C_{1-8}$ alkyl, amino, $C_{1-6}$ alkyl-amino, di($C_{1-6}$ alkyl)-amino, $C_{3-6}$ cycloalkyl-amino, $C_{1-6}$ alkyl-amino-acyl, di($C_{1-6}$ alkyl)-amino-acyl, $C_{3-6}$ cycloalkyl-amino-acyl, $C_{1-6}$ acyl-amino, substituted or unsubstituted heterocyclyl, and substituted or unsubstituted heterocyclyl-alkyl, wherein the substituent can optionally form a ring together with the carbon atom to which they are linked;

$R^6$ is hydrogen, halogen, hydroxyl, cyano, $C_{1-3}$ alkyl, halogenated $C_{1-3}$ alkyl, $C_{3-6}$ cycloalkyl, halogenated $C_{3-6}$ cycloalkyl, $C_{1-3}$ alkoxy, halogenated $C_{1-3}$ alkoxy, $C_{3-6}$ cycloalkoxy, and halogenated $C_{3-6}$ cycloalkoxy;

$Z^1$ is C—$R^7$, $Z^2$ is N, or $Z^1$ is N, $Z^2$ is C—$R^7$ (wherein $Z^1$ and $Z^2$ cannot be N simultaneously), wherein $R^7$ is hydrogen, halogen, cyano, $C_{1-3}$ alkyl, halogenated $C_{1-3}$ alkyl, $C_{3-6}$ cycloalkyl, halogenated $C_{3-6}$ cycloalkyl.

In some embodiments, $R^2$ is $OR^8$, wherein $OR^8$ is $C_{1-5}$ alkyl, halogenated $C_{1-5}$ alkyl, $C_{3-7}$ cycloalkyl, halogenated $C_{3-7}$ cycloalkyl or $C_{3-7}$ cycloalkyl-methyl; preferably, $R^2$ is $OR^8$, $R^8$ is methyl, ethyl, n-propyl, isopropyl, cyclopropyl, difluoromethyl, trifluoromethyl, cyclobutyl, or cyclopropylmethyl.

In some embodiments, X is a chemical bond or $NR^3$, wherein $R^3$ is hydrogen, methyl, ethyl, and methoxyethyl.

In some embodiments, $R^4$ is $C_{1-3}$ alkyl, $C_{3-6}$ cycloalkyl, 4-7 membered heterocyclyl or 4-7 membered bicyclo-bridged heterocyclyl containing 1-2 heteroatoms selected from N, O and S, which can be optionally substituted by 1-3 substituents independently selected from the group consisting of: $C_{1-6}$ alkyl, halogenated $C_{1-6}$ alkyl, $C_{1-6}$ alkoxy, halogenated $C_{1-6}$ alkoxy, $C_{3-6}$ cycloalkyl, halogenated $C_{3-6}$ cycloalkyl, $C_{3-6}$ cycloalkoxy, halogenated $C_{3-6}$ cycloalkoxy, $C_{1-6}$ alkoxy-$C_{1-6}$ alkyl, hydroxyl-$C_{1-6}$ alkyl, amino-$C_{1-6}$ alkyl, $C_{1-6}$ alkyl-amino-$C_{1-6}$ alkyl, halogen, hydroxyl, cyano, cyano-$C_{1-8}$ alkyl, amino, $C_{1-6}$ alkyl-amino, di($C_{1-6}$ alkyl)-amino, $C_{3-6}$ cycloalkyl-amino, $C_{1-6}$ alkylcarbonyl, $C_{1-6}$ alkyl-amino-acyl, di($C_{1-6}$ alkyl)-amino-acyl, $C_{3-6}$ cycloalkyl-amino-acyl, $C_{1-6}$ acyl-amino, and substituted or unsubstituted 4-7 membered heterocyclyl;

preferably, $R^4$ is selected from the group consisting of:

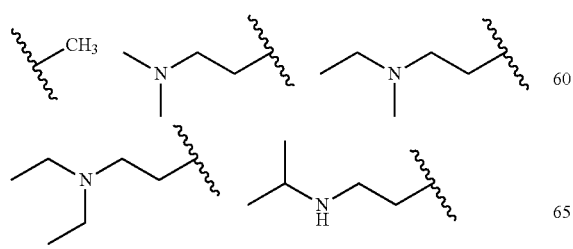
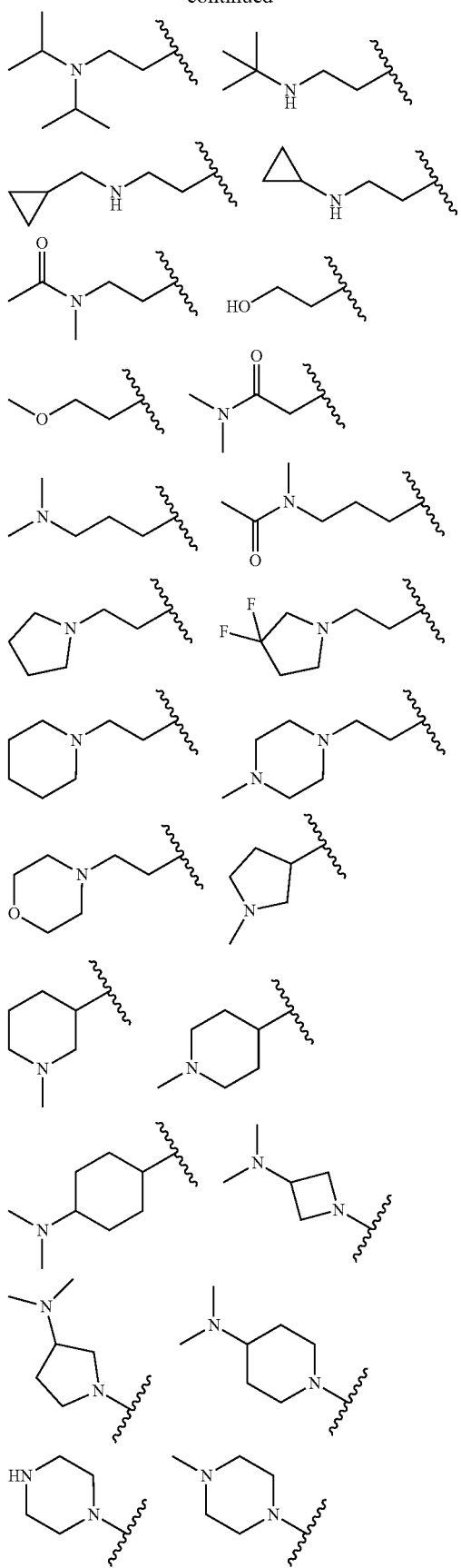

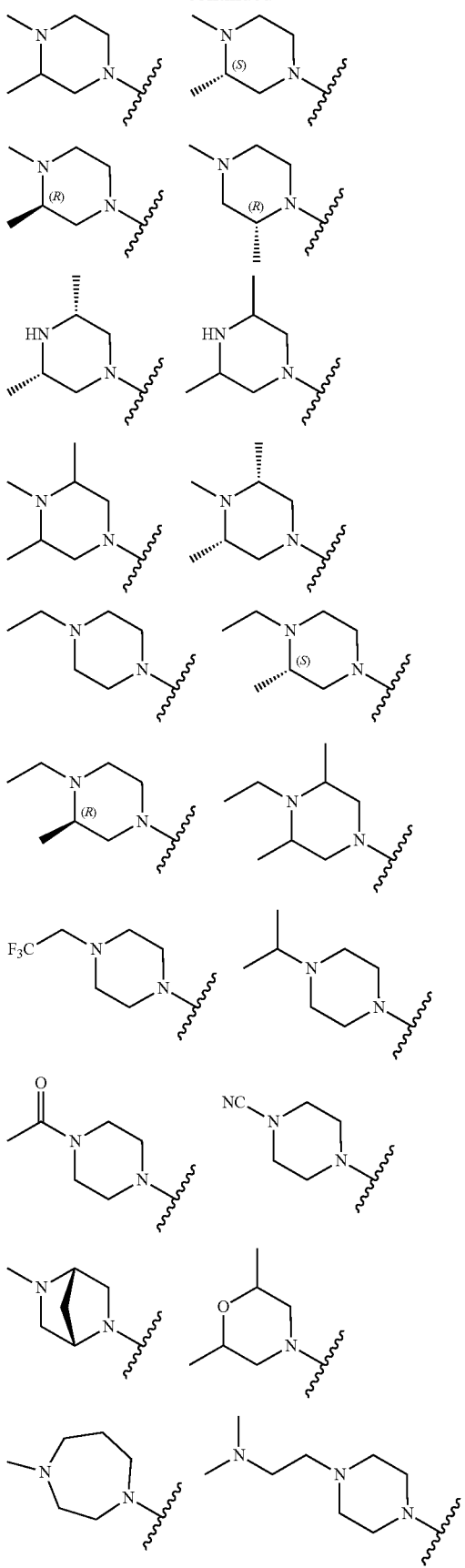
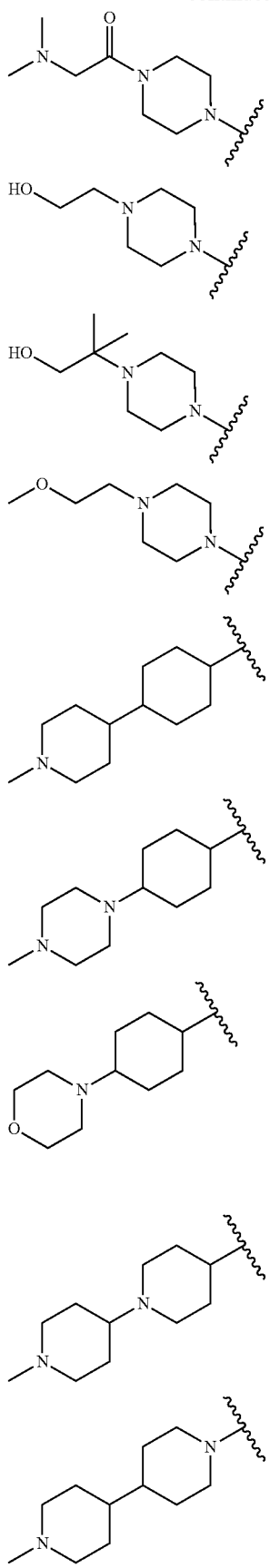

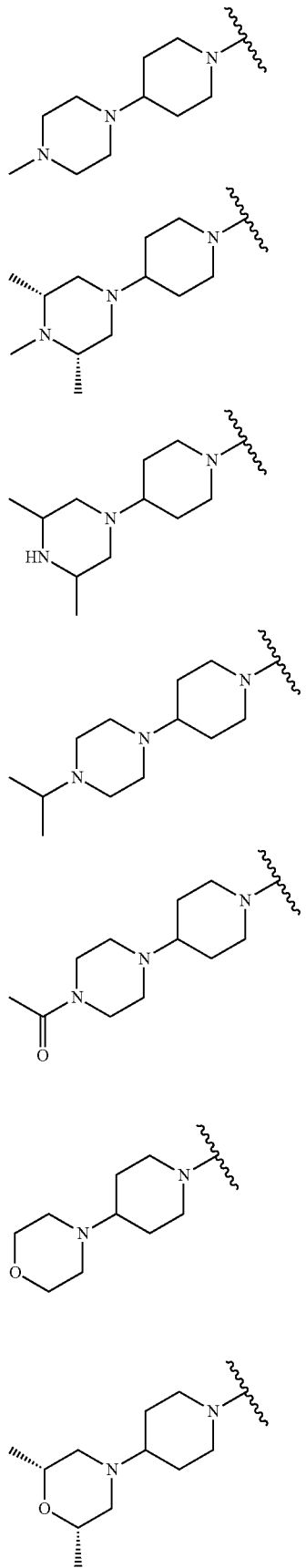
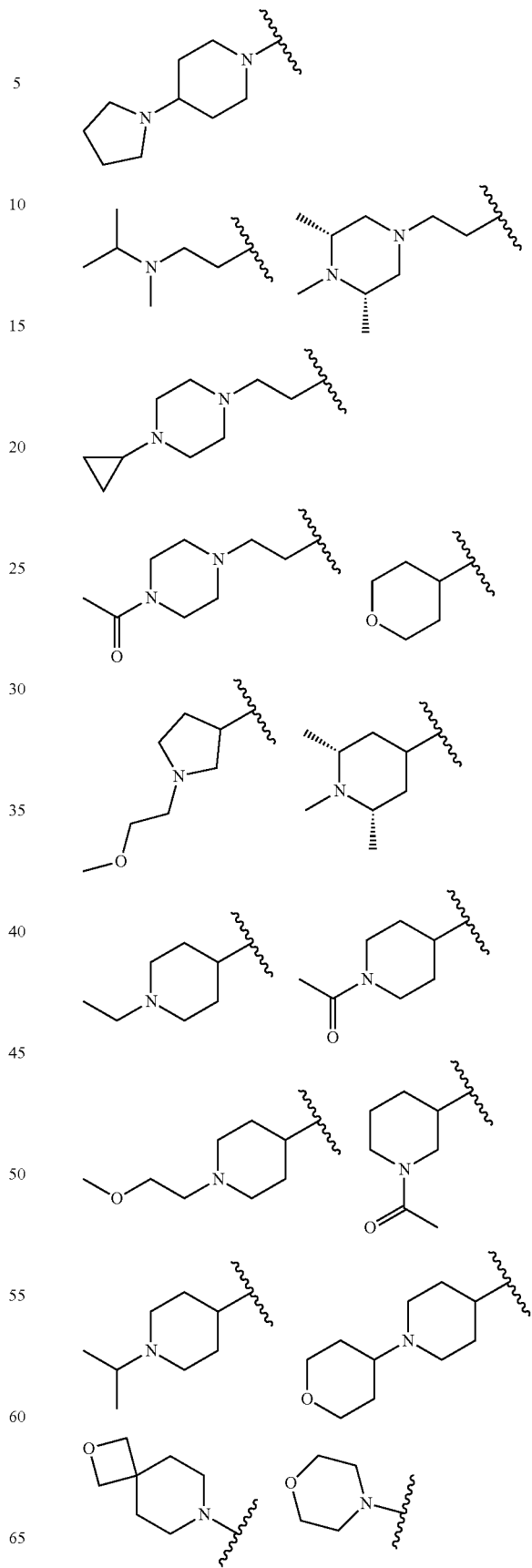

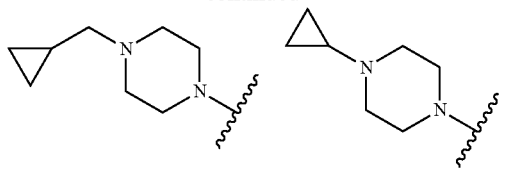
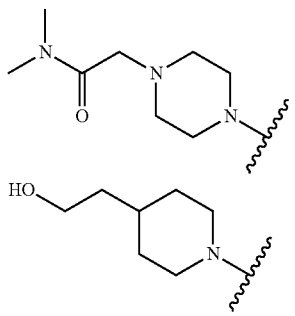
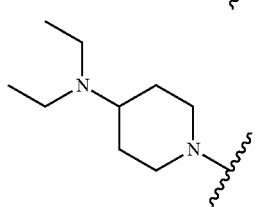
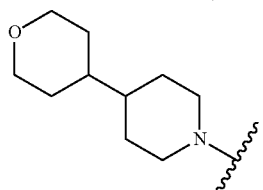
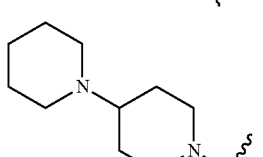
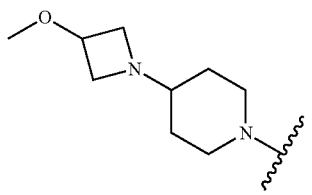
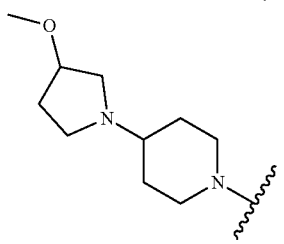
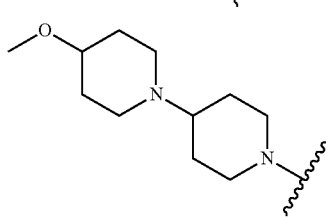
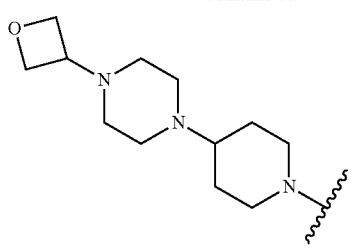
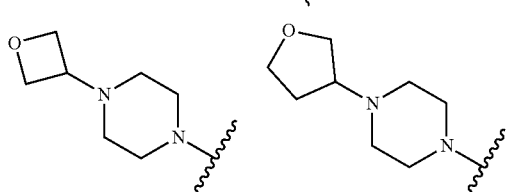
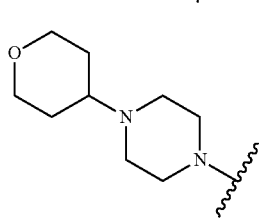
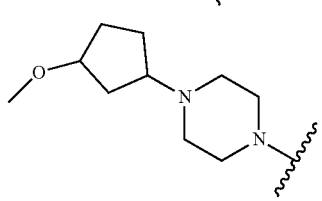
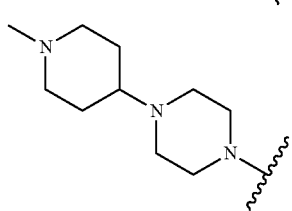
In some embodiments, R⁵ is
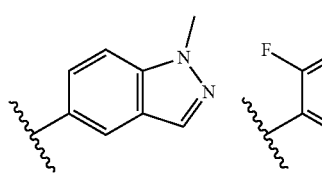
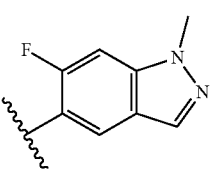
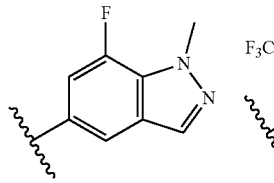
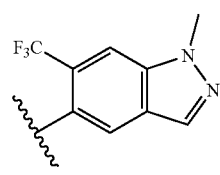
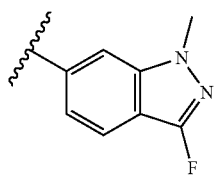
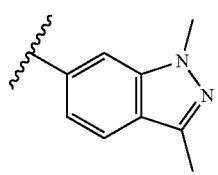

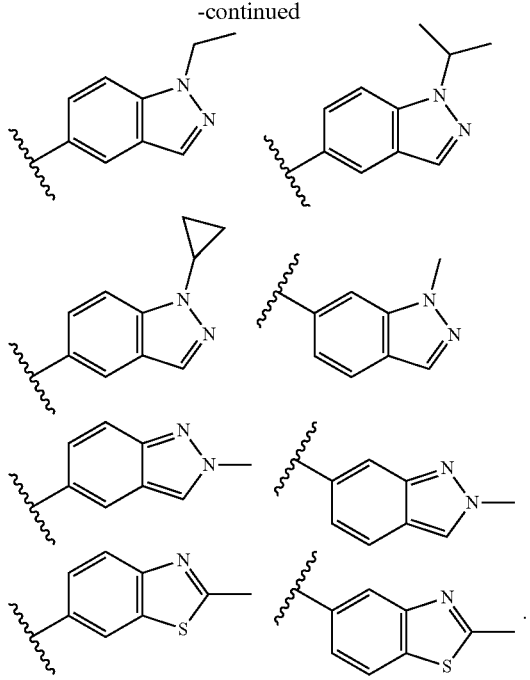

In some embodiments, $R^6$ is hydrogen, halogen, hydroxyl, cyano, $C_{1-3}$ alkyl, halogenated $C_{1-3}$ alkyl, $C_{1-3}$ alkoxy, and halogenated $C_{1-3}$ alkoxy.

In some embodiments, $Z^1$ is C—$R^7$, $Z^2$ is N, or $Z^1$ is N, $Z^2$ is C—$R^7$, wherein $R^7$ is hydrogen.

Unless otherwise indicated, the following definitions are set forth to illustrate and define the meaning and scope of various terms used to describe the present invention.

The minimum and maximum values of carbon atoms content in hydrocarbon groups are represented by a prefix, for example, the prefix $(C_{a-b})$alkyl refers to any alkyl containing "a" to "b" carbon atoms. Therefore, for example, $(C_{1-6})$alkyl means an alkyl containing one to six carbon atoms. The alkyl is branched or linear-chain.

The atoms in the compounds of the present application include isotopic atoms, for example, hydrogen may be deuterium or tritium.

"Alkyl" refers to a linear or branched, monovalent, saturated aliphatic radical, including but not limited to, e.g. methyl, ethyl, n-propyl, isopropyl, n-butyl, isobutyl, sec-butyl, tert-butyl, pentyl, isopentyl, hexyl and other similar groups, preferably $C_{1-8}$ alkyl, more preferably $C_{1-6}$ alkyl, more preferably $C_{1-4}$ alkyl.

"Cycloalkyl" refers to a saturated monocyclic or polycyclic alkyl, possibly in combination with other groups. Cycloalkyl includes but not limited to such as cyclopropyl, cyclobutyl, cyclopentyl, cyclohexyl, cycloheptyl, preferably $C_{3-8}$ cycloalkyl, more preferably $C_{3-6}$ cycloalkyl, more preferably $C_{3-4}$ cycloalkyl.

"Alkoxy" refers to linear chain or branched chain, monovalent, saturated aliphatic radical bonding with an oxygen atom, including but not limited to such as methoxy, ethoxy, propoxy, butoxy, isobutoxy, tert-butoxy, and other similar groups, preferably $C_{1-8}$ alkoxy, more preferably $C_{1-6}$ alkoxy, more preferably $C_{1-4}$ alkoxy.

"Halogen" refers to fluorine, chlorine, bromine and iodine, preferably fluorine and chlorine.

"Haloalkyl" (or halogenated alkyl) means alkyl as defined herein, wherein one or more hydrogen have been substituted with the same or different halogens. Exemplary haloalkyls include —$CH_2Cl$, —$CH_2CF_3$, $CH_2CCl_3$, perfluoroalkyl (e.g., —$CF_3$) and the like.

"Heterocyclyl" refers to non-aromatic monocyclic groups, containing heteroatoms selected from the group consisting of N, O, or S, and the remaining atoms are C. Examples of heterocyclic moieties include, but not limited to: piperidinyl, piperazinyl, homopiperazinyl, pyrrolidinyl, pyrazolidinyl, imidazolidinyl, imidazolinyl, morpholinyl, pyridyl, pyridazinyl, pyrimidinyl, oxazolidinyl, isoxazolidinyl, thiazolidinyl, isothiazolidinyl, quinuclidinyl, thiadiazolizinyl, dihydrofuranyl, tetrahydrofuranyl, dihydropyranyl, tetrahydropyranyl, thiomorpholinyl, thiomorpholinylsulfoxide, thiomorpholinyl sulfone, preferably 4-7 membered heterocyclyl, more preferably 4-6 membered heterocyclyl.

A cyclic group may bond with another group by a variety of ways. If the bonding way is not indicated, it is meant to include all possible ways. For example, "pyridyl" includes 2-, 3-, or 4-pyridyl, and "thienyl" includes 2- or 3-thienyl.

"Pharmaceutically salts" refer to conventional acid addition salts or base addition salts which keep biological effectiveness and properties of the compounds expressed by Formula I, which are formed by suitable non-toxic organic or inorganic acids or organic or inorganic bases. Examples of acid addition salts include those salts derived from inorganic acids and organic acids, wherein the inorganic acids include such as hydrochloric acid, hydrobromic acid, hydroiodic acid, sulfuric acid, sulfamic acid, phosphoric acid and nitric acid. The organic acids include such as p-methyl benzenesulfonic acid, salicylic acid, methanesulfonic acid, oxalic acid, succinic acid, citric acid, maleic acid, lactic acid, fumaric acid and the like. Examples of alkali addition salts include salts derived from ammonium, potassium, sodium and quaternary ammonium hydroxide, such as tetramethylammonium hydroxide. It is well known for pharmacists to change pharmaceutical compounds (i.e. drugs) into salts to improve physical and chemical stability, hygroscopicity, flowability and solubility of the compounds.

Method for Preparing the Compounds as EGFR Kinase Inhibitors

The present application also relates to a method for preparing the compounds as shown in Formula I. The compounds of the present invention can be prepared through any conventional means. Appropriate methods for synthesizing these compounds are provided in Examples. In a multi-step synthetic route, the reaction order can be adjusted under certain circumstances.

In some embodiments, the present invention provides a method for preparing the compounds as shown in Formula I comprising reacting compound 1 with compound M to form compound 2 in the presence of base, after that reacting the compound 2 with compound 3 to give the compounds as shown in Formula I in the presence of acid;

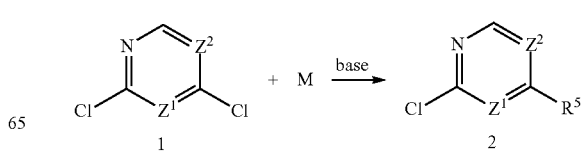

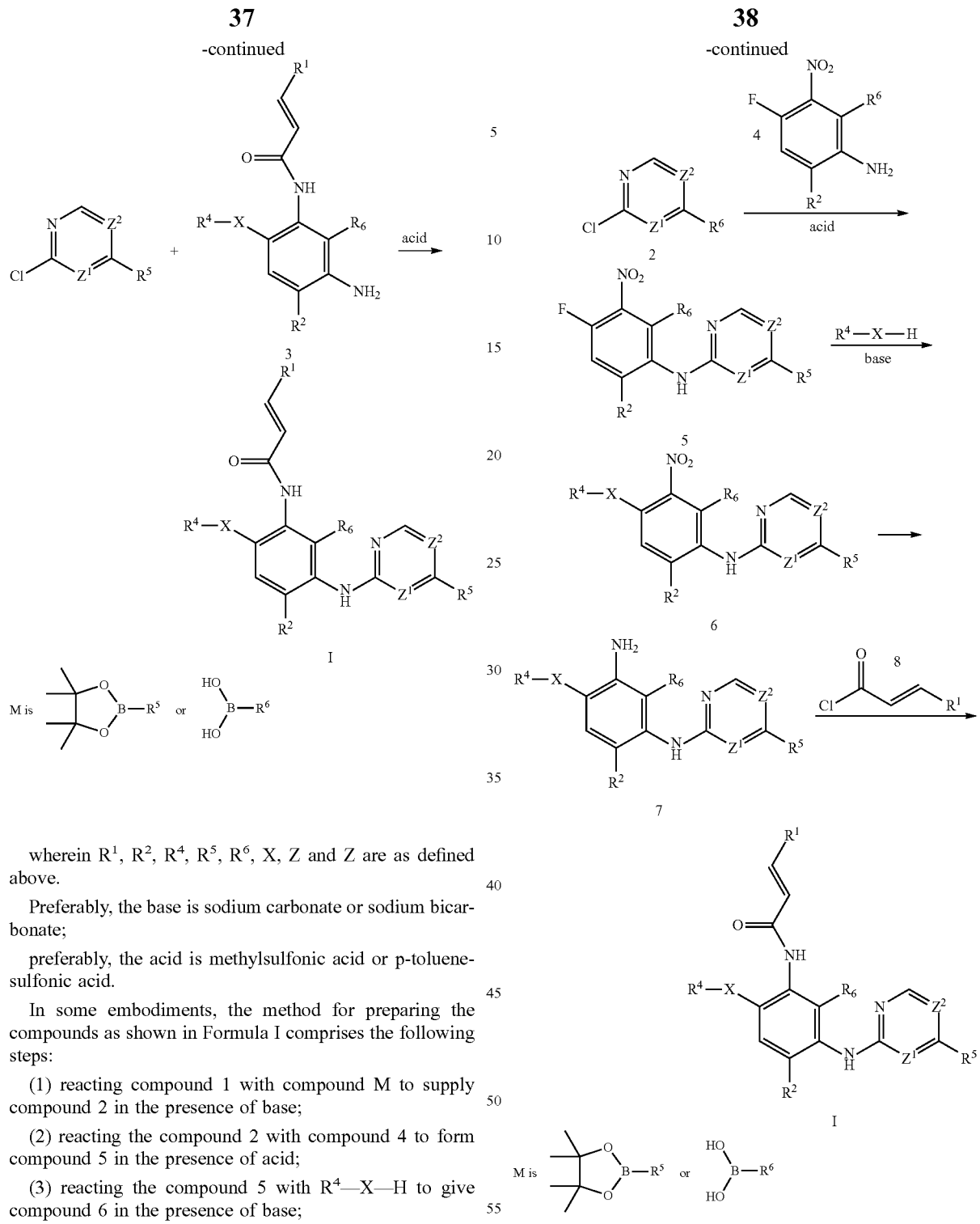

wherein $R^1$, $R^2$, $R^4$, $R^5$, $R^6$, X, Z and Z are as defined above.

Preferably, the base is sodium carbonate or sodium bicarbonate;

preferably, the acid is methylsulfonic acid or p-toluenesulfonic acid.

In some embodiments, the method for preparing the compounds as shown in Formula I comprises the following steps:

(1) reacting compound 1 with compound M to supply compound 2 in the presence of base;

(2) reacting the compound 2 with compound 4 to form compound 5 in the presence of acid;

(3) reacting the compound 5 with $R^4$—X—H to give compound 6 in the presence of base;

(4) reducing the compound 6 to provide compound 7;

(5) reacting the compound 7 with compound 8 to give the compounds as shown in Formula I;

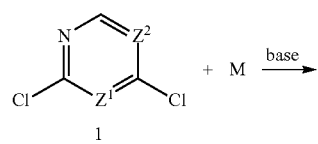

wherein $R^1$, $R^2$, $R^4$, $R^5$, $R^6$, X, $Z^1$ and $Z^2$ are as defined above preferably, in step (3), the base is selected from diisopropylethylamine, sodium carbonate and triethylamine.

Preferably, in step (1), the base is sodium carbonate or sodium bicarbonate;

preferably, in step (2), the acid is methylsulfonic acid or p-toluene sulfonic acid;

preferably, in step (3), the base is selected from diisopropylethylamine, sodium carbonate and triethylamine.

Pharmaceutical Compositions as EGFR Kinase Inhibitors

The present invention also provides a pharmaceutical composition comprising the compounds as EGFR kinase inhibitors and pharmaceutically acceptable carriers or excipients.

The term "pharmaceutically acceptable carrier" herein refers to a pharmaceutically acceptable substance, component or medium, such as liquid or solid filler, diluting agent, excipient, solvent or encapsulating material, which participates in loading or delivering the compounds of the present invention from one location, body fluids, tissues, organs (internal or external), or part of body to another location, body fluids, tissues, organs (internal or external), or part of body. The pharmaceutically acceptable carrier can be a medium, diluting agent, excipient or other materials which do not have excessive toxicity or side effects and can be used to contact animal tissues. Typical pharmaceutically acceptable carrier includes saccharides, starches, cellulose, maltose, gum tragacanth, gelatin, Ringer's solution, alginic acid, physiological saline and buffers and so on.

Each pharmaceutically acceptable carrier should be compatible with other components, for example, they may form preparations with the compounds of the present invention, do not have excessive toxicity, stimulus, allergic response, immunogenicity or other problems or complications to living biological tissues or organs, and have a reasonable benefit-risk ratio.

Some of the pharmaceutically acceptable carriers include: (1) saccharides, such as lactose, glucose and sucrose; (2) starches, such as corn starch and potato starch; (3) cellulose and its derivatives, such as sodium carboxymethylcellulose, ethyl cellulose and acetyl cellulose; (4) gum tragacanth powder; (5) maltose; (6) gelatin; (7) talcum powder; (8) excipients, such as cocoa butter and suppository wax; (9) oils, such as peanut oil, cottonseed oil, safflower oil, sesame oil, olive oil, corn oil and soybean oil; (10) glycols, such as propylene glycol; (11) polyols, such as glycerol, sorbitol, mannitol and polyethylene glycol; (12) lipids, such as ethyl oleate and ethyl laurate; (13) agaropectin; (14) buffers, such as magnesium hydroxide and aluminium hydroxide; (15) alginic acid; (16) sterile pyrogen-free water; (17) physiological saline; (18) Ringer's solution; (19) alcohols, such as ethanol and propanol; (20) phosphate buffer; (21) other non-toxic compatible substances in pharmaceutical formulations, such as acetone.

The pharmaceutical compositions may comprise pharmaceutically acceptable ingredients to simulate physiological conditions, such as pH adjusting and buffering agents, toxicity adjusting agents, and so on, such as sodium acetate, sodium chloride, potassium chloride, calcium chloride, sodium lactate and the like.

Pharmaceutical ingredients can be prepared into any suitable formulation, such as solid dosage form (e.g. tablets, capsules, powder, granules, etc.) and liquid dosage form (e.g. aqueous solution, emulsion, elixir, syrup, etc.). The methods for preparing pharmaceutical compositions has been well known, which can be prepared according to conventional processes, for example, provided by Remington in The Science and Practice of Pharmacy (Gennaro ed. 20th edition, Williams & Wilkins PA, USA) (2000).

In some embodiments, the compounds or pharmaceutical compositions of the present invention can be formulated into dosage forms suitable for drug release, which are administered by injection (e.g. subcutaneous, intravenous, intramuscular, intraarterial, hydrocele, intracystic, box, intracardiac, intradermal, intraperitoneal, intratracheal, epidermis, intraarticular, subcapsular, subarachnoid, intraspinal, intraster- nal, and/or infusion) and by non-injection route (e.g. oral, parenteral, buccal, nasal, intranasal, mucosal, epidermal, plaster, dermal, ophthalmic, pulmonary, sublingual, rectal, vaginal or surface skin local application).

Suitable formulations include (but not limited to) injectable dosage forms, such as emulsion, solution and suspension, oral dosage forms such as tablet, capsule, pill, sugar coated pill, powder and granule, topical dosage forms or transdermal absorption dosage forms such as spray, ointment, paste, cream, lotion, gel, solution, drug patch and inhaler, and those for vaginal or rectal dosage forms such as suppository. These formulations can be prepared under appropriate conditions according to the compounds and suitable excipients, while the preparation methods and processes are well known in the art, for example provided by Remington in The Science and Practice of Pharmacy (Gennaro ed. 20th edition, Williams & Wilkins PA, USA) (2000).

In some embodiments, the present application provides a pharmaceutical composition comprising the above-mentioned compounds and pharmaceutically acceptable carriers or excipients. In some embodiments, the pharmaceutical composition is tablet, capsule, pill, granule, powder, suppository, injection, solution, suspension, ointment, patch, lotion, drop, liniment and spray.

Use of the Pharmaceutical Compositions of as EGFR Kinase Inhibitors

In another aspect, the present invention provides a use of the above-mentioned compounds and/or the pharmaceutical compositions in the preparation of drugs and the treatment of diseases.

In some embodiments, the present invention provides a use of the above-mentioned compounds and/or the pharmaceutical compositions in the preparation of antitumor drugs.

In some embodiments, the present application provides a use of the above-mentioned compounds and/or the pharmaceutical compositions in the preparation of antitumor drugs. In some embodiments, the antitumor drugs are applied for the following conditions: head and neck cancer, melanoma, bladder cancer, esophageal cancer, anaplastic large cell lymphoma, renal cell cancer, breast cancer, colorectal cancer, ovarian cancer, cervical cancer, pancreatic cancer, glioma, glioblastoma, prostate cancer, leukemia, lymphoma, non-Hodgkin's lymphoma, stomach cancer, lung cancer, hepatocellular cancer, gastrointestinal stromal tumors, thyroid cancer, cholangiocarcinoma, uterus endometrial cancer, multiple myeloma or mesothelioma.

In some embodiments, the present application provides a method for treating tumors in a subject, comprising administering to the subject a therapeutically effective amount of the above-mentioned compounds or the pharmaceutical compositions, wherein the subject is preferably a mammal, and the mammal is preferably a human being. In some embodiments, the administration method includes oral, mucosal, sublingual, ophthalmic, topical, parenteral, rectal, cisterna, vaginal, peritoneal, bladder and nasal administration.

The compounds or the pharmaceutical compositions of the present invention can enter the organism through any suitable ways, such as oral, intravenous injection, intranasal, external, intramuscular injection, intradermal injection, transdermal administration or subcutaneous route. In some embodiments, the administration method of the compounds or the pharmaceutical compositions of the present invention includes oral, mucosal, sublingual, ophthalmic, topical, parenteral, rectal, cisterna, vaginal, peritoneal, bladder and nasal administration.

In some embodiments, the compounds or the pharmaceutical compositions of the present invention can be administrated simultaneously with a second active substance to achieve additive or even synergetic effects in organisms. For example, the compounds of the present invention may be combined with a second active substance into a pharmaceutical composition, or administrated simultaneously with a second active substance in an independent composition, or administrated in turn with a second active substance. The second active substance which can be administrated simultaneously with the compounds of the invention for the treatment of cancer includes but are not limited to: fluorouracil, adriamycin, daunorubicin, tamoxifen, leuprorelin, goserelin, flutamide, nilumite, finasteride, dexamethasone, aminoglutethimide, amsacrine, anastrozole, asparaginase, *Bacillus* Calmette-Guerin vaccine, bicalutamide, bleomycin, busulfan, camptothecin, capecitabine, carboplatin, carmustine, chlorambucil, cisplatin, cladribine, colchicine, cyclophosphamide, cyproterone, cytarabine, dacarbazine, actinomycin d, daunomycin, dienestrol, diethylstilbestrol, docetaxel, adriamycin, epirubicin, estradiol, estramustine, etoposide, exemestane, filgrastim, fludarabine, hydrocortisone, fluorouracil, flurotestosterone, flutamide, gemcitabine, genistein, goserelin, tamoxifen, teniposide, testosterone, titanium dichloride, topotecan, trastuzumab, retinoic acid, vinblastine, hydroxyurea, idarubicin, ifosfamide, imatinib, interferon, irinotecan, letrozole, formyltetrahydrofolate, penastatin, mithramycin, procarbazine, raltitrexed, porfi mer sodium, rituximab, streptozotocin, suramin, leuprorelin, levamisole, lomustine, mustargen, medroxyprogesterone, megestrol acetate, melphalan, mercaptopurine, mesna, methotrexate, mitomycin, mitotane, mitoxantrone, nilutamide, nocodazole, octreotide, platinum, paclitaxel, pamidronic acid, thioguanine, thiophosphoramide, chloromethane, topotecan ferrocene, trastuzumab, retinoic acid, vinblastine, vincristine, vindesine, vinorelbine.

In some embodiments, the compounds provided by the present invention can be used simultaneously with a non-chemical method for the treatment of cancer. In some embodiments, the compounds provided by the present invention can be applied simultaneously with radiotherapy. In some embodiments, the compounds provided by the invention can be used in combination with surgical operation, tumor thermotherapy, ultrasound focusing therapy, cryotherapy or their combination.

In some embodiments, the compounds provided by the present invention can be used simultaneously with a steroid. Appropriate steroid includes but not limited to: amcinonide, beclomethasone, betamethasone, budesonide, chlorprednisone, clobetasol, corticosterone, cortisone, hydroxyprednisone, dexamethasone, difluorosathon, difluoromethasone, difluprednate, glycyrrhetinic acid, fluazacort, flumetasone, fluorinone, flucloronide, lidex, fluororelaxant acetate, fluorobutyl ester, fluorocorone, hydroxyfluoroacetone, fluperone acetate, fluprednidine acetate, fluprednisolone, flurandrenolide, fluorine propionate, formocortal, clobetasol propionate, halcinonide, halometasone, hydrocortisone, loteprednol etabonate, mazipredone, medrysone, meprednisone, 6-methylprednisone, zairen furoate, paramethasone, prednisolone, dexamethasone, and prednisolone 25-diethylamine acetate.

In some embodiments, the compounds provided by the present invention can be used simultaneously with an immunotherapeutic agent. Appropriate immunotherapeutic agent includes: tumor cells multidrug resistance reversal agent (such as verapamil), rapamycin, mycophenolate mofetil, thalidomide, cyclophosphamide, cyclosporine, and monoclonal antibodies.

DETAILED DESCRIPTION OF THE EMBODIMENTS

EXAMPLE 1

Preparation of 1,2,6-trimethylpiperazine trifluoroacetate

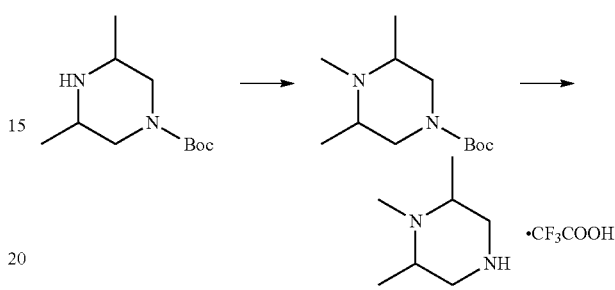

Step 1: tert-butyl 3,4,5-trimethylpiperazine-1-carboxylate

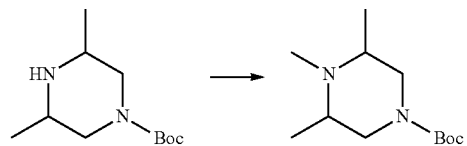 [SMILES: CC1CN(C(=O)OC(C)(C)C)CC(C)N1 ; CC1CN(C(=O)OC(C)(C)C)CC(C)N1C]

Tert-butyl 3,5-dimethylpiperazine-1-carboxylate (520 mg, 2.43 mmol) and THF (10 mL) were added to a 100 mL three-necked bottle under the protection of argon and cooled to about 0° C. NaH (70 mg, 2.91 mmol) was added thereinto, stirred at 0° C. for half an hour, and then CH$_3$I (690 mg, 4.86 mmol) in THF (1 mL) was added dropwise thereinto. After the addition, the reaction mixture was stirred at 0° C. for 1 hour, and then warmed to room temperature and kept stirring. The reaction was monitored by TLC, after the reaction completed, 50 mL water and 30 mL ethyl acetate were added thereinto, stirred to separate into layers, aqueous phase was extracted with ethyl acetate (30 mL×2) twice, organic phases were combined, washed with saturated brine (50 mL×2) twice, dried with anhydrous sodium sulfate, and filtered, and filtrate was concentrated to give a product of 510 mg.

Step 2: 1,2,6-trimethylpiperazine trifluoroacetate

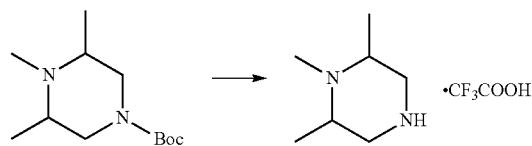

Tert-butyl 3,4,5-trimethylpiperazine-1-carboxylate, dichloromethane (10 mL) and trifluoroacetic acid (4 mL) were added in order into a 100 mL single-necked bottle, stirred at room temperature, the reaction was monitored by TLC, after the reaction completed, the reaction mixture was concentrated to give 870 mg 1,2,6-trimethylpiperazine trifluoroacetate (280 mg in theory).

EXAMPLE 2

Preparation of cis 1,2,6-trimethylpiperazine trifluoroacetate

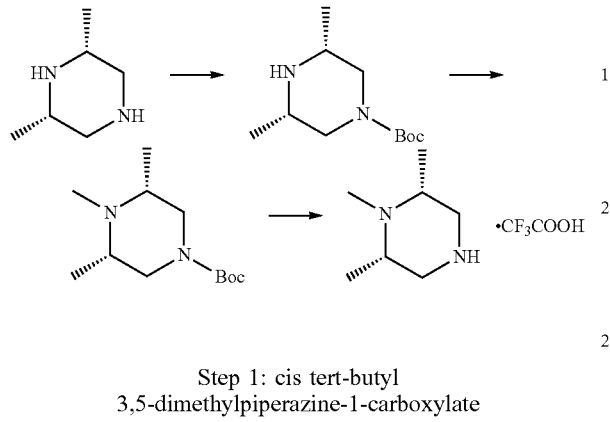

Step 1: cis tert-butyl 3,5-dimethylpiperazine-1-carboxylate

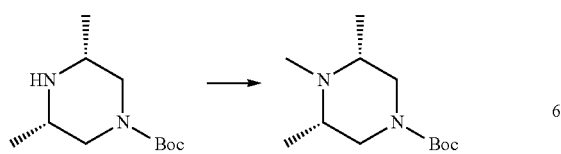

Cis 2,6-dimethylpiperazine (1.0 g, 8.76 mmol) and dichloromethane (20 mL) were added to a 100 mL single-necked bottle, cooled to 0-5° C. Triethylamine (2.22 g, 21.89 mmol) was added thereinto, and then (Boc)₂O (1.92 g, 8.76 mmol) in dichloromethane (10 mL) was added dropwise thereinto, then, the reaction mixture was warmed to room temperature and stirred overnight. The reaction was monitored by TLC, after the reaction completed, the reaction mixture was concentrated under reduced pressure, purified by column chromatography with DCM/MeOH=30/1 as eluent, the product was collected and concentrated to give a product of 1.9 g.

Step 2: cis tert-butyl 3,4,5-trimethylpiperazine-1-carboxylate

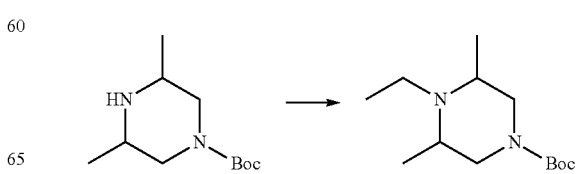

The compound was synthesized with cis tert-butyl 3,5-dimethylpiperazine-1-carboxylate and CH₃I as the starting materials according to the method in the step 1 of EXAMPLE 1.

Step 3: cis 1,2,6-trimethylpiperazine trifluoroacetate

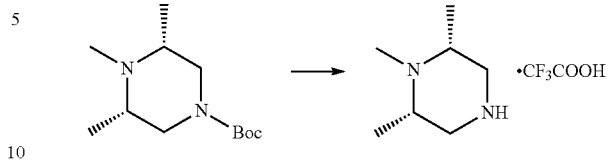

The compound was synthesized with cis tert-butyl 3,4,5-trimethylpiperazine-1-carboxylate as the starting material according to the method in the step 2 of EXAMPLE 1.

EXAMPLE 3

Preparation of (1S,4S)-2-methyl-2,5-diazabicyclo[2.2.1]heptane trifluoroacetate

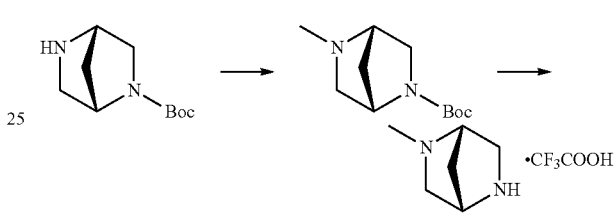

The compound was synthesized with cis tert-butyl (1S, 4S)-2,5-diazabicyclo[2.2.1]heptane-2-carboxylate and CH₃I as the starting materials according to the method of EXAMPLE 1.

EXAMPLE 4

Preparation of 1-ethyl-2,6-dimethylpiperazine trifluoroacetate

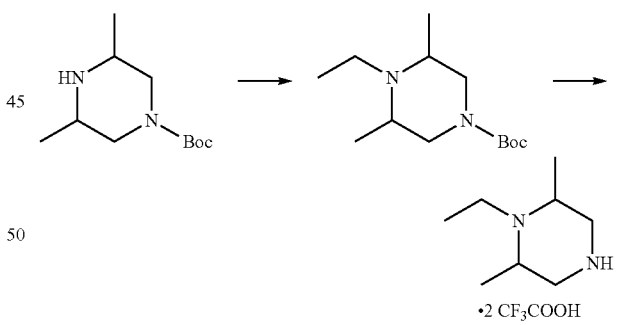

Step 1: tert-butyl 4-ethyl-3,5-dimethylpiperazine-1-carboxylate

The compound was synthesized with tert-butyl 3,5-dimethylpiperazine-1-carboxylate and C₂H₅I as the starting materials, DMF as the solvent with a temperature of 80° C. for 7-8 hours according to the method in the step 1 of EXAMPLE 1.

Step 2: 1-ethyl-2,6-dimethylpiperazine trifluoroacetate

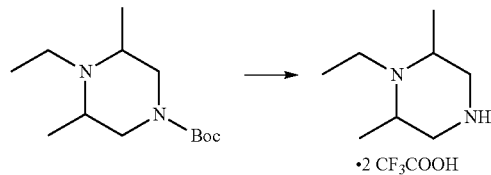

The compound was synthesized with tert-butyl 4-ethyl-3,5-dimethylpiperazine-1-carboxylate as the starting material according to the method in the step 2 of EXAMPLE 1.

EXAMPLE 5

Preparation of (S)-1-ethyl-2-methylpiperazine trifluoroacetate

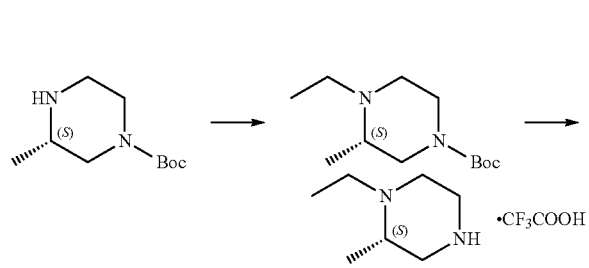

The compound was synthesized according to the method of EXAMPLE 1 except that tert-butyl (S)-3-methylpiperazine-1-carboxylate and C₂H₅I were used as the starting materials.

EXAMPLE 6

Preparation of (R)-1-ethyl-2-methylpiperazine trifluoroacetate

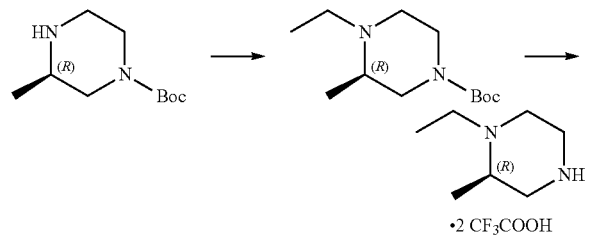

The compound was synthesized according to the method of EXAMPLE 1 except that tert-butyl (R)-3-methylpiperazine-1-carboxylate and C₂H₅I were used as the starting materials.

EXAMPLE 7

Preparation of (S)-1,2-dimethylpiperazine trifluoroacetate

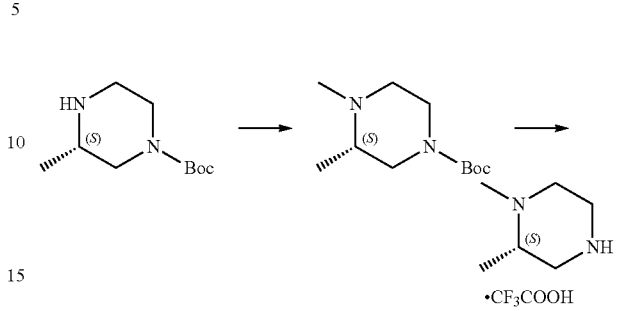

The compound was synthesized according to the method of EXAMPLE 1 except that tert-butyl (S)-3-methylpiperazine-1-carboxylate was used as the staring material.

EXAMPLE 8

Preparation of (R)-1,2-dimethylpiperazine trifluoroacetate

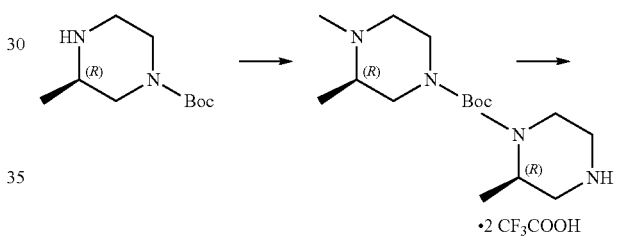

The compound was synthesized according to the method of EXAMPLE 1 except that tert-butyl (R)-3-methylpiperazine-1-carboxylate was used as the staring material.

EXAMPLE 9

Preparation of (R)-1,3-dimethylpiperazine

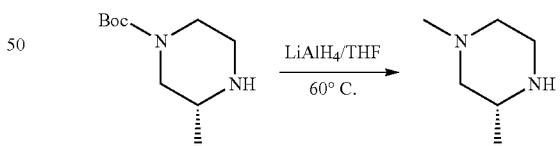

Lithium aluminum hydride (1.36 g, 36 mmol) was added to a 250 mL three-necked bottle under the protection of argon and cooled to about 0° C., and then THF (100 mL) was added dropwise thereinto, after the addition completed, tert-butyl (R)-3-methyl-piperazine-1-carboxylate (3.60 g, 18 mmol) in THF (10 mL) was added dropwise thereinto, the temperature was kept at −5~0° C., after the addition completed, the temperature was raised to 60° C. and reacted under reflux for 2 h. The reaction was monitored by TLC. The starting materials reacted completely, and then the temperature was cooled to about 0° C., water (1.37 mL), aqueous sodium hydroxide solution (2 N, 1.37 mL) and water (2.74 mL) were added dropwise slowly in order to quench the reaction, stirred for 5 min, and filtered, the filter cake was washed with 15 mL methanol, the filtrate was concentrated at 40° C. to give a 2 g colorless oil. The crude product was purified by column chromatography with neutral alumina as the adsorbent and DCM/MeOH=20/1 as eluent, the product was collected and concentrated to give a 1.3 g colorless oil with a yield of 65%.

EXAMPLE 10

Preparation of N,1-dimethylpyrrolodin-3-amine

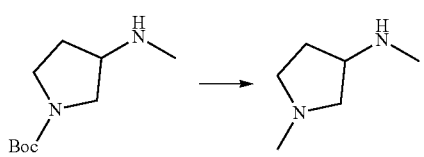

The compound was synthesized according to the method of EXAMPLE 9 except that tert-butyl 3-(methylamino)pyrrolodin-1-carboxylate was used as the starting material.

EXAMPLE 11

Preparation of N-methyl-2-(4-methylpiperazine-1-yl)ethyl-1-amine

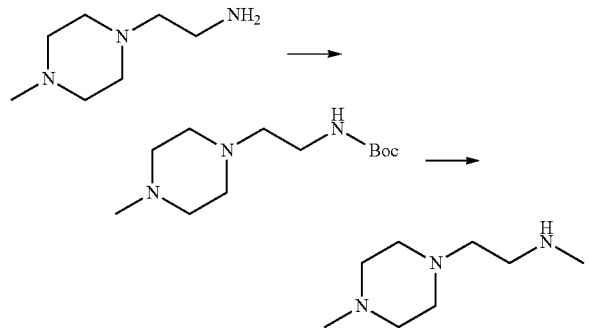

Step 1: tert-butyl methyl(2-(4-methylpiperazine-1-yl)ethyl)amine Carboxylate

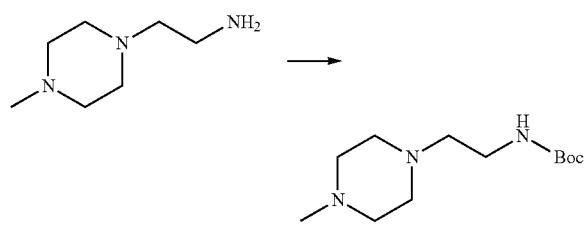

2-(4-methylpiperazine-1-yl)ethyl-1-amine (1.0 g, 6.98 mmol) and DCM (15 mL) were added to a 100 mL three-necked bottle. The mixture was cooled to 0° C. in an ice-water bath. Trimethylamine (1.41 g, 13.96 mmol) was added thereinto, stirred for 0.5 h, and then (Boc)₂O (1.53 g, 6.98 mmol) in DCM (5 mL) was added dropwise. After the addition completed, the temperature was raised to room temperature and reacted with stirring. The reaction was monitored by TLC. After the reaction completed, the reaction mixture was concentrated. The crude product was purified by column chromatography with DCM/MeOH=30/1 as eluent, the product was collected and concentrated to give the target compound of 1.4 g.

Step 2: N-methyl-2-(4-methylpiperazine-1-yl)ethyl-1-amine

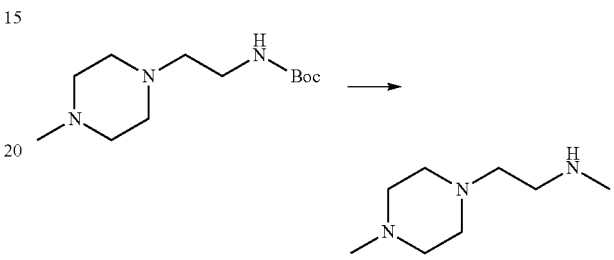

The compound was synthesized with tert-butyl methyl(2-(4-methylpiperazine-1-yl) ethyl)amine carboxylate as the starting material according to the method of EXAMPLE 9.

EXAMPLE 12

N-methyl-2-(piperazine-1-yl)ethylamine trifluoroacetate

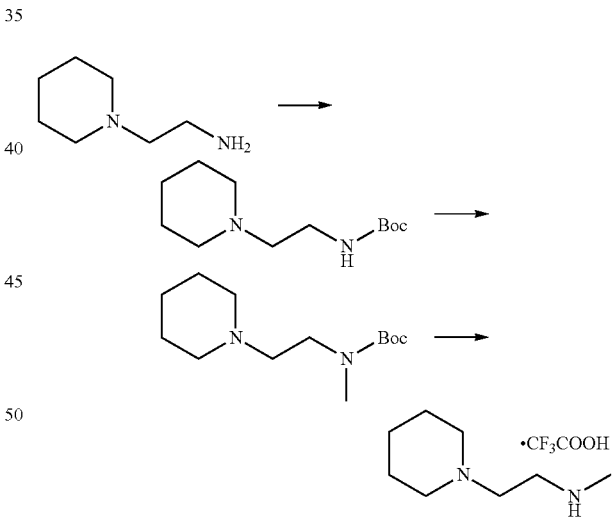

Step 1: tert-butyl (2-piperazine-1-yl) ethyl)amine carboxylate

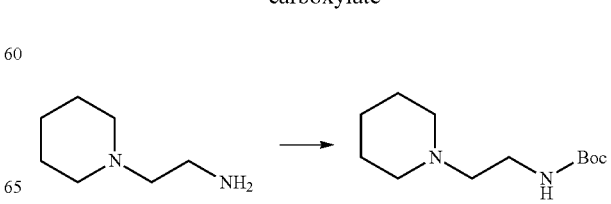

1-(2-aminoethyl)piperazine (500 mg, 3.84 mmol) and THF (10 mL) were added to a 100 mL three-necked bottle under the protection of argon and cooled to 0-5° C., and then (Boc)₂O (1.05 g, 4.81 mmol) in THF (2 mL) was added dropwise thereinto, after the addition completed, the reaction mixture was warmed to room temperature, and reacted with stirring. The reaction was monitored by TLC, after the reaction completed, 50 mL water and 50 mL ethyl acetate were added, stirred to separate into layers, the aqueous phase was extracted with ethyl acetate (40 mL) once, the organic phase were combined and washed with saturated brine (50 mL×2) twice, dried with anhydrous sodium sulfate for 30 min, and filtered, concentrated to give 891 mg of product.

Step 2: tert-butyl methyl(2-(piperazine-1-yl) ethyl)amine carboxylate

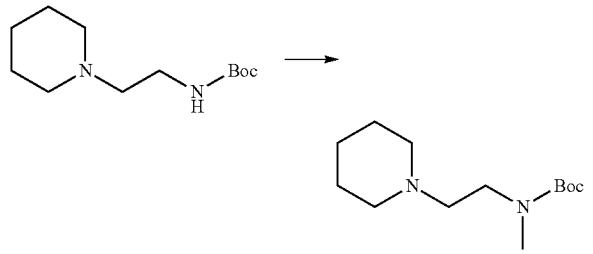

DMF (10 mL) and NaH (220 mg, 5.50 mmol) were added to a 100 mL three-necked bottle under the protection of argon and cooled to about 0-5° C. in an ice-salt bath, tert-butyl (2-piperazine-1-yl) ethyl)amine carboxylate (890 mg, 3.67 mmol) in DMF (5 mL) was added dropwise, after the addition completed, the reaction mixture was stirred at 0-5° C. for 1 h. CH₃I (780 mg, 5.50 mmol) in DMF (1 mL) was added dropwise, after the addition completed, the reaction mixture was stirred at 0-5° C. for 1 h, and then warmed to room temperature to react for 1 d. TLC was used to monitor the reaction, after the reaction completed, 50 mL aqueous ammonium chloride solution and 40 mL ethyl acetate were added, stirred to separate into layers, the aqueous phase was extracted with ethyl acetate (30 mL×2) twice, the organic phase were combined, washed with saturated brine (50 mL×2) twice, dried with anhydrous sodium sulfate for 30 min, and filtered, the filtrate was concentrated to give crude product. The crude product was purified by column chromatography with DCM/MeOH=30/1 as eluent, the product was collected and concentrated to give 140 mg.

Step 3: N-methyl-2-(piperazine-1-yl)ethylamine trifluoroacetate

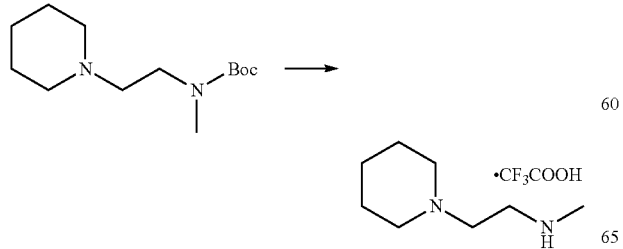

Methyl(2-(piperazine-1-yl)ethyl)amine carboxylate (130 mg, 0.54 mmol), dichloromethane (3 mL) and trifluoroacetic acid (2 mL) were sequentially added into a 100 mL single-necked bottle, stirred at room temperature, TLC was used to monitor the reaction, after the reaction was completed, the reaction mixture was concentrated to give 148 mg of N-methyl-2-(piperazine-1-yl)ethylamine trifluoroacetate, which was directly used to the next step without further purification.

EXAMPLE 13

Preparation of N-methyl-2-(pyrrolidine-1-yl) ethylamine trifluoroacetate

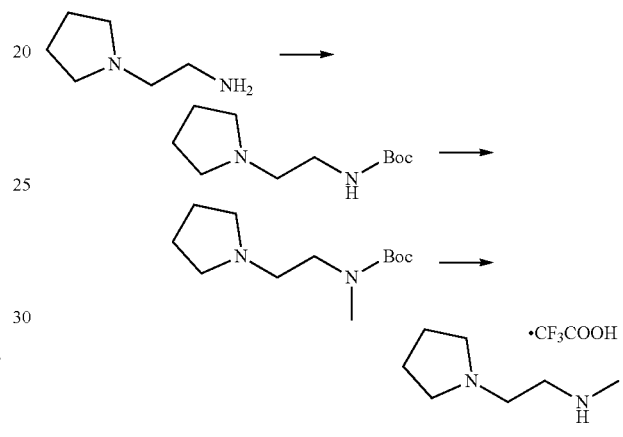

The compound was synthesized according to the method of EXAMPLE 12 except that 1-(2-aminoethyl)pyrrolidine was used as the starting material.

EXAMPLE 14

Preparation of N-methyl-2-morpholine ethyl-1-amine trifluoroacetate

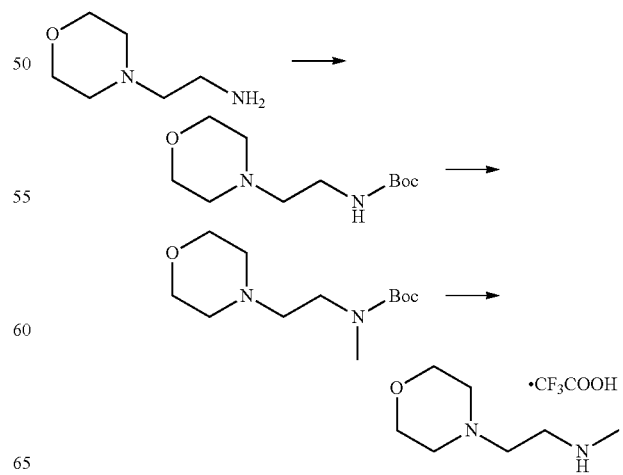

Step 1: tert-butyl (2-morpholineethyl)amine carboxylate 1-(2-aminoethyl)morpholine (500 mg, 3.84 mmol), dioxane 10 mL, sodium carbonate (814 mg, 7.68 mmol) and water (2 mL) were sequentially added to 100 mL three-necked bottle under the protection of argon and cooled to 0° C. in an ice-salt bath. (Boc)₂O (992 mg, 4.55 mmol) in dioxane (1 mL) was added dropwise, reacted with stirring. TLC was used to monitor the reaction, when the reaction completed, water (50 mL) and ethyl acetate (40 mL) were added thereinto, stirred to separate into layers, the aqueous phase was extracted with ethyl acetate (40 mL) once, the organic phase were combined, washed with saturated brine (50 mL×2) twice, dried with anhydrous sodium sulfate for 30 min, and filtered, the filtrate was concentrated to give a 885 mg of product.

Step 2: tert butyl methyl(2-morpholineethyl)amine carboxylate

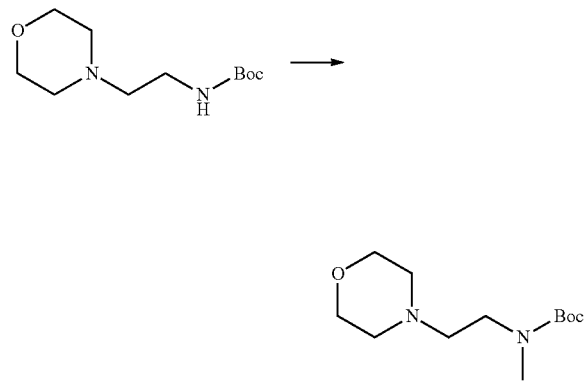

The compound was synthesized according to the method in step 2 of EXAMPLE 12 except that tert-butyl (2-morpholineethyl)amine carboxylate was used as the starting material.

Step 3: N-methyl-2-(pyrrolidine-1-yl)ethylamine trifluoroacetate

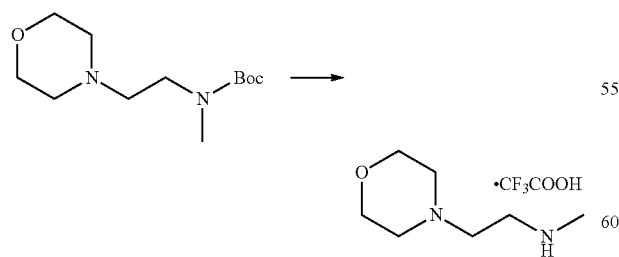

The compound was synthesized according to the method in step 3 of EXAMPLE 12 except that tert-butyl methyl(2-morpholineethyl)amine carboxylate was used as the starting material.

EXAMPLE 15

Preparation of 1-(tetrahydro-2H-pyran-4-yl)piperazine trifluoroacetate

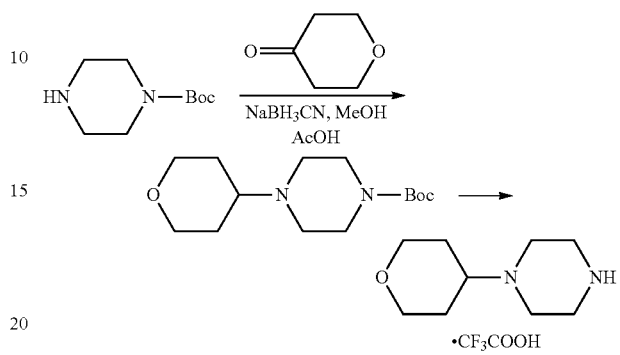

Step 1: tert-butyl 4-(tetrahydro-2H-pyran-4-yl)piperazine-1-carboxylate

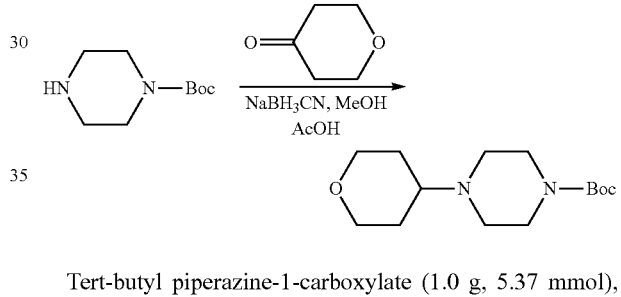

Tert-butyl piperazine-1-carboxylate (1.0 g, 5.37 mmol), tetrahydro-4H-pyran-4-one (1.07 g, 10.7 mmol) and methanol (20 mL) were sequentially added to a 100 mL single-necked bottle, and then sodium cyanoborohydride (507 mg, 8.06 mmol) was added in batch, after the addition completed, 0.5 mL acetic acid was added, stirred at room temperature for 6-7 h. TLC was used to monitor the reaction. After the reaction completed, saturated aqueous sodium bicarbonate solution was added to quench the reaction, the aqueous phase was extracted with ethyl acetate (100 mL×3) for three times, the organic phase were combined, concentrated. The crude product was purified by column chromatography with DCM/MeOH=20/1 as eluent, the product was collected and concentrated to give a 1.5 g colorless oil.

Step 2: 1-(tetrahydro-2H-pyran-4-yl)piperazine trifluoroacetate

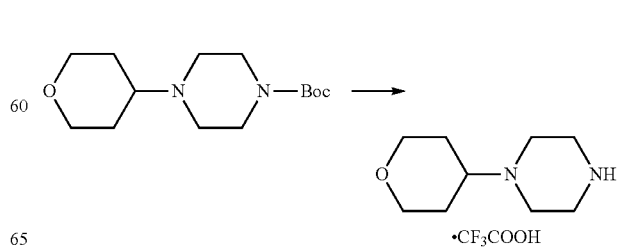

Tert-butyl 4-(tetrahydro-2H-pyran-4-yl)piperazine-1-carboxylate (1.5 g, 5.55 mmol) and dichloromethane (20 mL) were added to a 100 mL single-necked bottle, trifluoroacetic acid (6 mL) was added with stirring, after the addition completed, the mixture was reacted with stirring at room temperature for 2-3 h. TLC was used to monitor the reaction. After the reaction completed, concentrated, precipitated with Methyl tert-butyl ether and stirred for 5 min, filtered, the filter cake was dried to give a 1.75 g of white solid.

EXAMPLE 16

Preparation of N1-(tert-butyl)-N2-methylethane-1,2-diamine

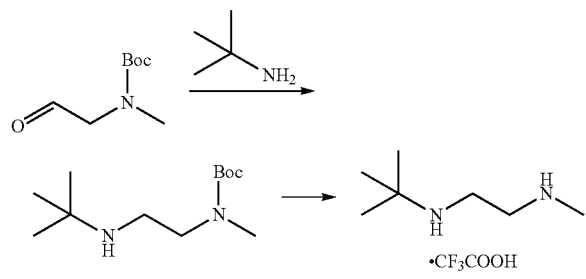

The compound was synthesized according to the method of EXAMPLE 15 except that N-Boc-(methylamino)acetaldehyde and tert-butyl amine were used as the starting materials, sodium triacetoxyborohydride were used as the reducing agent and trichloromethane were used as the solvent.

EXAMPLE 17

Preparation of 1-methyl-4-(piperidine-4-yl)piperazine trifluoroacetate

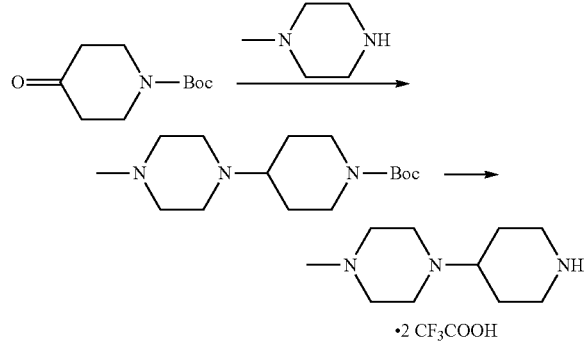

The compound was synthesized according to the method of EXAMPLE 15 except that N-tert-butoxycarbonyl-4-piperidone and 1-methylpiperazine was used as the starting materials.

EXAMPLE 18

Preparation of 1-methyl-4,4'-bipiperidine hydrochloride

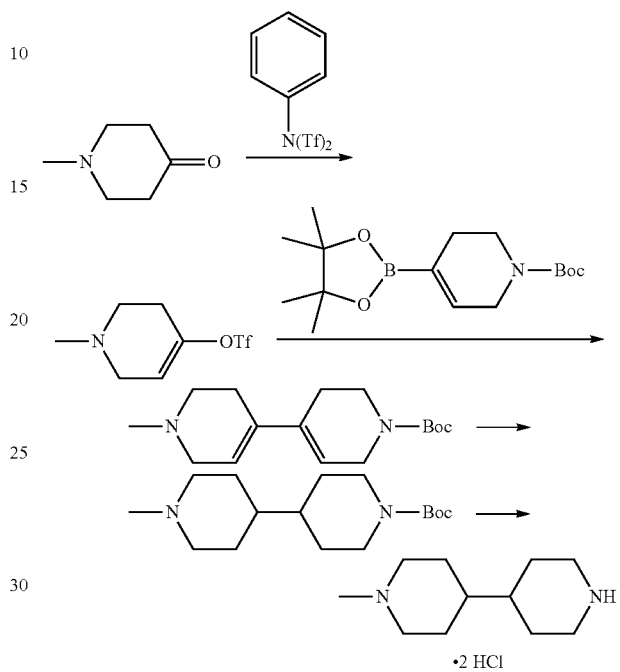

Step 1: trifluoromethanesulfonic acid 1-methyl-1,2,3,6-tetrahydropyridine-4-yl ester

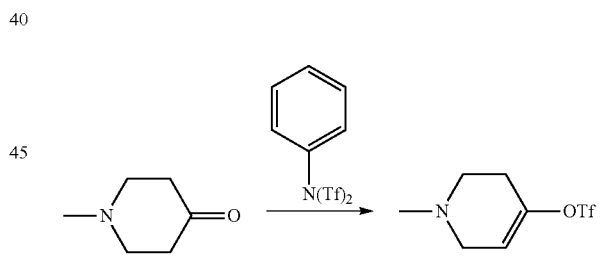

THF (30 mL) was added to a 250 mL three-necked bottle under the protection of argon, cooled to −78° C., LDA (30.4 mL, 60.8 mmol) was added dropwise, the temperature was kept at −78° C., 1-methylpiperidine-4-one (4.0 mL, 30.4 mmol) in THF (10 mL) was added dropwise, after the addition completed, the mixture was warmed to −10° C. to react for 30 min. The reaction mixture was cooled to −78° C., N-phenyl-bis(trifluoromethanesulfonyl)aniline (16.29 g, 45.63 mmol) in THF (50 mL) was added dropwise, after the addition completed, the mixture was warmed to room temperature to react for 1-2 h. TLC was used to monitor the reaction. After the reaction completed, the reactant was concentrated. The crude product was purified by column chromatography with PE/EA=5/1 (neutral alumina) as eluent, the product was collected and concentrated to give a 8.0 g pale yellow oil with a yield of 74.07%.

Step 2: tert-butyl 1'-methyl-1',2',3,3',6,6'-hexahydro-(4,4'-bipyridine)-1(2H)-carboxylate

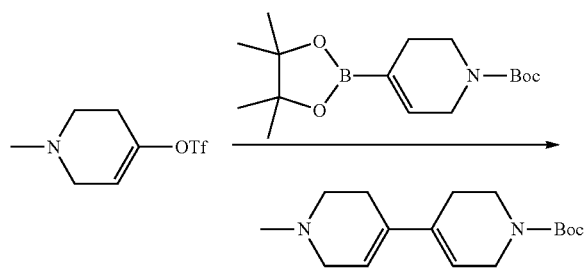

Trifluoromethanesulfonic acid 1-methyl-1,2,3,6-tetrahydropyridine-4-yl ester (1.0 g, 4.08 mmol), N-tert-butoxycarbonyl-1,2,5,6-tetrahydropyridine-4-boronic acid pinacol ester (2.5 g, 8.1 mmol), sodium carbonate (865 mg, 8.1 mmol), Pd(PPh$_3$)$_4$ (940 mg, 0.81 mmol), toluene (24 mL), ethanol (4 mL) and water (4 mL) were sequentially added to a 100 mL single-necked bottle, after the addition completed, the reaction mixture was heated to 120° C. to react for 7-8 h. TLC was used to monitor the reaction. After the reaction completed, 5 mL water was added, the aqueous phase was extracted with ethyl acetate (100 mL×3) for three times, the organic phases were combined and concentrated. The crude product was purified by column chromatography eluting with DCM/MeOH=10/1, the product was collected and concentrated to give a 500 mg pale yellow oil with a yield of 44.24%.

Step 3: tert-butyl 1'-methyl-(4,4'-bipiperidine)-1-carboxylate

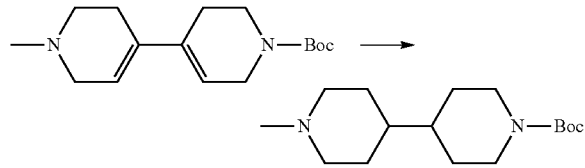

Tert-butyl 1'-methyl-1',2',3,3',6,6'-hexahydro-(4,4'-bipyridine)-1(2H)-carboxylate (500 mg, 1.79 mmol) and methanol (20 mL) were added to a 100 mL single-necked bottle in order, Pd/C (200 mg, 50%) was added with stirring, after the addition completed, the mixture was reacted under the pressure of hydrogen at room temperature for 14-16 h with stirring, filtered, the filtrate was concentrated to give a 450 mg yellow oil with a yield of 88.75%.

Step 4: 1-methyl-4,4'-bipiperidine hydrochloride

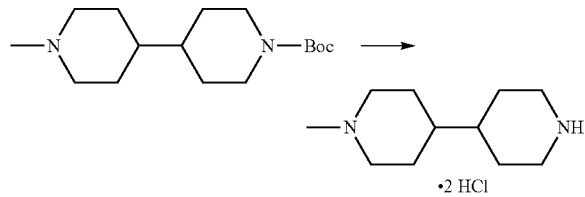

Tert-butyl 1'-methyl-(4,4'-bipiperidine)-1-carboxylate (450 mg, 1.59 mmol) and dichloromethane (10 mL) were added to a 100 mL single-necked bottle, and then trifluoroacetic acid (5 mL) was slowly added with stirring, after the addition completed, the mixture was reacted at room temperature for 2-3 h with stirring. The reactant was concentrated. Methyl tert-butyl ether (20 mL) and concentrated hydrochloric acid (2 mL) were added to the residue, concentrated to give a 380 mg white-like solid with a yield of 93.82%.

EXAMPLE 19

Preparation of N,1-dimethylpiperidine-3-amine

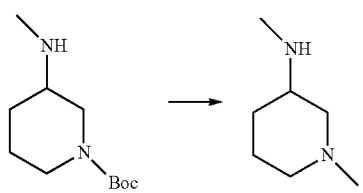

The compound was synthesized according to the method of EXAMPLE 9 except that tert-butyl 3-(methylamino)piperidine-1-carboxylate was used as the starting material.

EXAMPLE 20

Preparation of N,1'-dimethyl-[1,4'-bipiperidine]-4-amine

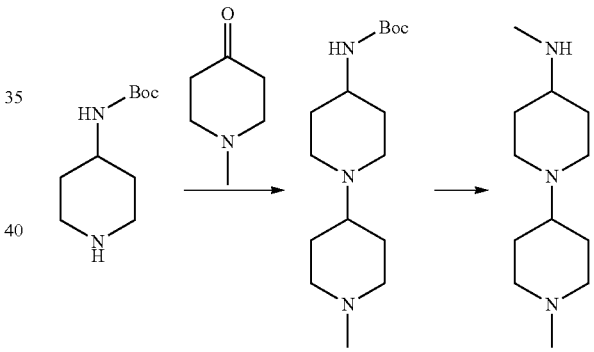

Step 1: tert-butyl (1'-methyl-[1,4'-bipiperidine]-4-yl) amino carboxylate

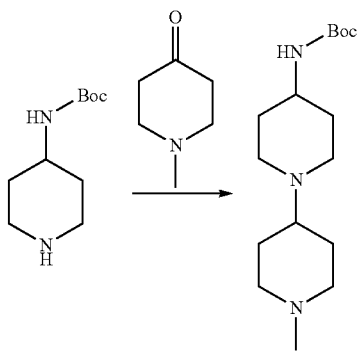

The compound was synthesized according to the method in step 1 of EXAMPLE 15 except that tert-butyl piperidine- 4-ylamino carboxylate and 1-methyl-piperidine-4-one were used as the starting materials.

Step 2: N,1'-dimethyl-[1,4'-bipiperidine]-4-amine

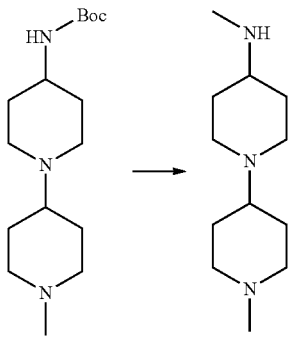 [SMILES: CN1CCC(N2CCC(NC(=O)OC(C)(C)C)CC2)CC1 ; CNC1CCN(C2CCN(C)CC2)CC1]

The compound was synthesized according to the method of EXAMPLE 9 except that using tert-butyl (1'-methyl-[1,4'-bipiperidine]-4-yl) amino carboxylate was used as the starting material.

EXAMPLE 21

Preparation of N1,N1,N4-trimethyl-cyclohexane-1,4-diamine

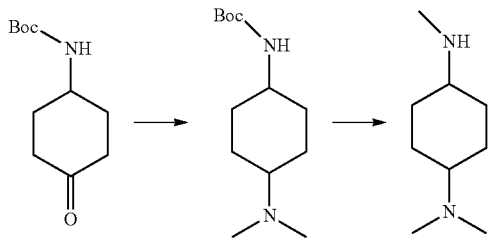 [SMILES: CC(C)(C)OC(=O)NC1CCC(=O)CC1 ; CN(C)C1CCC(NC(=O)OC(C)(C)C)CC1 ; CNC1CCC(N(C)C)CC1]

The compound was synthesized according to the method of EXAMPLE 20 except that tert-butyl (4-oxycyclohexyl) amine carboxylate and dimethylamine hydrochloride were used as the starting materials.

EXAMPLE 22

N-methyl-4-(4-methylpiperazine-1-yl) cyclohexane-1-amine

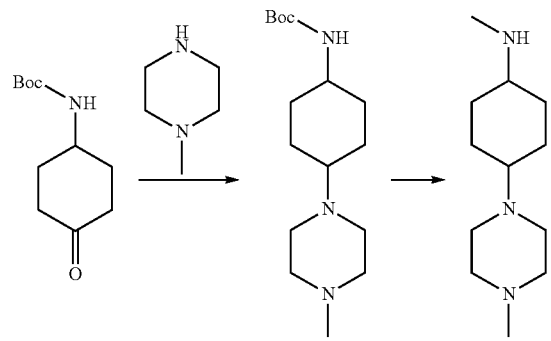

The compound was synthesized according to the method of EXAMPLE 20 except that tert-butyl (4-oxycyclohexyl) amine carboxylate and 1-methylpiperazine were used as the starting materials.

EXAMPLE 23

N-methyl-4-(1-methylpiperidine-4-yl) cyclohexyl-1-amine

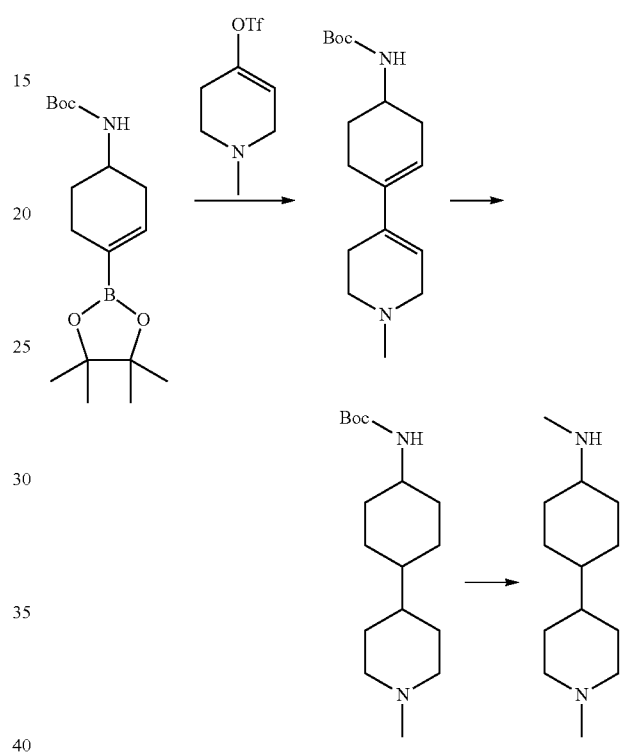

Step 1: tert-butyl (4-(1-methyl-1,2,3,6-tetrahydro-pyridine-4-yl) cyclohexyl-3-ene-1-yl) amino carboxylate

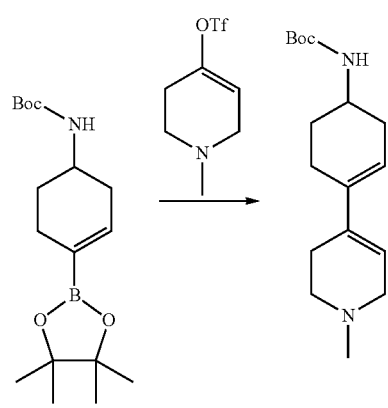

The compound was synthesized according to the method in step 2 of EXAMPLE 18 except that N-tert-butoxycarbonyl-cyclohexyl-3-eneamino-4-boronic acid pinacol ester and 1-methyl-1,2,3,6-tetrahydropyridine-4-yl trifluoromethanesulfonate were used as the starting materials.

Step 2: tert-butyl (4-(1-methylpiperidine-4-yl)cyclohexyl)amino carboxylate

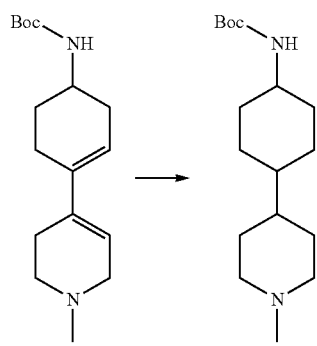 [SMILES: CN1CC=C(C2=CCC(NC(=O)OC(C)(C)C)CC2)CC1 ; CN1CCC(C2CCC(NC(=O)OC(C)(C)C)CC2)CC1]

The compound was synthesized according to the method in step 3 of EXAMPLE 18 except that tert-butyl (4-(1-methyl-1,2,3,6-tetrahydropyridine-4-yl)cyclohexyl-3-ene-1-yl)amino carboxylate was used as the starting material.

Step 3: N-methyl-4-(1-methylpiperidine-4-yl)cyclohexyl-1-amine

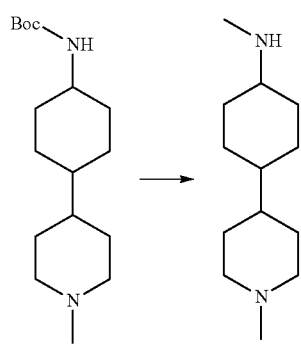 [SMILES: CN1CCC(C2CCC(NC(=O)OC(C)(C)C)CC2)CC1 ; CNC1CCC(C2CCN(C)CC2)CC1]

The compound was synthesized according to the method of EXAMPLE 19 except that tert-butyl (4-(1-methylpiperidine-4-yl) cyclohexyl)amino carboxylate was used as the starting material.

EXAMPLE 24

N-methyl-N-(2-(methylamino)ethyl)acetamide trifluoroacetate

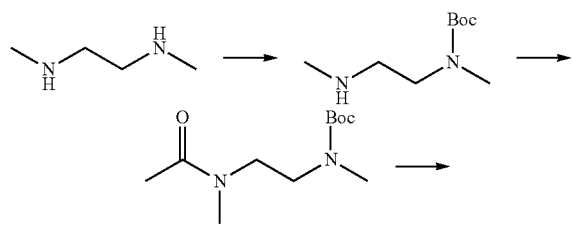

-continued

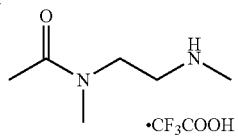

Step 1: tert-butyl methyl(2-(methylamino)ethyl)amino carboxylate

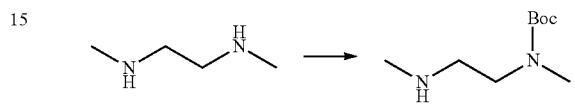

N1,N2-dimethylethyl-1,2-diamine (4 g, 45 mmol) was added to a 100 mL single-necked bottle, cooled to about 0° C. in an ice-water bath, and then (Boc)$_2$O (5 g, 23 mmol) in DCM (20 mL) was added dropwise, after the addition completed, the mixture was warmed to 25° C. and reacted for 4 h with stirring, the reaction mixture was concentrated, saturated sodium carbonate was added to the residue, extracted by ethyl acetate (30 mL×3) for three times, the organic phases were combined, washed with saturated brine (20 mL×3) for three times, dried with anhydrous sodium sulfate for 30 min, and filtered, the filtrate was concentrated at 45° C. to give a crude product. The crude product was purified by column chromatography eluting with DCM/MeOH=30/1, the product was collected and concentrated to give a 2.1 g of yellow oil.

Step 2: tert-butyl methyl(2-(N-methylacetamino)ethyl)amino carboxylate

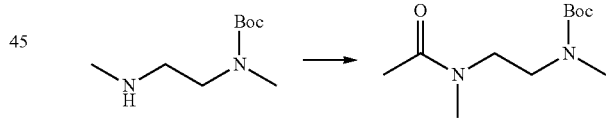

Tert-butyl methyl(2-(methylamino)ethyl)amino carboxylate (2.15 g, 11.4 mmol), DCM (10 mL) and trimethylamine (2.3 g, 23 mmol) were added to a 100 mL three-necked bottle in order, cooled to −5-0° C. in an ice-salt bath, and then acetic anhydride (1.4 g, 14.7 mmol) was added dropwise, after the addition completed, the mixture was warmed to 25° C. and reacted for 1 h with stirring. Water (20 mL) was added to the reaction mixture mixture, extracted with DCM (30 mL×3) for three times, the organic phases were combined, washed with saturated brine (20 mL×3) for three times, dried with anhydrous sodium sulfate for 30 min, and filtered, the filtrate was concentrated under reduced pressure at 45° C. to give a crude product. The crude product was purified by column chromatography with DCM/MeOH=50/1 as eluent, the product was collected and concentrated under reduced pressure to give a 2.3 g of yellow oil.

Step 3: N-methyl-N-(2-(methylamino)ethyl)acetamide trifluoroacetate

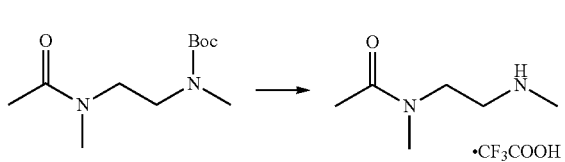

Tert-butyl methyl(2-(N-methylacetamido)ethyl)amino carboxylate (2.4 g, 0.01 mol) and DCM (10 mL) were added to a 100 mL single-necked bottle, trifluoroacetic acid (3.0 g, 0.026 mol) was added dropwise with stirring, reacted at 25° C. for 3 h with stirring. The reaction mixture was concentrated at 50° C. under reduced pressure, anhydrous ethanol (10 mL×2) was added, concentrated twice, methyl tert-butyl ether was added to the residue, stirred, and filtered, the filter cake was dried under reduced pressure to give a 3.1 g green oil.

EXAMPLE 25

Tert-butyl cyclopropyl(2-(methylamino)ethyl)amino carboxylate

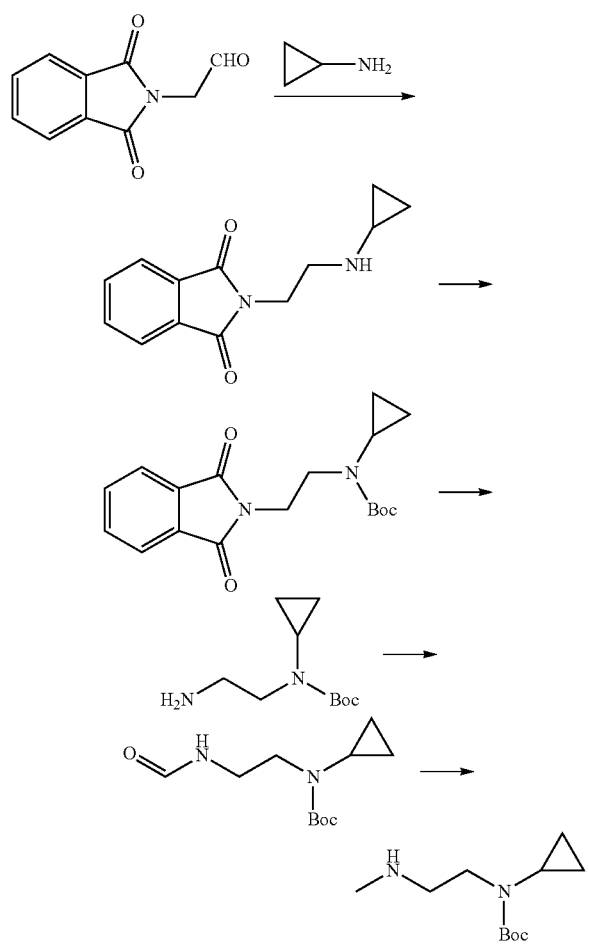

Step 1: N-(2-(cyclopropylamino)ethyl)phthalimide

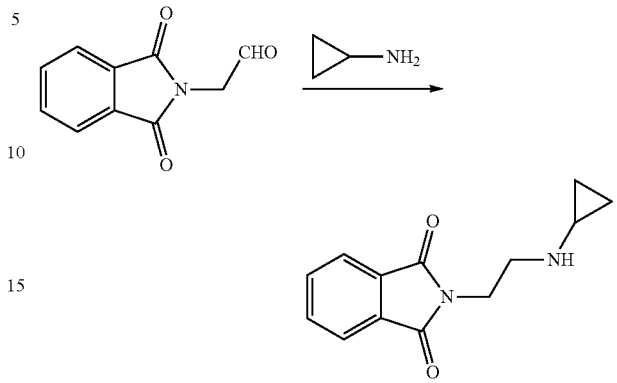

N-(2-acetaldehyde)phthalimide, cyclopropylamine (663 mg, 11.6 mmol) and trichloromethane (30 mL) were added to a 100 mL single-necked bottle, stirred at room temperature for 1 h, and then sodium triacetoxyborohydride (6.73 g, 31.7 mmol) was added, after the addition completed, the mixture was reacted at room temperature for 5-6 h. Saturated sodium bicarbonate was added to adjust the pH into pH>8, the aqueous phase was extracted with DCM (100 mL×3) for three times, combined the organic phases and concentrated under reduced pressure to give a crude product. The crude product was purified by column chromatography with DCM/MeOH=50/1 as eluent, the product was collected and concentrated to give a 1.0 g of pale yellow solid with a yield of 28.7%.

Step 2: tert-butyl cyclopropyl(2-(phthalimide-2-yl)ethyl)amino carboxylate

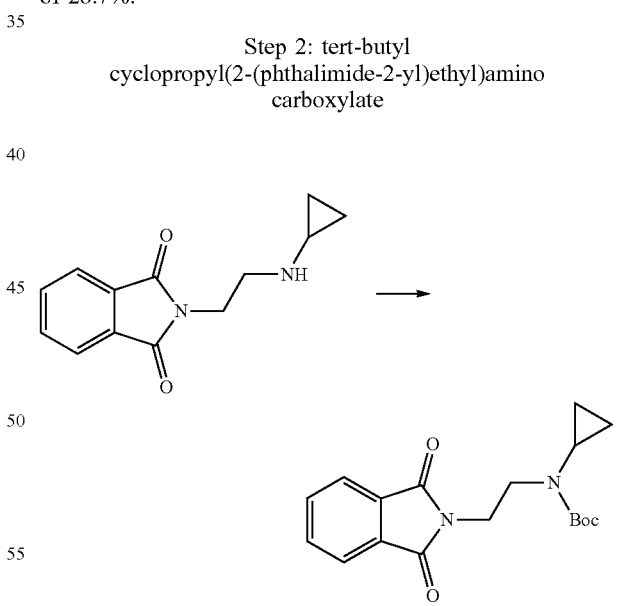

N-(2-(cyclopropylamino)ethyl)phthalimide (1.0 g, 4.34 mmol), DCM (20 mL), DIPEA (616 mg, 4.78 mmol) and (Boc)$_2$O (1.04 g, 4.78 mmol) were added to a 100 mL single-necked bottle. The mixture was stirred at 25° C. for 3-4 h. Water (50 mL) was added to the reaction mixture, extracted with DCM (30 mL×3) for three times, the organic phases were combined, washed with saturated brine (20 mL×3) for three times, dried with anhydrous sodium sulfate for 30 min, and filtered under reduced pressure, the filtrate was concentrated at 45° C. to give a crude product which was purified by column chromatography with DCM/MeOH=50/1 as eluent, the product was collected and concentrated under reduced pressure to give a 1.0 g of white solid with a yield of 69.9%.

Step 3: tert-butyl (2-aminoethyl)(cyclopropyl)amino carboxylate

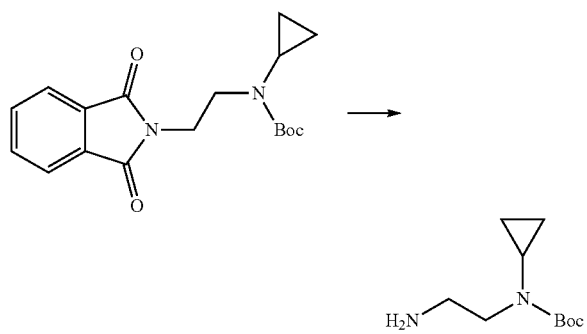

Tert-butyl cyclopropyl(2-(phthalimide-2-yl)ethyl)amino carboxylate (1.0 g, 3.0 mmol) and anhydrous ethanol (100 mL) were added to a 100 mL single-necked bottle in order, and then hydrazine hydrate (1.89 g, 30 mmol) was added thereinto with stirring, the mixture reacted at 25° C. for 2-3 h with stirring, filtered, the filtrate was concentrated under reduced pressure at 45° C. to give a 700 mg of yellow oil with a yield of 115%.

Step 4: tert-butyl cyclopropyl (2-formylaminoethyl) amino carboxylate

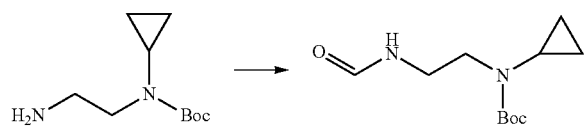

Tert-butyl (2-aminoethyl)(cyclopropyl)amino carboxylate (650 mg, 3.25 mmol) and ethyl formate (15 mL) were added to a 100 mL single-necked bottle, reacted at 25° C. for 15 h with stirring. The reaction mixture was concentrated under reduced pressure to give a 700 mg of yellow oil with a yield of 94.5%.

Step 5: tert-butyl cyclopropyl(2-(methylamino)ethyl)amino carboxylate

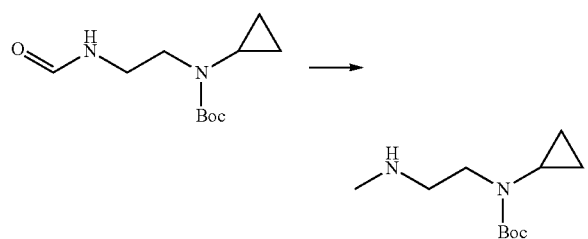

Tert-butyl cyclopropyl(2-formylaminoethyl)amino carboxylate (700 mg, 3.07 mmol) and tetrahydrofuran (15 mL) were added to a 100 mL single-necked bottle in order under the protection of argon, $BH_3(Me_2S)$ (3 mL) was added dropwise slowly, and then heated to 65° C. The reaction mixture was stirred for 3 h. The reaction mixture was cooled to room temperature and concentrated under reduced pressure. Anhydrous ethanol (15 mL) and potassium carbonate (1.0 g) were added to the residue, stirred at 25° C. to react for 15 h. Filtered, the filtrate was concentrated under reduced pressure, water (30 mL) was added to the residue, the aqueous phase was extracted with ethyl acetate (50 mL×3) for three times, the organic phases were combined and concentrated under reduced pressure to give a crude product. The crude product was purified by column chromatography with DCM/MeOH=30/1 as eluent, the product was collected and concentrated under reduced pressure to give a 210 mg of pale yellow oil with a yield of 31.9%.

EXAMPLE 26

2-(3,3-difluoropyrrolidin-1-yl)-N-methylethan-1-amine

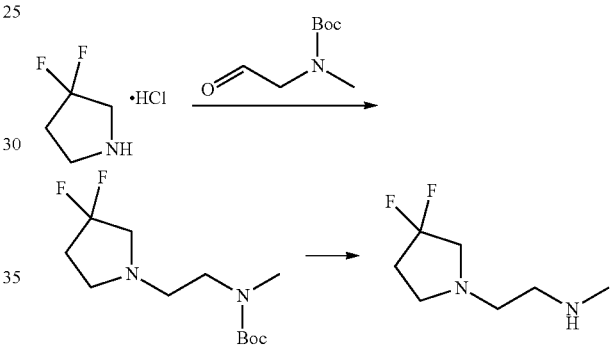

The compound was synthesized according to the method of EXAMPLE 15 except that tert-butyl methyl(2-oxoethyl)amino carboxylate and 3,3-difluoropyrrolidin hydrochloride were used as the starting materials.

EXAMPLE 27

N-methyl-N-(3-(methylamino)propyl)acetamide trifluoroacetate

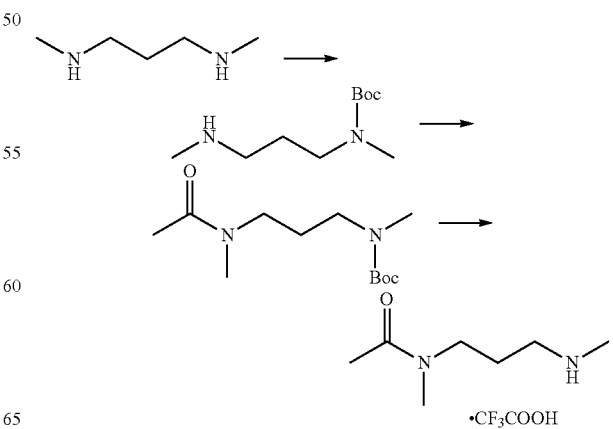

The compound was synthesized according to the method of EXAMPLE 24 except that N1,N3-dimethylpropyl-1,3-diamine was used as the starting material.

EXAMPLE 28

Tert-butyl isopropyl(2-(methylamino)ethyl)amino carboxylate

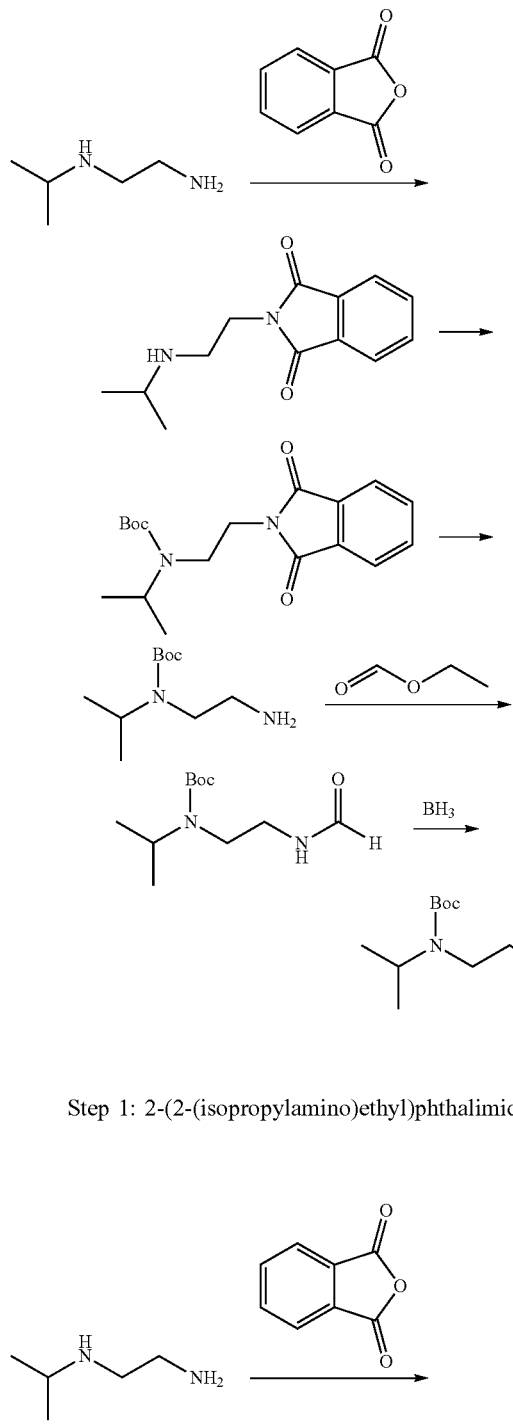

Step 1: 2-(2-(isopropylamino)ethyl)phthalimide

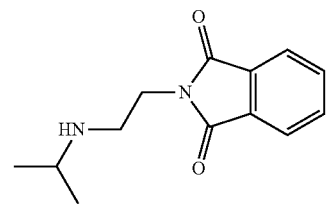

N-isopropylethylenediamine, phthalic anhydride (4.5 g, 0.03 mol), p-toluene sulfonic acid (500 mg, 3 mmol) and toluene (20 mL) were added to a 100 mL three-necked bottle in order, heated to 115° C. to react under reflux for 4 h. The reaction mixture was cooled to room temperature, and saturated sodium bicarbonate was added to adjust the pH into pH>8, extracted with ethyl acetate (30 mL×3) for three times, the organic phases were combined, washed with saturated brine (20 mL×3) for three times, dried with anhydrous sodium sulfate for 30 min, and filtered, then the filtrate was concentrated under reduced pressure at 45° C. to give a 4.2 g of pale yellow oil.

Steps 2, 3, 4, 5: Tert-butyl isopropyl(2-(methylamino)ethyl)amino carboxylate

The compound was synthesized according to the method in steps 2, 3, 4 and 5 of EXAMPLE 25 except that 2-(2-(isopropylamino)ethyl)phthalimide was used as the starting material.

EXAMPLE 29

N1,N1-diisopropyl-N2-methylethylenediamine

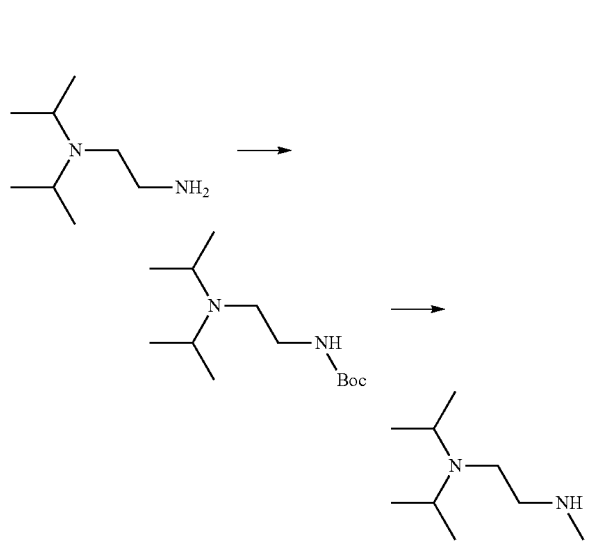

The compound was synthesized according to the method of EXAMPLE 11 except that N1,N1-diisopropyl ethylenediamine was used as the starting material.

EXAMPLE 30

1-(1-((tert-butyldimethylsilyl)oxy)-2-methylpropyl-2-yl)piperazine

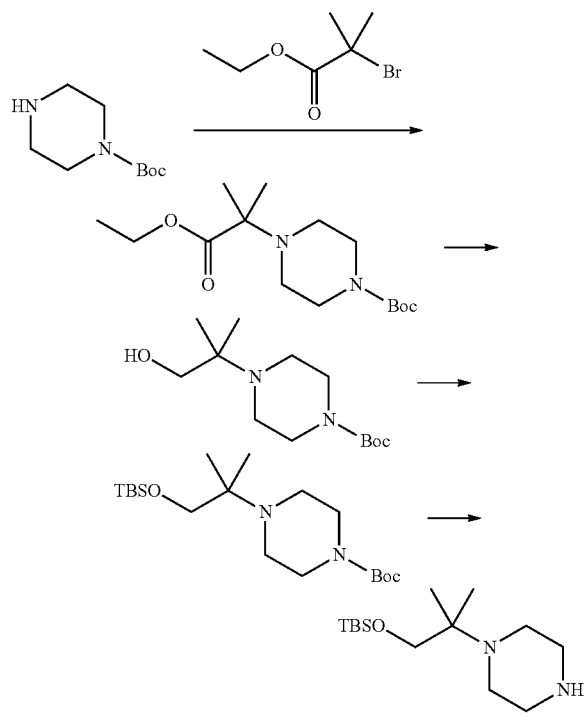

Step 1: tert-butyl 4-(1-ethoxy-2-methyl-1-oxopropyl-2-yl) piperazine-1-carboxylate

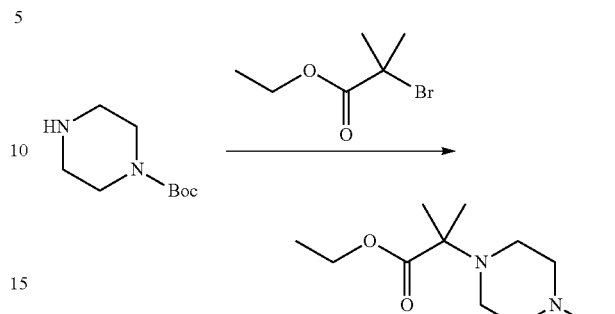

Tert-butyl 1-piperazinecarboxylate (2.5 g, 13.4 mmol), potassium carbonate (2.78 g, 20.1 mmol) and DMF (60 mL) were added to a 100 mL single-necked bottle in order, stirred for 10 min, and then ethyl 2-bromo-2-methylpropionate (2.86 g, 14.7 mmol) was added thereinto, the reaction mixture was stirred overnight at room temperature. Water (100 mL) was added to the reaction mixture, and the aqueous phase was extracted with ethyl acetate (100 mL×3) for three times, the organic phases were combined and concentrated under reduced pressure to give a crude product. The crude product was purified by column chromatography with DCM/MeOH=30/1 as eluent. The product was collected and concentrated under reduced pressure to give a 1.0 g of yellow with a yield of 30.3%.

Step 2: tert-butyl 4-(1-hydroxy-2-methylpropyl-2-yl)piperazine)-1-carboxylate

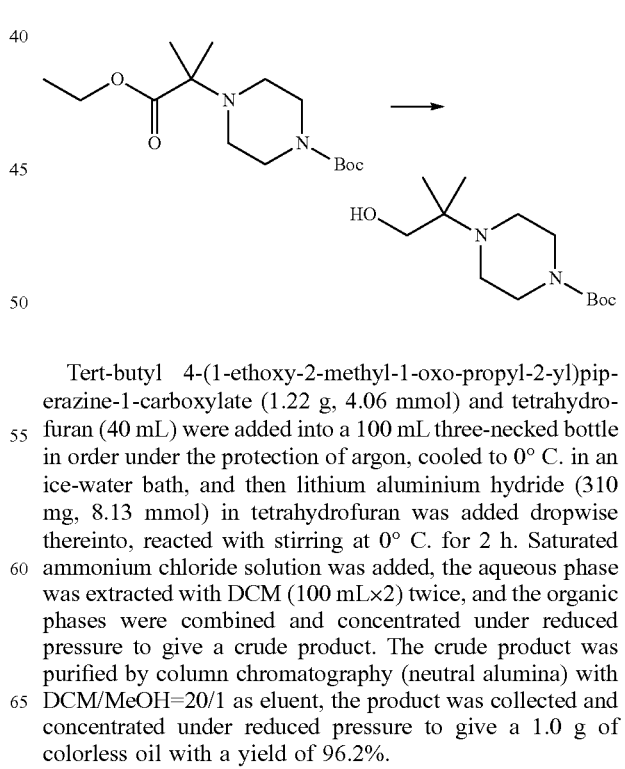

Tert-butyl 4-(1-ethoxy-2-methyl-1-oxo-propyl-2-yl)piperazine-1-carboxylate (1.22 g, 4.06 mmol) and tetrahydrofuran (40 mL) were added into a 100 mL three-necked bottle in order under the protection of argon, cooled to 0° C. in an ice-water bath, and then lithium aluminium hydride (310 mg, 8.13 mmol) in tetrahydrofuran was added dropwise thereinto, reacted with stirring at 0° C. for 2 h. Saturated ammonium chloride solution was added, the aqueous phase was extracted with DCM (100 mL×2) twice, and the organic phases were combined and concentrated under reduced pressure to give a crude product. The crude product was purified by column chromatography (neutral alumina) with DCM/MeOH=20/1 as eluent, the product was collected and concentrated under reduced pressure to give a 1.0 g of colorless oil with a yield of 96.2%.

Step 3: tert-butyl (1-((tert-butyl dimethylsilyl)oxy)-2-methylpropyl-2-yl)piperazine-1-carboxylate

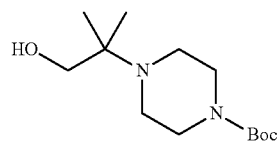

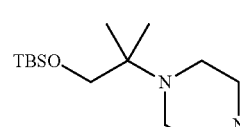

Tert-butyl 4-(1-hydroxy-2-methylpropyl-2-yl)piperazine-1-carboxylate (780 mg, 3.02 mmol), imidazole (617 mg, 9.06 mmol) and DMF (20 mL) were added to a 100 mL single-necked bottle in order under the protection of argon, after all materials were dissolved with stirring, tert-butyl dimethylchlorosilane (1.0 g, 6.04 mmol) was added thereinto, and the reaction mixture was heated to 80° C. in an oil bath and reacted for 4-5 h with stirring. cooled to room temperature, water (50 mL) was added to the reaction mixture, the aqueous phase was extracted with ethyl acetate (80 mL×3) for three times, and then the organic phases were combined and concentrated under reduced pressure to give a crude product. The crude product was purified by column chromatography with DCM/MeOH=20/1 as eluent, the product was collected and concentrated under reduced pressure to give a 1.4 g of pale yellow oil with a yield of 125%.

Step 4: 1-(1-(tert-butyl dimethylsilyl)oxy)-2-methylpropyl-2-yl)piperazine

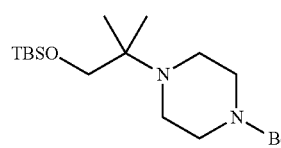

Tert-butyl (1-((tert-butyl dimethylsilyl)oxy)-2-methylpropyl-2-yl)piperazine-1-carboxylate (1.4 g, 3.76 mmol) and DCM (20 mL) were added to a 100 mL single-necked bottle in order, cooled to 0° C., trifluoroacetic acid (5 mL) was added dropwise thereinto, the mixture was stirred for 4-5 h at 0° C. Saturated sodium carbonate was added thereinto to adjust pH to pH>7, the aqueous phase was extracted with DCM (80 mL×3) for three times, the organic phases were combined and concentrated under reduced pressure to give a 1.0 g of pale yellow oil with a yield of 98.0%.

EXAMPLE 31

(2S,6R)-1,2,6-trimethyl-4-(piperidine-4-yl)piperazine trifluoroacetate

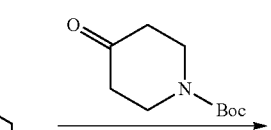

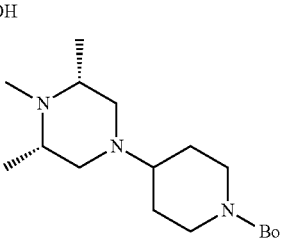

The compound was synthesized according to the method of EXAMPLE 15 except that (2S,6R)-1,2,6-trimethylpiperazine trifluoroacetate and N-tert-butoxycarbonyl-4-piperidone were used as the starting materials.

EXAMPLE 32

1-isopropyl-4-(piperidine-4-yl)piperazine trifluoroacetate

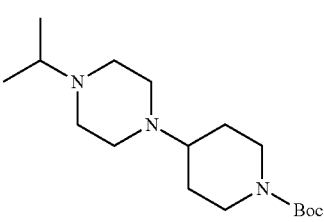

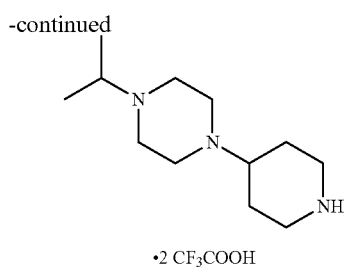

The compound was synthesized according to the method of EXAMPLE 15 except that 1-isopropylpiperazine and N-tert-butoxycarbonyl-4-piperidone were used as the starting materials.

EXAMPLE 33

Ally (2R,6S)-2,6-dimethylpiperazine-1-carboxylate hydrochloride

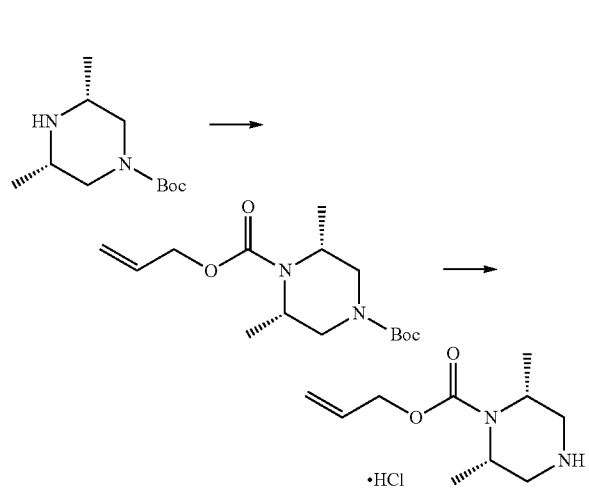

Step 1: 4-(tert-butyl)(2R,6S)-2,6-dimethylpiperazine-1,4-dicarboxylic acid 1-allyl ester Tert-butyl cis-3,5-dimethylpiperazine-1-carboxylate (2 g, 9.34 mmol), pyridine (1.47 g, 18.6 mmol) and DCM (10 mL) were added to a 100 mL three-necked bottle in order, cooled to 0° C., and then allyl chloroformate (1.68 g, 14 mmol) in DCM was added dropwise thereinto, warmed to room temperature to react overnight. Water (20 mL) was added to the reaction mixture, allowed to separate into layers, and then the organic phase was concentrated to give a crude product. The crude product was purified by column chromatography with PE/EA=5/1 as eluent, the product was collected and concentrated under reduced pressure to give a 1.2 g of colorless oil with a yield of 43.2%.

Step 2: ally (2R,6S)-2,6-dimethylpiperazine-1-carboxylate hydrochloride

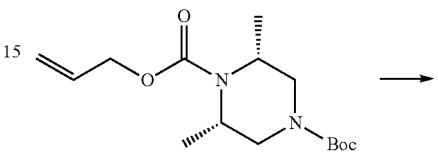

4-(tert-butyl)(2R,6S)-2,6-dimethylpiperazine-1,4-dicarboxylic acid-1-allyl ester (1.1 g, 3.69 mmol) and DCM (10 mL) were added in a 100 mL single-necked bottle in order, and then trifluoroacetic acid (5 mL) was added thereinto with stirring, reacted at room temperature for 2-3 h, and the reaction mixture was concentrated under reduced pressure. Concentrated hydrochloric acid (1 mL) and ethanol (5 mL) were added thereinto, and concentrated continuously. Isopropyl ether (10 mL) was added to the residue, stirred for 10 minutes, and filtered, the filter cake was dried to give a 640 mg of yellow solid with a yield of 74.15%.

EXAMPLE 34

N1-ethyl-N1,N2-dimethylethylenediamine hydrochloride

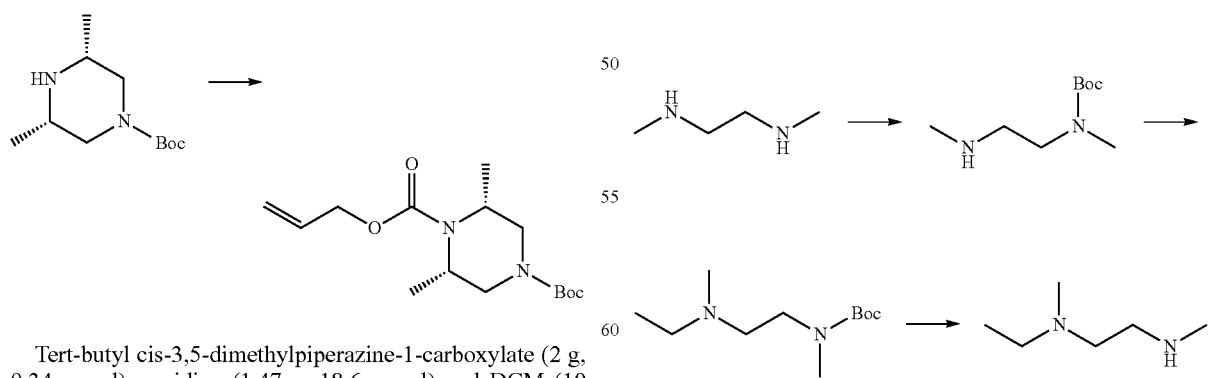

The compound was synthesized according to the method of EXAMPLE 2 except that N1,N2-dimethylethylenediamine was used as the starting material.

EXAMPLE 35

Cis-2,6-dimethyl-4-(piperidine-4-yl)morpholine trifluoroacetate

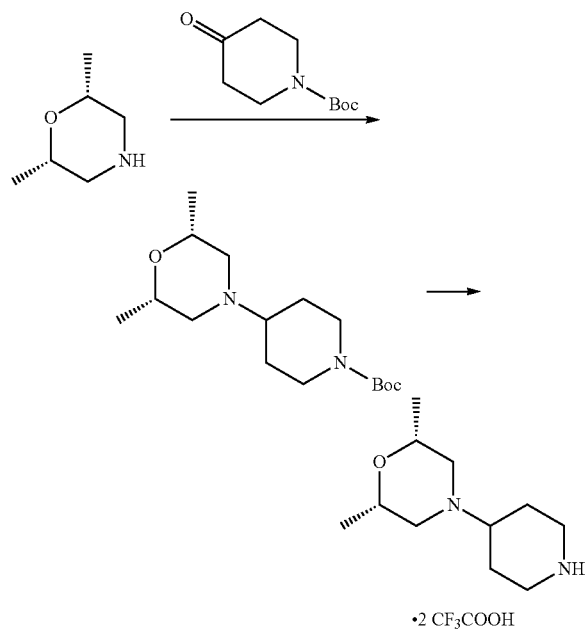

The compound was synthesized according to the method of EXAMPLE 15 except that cis-2,6-dimethylmorpholine and N-tert-butoxycarbonyl-4-piperidone were used as the starting materials.

EXAMPLE 36

3-((tert-butyldimethylsilyl)oxy)-N-methylpropan-1-amine

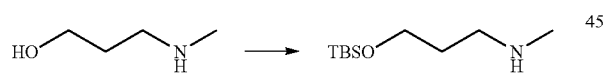

The compound was synthesized according to the method in the step 3 of EXAMPLE 30 except that 3-(methylamino)propanol was used as the starting material.

EXAMPLE 37

4-(2-((tert-butyl dimethylsilyl)oxy)ethyl)piperidine

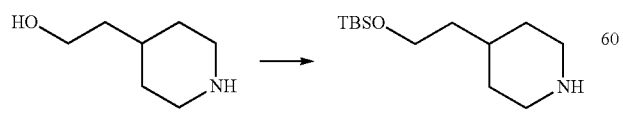

The compound was synthesized according to the method in the step 3 of EXAMPLE 30 except that 2-(piperidine-4-yl)ethan-1-ol was used as the starting material.

EXAMPLE 38

(R)—N,1-dimethylpyrrolidin-3-amine

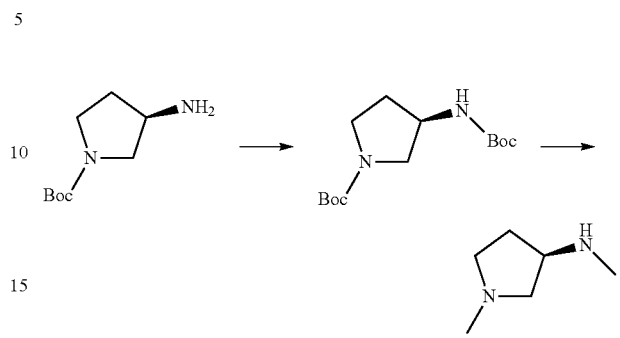

The compound was synthesized according to the method of EXAMPLE 11 except that tert-butyl (R)-3-aminopyrrolidin-1-carboxylate was used as the starting material.

EXAMPLE 39

N-methyl-2-((3S,5R)-3,4,5-trimethylpiperazine-1-yl)ethylamine trifluoroacetate

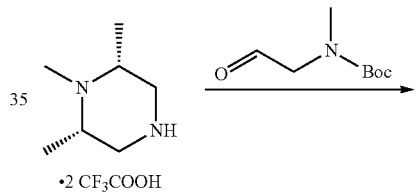

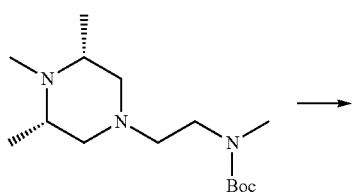

The compound was synthesized according to the method of EXAMPLE 15 except that N-Boc-(methylamino)acetaldehyde and (2S,6R)-1,2,6-trimethylpiperazine trifluoroacetate were used as the starting materials.

EXAMPLE 40

2-(4-cyclopropylpiperazine-1-yl)-N-methylethylamine Hydrochloride

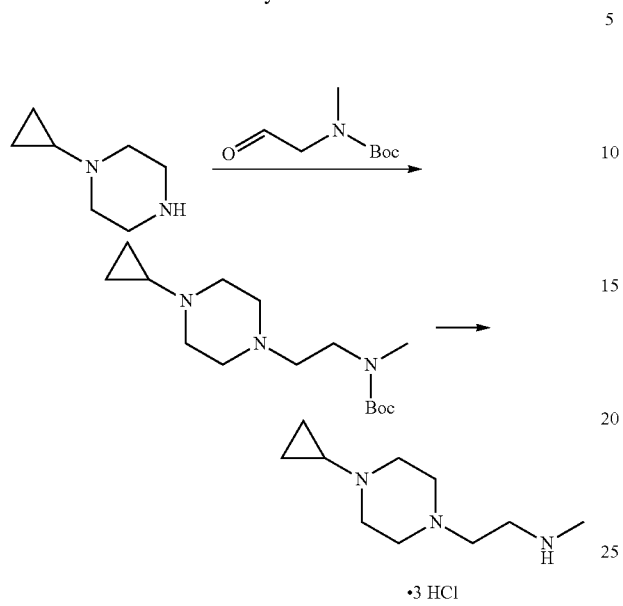

·3 HCl

The compound was synthesized according to the method of EXAMPLE 15 except that N-Boc-(methylamino)acetaldehyde and 1-cyclopropylpiperazine were used as the starting materials.

EXAMPLE 41

1-(4-piperidine-4-yl)piperazine-1-yl)ethyl-1-one Hydrochloride

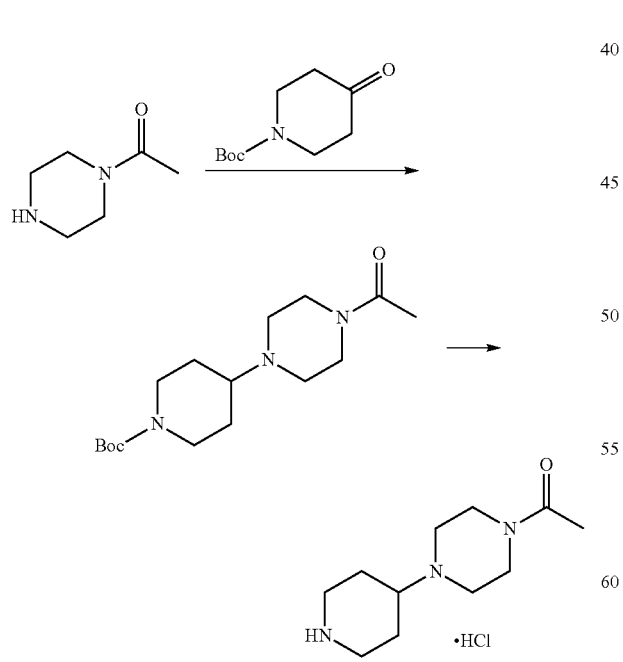

·HCl

The compound was synthesized according to the method of EXAMPLE 15 except that 1-(piperazine-1-yl)acetone and N-Boc-4-piperidone were used as the starting materials.

EXAMPLE 42

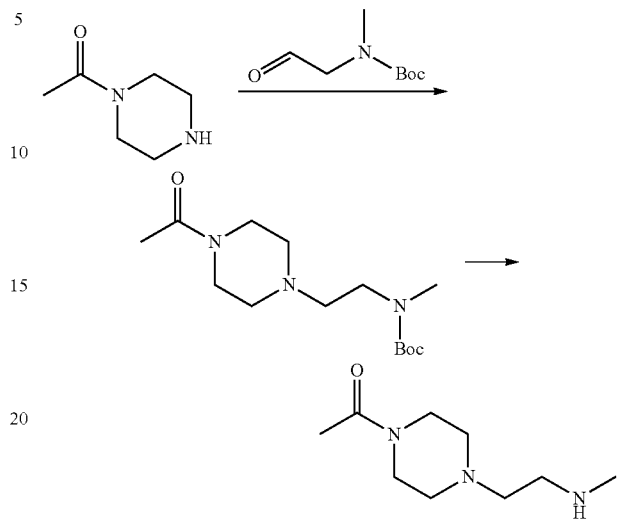

The compound was synthesized according to the method of EXAMPLE 15 except that 1-(piperazine-1-yl)acetone and N-Boc-(methylamino) acetaldehyde were used as the starting materials.

EXAMPLE 43

1-(1-methylpiperidine-4-yl)piperazine

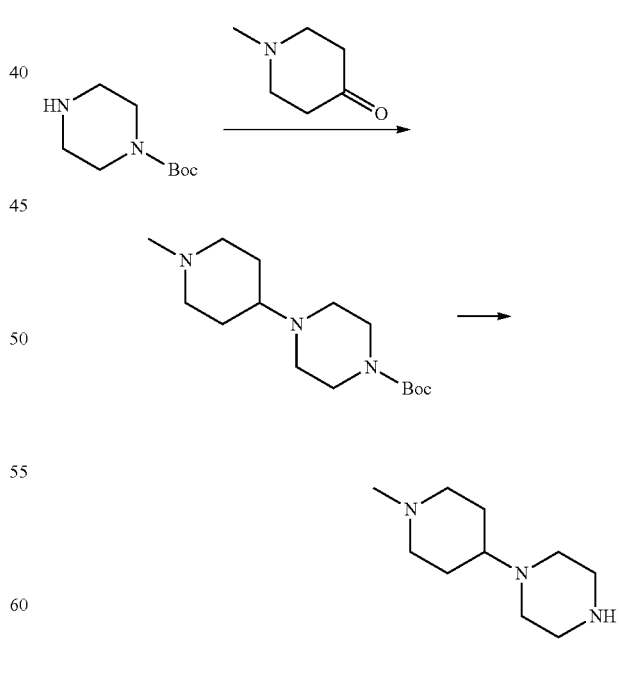

The compound was synthesized according to the method of EXAMPLE 15 except that 1-methyl-4-piperidone and tert-butyl piperazine-1-carboxylate were used as the starting materials.

EXAMPLE 44

2-(dimethylamino)-1-(piperazine-1-yl)acetone hydrochloride

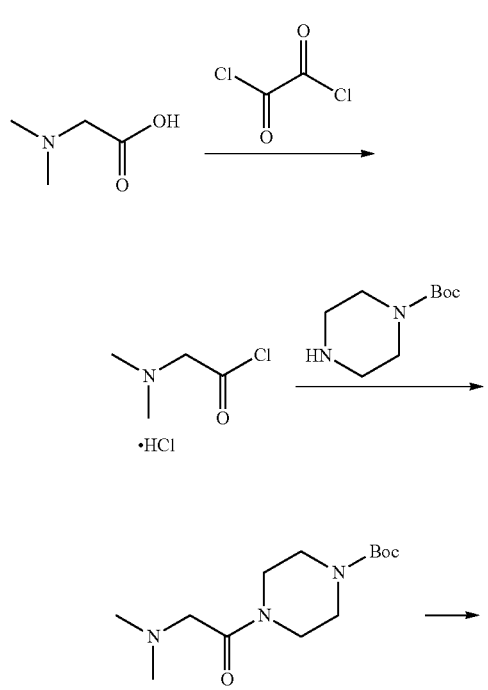

Step 1: N,N-dimethylaminoacetyl chloride hydrochloride

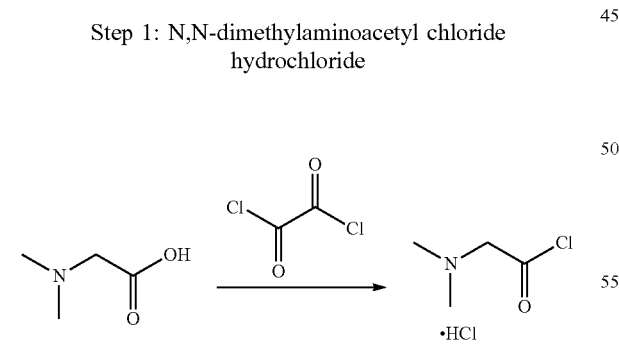

N,N-dimethylglycine (1 g, 10 mmol), acetonitrile (15 mL) and DMF (5 d) were added to a 100 mL three-necked bottle in order under the protection of argon, and then oxalyl chloride (1.23 g, 10 mmol) was added dropwise thereinto at room temperature, warmed to 30° C. in an oil bath to react for 3 h. The reaction mixture was cooled to room temperature. The reaction mixture was used to the next step directly without any further processing.

Steps 2-3: 2-(dimethylamino)-1-(piperazine-1-yl)acetone hydrochloride

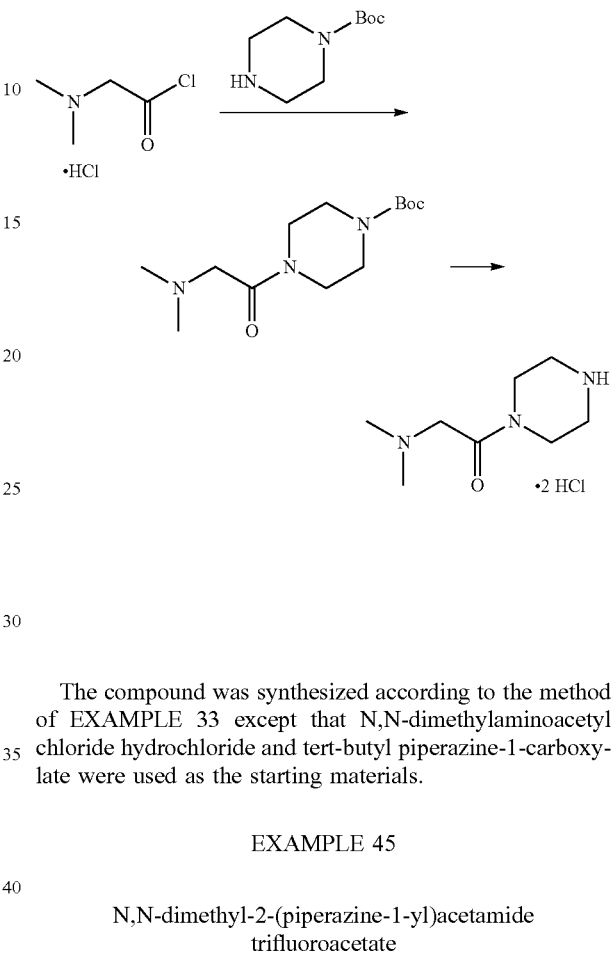

The compound was synthesized according to the method of EXAMPLE 33 except that N,N-dimethylaminoacetyl chloride hydrochloride and tert-butyl piperazine-1-carboxylate were used as the starting materials.

EXAMPLE 45

N,N-dimethyl-2-(piperazine-1-yl)acetamide trifluoroacetate

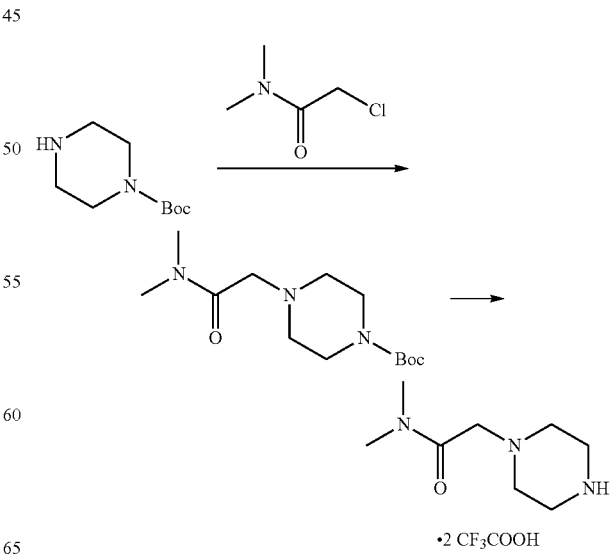

Step 1: tert-butyl 4-(2-(dimethylamino)-2-oxoethyl)piperazine-1-carboxylate

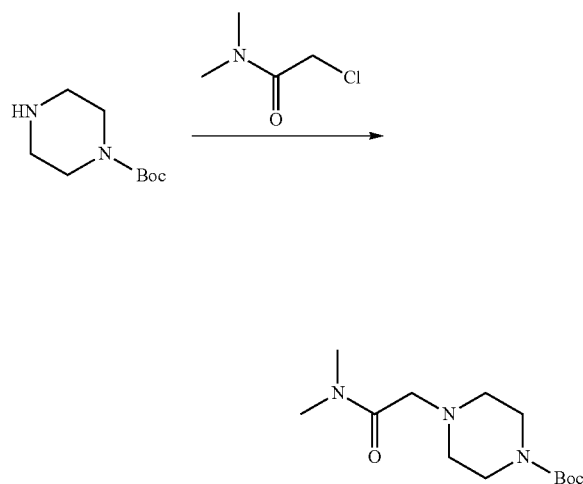

N,N-dimethyl-2-chloroacetamide (200 mg, 1.65 mmol), THF (10 mL), triethylamine (334 mg, 2 eq) and tert-butyl piperazine-1-carboxylate (337 mg, 1.1 eq) were added to a 100 mL single-necked bottle in order, reacted at room temperature with stirring. TLC was used to monitor the reaction, when the reaction completed, the reaction mixture was concentrated under reduced pressure to give a crude product, the crude product was purified by column chromatography with DCM/MeOH=20/1 as eluent, the product was collected and concentrated under reduced pressure to give 410 mg.

Step 2: N,N-dimethyl-2-(piperazine-1-yl) acetamide trifluoroacetate

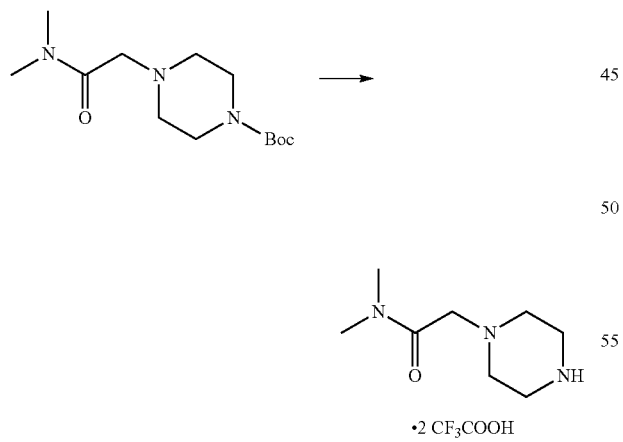

tert-butyl 4-(2-(dimethylamino)-2-oxoethyl)piperazine-1-carboxylate, DCM (10 mL) and trifluoroacetic acid (2 mL) were added to a 100 mL single-necked bottle in order, reacted at room temperature with stirring, TLC was used to monitor the reaction, when the reaction completed, the reaction mixture was concentrated under reduced pressure to give a 600 mg of trifluoroacetate.

EXAMPLE 46

4-(diethylamino)piperidine

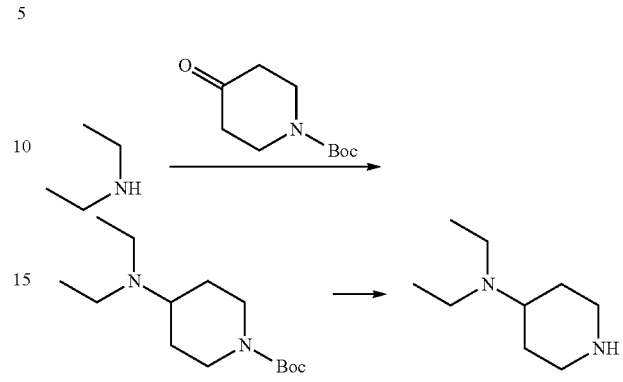

The compound was synthesized according to the method of EXAMPLE 15 except that diethylamine and N-(tert-butoxycarbonyl)-4-piperidone were used as the starting materials.

EXAMPLE 47

Allyl isopropyl(2-methylamino)ethyl)aminocarboxylate hydrochloride

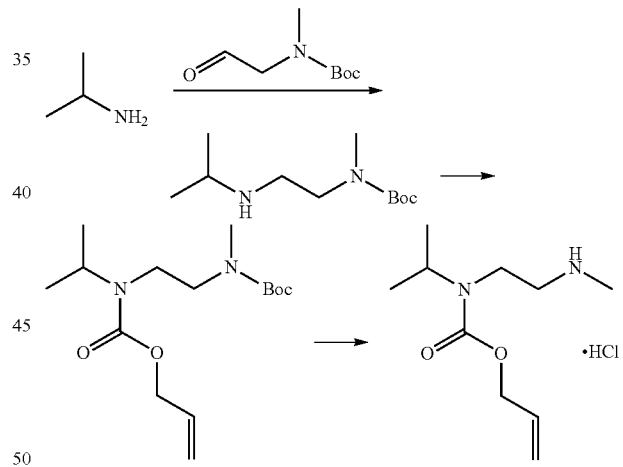

Step 1: tert-butyl (2-(isopropylamino)ethyl)(methyl)carbamate

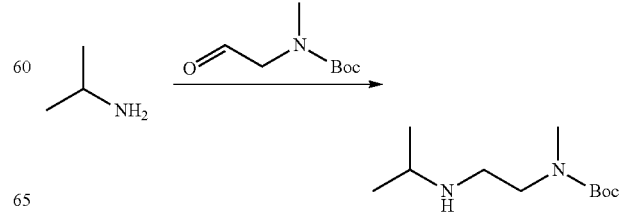

The compound was synthesized according to the method in the step 1 of EXAMPLE 15 except that isopropylamine and N-Boc-(methylamino)acetaldehyde were used as the starting materials.

Steps 2-3: Allyl isopropyl(2-methylamino)ethyl)aminocarboxylate hydrochloride

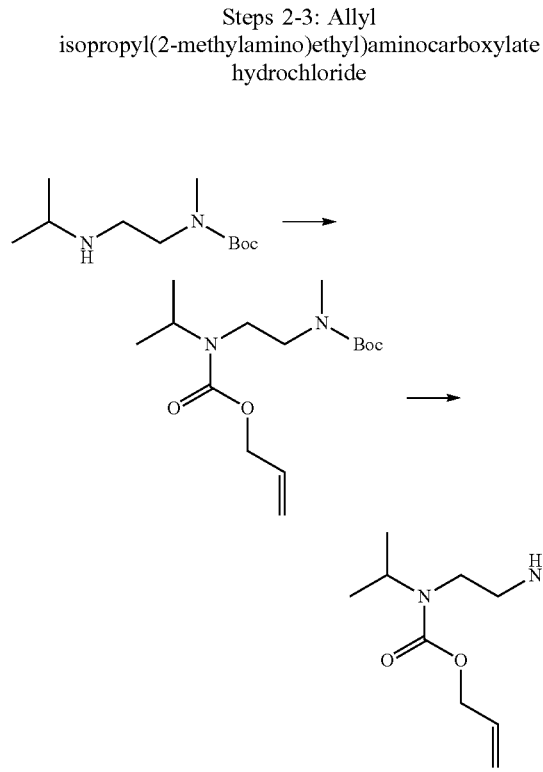

The compound was synthesized according to the method of EXAMPLE 33 except that tert-butyl (2-(isopropylamino)ethyl)(methyl)carbamate and allyl chloroformate were used as the starting materials.

EXAMPLE 48

N1-isopropyl-N1,N2-dimethylethylenediamine

Step 1: tert-butyl methyl(2-(isopropylamino)ethyl)carbamate

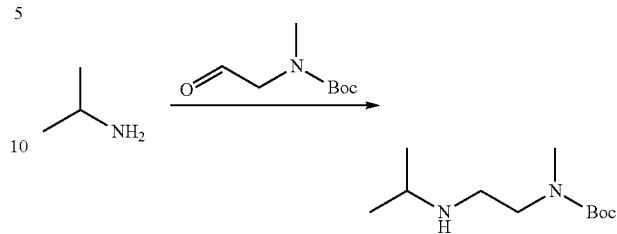

The compound was synthesized according to the method in the step 1 of EXAMPLE 15 except that isopropylamine and N-Boc-(methylamino)acetaldehyde were used as the starting materials.

Steps 2, 3: N1-isopropyl-N1,N2-dimethylethylenediamine

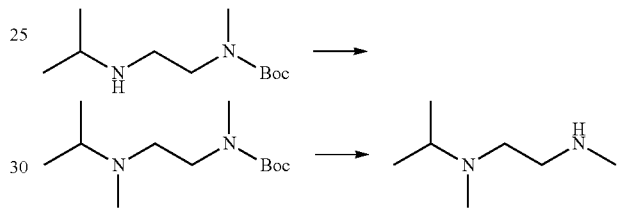

The compound was synthesized according to the method in the steps 2, 3 of EXAMPLE 2 except that tert-butyl methyl(2-(isopropylamino)ethyl)carbamate and CH₃I were used as the starting materials.

EXAMPLE 49

N,1,2,6-tetramethylpiperidine-4-amine trifluoracetate

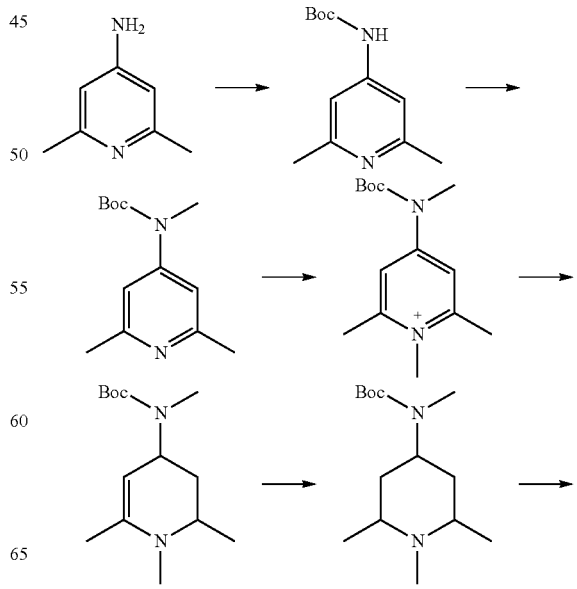

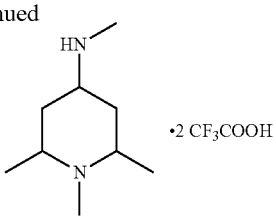

·2 CF₃COOH

Step 1: tert-butyl (2,6-dimethylpyridine-4-yl)carbamate

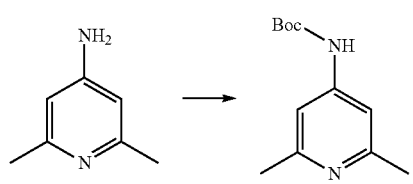

2,6-dimethylpyridine-4-amine (1 g, 8.2 mmol), DCM (20 mL), trimethylamine (1.66 g, 16.4 mmol) and DMAP (0.1 g, 0.82 mmol) were added to a 100 mL three-necked bottle in order, and then (Boc)₂O (1.79 g, 8.2 mmol) in DCM (5 mL) was added dropwise at room temperature with stirring, after the addition was completed, the mixture was reacted at room temperature with stirring for 1-2 h. Water (50 mL) and DCM (30 mL) were added to the reaction mixture thereinto, filtered, the filtrate was allowed to separate into layers, the aqueous phase was extracted with DCM twice, the organic phases were combined, washed with saturated brine twice, dried with anhydrous sodium sulfate, and then concentrated under reduced pressure to give a crude product, the crude product was purified by column chromatography with DCM/MeOH=25/1 as eluent, the product was collected and concentrated under reduced pressure to give a 750 mg of white solid.

Step 2: tert-butyl (2,6-dimethylpiperidine-4-yl)(methyl)carbamate

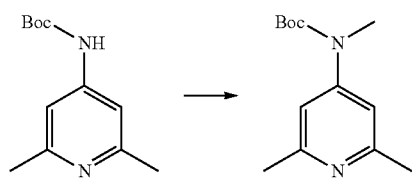

DMF (30 mL) and NaH (406 mg, 10.13 mmol) were added to a 100 mL three-necked bottle in order under the protection of argon, cooled to 0-5° C. in an ice-water bath, and then tert-butyl (2,6-dimethylpyridine-4-yl)carbamate (750 mg. 3.38 mmol) in DMF (5 mL) was added dropwise thereinto, after the addition was completed, the mixture was reacted at 0-5° C. for 1 h. CH₃I (720 mg, 1.5 eq) in DMF (5 mL) was added dropwise thereinto, and then the mixture was warmed to room temperature and reacted with stirring for 1-2 h. When the reaction completed, the reaction mixture was cooled to 0-10° C., water (15 mL) was added dropwise thereinto, extracted with ethyl acetate (20 mL×3) for three times, the organic phases were combined, washed with saturated brine twice, dried with anhydrous sodium sulfate, and concentrated under reduced pressure to give a 900 mg of pale yellow liquid.

Step 3: 4-((tert-butoxycarbonyl)(methyl)amino)-1,2,6-trimethylpyridinium

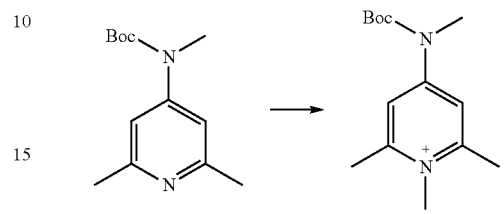

Tert-butyl (2,6-dimethylpyridine-4-yl)(methyl)carbamate (400 mg, 1.69 mmol), DMF (10 mL) and CH₃I (1.2 g, 8.47 mmol) were sequentially added to a 50 mL sealed tube, heated to 75-80° C. in an oil bath, stirred for 7-8 h. Then the mixture was cooled to room temperature and was applied to the next step directly without any further purification.

Step 4: tert-butyl (1,2,6-trimethyl-1,2,3,4-tetrahydropyridine-4-yl)(methyl) carbamate

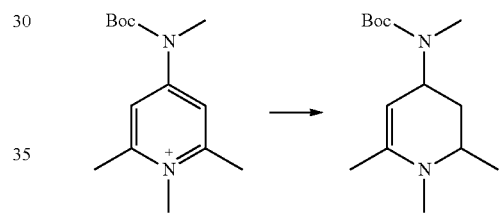

The reaction mixture derived from the last step, ethanol (30 mL) and water (3 mL) were added to a 250 mL three-necked bottle in order, cooled to 0-5° C. in an ice-water bath, and then NaBH₄ (241 mg, 6.37 mmol) was added in batches thereinto, warmed to room temperature and reacted overnight with stirring. Water (50 mL) was added to the reaction mixture, extracted with ethyl acetate (50 mL×3) for three times, combined the organic phases, washed with saturated brine twice, dried with anhydrous sodium sulfate, and then concentrated under reduced pressure to give a crude product, the crude product was purified by column chromatography with DCM/MeOH=10/1 as eluent, the product was collected and concentrated under reduced pressure to give a 110 mg of oil.

Step 5: tert-butyl (1,2,6-trimethylpiperidine-4-yl)(methyl)carbamate

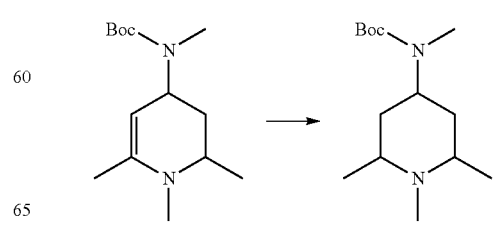

Tert-butyl (1,2,6-trimethyl-1,2,3,4-tetrahydropyridine-4-yl)(methyl)carbamate (110 mg, 0.43 mmol), methanol (10 mL) and Pd/C (20 mg) were added to a 100 mL single-necked bottle in order, hydrogen was substituted for three times, the mixture reacted at room temperature with stirring for 2-3 h. Then the mixture was filtered, the filtrate was concentrated under reduced pressure to give a 115 mg of oily product.

Step 6: N,1,2,6-tetramethylpiperidine-4-amine trifluoroacetate

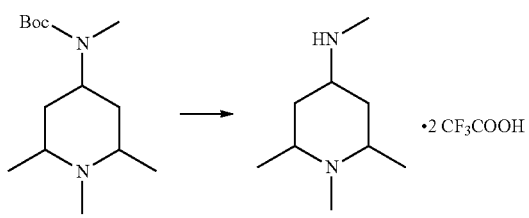

Tert-butyl (1,2,6-trimethylpiperidine-4-yl)(methyl)carbamate (115 mg, 0.45 mmol) and DCM (5 mL) were added to a 100 mL three-necked bottle in order, and then trifluoroacetic acid (3 mL) was added dropwise thereinto at room temperature, after the addition completed, the mixture was stirred at room temperature. When the reaction completed, the reaction mixture was concentrated under reduced pressure, the residue was dissolved in ethyl acetate and continued to concentrated under reduced pressure to give a 180 mg of residue, and the residue was applied to the next step directly without further purification.

EXAMPLE 50

1-isopropyl-N-methylpiperidine-4-amine

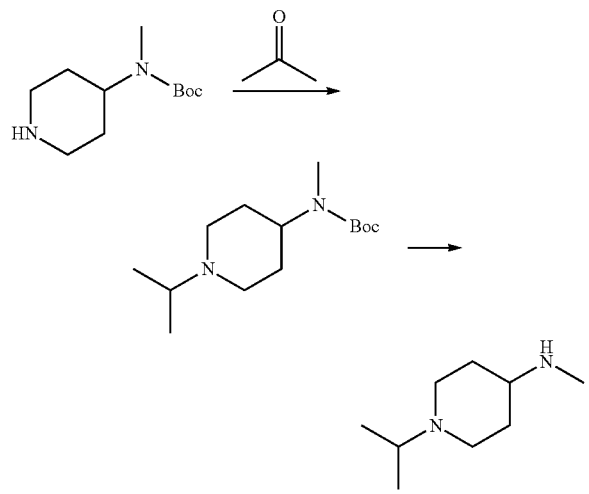

The compound was synthesized according to the method of EXAMPLE 15 except that tert-butyl methyl(piperidine-4-yl)carbamate and acetone were used as the starting materials.

EXAMPLE 51

4-piperidinopiperidine

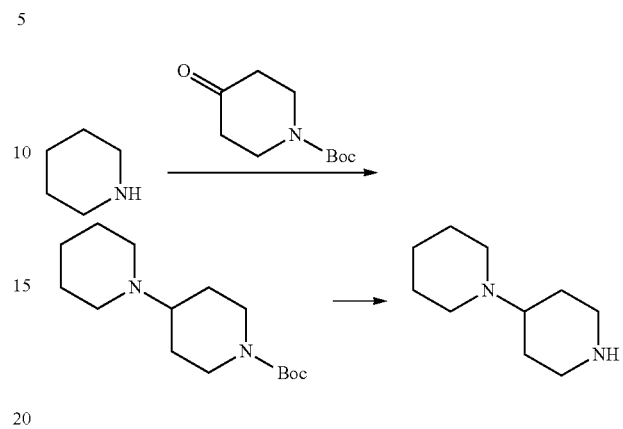

The compound was synthesized according to the method of EXAMPLE 15 except that N-(tert-butoxycarbonyl)-4-piperidone and piperidine were used as the starting materials.

EXAMPLE 52

1-(2-((tert-butyldimethylsilyl)oxy)ethyl)piperazine

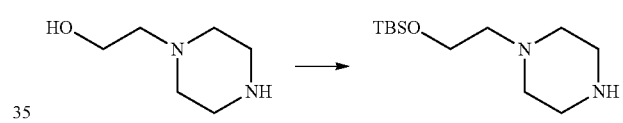

The compound was synthesized according to the method in the step 3 of EXAMPLE 30 except that 1-(2-hydroxyethyl)piperazine was used as the starting material.

EXAMPLE 53

N,N-diethyl-N'-methylethylenediamine trifluoroacetate

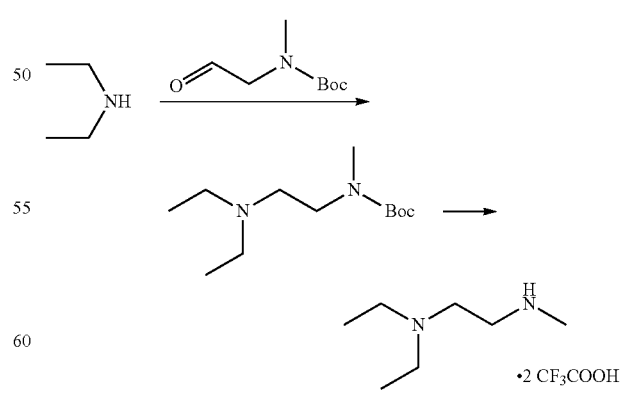

The compound was synthesized according to the method of EXAMPLE 15 except that ethylenediamine and N-Boc-(methylamino)acetaldehyde were used as the starting materials.

EXAMPLE 54

1-hydroxyethylpiperidine

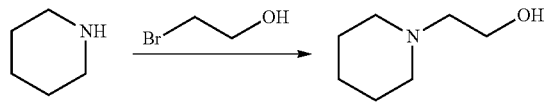

2-bromoethanol (1 g) and DCM (24 mL) were added to a 100 mL three-necked bottle, and then piperidine (2 mL) was added thereinto with stirring, and reacted at room temperature overnight. The reaction mixture was concentrated under reduced pressure, tert-butyl methyl ether (10 mL) was added to the residue, stirred, and filtered, the filtrate was concentrated under reduced pressure to give a crude product, the crude product was purified by column chromatography with DCM/MeOH=10/1 as eluent, the product was collected and concentrated under reduced pressure to give 570 mg.

EXAMPLE 55

N-methyl-2-(4-methylpiperazine-1-yl)ethylamine trifluoroacetate

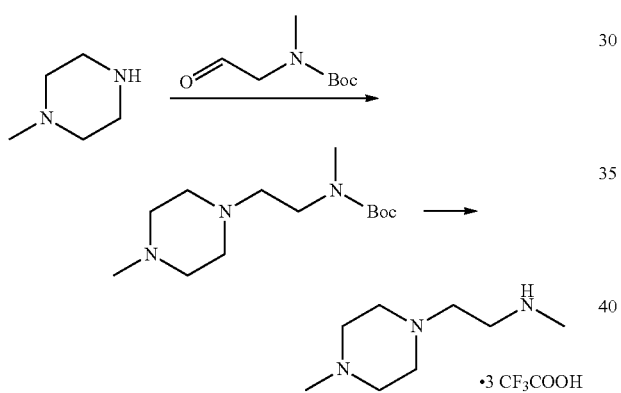

The compound was synthesized according to the method of EXAMPLE 15 except that N-Boc-(methylamino)acetaldehyde and methylpiperazine were used as the starting materials.

EXAMPLE 56

N-isopropyl-N,N'-dimethylethylenediamine hydrochloride

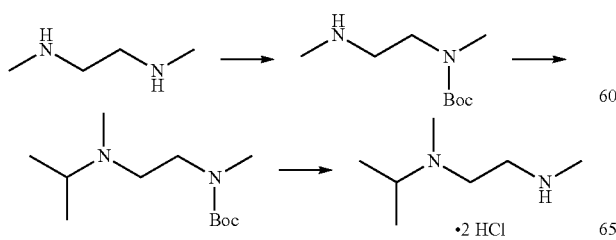

The compound was synthesized according to the method of EXAMPLE 2 except that N,N'-dimethylethylenediamine was used as the starting material.

EXAMPLE 57

4-(3-methoxypyrrolidine-1-yl)piperidine

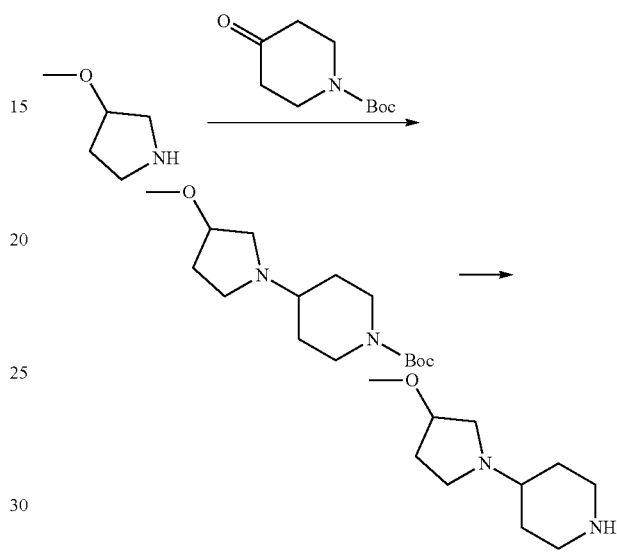

The compound was synthesized according to the method of EXAMPLE 15 except that 3-methoxypyrrolidine and N-tert-butoxycarbonyl-4-piperidone were used as the starting materials.

EXAMPLE 58

4-(4-methoxypiperidine-1-yl)piperidine hydrochloride

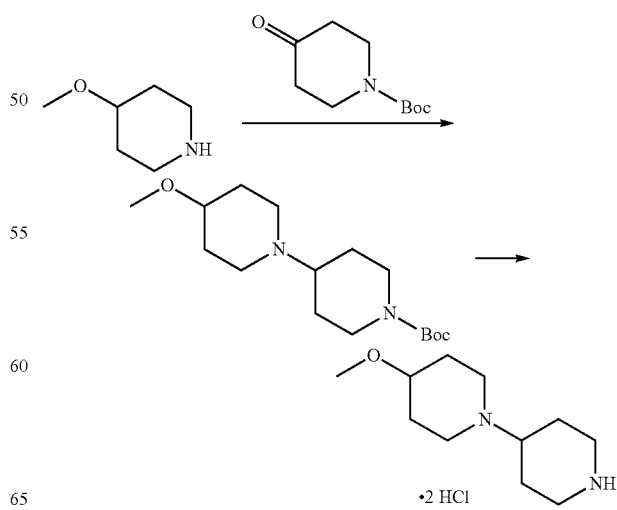

The compound was synthesized according to the method of EXAMPLE 15 except that 4-methoxypiperidine and N-tert-butoxycarbonyl-4-piperidone were used as the starting materials.

EXAMPLE 59

4-(3-methoxyacridine-1-yl)piperidine

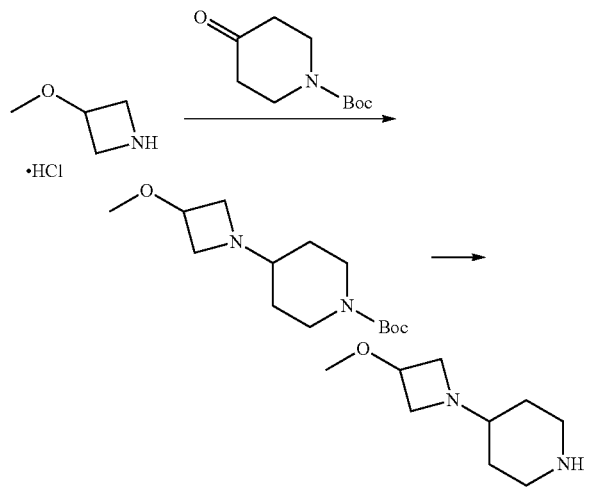

The compound was synthesized according to the method of EXAMPLE 15 except that 3-methoxyacridine hydrochloride and N-tert-butoxycarbonyl-4-piperidone were used as the starting materials.

EXAMPLE 60

4-(tetrahydro-pyran-4-yl)piperidine

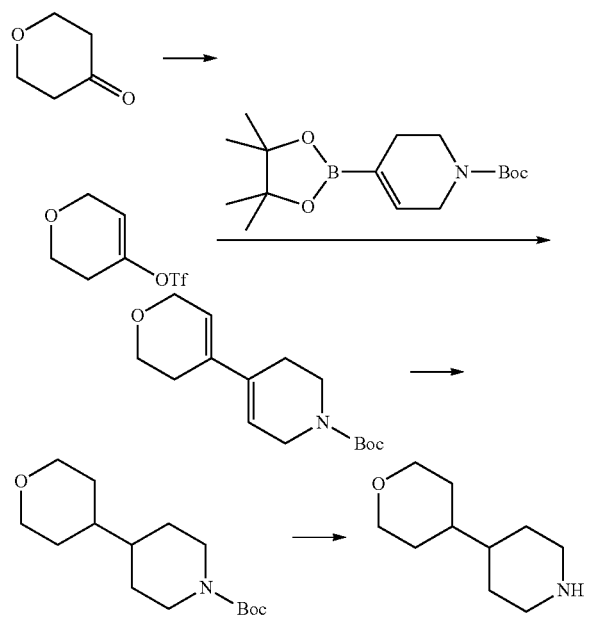

The compound was synthesized according to the method of EXAMPLE 18 except that tetrahydro-4H-pyran-4-one was used as the starting material.

EXAMPLE 61

1-(oxethan-3-yl)-4-(piperidine-4-yl)piperazine trifluoroacetate

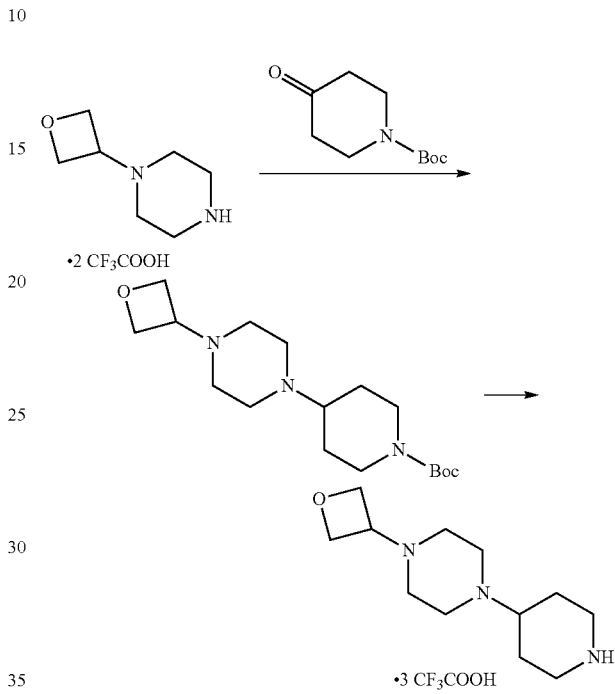

The compound was synthesized according to the method of EXAMPLE 15 except that 1-(oxethan-3-yl)piperazine trifluoroacetate and N-tert-butoxycarbonyl-4-piperidone were used as the starting materials.

EXAMPLE 62

1-(piperidine-4-yl)pyrrolidin-2-one

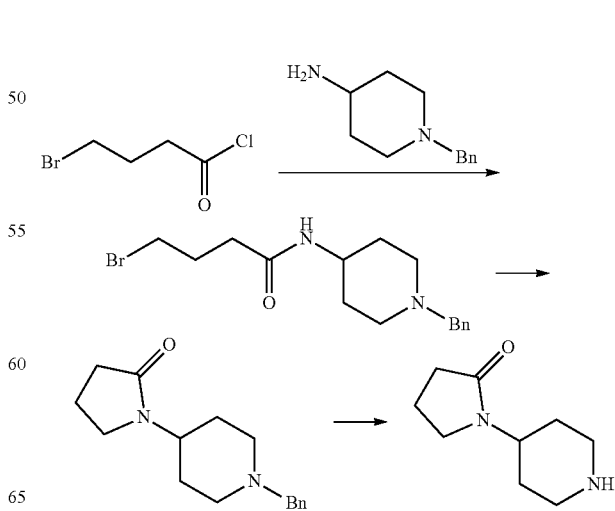

Step 1:
N-(1-benzylpiperidine-4-yl)-4-bromobutanamide

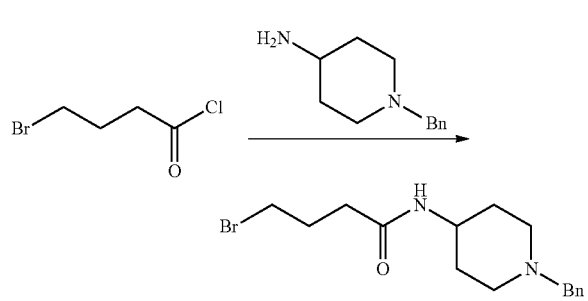

1-benzylpiperidine-4-amine (2.5 g, 1.0 eq), DCM (30 mL) and pyridine (1.5 eq) were added to a 100 mL three-necked bottle in order, cooled to 0° C., and then 4-bromobutyryl chloride (1.2 eq) was added dropwise thereinto, reacted at 0° C., TLC was used to monitor the reaction. When the reaction completed, saturated potassium carbonate (30 mL) was added, extracted with DCM (30 mL×2) twice, the organic phases were combined, dried with anhydrous sodium sulfate, and filtered, the filtrate was concentrated under reduced pressure to give a crude product, the crude product was purified by column chromatography with gradient elution of DCM/MeOH=80/1-25/1, the product was collected and concentrated under reduced pressure to give a 4 g of oil.

Step 2: 1-(1-benzylpiperidine-4-yl) pyrrolidin-2-one

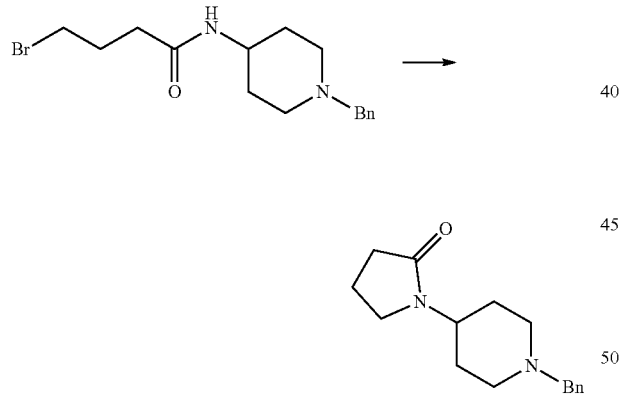

N-(1-benzylpiperidine-4-yl)-4-bromobutanamide (4 g, 1.0 eq) and THF (30 mL) were added to a 100 mL single-necked bottle, cooled to 0° C., and then sodium hydride (2.0 eq) was added in batches, the reaction was stirred at room temperature which was monitored by TLC. saturated potassium carbonate (30 mL) was added to quench the reaction, extracted with DCM (30 mL×2) twice, the organic phases were combined, washed with saturated brine twice, dried with anhydrous sodium sulfate, and filtered, the filtrate was concentrated under reduced pressure to give a crude product, the crude product was purified by column chromatography with DCM/MeOH=100/1→25/1 as eluent, the product was collected and concentrated under reduced pressure to give a 1.6 g of oil.

Step 3: 1-(piperidine-4-yl)pyrrolidin-2-one

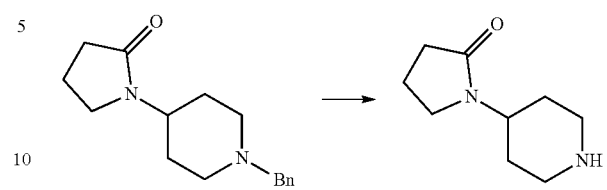

1-(1-benzylpiperidine-4-yl)pyrrolidin-2-one (1.6 g, 1.0 eq) and methanol (30 mL) were added to a 100 mL single-necked bottle, after dissolving with stirring, 10% Pd/C and ammonium formate (6.5 eq) were added, heated to reflux, TLC was used to monitor the reaction, and filtered, the filtrate was concentrated under reduced pressure to give a 1.1 g of oily residue which was applied to next step directly.

EXAMPLE 63

1-(tetrahydro-pyran-3-yl)piperazine

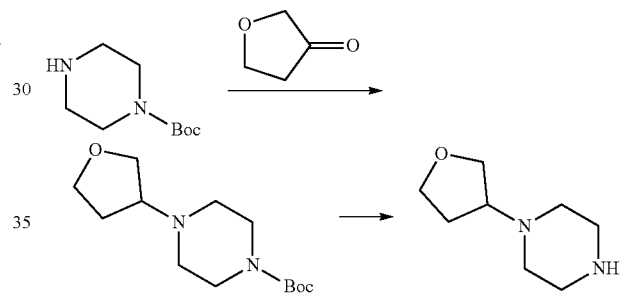

The compound was synthesized according to the method of EXAMPLE 15 except that dihydrofuran-3(2H)-one and tert-butyl piperazine-1-carboxylate were used as the starting materials.

EXAMPLE 64

1-(3-methoxycyclopentyl)piperazine

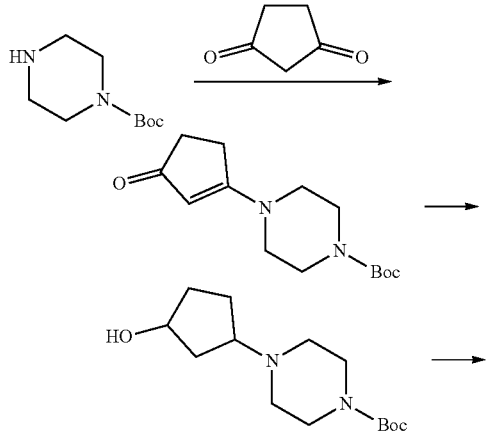

-continued

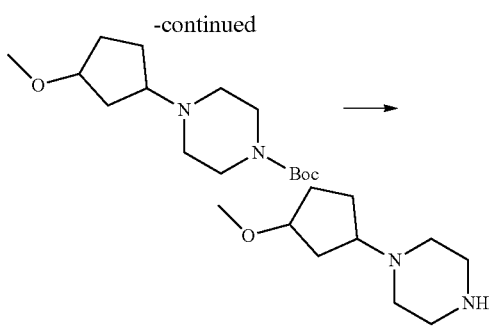

Step 1: tert-butyl 4-(3-oxocyclopent-1-en-1-yl)piperazine-1-carboxylate

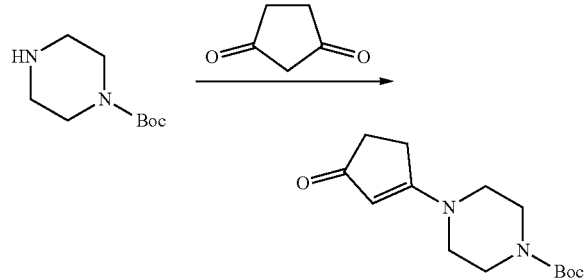

1,3-cyclopentanedione (7 g, 38 mmol), tert-butyl piperazine-1-carboxylate (7.4 g, 75 mmol) and DCM (100 mL) were added to a 250 mL single-necked bottle in order, stirred at room temperature for 24 h. The reaction mixture was concentrated under reduced pressure to give a crude product, the crude product was purified by column chromatography with DCM/MeOH=10/1 as eluent, the product was collected and concentrated under reduced pressure to give a 12 g of white solid.

Step 2: tert-butyl 4-(3-hydroxycyclopentyl)piperazine-1-carboxylate

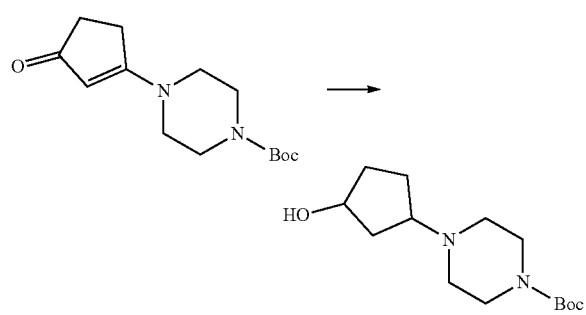

Lithium aluminium hydride (6.8 g, 180 mmol) and tetrahydrofuran (200 mL) were added to a 1 L three-necked bottle, cooled to −5-0° C. in an ice-salt bath, and then tert-butyl 4-(3-oxocyclopent-1-en-1-yl)piperazine-1-carboxylate (12 g, 45 mmol) in tetrahydrofuran (200 mL) was added dropwise, reacted at 0° C. for 30 min. Water was added dropwise slowly to the reaction mixture at −5-0° C. in an ice-salt bath, extracted with DCM (50 mL×3) for three times, the organic phases were combined, washed with saturated brine (100 mL×3) for three times, dried with anhydrous sodium sulfate for 30 min, and filtered under reduced pressure, the filtrate was concentrated at 45° C. to give a crude product, the crude product was purified by column chromatography with DCM/MeOH=10/1 as eluent, the product was collected and concentrated under reduced pressure to give a 1.76 g of red brown solid.

Step 3: tert-butyl 4-(3-methoxycyclopentyl)piperazine-1-carboxylate

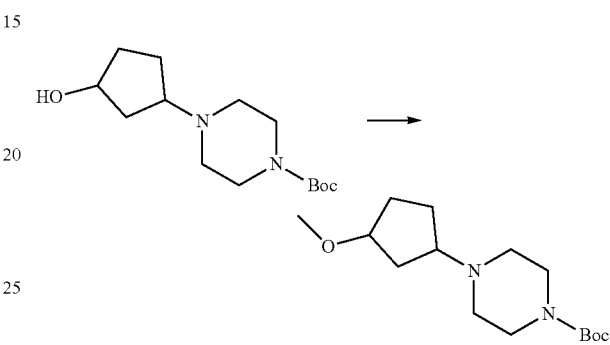

Tert-butyl 4-(3-hydroxycyclopentyl)piperazine-1-carboxylate (1.73 g, 6.4 mmol) and DMF (50 mL) were added to a 100 mL single-necked bottle, stirred to dissolve, cooled to −5-0° C. in an ice-salt bath, and then sodium tert-butoxide (1.23 g, 12.8 mmol) was added in batches, reacted at this temperature for 30 min. Water (30 mL) was added, extracted with ethyl acetate (30 mL×3) for three times, the organic phases were combined, washed with saturated brine (20 mL×3) for three times, dried with anhydrous sodium sulfate for 30 min, and filtered under reduced pressure, then the filtrate was concentrated under reduced pressure at 45° C. to give a crude product, the crude product was purified by column chromatography with DCM/MeOH=50/1 as eluent, the product was collected and concentrated under reduced pressure to give a 1.25 g of yellow oil.

Step 4: 1-(3-methoxycyclopentyl)piperazine

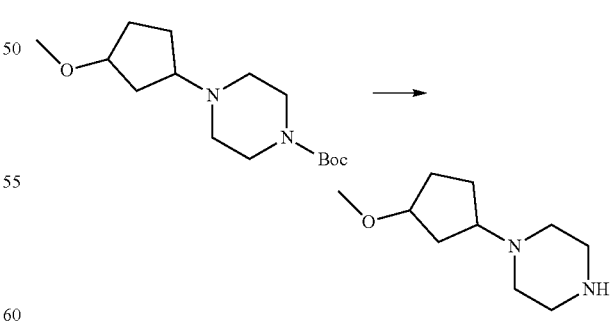

Tert-butyl 4-(3-methoxycyclopentyl)piperazine-1-carboxylate (1.25 g, 4.4 mmol) and DCM (20 mL) were added to a 100 mL single-necked bottle, stirred to dissolve, and then trifluoroacetic acid (10 g, 88 mmol) was added dropwise, reacted at room temperature for 2 h. The reaction mixture was concentrated under reduced pressure at 50° C., anhydrous ethanol (10 mL) was added to the residue, and then concentration under reduced pressure at 50° C., isopropyl ether was added to the residue, stirred at room temperature for 1 h, a white solid was precipitated, and filtered, the filter cake was dried at 50° C. to give a 1.6 g of white solid.

EXAMPLE 65

1-(oxethan-3-yl)piperazine trifluoroacetate

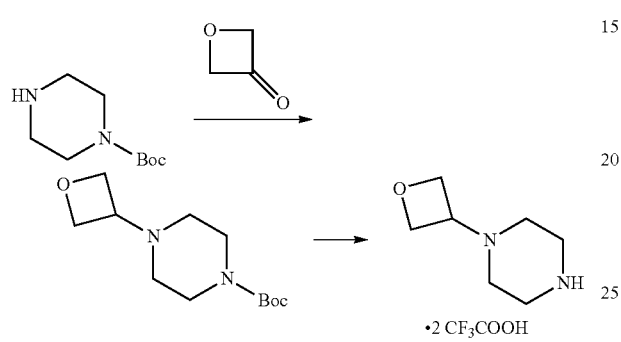

The compound was synthesized according to the method of EXAMPLE 15 except that 3-oxetanone and 1-Boc-piperazine were used as the starting materials.

EXAMPLE 66

N-methyl-1-(tetrahydro-2H-pyran-4-yl)piperidine-4-amine trifluoracetate

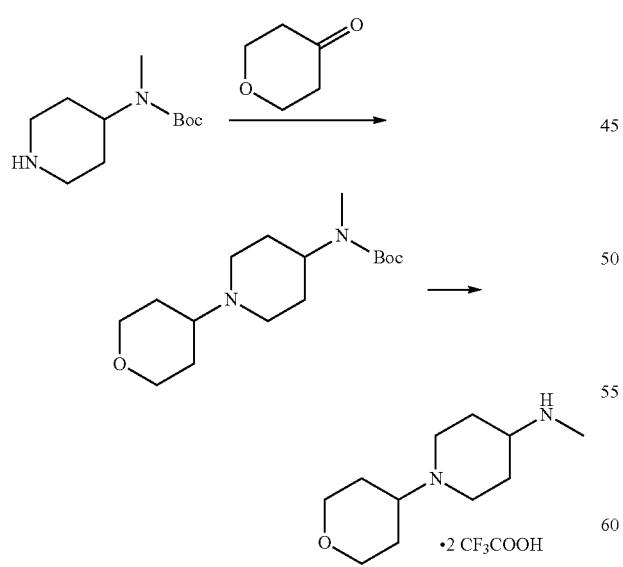

The compound was synthesized according to the method of EXAMPLE 15 except that 4-N-tert-butoxycarbonyl-4-N-methylaminopiperidine and tetrahydro-4H-pyran-4-one were used as the starting materials.

EXAMPLE 67

1-(2-methoxyethyl)-N-methylpyrrolidin-3-amine

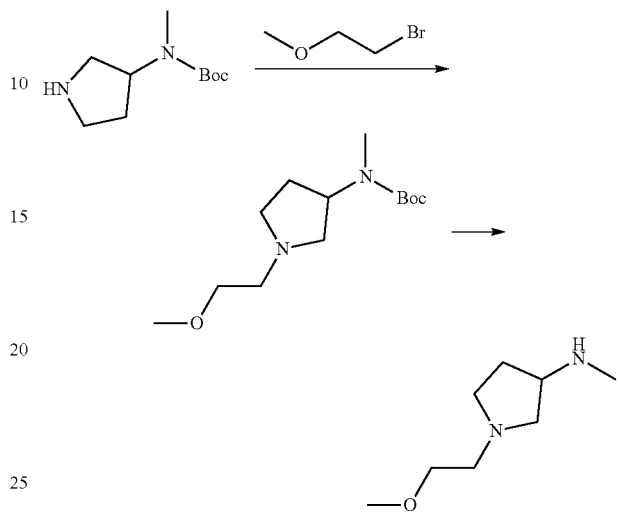

The compound was synthesized according to the method of EXAMPLE 45 except that tert-butyl methyl(pyrrolidin-3-yl)carbamate and 1-bromo-2-methoxyethane were used as the starting materials.

EXAMPLE 68

1-(2-methoxyethyl)-N-methylpiperidine-4-amine trifluoroacetate

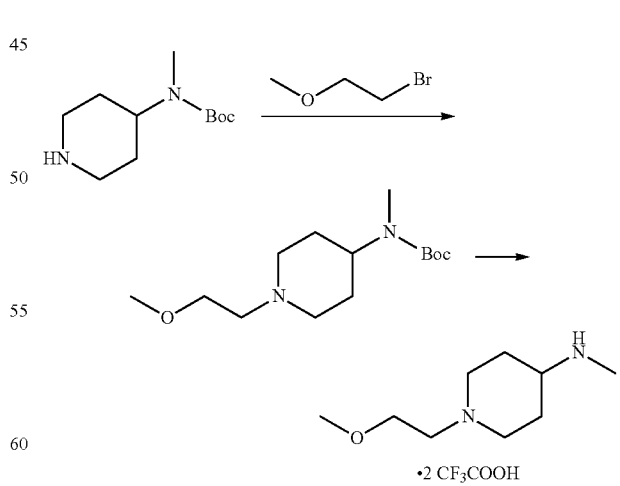

The compound was synthesized according to the method of EXAMPLE 45 except that tert-butyl methyl(piperidin-4-yl)carbamate and 1-bromo-2-methoxyethane were used as the starting materials.

EXAMPLE 69

1-N-ethyl-N-methylpiperazine-4-amine

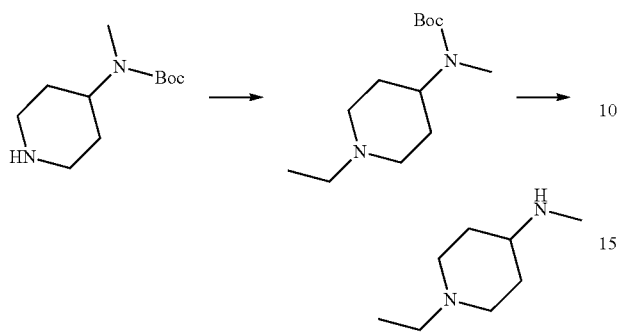

The compound was synthesized according to the method of EXAMPLE 1 except that tert-butyl methyl(piperidin-4-yl)carbamate and iodoethane were used as the starting materials.

EXAMPLE 70

Preparation of 1-methyl-6-(trifluoromethyl)indole-5-boronic acid pinacol ester

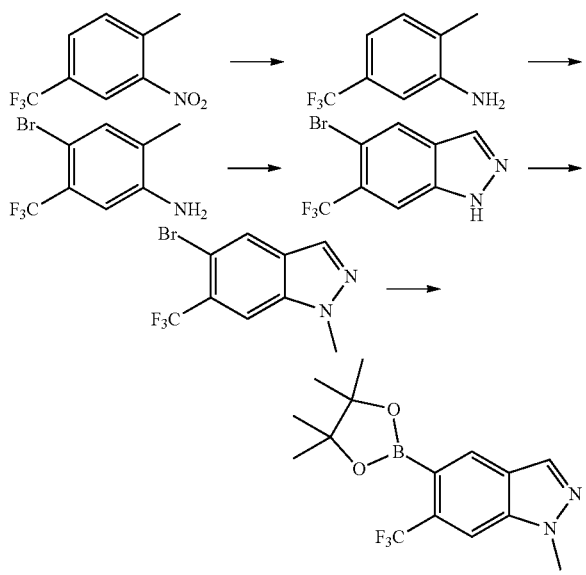

Step 1: 2-methyl-5-(trifluoromethyl)aniline

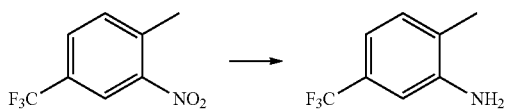

1-methyl-2-nitro-4-(trifluoromethyl)benzene (3 g, 14 mmol), ethanol (30 mL) and Pd/C (100 mg) were added to a 100 mL single-necked bottle in order. The mixture was stirred at room temperature under the pressure of hydrogen for 12-14 h, filtered, the filtrate was concentrated under reduced pressure to give a 2.6 g of pale yellow oil with a yield of 101.5%.

Step 2: 4-bromo-2-methyl-5-(trifluoromethyl)aniline

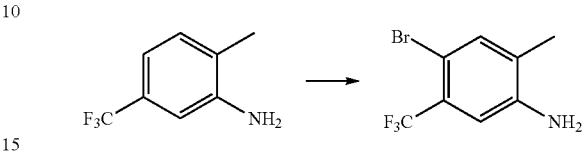

2-methyl-5-(trifluoromethyl)aniline (2.6 g, 14 mmol) and acetonitrile (40 mL) were added to a 100 mL single-necked bottle in order, cooled to 10° C., and then NBS (2.9 g, 16 mmol) was added in batches. When the addition completed, the mixture was stirred at 25° C. for 1.5 h. 50 mL saturated sodium thiosulfate solution was added to quench the reaction, the aqueous phase was extracted with ethyl acetate (80 mL×3) for three times, the organic phases were combined and concentrated under reduced pressure to give a crude product, the crude product was purified by column chromatography with PE/EA=6/1 as eluent, the product was collected and concentrated under reduced pressure to give a 3.43 g of pale yellow oil with a yield of 91.5%.

Step 3: 5-bromo-6-(trifluoromethyl)-1H-indole

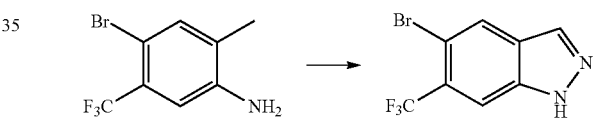

4-bromo-2-methyl-5-(trifluoromethyl)aniline (3.43 g, 13.55 mmol) and acetic acid (130 mL) were added to a 100 mL single-necked bottle in order, and then sodium nitrite (1.02 g, 14.91 mmol) in water (3.5 mL) was added dropwise thereinto. After the addition completed, the mixture was reacted at room temperature for 12-14 h. Saturated sodium carbonate (PH>7) was added, and filtered, the filter cake was collected, precipitate with 30 mL petroleum ether and stirred for 20 min, filtered, dried to give a 2.2 g of pale solid with a yield of 61.6%.

Step 4: 5-bromo-1-methyl-6-(trifluoromethyl)-1H-indole

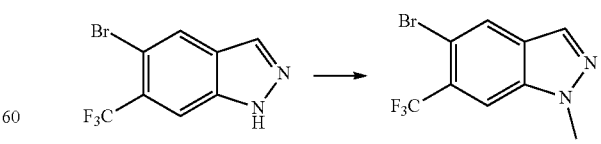

5-bromo-6-(trifluoromethyl)-1H-indole (2.2 g, 8.33 mmol) and tetrahydrofuran (20 mL) were added to a 100 mL single-necked bottle in order, cooled to 10° C., and then sodium hydride (433 mg, 10.83 mmol) was added thereinto. After the addition completed, the mixture was reacted at 0°

C. for 30 min. Iodomethane (1.77 g, 12.5 mmol) in THF (4 mL) was added dropwise while the temperature of the mixture was kept at 0° C., after the addition completed, the mixture was warmed to room temperature and reacted for 2 h with stirring. Then 20 mL water was added to quench the reaction, the aqueous phase was extracted with ethyl acetate (60 mL×3) for three times, the organic phases were combined and concentrated under reduced pressure to give a crude product. The crude product was purified by column chromatography with PE/EA=10/1 as eluent, the product was collected and concentrated to give a 600 mg of pale yellow solid with a yield of 26.1%.

Step 5:
1-methyl-6-(trifluoromethyl)indole-5-boronic acid pinacol ester

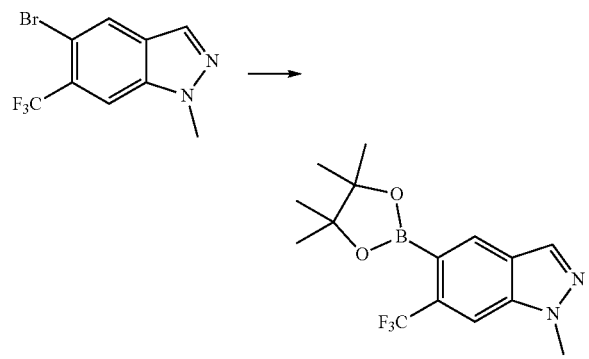

5-bromo-1-methyl-6-(trifluoromethyl)-1H-indole (500 mg, 1.79 mmol), bis(pinacolato)diboron (685.2 mg, 2.69 mmol), potassium acetate (352.5 mg, 3.58 mmol), Pd(dppf)Cl$_2$ (131.6 mg, 0.179 mmol) and 1,4-dioxane (15 mL) were added to a 100 mL single-necked bottle in order under the protection of argon, after the addition completed, the mixture was heated to 100° C. to react for 7 h. Then the reaction mixture was cooled to room temperature, 20 mL water was added thereinto, the aqueous phase was extracted with ethyl acetate (50 mL×3) for three times, the organic phases were combined and concentrated to give a crude product. The crude product was purified by column chromatography with PE/EA=10/1 as eluent, the product was collected and concentrated to give a 300 mg of pale yellow oil with a yield of 51.1%.

EXAMPLE 71

Preparation of 1-methyl-7-fluoroindole-5-boronic acid pinacol ester

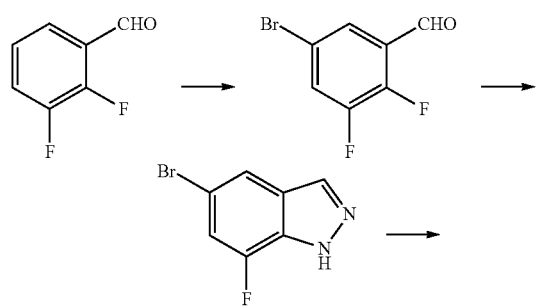

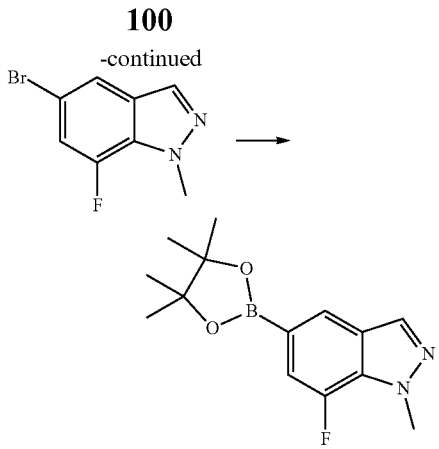

Step 1: 5-bromo-2,3-difluorobenzaldehyde

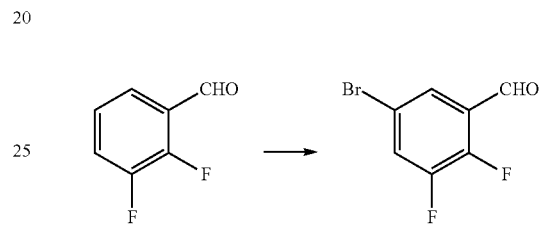

1,3-difluorobenzaldehyde (1 g, 7.04 mmol) and concentrated sulfuric acid (50 mL) were added to a 100 mL three-necked bottle in order, stirred at room temperature to give a brown yellow solution. Then NBS (1.05 g, 5.90 mmol) was added in batches slowly, after the addition completed, the mixture was heated to 45-50° C. to react for 2-3 h. The reaction mixture was dropped slowly to a 200 mL ice water, extracted with ethyl acetate (50 mL×2) twice, the organic phases were combined, washed with saturated brine twice, dried with anhydrous sodium sulfate for 30 min, and filtered, the filtrate was concentrated under reduced pressure to give a crude product, the crude product was purified by column chromatography to give a 280 mg of product. The materials were recycled.

Step 2: 5-bromo-7-fluoro-1H-indole

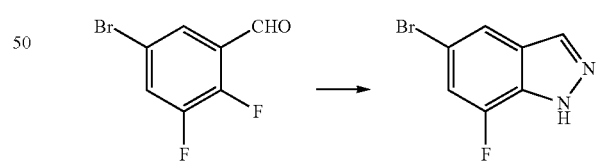

5-bromo-2,3-difluorobenzaldehyde (200 mg) and hydrazine hydrate (10 mL) were added to a 100 mL three-necked bottle in order, heated to 100-110° C. to react for 3-4 h with stirring, cooled to room temperature, and then 30 mL water and 30 mL ethyl acetate were added thereinto, stirred to separate into layers, the aqueous phase was extracted with ethyl acetate (20 mL×3) for three times, the organic phases were combined, washed with saturated brine (30 mL×2) twice, dried with anhydrous sodium sulfate for 30 min, and filtered, the filtrate was concentrated under reduced pressure to give a crude product, the crude product was accordingly purified by column chromatography with PE/EA=4/1 as eluent, the product was collected and concentrated to give 32 mg.

Step 3: 1-methyl-5-bromo-7-fluoro-1H-indole

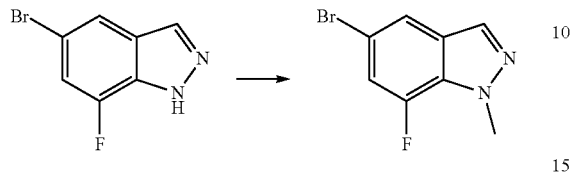

The compound was synthesized according to the method in the step 4 of EXAMPLE 70 except that 5-bromo-7-fluoro-1H-indole was used as the starting material.

Step 4: 1-methyl-7-fluoroindole-5-boronic acid pinacol ester

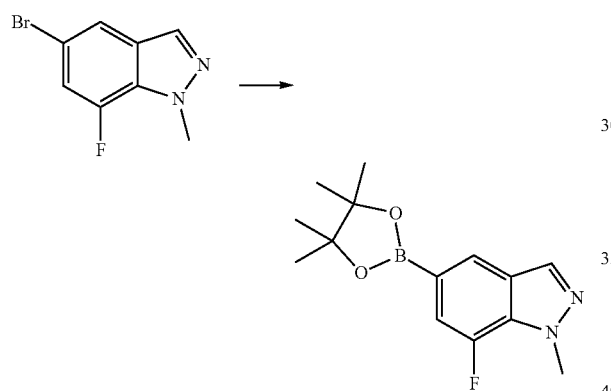

The compound was synthesized according to the method in the step 5 of EXAMPLE 70 except that 1-methyl-5-bromo-7-fluoro-1H-indole was used as the starting material.

EXAMPLE 72

Preparation of 1-methyl-7-(trifluoromethyl)indole-5-boronic acid pinacol ester

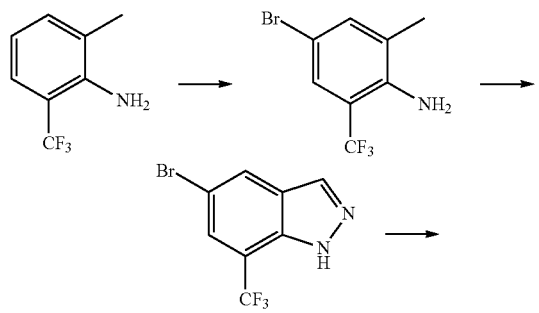

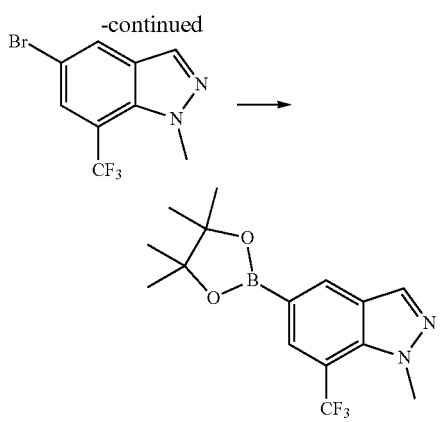

The compound was synthesized according to the method in the steps 2-5 of EXAMPLE 70 except that 2-methyl-6-(trifluoromethyl)aniline was used as the starting material.

EXAMPLE 73

Preparation of 1-methyl-6-fluoroindole-5-boronic acid pinacol ester

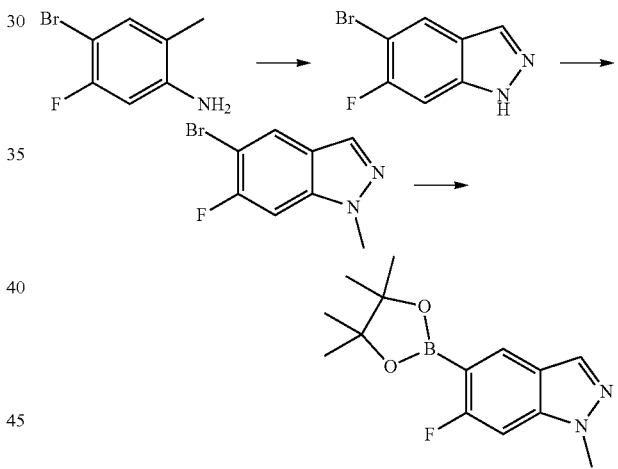

The compound was synthesized according to the method in the steps 2-5 of EXAMPLE 70 except that 4-bromo-5-fluoro-2-methylaniline was used as the starting material.

EXAMPLE 74

Preparation of 1,3-dimethylindole-6-boronic acid pinacol ester

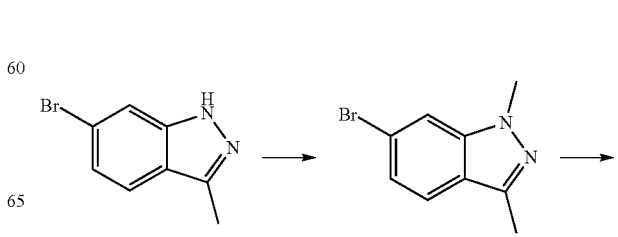

-continued

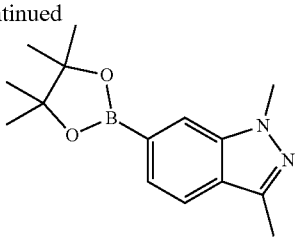

The compound was synthesized according to the method in the steps 4-5 of EXAMPLE 70 except that 6-bromo-3-methyl-1H-indole was used as the starting material.

EXAMPLE 75

Preparation of 1-methyl-3-fluoroindole-6-boronic acid pinacol ester

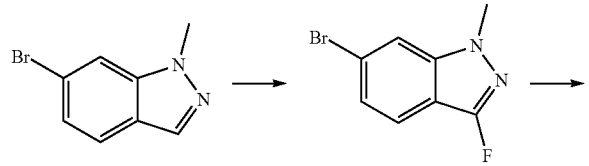

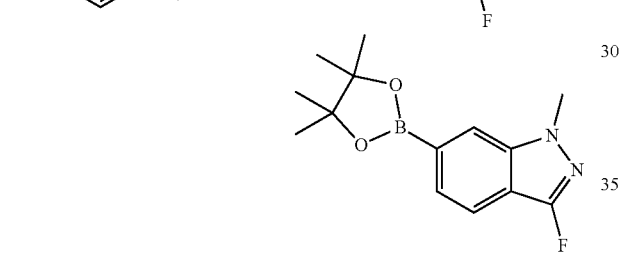

Step 1: 1-methyl-6-bromo-3-fluoro-1H-indole

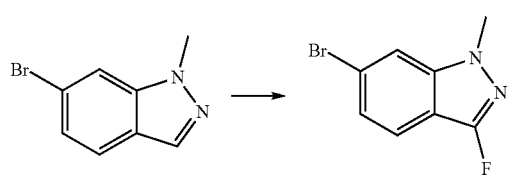

6-bromo-1-methyl-1H-indole (2 g, 9.48 mmol), select flour (fluorinated reagent) (4.4 g, 12.32 mmol) and acetonitrile (40 mL) were added to a 100 mL single-necked bottle in order, heated to 100° C. in an oil bath and reacted with stirring. TLC was used to monitor the reaction. When the reaction completed, the mixture was cooled to room temperature, water (60 mL) and ethyl acetate (80 mL) were added thereinto, extracted with ethyl acetate, the organic phase was washed with saturated brine (50 mL×2) twice, dried with anhydrous sodium sulfate for 30 min. Filtered, the filtrate was concentrated under reduced pressure to give a crude product, the crude product was purified by column chromatography with PE/EA=10/1 as eluent, the product was collected and concentrated under reduced pressure to give a 620 mg of white solid.

Step 2: 1-methyl-3-fluoroindole-6-boronic acid pinacol ester

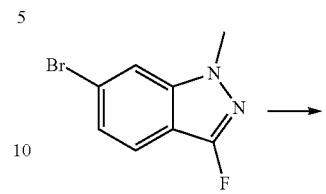

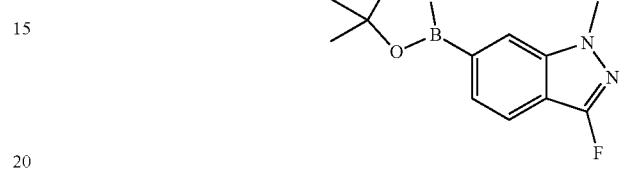

The compound was synthesized according to the method in the step 5 of EXAMPLE 70 except that 1-methyl-6-bromo-3-fluoro-1H-indole was used as the starting material.

EXAMPLE 76

Preparation of 2-methyl-2H-indole-6-boronic acid pinacol ester

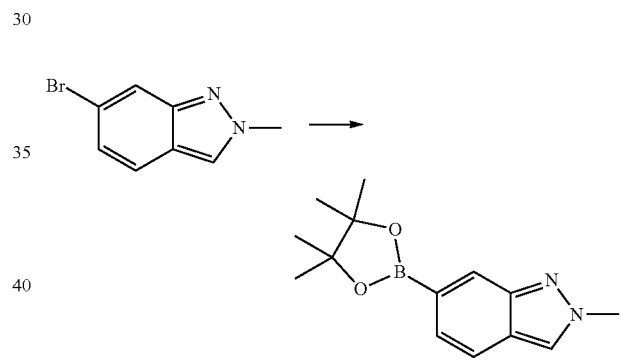

The compound was synthesized according to the method in the step 5 of EXAMPLE 70 except that 6-bromo-2-methyl-2H-indole was used as the starting material.

EXAMPLE 77

Preparation of benzothiazole-5-boronic acid pinacol ester

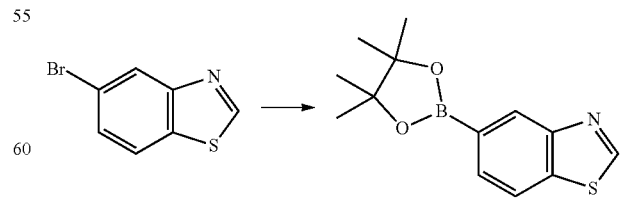

The compound was synthesized according to the method in the step 5 of EXAMPLE 70 except that 5-bromobenzothiazole was used as the starting material and DMF was used as the solvent.

EXAMPLE 78

Preparation of benzothiazole-6-boronic acid pinacol ester

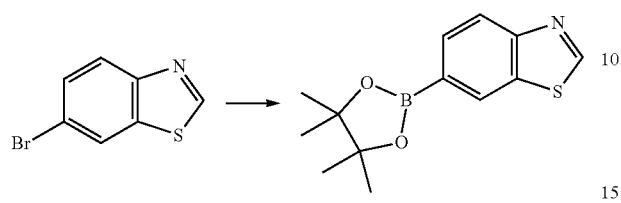

The compound was synthesized according to the method in the step 5 of EXAMPLE 70 except that 6-bromo benzothiazole was used as the starting material and DMF was used as the solvent.

EXAMPLE 79

Preparation of 2-methyl-benzothiazole-6-boronic acid pinacol ester

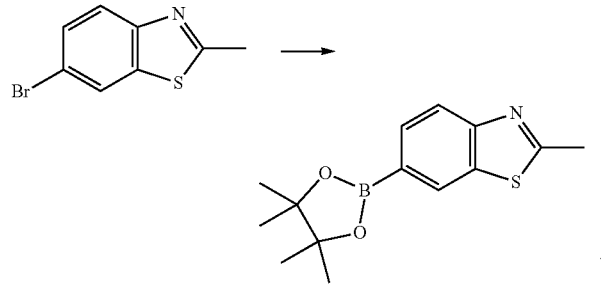

The compound was synthesized according to the method in the step 5 of EXAMPLE 70 except that 6-bromo-2-methylbenzothiazole was used as the starting material.

EXAMPLE 80

Preparation of 1-ethylindole-5-boric acid pinacol ester

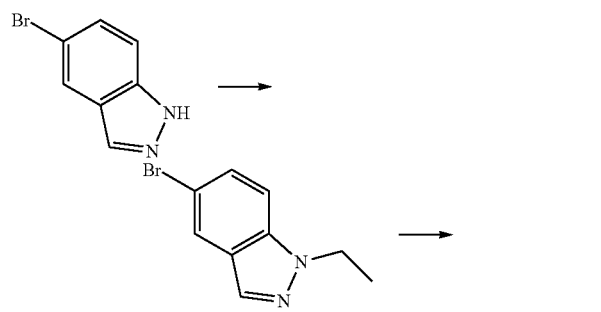

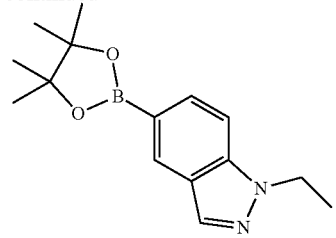

The compound was synthesized according to the method in the step 5 of EXAMPLE 70 except that 5-bromoindole and $C_2HI$ were used as the starting materials.

EXAMPLE 81

Preparation of 1-isopropylindole-5-boric acid pinacol ester

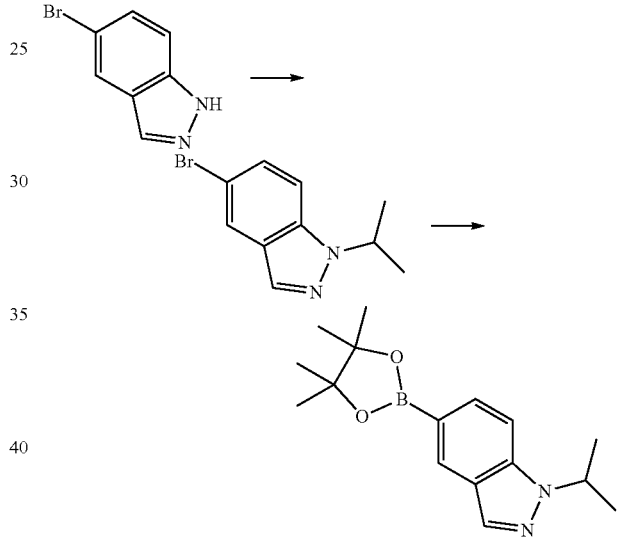

The compound was synthesized according to the method in the steps 4-5 of EXAMPLE 70 except that 5-bromoindole and iodoisopropane were used as the starting materials.

EXAMPLE 82

Preparation of 1-isopropylindole-6-boric acid pinacol ester

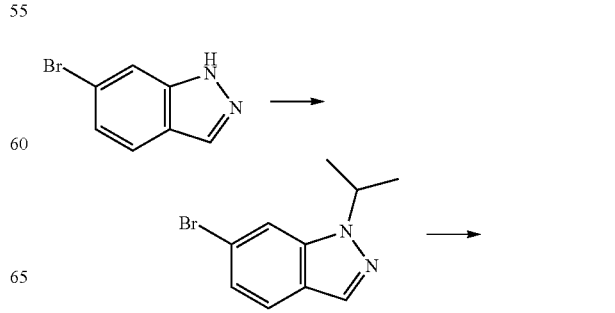

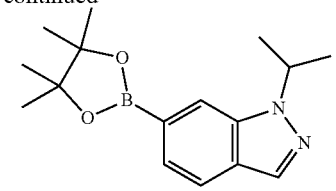

The compound was synthesized according to the method in the step 5 of EXAMPLE 70 except that 6-bromoindole and iodoisopropane were used as the starting materials.

EXAMPLE 83

4-(2-(dimethylamino)ethoxy)-2-methoxy-5-nitroaniline

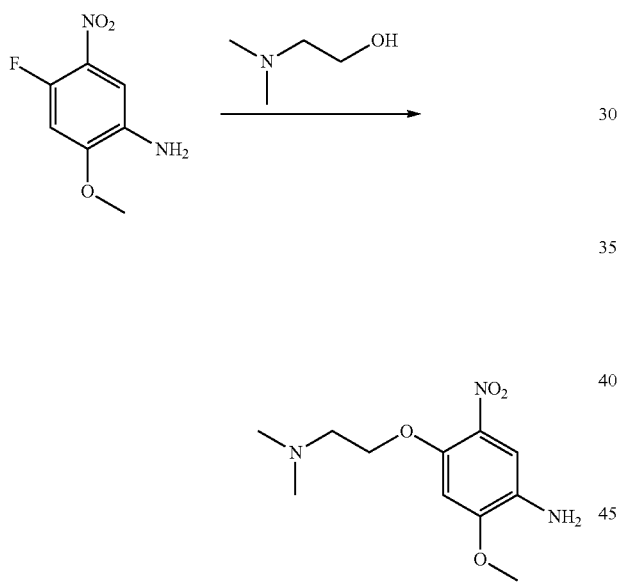

2-(dimethylamino)ethanol (718 mg, 8.06 mmol) and DMF (30 mL) were added to a 100 mL three-necked bottle, cooled to 0-5° C. in an ice-water bath, potassium tert-butoxide (1.5 g, 13.4 mmol) was added in batches thereinto, reacted at the same temperature for 30 min, then 4-fluoro-2-methoxy-5-nitroaniline (500 mg, 2.69 mmol) was added thereinto, reacted at this temperature for 20 min. TLC was used to monitored the reaction until the reaction completed, then the mixture was cooled to room temperature. Water (50 mL) was added, the mixture was extracted with ethyl acetate (50 mL×3) for three time, the organic phases were combined, washed with saturated brine (20 mL×3) for three times, dried with sodium sulfate for 30 min, and filtered, the filtrate was concentrated under reduced pressure at 45° C. to give a crude product, the crude product was purified by column chromatography with DCM/MeOH=10/1 as eluent, the product was collected and concentrated under reduced pressure to give a 265 mg of brown oil.

EXAMPLE 84

N-(4-amino-5-methoxy-2-nitrophenyl)-2-(dimethylamino)-N-methylacetamide

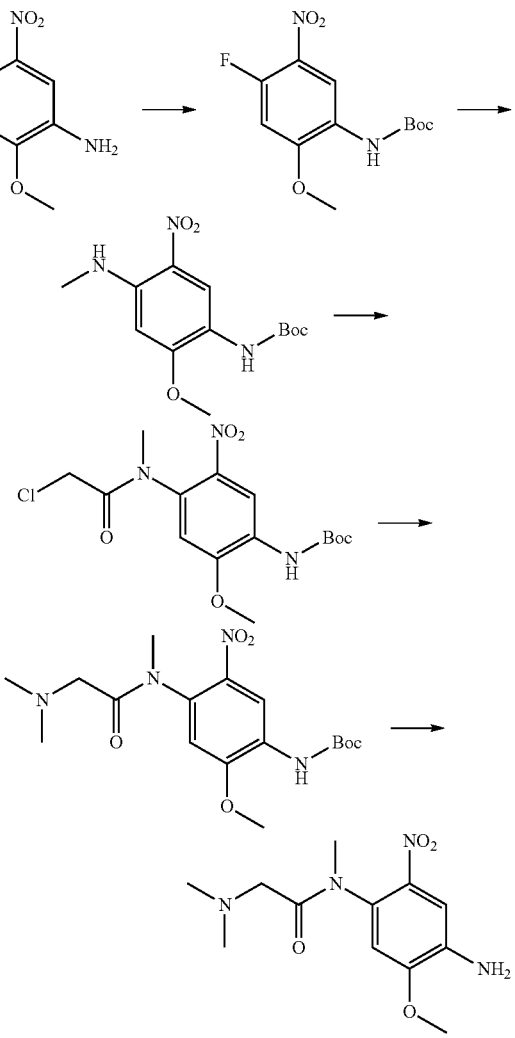

Step 1: tert-butyl (4-fluoro-2-methoxy-5-nitrophenyl)carbamate

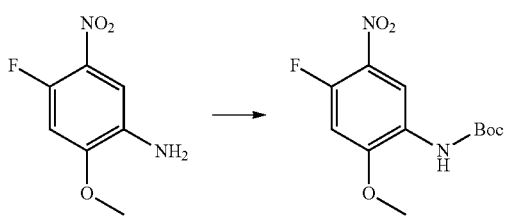 [SMILES: COc1cc(F)c([N+](=O)[O-])cc1N ; COc1cc(F)c([N+](=O)[O-])cc1NC(=O)OC(C)(C)C]

4-fluoro-2-methoxy-5-nitroaniline (5 g, 27 mmol), 4-dimethylaminopyridine (0.33 g, 2.7 mmol) and DCM (50 mL) were added to a 250 mL single-necked bottle, stirred for 10 min, then trimethylamine (5.4 g, 53.75 mmol) and (Boc)$_2$O (5.87 g, 27 mmol) were added thereinto, after the addition completed, reacted at room temperature for 4.5 h. Water (30 mL) was added thereinto, the mixture was extracted with DCM (40 mL×3) for three time, the organic phases were combined, washed with saturated brine (20 mL×3) for three times, dried with sodium sulfate for 30 min, and filtered, the filtrate was concentrated under reduced pressure at 45° C. to give a crude product, the crude product was purified by column chromatography with PE/EA=10/1 as eluent, the product was collected and concentrated under reduced pressure to give a 5.34 g of brown yellow solid.

Step 2: tert-butyl (2-methoxy-4-(methylamino)-5-nitrophenyl)carbamate

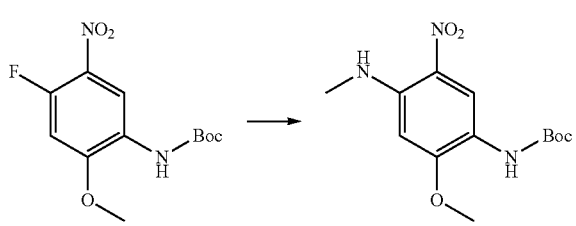 [SMILES: COc1cc(F)c([N+](=O)[O-])cc1NC(=O)OC(C)(C)C ; CNc1cc(OC)c(NC(=O)OC(C)(C)C)cc1[N+](=O)[O-]]

Tert-butyl (4-fluoro-2-methoxy-5-nitrophenyl)carbamate (1.7 g, 5.9 mmol), methylamine hydrochloride (1.2 g, 17.8 mmol), sodium carbonate (3.15 g, 29.7 mmol), potassium iodide (986 mg, 5.9 mmol) and N-methylpyrrolidone (30 mL) were added to a 100 mL sealed tube in order, heated to 60° C. in an oil bath to react for 7 h. The mixture was cooled to room temperature, water (30 mL) was added thereinto, extracted with ethyl acetate (20 mL×3) for three time, the organic phases were combined, washed with saturated brine (20 mL×3) for three times, dried with sodium sulfate for 0.5 h, and filtered under reduced pressure, the filtrate was concentrated under reduced pressure at 45° C. to give a 1.9 g of red brown solid of crude product.

Step 3: tert-butyl (4-(2-chloro-N-methylacetamido)-2-methoxy-5-nitrophenyl)-carbamate

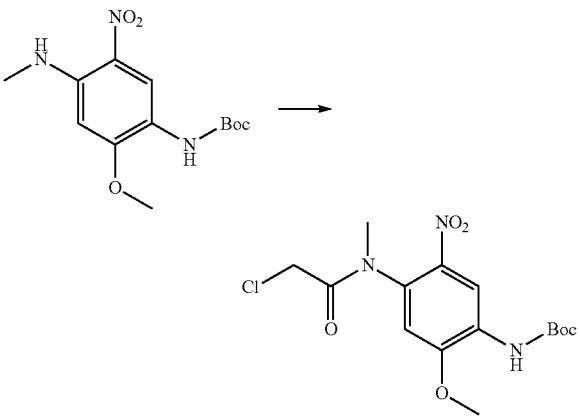

Tert-butyl (2-methoxy-4-(methylamino)-5-nitrophenyl) carbamate (1.7 g, 6 mmol), potassium carbonate (4 g, 28.6 mmol), 30 mL tetrahydrofuran and chloroacetyl chloride (1.9 g, 17 mmol) were added to a 100 mL three-necked bottle in order under the protection of argon, heated to 70° C. in an oil bath to react for 3 h. Water (30 mL) was added to the reaction mixture, extracted with ethyl acetate (30 mL×3) for three time, washed with saturated brine (20 mL×3) for three times, dried with sodium sulfate for 0.5 h, filtered under reduced pressure, the filtrate was concentrated under reduced pressure at 45° C. to give a crude product, the crude product was purified by column chromatography with PE/EA=1/1 as eluent, the product was collected and concentrated under reduced pressure to give a 1.5 g of pale yellow solid.

Step 4: tert-butyl (4-(2-(dimethylamino)-N-methylacetamido)-2-methoxy-5-nitrophenyl)carbamate

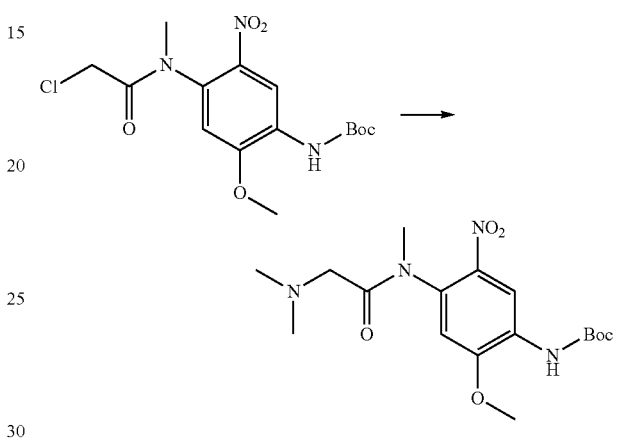

Tert-butyl (4-(2-chloro-N-methylacetamido)-2-methoxy-5-nitrophenyl) carbamate (1.5 g, 4 mmol), dimethylamine hydrochloride (982 mg, 12 mmol), potassium carbonate (2.8 g, 20 mmol) and acetone (30 mL) were added to a 100 mL sealed tube in order, heated to 50° C. in an oil bath to react for 15 h. Water (30 mL) was added to the reaction mixture, extracted with ethyl acetate (30 mL×3) for three time, the reaction mixture was washed with saturated brine (20 mL×3) for three times, dried with sodium sulfate for 0.5 h, filtered under reduced pressure, the filtrate was concentrated under reduced pressure at 45° C. to give a crude product, the crude product was purified by column chromatography, the product was collected and concentrated under reduced pressure to give a 1.2 g of red brown oil.

Step 5: N-(4-amino-5-methoxy-2-nitrophenyl)-2-(dimethylamino)-N-methylacetamide

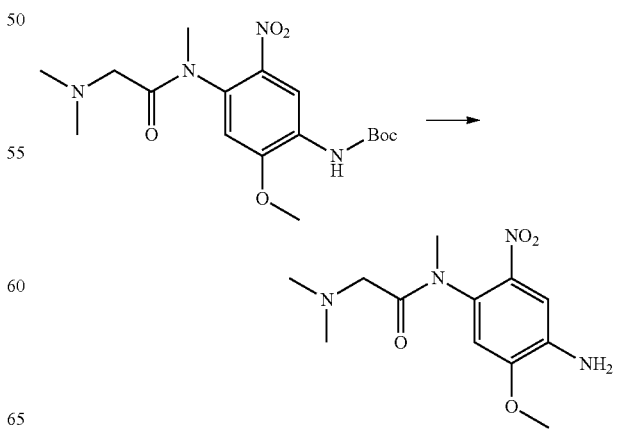

Tert-butyl (4-(2-(dimethylamino)-N-methylacetamido)-2-methoxy-5-nitrophenyl)carbamate (1.2 g, 3.1 mmol) and DCM (20 mL) were added to a 100 mL single-necked bottle, stirred to dissolve, then trifluoroacetic acid (7.2 g, 62.8 mmol) was added dropwise thereinto, reacted at room temperature for 2.5 h. Water (30 mL) was added to the reaction mixture, sodium carbonate was added in batches to adjust pH to pH>8, extracted with ethyl acetate (30 mL×3) for three time, the organic phases were combined, washed with saturated brine (20 mL×3) for three times, dried with sodium sulfate for 0.5 h, filtered under vacuum, the filtrate was concentrated under reduced pressure at 45° C. to give a 673 mg of yellow solid.

EXAMPLE 85

N-(4-amino-5-methoxy-2-nitrophenyl)-2-(dimethylamino)-N-methylpropanamide

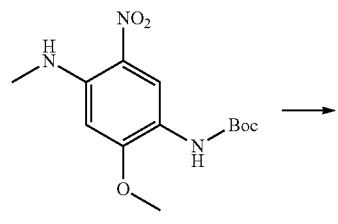

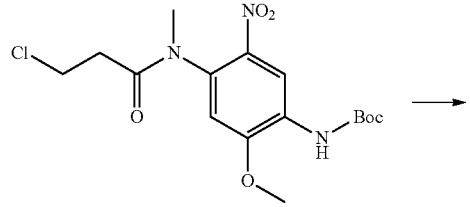

The compound was synthesized according to the method of EXAMPLE 84 except that tert-butyl (2-methoxy-4-(methylamino)-5-nitrophenyl) carbamate and chloropropyl chloride were used as the starting materials.

EXAMPLE 86

5-(difluoromethoxy)-N1-(2-(dimethylamino)ethyl)-N1-methyl-2-nitrobenzene-1,4-diamine

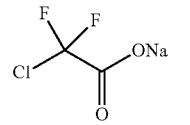

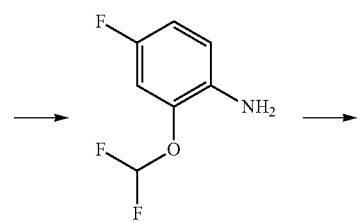

Step 1: 4-fluoro-2-difluoromethoxynitrobenzene

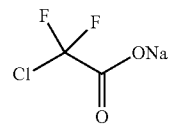

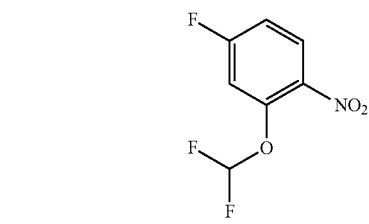

5-fluoro-2-nitrophenol (3 g, 19.1 mmol), sodium chlorodifluoroacetate (3.8 g, 28.6 mmol), potassium carbonate (5.28 g, 38.2 mmol) and DMF (100 mL) were added to a 100 mL single-necked bottle in order under the protection of argon, heated to 80° C. to react for 7-8 h. Then the mixture was cooled to room temperature, ice water was added thereinto, the aqueous phase was extracted with ethyl acetate (80 mL×3) for three times, the organic phases were combined and concentrated under reduced pressure. Crude product was purified by column chromatography with PE/EA=20/1 as eluent, the product was collected and concentrated under reduced pressure to give a 3.26 g of pale oil with a yield of 82.5%.

Step 2: 2-(difluoromethoxy)-4-fluoroaniline

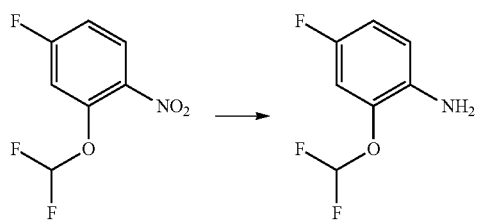 [SMILES: O=[N+]([O-])c1ccc(F)cc1OC(F)F ; Nc1ccc(F)cc1OC(F)F]

4-fluoro-2-difluoromethoxynitrobenzene (3.26 g, 15.7 mmol), Pd/C (800 mg, 20%) and methanol (50 mL) were added to a 100 mL single-necked bottle in order, substitution with hydrogen twice, and then reacted under the pressure of hydrogen at room temperature for 2-3 h. The reaction mixture was filtered, the filtrate was concentrated under reduced pressure to give a 2.6 g of colorless oil with a yield of 93.5%.

Step 3: 2-(difluoromethoxy)-4-fluoro-5-nitroaniline

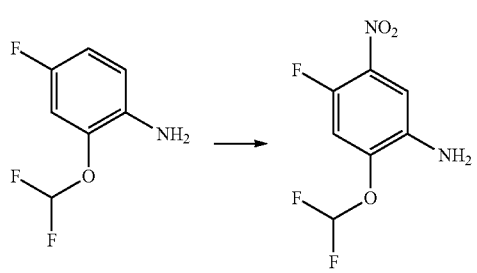 [SMILES: Nc1ccc(F)cc1OC(F)F ; Nc1cc([N+](=O)[O-])c(F)cc1OC(F)F]

Concentrated sulfuric acid (15 mL) was added to a 100 mL three-necked bottle, cooled to 0° C., 2-(difluoromethoxy)-4-fluoroaniline (2.56 g, 14.4 mmol) was added thereinto, reacted at 0° C. for 15 min, and then potassium nitrate (1.60 g, 15.9 mmol) was added in batches, reacted at 0° C. for 2-3 h. The reaction mixture was poured into sodium carbonate solution slowly to adjust pH>7, the aqueous phase was extracted with ethyl acetate (80 mL×2) twice, the organic phases were combined and concentrated under reduced pressure to give a crude product. The crude product was purified by column chromatography with PE/EA=10/1 as eluent, the product was collected and concentrated under reduced pressure to give a 1.8 g of pale yellow solid with a yield of 56.3%.

Step 4: 5-(difluoromethoxy)-N1-(2-(dimethylamino)ethyl)-N1-methyl-2-nitrobenzene-1,4-diamine

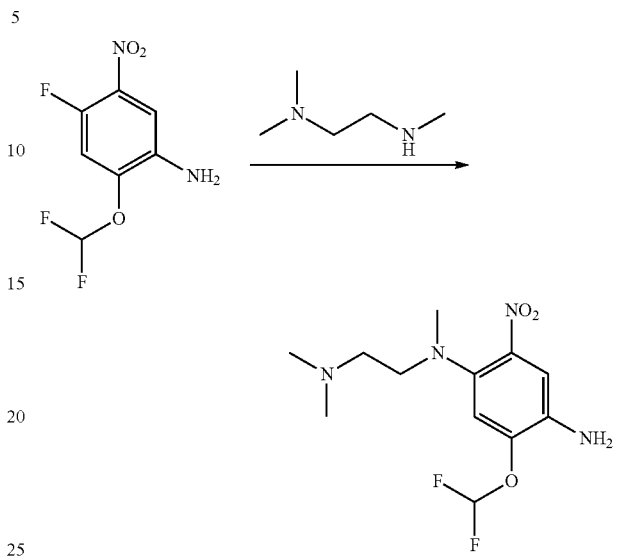

2-(difluoromethoxy)-4-fluoro-5-nitroaniline (1 g, 4.5 mmol), N1,N1,N2-trimethylethylenediamine (2.3 g, 22.5 mmol), DIPEA (2.9 g, 22.5 mmol) and NMP (20 mL) were added to a 100 mL single-necked bottle in order under the protection of argon. The mixture was heated to 100° C. to react for 4-5 h. Cooled to room temperature, water (100 mL) was added to the reaction mixture, the aqueous phase was extracted with ethyl acetate (80 mL×3) for three times, the organic phases were combined and concentrated under reduced pressure to give a crude product. The crude product was purified by column (neutral Al₂O₃) with DCM/MeOH=50/1 as eluent, the product was collected and concentrated under reduced pressure to give a 1.2 g of pale red oil with a yield of 88.2%.

EXAMPLE 87

5-ethyoxyl-N1-(2-(dimethylamino)ethyl)-N-methyl-2-nitrophenyl-1,4-diamine

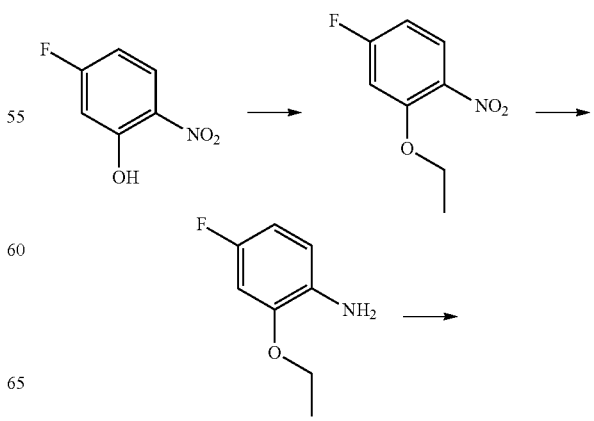

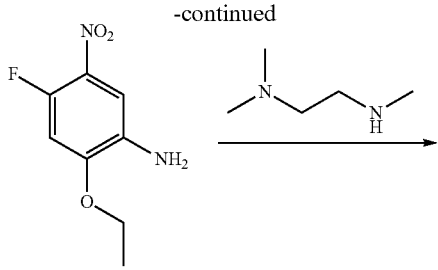

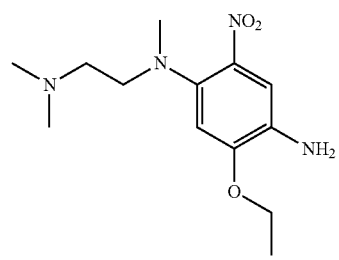

The compound was synthesized according to the method of EXAMPLE 86 except that 5-fluoro-2-nitrophenol and $C_2H_5I$ were used as the starting materials.

EXAMPLE 88

4-fluoro-5-nitro-2-(trifluoromethoxy)aniline

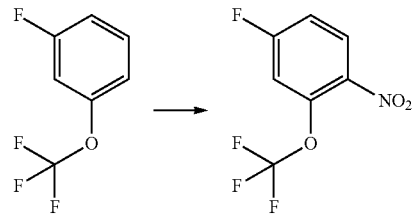 [SMILES: Fc1cccc(OC(F)(F)F)c1 ; O=[N+]([O-])c1ccc(F)cc1OC(F)(F)F]

Step 1: 4-fluoro-2-(trifluoromethoxy)nitrobenzene

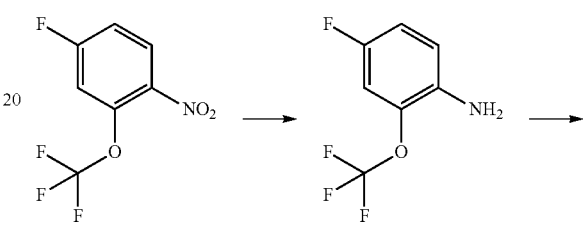

Concentrated sulfuric acid (20 mL) was added to a 250 mL three-necked bottle, cooled to −5-0° C. in an ice-salt bath, 3-(trifluoromethoxy)fluorobenzene (10 g, 60 mmol) was added thereinto, and then potassium nitrate (5.9 g, 60 mmol) was added in batches, reacted at 0° C. for 1 h with stirring. The reaction mixture was poured into an ice water slowly, the mixture was extracted with ethyl acetate (40 mL×3) for three times, the organic phases were combined, washed with saturated brine (20 mL×3) for three times, dried with sodium sulfate for 30 min, and filtered under reduced pressure, the filtrate was concentrated at 45° C. under reduced pressure to give a 8.5 g of pale yellow oil.

Steps 2-3:
4-fluoro-5-nitro-2-(trifluoromethoxy)aniline

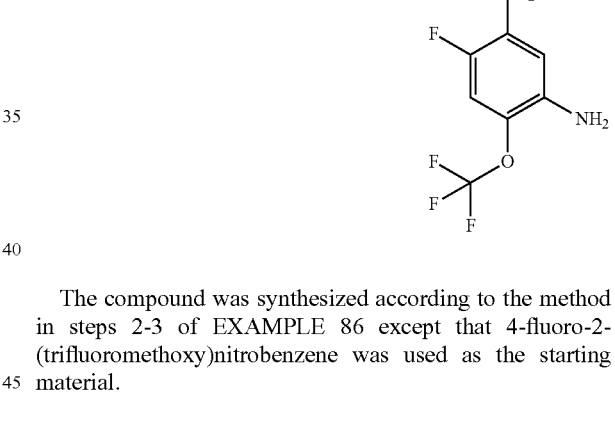

The compound was synthesized according to the method in steps 2-3 of EXAMPLE 86 except that 4-fluoro-2-(trifluoromethoxy)nitrobenzene was used as the starting material.

EXAMPLE 89

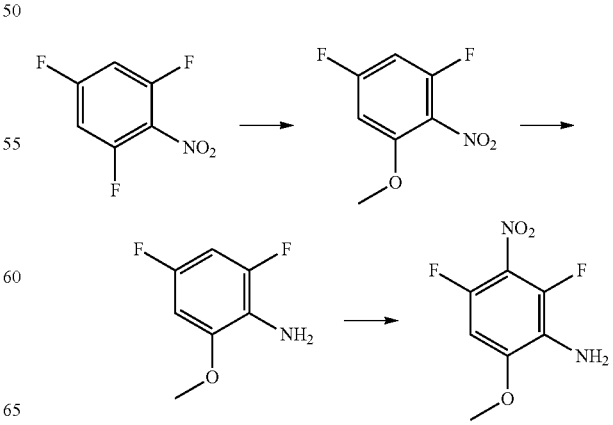

Step 1: 1,5-difluoro-3-methoxy-2-nitrobenzene

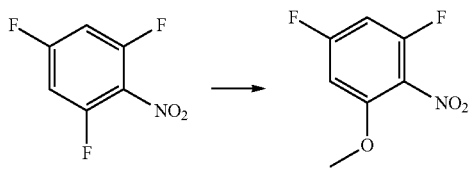

Methanol (60 mL) was added to a 100 mL single-necked bottle, cooled to 0-10° C. in an ice-water bath, sodium (2.6 g, 112.94 mmol) was added in batches, stirred to dissolve to give 2 N sodium methoxide methanol solution, which was reserved under the protection of argon.

1,3,5-trifluoro-2-nitrobenzene (10 g, 56.47 mmol) and methanol (100 mL) were added to another 250 mL dry three-necked bottle in order, stirred to dissolve, and cooled to 0-5° C. The prepared sodium methoxide methanol solution was added dropwise to the reaction mixture, after the addition completed, the mixture was reacted at the same temperature for 2-3 h. 2 N HCl was added dropwise to adjust the pH to 7, then the reaction mixture was poured into 200 mL water, extracted with ethyl acetate (100 mL×3) for three times, the organic phases were combined, washed with saturated brine (100 mL×2) twice, dried with sodium sulfate for 30 min, and filtered, the filtrate was concentrated to give a 10 g of crude product, the crude product was dissolved with petroleum ether (30 mL) and stirred at room temperature, filtered, the filtrate was concentrated under reduced pressure to give a 4 g of oily product which was purified by column chromatography with PE/EA=10/1 as eluent, the product was collected and concentrated to give 2.2 g.

Step 2: 2,4-difluoro-6-methoxyaniline

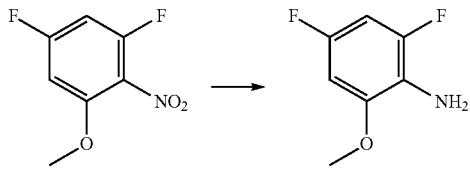

1,5-difluoro-3-methoxy-2-nitrobenzene (4.3 g, 1 eq), methanol (50 mL), ammonium acetate (3.5 g, 2 eq) and Pd/C (430 mg, 0.1 eq) were added to a 250 mL single-necked bottle in order, substitution with hydrogen for three times, the mixture was reacted at room temperature with stirring, TLC was used to monitor the reaction, when the reaction completed, filtered, the filtrate was concentrated under reduced pressure to give a crude product, the crude product was purified by column chromatography with PE/EA=20/1 as eluent, the product was collected and concentrated under reduced pressure to give 3.8 g.

Step 3: 2,4-difluoro-6-methoxy-3-nitroaniline

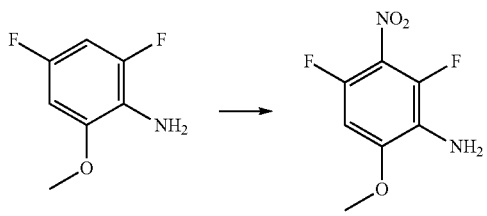

Concentrated sulfuric acid (20 mL) was added to a 100 mL three-necked bottle, cooled to about 0° C. in an ice-salt bath, 2,4-difluoro-6-methoxyaniline (3.8 g, 1 eq) was added thereinto, stirred to dissolve, and then potassium nitrate (2.42 g, 1 eq) was added in batches thereinto, reacted at the same temperature. TLC was used to monitor the reaction. When the reaction completed, the reaction mixture was poured into an ice water, the pH of the solution was adjusted to pH>7 with sodium carbonate, the solution was extracted with ethyl acetate (100 mL×2) twice, the organic phases were combined, dried with sodium sulfate for 30 min, and filtered, the filtrate was concentrated under reduced pressure to give a crude product which was purified by column chromatography with PE/EA=10/1 as eluent, the product was collected and concentrated to give 2.1 g

EXAMPLE 90

4-amino-N-(2-(dimethylamino)ethyl)-5-methoxy-N-methyl-2-nitrobenzamide

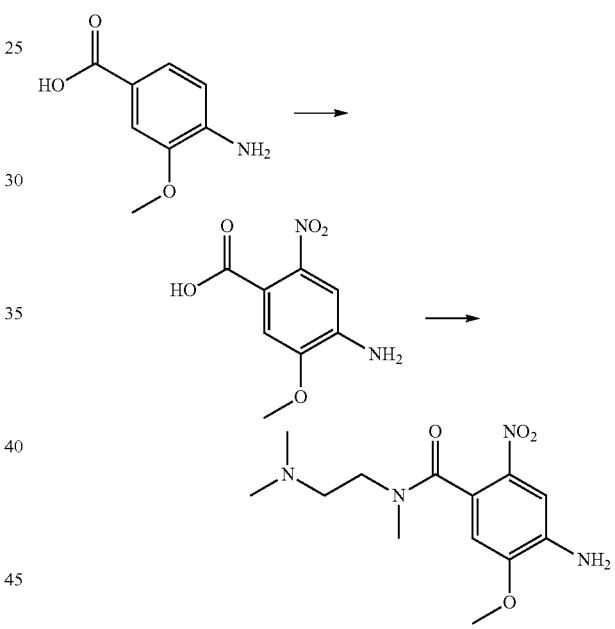

Step 1: 4-amino-5-methoxy-2-nitrobenzonic acid

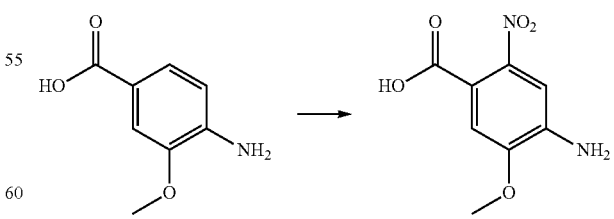

Concentrated sulfuric acid (10 mL) was added to a 100 mL three-necked bottle, cooled to 0° C. in an ice-salt bath, 4-amino-3-methoxybenzonic acid (1.1 g, 6.58 mmol) was added in batches thereinto, after the addition completed, stirred at 0° C. for 30 min. Then potassium nitrate (700 mg, 1.05 eq) was added in batches thereinto, reacted at the same temperature. TLC was used to monitor the reaction. When the reaction completed, the reaction mixture was poured into an ice water (500 mL), the pH of the solution was adjusted to 3-4 with sodium carbonate, the solution was extracted with ethyl acetate (300 mL×3) for three times, the organic phases were combined, washed with saturated brine (500 mL×2) twice, dried with sodium sulfate for 30 min, and filtered, the filtrate was concentrated under reduced pressure, precipitation with DCM (30 mL), filtered, the filter cake was dried to give a 1.1 g.

Step 2: 4-amino-N-(2-(dimethylamino)ethyl)-5-methoxy-N-methyl-2-nitrobenzamide

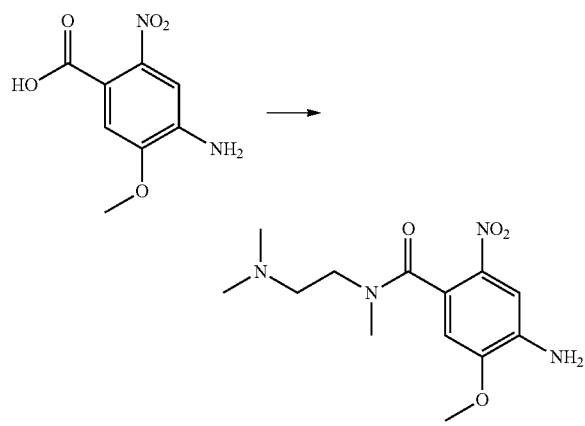

4-amino-5-methoxy-2-nitrobenzonic acid (400 mg, 1.89 mmol), DMF (20 mL), EDCI (543 mg. 1.5 eq), HOBt (384 mg, 1.5 eq), triethylamine (574 mg, 3 eq) and N1,N1,N2-trimethylethylenediamine (386 mg, 2 eq) were added to a 100 mL single-necked bottle in order, heated to 50-55° C. in an oil bath and stirred. TLC was used to monitor the reaction, when the reaction completed, the mixture was cooled to room temperature, water (100 mL) was added thereinto, extracted with ethyl acetate (50 mL×4) for four times, the organic phases were combined, washed with saturated brine (50 mL×2) twice, dried with anhydrous sodium sulfate for 30 min, and filtered, the filtrate was concentrated under reduced pressure to give a crude product which was purified by column chromatography with DCM/MeOH=10/1 as eluent, the product was collected and concentrated under reduced pressure to give 370 mg.

EXAMPLE 91

PREPARATION OF INTERMEDIATE A1

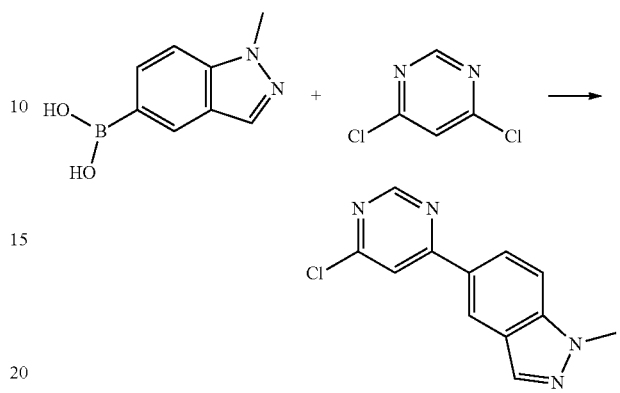

1-methylinazole-5-boric acid (300 mg, 1.70 mmol), 4,6-dichloropyrimidine (330 mg, 2.216 mmol), sodium carbonate (360 mg, 3.41 mmol) and acetonitrile/water=4/1 (15 mL) were added to a 100 mL three-necked bottle in order. Tetra(triphenylphosphine)palladium (200 mg, 0.171 mmol) was added in batches under the protection of argon, heated to 65-70° C. in an oil bath to react for about 7 h, then cooled to room temperature. Water (50 mL) and dichloromethane (50 mL) were added thereinto, stirred for 5 min, organic layer was separated, the aqueous phase was extracted with dichloromethane (30 mL×2) twice. The organic phases were combined, washed with saturated brine (50 mL×2) twice, dried with anhydrous sodium sulfate for 30 min. Filtered, the filtrate was concentrated under reduced pressure to give a crude product which was purified by column chromatography with PE/EA=6/1 as eluent. The product was collected and concentrated under reduced pressure to give the intermediate A1: 330 mg.

Examples 92-112

PREPARATION OF INTERMEDIATES A2-A22

Intermediates A2-A22 were prepared by the method of synthesizing the intermediate A1 in EXAMPLE 91 except that boric esters or boric acid compounds commercially available or prepared by EXAMPLES 70-82 and 4,6-dichloropyrimidine or 2,4-dichloropyrimidine were used as the starting materials. (Table 1)

TABLE 1

| Intermediates A2-A22 | | | |
|---|---|---|---|
| Intermediate | Starting material | Structure of Intermediates | Molecular ion peaks [M + 1]+ |
| A2 | ![structure] | ![structure] | 245.20 |

TABLE 1-continued
Intermediates A2-A22
| Intermediate | Starting material | Structure of Intermediates | Molecular ion peaks [M + 1]+ |
|---|---|---|---|
| A3 | 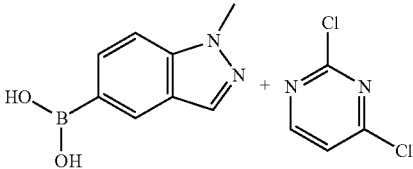 | 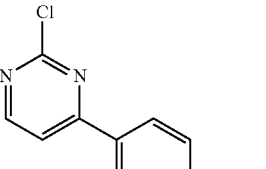 | 245.23 |
| A4 | 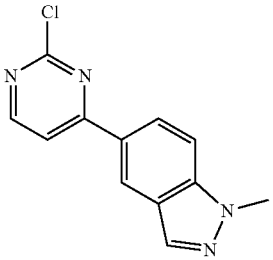 [SMILES: Cn1ncc2cc(-c3ccnc(Cl)n3)ccc21] | 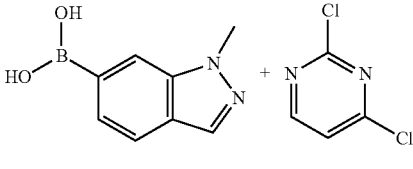 | 245.19 |
| A5 | 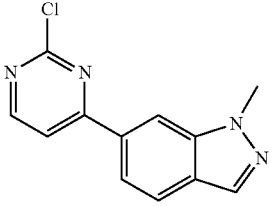 [SMILES: Cn1ncc2ccc(-c3ccnc(Cl)n3)cc21] | 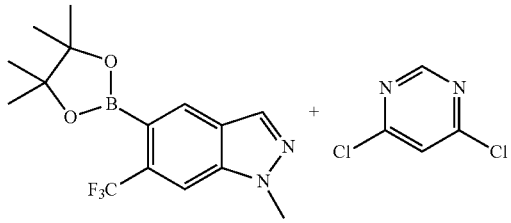 | 313.19 |
| A6 | 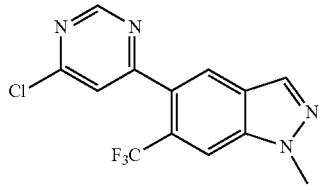 [SMILES: Cn1ncc2cc(-c3cc(Cl)ncn3)c(C(F)(F)F)cc21] | 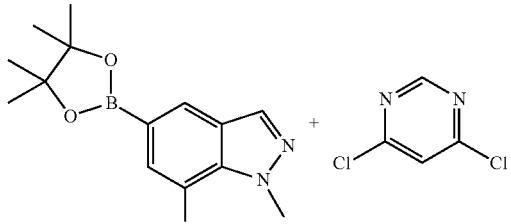 | 313.20 |
| A7 | 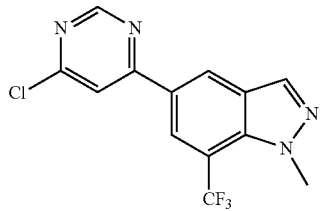 [SMILES: Cn1ncc2cc(-c3cc(Cl)ncn3)cc(C(F)(F)F)c21] | 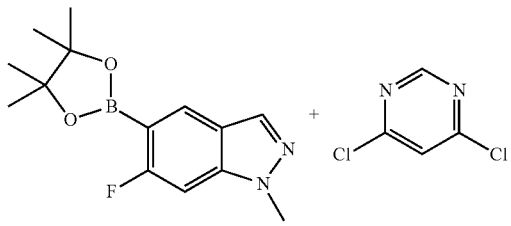 [SMILES: Cn1ncc2cc(B3OC(C)(C)C(C)(C)O3)c(F)cc21 ; Clc1cc(Cl)ncn1] | 263.17 |
| A8 | 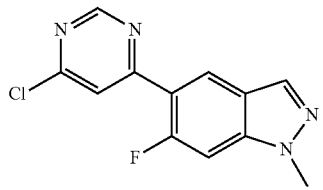 [SMILES: Cn1ncc2cc(-c3cc(Cl)ncn3)c(F)cc21] | 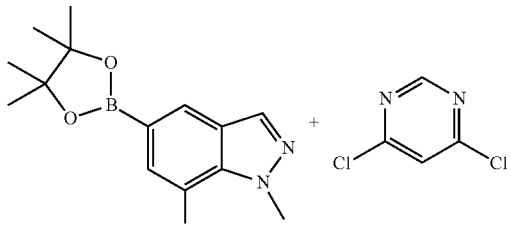 | 263.15 |

TABLE 1-continued

Intermediates A2-A22

| Intermediate | Starting material | Structure of Intermediates | Molecular ion peaks [M + 1]+ |
|---|---|---|---|
| A9 | | | 259.20 |
| A10 | | | 263.16 |
| A11 | | | 245.19 |
| A12 | | | 245.20 |
| A13 | | | 248.13 |
| A14 | | | 248.14 |

TABLE 1-continued
Intermediates A2-A22
| Intermediate | Starting material | Structure of Intermediates | Molecular ion peaks [M + 1]+ |
|---|---|---|---|
| A15 | 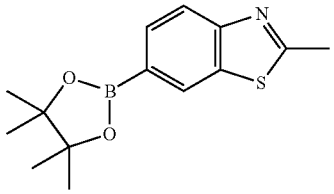 + 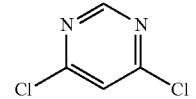 | 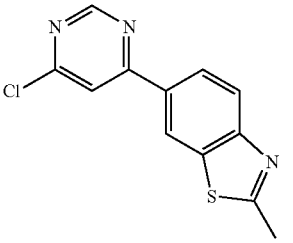 [SMILES: Cc1nc2ccc(-c3cc(Cl)ncn3)cc2s1] | 262.7 |
| A16 | 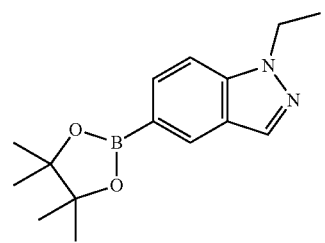 + 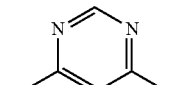 | 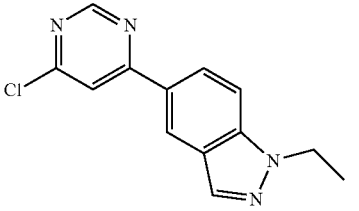 [SMILES: CCn1ncc2cc(-c3cc(Cl)ncn3)ccc21] | 259.11 |
| A17 | 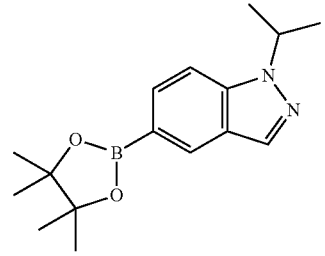 + 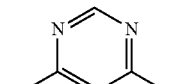 | 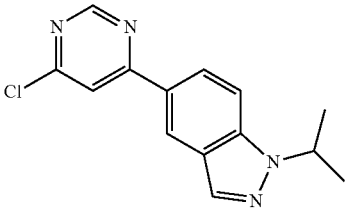 [SMILES: CC(C)n1ncc2cc(-c3cc(Cl)ncn3)ccc21] | 273.24 |
| A18 | 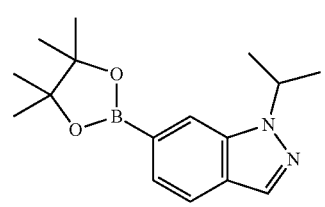 + 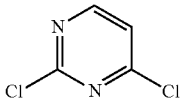 | 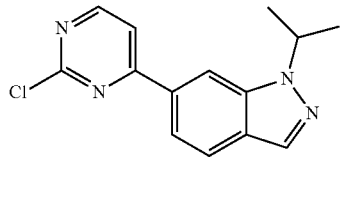 [SMILES: CC(C)n1ncc2ccc(-c3ccnc(Cl)n3)cc21] | 273.16 |
| A19 | 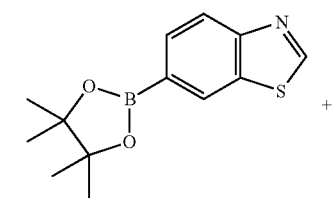 + 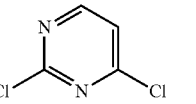 | 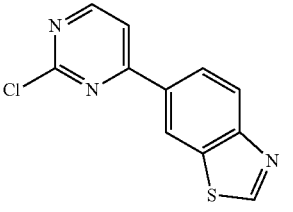 [SMILES: Clc1nccc(-c2ccc3ncsc3c2)n1] | 278.17 |
| A20 | 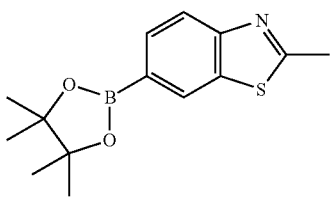 + 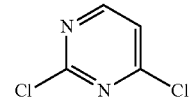 | 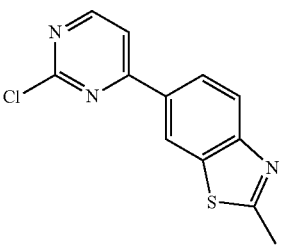 [SMILES: Cc1nc2ccc(-c3ccnc(Cl)n3)cc2s1] | 292.20 |

TABLE 1-continued
Intermediates A2-A22
| Intermediate | Starting material | Structure of Intermediates | Molecular ion peaks [M + 1]+ |
|---|---|---|---|
| A21 | 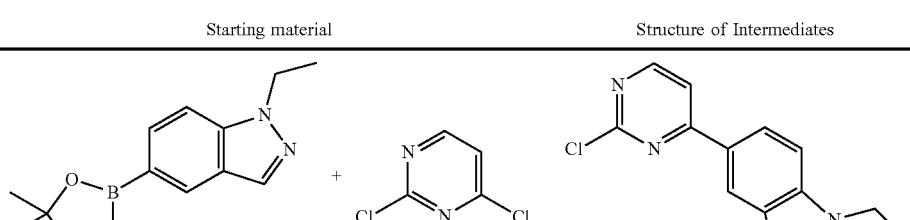 | 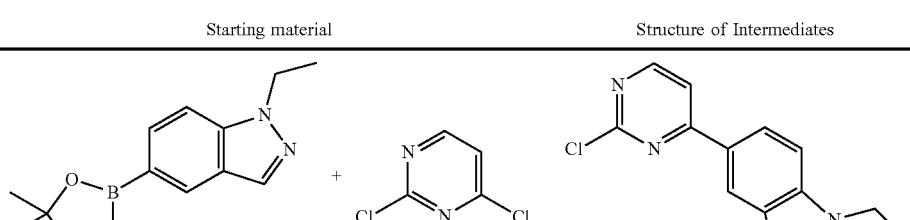 | 259.31 |
| A22 | 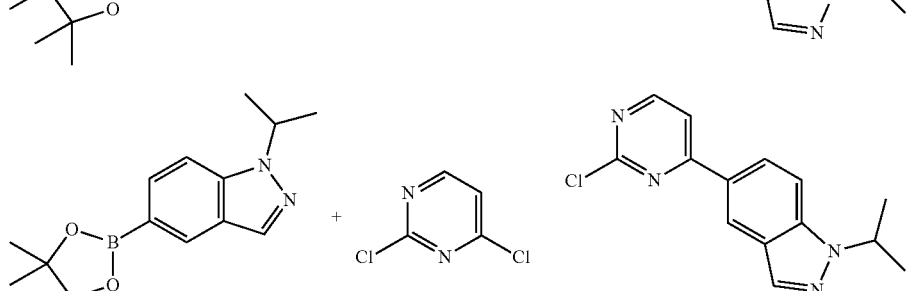 | 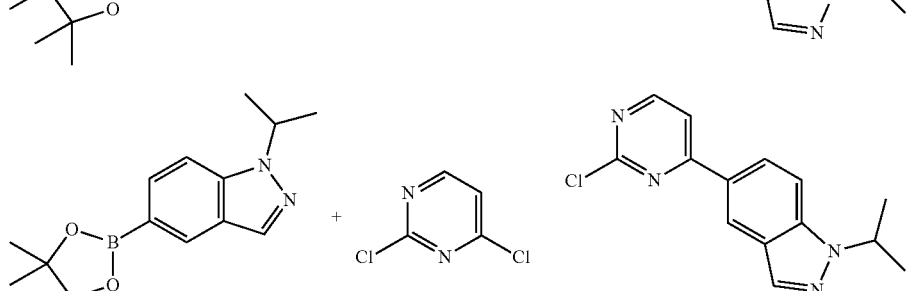 | 273.14 |
EXAMPLE 113
PREPARATION OF INTERMEDIATE B1
N-(5-amino-4-methoxy-2-(4-methylpiperazine-1-yl)phenyl)acrylamide
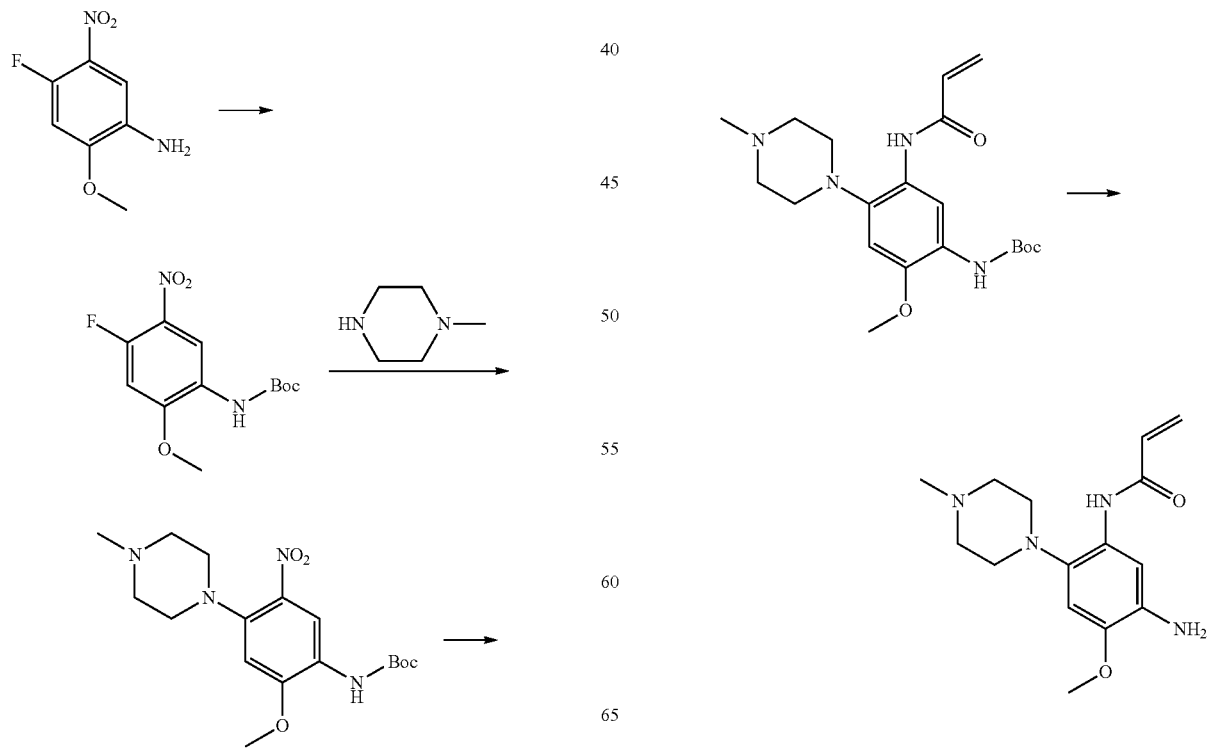

Step 1: tert-butyl (4-fluoro-2-methoxy-5-nitrophenyl)carbamate

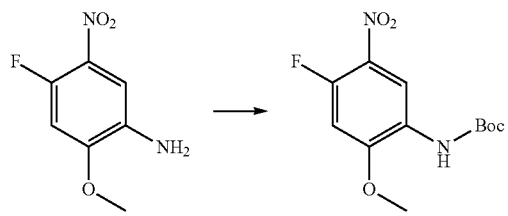 [SMILES: COc1cc(F)c([N+](=O)[O-])cc1N ; COc1cc(F)c([N+](=O)[O-])cc1NC(=O)OC(C)(C)C]

4-fluoro-2-methoxy-5-nitroaniline (3 g, 16 mmol), DCM (50 mL), pyridine (2.5 g, 32.2 mmol) and DMAP (0.19 g, 1.6 mmol) were added to a 100 mL three-necked bottle, and then (Boc)₂O (3.5 g, 0.016 mol) in DCM (10 mL) was added dropwise thereinto, after the addition completed, the mixture was reacted at 40° C., when the reaction completed, concentration under reduced pressure, then water (100 mL) and ethyl acetate (100 mL) were added, stirred and then separated the organic phase, the aqueous phase was extracted with ethyl acetate twice, the organic phases were combined, washed with water (100 mL×2) twice, dried with anhydrous sodium sulfate for 30 min, and filtered, the filtrate was concentrated under reduced pressure to give a 3.6 g of product with a yield of 78%.

Step 2: tert-butyl (2-methoxy-4-(4-methylpiperazine-1-yl)-5-nitrophenyl) carbamate

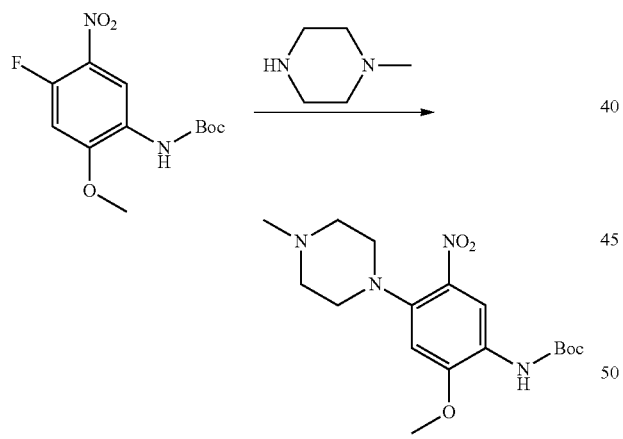

Tert-butyl (4-fluoro-2-methoxy-5-nitrophenyl)carbamate (2.1 g, 7.3 mmol), DMF (50 mL), N-methylpiperazine (808 mg, 8.06 mmol) and DIPEA (1.03 g, 8.03 mmol) were added to a 250 mL single-necked bottle in order, stirred at room temperature, when the reaction completed, saturated ammonium chloride (150 mL) and ethyl acetate (50 mL) were added thereinto, stirred and then separated organic phase, the aqueous phase was discarded, the organic phase was washed with water till the pH to neutral, then washed with saturated brine (30 mL×2) twice, dried with anhydrous sodium sulfate for 30 min, and filtered, the filtrate was concentrated under reduced pressure, and purified by column chromatography with gradient eluent of PE/EA=5/1→1/1 and DCM/MeOH=10/1, the product was collected and concentrated under reduced pressure to give 2.65 g with a yield of 98%.

Step 3: tert-butyl (5-amino-2-methoxy-4-(4-methylpiperazine-1-yl)phenyl) carbamate

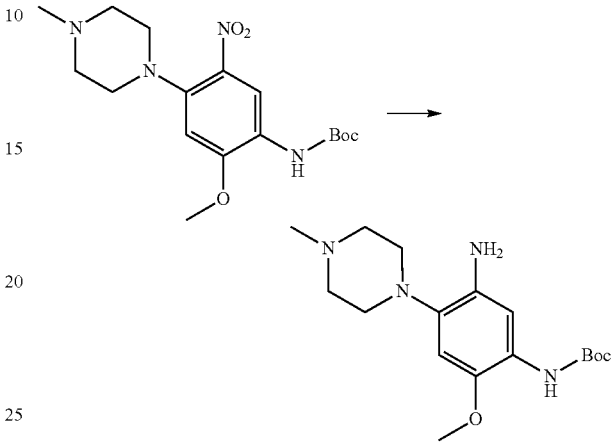

Tert-butyl (2-methoxy-4-(4-methylpiperazine-1-yl)-5-nitrophenyl) carbamate (2.65 g, 7.23 mmol), methanol (10 mL) and 10% Pd/C (265 mg) were added to a 250 mL single-necked bottle, reacted under the pressure of hydrogen at room temperature with stirring, when the reaction completed, filtered, the filtrate was concentrated under reduced pressure to give a 2.35 g of product with a yield of 96.7%.

Step 4: tert-butyl (5-acrylamido-2-methoxy-4-(4-methylpiperazine-1-yl)phenyl) carbamate

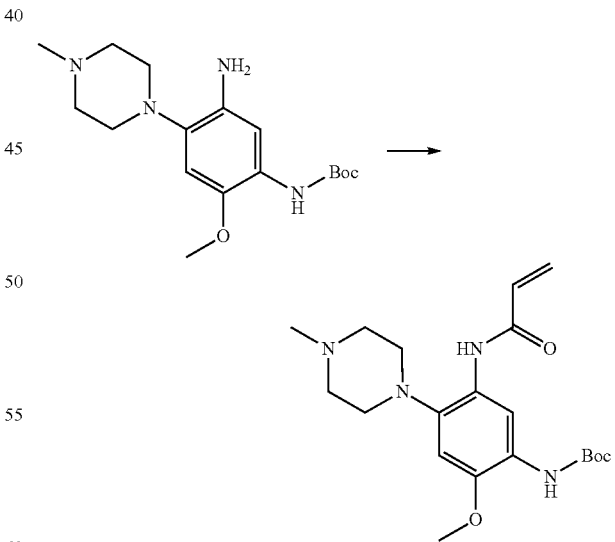

Tert-butyl (5-amino-2-methoxy-4-(4-methylpiperazine-1-yl)phenyl)carbamate (2.3 g, 6.8 mmol), and THF (20 mL) were added to a 250 mL three-necked bottle, cooled to 0° C., acryl chloride (680 mg, 7.5 mmol) was added dropwise thereinto, after the addition completed, the mixture was warmed to room temperature to react, when the reaction completed, the pH of the reaction mixture was adjusted with saturated sodium bicarbonate to neutral, then DCM (20 mL) and water (20 mL) were added, separated organic phase, the aqueous phase was discarded, the organic phase was washed with saturated brine (50 mL×2) twice, dried with anhydrous sodium sulfate for 30 min, and filtered, the filtrate was concentrated under reduced pressure to give a 2.3 g of product with a yield of 100%.

Step 5: N-(5-amino-4-methoxy-2-(4-methylpiperazine-1-yl)phenyl)acrylamide

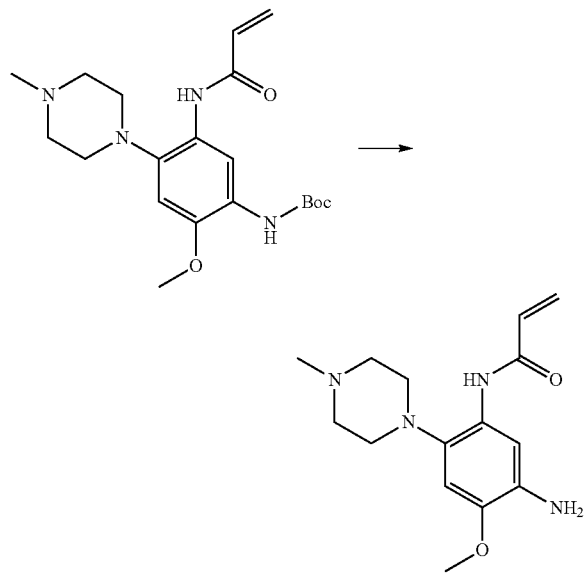

Tert-butyl (5-acrylamido-2-methoxy-4-(4-methylpiperazine-1-yl)phenyl)carbamate (1.9 g, 6.88 mmol), 4 mol/L hydrochloric acid (16 mL) and THF (30 mL) were added to a 250 mL single-necked bottle, reacted at room temperature with stirring, after the reaction completed, the pH of the reaction mixture was adjusted with saturated sodium bicarbonate to neutral, then water (20 mL) and DCM (20 mL) were added thereinto, separated organic phase, the aqueous phase was extracted with DCM (20 mL×2) twice, the organic phases were combined, washed with water (20 mL×2) twice and then with saturated brine (20 mL×2) twice, dried with anhydrous sodium sulfate for 30 min, and filtered, the filtrate was concentrated under reduced pressure to give a 472 mg of product.

EXAMPLE 114

PREPARATION OF INTERMEDIATE B2

N-(5-amino-2-((2-(dimethylamino)ethyl)(methyl)amino-4-methoxyphenyl)acrylamide

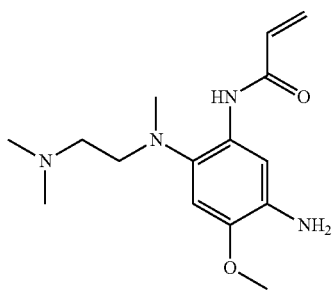 [SMILES: C=CC(=O)Nc1cc(N)c(OC)cc1N(C)CCN(C)C]

Intermediate B2 was synthesized according to the method of EXAMPLE 113 except that N-methylpiperazine was replaced with N,N,N'-trimethylethylenediamine.

EXAMPLE 115

PREPARATION OF INTERMEDIATE B3

N-(5-amino-2-(3-(dimethylamino)azetidin)-1-yl)-4-methoxyphenyl)acrylamide

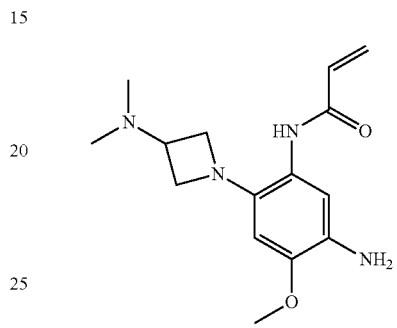

Intermediate B3 was synthesized according to the method of EXAMPLE 113 except that N-methylpiperazine was replaced with 3-(dimethylamino)azetidine hydrochloride.

EXAMPLE 116

PREPARATION OF INTERMEDIATE B4

N-(5-amino-4-methoxy-2-(1-methylpiperidine-4-yl)phenyl)acrylamide

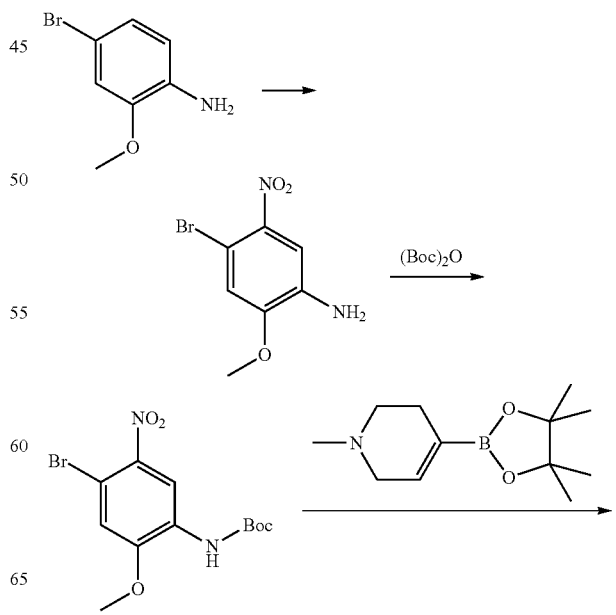

133
-continued

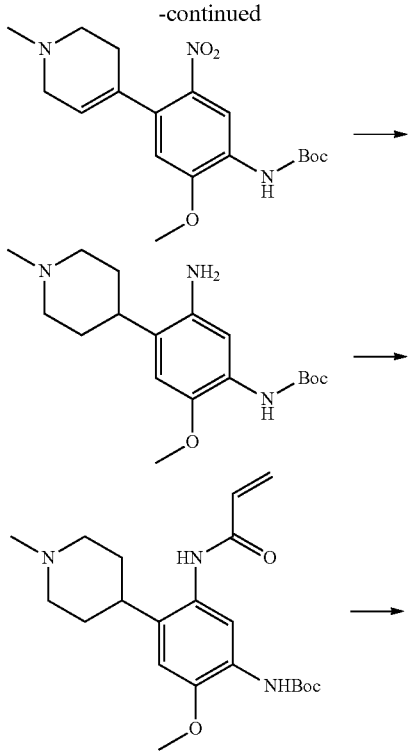

134

Step 2: tert-butyl (4-bromo-2-methoxy-5-nitrophenyl)carbamate

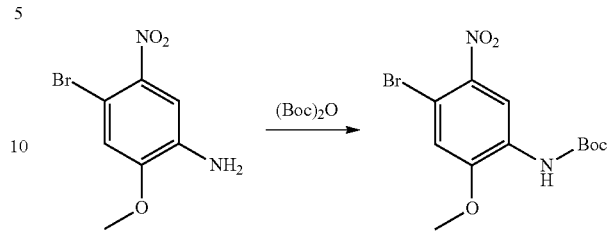

4-bromo-2-methoxy-5-nitroaniline (4.9 g, 19 mmol), dichloromethane (50 mL), triethylamine (4.0 g, 38 mmol), DMAP (243 mg, 1.9 mmol) and (Boc)₂O (5.21 g, 23 mmol) were added to a 250 mL single-necked bottle in order, reacted at 25° C. with stirring for 4 h. Water (100 mL) was added thereinto to quench the reaction, the aqueous phase was extracted with dichloromethane (100 mL×2) twice, the organic phases were combined and concentrated under reduced pressure to give a crude product. The crude product was purified by column chromatography with PE/EA=10/1 as eluent, the product was collected and concentrated to give a 1.4 g of yellow solid with a yield of 20.31%.

Step 3: tert-butyl (2-methoxy-4-(1-methyl-1,2,3,6-tetrahydropyridine-4-yl)-5-nitrophenyl)carbamate

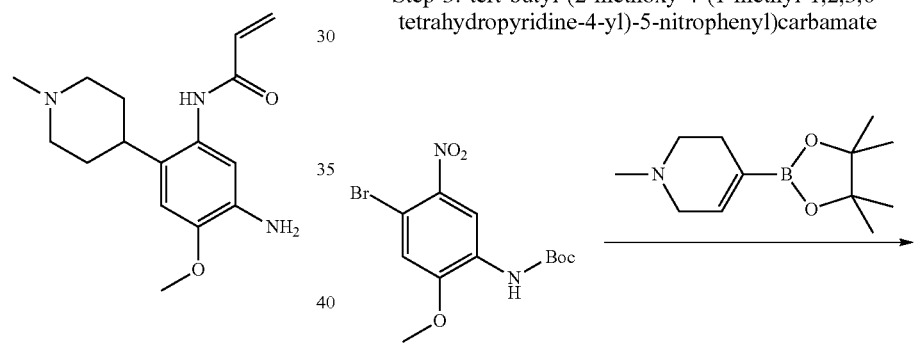

Step 1: 4-bromo-2-methoxy-5-nitroaniline

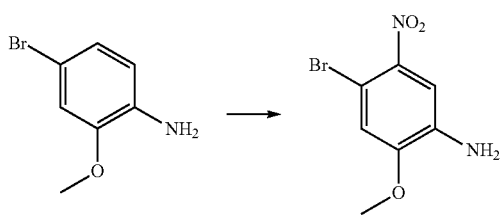

85% sulphuric acid (39 mL) and 4-bromo-2-methoxyaniline (5 g, 24.8 mmol) were added to a 100 mL single-necked bottle in order, cooled to 0-5° C., guanidine nitrate (3.2 g, 26.1 mmol) was added thereinto in batches, after the addition completed, the mixture was reacted at the same temperature for 45 min. The reaction mixture was poured into 50% aqueous sodium hydroxide solution (100 mL, pH>8), stirred at 5-10° C., and filtered, the filter cake was rinsed with 100 mL water and dried. The crude product was washed with 50 mL n-hexane and filtered, the filter cake was dried to give a 4.9 g of yellow solid with a yield of 80.19%.

Tert-butyl (4-bromo-2-methoxy-5-nitrophenyl) carbamate (450 mg, 1.44 mmol), 1-methyl-1,2,3,6-tetrahydropyridine-4-boronic acid pinacol ester (322 mg, 1.44 mmol), acetonitrile (40 mL), sodium carbonate (306 mg, 2.88 mmol), water (8 mL) and Pd(PPh₃)₄ (167 mg, 0.144 mmol) were added to a 100 mL single-necked bottle in order under the protection of argon, reacted at 80° C. with stirring for 3.5 h. The reaction mixture was cooled to room temperature, water (50 mL) was added thereinto, the aqueous phase was extracted with ethyl acetate (50 mL×2) twice, the organic phases were combined and concentrated under reduced pressure to give a crude product. The crude product was purified by column chromatography with DCM/MeOH=20/1 as eluent, the product was collected and concentrated to give a 480 mg of yellow solid with a yield of 91.5%.

Step 4: tert-butyl (5-amino-2-methoxy-4-(1-methylpiperidine-4-yl)phenyl)-carbamate

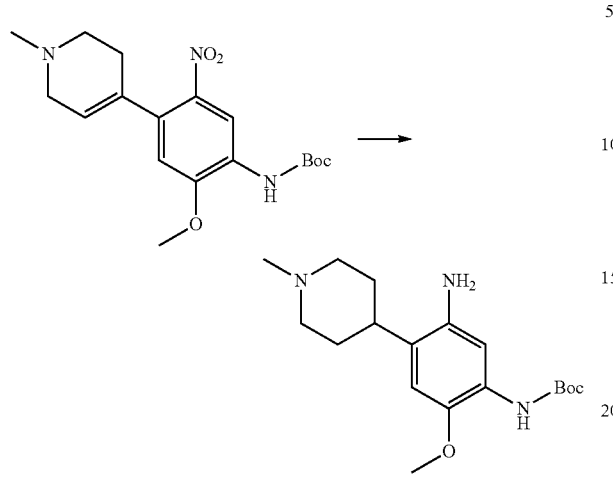

Tert-butyl (2-methoxy-4-(1-methyl-1,2,3,6-tetrahydropyridine-4-yl)-5-nitrophenyl) carbamate (480 mg, 1.32 mmol), tetrahydrofuran (20 mL) and Pd/C (50 mg) were added to a 100 mL single-necked bottle in order. The mixture was reacted under the pressure of hydrogen at room temperature with stirring for 12-14 h. Filtered, the filtrate was concentrated to give a 340 mg of pale yellow oil with a yield of 76.8%.

Step 5: tert butyl (5-acryloylamino-2-methoxy-4-(1-methylpiperidine-4-yl)phenyl) carbamate

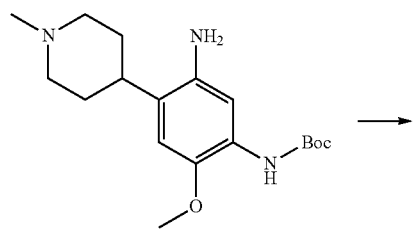

The compound was synthesized according to the method in the step 4 of EXAMPLE 113 except that tert-butyl (5-amino-2-methoxy-4-(1-methylpiperidine-4-yl)phenyl) carbamate was used as the starting material.

Step 6: N-(5-amino-4-methoxy-2-(1-methylpiperidine-4-yl)phenyl)acrylamide

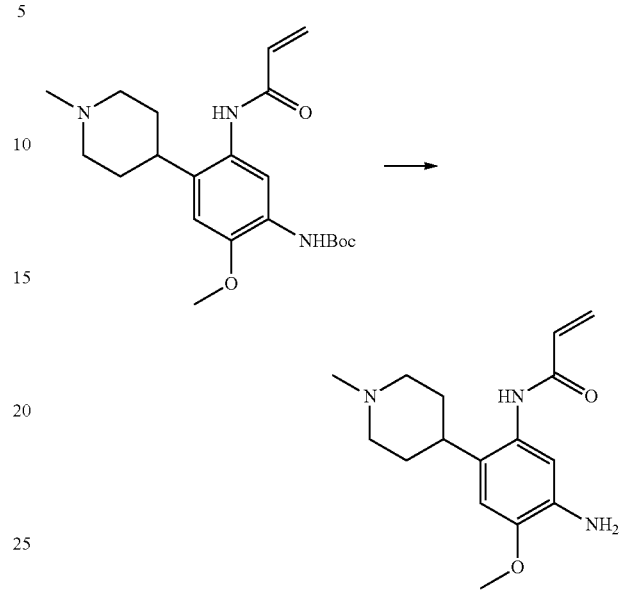

Tert butyl (5-acryloylamino-2-methoxy-4-(1-methylpiperidine-4-yl)phenyl) carbamate (300 mg, 0.77 mmol) and dichloromethane (20 mL) were added to a 100 mL single-necked bottle in order, then trifluoroacetic acid (4 mL) was added dropwise.

After the addition completed, the mixture was reacted at room temperature for 30 min. Saturated sodium bicarbonate (50 mL) was added to the reaction mixture, then separated organic phase, the aqueous phase was extracted with dichloromethane (50 mL×2) twice, the organic phases were combined and concentrated to give a 170 mg of pale gray solid with a yield of 76.6%.

EXAMPLE 117

PREPARATION OF INTERMEDIATE B5

N-(5-amino-4-methoxy-2-(1-methylpiperazine-1-carbonyl)phenyl)acrylamide

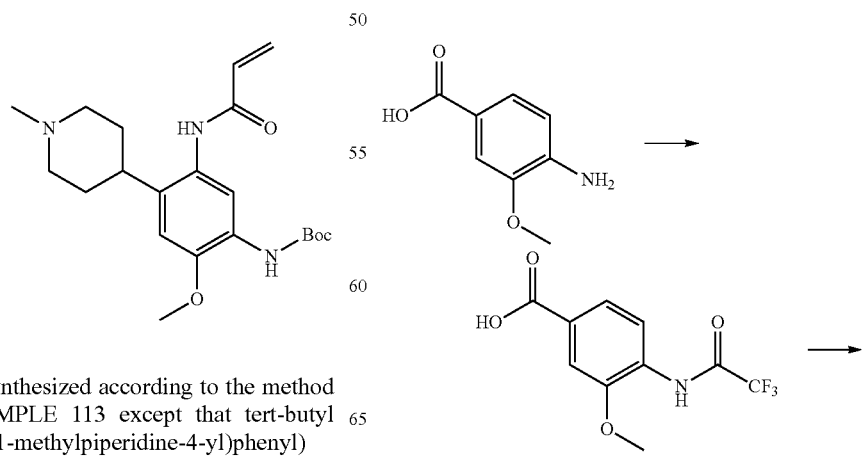

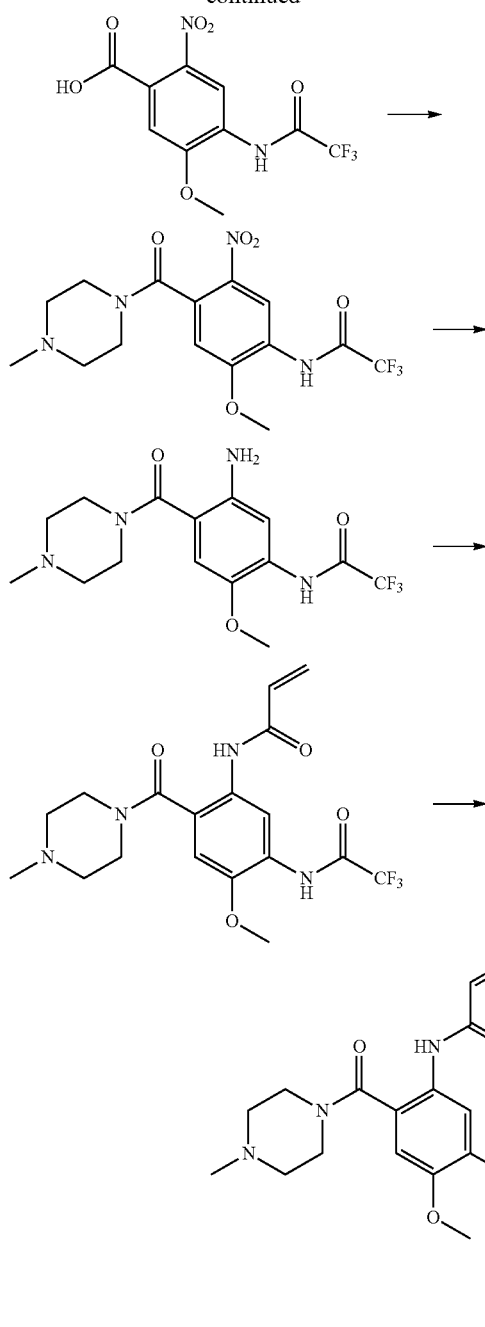

Step 1:
3-methoxy-4-(2,2,2-trifluoroacetamido)benzoic acid

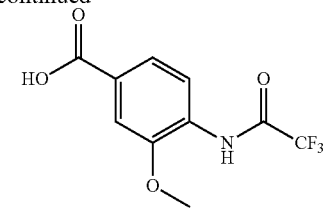

4-amino-3-methoxybenzoic acid (5 g, 29.9 mmol) and ethyl acetate (200 mL) were added to a 500 mL three-necked bottle, cooled to 0° C. in an ice-salt bath, then TFAA (5 mL) in ethyl acetate (5 mL) was added dropwise. The mixture was reacted with stirring at the same temperature for 2 h, then warmed to room temperature and continued to stir for 2 h. Water (200 mL) was added thereinto and separated organic phase, the aqueous phase was extracted with ethyl acetate (50 mL×2) twice, the organic phases were combined, washed with saturated brine (100 mL×2) twice, dried with anhydrous sodium sulfate for 30 min, and filtered under reduced pressure, the filtrate was concentrated under reduced pressure to give a 7.8 g of product.

Step 2: 5-methoxy-2-nitro-4-(2,2,2-trifluoroacetamido)benzoic acid

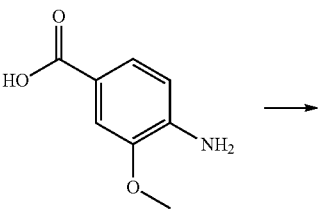

3-methoxy-4-(2,2,2-trifluoroacetamido)benzoic acid (1 g, 3.8 mmol) and concentrated sulfuric acid (10 mL) were added to a 100 mL three-necked bottle, cooled to 0° C. in an ice-salt bath, then potassium nitrate (840 mg, 5.7 mmol) was added in batches, reacted with at 0° C. with stirring for 1 h. The reaction mixture was added dropwise slowly to a 100 mL ice water, then 100 mL ethyl acetate was added thereinto, Separated organic phase, the aqueous phase was extracted with ethyl acetate (50 mL×2) twice, the organic phases were combined, washed with saturated brine (50 mL×2) twice, dried with anhydrous sodium sulfate for 30 min, and filtered under reduced pressure, the filtrate was concentrated under reduced pressure to give a 500 mg of product.

Step 3: 2,2,2-trifluoro-N-(2-methoxy-4-(4-methylpiperazine-1-carbonyl)-5-nitrophenyl)acetamide

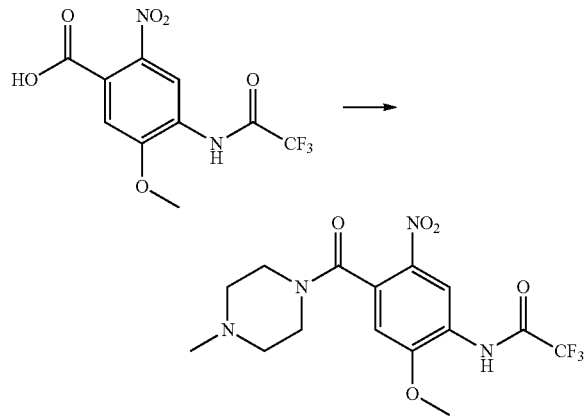

5-methoxy-2-nitro-4-(2,2,2-trifluoroacetamido)benzoic acid (500 mg, 1.622 mmol), dichloromethane (30 mL), N-methylpiperazine (325 mg, 3.245 mmol), EDCI (436 mg, 2.271 mmol), HOBt (313 mg, 2.044 mmol) and trimethylamine (656 mg, 6.49 mmol) were added to a 100 mL three-necked bottle, stirred at room temperature for about 2 h, the pH of the reaction mixture was adjusted to neutral, extracted with ethyl acetate (30 mL×3) for three times. The organic phases were combined, washed with saturated brine (50 mL×2) twice, dried with anhydrous sodium sulfate for 30 min. Filtration under reduced pressure was carried out, the filtrate was concentrated under reduced pressure to give a 250 mg of brown yellow oily product.

Step 4: N-(5-amino-2-methoxy-4-(4-methylpiperazine-1-carbonyl)phenyl)-2,2,2-trifluoroacetamide

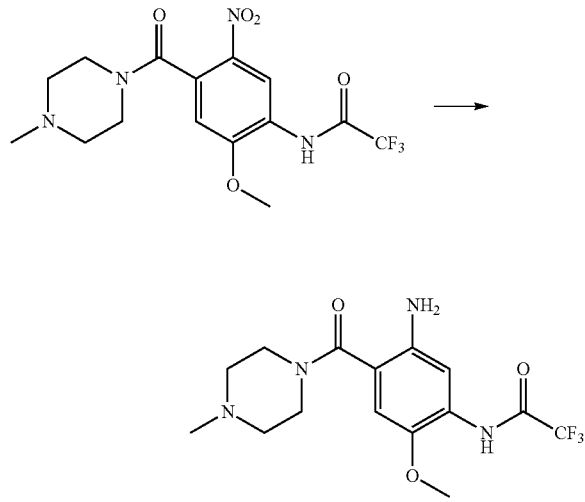

The compound was synthesized according to the method in the step 3 of EXAMPLE 113 except that 2,2,2-trifluoro-N-(2-methoxy-4-(4-methylpiperazine-1-carbonyl)-5-nitrophenyl)acetamide was used as the starting material.

Step 5: N-(4-methoxy-2-(4-methylpiperazine-1-carbonyl)-5-(2,2,2-trifluoro-acetamido)phenyl)acrylamide

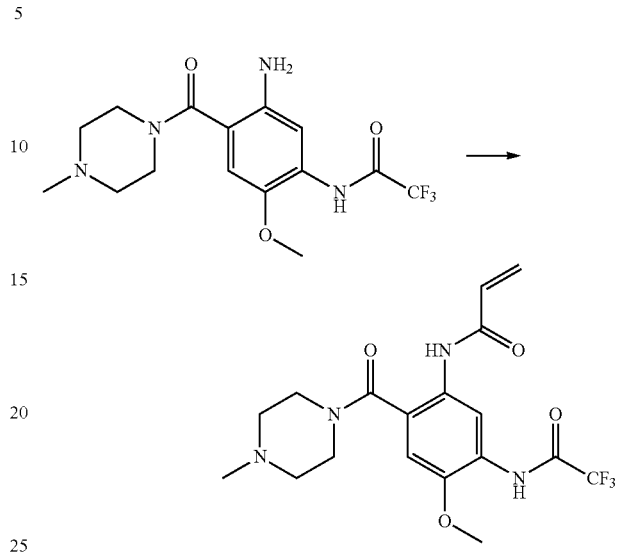

The compound was synthesized according to the method in the step 4 of EXAMPLE 113 except that N-(5-amino-2-methoxy-4-(4-methylpiperazine-1-carbonyl)-2,2,2-trifluoroacetamide was used as the starting material.

Step 6: N-(5-amino-4-methoxy-2-(1-methylpiperazine-1-carbonyl)phenyl) acrylamide

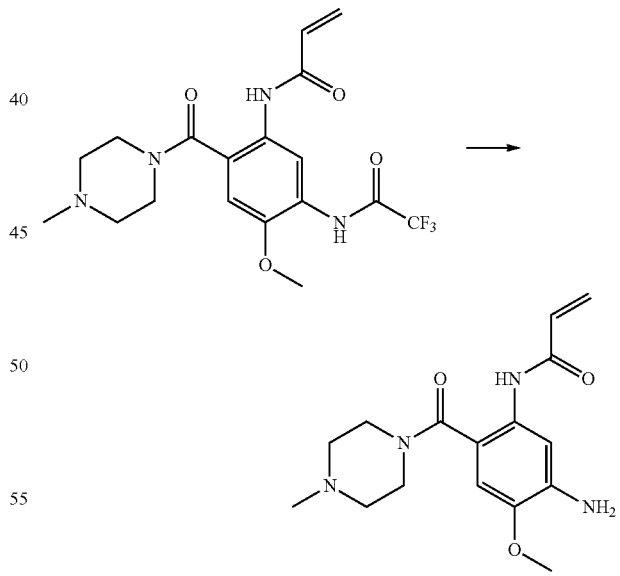

N-(4-methoxy-2-(4-methylpiperazine-1-carbonyl)-5-(2,2,2-trifluoroacetamido)phenyl)acrylamide (410 mg, 0.99 mmol), acetonitrile (30 mL) and aqueous potassium carbonate (683 mg, 4.95 mmol) solution (30 mL) were added to a 250 mL single-necked bottle, stirred at room temperature overnight. After the reaction completed, 30 mL water and 50 mL dichloromethane were added thereinto to separate organic phase, the aqueous phase was extracted with dichloromethane (30 mL×2) twice, the organic phases were combined, washed with saturated brine (30 mL×2) twice, dried with anhydrous sodium sulfate for 30 min, and filtered under reduced pressure, the filtrate was concentrated under reduced pressure to give a 290 mg of product.

EXAMPLE 118

PREPARATION OF INTERMEDIATE B6

N-(3-amino-6-((2-(dimethylamino)ethyl)(methyl)amino)-2-fluoro-4-methoxyphen yl)acrylamide

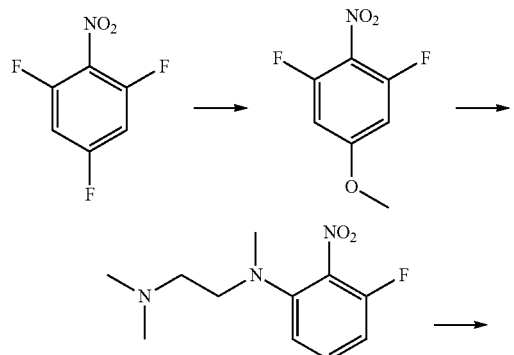

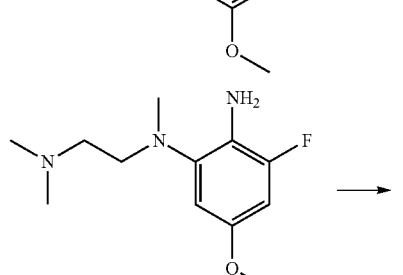

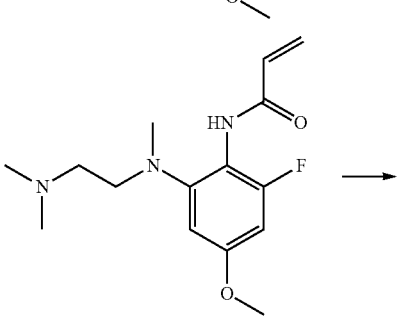

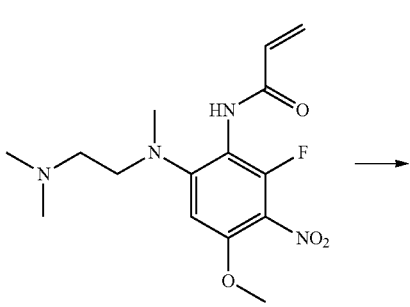

Step 1: 1,3-difluoro-5-methoxy-2-nitrobenzene

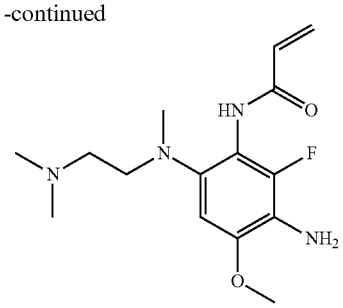

The compound was synthesized according to the method in the step 1 of EXAMPLE 89 except that 1,3,5-trifluoro-2-nitrobenzene was used as the starting material.

Step 2: N1-(3-fluoro-5-methoxy-2-nitrophenyl)-N1,N2,N2-trimethylethane-1,2-diamine

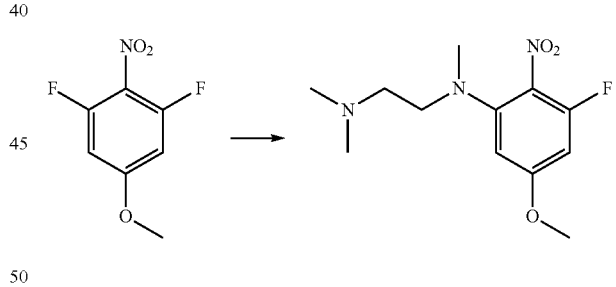

1,3-difluoro-5-methoxy-2-nitrobenzene (1.27 g, 6.72 mmol) and DMF (50 mL) were added to a 100 mL three-necked bottle in order, stirred to dissolve, then DIPEA (1.13 g, 1.3 eq) and N,N,N'-trimethylethylenediamine (686 mg, 1 eq) were added thereinto, heated to 50-55° C. in an oil bath to reflux for 4-5 h. The reaction mixture was cooled to room temperature, and then poured into a 150 mL water, extracted with ethyl acetate (100 mL, 50 mL, 50 mL) for three times, the organic phases were combined, washed with saturated sodium chloride solution (50 mL×2) twice, dried with anhydrous sodium sulfate for 30 min, and filtered, the filtrate was concentrated under reduced pressure to give a 1.8 g of oily crude product.

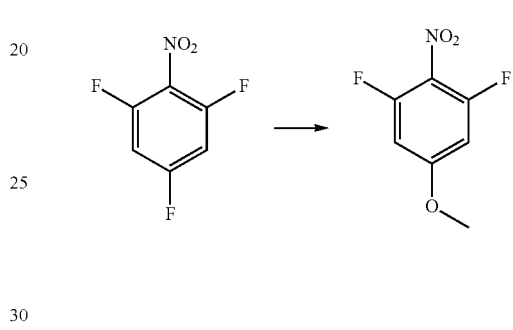

Step 3: N1-(2-(dimethylamino)ethyl)-3-fluoro-5-methoxy-N1-methylbenzene-1,2-diamine

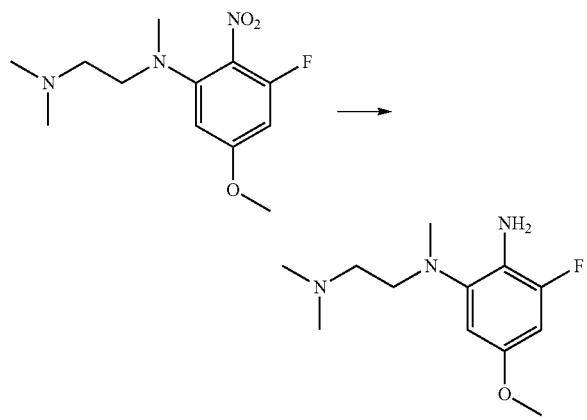

N1-(3-fluoro-5-methoxy-2-nitrophenyl)-N1,N2,N2-trimethylethane-1,2-diamine (1.8 g, 6.63 mmol) and methanol (36 mL) were added to a 100 mL single-necked bottle in order, stirred to dissolve, then 180 mg Pd/C was added thereinto, the mixture was stirred at room temperature for 5-6 h under the pressure of hydrogen. Pd/C was removed through filtration, the filtrate was concentrated under reduced pressure to give a 1.7 g of product.

Step 4: N-(2-((2-(dimethylamino)ethyl)(methyl)amino)-6-fluoro-4-methoxyphenyl) acrylamide

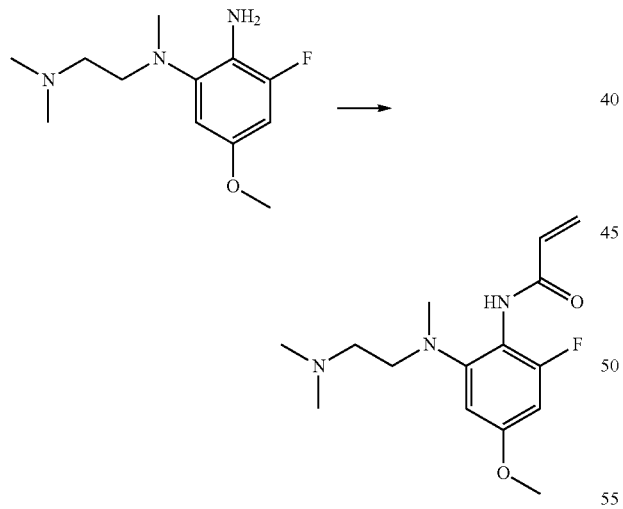

N1-(2-(dimethylamino)ethyl)-3-fluoro-5-methoxy-N1-methylbenzene-1,2-diamine (920 mg, 3.81 mmol) and dry THF (20 mL) were added to a 100 mL three-necked bottle, stirred to dissolve. The reaction mixture was cooled to 0-5° C. Acrylamide (379 mg, 1.1 eq) in THF (1 mL) was added thereinto dropwise, after the addition completed, the mixture was reacted at the same temperature for 30 min. The reaction mixture was poured into a 100 mL saturated sodium bicarbonate solution, extracted with DCM (50 mL×3) for three times, the organic phases were combined, dried with anhydrous sodium sulfate for 30 min, and filtered, the filtrate was concentrated under reduced pressure to give a crude product which was purified by column chromatography with gradient eluent of DCM/MeOH=20/1→10/1, the product was collected and concentrated under reduced pressure to give a 596 mg of gray solid.

Step 5: N-(6-((2-(dimethylamino)ethyl)(methyl)amino)-2-fluoro-4-methoxy-3-nitrophenyl)acrylamide

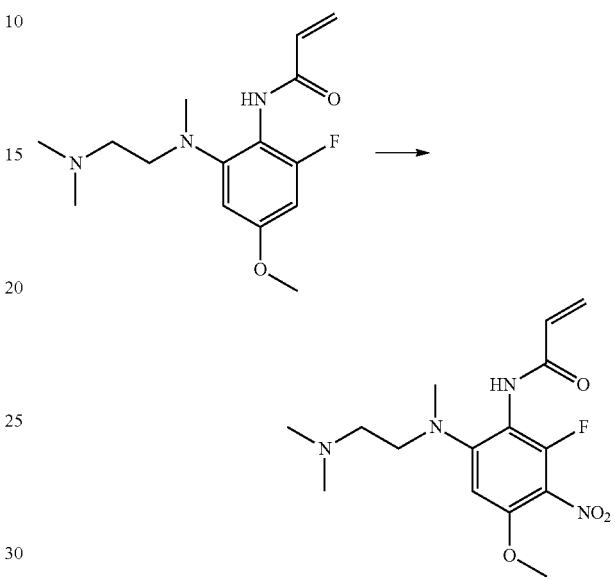

N-(2-((2-(dimethylamino)ethyl)(methyl)amino)-6-fluoro-4-methoxyphenyl) acrylamide (519 mg, 1.76 mmol) and concentrated sulfuric acid (10 mL) were added to a 100 mL three-necked bottle, stirred to dissolve, and cooled to 0-5° C. Potassium nitrate (195 mg, 1.93 mmol) was slowly added in batches into the reaction mixture, after the addition completed, the mixture was reacted at the same temperature with stirring for 30 min, then warmed to room temperature and stirred for 1-2 h. The reaction mixture was slowly added dropwise to 200 mL ice water for quenching, the pH was adjusted to neutral with sodium carbonate, extracted with ethyl acetate (100 mL×3) for three times, the organic phases were combined, dried with anhydrous sodium sulfate for 30 min, and filtered, the filtrate was concentrated under reduced pressure to give a crude product. The crude product was purified by column chromatography, the product was collected to give a 137 mg of product.

Step 6: N-(3-amino-6-((2-(dimethylamino)ethyl)(methyl)amino)-2-fluoro-4-methoxyphenyl)acrylamide

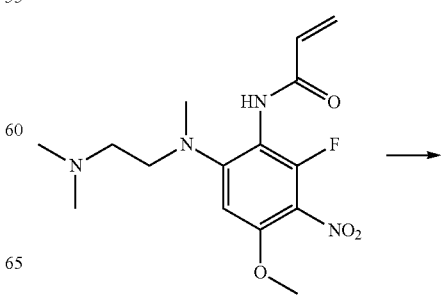

-continued

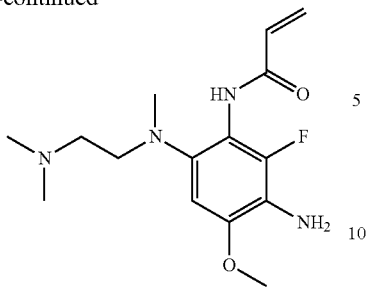

N-(6-((2-(dimethylamino)ethyl)(methyl)amino)-2-fluoro-4-methoxy-3-nitrophenyl)acrylamide (137 mg, 0.4 mmol), Fe (135 mg, 6 eq), ammonium chloride (127 mg, 6 eq), anhydrous ethanol (8 mL) and water (2 mL) were added to a 100 mL three-necked bottle in order, heated to 90-100° C. in an oil bath to react for 2-3 h. The mixture was cooled to room temperature, and the reaction mixture was poured into 30 mL water, extracted with ethyl acetate (30 mL×3) for three times, the organic phases were combined, dried with anhydrous sodium sulfate for 30 min, and filtered, the filtrate was concentrated under reduced pressure to give a crude product which was accordingly purified by column chromatography with DCM/MeOH=5/1 as eluent, the product was collected and concentrated under reduced pressure to give 90 mg.

EXAMPLE 119

PREPARATION OF INTERMEDIATE C1

N-(4-fluoro-2-methoxy-5-nitrophenyl)-6-(1-methyl-1H-indol-5yl)pyrimidine-4-amine

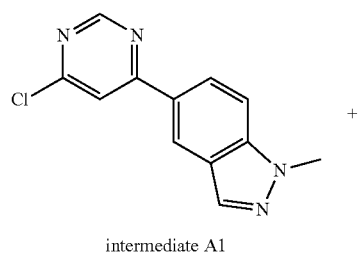

intermediate A1

+

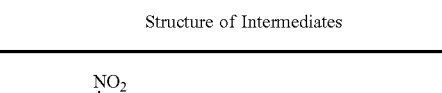

intermediate C1

4-fluoro-2-methoxy-5-nitroaniline (2 g, 10.75 mmol), intermediate A1 (2.38 g, 9.77 mmol), 1,4-dioxane (100 mL) and methanesulfonic acid (2.82 g, 29.32 mmol) were added to a 250 mL single-necked bottle in order. The mixture was heated to reflux in an oil bath, stirred for about 4 h, and then cooled naturally to room temperature. The reaction mixture was stirred at room temperature for 30 min and filtered, the residue was rinsed with petroleum ether and dried at 40-45° C. for 2-3 h to give a 3.8 g of yellow solid.

Examples 120-149

PREPARATION OF INTERMEDIATES C2-C31

Intermediates C2-C31 were prepared by the method of synthesizing the intermediate C1 except that the intermediates A and substituted nitroanilines were used as the starting materials. (Table 2)

TABLE 2

Intermediates C2-C31

| EXAMPLE | Intermediate | Starting material | Structure of Intermediates | Molecular ion peak [M + 1]+ |
|---|---|---|---|---|
| 120 | Intermediate C2 | A2 | (structure shown) | 395.19 |

147
148
TABLE 2-continued
Intermediates C2-C31
| EXAMPLE | Intermediate | Starting material | Structure of Intermediates | Molecular ion peak [M + 1]+ |
|---|---|---|---|---|
| 121 | Intermediate C3 | A3 | 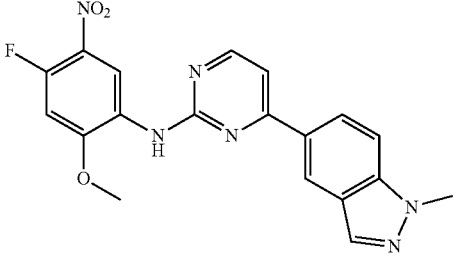 [SMILES: COc1cc(F)c([N+](=O)[O-])cc1Nc1nccc(-c2ccc3c(cnn3C)c2)n1] | 395.13 |
| 122 | Intermediate C4 | A4 | 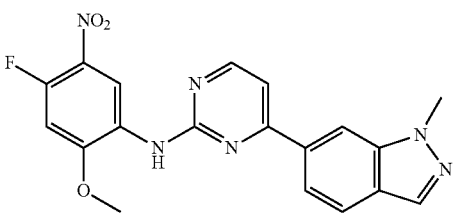 [SMILES: COc1cc(F)c([N+](=O)[O-])cc1Nc1nccc(-c2ccc3cnn(C)c3c2)n1] | 395.19 |
| 123 | Intermediate C5 | A9 | 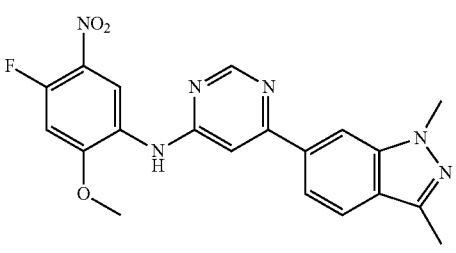 [SMILES: COc1cc(F)c([N+](=O)[O-])cc1Nc1cc(-c2ccc3c(C)nn(C)c3c2)ncn1] | 409.15 |
| 124 | Intermediate C6 | A10 | 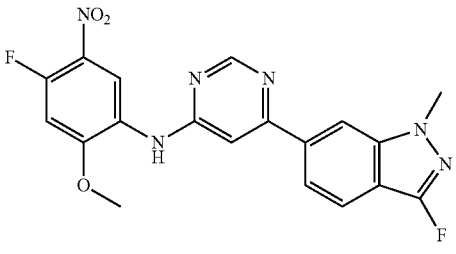 [SMILES: COc1cc(F)c([N+](=O)[O-])cc1Nc1cc(-c2ccc3c(F)nn(C)c3c2)ncn1] | 413.12 |
| 125 | Intermediate C7 | A12 | 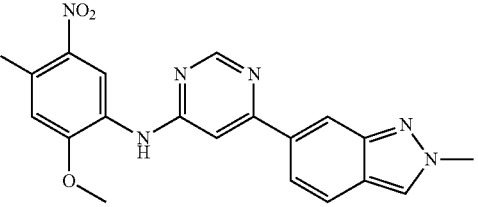 | 395.12 |
| 126 | Intermediate C8 | A14 | 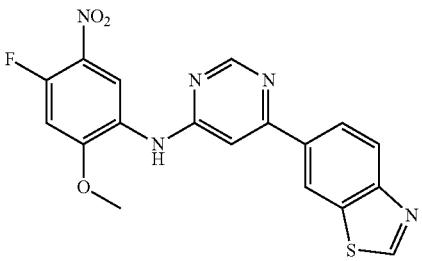 [SMILES: COc1cc(F)c([N+](=O)[O-])cc1Nc1cc(-c2ccc3ncsc3c2)ncn1] | 428.15 |

TABLE 2-continued
| | | Intermediates C2-C31 | | |
|---|---|---|---|---|
| EXAMPLE | Intermediate | Starting material | Structure of Intermediates | Molecular ion peak [M + 1]+ |
| 127 | Intermediate C9 | A15 | 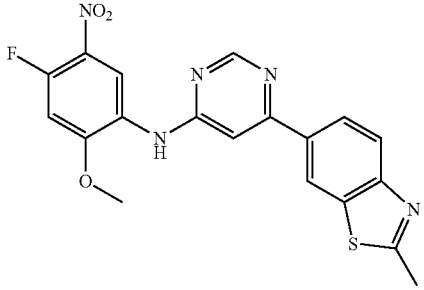 [SMILES: COc1cc(F)c([N+](=O)[O-])cc1Nc1cc(-c2ccc3nc(C)sc3c2)ncn1] | 442.18 |
| 128 | Intermediate C10 | A1 | 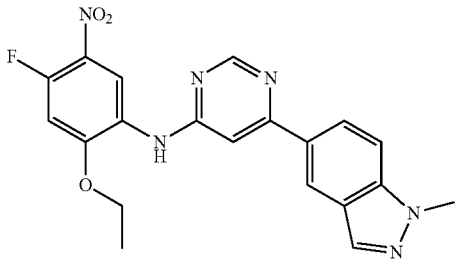 [SMILES: CCOc1cc(F)c([N+](=O)[O-])cc1Nc1cc(-c2ccc3c(cnn3C)c2)ncn1] | 409.19 |
| 129 | Intermediate C11 | A1 | 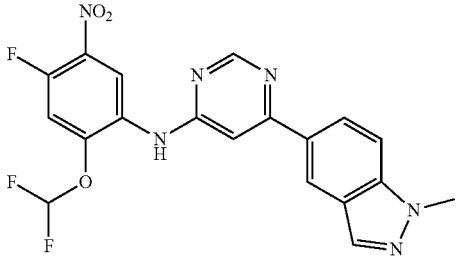 [SMILES: Cn1ncc2cc(-c3cc(Nc4cc([N+](=O)[O-])c(F)cc4OC(F)F)ncn3)ccc21] | 431.25 |
| 130 | Intermediate C12 | A7 | 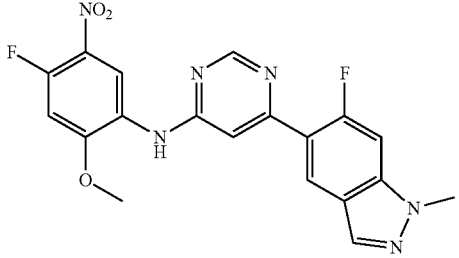 [SMILES: COc1cc(F)c([N+](=O)[O-])cc1Nc1cc(-c2cc3cnn(C)c3cc2F)ncn1] | 413.06 |
| 131 | Intermediate C13 | A20 | 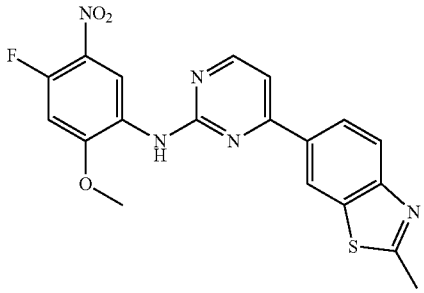 [SMILES: COc1cc(F)c([N+](=O)[O-])cc1Nc1nccc(-c2ccc3nc(C)sc3c2)n1] | 412.11 |

TABLE 2-continued

Intermediates C2-C31

| EXAMPLE | Intermediate | Starting material | Structure of Intermediates | Molecular ion peak [M + 1]+ |
|---|---|---|---|---|
| 132 | Intermediate C14 | A1 | | 449.34 |
| 133 | Intermediate C15 | A4 | | 431.15 |
| 134 | Intermediate C16 | A1 | | 413.06 |
| 135 | Intermediate C17 | A2 | | 413.22 |
| 136 | Intermediate C18 | A4 | | 413.06 |
| 137 | Intermediate C19 | A17 | | 423.02 |

TABLE 2-continued
Intermediates C2-C31
| EXAMPLE | Intermediate | Starting material | Structure of Intermediates | Molecular ion peak [M + 1]+ |
|---|---|---|---|---|
| 138 | Intermediate C20 | A16 | 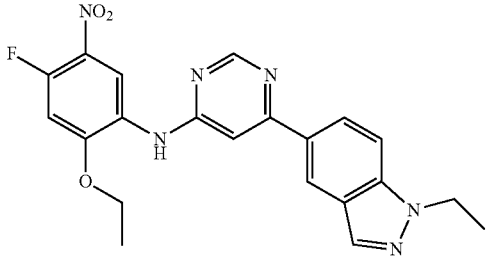 [SMILES: CCOc1cc(F)c([N+](=O)[O-])cc1Nc1cc(-c2ccc3c(cnn3CC)c2)ncn1] | 423.15 |
| 139 | Intermediate C21 | A22 | 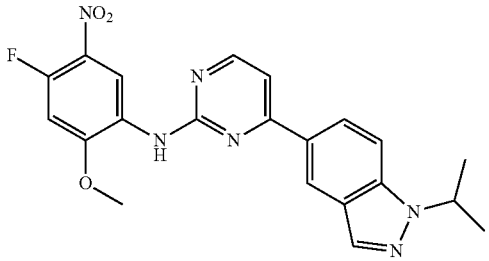 [SMILES: COc1cc(F)c([N+](=O)[O-])cc1Nc1nccc(-c2ccc3c(cnn3C(C)C)c2)n1] | 423.07 |
| 140 | Intermediate C22 | A21 | 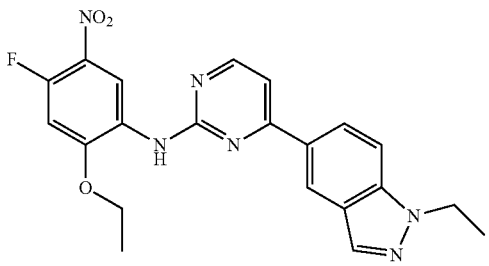 [SMILES: CCOc1cc(F)c([N+](=O)[O-])cc1Nc1nccc(-c2ccc3c(cnn3CC)c2)n1] | 423.19 |
| 141 | Intermediate C23 | A19 | 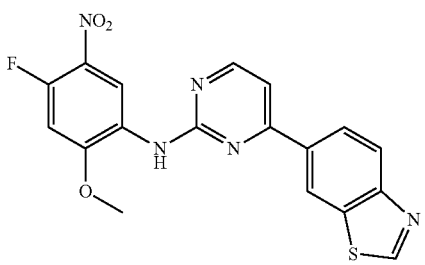 [SMILES: COc1cc(F)c([N+](=O)[O-])cc1Nc1nccc(-c2ccc3ncsc3c2)n1] | 428.25 |
| 142 | Intermediate C24 | A1 | 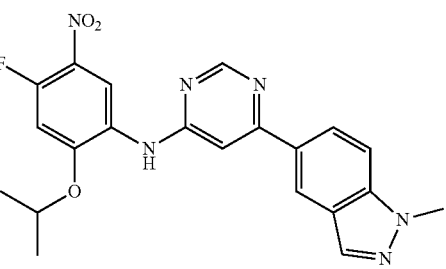 | 423.22 |

TABLE 2-continued

Intermediates C2-C31

| EXAMPLE | Intermediate | Starting material | Structure of Intermediates | Molecular ion peak [M + 1]+ |
|---------|--------------|-------------------|----------------------------|------------------------------|
| 143 | Intermediate C25 | A16 | | 445.07 |
| 144 | Intermediate C26 | A16 | | 409.10 |
| 145 | Intermediate C27 | A3 | | 431.35 |
| 146 | Intermediate C28 | A2 | | 431.18 |
| 147 | Intermediate C29 | A21 | | 409.20 |

TABLE 2-continued

Intermediates C2-C31

| EXAMPLE | Intermediate | Starting material | Structure of Intermediates | Molecular ion peak [M + 1]+ |
|---|---|---|---|---|
| 148 | Intermediate C30 | A3 | | 409.24 |
| 149 | Intermediate C31 | A3 | | 413.16 |

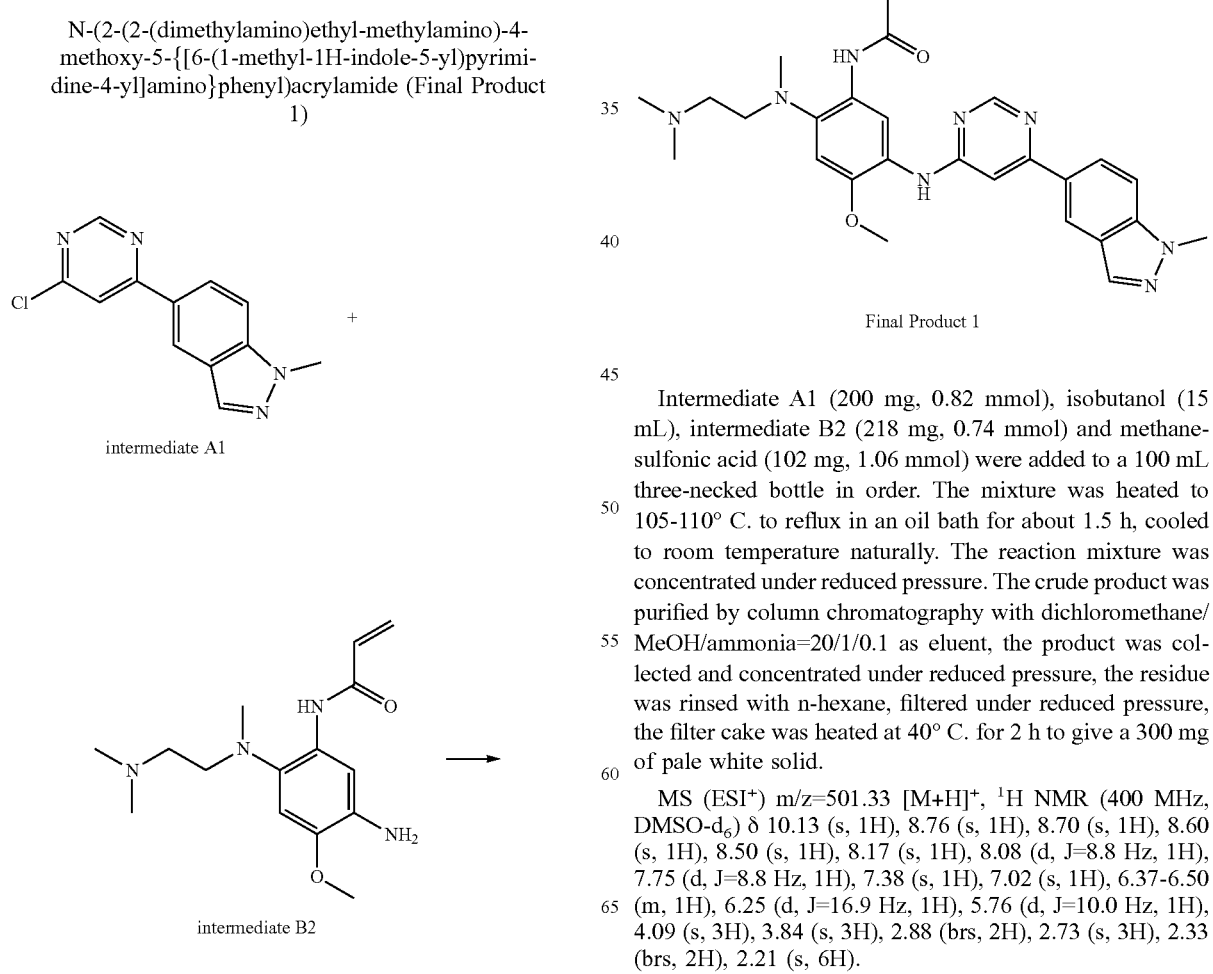

EXAMPLE 150

N-(2-(2-(dimethylamino)ethyl-methylamino)-4-methoxy-5-{[6-(1-methyl-1H-indole-5-yl)pyrimidine-4-yl]amino}phenyl)acrylamide (Final Product 1)

Intermediate A1 (200 mg, 0.82 mmol), isobutanol (15 mL), intermediate B2 (218 mg, 0.74 mmol) and methanesulfonic acid (102 mg, 1.06 mmol) were added to a 100 mL three-necked bottle in order. The mixture was heated to 105-110° C. to reflux in an oil bath for about 1.5 h, cooled to room temperature naturally. The reaction mixture was concentrated under reduced pressure. The crude product was purified by column chromatography with dichloromethane/MeOH/ammonia=20/1/0.1 as eluent, the product was collected and concentrated under reduced pressure, the residue was rinsed with n-hexane, filtered under reduced pressure, the filter cake was heated at 40° C. for 2 h to give a 300 mg of pale white solid.

MS (ESI+) m/z=501.33 [M+H]+, 1H NMR (400 MHz, DMSO-d6) δ 10.13 (s, 1H), 8.76 (s, 1H), 8.70 (s, 1H), 8.60 (s, 1H), 8.50 (s, 1H), 8.17 (s, 1H), 8.08 (d, J=8.8 Hz, 1H), 7.75 (d, J=8.8 Hz, 1H), 7.38 (s, 1H), 7.02 (s, 1H), 6.37-6.50 (m, 1H), 6.25 (d, J=16.9 Hz, 1H), 5.76 (d, J=10.0 Hz, 1H), 4.09 (s, 3H), 3.84 (s, 3H), 2.88 (brs, 2H), 2.73 (s, 3H), 2.33 (brs, 2H), 2.21 (s, 6H).

EXAMPLE 151-166

Preparation of Final Products 2-17

Final products 2-17 were prepared by the method of synthesizing the above-mentioned final product 1 except that the intermediates A and B (Table 3) were used.

TABLE 3

Final Products 2-17

| No. of Final Products | No. of Intermediates | Structure of Final Products | NMR or MS |
|---|---|---|---|
| Final Product 2 | A2 + B2 | | yield: 42.3%. MS (ESI+) m/z = 501.25 [M + H]+. $^1$H NMR (400 MHz, DMSO-d$_6$) δ 10.17 (s, 1H), 8.84 (s, 1H), 8.71 (s, 1H), 8.65 (s, 1H), 8.34 (s, 1H), 8.11 (s, 1H), 7.86 (d, J = 8.0 Hz, 1H), 7.79 (d, J = 8.0 Hz, 1H), 7.48 (s, 1H), 7.03 (s, 1H), 6.37-6.50 (m, 1H), 6.22 (d, J = 20.0 Hz, 1H), 5.75 (d, J = 8.0 Hz, 1H), 4.13 (s, 3H), 3.85 (s, 3H), 2.88 (brs, 2H), 2.73 (s, 3H), 2.33 (brs, 2H), 2.22 (s, 6H). |
| Final Product 3 | A3 + B2 | | yield: 45%. MS (ESI+) m/z = 501.25 [M + H]+. $^1$H NMR (400 MHz, DMSO-d$_6$) δ 10.20 (s, 1H), 9.28 (s, 1H), 8.94 (s, 1H), 8.49 (d, J = 4.0 Hz, 1H), 8.32 (d, J = 8.0 Hz, 1H), 8.14 (s, 1H), 8.02 (s, 1H), 7.72 (d, J = 8.0 Hz, 1H), 7.50 (d, J = 8.0 Hz, 1H), 7.04 (s, 1H), 6.43-6.50 (m, 1H), 6.35 (d, J = 16.0 Hz, 1H), 5.82 (d, J = 8.0 Hz, 1H), 4.10 (s, 3H), 3.89 (s, 3H), 2.88 (brs, 2H), 2.72 (s, 3H), 2.29 (brs, 2H), 2.21 (s, 6H). |
| Final Product 4 | A6 + B2 | | MS (ESI+) m/z = 569.18 [M + H]+. $^1$H NMR (500 MHz, DMSO-d$_6$) δ 10.14 (s, 1H), 8.87 (s, 1H), 8.83 (s, 1H), 8.72 (s, 1H), 8.65 (s, 1H), 8.51 (s, 1H), 8.43 (s, 1H), 7.50 (s, 1H), 7.03 (s, 1H), 6.37-6.43 (m, 1H), 6.25 (dd, J = 1.5, 16.5 16.5 Hz, 1H), 5.76 (dd, J = 1.5, 10.0 Hz, 1H), 4.19 (s, 3H), 3.85 (s, 3H), 2.88 (t, J = 5.5 Hz, 2H), 2.73 (s, 3H), 2.33 (t, J = 6.0 Hz, 2H), 2.21 (s, 6H). |
| Final Product 5 | A7 + B2 | | MS (ESI+) m/z = 519.26 [M + H]+. $^1$H NMR (400 MHz, DMSO-d$_6$) δ 10.07 (s, 1H), 8.97 (s, 1H), 8.60 (s, 2H), 8.47 (d, J = 7.6 Hz, 1H), 8.19 (s, 1H), 7.68 (d, J = 12.0 Hz, 1H), 7.20 (s, 1H), 7.01 (s, 1H), 6.35-6.43 (m, 1H), 6.22 (d, J = 15.2 Hz, 1H), 5.74 (d, J = 11.5 Hz, 1H), 4.05 (s, 3H), 3.82 (s, 3H), 2.87 (t, J = 5.2 Hz, 2H), 2.72 (s, 3H), 2.32 (t, J = 5.2 Hz, 2H), 2.21 (s, 6H). |

TABLE 3-continued

Final Products 2-17

| No. of Final Products | No. of Intermediates | Structure of Final Products | NMR or MS |
|---|---|---|---|
| Final Product 6 | A8 + B2 | | MS (ESI+) m/z = 519.22 [M + H]+. 1H NMR (400 MHz, DMSO-d6) δ 10.14 (s, 1H), 8.78 (s, 1H), 8.68 (s, 1H), 8.61 (d, J = 0.4 Hz, 1H), 8.33 (d, J = 0.8 Hz, 1H), 8.25 (d, J = 2.4 Hz, 1H), 7.87 (dd, J = 0.8, 13.6 Hz, 1H), 7.40 (s, 1H), 7.03 (s, 1H), 6.37-6.44 (m, 1H), 6.26 (dd, J = 1.6, 16.8 Hz, 1H), 5.76 (dd, J = 2.0, 10.0 Hz, 1H), 4.21 (s, 3H), 3.85 (s, 3H), 2.89 (t, J = 5.6 Hz, 2H), 2.73 (s, 3H), 2.34 (d, J = 5.6 Hz, 2H), 2.22 (s, 6H). |
| Final Product 7 | A11 + B2 | | MS (ESI+) m/z = 501.18 [M + H]+. 1H NMR (500 MHz, DMSO-d6) δ 10.10 (s, 1H), 8.75 (s, 1H), 8.69 (s, 1H), 8.59 (s, 1H), 8.49 (s, 2H), 7.88 (dd, J = 1.5, 9.0 Hz, 1H), 7.68 (d, J = 9.0 Hz, 1H), 7.36 (s, 1H), 7.02 (s, 1H), 6.38-6.44 (m, 1H), 6.25 (dd, J = 1.5, 17.0 Hz, 1H), 5.75 (dd, J = 2.0, 10.5 Hz, 1H), 4.20 (s, 3H), 3.84 (s, 3H), 2.90 (brs, 2H), 2.72 (s, 3H), 2.36 (brs, 2H), 2.24 (brs, 6H). |
| Final Product 8 | A1 + B1 | | MS (ESI+) m/z = 499.29 [M + H]+. 1H NMR (400 MHz, DMSO-d6) δ 9.04 (s, 1H), 8.77 (s, 1H), 8.59 (s, 1H), 8.50 (s, 1H), 8.34 (s, 1H), 8.18 (s, 1H), 8.08 (d, J = 8.7 Hz, 1H), 7.75 (d, J = 8.8 Hz, 1H), 7.38 (s, 1H), 6.87 (s, 1H), 6.59-6.70 (m, 1H), 6.23 (d, J = 20.0 Hz, 1H), 5.74 (d, J = 8.0 Hz, 1H), 4.09 (s, 3H), 3.86 (s, 3H), 2.88 (s, 4H), 2.26 (s, 3H). |
| Final Product 9 | A14 + B1 | | MS (ESI+) m/z = 502.16 [M + H]+. 1H NMR (500 MHz, DMSO-d6) δ 9.50 (s, 1H), 9.05 (s, 1H), 8.90 (s, 1H), 8.87 (s, 1H), 8.64 (s, 1H), 8.30 (s, 1H), 8.17-8.21 (m, 2H), 7.43 (s, 1H), 6.88 (s, 1H), 6.60-6.66 (m, 1H), 6.26 (d, J = 17.5 Hz, 1H), 5.75 (d, J = 11.0 Hz, 1H), 3.86 (s, 3H), 2.89 (t, J = 4.0 Hz, 4H), 2.55 (s, 4H), 2.27 (s, 3H). |

TABLE 3-continued

Final Products 2-17

| No. of Final Products | No. of Intermediates | Structure of Final Products | NMR or MS |
|---|---|---|---|
| Final Product 10 | A1 + B3 | | MS (ESI+) m/z = 499.21 [M + H]+. 1H NMR (500 MHz, DMSO-d6) δ 9.36 (s, 1H), 8.64 (s, 1H), 8.54 (s, 1H), 8.46 (s, 1H), 8.16 (s, 1H), 8.05 (d, J = 9.0 Hz, 1H), 7.74 (d, J = 8.5 Hz, 1H), 7.52 (brs, 1H), 7.21 (brs, 1H), 6.44-6.50 (m, 1H), 6.21 (d, J = 18.5 Hz, 2H), 5.70 (d, J = 10.5 Hz, 1H), 4.08 (s, 3H), 3.96 (t, J = 6.5 Hz, 2H), 3.83 (s, 3H), 3.58 (t, J = 6.0 Hz, 2H), 3.05 (t, J = 6.0 Hz, 1H), 2.07 (m, 6H). |
| Final Product 11 | A1 + B4 | | yield: 18.9%. MS (ESI+) m/z = 498.30 [M + H]+. 1H NMR (400 MHz, DMSO-d6) δ 9.58 (s, 1H), 8.77 (s, 1H), 8.64 (s, 1H), 8.52 (s, 1H), 8.18 (s, 1H), 8.08 (d, J = 8.6 Hz, 1H), 7.99 (s, 1H), 7.78 (d, J = 8.6 Hz, 1H), 7.57 (s, 1H), 6.95 (s, 1H), 6.47-6.60 (m, 1H), 6.24 (d, J = 20.0 Hz, 1H), 5.75 (d, J = 8.8 Hz, 1H), 4.09 (s, 3H), 3.90 (s, 3H), 2.88 (d, J = 10.8 Hz, 2H), 2.51-2.70 (m, 1H), 2.21 (s, 3H), 1.95 (brs, 2H), 1.68-1.80 (m, 4H). |
| Final Product 12 | A1 + B5 | | MS (ESI+) m/z = 527.18 [M + H]+. 1H NMR (400 MHz, DMSO-d6) δ 9.77 (s, 1H), 8.92 (s, 1H), 8.71 (s, 1H), 8.54 (s, 1H), 8.42 (s, 1H), 8.20 (s, 1H), 8.11 (d, J = 8.8 Hz, 1H), 7.78 (d, J = 8.9 Hz, 1H), 7.71 (s, 1H), 6.95 (s, 1H), 6.47-6.60 (m, 1H), 6.23 (d, J = 16.0 Hz, 1H), 5.74 (d, J = 8.0 Hz, 1H), 4.09 (s, 3H), 3.91 (s, 3H), 3.56 (brs, 2H), 3.23 (brs, 2H), 2.17-2.33 (m, 7H). |
| Final Product 13 | A1 + B6 | | MS (ESI+) m/z = 519.23 [M + H]+. 1H NMR (500 MHz, DMSO-d6) δ 9.51 (s, 1H), 8.72 (s, 1H), 8.50 (s, 1H), 8.47 (s, 1H), 8.16 (s, 1H), 8.06 (dd, J = 8.9, 1.1 Hz, 1H), 7.73 (d, J = 8.9 Hz, 1H), 6.94 (s, 1H), 6.57 (s, 1H), 6.46-6.51 (m, 1H), 6.22 (d, J = 16.9 Hz, 1H), 5.73 (d, J = 11.5 Hz, 1H), 4.08 (s, 3H), 3.81 (s, 3H), 3.02 (t, J = 7.0 Hz, 2H), 2.80 (s, 3H), 2.43 (q, J = 7.0 Hz, 2H), 2.14 (s, 6H). |

TABLE 3-continued

Final Products 2-17

| No. of Final Products | No. of Intermediates | Structure of Final Products | NMR or MS |
|---|---|---|---|
| Final Product 14 | A16 + B2 | | MS (ESI+) m/z = 515.17 [M + H]+. 1H NMR (400 MHz, DMSO-$d_6$) δ 10.05 (s, 1H), 8.77 (s, 1H), 8.63 (s, 1H), 8.60 (s, 1H), 8.50 (s, 1H), 8.18 (s, 1H), 8.06 (dd, J = 8.8, 1.2 Hz, 1H), 7.79 (d, J = 9.2 Hz, 1H), 7.40 (s, 1H), 7.01 (s, 1H), 6.47-6.65 (m, 1H), 6.26 (d, J= 16.8, 1.2 Hz, 1H), 5.75 (d, J = 12.0 Hz, 1H), 4.48 (q, J = 7.2 Hz, 2H), 3.85 (s, 3H), 2.97 (s, 2H), 2.69 (s, 3H), 2.50-2.51 (m, 2H), 2.33 (brs, 6H), 1.42 (t, J = 7.2 Hz, 3H). |
| Final Product 15 | A17 + B2 | | MS (ESI+) m/z = 529.20 [M + H]+. 1H NMR (400 MHz, DMSO-$d_6$) δ 10.08 (s, 1H), 8.77 (s, 1H), 8.65 (s, 1H), 8.60 (s, 1H), 8.49 (s, 1H), 8.19 (s, 1H), 8.05 (d, J = 9.2 Hz, 1H), 7.81 (d, J = 9.2 Hz, 1H), 7.39 (s, 1H), 7.01 (s, 1H), 6.45-6.65 (m, 1H), 6.25 (d, J = 15.6 Hz, 1H), 5.76 (d, J = 12.0 Hz, 1H), 5.00-5.07 (m, 1H), 3.85 (s, 3H), 2.94 (brs, 2H), 2.71 (s, 3H), 2.28-2.50 (m, 8H), 1.50 (d, J = 5.6 Hz, 6H). |
| Final Product 16 | A4 + B2 | | MS (ESI+) m/z = 501.16 [M + H]+. 1H NMR (500 MHz, DMSO-$d_6$) δ 10.19 (s, 1H), 9.20 (s, 1H), 8.54-8.56 (m, 2H), 8.12 (s, 2H), 8.05 (d, J = 8.5 Hz, 1H), 7.86 (d, J = 8.5 Hz, 1H), 7.56 (d, J = 5.0 Hz, 1H), 7.05 (s, 1H), 6.39-6.45 (m, 1H), 6.25 (d, J = 17.0 Hz, 1H), 5.78 (d, J = 10.0 Hz, 1H), 4.12 (s, 3H), 3.88 (s, 3H), 2.89 (m, 2H), 2.72 (s, 3H), 2.31 (brs, 2H), 2.22 (s, 6H). |
| Final Product 17 | A18 + B2 | | MS (ESI+) m/z = 529.23 [M + H]+. 1H NMR (500 MHz, DMSO-$d_6$) δ 10.13 (s, 1H), 9.10 (s, 1H), 8.50-8.55 (m, 2H), 8.14 (d, J = 4.0 Hz, 2H), 8.06 (d, J = 8.5 Hz, 1H), 7.85 (d, J = 8.5 Hz, 1H), 7.57 (d, J = 5.0 Hz, 1H), 7.03 (s, 1H), 6.42-6.45 (m, 1H), 6.28 (d, J = 13.2 Hz, 1H), 5.77 (d, J = 11.0 Hz, 1H), 5.10-5.17 (m, 1H), 3.88 (s, 3H), 2.91 (s, 2H), 2.71 (s, 3H), 2.25-2.34 (m, 8H), 1.50 (t, J = 6.5 Hz, 6H). |

EXAMPLE 167

Preparation of Final Product 18

N-(2-(4-ethylpiperazine-1-yl)-4-methoxy-5-{[6-(1-methyl-1H-indole-5-yl)pyrimidine-4-yl]amino}phenyl) acrylamide (Final Product 18)

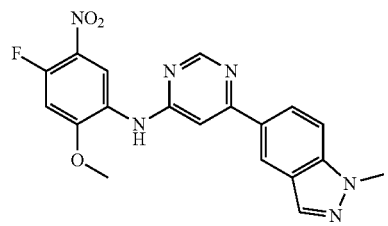

Intermediate C1

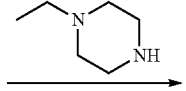

Step 1: N-(4-(4-ethylpiperazine-1-yl)-2-methoxy-5-nitrophenyl)-6-(1-methyl-1H-indole-5-yl)pyrimidine-4-amine

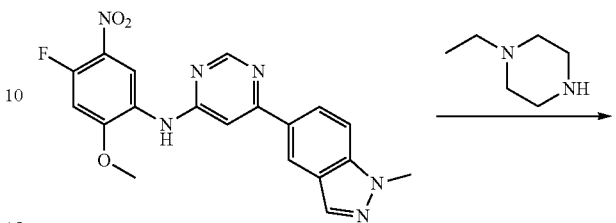

Intermediate C1

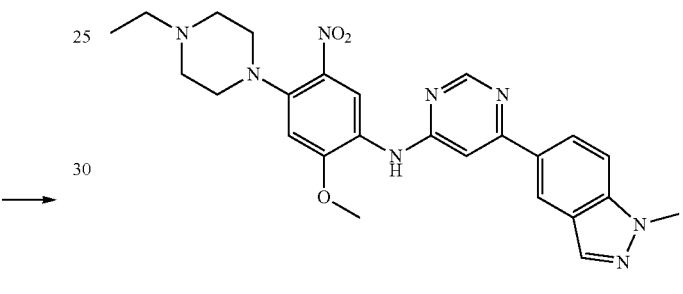

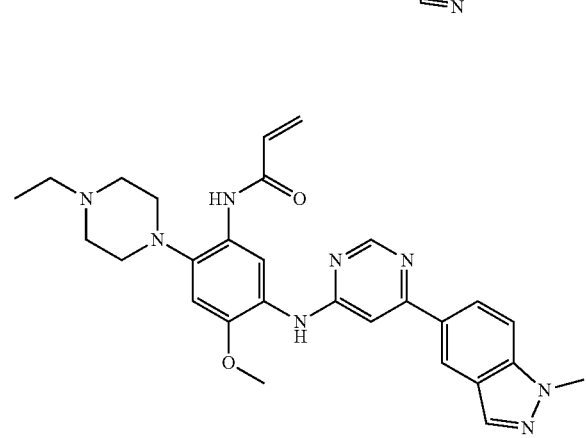

Final Product 18

N-(4-fluoro-2-methoxy-5-nitrophenyl)-6-(1-methyl-1H-indole-5-yl)pyrimidine-4-amine (Intermediate C1) (400 mg, 1.014 mmol) and DMF (20 mL) were added to a 100 mL single-necked bottle, 1-ethylpiperazine (150 mg, 1.319 mmol) and DIPEA (196 mg, 1.521 mmol) were added thereinto with stirring at room temperature. The mixture was heated to 45-50° C. in an oil bath to react with stirring, the reaction was monitored by TLC. After the reaction completed, 50 mL water and 30 mL ethyl acetate were added thereinto, separated organic phase, the aqueous phase was extracted with ethyl acetate (30 mL×2) twice, the organic phases were combined and washed with water (50 mL×2) twice, and then with saturated brine (50 mL×2) twice. The organic phase was dried by anhydrous sodium sulfate for 30 min and filtered under reduced pressure, the filtrate was concentrated under reduced pressure to give a crude product. The crude product was purified by column chromatography with gradient eluent of DCM/MeOH=10/1→5/1, the product was collected and concentrated under reduced pressure to give 390 mg, the base added to the reaction mixture could be TEA or Na$_2$CO$_3$/KI.

Step 2: 4-(4-ethylpiperazine-1-yl)-6-methoxy-N1-(6-(1-methyl-1H-indole-5-yl) pyrimidine-4-yl)benzene-1,3-diamine

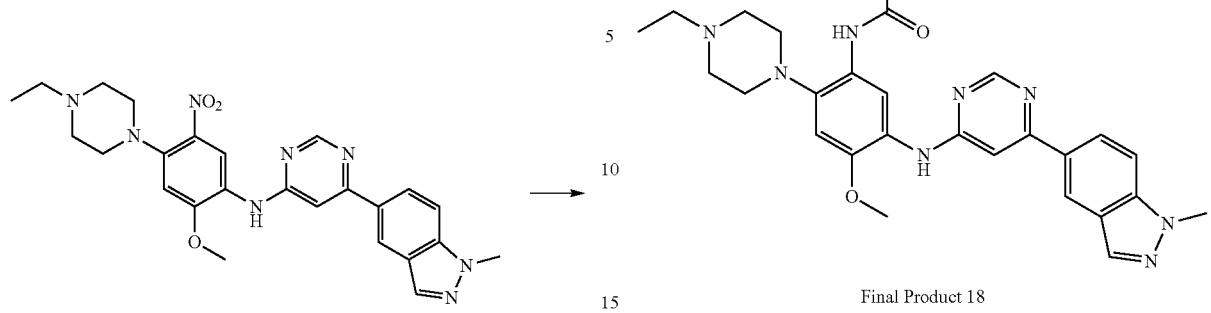

Final Product 18

N-(4-(4-ethylpiperazine-1-yl)-2-methoxy-5-nitrophenyl)-6-(1-methyl-1H-indole-5-yl) pyrimidine-4-amine (390 mg, 0.798 mmol), DCM (10 mL), THF (10 mL) and 10% Pd/C (80 mg) were added to a 100 mL single-necked bottle in order, reacted for about 10 h under the pressure of hydrogen with stirring at room temperature. The mixture was filtered, the filtrate was concentrated under reduced pressure to give a 300 mg of product. Or iron powder and NH₄Cl were used as the reducing agents and ethanol and water were used as the solvents to reduce the nitro group at 85-90° C. with stirring.

Step 3: N-(2-(4-ethylpiperazine-1-yl)-4-methoxy-5{[6-(1-methyl-1H-indole-5-yl) pyrimidine-4-yl]amino}phenyl)acrylamide

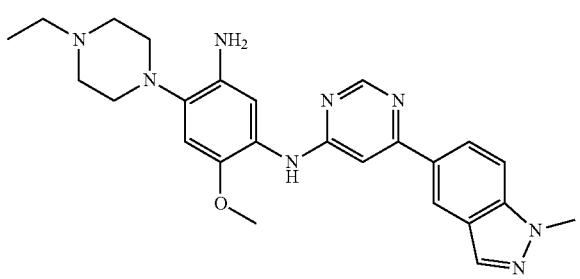

4-(4-ethylpiperazine-1-yl)-6-methoxy-N1-(6-(1-methyl-1H-indole-5-yl)pyrimidine-4-yl)benzene-1,3-diamine (300 mg, 0.654 mmol) and THF (10 mL) were added to a 100 mL single-necked bottle, cooled in an ice salt bath, acrylyl chloride (65 mg, 0.72 mmol) was added dropwise thereinto, after the addition completed, the system changed from clear to turbid, TLC was used to monitor the reaction, when the starting materials reacted completely, 30 mL saturated sodiumbicarbonate solution was added thereinto, and then 30 mL dichloromethane was added thereinto, stirred and separated organic phase, the aqueous phase was extracted with dichloromethane (30 mL×2) twice, the organic phases were combined and washed with saturated brine (30 mL×2) twice. The organic phase was dried by anhydrous sodium sulfate for 30 min and filtered under reduced pressure, the filtrate was concentrated under reduced pressure to give a crude product. The crude product was purified by column chromatography with DCM/MeOH=10/1 as eluent, the product was collected and concentrated under reduced pressure, the residue was rinsed with n-hexane and filtered under reduced pressure, the residue was dried at 45° C. for 2 h to give a 76 mg of pale yellow solid.

MS (ESI⁺) m/z=459.21[M+H]⁺. ¹H NMR (400 MHz, DMSO-d₆) δ 9.03 (s, 1H), 8.75 (s, 1H), 8.59 (s, 1H), 8.49 (s, 1H), 8.35 (s, 1H), 8.17 (d, J=0.8 Hz, 1H), 8.08 (dd, J=1.2, 8.8 Hz, 1H), 7.75 (d, J=8.8 Hz, 1H), 7.38 (s, 1H), 6.89 (s, 1H), 6.58-6.70 (m, 1H), 6.23 (dd, J=1.6, 17.2 Hz, 1H), 5.73 (d, J=10.8 Hz, 1H), 4.08 (s, 3H), 3.85 (s, 3H), 2.87 (t, J=4.3 Hz, 4H), 2.58 (brs, 4H), 2.40-2.42 (m, 2H), 1.04 (t, J=7.2 Hz, 3H).

Examples 168-411

Preparation of Final Products 19-262

Final Products 19-262 were prepared by the method of synthesizing the Final Product 18 (EXAMPLE 167) except that the intermediate C and amines or alcohols which are commercially available or synthesized by EXAMPLES 1-69 were used as the starting materials. (Table 4)

TABLE 4

Final Products 19-262

| No. of Final Products | No. of Intermediates | Structure of Final Products | NMR or MS |
|---|---|---|---|
| Final Product 19 | C1 | | MS (ESI$^+$) m/z = 527.22 [M + H]$^+$. $^1$H NMR (400 MHz, DMSO-d$_6$) δ 9.03 (s, 1H), 8.74 (s, 1H), 8.59 (s, 1H), 8.49 (s, 1H), 8.36 (s, 1H), 8.17 (d, J = 0.4 Hz, 1H), 8.08 (dd, J = 1.2, 8.8 Hz, 1H), 7.75 (d, J = 8.8 Hz, 1H), 7.38 (s, 1H), 6.89 (s, 1H), 6.59-6.67 (m, 1H), 6.23 (dd, J = 1.6, 14.4 Hz, 1H), 5.74 (d, J = 11.6 Hz, 1H), 4.08 (s, 3H), 3.85 (s, 3H), 2.87 (d, J = 4.7 Hz, 4H), 2.65-2.80 (m, 5H), 1.02 (d, J = 6.8 Hz, 6H). |
| Final Product 20 | C1 | | MS (ESI$^+$) m/z = 527.27 [M + H]$^+$. $^1$H NMR (500 MHz, DMSO-d$_6$) δ 9.15 (s, 1H), 8.77 (s, 1H), 8.60 (d, J = 1.0 Hz, 1H), 8.50 (d, J = 1.0 Hz, 1H), 8.47 (s, 1H), 8.18 (d, J = 0.5 Hz, 1H), 8.08 (dd, J = 1.5, 9.0 Hz, 1H), 7.76 (d, J = 9.0 Hz, 1H), 7.41 (s, 1H), 6.91 (s, 1H), 6.65-6.71 (m, 1H), 6.26 (dd, J = 1.5, 17.0 Hz, 1H), 5.76 (d, J = 11.0 Hz, 1H), 4.09 (s, 3H), 3.85 (s, 3H), 3.65 (brs, 4H), 2.82-2.88 (m, 4H), 2.06 (s, 3H). |
| Final Product 21 | C1 | | yield: 18%. MS (ESI$^+$) m/z = 513.22 [M + H]$^+$. $^1$H NMR (400 MHz, DMSO-d$_6$) δ 9.08 (s, 1H), 8.78 (s, 1H), 8.75 (s, 1H), 8.62 (s, 1H), 8.50 (s, 1H), 8.18 (s, 1H), 8.08 (dd, J = 1.2, 7.2 Hz, 1H), 7.76 (d, J = 7.2 Hz, 1H), 7.45 (s, 1H), 7.03 (s, 1H), 6.57-6.63 (m, 1H), 6.23 (dd, J = 1.2, 13.2 Hz, 1H), 5.76 (d, J = 8.4 Hz, 1H), 4.09 (s, 3H), 3.85 (s, 3H), 3.17 (t, J = 4.8 Hz, 1H), 2.72-2.87 (m, 4H), 2.32-2.35 (m, 1H), 2.26 (s, 3H), 2.01-2.06 (t, J = 10 Hz, 1H), 0.78 (d, J = 5.2 Hz, 3H). |
| Final Product 22 | C1 | | yield: 27%. MS (ESI$^+$) m/z = 513.25 [M + H]$^+$. $^1$H NMR (500 MHz, DMSO-d$_6$) δ 9.04 (s, 1H), 8.76 (s, 1H), 8.60 (s, 1H), 8.50 (s, 1H), 8.35 (s, 1H), 8.18 (s, 1H), 8.08 (d, J = 9.0 Hz, 1H), 7.75 (d, J = 8.5 Hz, 1H), 7.38 (s, 1H), 6.85 (s, 1H), 6.57-6.63 (m, 1H), 6.24 (d, J = 17.0 Hz, 1H), 5.74 (d, J = 10.0 Hz, 1H), 4.09 (s, 3H), 3.86 (s, 3H), 2.78-2.94 (m, 4H), 2.25-2.50 (m, 6H), 1.02 (d, J = 5.5 Hz, 3H). |

TABLE 4-continued

Final Products 19-262

| No. of Final Products | No. of Intermediates | Structure of Final Products | NMR or MS |
|---|---|---|---|
| Final Product 23 | C1 | | MS (ESI+) m/z = 527.23 [M + H]+. 1H NMR (400 MHz, DMSO-d6) δ 9.06 (s, 1H), 8.76 (s, 1H), 8.60 (s, 1H), 8.50 (s, 1H), 8.36 (s, 1H), 8.18 (s, 1H), 8.08 (d, J = 8.8 Hz, 1H), 7.76 (d, J = 8.8 Hz, 1H), 7.38 (s, 1H), 6.84 (s, 1H), 6.57-6.64 (m, 1H), 6.24 (d, J = 7.2 Hz, 1H), 5.74 (d, J = 10.0 Hz, 1H), 4.09 (s, 3H), 3.86 (s, 3H), 2.89 (d, J = 10.0 Hz, 2H), 2.54 (d, J = 10.8 Hz, 2H), 2.45 (brs, 2H), 2.24 (s, 3H), 1.03 (d, J = 5.6 Hz, 6H). |
| Final Product 24 | C1 | | MS (ESI+) m/z = 527.17 [M + H]+. 1H NMR (500 MHz, DMSO-d6) δ 9.05 (s, 1H), 8.75 (s, 1H), 8.59 (s, 1H), 8.49 (s, 1H), 8.35 (s, 1H), 8.17 (s, 1H), 8.07 (dd, J = 1.0, 9.0 Hz, 1H), 7.75 (d, J = 9.0 Hz, 1H), 7.37 (s, 1H), 6.84 (s, 1H), 6.57-6.63 (m, 1H), 6.23 (d, J = 16.5 Hz, 1H), 5.74 (d, J = 10.5 Hz, 1H), 4.08 (s, 3H), 3.86 (s, 3H), 2.88 (d, J = 10.0 Hz, 2H), 2.53 (d, J = 10.5 Hz, 2H), 2.44 (brs, 2H), 2.23 (s, 3H), 1.02 (d, J = 5.5 Hz, 6H). |
| Final Product 25 | C1 | | MS (ESI+) m/z = 511.19 [M + H]+. 1H NMR (400 MHz, DMSO-d6) δ 9.32 (s, 1H), 8.63 (s, 1H), 8.56 (s, 1H), 8.47 (s, 1H), 8.17 (s, 1H), 8.06 (dd, J = 1.2, 8.8 Hz, 1H), 7.74 (d, J = 8.8 Hz, 1H), 7.59 (s, 1H), 7.25 (s, 1H), 6.42-6.51 (m, 2H), 6.22 (dd, J = 1.6, 16.8 Hz, 1H), 5.70 (dd, J = 2.0, 10.0 Hz, 1H), 4.20 (s, 1H), 4.08 (s, 3H), 3.83 (s, 3H), 3.39 (d, J = 8.8 Hz, 2H), 3.12 (d, J = 8.8 Hz, 1H), 2.84 (d, J = 6.8 Hz, 1H), 2.75 (d, J = 9.2 Hz, 1H), 2.30 (s, 3H), 1.83 (d, J = 9.2 Hz, 1H), 1.71 (d, J = 9.6 Hz, 1H). |
| Final Product 26 | C1 | | yield: 31.42%. MS (ESI+) m/z = 527.24 [M + H]+. 1H NMR (500 MHz, DMSO-d6) δ 9.03 (s, 1H), 8.74 (s, 1H), 8.59 (s, 1H), 8.50 (s, 1H), 8.36 (s, 1H), 8.17 (s, 1H), 8.08 (d, J = 9.0 Hz, 1H), 7.75 (d, J = 9.0 Hz, 1H), 7.37 (s, 1H), 6.86 (s, 1H), 6.65-6.70 (m, 1H), 6.25 (d, J = 17.0 Hz, 1H), 5.74 (d, J = 10.5 Hz, 1H), 4.09 (s, 3H), 3.85 (s, 3H), 3.07 (d, J = 10.5 Hz, 2H), 2.68 (t, J = 10.5 Hz, 2H), 2.50 (s, 1H), 2.25 (s, 6H), 1.85 (d, J = 11.0 Hz, 2H), 1.70 (d, J = 10.5 Hz, 2H). |

TABLE 4-continued

Final Products 19-262

| No. of Final Products | No. of Intermediates | Structure of Final Products | NMR or MS |
|---|---|---|---|
| Final Product 27 | C1 | | MS (ESI⁺) m/z = 569.23 [M + H]⁺. ¹H NMR (500 MHz, DMSO-d₆) δ 9.00 (s, 1H), 8.74 (s, 1H), 8.59 (s, 1H), 8.49 (s, 1H), 8.37 (s, 1H), 8.17 (s, 1H), 8.07 (dd, J = 1.0, 9.0 Hz, 1H), 7.75 (d, J = 8.0 Hz, 1H), 7.36 (s, 1H), 6.85 (s, 1H), 6.64-6.70 (m, 1H), 6.24 (d, J = 17.0 Hz, 1H), 5.74 (d, J = 11.0 Hz, 1H), 4.08 (s, 3H), 3.84 (s, 3H), 3.60 (s, 4H), 3.07 (d, J = 11.0 Hz, 2H), 2.68 (t, J = 11.0 Hz, 2H), 2.49 (s, 4H), 2.20-2.30 (m, 1H), 1.87 (d, J = 11.5 Hz, 2H), 1.69-1.73 (m, 2H). |
| Final Product 28 | C1 | | yield: 23%. MS (ESI⁺) m/z = 527.26 [M + H]⁺. ¹H NMR (500 MHz, DMSO-d₆) δ 9.04 (s, 1H), 8.76 (s, 1H), 8.60 (s, 1H), 8.50 (s, 1H), 8.35 (s, 1H), 8.18 (d, J = 0.8 Hz, 1H), 8.08 (dd, J = 1.5, 9.0 Hz, 1H), 7.76 (d, J = 9.0 Hz, 1H), 7.39 (s, 1H), 6.87 (s, 1H), 6.57-6.63 (m, 1H), 6.24 (dd, J = 1.0, 17.0 Hz, 1H), 5.75 (d, J = 11.5 Hz, 1H), 4.09 (s, 3H), 3.86 (s, 3H), 2.95-2.53 (m, 8H), 2.36-2.37 (m, 1H), 1.00-1.05 (m, 6H). |
| Final Product 29 | C1 | | MS (ESI⁺) m/z = 527.22 [M + H]⁺. ¹H NMR (500 MHz, DMSO-d₆) δ 9.04 (s, 1H), 8.76 (s, 1H), 8.60 (s, 1H), 8.50 (s, 1H), 8.35 (s, 1H), 8.18 (d, J = 1.0 Hz, 1H), 8.08 (dd, J = 1.5, 9.0 Hz, 1H), 7.76 (d, J = 9.0 Hz, 1H), 7.39 (s, 1H), 6.88 (s, 1H), 6.57-6.63 (m, 1H), 6.23 (d, J = 17.5 Hz, 1H), 5.75 (d, J = 10.0 Hz, 1H), 4.09 (s, 3H), 3.86 (s, 3H), 2.95-2.55 (m, 8H), 2.36-2.38 (m, 1H), 1.00-1.05 (m, 6H). |
| Final Product 30 | C1 | | yield: 50%. MS (ESI⁺) m/z = 513.25 [M + H]⁺. ¹H NMR (500 MHz, DMSO-d₆) δ 9.04 (s, 1H), 8.76 (s, 1H), 8.60 (s, 1H), 8.50 (s, 1H), 8.35 (s, 1H), 8.18 (d, J = 0.5 Hz, 1H), 8.08 (dd, J = 1.5, 9.0 Hz, 1H), 7.76 (d, J = 9.0 Hz, 1H), 7.38 (s, 1H), 6.85 (s, 1H), 6.57-6.63 (m, 1H), 6.24 (dd, J = 1.5, 17.0 Hz, 1H), 5.75 (d, J = 14.5 Hz, 1H), 4.09 (s, 3H), 3.88 (s, 3H), 2.78-2.92 (m, 4H), 2.46-2.25 (m, 6H), 1.02 (d, J = 6.0 Hz, 3H). |
| Final Product 31 | C1 | | MS (ESI⁺) m/z = 513.20 [M + H]⁺. ¹H NMR (400 MHz, DMSO-d₆) δ 9.03 (s, 1H), 8.75 (s, 1H), 8.59 (s, 1H), 8.49 (s, 1H), 8.34 (s, 1H), 8.17 (s, 1H), 8.07 (dd, J = 0.8, 7.2 Hz, 1H), 7.75 (d, J = 7.2 Hz, 1H), 7.37 (s, 1H), 6.85 (s, 1H), 6.57-6.63 (m, 1H), 6.23 (d, J = 13.6 Hz, 1H), 5.73 (d, J = 8.4 Hz, 1H), 4.08 (s, 3H), 3.85 (s, 3H), 2.77-2.93 (m, 4H), 2.45-2.24 (m, 6H), 1.01 (d, J = 4.8 Hz, 3H). |

TABLE 4-continued

Final Products 19-262

| No. of Final Products | No. of Intermediates | Structure of Final Products | NMR or MS |
|---|---|---|---|
| Final Product 32 | C1 | | yield: 45%. MS (ESI+) m/z = 567.29 [M + H]+. 1H NMR (500 MHz, DMSO-d6) δ 9.07 (s, 1H), 8.76 (s, 1H), 8.60 (s, 1H), 8.50 (s, 1H), 8.39 (s, 1H), 8.18 (d, J = 1.0 Hz, 1H), 8.08 (dd, J = 1.5, 9.0 Hz, 1H), 7.76 (d, J = 9.0 Hz, 1H), 7.40 (s, 1H), 6.93 (s, 1H), 6.60-6.65 (m, 1H), 6.24 (dd, J = 1.5, 17.0 Hz, 1H), 5.75 (d, J = 11.0 Hz, 1H), 4.09 (s, 3H), 3.86 (s, 3H), 3.27 (q, J = 10.2 Hz, 2H), 2.89 (dd, J = 4.5, 25.0 Hz, 8H). |
| Final Product 33 | C1 | | MS (ESI+) m/z = 582.22 [M + H]+. 1H NMR (400 MHz, DMSO-d6) δ 9.00 (s, 1H), 8.74 (s, 1H), 8.59 (s, 1H), 8.49 (s, 1H), 8.37 (s, 1H), 8.17 (s, 1H), 8.08 (dd, J = 1.2, 7.2 Hz, 1H), 7.75 (d, J = 7.2 Hz, 1H), 7.36 (s, 1H), 6.85 (s, 1H), 6.65-6.71 (m, 1H), 6.25 (dd, J = 1.2 13.6 Hz, 1H), 5.74 (d, J = 9.2 Hz, 1H), 4.08 (s, 3H), 3.84 (s, 3H), 3.06 (d, J = 8.8 Hz, 2H), 2.67 (t, J = 8.8 Hz, 2H), 2.52-2.53 (m, 4H), 2.26-2.36 (m, 5H), 2.16 (s, 3H), 1.85 (d, J = 8.8 Hz, 2H), 1.72-1.74 (m, 2H). |
| Final Product 34 | C1 | | yield: 60.60%. MS (ESI+) m/z = 581.24 [M + H]+. 1H NMR (400 MHz, DMSO-d6) δ 8.99 (s, 1H), 8.74 (s, 1H), 8.59 (s, 1H), 8.49 (s, 1H), 8.36 (s, 1H), 8.17 (s, 1H), 8.08 (dd, J = 1.2, 7.2 Hz, 1H), 7.75 (d, J = 7.2 Hz, 1H), 7.36 (s, 1H), 6.85 (s, 1H), 6.62-6.66 (m, 1H), 6.24 (dd, J = 1.2, 13.6 Hz, 1H), 5.73 (d, J = 9.2 Hz, 1H), 4.08 (s, 3H), 3.84 (s, 3H), 3.05 (d, J = 9.2 Hz, 2H), 2.80 (d, J = 8.4 Hz, 2H), 2.63 (t, J = 9.2 Hz, 2H), 2.14 (s, 3H), 1.75-1.82 (m, 4H), 1.68 (d, J = 9.2 Hz, 2H), 1.46-1.48 (m, 2H), 1.18-1.23 (m, 3H), 1.06-1.10 (m, 1H). |
| Final Product 35 | C1 | | MS (ESI+) m/z = 527.19 [M + H]+. 1H NMR (400 MHz, DMSO-d6) δ 9.13 (s, 1H), 8.74 (s, 1H), 8.60 (s, 1H), 8.50 (s, 2H), 8.17 (s, 1H), 8.08 (dd, J = 1.2, 8.8 Hz, 1H), 7.76 (d, J = 8.8 Hz, 1H), 7.42 (s, 1H), 6.93 (s, 1H), 6.59-6.93 (m, 1H), 6.23 (dd, J = 1.6, 16.8 Hz, 1H), 5.72 (d, J = 11.6 Hz, 1H), 4.09 (s, 3H), 3.84 (s, 3H), 2.69-2.76 (m, 3H), 2.64 (s, 3H), 2.12 (s, 3H), 1.54-1.78 (m, 6H). |
| Final Product 36 | C1 | | MS (ESI+) m/z = 527.17 [M + H]+. |

TABLE 4-continued

Final Products 19-262

| No. of Final Products | No. of Intermediates | Structure of Final Products | NMR or MS |
|---|---|---|---|
| Final Product 37 | C1 | | MS (ESI$^+$) m/z = 541.12 [M + H]$^+$. |
| Final Product 38 | C1 | | MS (ESI$^+$) m/z = 543.14 [M + H]$^+$. $^1$H NMR (500 MHz, DMSO-d$_6$) δ 9.33 (s, 1H), 8.76 (s, 1H), 8.60 (s, 1H), 8.50 (s, 1H), 8.46 (s, 1H), 8.17 (s, 1H), 8.08 (dd, J = 1.5, 8.5 Hz, 1H), 7.76 (d, J = 8.9 Hz, 1H), 7.38 (s, 1H), 6.97 (s, 1H), 6.59-6.65 (m, 1H), 6.25 (dd, J = 1.5, 17.0 Hz, 1H), 5.76 (d, J = 11.0 Hz, 1H), 4.09 (s, 3H), 3.86 (s, 3H), 3.55 (t, J = 4.5 Hz, 4H), 3.01 (t, J = 6.5 Hz, 2H), 2.72 (s, 3H), 2.34-2.41 (m, 2H). |
| Final Product 39 | C1 | | MS (ESI$^+$) m/z = 513.13 [M + H]$^+$. $^1$H NMR (400 MHz, DMSO-d$_6$) δ 9.19 (s, 1H), 8.72 (s, 1H), 8.58 (s, 1H), 8.48 (s, 1H), 8.17 (s, 2H), 8.07 (d, J = 7.2 Hz, 1H), 7.74 (d, J = 7.2 Hz, 1H), 7.35 (s, 1H), 6.85 (s, 1H), 6.57-6.63 (m, 1H), 6.24 (d, J = 13.2 Hz, 1H), 5.74 (d, J = 8.4 Hz, 1H), 4.08 (s, 3H), 3.84 (s, 3H), 3.14-3.17 (m, 4H), 2.75 (brs, 4H), 2.37 (s, 3H), 1.89 (s, 2H). |
| Final Product 40 | C1 | | yield: 57.6%. MS (ESI$^+$) m/z = 515.17 [M + H]$^+$. $^1$H NMR (500 MHz, DMSO-d$_6$) δ 9.13 (s, 1H), 8.75 (s, 1H), 8.59 (s, 1H), 8.48 (s, 1H), 8.41 (s, 1H), 8.17 (s, 1H), 8.07 (dd, J = 1.5, 9.0 Hz, 1H), 7.75 (d, J = 9.0 Hz, 1H), 7.37 (s, 1H), 6.91 (s, 1H), 6.62-6.67 (m, 1H), 6.23 (dd, J = 1.5, 17.0 Hz, 1H), 5.72 (d, J = 1.5, 11.5 1H), 4.08 (s, 3H), 3.85 (s, 3H), 2.85 (t, J = 7.0 Hz, 2H), 2.66 (s, 3H), 2.29 (s, 2H), 2.15 (s, 6H), 1.60-1.66 (m, 2H). |
| Final Product 41 | C2 | | MS (ESI$^+$) m/z = 513.21 [M + H]$^+$. $^1$H NMR (400 MHz, DMSO-d$_6$) δ 9.05 (s, 1H), 8.82 (s, 1H), 8.65 (s, 1H), 8.37 (s, 1H), 8.34 (s, 1H), 8.11 (d, J = 0.8 Hz, 1H), 7.87 (d, J = 8.4 Hz, 1H), 7.78 (dd, J = 0.8, 8.4 Hz, 1H), 7.48 (s, 1H), 6.87 (s, 1H), 6.57-6.64 (m, 1H), 6.23 (dd, J = 1.2, 16.8 Hz, 1H), 5.75 (dd, J = 2.0, 13.6 Hz, 1H), 4.14 (s, 3H), 3.87 (s, 3H), 2.78-2.91 (m, 4H), 2.43-2.53 (m, 2H), 2.33 (s, 1H), 2.25 (s, 3H), 1.02 (d, J = 6.0 Hz, 3H). |

TABLE 4-continued

Final Products 19-262

| No. of Final Products | No. of Intermediates | Structure of Final Products | NMR or MS |
|---|---|---|---|
| Final Product 42 | C2 | | yield: 45%. MS (ESI⁺) m/z = 527.23 [M + H]⁺. ¹H NMR (400 MHz, DMSO-d₆) δ 9.06 (s, 1H), 8.82 (s, 1H), 8.64 (s, 1H), 8.37 (s, 1H), 8.33 (s, 1H), 8.10 (d, J = 0.4 Hz, 1H), 7.87 (d, J = 8.4 Hz, 1H), 7.78 (dd, J = 0.8, 8.4 Hz, 1H), 7.47 (s, 1H), 6.84 (s, 1H), 6.57-6.64 (m, 1H), 6.23 (dd, J = 1.2, 16.8 Hz, 1H), 5.74 (dd, J = 2.0, 13.6 Hz, 1H), 4.13 (s, 3H), 3.86 (s, 3H), 2.88 (d, J = 10.4 Hz, 2H), 2.54 (d, J = 10.4 Hz, 2H), 2.44 (s, 2H), 2.23 (s, 3H), 1.03 (d, J = 6.0 Hz, 6H). |
| Final Product 43 | C2 | | yield: 52.04%. MS (ESI⁺) m/z = 499.22 [M + H]⁺. ¹H NMR (400 MHz, DMSO-d₆) δ 9.04 (s, 1H), 8.82 (s, 1H), 8.64 (s, 1H), 8.36 (s, 1H), 8.33 (s, 1H), 8.10 (s, 1H), 7.86 (d, J = 8.4 Hz, 1H), 7.78 (d, J = 8.4 Hz, 1H), 7.47 (s, 1H), 6.87 (s, 1H), 6.58-6.65 (m, 1H), 6.22 (d, J = 17.2 Hz, 1H), 5.73 (d, J = 10.4 Hz, 1H), 4.13 (s, 3H), 3.86 (s, 3H), 2.88 (t, J = 4.4 Hz, 4H), 2.53 (s, 4H), 2.26 (s, 3H). |
| Final Product 44 | C2 | | yield: 45%. MS (ESI⁺) m/z = 513.20 [M + H]⁺. ¹H NMR (400 MHz, DMSO-d₆) δ 9.09 (s, 1H), 8.85 (s, 1H), 8.77 (s, 1H), 8.67 (s, 1H), 8.34 (s, 1H), 8.11 (d, J = 0.8 Hz, 1H), 7.88 (d, J = 6.8 Hz, 1H), 7.79 (dd, J = 1.2, 6.8 Hz, 1H), 7.54 (s, 1H), 7.04 (s, 1H), 6.57-6.63 (m, 1H), 6.22 (dd, J = 1.2, 13.6 Hz, 1H), 5.75 (dd, J = 0.8, 8.4 Hz, 1H), 4.13 (s, 3H), 3.85 (s, 3H), 3.17 (t, J = 5.2 Hz, 1H), 2.71-2.87 (m, 4H), 2.30-2.37 (m, 1H), 2.25 (s, 3H), 1.90-2.10 (m, 1H), 0.78 (d, J = 4.8 Hz, 3H). |
| Final Product 45 | C2 | | yield: 45%. MS (ESI⁺) m/z = 514.23 [M + H]⁺. ¹H NMR (400 MHz, DMSO-d₆) δ 9.05 (s, 1H), 8.81 (s, 1H), 8.64 (s, 1H), 8.38 (s, 1H), 8.34 (s, 1H), 8.10 (d, J = 0.8 Hz, 1H), 7.87 (d, J = 8.4 Hz, 1H), 7.78 (dd, J = 0.8, 8.4 Hz, 1H), 7.46 (s, 1H), 6.86 (s, 1H), 6.64-6.70 (m, 1H), 6.23 (dd, J = 1.6, 16.8 Hz, 1H), 5.74 (dd, J = 2.4, 13.6 Hz, 1H), 4.13 (s, 3H), 3.87 (s, 3H), 3.32-3.35 (m, 1H), 3.29 (s, 3H), 2.99-3.02 (m, 2H), 2.68-2.74 (m, 2H), 1.98-2.01 (m, 2H), 1.70-1.73 (m, 2H). |
| Final Product 46 | C2 | | yield: 54.29%. MS (ESI⁺) m/z = 569.27 [M + H]⁺. ¹H NMR (400 MHz, DMSO-d₆) δ 9.07 (s, 1H), 8.81 (s, 1H), 8.64 (s, 1H), 8.38 (s, 1H), 8.34 (s, 1H), 8.10 (d, J = 0.8 Hz, 1H), 7.87 (d, J = 6.8 Hz, 1H), 7.78 (dd, J = 1.2, 6.8 Hz, 1H), 7.48 (s, 1H), 6.90 (s, 1H), 6.60-6.66 (m, 1H), 6.21 (dd, J = 1.2, 13.6 Hz, 1H), 5.74 (dd, J = 3.2, 9.2 Hz, 1H), 4.13 (s, 3H), 3.92 (dd, J = 2.4, 8.4 Hz, 2H), 3.86 (s, 3H), 3.25-3.33 (m, 2H), 2.89 (t, J = 3.2 Hz, 4H), 2.70 (brs, 4H), 2.40-2.50 (m, 1H), 1.76 (d, J = 10.8 Hz, 2H), 1.40-1.48 (m, 2H). |

TABLE 4-continued

Final Products 19-262

| No. of Final Products | No. of Intermediates | Structure of Final Products | NMR or MS |
|---|---|---|---|
| Final Product 47 | C2 | | MS (ESI+) m/z = 513.22 [M + H]+. 1H NMR (400 MHz, DMSO-d6) δ 9.20 (s, 1H), 8.79 (s, 1H), 8.63 (s, 1H), 8.33 (s, 1H), 8.20 (s, 1H), 8.10 (s, 1H), 7.87 (d, J = 6.8 Hz, 1H), 7.78 (d, J = 7.2 Hz, 1H), 7.45 (s, 1H), 6.86 (s, 1H), 6.57-6.63 (m, 1H), 6.23 (d, J = 13.6 Hz, 1H), 5.74 (d, J = 8.8 Hz, 1H), 4.13 (s, 3H), 3.85 (s, 3H), 3.16-3.18 (m, 4H), 2.73 (brs, 4H), 2.37 (s, 3H), 1.89 (s, 2H). |
| Final Product 48 | C2 | | yield: 8%. MS (ESI+) m/z = 527.26 [M + H]+. 1H NMR (500 MHz, DMSO-d6) δ 9.05 (s, 1H), 8.82 (s, 1H), 8.65 (s, 1H), 8.37 (s, 1H), 8.34 (s, 1H), 8.11 (s, 1H), 7.88 (d, J = 8.5 Hz, 1H), 7.79 (d, J = 8.5 Hz, 1H), 7.48 (s, 1H), 6.88 (s, 1H), 6.57-6.63 (m, 1H), 6.23 (d, J = 17.0 Hz, 1H), 5.75 (d, J = 10.0 Hz, 1H), 4.14 (s, 3H), 3.87 (s, 3H), 2.51-2.95 (m, 8H), 2.37 (s, 1H), 1.03 (d, J = 13.5 Hz, 6H). |
| Final Product 49 | C2 | | yield: 24.6%. MS (ESI+) m/z = 527.20 [M + H]+. 1H NMR (400 MHz, DMSO-d6) δ 9.05 (s, 1H), 8.82 (s, 1H), 8.64 (s, 1H), 8.37 (s, 1H), 8.37 (s, 1H), 8.10 (d, J = 0.4 Hz, 1H), 7.87 (d, J = 6.4 Hz, 1H), 7.78 (dd, J = 0.8, 6.8 Hz, 1H), 7.48 (s, 1H), 6.88 (s, 1H), 6.57-6.63 (m, 1H), 6.23 (dd, J = 1.2, 13.6 Hz, 1H), 5.73 (d, J = 8.8 Hz, 1H), 4.13 (s, 3H), 3.86 (s, 3H), 2.96 (d, J = 9.2 Hz, 1H), 2.76-2.88 (m, 4H), 2.66 (s, 1H), 2.52-2.57 (m, 2H), 2.37-2.39 (m, 1H), 1.01-1.05 (m, 6H). |
| Final Product 50 | C2 | | yield: 31%. MS (ESI+) m/z = 513.21 [M + H]+. 1H NMR (300 MHz, DMSO-d6) δ 9.05 (s, 1H), 8.82 (s, 1H), 8.65 (s, 1H), 8.37 (s, 1H), 8.34 (s, 1H), 8.11 (s, 1H), 7.88 (d, J = 8.5 Hz, 1H), 7.78 (d, J = 8.5 Hz, 1H), 7.48 (s, 1H), 6.87 (s, 1H), 6.61-6.70 (m, 1H), 6.23 (d, J = 17.0 Hz, 1H), 5.74 (d, J = 11.9 Hz, 1H), 4.17 (s, 3H), 3.87 (s, 3H), 2.70-2.90 (m, 4H), 2.25-2.46 (m, 6H), 1.02 (d, J = 6.1 Hz, 3H). |
| Final Product 51 | C2 | | yield: 35.7%. MS (ESI+) m/z = 513.23 [M + H]+. 1H NMR (400 MHz, DMSO-d6) δ 9.05 (s, 1H), 8.82 (s, 1H), 8.64 (s, 1H), 8.37 (s, 1H), 8.34 (s, 1H), 8.11 (d, J = 0.4 Hz, 1H), 7.87 (d, J = 6.8 Hz, 1H), 7.78 (dd, J = 0.8, 6.8 Hz, 1H), 7.47 (s, 1H), 6.86 (s, 1H), 6.58-6.64 (m, 1H), 6.23 (dd, J = 1.2, 13.6 Hz, 1H), 5.74 (d, J = 8.8 Hz, 1H), 4.13 (s, 3H), 3.86 (s, 3H), 2.78-2.94 (m, 4H), 2.44 (t, J = 8.0 Hz, 2H), 2.32 (s, 1H), 2.25 (s, 3H), 1.01 (d, J = 4.8 Hz, 3H). |

TABLE 4-continued

Final Products 19-262

| No. of Final Products | No. of Intermediates | Structure of Final Products | NMR or MS |
|---|---|---|---|
| Final Product 52 | C2 | 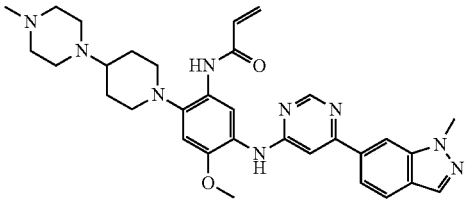 [SMILES: C=CC(=O)Nc1cc(Nc2cc(-c3ccc4cnn(C)c4c3)ncn2)c(OC)cc1N1CCC(N2CCN(C)CC2)CC1] | MS (ESI+) m/z = 582.27 [M + H]+. 1H NMR (400 MHz, DMSO-d6) δ 9.02 (s, 1H), 8.81 (s, 1H), 8.64 (s, 1H), 8.39 (s, 1H), 8.34 (s, 1H), 8.10 (d, J = 0.4 Hz, 1H), 7.87 (d, J = 6.8 Hz, 1H), 7.78 (dd, J = 0.8, 6.8 Hz, 1H), 7.46 (s, 1H), 6.85 (s, 1H), 6.65-6.71 (m, 1H), 6.22 (dd, J = 0.4, 13.6 Hz, 1H), 5.74 (d, J = 9.2 Hz, 1H), 4.13 (s, 3H), 3.85 (s, 3H), 3.07 (d, J = 8.0 Hz, 2H), 2.68 (t, J = 9.2 Hz, 2H), 2.56 (s, 4H), 2.30-2.40 (m, 5H), 2.20 (s, 3H), 1.85 (d, J = 8.8 Hz, 2H), 1.70-1.75 (m, 2H). |
| Final Product 53 | C2 | 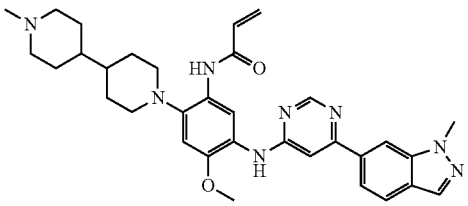 [SMILES: C=CC(=O)Nc1cc(Nc2cc(-c3ccc4cnn(C)c4c3)ncn2)c(OC)cc1N1CCC(C2CCN(C)CC2)CC1] | yield: 36.4%. MS (ESI+) m/z = 581.25 [M + H]+. 1H NMR (400 MHz, DMSO-d6) δ 9.01 (s, 1H), 8.80 (s, 1H), 8.63 (s, 1H), 8.37 (s, 1H), 8.34 (s, 1H), 8.10 (s, 1H), 7.87 (d, J = 6.8 Hz, 1H), 7.78 (dd, J = 0.8, 6.8 Hz, 1H), 7.46 (s, 1H), 6.85 (s, 1H), 6.62-6.68 (m, 1H), 6.23 (dd, J = 1.2, 13.6 Hz, 1H), 5.73 (d, J = 8.8 Hz, 1H), 4.13 (s, 3H), 3.85 (s, 3H), 3.05 (d, J = 9.2 Hz, 2H), 2.82 (d, J = 8.4 Hz, 2H), 2.63 (t, J = 9.2 Hz, 2H), 2.16 (s, 3H), 1.83 (t, J = 8.0 Hz, 2H), 1.76 (d, J = 9.2 Hz, 2H), 1.69 (d, J = 10.0 Hz, 2H), 1.47 (q, J = 7.6 Hz, 2H), 1.16-1.23 (m, 3H), 1.05-1.10 (m, 1H). |
| Final Product 54 | C2 | 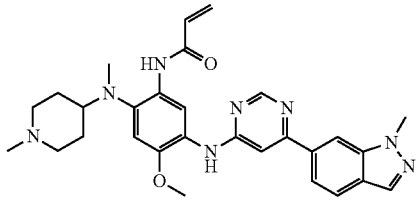 [SMILES: C=CC(=O)Nc1cc(Nc2cc(-c3ccc4cnn(C)c4c3)ncn2)c(OC)cc1N(C)C1CCN(C)CC1] | MS (ESI+) m/z = 527.25 [M + H]+. 1H NMR (500 MHz, DMSO-d6) δ 9.36 (s, 1H), 8.68 (s, 1H), 8.24 (s, 1H), 8.07 (s, 1H), 7.79 (d, J = 8.5 Hz, 1H), 7.54 (s, 1H), 7.21 (s, 1H), 6.71 (s, 1H), 6.45-6.70 (m, 2H), 6.22 (dd, J = 2.0, 17.0 Hz, 1H), 5.73 (dd, J = 1.5, 10.0 Hz, 1H), 4.96 (s, 1H), 4.10 (s, 3H), 3.77 (s, 3H), 3.43 (brs, 1H), 3.32 (s, 3H), 2.77 (brs, 2H), 2.22 (s, 3H), 2.14 (s, 2H), 1.95-2.01 (m, 2H), 1.46-1.54 (m, 2H). |
| Final Product 55 | C2 | 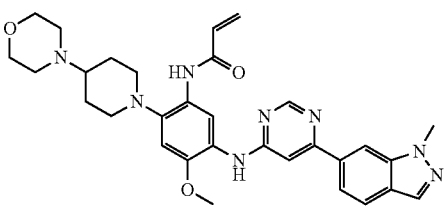 [SMILES: C=CC(=O)Nc1cc(Nc2cc(-c3ccc4cnn(C)c4c3)ncn2)c(OC)cc1N1CCC(N2CCOCC2)CC1] | MS (ESI+) m/z = 569.23 [M + H]+. 1H NMR (500 MHz, DMSO-d6) δ 9.03 (s, 1H), 8.81 (s, 1H), 8.64 (s, 1H), 8.39 (s, 1H), 8.34 (s, 1H), 8.11 (d, J = 0.5 Hz, 1H), 7.87 (d, J = 8.5 Hz, 1H), 7.79 (dd, J = 1.0, 8.5 Hz, 1H), 7.47 (s, 1H), 6.86 (s, 1H), 6.65-6.71 (m, 1H), 6.24 (dd, J = 1.5, 17.0 Hz, 1H), 5.74 (d, J = 11.5 Hz, 1H), 4.14 (s, 3H), 3.85 (s, 3H), 3.60 (t, J = 4.5 Hz, 4H), 3.08 (d, J = 7.5 Hz, 2H), 2.67 (t, J = 11.5 Hz, 2H), 2.52 (s, 4H), 2.26 (t, J = 11.0 Hz, 1H), 1.88 (d, J = 11.0 Hz, 2H), 1.69-1.74 (m, 2H). |

TABLE 4-continued

Final Products 19-262

| No. of Final Products | No. of Intermediates | Structure of Final Products | NMR or MS |
|---|---|---|---|
| Final Product 56 | C5 | | MS (ESI+) m/z = 541.24 [M + H]+. 1H NMR (500 MHz, DMSO-d6) δ 9.07 (s, 1H), 8.80 (s, 1H), 8.63 (s, 1H), 8.39 (s, 1H), 8.25 (s, 1H), 7.82 (d, J = 8.5 Hz, 1H), 7.74 (dd, J = 1.0, 8.5 Hz, 1H), 7.48 (s, 1H), 6.85 (s, 1H), 6.58-6.64 (m, 1H), 6.23 (dd, J = 1.0, 17.0 Hz, 1H), 5.74 (dd, J = 4.5, 15.5 Hz, 1H), 4.02 (s, 3H), 3.87 (s, 3H), 2.88 (d, J = 10.5 Hz, 2H), 2.54 (d, J = 10.5 Hz, 2H), 2.50 (d, J = 1.7 Hz, 3H), 2.44 (brs, 2H), 2.23 (s, 3H), 1.03 (d, J = 6.0 Hz, 6H). |
| Final Product 57 | C1 | | yield: 54%. MS (ESI+) m/z = 513.15 [M + H]+. 1H NMR (500 MHz, DMSO-d6) δ 9.33 (s, 1H), 8.76 (s, 1H), 8.63 (s, 1H), 8.61 (s, 1H), 8.51 (s, 1H), 8.18 (s, 1H), 8.08 (d, J = 9.0 Hz, 1H), 7.76 (d, J = 9.0 Hz, 1H), 7.43 (s, 1H), 6.98 (s, 1H), 6.58-6.64 (m, 1H), 6.24 (d, J = 17.0 Hz, 1H), 5.75 (d, J = 10.5 Hz, 1H), 4.09 (s, 3H), 3.85 (s, 3H), 3.59-3.64 (m, 1H), 2.53-2.58 (m, 4H), 2.46-2.50 (m, 3H), 2.26 (s, 3H), 1.90-1.97 (m, 1H), 1.72-1.79 (m, 1H). |
| Final Product 58 | C1 | | MS (ESI+) m/z = 487.11 [M + H]+. 1H NMR (500 MHz, DMSO-d6) δ 9.43 (s, 1H), 8.59 (s, 1H), 8.53 (s, 1H), 8.44 (s, 1H), 8.16 (s, 1H), 8.04 (dd, J = 1.2, 9.0 Hz, 1H), 7.72 (d, J = 9.0 Hz, 1H), 7.48 (s, 1H), 7.14 (s, 1H), 6.44-6.50 (m, 1H), 6.41 (s, 1H), 6.22 (dd, J = 2.0, 17.0 Hz, 1H), 5.71 (dd, J = 2.0, 10.5 Hz, 1H), 4.89 (s, 1H), 4.07 (s, 3H), 3.83 (s, 3H), 3.20 (q, J = 6.0 Hz, 2H), 2.49 (s, 2H), 2.21 (s, 6H). |
| Final Product 59 | C1 | | MS (ESI+) m/z = 556.19 [M + H]+. 1H NMR (500 MHz, DMSO-d6) δ 9.05 (s, 1H), 8.78 (s, 1H), 8.59 (s, 1H), 8.50 (s, 1H), 8.35 (s, 1H), 8.18 (s, 1H), 8.08 (d, J = 9.0 Hz, 1H), 7.76 (d, J = 9.0 Hz, 1H), 7.40 (s, 1H), 6.88 (s, 1H), 6.60-6.66 (m, 1H), 6.24 (d, J = 17.0 Hz, 1H), 5.74 (d, J = 10.5 Hz, 1H), 4.09 (s, 3H), 3.86 (s, 3H), 2.88 (s, 4H), 2.64 (s, 4H), 2.53 (s, 4H), 2.28 (s, 6H). |
| Final Product 60 | C1 | | MS (ESI+) m/z = 556.14 [M + H]+. 1H NMR (500 MHz, DMSO-d6) δ 9.34 (s, 1H), 8.75 (s, 1H), 8.60 (s, 1H), 8.49 (s, 1H), 8.47 (s, 1H), 8.17 (s, 1H), 8.07 (dd, J = 1.5, 9.0 Hz, 1H), 7.75 (d, J = 9.0 Hz, 1H), 7.38 (s, 1H), 6.96 (s, 1H), 6.58-6.64 (m, 1H), 6.23 (dd, J = 1.5, 18.5 Hz, 1H), 5.74 (s, 1H), 4.08 (s, 3H), 3.85 (s, 3H), 2.98 (t, J = 6.5 Hz, 2H), 2.70 (s, 3H), 2.30-2.39 (m, 10H), 2.13 (s, 3H). |

TABLE 4-continued

Final Products 19-262

| No. of Final Products | No. of Intermediates | Structure of Final Products | NMR or MS |
|---|---|---|---|
| Final Product 61 | C1 | 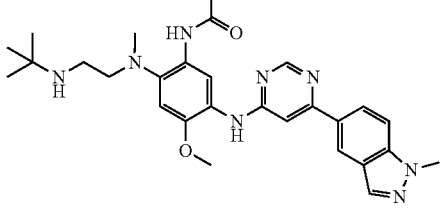 | yield: 65.4%. MS (ESI+) m/z = 529.14 [M + H]+. $^1$H NMR (500 MHz, DMSO-$d_6$) δ 9.46 (s, 1H), 8.75 (s, 1H), 8.60 (s, 1H), 8.55 (s, 1H), 8.49 (s, 1H), 8.17 (s, 1H), 8.07 (d, J = 8.5 Hz, 1H), 7.75 (d, J = 8.5 Hz, 1H), 7.35 (s, 1H), 6.94 (s, 1H), 6.64-6.69 (m, 1H), 6.25 (d, J = 17.5 Hz, 1H), 5.73 (d, J = 9.0 Hz, 1H), 4.09 (s, 3H), 3.85 (s, 3H), 3.32 (s, 1H), 2.89 (s, 2H), 2.68 (s, 3H), 2.64 (s, 2H), 1.04 (s, 9H). |
| Final Product 62 | C1 | 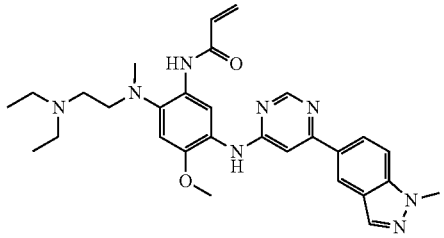 [SMILES: C=CC(=O)Nc1cc(Nc2cc(-c3ccc4c(cnn4C)c3)ncn2)c(OC)cc1N(C)CCN(CC)CC] | yield: 35.0%. MS (ESI+) m/z = 529.13 [M + H]+. $^1$H NMR (400 MHz, DMSO-$d_6$) δ 9.73 (s, 1H), 8.75 (s, 1H), 8.60 (s, 2H), 8.49 (s, 1H), 8.16 (s, 1H), 8.07 (dd, J = 1.2, 8.8 Hz, 1H), 7.74 (d, J = 9.2 Hz, 1H), 7.35 (s, 1H), 6.98 (s, 1H), 6.43-6.50 (m, 1H), 6.25 (d, J = 16.0 Hz, 1H), 5.75 (d, J = 10.8 Hz, 1H), 4.08 (s, 3H), 3.84 (s, 3H), 2.86 (s, 2H), 2.72 (s, 3H), 2.53 (s, 6H), 0.95 (t, J = 6.8 Hz, 6H). |
| Final Product 63 | C8 | 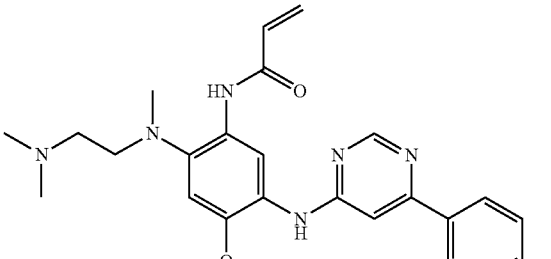 | yield: 29.7%. MS (ESI+) m/z = 504.13 [M + H]+. $^1$H NMR (300 MHz, DMSO-$d_6$) δ 10.13 (s, 1H), 9.50 (s, 1H), 8.90 (s, 1H), 8.86 (s, 1H), 8.65 (s, 2H), 8.19 (s, 2H), 7.44 (s, 1H), 7.03 (s, 1H), 6.37-6.47 (m, 1H), 6.27 (d, J = 16.2 Hz, 1H), 5.77 (d, J = 9.6 Hz, 1H), 3.85 (s, 3H), 2.89 (brs, 2H), 2.73 (s, 3H), 2.36 (brs, 2H), 2.24 (s, 6H). |
| Final Product 64 | C8 | 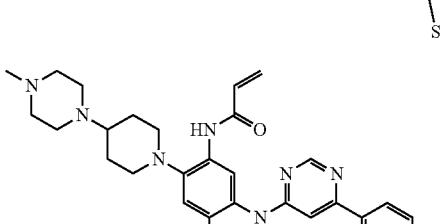 | yield: 22.7%. MS (ESI+) m/z = 585.21 [M + H]+. $^1$H NMR (500 MHz, DMSO-$d_6$) δ 9.49 (s, 1H), 9.01 (s, 1H), 8.90 (s, 1H), 8.85 (s, 1H), 8.63 (s, 1H), 8.32 (s, 1H), 8.19 (s, 2H), 7.41 (s, 1H), 6.86 (s, 1H), 6.66-6.72 (m, 1H), 6.26 (d, J = 16.5 Hz, 1H), 5.75 (d, J = 11.0 Hz, 1H), 3.84 (s, 3H), 3.07 (d, J = 11.5 Hz, 2H), 2.68 (t, J = 11.0 Hz, 2H), 2.52 (s, 4H), 2.26-2.36 (m, 5H), 2.16 (s, 3H), 1.85 (d, J = 11.5 Hz, 2H), 1.68-1.74 (m, 2H). |
| Final Product 65 | C9 | 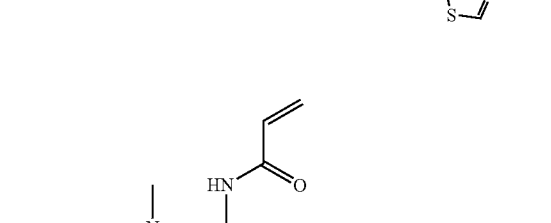 | MS (ESI+) m/z = 518.26 [M + H]+. $^1$H NMR (400 MHz, DMSO-$d_6$) δ 10.12 (s, 1H), 8.82 (s, 1H), 8.75 (d, J = 1.6 Hz, 1H), 8.64 (s, 1H), 8.62 (s, 1H), 8.11 (dd, J = 1.6, 8.8 Hz, 1H), 8.00 (d, J = 8.8 Hz, 1H), 7.40 (s, 1H), 7.02 (s, 1H), 6.37-6.45 (m, 1H), 6.24 (dd, J = 1.6, 16.8 Hz, 1H), 5.75 (dd, J = 2.0, 12.0 Hz, 1H), 3.84 (s, 3H), 2.89 (s, 2H), 2.83 (s, 3H), 2.72 (s, 3H), 2.34 (m, 2H), 2.22 (s, 6H). |

TABLE 4-continued

Final Products 19-262

| No. of Final Products | No. of Intermediates | Structure of Final Products | NMR or MS |
|---|---|---|---|
| Final Product 66 | C10 | | MS (ESI+) m/z = 527.31 [M + H]+. 1H NMR (400 MHz, DMSO-d6) δ 9.32 (s, 1H), 8.64 (s, 1H), 8.62 (s, 1H), 8.60 (s, 1H), 8.53 (s, 1H), 8.18 (s, 1H), 8.11 (d, J = 8.8 Hz, 1H), 7.76 (d, J = 8.8 Hz, 1H), 7.42 (s, 1H), 6.97 (s, 1H), 6.56-6.68 (m, 1H), 6.25 (d, J = 17.1 Hz, 1H), 5.75 (d, J = 10.0 Hz, 1H), 4.09-4.14 (m, 5H), 3.61 (s, 1H), 2.58 (s, 3H), 2.53-2.51 (m, 1H), 2.49-2.48 (m, 1H), 2.41 (t, J = 6.3 Hz, 2H), 2.23 (s, 3H), 1.89-1.91 (m, 1H), 1.73-1.75 (m, 1H), 1.32 (t, J = 6.9 Hz, 3H). |
| Final Product 67 | C11 | | MS (ESI+) m/z = 592.26 [M + H]+. 1H NMR (400 MHz, DMSO-d6) δ 9.44 (s, 1H), 9.03 (s, 1H), 8.60 (s, 1H), 8.50 (s, 1H), 8.45 (s, 1H), 8.17 (s, 1H), 8.08 (d, J = 9.2 Hz, 1H), 7.75 (d, J = 8.4 Hz, 1H), 7.35 (s, 1H), 7.32 (s, 0.3H), 7.13 (s, 0.5H), 7.11 (s, 1H), 6.95 (s, 0.2H), 6.61-6.68 (m, 1H), 6.6 (d, J = 16.8 Hz, 1H), 5.79 (d, J = 10.0 Hz, 1H), 4.08 (s, 3H), 2.97 (s, 2H), 2.69 (s, 3H), 2.27-2.39 (m, 10H), 2.11 (s, 3H). |
| Final Product 68 | C3 | | MS (ESI+) m/z = 553.46 [M + H]+. 1H NMR (400 MHz, DMSO-d6) δ 9.02 (s, 1H), 9.00 (s, 1H), 8.87 (s, 1H), 8.48 (d, J = 4.8 Hz, 1H), 8.28 (d, J = 8.8 Hz, 1H), 8.15 (s, 1H), 7.98 (s, 1H), 7.71 (d, J = 8.8 Hz, 1H), 7.48 (d, J = 5.2 Hz, 1H), 6.87 (s, 1H), 6.68-6.75 (m, 1H), 6.32 (d, J = 16.4 Hz, 1H), 5.79 (d, J = 10.4 Hz, 1H), 4.09 (s, 3H), 3.88 (s, 3H), 3.00 (d, J = 10.4 Hz, 2H), 2.70 (t, J = 10.8 Hz, 2H), 2.50 (s, 4H), 2.09 (s, 1H), 1.94 (d, J = 11.2 Hz, 2H), 1.69 (s, 6H). |
| Final Product 69 | C1 | | MS (ESI+) m/z = 527.16 [M + H]+. 1H NMR (400 MHz, DMSO-d6) δ 9.57 (s, 1H), 8.74 (s, 1H), 8.61 (s, 1H), 8.56 (s, 1H), 8.50 (s, 1H), 8.17 (s, 1H), 8.07 (dd, J = 7.2, 0.8 Hz, 1H), 7.76 (d, J = 7.2 Hz, 1H), 7.43 (s, 1H), 6.99 (s, 1H), 6.49-6.55 (m, 1H), 6.23 (d, J = 13.6 Hz, 1H), 5.73 (d, J = 8.4 Hz, 1H), 4.08 (s, 3H), 3.84 (s, 3H), 2.90 (s, 1H), 2.65 (s, 3H), 2.57 (s, 1H), 2.00-2.02 (m, 4H), 1.98-1.99 (d, J = 2.0 Hz, 2H), 1.72 (d, J = 5.6 Hz, 2H), 1.40-1.51 (m, 2H). |
| Final Product 70 | C1 | | MS (ESI+) m/z = 610.18 [M + H]+. 1H NMR (400 MHz, DMSO-d6) δ 9.12 (s, 1H), 8.73 (s, 1H), 8.59 (s, 1H), 8.51 (s, 1H), 8.49 (s, 1H), 8.17 (s, 1H), 8.07 (dd, J = 9.2, 1.6 Hz, 1H), 7.75 (d, J = 8.8 Hz, 1H), 7.41 (s, 1H), 6.92 (s, 1H), 6.59-6.70 (m, 1H), 6.24 (dd, J = 16.8, 1.6 Hz, 1H), 5.71 (dd, J = 10.0, 1.6 Hz, 1H), 4.08 (s, 3H), 3.83 (s, 3H), 2.85 (d, J = 11.2 Hz, 2H), 2.74 (d, J = 11.2 Hz, 2H), 2.67 (s, |

TABLE 4-continued

Final Products 19-262

| No. of Final Products | No. of Intermediates | Structure of Final Products | NMR or MS |
|---|---|---|---|
| | | | 1H), 2.63 (s, 3H), 2.04-2.10 (m, 4H), 2.00 (t, J = 11.6 Hz, 2H), 1.79 (t, J = 11.2 Hz, 2H), 1.70 (d, J = 10.8 Hz, 2H), 1.62 (d, J = 11.6 Hz, 2H), 1.50-1.52 (m, 2H), 1.36-1.38 (m, 2H) |
| Final Product 71 | C1 | | yield: 18.79%. MS (ESI+) m/z = 555.19 [M + H]+. 1H NMR (400 MHz, DMSO-d6) δ 9.10 (s, 1H), 8.73 (s, 1H), 8.60 (s, 1H), 8.50 (s, 1H), 8.43 (s, 1H), 8.18 (s, 1H), 8.08 (d, J = 7.2 Hz, 1H), 7.76 (d, J = 6.8 Hz, 1H), 7.41 (s, 1H), 6.89 (s, 1H), 6.59-6.65 (m, 1H), 6.24 (d, J = 13.2 Hz, 1H), 5.73 (d, J = 8.4 Hz, 1H), 4.09 (s, 3H), 3.84 (s, 3H), 2.65-2.69 (m, 1H), 2.64 (s, 3H), 2.50-2.51 (m, 1H), 2.00-2.14 (m, 6H), 1.82 (t, J = 9.6 Hz, 4H), 1.35-1.42 (m, 2H), 1.05-1.12 (m, 2H). |
| Final Product 72 | C1 | | yield: 27.52%. MS (ESI+) m/z = 610.23 [M + H]+. 1H NMR (400 MHz, DMSO-d6) δ 9.14 (s, 1H), 8.76 (s, 1H), 8.69 (s, 1H), 8.61 (s, 1H), 8.50 (s, 1H), 8.18 (s, 1H), 8.08 (dd, J = 7.2, 1.2 Hz, 1H), 7.76 (d, J = 7.2 Hz, 1H), 7.43 (s, 1H), 6.99 (s, 1H), 6.56-6.62 (m, 1H), 6.22 (dd, J = 13.6, 0.8 Hz, 1H), 5.74 (d, J = 8.8 Hz, 1H), 4.09 (s, 3H), 3.83 (s, 3H), 2.99 (s, 1H), 2.59 (s, 3H), 2.42 (s, 3H), 2.32-2.40 (m, 5H), 2.16 (brs, 4H), 1.77 (brs, 4H), 1.41 (t, J = 5.6 Hz, 2H), 1.25-1.29 (m, 2H). |
| Final Product 73 | C2 | | MS (ESI+) m/z = 527.17 [M + H]+. 1H NMR (500 MHz, DMSO-d6) δ 9.60 (s, 1H), 8.81 (s, 1H), 8.66 (s, 1H), 8.58 (s, 1H), 8.34 (s, 1H), 8.10 (s, 1H), 7.88 (d, J = 8.5 Hz, 1H), 7.78 (d, J = 8.5 Hz, 1H), 7.52 (s, 1H), 7.00 (s, 1H), 6.50-6.55 (m, 1H), 6.22 (dd, J = 16.5 Hz, 1H), 5.71 (dd, J = 11.0 1H), 4.13 (s, 3H), 3.85 (s, 3H), 2.91 (s, 1H), 2.65 (s, 3H), 2.56 (brs, 1H), 2.11 (s, 4H), 1.99-2.03 (m, 2H), 1.72 (s, 2H), 1.40-1.52 (m, 2H). |
| Final Product 74 | C2 | | yield: 54%. MS (ESI+) m/z = 513.15 [M + H]+. 1H NMR (500 MHz, DMSO-d6) δ 9.34 (s, 1H), 8.82 (s, 1H), 8.65 (s, 1H), 8.63 (s, 1H), 8.34 (s, 1H), 8.11 (s, 1H), 7.88 (d, J = 8.5 Hz, 1H), 7.79 (d, J = 8.5 Hz, 1H), 7.52 (s, 1H), 6.99 (s, 1H), 6.58-6.63 (m, 1H), 6.24 (d, J = 17.0 Hz, 1H), 5.75 (d, J = 11.0 Hz, 1H), 4.14 (s, 3H), 3.85 (s, 3H), 3.58-3.63 (m, 1H), 2.60-2.70 (s, 1H), 2.59 (s, 3H), 2.50-2.52 (s, 1H), 2.42-2.45 (m, 2H), 2.25 (s, 3H), 1.89-1.97 (m, 1H), 1.73-1.79 (m, 1H). |

TABLE 4-continued

Final Products 19-262

| No. of Final Products | No. of Intermediates | Structure of Final Products | NMR or MS |
|---|---|---|---|
| Final Product 75 | C24 | | MS (ESI⁺) m/z = 529.17 [M + H]⁺. ¹H NMR (500 MHz, DMSO-d₆) δ 10.11 (s, 1H), 8.69 (s, 1H), 8.62 (s, 1H), 8.56 (s, 1H), 8.53 (s, 1H), 8.17 (s, 1H), 8.11 (dd, J = 9.0, 1.5 Hz, 1H), 7.76 (d, J = 9.0 Hz, 1H), 7.40 (s, 1H), 7.02 (s, 1H), 6.38-6.44 (m, 1H), 6.26 (dd, J = 16.5, 1.5 Hz, 1H), 5.76 (dd, J = 10.0, 2.0 Hz, 1H), 4.61 (q, J = 12.0 Hz, 1H), 4.09 (s, 3H), 2.88 (s, 2H), 2.71 (s, 3H), 2.33 (brs, 2H), 2.22 (brs, 6H), 1.25 (d, J = 6.0 Hz, 6H). |
| Final Product 76 | C1 | | MS (ESI⁺) m/z = 529.27 [M + H]⁺. ¹H NMR (400 MHz, DMSO-d₆) δ 8.92 (s, 1H), 8.61 (s, 1H), 8.50 (d, J = 0.8 Hz, 1H), 8.45 (s, 1H), 8.13 (d, J = 0.8 Hz, 1H), 8.10 (dd, J = 8.8, 1.6 Hz, 1H), 7.70 (d, J = 8.8 Hz, 1H), 7.35 (s, 1H), 6.97 (s, 1H), 6.57- 6.60 (m, 1H), 6.25 (dd, J = 16.8, 1.6 Hz, 1H), 5.73 (dd, J = 10.0, 2.0 Hz, 1H), 4.08 (s, 3H), 3.87 (s, 3H), 3.46 (brs, 2H), 3.10 (brs, 2H), 2.82-2.92 (m, 3H), 2.72 (s, 3H), 1.95 (s, 3H). |
| Final Product 77 | C2 | | yield: 18%. MS (ESI⁺) m/z = 556.22 [M + H]⁺. ¹H NMR (500 MHz, DMSO-d₆) δ 9.05 (s, 1H), 8.82 (s, 1H), 8.64 (s, 1H), 8.38 (s, 1H), 8.34 (s, 1H), 8.11 (s, 1H), 7.87 (d, J = 8.5 Hz, 1H), 7.79 (d, J = 8.5 Hz, 1H), 7.48 (s, 1H), 6.90 (s, 1H), 6.60-6.66 (m, 1H), 6.23 (d, J = 17.0 Hz, 1H), 5.74 (d, J = 10.5 Hz, 1H), 4.14 (s, 3H), 3.86 (s, 3H), 2.88 (brs, 4H), 2.62 (brs, 4H), 2.46-2.50 (m, 2H), 2.36-2.40 (m, 2H), 2.17 (s, 6H). |
| Final Product 78 | C2 | | MS (ESI⁺) m/z = 556.18 [M + H]⁺. ¹H NMR (500 MHz, DMSO-d₆) δ 9.36 (s, 1H), 8.81 (s, 1H), 8.64 (s, 1H), 8.47 (s, 1H), 8.34 (s, 1H), 8.10 (s, 1H), 7.87 (d, J = 8.5 Hz, 1H), 7.78 (d, J = 8.5 Hz, 1H), 7.47 (s, 1H), 6.95 (s, 1H), 6.58-6.64 (m, 1H), 6.23 (dd, J = 18.5, 1.5 Hz, 1H), 5.75 (d, J = 10.3 Hz, 1H), 4.13 (s, 3H), 3.85 (s, 3H), 2.98 (t, J = 6.5 Hz, 2H), 2.49-2.50 (m, 3H), 2.29-2.39 (m, 10H), 2.12 (s, 3H). |
| Final Product 79 | C2 | | yield: 57.6%. MS (ESI⁺) m/z = 515.18 [M + H]⁺. ¹H NMR (400 MHz, DMSO-d₆) δ 9.16 (s, 1H), 8.81 (s, 1H), 8.64 (s, 1H), 8.44 (s ,1H), 8.32 (s, 1H), 8.10 (d, J = 0.80 Hz, 1H), 7.87 (d, J = 8.4 Hz, 1H), 7.78 (dd, J = 8.4, 1.2 Hz, 1H), 7.46 (s, 1H), 6.91 (s, 1H), 6.61-6.68 (m, 1H), 6.23 (dd, J = 16.8, 1.6 Hz, 1H), 5.72 (dd, J = 12.0, 2.0 Hz, 1H), 4.13 (s, 3H), 3.85 (s, 3H), 2.83-2.87 (m, 2H), 2.67 (s, 3H), 2.27 (t, J = 6.8 Hz, 2H), 2.13 (s, 6H), 1.61-1.66 (m, 2H). |

TABLE 4-continued

Final Products 19-262

| No. of Final Products | No. of Intermediates | Structure of Final Products | NMR or MS |
|---|---|---|---|
| Final Product 80 | C2 | | MS (ESI+) m/z = 529.16 [M + H]+. 1HNMR (400 MHz, DMSO-d6) δ 9.75 (s, 1H), 8.81 (s, 1H), 8.64 (s, 1H), 8.61 (s, 1H), 8.33 (s, 1H), 8.10 (d, J = 0.8 Hz, 1H), 7.86 (d, J = 8.4 Hz, 1H), 7.77 (dd, J = 8.8, 1.2 Hz, 1H), 7.45 (s, 1H), 6.98 (s, 1H), 6.44-6.51 (m, 1H), 6.24 (d, J = 16.8 Hz, 1H), 5.75 (t, J = 6.4 Hz, 1H), 4.12 (s, 3H), 3.84 (s, 3H), 2.86 (s, 2H), 2.71 (s, 3H), 2.51-2.53 (m, 6H), 0.95 (t, J = 6.8 Hz, 6H). |
| Final Product 81 | C8 | | MS (ESI+) m/z = 530.09 [M + H]+. 1H NMR (500 MHz, DMSO-d6) δ 9.50 (s, 1H), 9.15 (s, 1H), 8.89 (s, 1H), 8.85 (s, 1H), 8.64 (s, 1H), 8.45 (s, 1H), 8.17-8.22 (m, 2H), 7.47 (s, 1H), 6.93 (s, 1H), 6.61-6.67 (m, 1H), 6.24 (dd, J = 17.0, 1.5 Hz, 1H), 5.73 (dd, J = 11.5, 1.5 Hz, 1H), 3.84 (s, 3H), 2.76 (d, J = 10.5 Hz, 2H), 2.69 (t, J = 11.0 Hz, 1H), 2.64 (s, 3H), 2.11 (s, 3H), 1.77 (t, J = 10.5 Hz, 2H), 1.68 (d, J = 11.0 Hz, 2H), 1.55-1.62 (m, 2H). |
| Final Product 82 | C8 | | MS (ESI+) m/z = 530.19 [M + H]+. 1H NMR (500 MHz, DMSO-d6) δ 9.50 (s, 1H), 9.07 (s, 1H), 8.90 (s, 1H), 8.86 (s, 1H), 8.64 (s, 1H), 8.31 (s, 1H), 8.17-8.21 (m, 2H), 7.42 (s, 1H), 6.85 (s, 1H), 6.58-6.64 (m, 1H), 6.26 (d, J = 17.0 Hz, 1H), 5.75 (d, J = 10.5 Hz, 1H), 3.86 (s, 3H), 2.89 (d, J = 10.5 Hz, 2H), 2.54-2.60 (m, 2H), 2.44 (brs, 2H), 2.24 (s, 3H), 1.04 (d, J = 6.0 Hz, 6H). |
| Final Product 83 | C19 | | MS (ESI+) m/z = 555.25 [M + H]+. 1H NMR (500 MHz, DMSO-d6) δ 9.05 (s, 1H), 8.75 (s, 1H), 8.60 (s, 1H), 8.49 (s, 1H), 8.35 (s, 1H), 8.20 (s, 1H), 8.05 (dd, J = 9.0, 1.5 Hz, 1H), 7.81 (d, J = 9.0 Hz, 1H), 7.37 (s, 1H), 6.85 (s, 1H), 6.58-6.63 (m, 1H), 6.24 (d, J = 17.0 Hz, 1H), 5.74 (d, J = 10.5 Hz, 1H), 5.01-5.06 (m, 1H), 3.86 (s, 3H), 2.88 (d, J = 10.5 Hz, 2H), 2.54 (t, J = 10.5 Hz, 2H), 2.23-2.45 (m, 3H), 1.51 (d, J = 7.0 Hz, 6H), 1.04 (t, J = 6.0 Hz, 6H). |
| Final Product 84 | C19 | | yield: 24.39%. MS (ESI+) m/z = 610.29 [M + H]+. 1H NMR (500 MHz, DMSO-d6) δ 9.00 (s, 1H), 8.74 (s, 1H), 8.59 (s, 1H), 8.49 (s, 1H), 8.36 (s, 1H), 8.19 (s, 1H), 8.05 (d, J = 8.5 Hz, 1H), 7.80 (d, J = 8.5 Hz, 1H), 7.35 (s, 1H), 6.85 (s, 1H), 6.65-6.71 (m, 1H), 6.24 (d, J = 16.5 Hz, 1H), 5.74 (d, J = 10.5 Hz, 1H), 5.01-5.06 (m, 1H), 3.84 (s, 3H), 3.06 (d, J = 10.5 Hz, 2H), 2.68 (t, J = 11.5 Hz, 2H), 2.53 (brs, 4H), 2.26-2.33 (m, 5H), 2.16 (s, 3H), 1.84 (d, J = 11.0 Hz, 2H), 1.68-1.74 (m, 2H), 1.55 (d, J = 6.0 Hz, 6H). |

TABLE 4-continued

Final Products 19-262

| No. of Final Products | No. of Intermediates | Structure of Final Products | NMR or MS |
|---|---|---|---|
| Final Product 85 | C19 | | MS (ESI+) m/z = 555.28 [M + H]+. 1H NMR (500 MHz, DMSO-d6) δ 9.14 (s, 1H), 8.75 (s, 1H), 8.60 (s, 1H), 8.50 (s, 2H), 8.20 (s, 1H), 8.05 (dd, J = 9.0, 1.0 Hz, 1H), 7.82 (d, J = 9.0 Hz, 1H), 7.42 (s, 1H), 6.94 (s, 1H), 6.60-6.66 (m, 1H), 6.23 (m, 1H), 5.73 (d, J = 11.5, 1.5 Hz, 1H), 5.02-5.06 (m, 1H), 3.85 (s, 3H), 2.77 (d, J = 9.5 Hz, 2H), 2.65-2.68 (m, 1H), 2.65 (s, 3H), 2.13 (s, 3H), 1.81 (brs, 2H), 1.69 (d, J = 10.5 Hz, 2H), 1.61 (t, J = 9.0 Hz, 2H), 1.51 (d, J = 6.6 Hz, 6H). |
| Final Product 86 | C19 | | yield: 40%. MS (ESI+) m/z = 609.32 [M + H]+. 1H NMR (500 MHz, DMSO-d6) δ 8.99 (s, 1H), 8.75 (s, 1H), 8.59 (s, 1H), 8.49 (s, 1H), 8.36 (s, 1H), 8.19 (s, 1H), 8.05 (d, J = 8.5 Hz, 1H), 7.81 (d, J = 9.0 Hz, 1H), 7.36 (s, 1H), 6.85 (s, 1H), 6.62-6.66 (m, 1H), 6.24 (d, J = 16.5 Hz, 1H), 5.74 (d, J = 10.0 Hz, 1H), 5.02-5.05 (m, 1H), 3.84 (s, 3H), 3.06 (d, J = 11.0 Hz, 2H), 2.83 (d, J = 9.5 Hz, 2H), 2.63 (t, J = 11.5 Hz, 2H), 2.18 (s, 3H), 1.86 (brs, 2H), 1.76 (d, J = 11.5 Hz, 2H), 1.70 (d, J = 12.5 Hz, 2H), 1.46-1.51 (m, 8H), 1.16-1.24 (m, 4H). |
| Final Product 87 | C19 | | MS (ESI+) m/z = 638.22 [M + H]+. 1H NMR (400 MHz, DMSO-d6) δ 9.13 (s, 1H), 8.74 (s, 1H), 8.60 (s, 1H), 8.52 (s, 1H), 8.50 (s, 1H), 8.19 (s, 1H), 8.05 (d, J = 7.2 Hz, 1H), 7.81 (d, J = 6.8 Hz, 1H), 7.41 (s, 1H), 6.93 (s, 1H), 6.61-6.66 (m, 1H), 6.23 (d, J = 13.6 Hz, 1H), 5.72 (d, J = 8.8 Hz, 1H), 5.04 (t, J = 5.6 Hz, 1H), 3.84 (s, 3H), 2.85 (d, J = 8.8 Hz, 2H), 2.75 (d, J = 8.8 Hz, 2H), 2.64-2.68 (m, 1H), 2.63 (s, 3H), 2.10 (brs, 4H), 2.00 (t, J = 8.8 Hz, 2H), 1.79 (t, J = 8.8 Hz, 2H), 1.70 (d, J = 8.8 Hz, 2H), 1.61 (d, J = 8.8 Hz, 2H), 1.50 (d, J = 5.2 Hz, 8H), 1.36-1.40 (m, 2H). |
| Final Product 88 | C1 | | MS (ESI+) m/z = 515.23 [M + H]+. 1H NMR (500 MHz, DMSO-d6) δ 9.90 (s, 1H), 8.76 (s, 1H), 8.64 (s, 1H), 8.60 (s, 1H), 8.49 (s, 1H), 8.17 (s, 1H), 8.07 (dd, J = 8.9, 1.1 Hz, 1H), 7.75 (d, J = 8.9 Hz, 1H), 7.37 (s, 1H), 7.00 (s, 1H), 6.43 (s, 1H), 6.25 (d, J = 17.0 Hz, 1H), 5.76 (d, J = 10.4 Hz, 1H), 4.08 (s, 3H), 3.85 (s, 3H), 2.88 (s, 2H), 2.71 (s, 3H), 2.40-2.45 (m, 4H), 2.20 (s, 3H), 1.00 (brs, 3H). |
| Final Product 89 | C20 | | MS (ESI+) m/z = 529.19 [M + H]+. 1H NMR (500 MHz, DMSO-d6) δ 10.12 (s, 1H), 8.66 (s, 2H), 8.61 (s, 1H), 8.51 (s, 1H), 8.18 (s, 1H), 8.08 (d, J = 9.0 Hz, 1H), 7.78 (d, J = 9.0 Hz, 1H), 7.37 (s, 1H), 7.01 (s, 1H), 6.37-6.43 (m, 1H), 6.25 (d, J = 17.0 Hz, 1H), 5.76 (d, J = 10.0 Hz, 1H), 4.48 (q, J = 7.5 Hz, 2H), 4.11 (q, J = 6.5 Hz, 2H), 2.87 (t, J = 5.5 Hz, 2H), 2.71 (s, 3H), 2.32 (t, J = 5.5 Hz, 2H), 2.21 (s, 6H), 1.42 (t, J = 7.0 Hz, 3H), 1.30 (t, J = 6.5 Hz, 3H). |

TABLE 4-continued

Final Products 19-262

| No. of Final Products | No. of Intermediates | Structure of Final Products | NMR or MS |
|---|---|---|---|
| Final Product 90 | C10 | 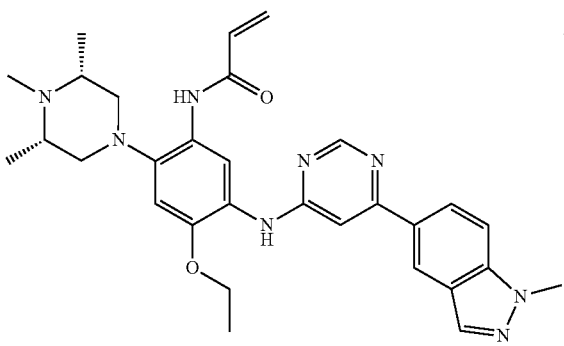 | MS (ESI+) m/z = 541.25 [M + H]+. 1H NMR (500 MHz, DMSO-d6) δ 9.04 (s, 1H), 8.65 (s, 1H), 8.60 (s, 1H), 8.51 (s, 1H), 8.32 (s, 1H), 8.17 (s, 1H), 8.09 (d, J = 8.5 Hz, 1H), 7.75 (d, J = 9.0 Hz, 1H), 7.36 (s, 1H), 6.82 (s, 1H), 6.57-6.63 (m, 1H), 6.24 (d, J = 17.0 Hz, 1H), 5.74 (d, J = 10.5 Hz, 1H), 4.12 (q, J = 7.0 Hz, 2H), 4.08 (s, 3H), 2.87 (d, J = 10.5 Hz, 2H), 2.51 (brs, 2H), 2.43 (brs, 2H), 2.23 (s, 3H), 1.31 (t, J = 7.0 Hz, 3H), 1.03 (d, J = 6.5 Hz, 6H). |
| Final Product 91 | C20 | 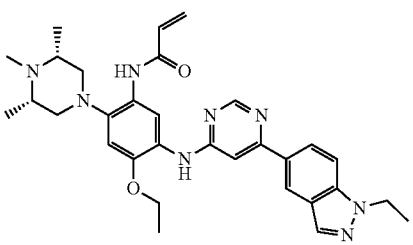 [SMILES: C=CC(=O)Nc1cc(Nc2cc(-c3ccc4c(cnn4CC)c3)ncn2)c(OCC)cc1N1C[C@@H](C)N(C)[C@@H](C)C1] | MS (ESI+) m/z = 555.31 [M + H]+. 1H NMR (500 MHz, DMSO-d6) δ 9.04 (s, 1H), 8.65 (s, 1H), 8.60 (s, 1H), 8.51 (s, 1H), 8.31 (s, 1H), 8.18 (s, 1H), 8.08 (dd, J = 9.0, 1.5 Hz, 1H), 7.78 (d, J = 9.0 Hz, 1H), 7.36 (s, 1H), 6.82 (s, 1H), 6.50-6.60 (m, 1H), 6.24 (d, J = 17.0 Hz, 1H), 5.74 (d, J = 10.7 Hz, 1H), 4.48 (q, J = 7.0 Hz, 2H), 4.12 (q, J = 7.0 Hz, 2H), 2.87 (d, J = 10.0 Hz, 2H), 2.52 (brs, 2H), 2.48 (brs, 2H), 2.23 (s, 3H), 1.42 (t, J = 7.5 Hz, 3H), 1.31 (t, J = 7.0 Hz, 3H), 1.02 (d, J = 6.0 Hz, 6H). |
| Final Product 92 | C25 | 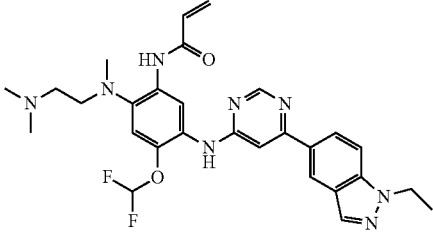 [SMILES: C=CC(=O)Nc1cc(Nc2cc(-c3ccc4c(cnn4CC)c3)ncn2)c(OC(F)F)cc1N(C)CCN(C)C] | yield: 6.34%. MS (ESI+) m/z = 551.16 [M + H]+. 1H NMR (500 MHz, DMSO-d6) δ 10.24 (s, 1H), 9.05 (s, 1H), 8.70 (s, 1H), 8.61 (s, 1H), 8.51 (s, 1H), 8.18 (s, 1H), 8.07 (s, 1H), 7.79 (s, 1H), 6.97-7.35 (m, 3H), 6.41 (s, 1H), 6.29 (s, 1H), 5.80 (s, 1H), 4.48 (s, 2H), 2.85 (s, 2H), 2.71 (s, 3H), 2.36 (s, 2H), 2.21 (s, 6H), 1.42 (s, 3H). |
| Final Product 93 | C10 | 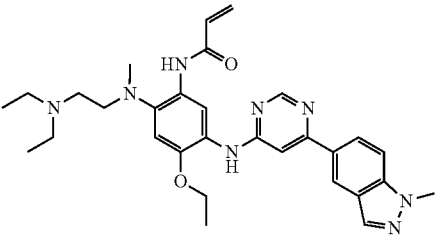 [SMILES: C=CC(=O)Nc1cc(Nc2cc(-c3ccc4c(cnn4C)c3)ncn2)c(OCC)cc1N(C)CCN(CC)CC] | MS (ESI+) m/z = 543.16 [M + H]+. 1H NMR (400 MHz, DMSO-d6) δ 9.73 (s, 1H), 8.66 (s, 1H), 8.59 (s, 1H), 8.57 (s, 1H), 8.50 (s, 1H), 8.16 (s, 1H), 8.09 (d, J = 8.8 Hz, 1H), 7.75 (d, J = 8.8 Hz, 1H), 7.34 (s, 1H), 6.97 (s, 1H), 6.43-6.50 (m, 1H), 6.25 (dd, J = 16.2, 1.2 Hz, 1H), 5.75 (d, J = 11.6 Hz, 1H), 4.11 (t, J = 6.8 Hz, 2H), 4.08 (s, 3H), 2.85 (t, J = 5.2 Hz, 2H), 2.70 (s, 3H), 2.50-2.55 (m, 6H), 1.30 (t, J = 6.8 Hz, 3H), 0.95 (t, J = 6.8 Hz, 6H). |
| Final Product 94 | C20 | 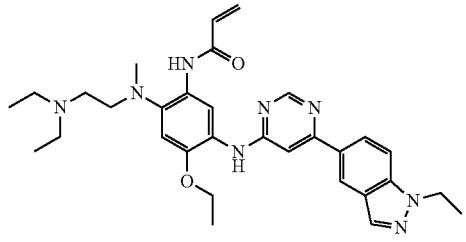 [SMILES: C=CC(=O)Nc1cc(Nc2cc(-c3ccc4c(cnn4CC)c3)ncn2)c(OCC)cc1N(C)CCN(CC)CC] | MS (ESI+) m/z = 557.21 [M + H]+. 1H NMR (500 MHz, DMSO-d6) δ 9.73-9.89 (m, 1.4H), 8.67 (s, 1H), 8.60-8.62 (m, 1H), 8.51 (s, 1H), 8.37 (s, 0.4H), 8.18 (s, 1H), 8.08 (d, J = 8.5 Hz, 1H), 7.79 (d, J = 8.5 Hz, 1H), 7.33-7.45 (m, 1H), 6.97 (s, 1H), 6.91-6.40 (m, 1H), 6.26 (d, J = 13.5 Hz, 1H), 5.77 (s, 1H), 4.48 (q, J = 7.5 Hz, 2H), 4.10-4.16 (m, 2H), 3.33 (s, 1H), 3.07-3.20 (m, 3H), 2.85 (s, 1H), 2.62-2.70 (m, 3H), 2.51 (s, 3H), 1.42 (t, J = 7.0 Hz, 3H), 1.10-1.32 (m, 6H), 0.95 (s, 3H). |

TABLE 4-continued

Final Products 19-262

| No. of Final Products | No. of Intermediates | Structure of Final Products | NMR or MS |
|---|---|---|---|
| Final Product 95 | C11 | | yield: 37.23%. MS (ESI+) m/z = 565.17 [M + H]+. 1H NMR (500 MHz, DMSO-d6) δ 9.88 (s, 1H), 9.04 (s, 1H), 8.62 (s, 1H), 8.60 (s, 1H), 8.50 (s, 1H), 8.17 (s, 1H), 8.08 (d, J = 9.0 Hz, 1H), 7.75 (d, J = 9.0 Hz, 1H), 7.12-7.33 (m, 3H), 6.46-6.51 (m, 1H), 6.27 (d, J = 17.0 Hz, 1H), 5.79 (d, J = 11.0 Hz, 1H), 4.08 (s, 3H), 2.84 (s, 2H), 2.71 (s, 3H), 2.52 (s, 6H), 0.96 (t, J = 7.0 Hz, 6H). |
| Final Product 96 | C25 | | MS (ESI+) m/z = 579.06 [M + H]+. 1H NMR (500 MHz, DMSO-d6) δ 9.88 (s, 1H), 9.05 (s, 1H), 8.62 (s, 1H), 8.60 (s, 1H), 8.50 (s, 1H), 8.19 (s, 1H), 8.07 (dd, J = 8.5, 1.0 Hz, 1H), 7.79 (d, J = 9.0 Hz, 1H), 6.97-7.33 (m, 3H), 6.46-6.51 (m, 1H), 6.28 (dd, J = 17.0, 1.5 Hz, 1H), 5.79 (dd, J = 11.5, 1.5 Hz, 1H), 4.48 (q, J = 7.0 Hz, 2H), 2.84 (t, J = 6.0 Hz, 2H), 2.71 (s, 3H), 2.51-2.54 (m, 6H), 1.42 (t, J = 7.0 Hz, 3H), 0.96 (t, J = 7.0 Hz, 6H). |
| Final Product 97 | C11 | | MS (ESI+) m/z = 563.25 [M + H]+. 1H NMR (500 MHz, DMSO-d6) δ 9.17 (s, 1H), 9.03 (s, 1H), 8.60 (s, 1H), 8.51 (s, 1H), 8.37 (s, 1H), 8.18 (s, 1H), 8.09 (dd, J = 9.0, 1.0 Hz, 1H), 7.76 (d, J = 9.0 Hz, 1H), 7.00-7.36 3H), 6.60-6.66 (m, 1H), 6.26 (dd, J = 17.5, 1.5 Hz, 1H), 5.78 (dd, J = 16.0, 4.5 Hz, 1H), 4.09 (s, 3H), 2.89 (d, J = 7.5 Hz, 2H), 2.45-2.47 (m, 4H), 2.23 (s, 3H), 1.02 (d, J = 5.0 Hz, 6H). |
| Final Product 98 | C25 | | MS (ESI+) m/z = 577.26 [M + H]+. 1H NMR (500 MHz, DMSO-d6) δ 9.17 (s, 1H), 9.03 (s, 1H), 8.60 (s, 1H), 8.51 (s, 1H), 8.37 (s, 1H), 8.19 (s, 1H), 8.07 (dd, J = 8.5, 1.0 Hz, 1H), 7.79 (d, J = 9.0 Hz, 1H), 7.00-7.36 (m, 3H), 6.60-6.64 (m, 1H), 6.26 (dd, J = 17.0, 1.5 Hz, 1H), 5.78 (q, J = 11.0 Hz, 1H), 4.48 (q, J = 7.0 Hz, 2H), 2.89 (d, J = 7.5 Hz, 2H), 2.45-2.47 (m, 4H), 2.23 (s, 3H), 1.43 (t, J = 7.0 Hz, 3H), 1.03 (t, J = 6.0 Hz, 6H). |
| Final Product 99 | C1 | | MS (ESI+) m/z = 543.19 [M + H]+. 1H NMR (400 MHz, DMSO-d6) δ 9.03 (s, 1H), 8.75 (s, 1H), 8.59 (s, 1H), 8.49 (s, 1H), 8.35 (s, 1H), 8.17 (s, 1H), 8.07 (d, J = 8.8 Hz, 1H), 7.75 (d, J = 8.8 Hz, 1H), 7.38 (s, 1H), 6.89 (s, 1H), 6.58-6.65 (m, 1H), 6.23 (d, J = 16.8 Hz, 1H), 5.74 (d, J = 10.8 Hz, 1H), 4.08 (s, 3H), 3.85 (s, 3H), 3.48 (t, J = 5.2 Hz, 2H), 3.25 (s, 3H), 2.88 (brs, 4H), 2.64 (brs, 4H), 2.56 (brs, 2H). |

TABLE 4-continued

Final Products 19-262

| No. of Final Products | No. of Intermediates | Structure of Final Products | NMR or MS |
|---|---|---|---|
| Final Product 100 | C1 | | MS (ESI+) m/z = 610.27 [M + H]+. 1H NMR (400 MHz, DMSO-d6) δ 9.00 (s, 1H), 8.74 (s, 1H), 8.59 (s, 1H), 8.49 (s, 1H), 8.35 (s, 1H), 8.17 (s, 1H), 8.07 (dd, J = 8.8, 1.2 Hz, 1H), 7.75 (d, J = 8.8 Hz, 1H), 7.36 (s, 1H), 6.84 (s, 1H), 6.65-6.72 (m, 1H), 6.24 (d, J = 18.0 Hz, 1H), 5.74 (d, J = 10.6 Hz, 1H), 4.08 (s, 3H), 3.84 (s, 3H), 3.07 (d, J = 11.6 Hz, 2H), 2.80 (brs, 2H), 2.66 (t, J = 10.8 Hz, 2H), 1.69-2.41 (m, 12H), 1.00 (brs, 6H). |
| Final Product 101 | C1 | | yield: 28.99%. MS (ESI+) m/z = 610.21 [M + H]+. 1H NMR (500 MHz, DMSO-d6) δ 9.00 (s, 1H), 8.73 (s, 1H), 8.58 (s, 1H), 8.49 (s, 1H), 8.36 (s, 1H), 8.16 (s, 1H), 8.07 (d, J = 9.0 Hz, 1H), 7.74 (d, J = 9.0 Hz, 1H), 7.36 (s, 1H), 6.85 (s, 1H), 6.64-6.70 (m, 1H), 6.24 (d, J = 17.0 Hz, 1H), 5.72-5.74 (d, J = 10.5 Hz, 1H), 4.08 (s, 3H), 3.83 (s, 3H), 3.06 (d, J = 12.5 Hz, 2H), 2.67 (t, J = 11.0 Hz, 2H), 2.56-2.59 (m, 4H), 2.51 (s, 1H), 2.44 (brs, 4H), 2.25 (s, 1H), 1.84 (d, J = 11.0 Hz, 2H), 1.71 (q, J = 10.5 Hz, 2H), 0.97 (d, J = 6.0 Hz, 6H). |
| Final Product 102 | C1 | | MS (ESI+) m/z = 486.27 [M + H]+. 1H NMR (500 MHz, DMSO-d6) δ 9.13 (s, 1H), 8.76 (s, 1H), 8.60 (s, 1H), 8.50 (s, 1H), 8.40 (s, 1H), 8.17 (s, 1H), 8.08 (d, J = 8.5 Hz, 1H), 7.75 (d, J = 9.0 Hz, 1H), 7.39 (s, 1H), 6.90 (s, 1H), 6.62-6.68 (m, 1H), 6.24 (d, J = 17.0 Hz, 1H), 5.74 (d, J = 14.0 Hz, 1H), 4.08 (s, 3H), 3.87 (s, 3H), 3.80 (m, 4H), 2.87 (s, 4H). |
| Final Product 103 | C1 | | yield: 34%. MS (ESI+) m/z = 597.23 [M + H]+. 1H NMR (400 MHz, DMSO-d6) δ 8.99 (s, 1H), 8.74 (s, 1H), 8.59 (s, 1H), 8.49 (s, 1H), 8.36 (s, 1H), 8.17 (s, 1H), 8.07 (d, J = 8.8 Hz, 1H), 7.75 (d, J = 8.8 Hz, 1H), 7.36 (s, 1H), 6.85 (s, 1H), 6.65-6.72 (m, 1H), 6.24 (d, J = 16.8 Hz, 1H), 5.74 (d, J = 10.0 Hz, 1H), 4.08 (s, 3H), 3.84 (s, 3H), 3.55 (brs, 2H), 3.07 (d, J = 9.2 Hz, 2H), 2.81 (d, J = 10.8 Hz, 2H), 2.67 (t, J = 10.8 Hz, 2H), 2.26 (brs, 1H), 1.70-2.00 (m, 6H), 1.07 (d, J = 5.6 Hz, 3H), 1.03 (d, J = 6.0 Hz, 3H). |
| Final Product 104 | C1 | | MS (ESI+) m/z = 488.18 [M + H]+. 1H NMR (500 MHz, DMSO-d6) δ 9.68 (s, 1H), 8.74 (s, 1H), 8.58 (s, 1H), 8.47 (s, 1H), 8.37 (s, 1H), 8.17 (s, 1H), 8.06 (d, J = 9.0 Hz, 1H), 7.74 (d, J = 8.5 Hz, 1H), 7.28 (s, 1H), 6.94 (s, 1H), 6.45-6.51 (m, 1H), 6.23 (dd, J = 17.0, 1.5 Hz, 1H), 5.74 (dd, J = 11.5, 1.5 Hz, 1H), 4.19 (t, J = 5.5 Hz, 2H), 4.08 (s, 3H), 3.85 (s, 3H), 2.61 (t, J = 5.5 Hz, 2H), 2.27 (s, 6H). |

TABLE 4-continued

Final Products 19-262

| No. of Final Products | No. of Intermediates | Structure of Final Products | NMR or MS |
|---|---|---|---|
| Final Product 105 | C1 | | MS (ESI⁺) m/z = 539.26 [M + H]⁺. ¹H NMR (500 MHz, DMSO-d₆) δ 8.92 (s, 1H), 8.64 (s, 1H), 8.48 (s, 1H), 8.38 (s, 1H), 8.25 (s, 1H), 8.06 (s, 1H), 7.96 (d, J = 9.0 Hz, 1H), 7.64 (d J = 9.0 Hz, 1H), 7.27 (s, 1H), 6.79 (s, 1H), 6.47-6.53 (m, 1H), 6.12 (d, J = 17.0 Hz, 1H), 5.62 (d, J = 10.0 Hz, 1H), 3.97 (s, 3H), 3.74 (s, 3H), 2.78 (brs, 4H), 2.54 (brs, 4H), 2.15 (d, J = 5.5 Hz, 2H), 0.76 (brs, 1H), 0.37 (d, J = 7.5 Hz, 2H), 0.00 (d, J = 3.5 Hz, 2H). |
| Final Product 106 | C1 | | MS (ESI⁺) m/z = 514.26 [M + H]⁺. ¹H NMR (500 MHz, DMSO-d₆) δ 9.15 (s, 1H), 8.75 (s, 1H), 8.60 (s, 1H), 8.56 (s, 1H), 8.50 (s, 1H), 8.17 (s, 1H), 8.08 (dd, J = 9.0, 1.0 Hz, 1H), 7.76 (d, J = 9.0 Hz, 1H), 7.42 (s, 1H), 6.96 (s, 1H), 6.62-6.68 (m, 1H), 6.25 (dd, J = 17.0, 1.0 Hz, 1H), 5.73 (d, J = 12.0 Hz, 1H), 4.08 (s, 3H), 3.87 (m, 2H), 3.84 (s, 3H), 3.20 (t, J = 11.0 Hz, 2H), 2.92-2.97 (m, 1H), 2.64 (s, 3H), 1.68 (d, J = 11.0 Hz, 2H), 1.51-1.60 (m, 2H). |
| Final Product 107 | C1 | | MS (ESI⁺) m/z = 526.27 [M + H]⁺. ¹H NMR (500 MHz, DMSO-d₆) δ 9.02 (s, 1H), 8.74 (s, 1H), 8.59 (s, 1H), 8.49 (s, 1H), 8.39 (s, 1H), 8.17 (s, 1H), 8.07 (dd, J = 8.9, 1.1 Hz, 1H), 7.75 (d, J = 8.9 Hz, 1H), 7.37 (s, 1H), 6.84 (s, 1H), 6.61-6.67 (m, 1H), 6.24 (d, J = 16.9 Hz, 1H), 5.73 (d, J = 10.6 Hz, 1H), 4.38 (s, 4H), 4.08 (s, 3H), 3.84 (s, 3H), 2.75 (brs, 4H), 1.99 (brs, 4H). |
| Final Product 108 | C1 | | yield: 31.58%. MS (ESI⁺) m/z = 553.21 [M + H]⁺. ¹H NMR (500 MHz, DMSO-d₆) δ 9.01 (s, 1H), 8.74 (s, 1H), 8.59 (s, 1H), 8.49 (s, 1H), 8.37 (s, 1H), 8.17 (s, 1H), 8.07 (dd, J = 8.5, 1.0 Hz, 1H),7.75 (d, J = 9.0 Hz, 1H), 7.36 (s, 1H), 6.86 (s, 1H), 6.62-6.68 (m, 1H), 6.24 (d, J = 17.0 Hz, 1H), 5.73 (d, J = 11.0 Hz, 1H), 4.08 (s, 3H), 3.84 (s, 3H), 3.03 (d, J = 10.5 Hz, 2H), 2.69 (t, J = 11.0 Hz, 2H), 2.57 (brs, 4H), 2.09 (brs, 1H), 1.93 (brs, 2H), 1.70 (s, 6H). |
| Final Product 109 | C3 | | MS (ESI⁺) m/z = 513.39 [M + H]⁺. ¹H NMR (500 MHz, DMSO-d₆) δ 9.37 (s, 1H), 9.22 (s, 1H), 8.93 (s, 1H), 8.49 (d, J = 5.0 Hz, 1H), 8.31 (d, J = 9.0 Hz, 1H), 8.15 (s, 1H), 8.00 (s, 1H), 7.72 (d, J = 9.0 Hz, 1H), 7.50 (d, J = 5.0 Hz, 1H), 7.00 (s, 1H), 6.61-6.67 (m, 1H), 6.34 (d, J = 17.0 Hz, 1H), 5.81 (d, J = 10.5 Hz, 1H), 4.09 (s, 3H), 3.88 (s, 3H), 3.32-3.59 (m, 1H), 2.51-2.58 (m, 4H), 2.47-2.50 (m, 1H), 2.38-2.43 (m, 2H), 2.22 (s, 3H), 1.89-1.93 (m, 1H), 1.71-1.75 (m, 1H). |

TABLE 4-continued

Final Products 19-262

| No. of Final Products | No. of Intermediates | Structure of Final Products | NMR or MS |
|---|---|---|---|
| Final Product 110 | C1 | | MS (ESI⁺) m/z = 513.27 [M + H]⁺. ¹H NMR (400 MHz, DMSO-d₆) δ 9.32 (s, 1H), 8.74 (s, 1H), 8.62 (s, 1H), 8.61 (s, 1H), 8.50 (s, 1H), 8.17 (d, J = 0.8 Hz, 1H), 8.08 (dd, J = 8.8, 1.2 Hz, 1H), 7.76 (d, J = 8.8 Hz, 1H), 7.42 (s, 1H), 6.97 (s, 1H), 6.55-6.63 (m, 1H), 6.24 (dd, J = 17.2, 2.0 Hz, 1H), 5.74 (dd, J = 10.4, 1.6 Hz, 1H), 4.09 (s, 3H), 3.84 (s, 3H), 3.50-3.70 (m, 1H), 2.58 (s, 3H), 2.55-2.57 (m, 1H), 2.49-2.50 (m, 1H), 2.40-2.47 (m, 2H), 2.22 (s, 3H), 1.90-1.93 (m, 1H), 1.73-1.75 (m, 1H). |
| Final Product 111 | C11 | | MS (ESI⁺) m/z = 549.28 [M + H]⁺. ¹H NMR (500 MHz, DMSO-d₆) δ 9.44 (s, 1H), 9.04 (s, 1H), 8.62 (s, 1H), 8.60 (s, 1H), 8.52 (s, 1H), 8.18 (s, 1H), 8.09 (dd, J = 8.5, 1.0 Hz, 1H), 7.77 (d, J = 9.0 Hz, 1H), 7.40 (s, 1H), 6.99-7.29 (m, 2H), 6.60-6.66 (m, 1H), 6.26 (dd, J = 17.0, 1.5 Hz, 1H), 5.78 (d, J = 11.5 Hz, 1H), 4.09 (s, 3H), 3.59 (brs, 1H), 2.59 (brs, 4H), 2.40-2.47 (m, 3H), 2.22 (s, 3H), 1.91-1.93 (m, 1H), 1.73-1.75 (m, 1H). |
| Final Product 112 | C26 | | MS (ESI⁺) m/z = 527.31 [M + H]⁺. ¹H NMR (400 MHz, DMSO-d₆) δ 9.33 (s, 1H), 8.75 (s, 1H), 8.61 (s, 2H), 8.51 (s, 1H), 8.19 (s, 1H), 8.07 (d, J = 8.8 Hz, 1H), 7.80 (d, J = 8.8 Hz, 1H), 7.42 (s, 1H), 6.98 (s, 1H), 6.56-6.63 (m, 1H), 6.23 (d, J = 16.8 Hz, 1H), 5.75 (d, J = 10.4 Hz, 1H), 4.49 (q, J = 6.8 Hz, 2H), 3.85 (s, 3H), 3.62 (s, 1H), 2.59 (s, 3H), 2.55-2.37 (m, 4H), 2.23 (s, 3H), 1.90-1.95 (m, 1H), 1.73-1.75 (m, 1H), 1.43 (t, J = 6.8 Hz, 3H) |
| Final Product 113 | C3 | | MS (ESI⁺) m/z = 556.20 [M + H]⁺. ¹H NMR (500 MHz, DMSO-d₆) δ 9.04 (s, 1H), 8.98 (s, 1H), 8.87 (s, 1H), 8.48 (d, J = 5.5 Hz, 1H), 8.29 (d, J = 8.9 Hz, 1H), 8.15 (s, 1H), 8.00 (s, 1H), 7.71 (d, J = 8.9 Hz, 1H), 7.48 (d, J = 5.0 Hz, 1H), 6.91 (s, 1H), 6.65-6.70 (m, 1H), 6.32 (d, J = 17.0 Hz, 1H), 5.80 (d, J = 10.0 Hz, 1H), 4.09 (s, 3H), 3.89 (s, 3H), 2.86 (t, J = 5.5 Hz, 4H), 2.62 (s, 4H), 2.47 (t, J = 6.5 Hz, 2H), 2.38 (t, J = 6.5 Hz, 2H), 2.16 (s, 6H). |
| Final Product 114 | C27 | | MS (ESI⁺) m/z = 592.11 [M + H]⁺· ¹H NMR (500 MHz, DMSO-d₆) δ 9.15 (s, 1H), 8.77 (s, 2H), 8.46-8.48 (m, 2H), 8.25 (dd, J = 8.9, 1.2 Hz, 1H), 8.15 (s, 1H), 7.72 (d, J = 8.9 Hz, 1H), 7.49 (d, J = 5.3 Hz, 1H), 7.00-7.29 (m, 2H), 6.66-6.72 (m, 1H), 6.31 (dd, J = 17.0, 1.4 Hz, 1H), 5.81 (d, J = 11.3 Hz, 1H), 4.09 (s, 3H), 2.84 (t, J = 4.3 Hz, 4H), 2.63 (s, 4H), 2.47 (d, J = 7.6 Hz, 2H), 2.37 (d, J = 6.0 Hz, 2H), 2.16 (s, 6H). |

TABLE 4-continued

Final Products 19-262

| No. of Final Products | No. of Intermediates | Structure of Final Products | NMR or MS |
|---|---|---|---|
| Final Product 115 | C11 | 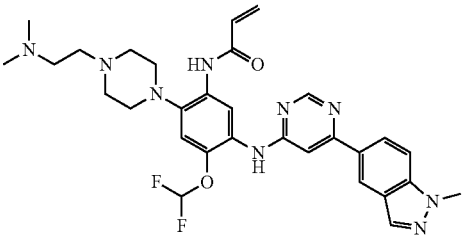 | MS (ESI+) m/z = 592.30 [M + H]+. 1H NMR (500 MHz, DMSO-d6) δ 9.14 (s, 1H), 9.04 (s, 1H), 8.60 (s, 1H), 8.51 (s, 1H), 8.37 (s, 1H), 8.18 (s, 1H), 8.09 (dd, J = 10.0, 1.0 Hz, 1H), 7.76 (d, J = 8.9 Hz, 1H), 7.37 (s, 1H), 7.00-7.30 (m, 2H), 6.62-6.68 (m, 1H), 6.26 (d, J = 17.0 Hz, 1H), 5.78 (d, J = 11.0 Hz, 1H), 4.09 (s, 3H), 2.84 (d, J = 4.5 Hz, 4H), 2.63 (brs, 4H), 2.44-2.49 (m, 2H), 2.37 (t, J = 7.5 Hz, 2H), 2.16 (s, 6H). |
| Final Product 116 | C26 | 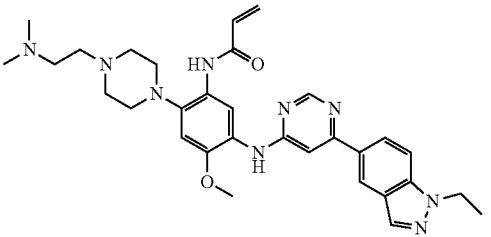 [SMILES: C=CC(=O)Nc1cc(Nc2cc(-c3ccc4c(cnn4CC)c3)ncn2)c(OC)cc1N1CCN(CCN(C)C)CC1] | MS (ESI+) m/z = 570.33 [M + H]+. 1H NMR (500 MHz, DMSO-d6) δ 9.03 (s, 1H), 8.76 (s, 1H), 8.59 (s, 1H), 8.49 (s, 1H), 8.35 (s, 1H), 8.18 (s, 1H), 8.06 (d, J = 8.5 Hz, 1H), 7.78 (d, J = 8.5 Hz, 1H), 7.38 (s, 1H), 6.89 (s, 1H), 6.59-6.64 (m, 1H), 6.23 (d, J = 17.0 Hz, 1H), 5.74 (d, J = 10.0 Hz, 1H), 4.48 (d, J = 6.5 Hz, 2H), 3.85 (s, 3H), 2.87 (brs, 4H), 2.62 (brs, 4H), 2.46-2.50 (m, 2H), 2.37 (brs, 2H), 2.16 (s, 6H), 1.42 (t, J = 6.0 Hz, 3H). |
| Final Product 117 | C10 | 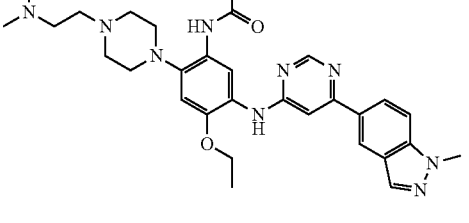 | MS (ESI+) m/z = 570.19 [M + H]+. 1H NMR (500 MHz, DMSO-d6) δ 9.02 (s, 1H), 8.65 (s, 1H), 8.60 (s, 1H), 8.51 (s, 1H), 8.33 (s, 1H), 8.17 (s, 1H), 8.09 (dd, J = 8.9, 1.3 Hz, 1H), 7.75 (d, J = 8.9 Hz, 1H), 7.37 (s, 1H), 6.87 (s, 1H), 6.59-6.64 (m, 1H), 6.23 (d, J = 18.1 Hz, 1H), 5.74 (d, J = 10.9 Hz, 1H), 4.12 (q, J = 9.0 Hz, 2H), 4.08 (s, 3H), 2.85 (t, J = 4.3 Hz, 4H), 2.61 (brs, 4H), 2.45-2.49 (m, 2H), 2.37 (t, J = 6.8 Hz, 2H), 2.16 (s, 6H), 1.31 (t, J = 6.9 Hz, 3H) |
| Final Product 118 | C26 | 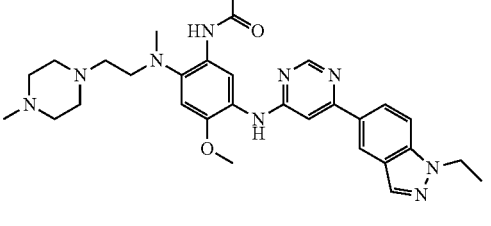 | MS (ESI+) m/z = 570.31 [M + H]+. 1H NMR (400 MHz, DMSO-d6) δ 9.33 (s, 1H), 8.74 (s, 1H), 8.60 (s, 1H), 8.49 (s 1H), 8.47 (s 1H), 8.18 (s, 1H), 8.06 (dd, J = 8.8, 1.2 Hz, 1H), 7.79 (d, J = 8.8 Hz, 1H), 7.38 (s, 1H), 6.96 (s, 1H), 6.57-6.64 (m, 1H), 6.25 (d, J = 16.9 Hz, 1H), 5.74 (d, J = 9.6 Hz, 1H), 4.48 (q, J = 7.2 Hz, 2H), 3.85 (s, 3H), 2.98 (t, J = 6.2 Hz, 2H), 2.70 (s, 3H), 2.30-2.38 (m, 10H), 2.13 (s, 3H), 1.42 (t, J = 7.2 Hz, 3H). |
| Final Product 119 | C10 | 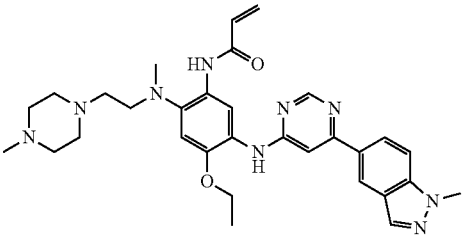 | MS (ESI+) m/z = 570.23 [M + H]+. 1H NMR (500 MHz, DMSO-d6) δ 9.34 (s, 1H), 8.65 (s, 1H), 8.61 (s, 1H), 8.52 (s, 1H), 8.45 (s, 1H), 8.17 (s, 1H), 8.10 (dd, J = 9.0, 1.0 Hz, 1H), 7.76 (d, J = 8.5 Hz, 1H), 7.38 (s, 1H), 6.96 (s, 1H), 6.59-6.65 (m, 1H), 6.25 (dd, J = 18.0, 1.0 Hz, 1H), 5.76 (d, J = 9.0 Hz, 1H), 4.11-4.14 (m, 2H), 4.09 (s, 3H), 2.98 (t, J = 6.0 Hz, 2H), 2.69 (s, 3H), 2.36-2.50 (m, 10H), 2.15 (s, 3H), 1.32 (t, J = 7.0 Hz, 3H). |

TABLE 4-continued

Final Products 19-262

| No. of Final Products | No. of Intermediates | Structure of Final Products | NMR or MS |
|---|---|---|---|
| Final Product 120 | C11 | | MS (ESI+) m/z = 565.12 [M + H]+. 1H NMR (500 MHz, DMSO-d6) δ 9.59 (s, 1H), 9.05 (s, 1H), 8.60 (s, 1H), 8.58 (s, 1H), 8.50 (s, 1H), 8.18 (s, 1H), 8.09 (dd, J = 8.9, 1.4 Hz, 1H), 7.76 (d, J = 8.9 Hz, 1H), 7.33 (s, 1H), 6.99-7.29 (m, 2H), 6.66-6.72 (m, 1H), 6.28 (dd, J = 17.0, 1.6 Hz, 1H), 5.77 (dd, J = 10.3, 1.5 Hz, 1H), 4.09 (s, 3H), 3.31 (s, 1H), 2.87 (t, J = 5.7 Hz, 2H), 2.60-2.70 (m, 5H), 1.04 (d, J = 8.5 Hz, 9H). |
| Final Product 121 | C10 | | MS (ESI+) m/z = 543.10 [M + H]+. 1H NMR (500 MHz, DMSO-d6) δ 9.45 (s, 1H), 8.66 (s, 1H), 8.60 (s, 1H), 8.54 (s, 1H), 8.50 (s, 1H), 8.16 (s, 1H), 8.08 (dd, J = 9.0, 1.5 Hz, 1H), 7.74 (d, J = 9.0 Hz, 1H), 7.33 (s, 1H), 6.93 (s, 1H), 6.63-6.68 (m, 1H), 6.24 (dd, J = 17.0, 2.0 Hz, 1H), 5.71 (dd, J = 11.5, 1.5 Hz, 1H), 4.10-4.12 (m, 2H), 4.08 (s, 3H), 2.88 (t, J = 5.5 Hz, 2H), 2.67 (s, 3H), 2.55-2.61 (m, 2H), 1.60 (s, 1H), 1.30 (t, J = 7.0 Hz, 3H), 1.03 (s, 9H). |
| Final Product 122 | C11 | | MS (ESI+) m/z = 523.29 [M + H]+. 1H NMR (500 MHz, DMSO-d6) δ 9.76 (s, 1H), 8.85 (s, 1H), 8.54 (s, 1H), 8.47 (s, 1H), 8.16 (s, 1H), 8.06 (d, J = 8.0 Hz, 1H), 7.73 (d, J = 7.5 Hz, 1H), 7.53 (s, 1H), 6.98-7.28 (m, 2H), 6.49-6.54 (m, 2H), 6.23 (d, J = 17.0 Hz, 1H), 5.74 (d, J = 9.5 Hz, 1H), 5.31 (s, 1H), 4.08 (s, 3H), 3.12 (brs, 2H), 3.07 (brs, 2H), 2.20 (s, 6H). |
| Final Product 123 | C10 | | MS (ESI+) m/z = 501.09 [M + H]+. 1H NMR (500 MHz, DMSO-d6) δ 9.41 (s, 1H), 8.54 (s, 1H), 8.52 (s, 1H), 8.46 (s, 1H), 8.15 (s, 1H), 8.06 (dd, J = 9.0, 1.5 Hz, 1H), 7.72 (d, J = 8.5 Hz, 1H), 7.46 (s, 1H), 7.13 (s, 1H), 6.44-6.50 (m, 1H), 6.40 (s, 1H), 6.22 (dd, J = 17.0, 1.5 Hz, 1H), 5.72 (dd, J = 10.0, 1.5 Hz, 1H), 4.88 (brs, 1H), 4.09-4.12 (m, 2H), 4.07 (s, 3H), 3.07-3.18 (m, 2H), 2.19-2.49 (m, 2H), 2.19 (s, 6H), 1.27 (t, J = 6.5 Hz, 3H). |
| Final Product 124 | C8 | | MS (ESI+) m/z = 559.40 [M + H]+. 1H NMR (500 MHz, DMSO-d6) δ 9.49 (s, 1H), 9.35 (s, 1H), 8.89 (s, 1H), 8.85 (s, 1H), 8.64 (s, 1H), 8.42 (s, 1H), 8.16-8.21 (m, 2H), 7.43 (s, 1H), 6.96 (s, 1H) 6.59-6.65 (m, 1H), 6.26 (d, J = 16.8 Hz, 1H), 5.75 (dd, J = 10.5, 6.0 Hz, 1H), 3.85 (s, 3H), 2.99 (s, 2H), 2.71 (s, 3H), 2.36-2.50 (m, 10H), 2.16 (s, 3H). |

TABLE 4-continued

Final Products 19-262

| No. of Final Products | No. of Intermediates | Structure of Final Products | NMR or MS |
|---|---|---|---|
| Final Product 125 | C1 | 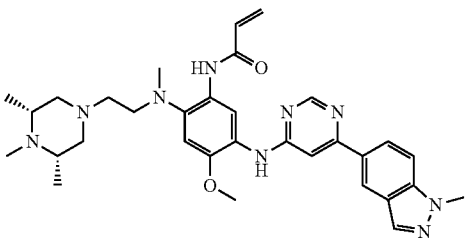 | MS (ESI+) m/z = 584.30 [M + H]+. 1H NMR (500 MHz, DMSO-d6) δ 9.34 (s, 1H), 8.74 (s, 1H), 8.60 (s, 1H), 8.50 (s, 1H), 8.46 (s, 1H), 8.17 (s, 1H), 8.08 (dd, J = 9.0, 1.5 Hz, 1H), 7.75 (d, J = 9.0 Hz, 1H), 7.39 (s, 1H), 6.96 (s, 1H), 6.57-6.63 (m, 1H), 6.25 (dd, J = 18.5, 1.5 Hz, 1H), 5.74 (d, J = 11.0 Hz, 1H), 4.08 (s, 3H), 3.85 (s, 3H), 2.97 (t, J = 6.5 Hz, 2H), 2.70 (s, 3H), 2.67 (d, J = 10.5 Hz, 2H), 2.32 (brs, 2H), 2.09-2.11 (m, 5H), 1.69 (t, J = 10.5 Hz, 2H), 0.92 (d, J = 5.5 Hz, 6H). |
| Final Product 126 | C8 | 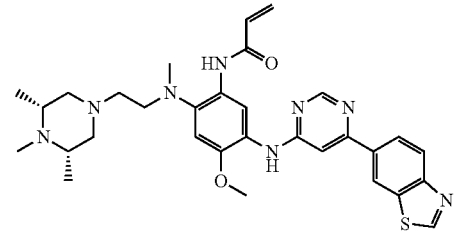 [SMILES: C=CC(=O)Nc1cc(Nc2cc(-c3ccc4ncsc4c3)ncn2)c(OC)cc1N(C)CCN1C[C@@H](C)N(C)[C@@H](C)C1] | MS (ESI+) m/z = 587.46 [M + H]+. 1H NMR (400 MHz, DMSO-d6) δ 9.49 (s, 1H), 9.35 (s, 1H), 8.90 (s, 1H), 8.84 (s, 1H), 8.64 (s, 1H), 8.42 (s, 1H), 8.16-8.21 (m, 2H), 7.44 (s, 1H), 6.96 (s, 1H), 6.57-6.64 (m, 1H), 6.27 (dd, J = 16.8, 1.2 Hz, 1H), 5.75 (d, J = 11.6 Hz, 1H), 3.85 (s, 3H), 2.97 (t, J = 6.0 Hz, 2H), 2.71 (s, 3H), 2.66 (d, J = 10.4 Hz, 2H), 2.33 (brs, 2H), 2.10 (s, 5H), 1.70 (t, J = 10.0 Hz, 2H), 0.92 (d, J = 5.2 Hz, 6H). |
| Final Product 127 | C1 | 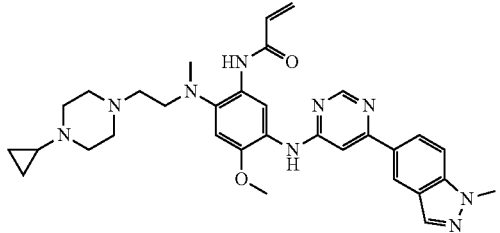 [SMILES: C=CC(=O)Nc1cc(Nc2cc(-c3ccc4c(cnn4C)c3)ncn2)c(OC)cc1N(C)CCN1CCN(C2CC2)CC1] | MS (ESI+) m/z = 582.46 [M + H]+. 1H NMR (500 MHz, DMSO-d6) δ 9.35 (s, 1H), 8.75 (s, 1H), 8.60 (s, 1H), 8.49 (s, 1H), 8.47 (s, 1H), 8.17 (s, 1H), 8.07 (d, J = 10.0, 1.0 Hz, 1H), 7.75 (d, J = 8.9 Hz, 1H), 7.38 (s, 1H), 6.97 (s, 1H), 6.61-6.65 (m, 1H), 6.25 (d, J = 17.0 Hz, 1H), 5.76 (d, J = 10.5 Hz, 1H), 4.08 (s, 3H), 3.85 (s, 3H), 2.98 (t, J = 6.5 Hz, 2H), 2.70 (s, 3H), 2.45 (brs, 4H), 2.31-2.37 (m, 6H), 1.55 (brs, 1H), 0.36 (d, J = 4.5 Hz, 2H), 0.24 (s, 2H). |
| Final Product 128 | C8 | 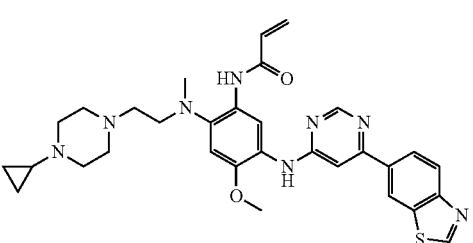 | MS (ESI+) m/z = 585.26 [M + H]+. 1H NMR (500 MHz, DMSO-d6) δ 9.49 (s, 1H), 9.36 (s, 1H), 8.89 (s, 1H), 8.85 (s, 1H), 8.64 (s, 1H), 8.43 (s, 1H), 8.16-8.21 (m, 2H), 7.43 (s, 1H), 6.97 (s, 1H), 6.60-6.65 (m, 1H), 6.27 (d, J = 17.0 Hz, 1H), 5.76 (d, J = 11.0 Hz, 1H), 3.85 (s, 3H), 2.98 (t, J = 6.5 Hz, 2H), 2.71 (s, 3H), 2.47 (brs, 4H), 2.37 (t, J = 6.5 Hz, 3H), 2.31 (brs, 3H), 1.51-1.55 (m, 1H), 0.36 (d, J = 4.5 Hz, 2H), 0.23 (d, J = 2.5 Hz, 2H). |
| Final Product 129 | C1 | 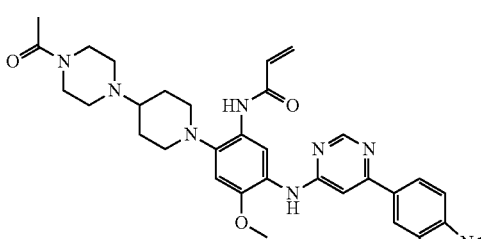 | yield: 30.39%. MS (ESI+) m/z = 610.35 [M + H]+. 1H NMR (500 MHz, DMSO-d6) δ 9.01 (s, 1H), 8.74 (s, 1H), 8.59 (s, 1H), 8.49 (s, 1H), 8.36 (s, 1H), 8.17 (s, 1H), 8.07 (d, J = 9.0 Hz, 1H), 7.76 (d, J = 9.0 Hz, 1H), 7.36 (s, 1H), 6.84 (s, 1H), 6.64-6.70 (m, 1H), 6.24 (d, J = 17.0 Hz, 1H), 5.73 (d, J = 10.0 Hz, 1H), 4.08 (s, 3H), 3.84 (s, 3H), 3.43 (brs, 4H), 3.07 (d, J = 10.0 Hz, 2H), 2.68 (t, J = 11.0 Hz, 2H), 2.53 (brs, 2H), 2.50 (s, 2H), 2.36 (brs, 1H), 1.99 (s, 3H), 1.83 (d, J = 10.5 Hz, 2H), 1.73 (d, J = 10.5 Hz, 2H). |

TABLE 4-continued

Final Products 19-262

| No. of Final Products | No. of Intermediates | Structure of Final Products | NMR or MS |
|---|---|---|---|
| Final Product 130 | C1 | | MS (ESI$^+$) m/z = 584.31 [M + H]$^+$. $^1$H NMR (500 MHz, DMSO-d$_6$) δ 9.31 (s, 1H), 8.75 (s, 1H), 8.59 (s, 1H), 8.49 (s, 1H), 8.45 (s, 1H), 8.17 (s, 1H), 8.07 (d, J = 9.0 Hz, 1H), 7.76 (d, J = 8.5 Hz, 1H), 7.38 (s, 1H), 6.96 (s, 1H), 6.57-6.63 (m, 1H), 6.26 (d, J = 17.5 Hz, 1H), 5.76 (d, J = 10.0 Hz, 1H), 4.08 (s, 3H), 3.85 (s, 3H), 3.36-3.38 (m, 4H), 3.01 (t, J = 6.5 Hz, 2H), 2.72 (s, 3H), 2.42 (t, J = 6.5 Hz, 2H), 2.34 (brs, 2H), 2.29 (brs, 2H), 1.95 (s, 3H). |
| Final Product 131 | C1 | | MS (ESI$^+$) m/z = 558.29 [M + H]$^+$. $^1$H NMR (500 MHz, DMSO-d$_6$) δ 10.05 (s, 1H), 8.75 (s, 1H), 8.71 (s, 1H), 8.60 (s, 1H), 8.50 (s, 1H), 8.17 (s, 1H), 8.07 (dd, J = 8.5, 1.0 Hz, 1H), 7.75 (d, J = 9.0 Hz, 1H), 7.37 (s, 1H), 7.02 (s, 1H), 6.69-6.76 (m, 1H), 6.21 (d, J = 15.5 Hz, 1H), 4.08 (s, 3H), 3.84 (s, 3H), 3.07 (d, J = 6.0 Hz, 2H), 2.85 (t, J = 5.0 Hz, 2H), 2.72 (s, 3H), 2.35 (t, J = 5.5 Hz, 2H), 2.23 (s, 6H), 2.18 (s, 6H). |
| Final Product 132 | C1 | | MS (ESI$^+$) m/z = 543.26 [M + H]$^+$. $^1$H NMR (500 MHz, DMSO-d$_6$) δ 9.21 (s, 1H), 8.73 (s, 1H), 8.57 (s, 1H), 8.47 (s, 1H), 8.24 (s, 1H), 8.16 (s, 1H), 8.06 (dd, J = 9.0, 1.5 Hz, 1H), 7.74 (d, J = 9.0 Hz, 1H), 7.25 (s, 1H), 6.91 (s, 1H), 6.56-6.61 (m, 1H), 6.22 (dd, J = 17.0, 1.5 Hz, 1H), 5.72 (dd, J = 11.5, 1.5 Hz, 1H), 4.21 (t, J = 5.5 Hz, 2H), 4.08 (s, 3H), 3.85 (s, 3H), 2.72 (t, J = 5.5 Hz, 2H), 2.51 (brs, 4H), 2.30 (brs, 4H), 2.15 (s, 3H). |
| Final Product 133 | C1 | | MS (ESI$^+$) m/z = 582.30 [M + H]$^+$. $^1$H NMR (500 MHz, DMSO-d$_6$) δ 9.03 (s, 1H), 8.75 (s, 1H), 8.60 (s, 1H), 8.50 (s, 1H), 8.36 (s, 1H), 8.18 (s, 1H), 8.09 (d, J = 9.0 Hz, 1H), 7.77 (d, J = 9.0 Hz, 1H), 7.39 (s, 1H), 6.90 (s, 1H), 6.60-6.65 (m, 1H), 6.25 (d, J = 17.0 Hz, 1H), 5.75 (d, J = 10.5 Hz, 1H), 4.09 (s, 3H), 3.85 (s, 3H), 2.88 (s, 4H), 2.81 (d, J = 10.5 Hz, 2H), 2.69 (s, 4H), 2.14-2.21 (m, 1H), 2.08 (s, 3H), 1.861 (t, J = 11.5 Hz, 2H), 1.775 (d, J = 11.0 Hz, 2H), 1.46 (q, J = 10.5 Hz, 2H). |
| Final Product 134 | C1 | | MS (ESI$^+$) m/z = 610.35 [M + H]$^+$. $^1$H NMR (300 MHz, DMSO-d$_6$) δ 9.04 (s, 1H), 8.74 (s, 1H), 8.60 (s, 1H), 8.50 (s, 1H), 8.36 (s, 1H), 8.18 (s, 1H), 8.08 (dd, J = 9.0, 1.5 Hz, 1H), 7.76 (d, J = 8.7 Hz, 1H), 7.39 (s, 1H), 6.89 (s, 1H), 6.58-6.67 (m, 1H), 6.24 (dd, J = 16.8, 1.5 Hz, 1H), 5.74 (d, J = 10.8 Hz, 1H), 4.39 (d, J = 12.6 Hz, 1H), 4.09 (s, 3H), 3.86 (s, 4H), 3.01 (d, J = 11.4 Hz, 1H), 2.89 (s, 4H), 2.71 (s, 4H), 2.51-2.60 (m, 1H), 2.01 (s, 3H), 1.70-1.90 (m, 2H), 1.24-1.43 (m, 3H). |

TABLE 4-continued

Final Products 19-262

| No. of Final Products | No. of Intermediates | Structure of Final Products | NMR or MS |
|---|---|---|---|
| Final Product 135 | C1 | | MS (ESI+) m/z = 570.30 [M + H]+. 1H NMR (500 MHz, DMSO-d6) δ 9.13 (s, 1H), 8.76 (s, 1H), 8.60 (s, 1H), 8.50 (s, 1H), 8.45 (s, 1H), 8.17 (s, 1H), 8.08 (dd, J = 8.9, 1.2 Hz, 1H), 7.75 (d, J = 8.9 Hz, 1H), 7.40 (s, 1H), 6.89 (s, 1H), 6.65-6.71 (m, 1H), 6.26 (d, J = 16.9 Hz, 1H), 5.75 (d, J = 10.9 Hz, 1H), 4.08 (s, 3H), 3.85 (s, 3H), 3.75 (brs, 2H), 3.67 (brs, 2H), 3.12 (s, 2H), 2.83-2.86 (m, 4H), 2.21 (s, 6H). |
| Final Product 136 | C1 | | MS (ESI+) m/z = 570.32 [M + H]+. 1H NMR (500 MHz, DMSO-d6) δ 9.03 (s, 1H), 8.76 (s, 1H), 8.59 (s, 1H), 8.50 (s, 1H), 8.37 (s, 1H), 8.18 (s, 1H), 8.08 (dd, J = 8.5, 1.0 Hz, 1H), 7.76 (d, J = 9.0 Hz, 1H), 7.39 (s, 1H), 6.89 (s, 1H), 6.59-6.65 (m, 1H), 6.24 (dd, J = 17.0, 1.5 Hz, 1H), 5.74 (d, J = 11.0 Hz, 1H), 4.09 (s, 3H), 3.86 (s, 3H), 3.21 (s, 2H), 3.08 (s, 3H), 2.90 (brs, 4H), 2.83 (s, 3H), 2.67 (brs, 4H). |
| Final Product 137 | C1 | | MS (ESI+) m/z = 555.38 [M + H]+. 1H NMR (500 MHz, DMSO-d6) δ 9.02 (s, 1H), 8.74 (s, 1H), 8.59 (s, 1H), 8.49 (s, 1H), 8.38 (s, 1H), 8.17 (s, 1H), 8.08 (dd, J = 10.0, 1.0 Hz, 1H), 7.75 (d, J = 9.0 Hz, 1H), 7.36 (s, 1H), 6.86 (s, 1H), 6.66-6.71 (m, 1H), 6.24 (d, J = 16.5 Hz, 1H), 5.74 (d, J = 11.0 Hz, 1H), 4.08 (s, 3H), 3.84 (s, 3H), 3.05 (d, J = 11.0 Hz, 2H), 2.66-2.71 (m, 2H), 2.53-2.60 (m, 5H), 1.74 (d, J = 2.5 Hz, 4H), 1.03 (d, J = 6.0 Hz, 2H), 0.99 (d, J = 7.0 Hz, 4H). |
| Final Product 138 | C1 | | MS (ESI+) m/z = 529.28 [M + H]+. 1H NMR (500 MHz, DMSO-d6) δ 9.83 (s, 1H), 8.82 (s, 1H), 8.68 (s, 1H), 8.64 (s, 1H), 8.40 (s, 1H), 8.11 (s, 1H), 7.88 (d, J = 8.5 Hz, 1H), 7.78 (dd, J = 8.5, 1.0 Hz, 1H), 7.44 (s, 1H), 6.99 (s, 1H), 6.40-6.46 (m, 1H), 6.27 (dd, J = 17.0, 1.5 Hz, 1H), 5.77 (dd, J = 11.5, 1.5 Hz, 1H), 4.13 (s, 3H), 3.85 (s, 3H), 2.81-2.88 (m, 3H), 2.73 (s, 3H), 2.43-2.46 (m, 2H), 2.20 (s, 3H), 0.97 (d, J = 6.5 Hz, 6H). |
| Final Product 139 | C10 | | MS (ESI+) m/z = 543.22 [M + H]+. 1H NMR (500 MHz, DMSO-d6) δ 9.81 (s, 1H), 8.67 (s, 1H), 8.64 (s, 1H), 8.60 (s, 1H), 8.51 (s, 1H), 8.17 (s, 1H), 8.09 (dd, J = 8.9, 1.4 Hz, 1H), 7.75 (d, J = 8.9 Hz, 1H), 7.33 (s, 1H), 6.98 (s, 1H), 6.40-6.43 (m, 1H), 6.26 (dd, J = 16.9, 1.7 Hz, 1H), 5.76 (dd, J = 11.5, 1.5 Hz, 1H), 4.10-4.13 (m, 2H), 4.09 (s, 3H), 2.80-2.86 (m, 3H), 2.72 (s, 3H), 2.44 (t, J = 6.0 Hz, 2H), 2.20 (s, 3H), 1.30 (t, J = 6.9 Hz, 3H), 0.98 (d, J = 6.5 Hz, 6H). |

TABLE 4-continued

Final Products 19-262

| No. of Final Products | No. of Intermediates | Structure of Final Products | NMR or MS |
|---|---|---|---|
| Final Product 140 | C10 | 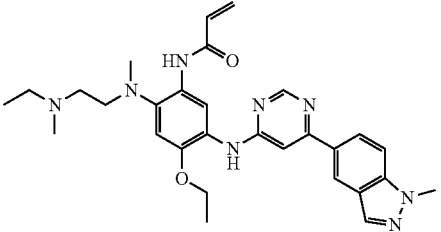 [SMILES: C=CC(=O)Nc1cc(Nc2cc(-c3ccc4c(cnn4C)c3)ncn2)c(OCC)cc1N(C)CCN(C)CC] | MS (ESI+) m/z = 529.21 [M + H]+. 1H NMR (500 MHz, DMSO-d6) δ 9.90 (s, 1H), 8.67 (s, 1H), 8.61 (s, 2H), 8.52 (s, 1H), 8.17 (s, 1H), 8.10 (dd, J = 8.9, 1.5 Hz, 1H), 7.76 (d, J = 8.9 Hz, 1H), 7.37 (s, 1H), 6.99 (s, 1H), 6.44 (brs, 1H), 6.26 (d, J = 16.7 Hz, 1H), 5.76 (d, J = 10.9 Hz, 1H), 4.09-4.12 (m, 5H), 2.88 (brs, 2H), 2.70 (brs, 3H), 2.41-2.45 (m, 4H), 2.10-2.30 (m, 3H), 1.31 (t, J = 6.6 Hz, 3H), 1.06 (brs, 3H). |
| Final Product 141 | C11 | 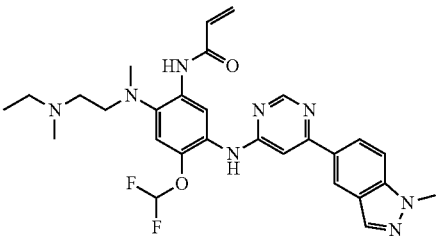 [SMILES: C=CC(=O)Nc1cc(Nc2cc(-c3ccc4c(cnn4C)c3)ncn2)c(OC(F)F)cc1N(C)CCN(C)CC] | MS (ESI+) m/z = 551.21 [M + H]+. 1H NMR (500 MHz, DMSO-d6) δ 10.04 (s, 1H), 9.05 (s, 1H), 8.67 (s, 1H), 8.61 (s, 1H), 8.51 (s, 1H), 8.18 (s, 1H), 8.09 (s, 1H), 7.77 (s, 1H), 7.23 (s, 1H), 6.98-7.28 (m, 2H), 6.45 (s, 1H), 6.29 (d, J = 15.0 Hz, 1H), 5.81 (s, 1H), 4.09 (s, 3H), 2.86 (s, 2H), 2.72 (s, 3H), 2.49 (brs, 4H), 2.20 (s, 3H), 1.01 (s, 3H). |
| Final Product 142 | C1 | 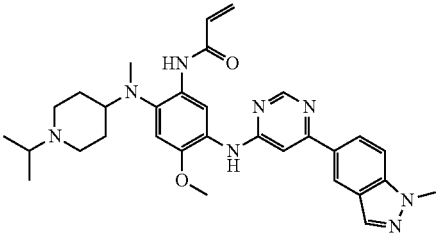 [SMILES: C=CC(=O)Nc1cc(Nc2cc(-c3ccc4c(cnn4C)c3)ncn2)c(OC)cc1N(C)C1CCN(C(C)C)CC1] | MS (ESI+) m/z = 555.28 [M + H]+. 1H NMR (500 MHz, DMSO-d6) δ 9.13 (s, 1H), 8.75 (s, 1H), 8.61 (s, 1H), 8.52 (s, 1H), 8.50 (s, 1H), 8.18 (s, 1H), 8.09 (dd, J = 9.0, 1.5 Hz, 1H), 7.74 (d, J = 9.0 Hz, 1H), 7.42 (s, 1H), 6.94 (s, 1H), 6.61-6.69 (m, 1H), 6.26 (dd, J = 17.0, 1.0 Hz, 1H), 5.74 (d, J = 11.0 Hz, 1H), 4.09 (s, 3H), 3.85 (s, 3H), 2.78 (s, 2H), 2.64-2.70 (m, 5H), 1.90-2.10 (m, 2H), 1.71-1.80 (m, 2H), 1.52-1.54 (m, 2H), 0.93 (brs, 6H). |
| Final Product 143 | C1 | 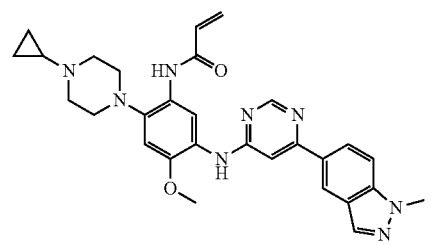 [SMILES: C=CC(=O)Nc1cc(Nc2cc(-c3ccc4c(cnn4C)c3)ncn2)c(OC)cc1N1CCN(C2CC2)CC1] | MS (ESI+) m/z = 525.30 [M + H]+. 1H NMR (500 MHz, DMSO-d6) δ 9.05 (s, 1H), 8.75 (s, 1H), 8.60 (s, 1H), 8.50 (s, 1H), 8.38 (s, 1H), 8.18 (s, 1H), 8.08 (dd, J = 9.0, 1.5 Hz, 1H), 7.76 (d, J = 9.0 Hz, 1H), 7.39 (s, 1H), 6.89 (s, 1H), 6.61-6.67 (m, 1H), 6.25 (dd, J = 17.5, 1.5 Hz, 1H), 5.75 (d, J = 11.0 Hz, 1H), 4.09 (s, 3H), 3.84 (s, 3H), 2.83 (d, J = 4.5 Hz, 4H), 2.76 (brs, 4H), 1.72 (q, J = 3.0 Hz, 1H), 0.45-0.47 (m, 2H), 0.32-0.34 (m, 2H). |
| Final Product 144 | C1 | 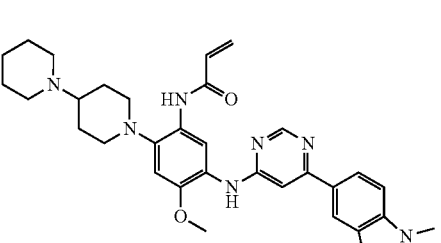 | MS (ESI+) m/z = 567.31 [M + H]+. 1H NMR (500 MHz, DMSO-d6) δ 9.01 (s, 1H), 8.75 (s, 1H), 8.60 (s, 1H), 8.50 (s, 1H), 8.37 (s, 1H), 8.18 (s, 1H), 8.08 (dd, J = 8.9, 1.4 Hz, 1H), 7.76 (d, J = 8.9 Hz, 1H), 7.37 (s, 1H), 6.85 (s, 1H), 6.65-6.70 (m, 1H), 6.25 (d, J = 17.1 Hz, 1H), 5.75 (d, J = 10.7 Hz, 1H), 4.09 (s, 3H), 3.85 (s, 3H), 2.64-2.70 (m, 2H), 2.40-2.49 (m, 4H), 2.33-2.37 (m, 1H), 1.79 (brs, 4H), 1.41-1.51 (m, 4H), 1.11 (s, 4H). |

TABLE 4-continued

Final Products 19-262

| No. of Final Products | No. of Intermediates | Structure of Final Products | NMR or MS |
|---|---|---|---|
| Final Product 145 | C11 | | MS (ESI+) m/z = 579.30 [M + H]+. 1H NMR (500 MHz, DMSO-d6) δ 9.15 (s, 1H), 9.05 (s, 1H), 8.61 (s, 1H), 8.52 (s, 1H), 8.37 (s, 1H), 8.18 (s, 1H), 8.10 (dd, J = 9.0, 1.5 Hz, 1H), 7.77 (d, J = 9.0 Hz, 1H), 7.37 (s, 1H), 7.01-7.31 (m, 2H), 6.63-6.69 (m, 1H), 6.27 (dd, J = 17.0, 1.5 Hz, 1H), 5.78 (d, J = 11.5 Hz, 1H), 4.09 (s, 3H), 3.48 (t, J = 5.5 Hz, 2H), 3.26 (s, 3H), 2.85 (d, J = 4.0 Hz, 4H), 2.65 (s, 4H), 2.57 (t, J = 5.5 Hz, 2H). |
| Final Product 146 | C11 | | MS (ESI+) m/z = 646.30 [M + H]+. 1H NMR (400 MHz, DMSO-d6) δ 9.11 (s, 1H), 9.03 (s, 1H), 8.60 (s, 1H), 8.51 (s, 1H), 8.37 (s, 1H), 8.18 (s, 1H), 8.09 (d, J = 8.8 Hz, 1H), 7.76 (d, J = 8.8 Hz, 1H), 7.35 (s, 1H), 6.95-7.32 (m, 2H), 6.69-6.76 (m, 1H), 6.25 (dd, J = 18.4, 1.6 Hz, 1H), 5.78 (d, J = 11.6 Hz, 1H), 4.09 (s, 3H), 3.07 (d, J = 10.8 Hz, 2H), 2.78 (d, J = 10.4 Hz, 2H), 2.61 (t, J = 11.2 Hz, 2H), 2.22-2.23 (m, 1H), 2.09-2.14 (m, 5H), 1.93 (t, J = 10.4 Hz, 2H), 1.84 (d, J = 10.8 Hz, 2H), 1.70-1.76 (m, 2H), 0.99 (d, J = 6.0 Hz, 6H). |
| Final Product 147 | C11 | | MS (ESI+) m/z = 646.36 [M + H]+. 1H NMR (400 MHz, DMSO-d6) δ 9.10 (s, 1H), 9.01 (s, 1H), 8.60 (s, 1H), 8.50 (s, 1H), 8.38 (s, 1H), 8.17 (s, 1H), 8.08 (dd, J = 8.8, 1.2 Hz, 1H), 7.75 (d, J = 8.8 Hz, 1H), 7.35 (s, 1H), 7.00-7.31 (m, 2H), 6.66-6.73 (m, 1H), 6.27 (d, J = 17.2 Hz, 1H), 5.77 (d, J = 11.6 Hz, 1H), 4.08 (s, 3H), 3.07 (d, J = 8.8 Hz, 2H), 2.51-2.66 (m, 7H), 2.45 (brs, 4H), 2.27 (brs, 1H), 1.84 (d, J = 11.6 Hz, 2H), 1.68-1.73 (m, 2H), 0.97 (d, J = 3.6 Hz, 6H). |
| Final Product 148 | C11 | | MS (ESI+) m/z = 633.25 [M + H]+. 1H NMR (400 MHz, DMSO-d6) δ 9.11 (s, 1H), 9.04 (s, 1H), 8.60 (s, 1H), 8.51 (s, 1H), 8.37 (s, 1H), 8.18 (s, 1H), 8.09 (d, J = 9.2 Hz, 1H), 7.76 (d, J = 8.8 Hz, 1H), 7.35 (s, 1H), 6.95-7.32 (m, 2H), 6.68-6.75 (m, 1H), 6.27 (d, J = 16.8 Hz, 1H), 5.78 (d, J = 10.4 Hz, 1H), 4.09 (s, 3H), 3.55 (s, 2H), 3.07 (d, J = 10.8 Hz, 2H), 2.81 (d, J = 10.4 Hz, 2H), 2.63 (t, J = 11.7 Hz, 2H), 2.27-2.31 (m, 1H), 1.65-1.83 (m, 6H), 1.07 (d, J = 6.0 Hz, 6H). |
| Product Final 149 | C11 | | MS (ESI+) m/z = 575.27 [M + H]+. 1H NMR (400 MHz, DMSO-d6) δ 9.14 (s, 1H), 9.04 (s, 1H), 8.60 (s, 1H), 8.51 (s, 1H), 8.37 (s, 1H), 8.18 (s, 1H), 8.09 (d, J = 9.0 Hz, 1H), 7.76 (d, J = 9.2 Hz, 1H), 7.37 (s, 1H), 6.96-7.33 (m, 2H), 6.61-6.67 (m, 1H), 6.26 (d, J = 17.1 Hz, 1H), 5.78 (d, J = 10.1 Hz, 1H), 4.09 (s, 3H), 2.87 (s, 4H), 2.67 (s, 4H), 2.27 (d, J = 6.0 Hz, 2H), 0.87 (brs, 1H), 0.49 (d, J = 6.6 Hz, 2H), 0.11 (d, J = 3.6 Hz, 2H). |

TABLE 4-continued

Final Products 19-262

| No. of Final Products | No. of Intermediates | Structure of Final Products | NMR or MS |
|---|---|---|---|
| Final Product 150 | C11 | | MS (ESI+) m/z = 589.26 [M + H]+. 1H NMR (400 MHz, DMSO-d6) δ 9.12 (s, 1H), 9.03 (s, 1H), 8.60 (s, 1H), 8.51 (s, 1H), 8.38 (s, 1H), 8.18 (s, 1H), 8.09 (d, J = 8.8 Hz, 1H), 7.76 (d, J = 9.2 Hz, 1H), 7.35 (s, 1H), 6.95-7.14 (m, 2H), 6.65-6.72 (m, 1H), 6.26 (d, J = 16.8 Hz, 1H), 5.78 (d, J = 10.4 Hz, 1H), 4.09 (s, 3H), 3.03 (d, J = 10.6 Hz, 2H), 2.66 (t, J = 11.2 Hz, 2H), 2.54 (brs, 4H), 2.12 (brs, 1H), 1.95 (d, J = 10.0 Hz, 2H), 1.70 (s, 6H). |
| Final Product 151 | C14 | | MS (ESI+) m/z = 555.25 [M + H]+. 1H NMR (500 MHz, DMSO-d6) δ 10.31 (s, 1H), 9.27 (s, 1H), 8.80 (s, 1H), 8.63 (s, 1H), 8.52 (s, 1H), 8.19 (s, 1H), 8.09 (dd, J = 8.9, 1.3 Hz, 1H), 7.77 (d, J = 8.9 Hz, 1H), 7.39 (s, 1H), 7.32 (s, 1H), 6.41-6.47 (m, 1H), 6.30 (dd, J = 16.9, 1.7 Hz, 1H), 5.83 (dd, J = 10.1, 1.7 Hz, 1H), 4.10 (s, 3H), 2.87 (t, J = 5.5 Hz, 2H), 2.72 (s, 3H), 2.37 (t, J = 5.1 Hz, 2H), 2.23 (s, 6H). |
| Final Product 152 | C1 | | MS (ESI+) m/z = 569.28 [M + H]+. 1H NMR (400 MHz, DMSO-d6) δ 9.03 (s, 1H), 8.73 (s, 1H), 8.59 (s, 1H), 8.49 (s, 1H), 8.36 (s, 1H), 8.17 (s, 1H), 8.07 (d, J = 8.8 Hz, 1H), 7.75 (d, J = 8.8 Hz, 1H), 7.38 (s, 1H), 6.89 (s, 1H), 6.58-6.65 (m, 1H), 6.23 (d, J = 16.8 Hz, 1H), 5.73 (d, J = 10.4 Hz, 1H), 4.08 (s, 3H), 3.90-3.92 (m, 2H), 3.85 (s, 3H), 3.27-3.33 (m, 2H), 2.88 (brs, 4H), 2.70 (brs, 4H), 2.41-2.45 (m, 1H), 1.73-1.77 (m, 2H), 1.39-1.48 (m, 2H). |
| Final Product 153 | C11 | | MS (ESI+) m/z = 605.35 [M + H]+. 1H NMR (400 MHz, DMSO-d6) δ 9.16 (s, 1H), 9.04 (s, 1H), 8.60 (s, 1H), 8.51 (s, 1H), 8.37 (s, 1H), 8.18 (s, 1H), 8.09 (dd, J = 9.2, 1.6 Hz, 1H), 7.76 (d, J = 8.8 Hz, 1H), 7.37 (s, 1H), 6.97-7.34 (m, 2H), 6.62-6.69 (m, 1H), 6.26 (d, J = 16.9 Hz, 1H), 5.77 (d, J = 11.6 Hz, 1H), 4.09 (s, 3H), 3.91 (d, J = 6.8 Hz, 2H), 3.27-3.32 (m, 2H), 2.86 (brs, 4H), 2.71 (brs, 4H), 2.44-2.50 (m, 1H), 1.75 (d, J = 13.0 Hz, 2H), 1.41-1.48 (m, 2H). |
| Final Product 154 | C2 | | MS (ESI+) m/z = 527.36 [M + H]+. 1H NMR (400 MHz, DMSO-d6) δ 9.06 (s, 1H), 8.81 (s, 1H), 8.64 (s, 1H), 8.37 (s, 1H), 8.33 (s, 1H), 8.10 (s, 1H), 7.87 (d, J = 8.5 Hz, 1H), 7.77 (d, J = 8.5 Hz, 1H), 7.47 (s, 1H), 6.84 (s, 1H), 6.57-6.64 (m, 1H), 6.22 (d, J = 16.7 Hz, 1H), 5.74 (d, J = 10.6 Hz, 1H), 4.13 (s, 3H), 3.88 (s, 3H), 2.88 (d, J = 10.5 Hz, 2H), 2.43-2.55 (m, 4H), 2.23 (s, 3H), 1.02 (t, J = 5.6 Hz, 6H). |

TABLE 4-continued

Final Products 19-262

| No. of Final Products | No. of Intermediates | Structure of Final Products | NMR or MS |
|---|---|---|---|
| Final Product 155 | C2 | | MS (ESI+) m/z = 597.39 [M + H]+. 1H NMR (400 MHz, DMSO-d6) δ 9.00 (s, 1H), 8.80 (s, 1H), 8.63 (s, 1H), 8.38 (s, 1H), 8.33 (s, 1H), 8.10 (s, 1H), 7.87 (d, J = 8.5 Hz, 1H), 7.78 (d, J = 8.5 Hz, 1H), 7.46 (s, 1H), 6.85 (s, 1H), 6.65-6.72 (m, 1H), 6.23 (d, J = 17.0 Hz, 1H), 5.74 (d, J = 11.3 Hz, 1H), 4.13 (s, 3H), 3.85 (s, 3H), 3.52-3.56 (m, 2H), 3.07 (d, J = 11.0 Hz, 2H), 2.81 (d, J = 10.3 Hz, 2H), 2.67 (t, J = 11.1 Hz, 2H), 2.23-2.26 (m, 1H), 1.79-1.85 (m, 4H), 1.70-1.76 (m, 2H), 1.07 (d, J = 6.2 Hz, 6H). |
| Final Product 156 | C2 | | MS (ESI+) m/z = 610.36 [M + H]+. 1H NMR (300 MHz, DMSO-d6) δ 9.02 (s, 1H), 8.81 (s, 1H), 8.62 (s, 1H), 8.36 (s, 1H), 8.11 (s, 1H), 7.88 (d, J = 8.7 Hz, 1H), 7.78 (d, J = 8.7 Hz, 1H), 7.47 (s, 1H), 6.86 (s, 1H), 6.64-6.70 (m, 1H), 6.25 (d, J = 15.6 Hz, 1H), 5.75 (d, J = 10.2 Hz, 1H), 4.14 (s, 3H), 3.86 (s, 3H), 3.09 (s, 3H), 2.86 (brs, 2H), 2.62-2.74 (m, 3H), 2.35 (brs, 3H), 2.15 (brs, 3H), 1.84-1.90 (m, 2H), 1.60-1.74 (m, 2H), 1.32 (brs, 3H), 1.04 (d, J = 6.2 Hz, 3H). |
| Final Product 157 | C2 | | MS (ESI+) m/z = 610.31 [M + H]+. 1H NMR (400 MHz, DMSO-d6) δ 8.99 (s, 1H), 8.77 (s, 1H), 8.63 (s, 1H), 8.39 (s, 1H), 8.33 (s, 1H), 8.09 (s, 1H), 7.86 (d, J = 8.4 Hz, 1H), 7.78 (d, J = 8.4 Hz, 1H), 7.46 (s, 1H), 6.86 (s, 1H), 6.63-6.67 (m, 1H), 6.23 (d, J = 17.2 Hz, 1H), 5.73 (d, J = 10.8 Hz, 1H), 4.13 (s, 3H), 3.84 (s, 3H), 3.06 (d, J = 10.8 Hz, 2H), 2.68 (t, J = 10.4 Hz, 2H), 2.52 (brs, 5H), 2.46 (brs, 4H), 2.27-2.30 (m, 1H), 1.85 (d, J = 10.9 Hz, 2H), 1.68-1.74 (m, 2H), 0.97 (d, J = 5.3 Hz, 6H). |
| Final Product 158 | C2 | | MS (ESI+) m/z = 553.30 [M + H]+. 1H NMR (300 MHz, DMSO-d6) δ 9.12 (s, 1H), 8.84 (s, 1H), 8.65 (s, 1H), 8.38 (s, 1H), 8.34 (s, 1H), 8.11 (d, J = 0.9 Hz, 1H), 7.88 (d, J = 8.7 Hz, 1H), 7.78 (d, J = 8.7 Hz, 1H), 7.49 (s, 1H), 6.87 (s, 1H), 6.58-6.64 (m, 1H), 6.25 (d, J = 17.4 Hz, 1H), 5.75 (d, J = 11.4 Hz, 1H), 4.14 (s, 3H), 3.86 (s, 3H), 3.41 (s, 4H), 3.08-3.13 (m, 3H), 2.71 (t, J = 11.1 Hz, 2H), 2.05 (s, 2H), 1.86 (s, 6H). |
| Final Product 159 | C2 | | MS (ESI+) m/z = 543.33 [M + H]+. 1H NMR (400 MHz, DMSO-d6) δ 9.03 (s, 1H), 8.80 (s, 1H), 8.64 (s, 1H), 8.37 (s, 1H), 8.33 (s, 1H), 8.10 (s, 1H), 7.87 (d, J = 8.5 Hz, 1H), 7.78 (d, J = 8.5 Hz, 1H), 7.47 (s, 1H), 6.89 (s, 1H), 6.58-6.65 (m, 1H), 6.22 (d, J = 17.1 Hz, 1H), 5.73 (d, J = 10.5 Hz, 1H), 4.13 (s, 3H), 3.86 (s, 3H), 3.47 (t, J = 5.8 Hz, 2H), 3.26 (s, 3H), 2.87 (d, J = 6.0 Hz, 4H), 2.64 (s, 4H), 2.56 (t, J = 5.7 Hz, 2H). |

TABLE 4-continued

Final Products 19-262

| No. of Final Products | No. of Intermediates | Structure of Final Products | NMR or MS |
|---|---|---|---|
| Final Product 160 | C28 | | MS (ESI+) m/z = 563.32 [M + H]+. 1H NMR (400 MHz, DMSO-d6) δ 9.18 (s, 1H), 9.12 (s, 1H), 8.65 (s, 1H), 8.38 (s, 1H), 8.35 (s, 1H), 8.11 (s, 1H), 7.88 (d, J = 8.4 Hz, 1H), 7.79 (d, J = 8.5 Hz, 1H), 7.45 (s, 1H), 6.99-7.36 (m, 2H), 6.60-6.67 (m, 1H), 6.25 (d, J = 16.6 Hz, 1H), 5.78 (d, J = 11.0 Hz, 1H), 4.13 (s, 3H), 2.88-2.91 (m, 2H), 2.45-2.47 (m, 4H), 2.23 (s, 3H), 1.02 (d, J = 4.5 Hz, 6H). |
| Final Product 161 | C28 | | MS (ESI+) m/z = 605.28 [M + H]+. 1H NMR (400 MHz, DMSO-d6) δ 9.19 (s, 1H), 9.15 (s, 1H), 8.64 (s, 1H), 8.38 (s, 1H), 8.35 (s, 1H), 8.11 (s, 1H), 7.88 (d, J = 8.5 Hz, 1H), 7.80 (d, J = 8.5 Hz, 1H), 7.46 (s, 1H), 6.96-7.33 (m, 2H), 6.68-6.75 (m, 1H), 6.26 (dd, J = 16.8, 1.6 Hz, 1H), 5.78 (dd, J = 11.7, 1.6 Hz, 1H), 4.13 (s, 3H), 3.60 (t, J = 4.4 Hz, 4H), 3.06-3.09 (m, 2H), 2.64 (t, J = 11.1 Hz, 2H), 2.50-2.51 (m, 4H), 2.20-2.30 (m, 1H), 1.88 (d, J = 11.8 Hz, 2H), 1.70-1.76 (m, 2H). |
| Final Product 162 | C28 | | MS (ESI+) m/z = 633.27 [M + H]+. 1H NMR (400 MHz, DMSO-d6) δ 9.17 (s, 1H), 9.13 (s, 1H), 8.64 (s, 1H), 8.37 (s, 1H), 8.35 (s, 1H), 8.11 (s, 1H), 7.88 (d, J = 8.5 Hz, 1H), 7.79 (d, J = 8.5 Hz, 1H), 7.45 (s, 1H), 6.96-7.33 (m, 2H), 6.69-6.73 (m, 1H), 6.26 (dd, J = 16.8, 1.6 Hz, 1H), 5.78 (d, J = 11.8 Hz, 1H), 4.13 (s, 3H), 3.52-3.56 (m, 2H), 3.07 (d, J = 11.4 Hz, 2H), 2.81 (m, J = 10.3 Hz, 2H), 2.63 (t, J = 11.0 Hz, 2H), 2.26-2.28 (m, 1H), 1.72-1.84 (m, 6H), 1.07 (d, J = 6.2 Hz, 6H). |
| Final Product 163 | C28 | | MS (ESI+) m/z = 646.35 [M + H]+. 1H NMR (400 MHz, DMSO-d6) δ 9.13 (s, 1H), 9.11 (s, 1H), 8.64 (s, 1H), 8.38 (s, 1H), 8.34 (s, 1H), 8.11 (s, 1H), 7.87 (d, J = 8.4 Hz, 1H), 7.79 (d, J = 8.0 Hz, 1H), 7.44 (s, 1H), 6.95-7.32 (m, 2H) 6.68-6.75 (m, 1H) 6.27 (d, J = 17.2 Hz, 1H), 5.78 (d, J = 11.6 Hz, 1H), 4.13 (s, 3H), 3.26-3.14 (m, 1H), 3.08 (s, 3H), 2.79 (s, 2H), 2.65 (t, J = 10.8 Hz, 3H), 2.33 (s, 2H), 2.16 (s, 3H), 1.84 (s, 2H), 1.75 (s, 2H), 1.32 (s, 3H), 1.01 (s, 3H). |
| Final Product 164 | C28 | | MS (ESI+) m/z = 589.29 [M + H]+. 1H NMR (400 MHz, DMSO-d6) δ 9.16 (s, 1H), 9.11 (s, 1H), 8.65 (s, 1H), 8.39 (s, 1H), 8.35 (s, 1H), 8.11 (s, 1H), 7.88 (d, J = 8.5 Hz, 1H), 7.79 (d, J = 8.5 Hz, 1H), 7.45 (s, 1H), 6.96-7.33 (m, 2H), 6.64-6.71 (m, 1H), 6.27 (d, J = 17.0 Hz, 1H), 5.78 (d, J = 11.6 Hz, 1H), 4.13 (s, 3H), 3.06 (d, J = 10.9 Hz, 2H), 2.63-2.69 (m, 7H), 1.98 (brs, 2H), 1.75 (brs, 6H). |

TABLE 4-continued

Final Products 19-262

| No. of Final Products | No. of Intermediates | Structure of Final Products | NMR or MS |
|---|---|---|---|
| Final Product 165 | C28 | | MS (ESI+) m/z = 549.29 [M + H]+. $^1$H NMR (500 MHz, DMSO-d$_6$) δ 9.46 (s, 1H), 9.12 (s, 1H), 8.66 (s, 1H), 8.60 (s, 1H), 8.35 (s, 1H), 8.11 (s, 1H), 7.88 (d, J = 8.5 Hz, 1H), 7.80 (d, J = 8.5 Hz, 1H), 7.48 (s, 1H), 6.99-7.29 (m, 2H), 6.60-6.64 (m, 1H), 6.26 (dd, J = 17.0, 1.4 Hz, 1H), 5.78 (d, J = 11.7 Hz, 1H), 4.13 (s, 3H), 3.59-3.60 (m, 1H), 2.57 (s, 4H), 2.40-2.49 (m, 3H), 2.23 (s, 3H), 1.91-1.93 (m, 1H), 1.73-1.75 (m, 1H). |
| Final Product 166 | C2 | | MS (ESI+) m/z = 555.28 [M + H]+. $^1$H NMR (400 MHz, DMSO-d$_6$) δ 9.06 (s, 1H), 8.83 (s, 1H), 8.64 (s, 1H), 8.45 (s, 1H), 8.34 (s, 1H), 8.11 (s, 1H), 7.87 (d, J = 8.5 Hz, 1H), 7.78 (d, J = 8.5 Hz, 1H), 7.48 (s, 1H), 6.87 (s, 1H), 6.65-6.72 (m, 1H), 6.25 (d, J = 17.1 Hz, 1H), 5.76 (d, J = 10.0 Hz, 1H), 4.16 (s, 3H), 3.85 (s, 3H), 3.25-3.29 (m, 1H), 3.10-3.20 (m, 4H), 2.81-2.85 (m, 2H), 2.51-2.55 (m, 2H), 1.76-2.04 (m, 4H), 1.23-1.30 (m, 6H). |
| Final Product 167 | C28 | | MS (ESI+) m/z = 591.25 [M + H]+. $^1$H NMR (400 MHz, DMSO-d$_6$) δ 9.14 (s, 1H), 9.09 (s, 1H), 8.64 (s, 1H), 8.39 (s, 1H), 8.34 (s, 1H), 8.11 (s, 1H), 7.88 (d, J = 8.4 Hz, 1H), 7.79 (d, J = 8.8 Hz, 1H), 7.43 (s, 1H), 6.95-7.32 (m, 2H), 6.68-6.75 (m, 1H), 6.27 (d, J = 18.0 Hz, 1H), 5.78 (d, J = 11.2 Hz, 1H), 4.13 (s, 3H), 3.06 (d, J = 11.2 Hz, 2H), 2.52-2.67 (m, 7H), 1.75 (s, 4H), 0.99 (t, J = 7.2 Hz, 6H). |
| Final Product 168 | C11 | | MS (ESI+) m/z = 591.26 [M + H]+. $^1$H NMR (400 MHz, DMSO-d$_6$) δ 9.12 (s, 1H), 9.01 (s, 1H), 8.60 (s, 1H), 8.51 (s, 1H), 8.39 (s, 1H), 8.17 (s, 1H), 8.08 (d, J = 9.2 Hz, 1H), 7.75 (d, J = 8.8 Hz, 1H), 7.35 (s, 1H), 6.94-7.31 (m, 2H), 6.68-6.75 (m, 1H), 6.27 (dd, J = 16.8, 1.2 Hz, 1H), 5.76 (dd, J = 6.8, 2.8 Hz, 1H), 4.09 (s, 3H), 3.06 (d, J = 11.2 Hz, 2H), 2.53-2.68 (m, 7H), 1.75 (brs, 4H), 0.99 (t, J = 7.2 Hz, 6H). |
| Final Product 169 | C2 | | MS (ESI+) m/z = 488.25 [M + H]+. $^1$H NMR (500 MHz, DMSO-d$_6$) δ 9.71 (s, 1H), 8.81 (s, 1H), 8.62 (s, 1H), 8.39 (s, 1H), 8.32 (s, 1H), 8.10 (s, 1H), 7.86 (d, J = 8.5 Hz, 1H), 7.76 (dd, J = 8.5, 1.0 Hz, 1H), 7.38 (s, 1H), 6.93 (d, J = 9.9 Hz, 1H), 6.45-6.51 (m, 1H), 6.22 (dd, J = 17.0, 1.7 Hz, 1H), 5.74 (dd, J = 10.2, 1.6 Hz, 1H), 4.19 (t, J = 5.6 Hz, 2H), 4.13 (s, 3H), 3.86 (s, 3H), 2.61 (t, J = 5.2 Hz, 2H), 2.27 (s, 6H). |

TABLE 4-continued

Final Products 19-262

| No. of Final Products | No. of Intermediates | Structure of Final Products | NMR or MS |
|---|---|---|---|
| Final Product 170 | C28 | | MS (ESI⁺) m/z = 524.19 [M + H]⁺. ¹H NMR (500 MHz, DMSO-d₆) δ 9.78 (s, 1H), 9.10 (s, 1H), 8.63 (s, 1H), 8.44 (s, 1H), 8.34 (s, 1H), 8.11 (s, 1H), 7.89 (d, J = 8.5 Hz, 1H), 7.78 (dd, J = 8.5, 1.0 Hz, 1H), 7.37 (s, 1H), 7.00-7.30 (m, 2H), 6.51-6.57 (m, 1H), 6.25 (dd, J = 17.0, 2.0 Hz, 1H), 5.77 (dd, J = 10.5, 1.5 Hz, 1H), 4.19 (t, J = 5.7 Hz, 2H), 4.13 (s, 3H), 2.64 (t, J = 5.2 Hz, 2H), 2.27 (s, 6H). |
| Final Product 171 | C11 | | MS (ESI⁺) m/z = 524.21 [M + H]⁺. ¹H NMR (500 MHz, DMSO-d₆) δ 9.76 (s, 1H), 9.02 (s, 1H), 8.59 (s, 1H), 8.50 (s, 1H), 8.44 (s, 1H), 8.18 (s, 1H), 8.09 (dd, J = 9.0, 1.5 Hz, 1H), 7.76 (d, J = 9.0 Hz, 1H), 7.00-7.30 (m, 3H), 6.51-6.57 (m, 1H), 6.26 (dd, J = 17.0, 1.5 Hz, 1H), 5.78 (dd, J = 10.0, 1.5 Hz, 1H), 4.19 (t, J = 5.5 Hz, 2H), 4.09 (s, 3H), 2.65 (d, J = 5.0 Hz, 2H), 2.27 (s, 6H) |
| Final Product 172 | C17 | | MS (ESI⁺) m/z = 519.21 [M + H]⁺. ¹H NMR (400 MHz, DMSO-d₆) δ 9.60 (s, 1H), 8.81 (s, 1H), 8.55 (s, 1H), 8.31 (s, 1H), 8.09 (s, 1H), 7.85 (d, J = 8.5 Hz, 1H), 7.76 (d, J = 8.7 Hz, 1H), 7.03 (s, 1H), 6.68 (s, 1H), 6.60-6.67 (m, 1H), 6.22 (d, J = 16.0 Hz, 1H), 5.74 (d, J = 10.4 Hz, 1H), 4.13 (s, 3H), 3.82 (s, 3H), 3.07-3.17 (m, 4H), 2.78 (s, 3H), 2.27 (brs, 6H). |
| Final Product 173 | C2 | | MS (ESI⁺) m/z = 527.22 [M + H]⁺. ¹H NMR (400 MHz, DMSO-d₆) δ 9.05 (s, 1H), 8.81 (s, 1H), 8.64 (s, 1H), 8.39 (s, 1H), 8.33 (s, 1H), 8.10 (s, 1H), 7.87 (d, J = 8.5 Hz, 1H), 7.78 (d, J = 8.6 Hz, 1H), 7.47 (s, 1H), 6.86 (s, 1H), 6.64-6.71 (m, 1H), 6.24 (dd, J = 17.0, 1.6 Hz, 1H), 5.75 (d, J = 10.9 Hz, 1H), 4.13 (s, 3H), 3.85 (s, 3H), 3.07-3.12 (m, 2H), 2.70 (t, J = 11.0 Hz, 2H), 2.40-2.49 (m, 7H), 1.90-1.93 (m, 2H), 1.75-1.77 (m, 2H). |
| Final Product 174 | C28 | | MS (ESI⁺) m/z = 563.27 [M + H]⁺. ¹H NMR (500 MHz, DMSO-d₆) δ 9.17 (s, 1H), 9.12 (s, 1H), 8.65 (s, 1H), 8.38 (s, 1H), 8.35 (s, 1H), 8.11 (s, 1H), 7.88 (d, J = 8.5 Hz, 1H), 7.79 (dd, J = 8.5, 1.0 Hz, 1H), 7.44 (s, 1H), 7.00-7.29 (m, 2H), 6.68-6.74 (m, 1H), 6.27 (dd, J = 17.0, 1.5 Hz, 1H), 5.78 (dd, J = 11.5, 1.0 Hz, 1H), 4.13 (s, 3H), 3.08 (d, J = 11.4 Hz, 2H), 2.63 (t, J = 11.4 Hz, 2H), 2.27 (brs, 7H), 1.86 (d, J = 11.0 Hz, 2H), 1.69-1.75 (m, 2H). |
| Final Product 175 | C11 | | MS (ESI⁺) m/z = 563.25 [M + H]⁺. ¹H NMR (500 MHz, DMSO-d₆) δ 9.15 (s, 1H), 9.03 (s, 1H), 8.60 (s, 1H), 8.51 (s, 1H), 8.37 (s, 1H), 8.18 (s, 1H), 8.09 (dd, J = 8.9, 1.2 Hz, 1H), 7.76 (d, J = 8.9 Hz, 1H), 7.35 (s, 1H), 7.00-7.29 (m, 2H), 6.68-6.73 (m, 1H), 6.27 (dd, J = 17.0, 1.5 Hz, 1H), 5.78 (d, J = 11.6 Hz, 1H), 4.09 (s, 3H), 3.07 (d, J = 8.4 Hz, 2H), 2.63 (t, J = 10.9 Hz, 2H), 2.27-2.14 (m, 7H), 1.84 (d, J = 11.2 Hz, 2H), 1.69-1.74 (m, 2H). |

TABLE 4-continued

Final Products 19-262

| No. of Final Products | No. of Intermediates | Structure of Final Products | NMR or MS |
|---|---|---|---|
| Final Product 176 | C28 | | MS (ESI+) m/z = 536.81 [M + H]+. |
| Final Product 177 | C15 | | MS (ESI+) m/z = 537.23 [M + H]+. $^1$H NMR (300 MHz, DMSO-d$_6$) δ 10.28 (s, 1H), 9.06 (s, 1H), 8.64 (s, 1H), 8.56 (s, 1H), 8.54 (s, 1H), 8.51 (s, 1H), 8.12 (d, J = 0.9 Hz, 1H), 7.99 (dd, J = 8.4, 1.2 Hz, 1H), 7.86 (d, J = 8.7 Hz, 1H), 7.58 (d, J = 5.4 Hz, 1H), 6.88-7.37 (m, 1H), 6.59-6.37 (m, 1H), 6.31 (d, J = 1.8 Hz, 1H), 5.83 (dd, J = 10.2, 2.1 Hz, 1H), 4.12 (d, J = 10.8 Hz, 3H), 2.88 (s, 2H), 2.72 (s, 3H), 2.37 (s, 2H), 2.25 (s, 6H). |
| Final Product 178 | C16 | | MS (ESI+) m/z = 506.24 [M + H]+. $^1$H NMR (300 MHz, DMSO-d$_6$) δ 9.43 (s, 1H), 8.77 (s, 1H), 8.52 (s, 1H), 8.48 (s, 1H), 8.18 (s, 1H), 8.08 (dd, J = 9.0, 1.5 Hz, 1H), 7.74 (d, J = 9.0 Hz, 1H), 6.97 (brs, 1H), 6.74 (s, 1H), 6.42-6.51 (m, 1H), 6.22 (dd, J = 16.8, 1.8 Hz, 1H), 5.73 (d, J = 10.2, 1.8 Hz, 1H), 4.19 (t, J = 5.7 Hz, 2H), 4.09 (s, 3H), 3.86 (s, 3H), 2.65 (t, J = 5.7 Hz, 2H), 2.24 (s, 6H). |
| Final Product 179 | C2 | | MS (ESI+) m/z = 567.28 [M + H]+. $^1$H NMR (400 MHz, DMSO-d$_6$) δ 9.03 (s, 1H), 8.81 (s, 1H), 8.64 (s, 1H), 8.39 (s, 1H), 8.34 (s, 1H), 8.11 (s, 1H), 7.87 (d, J = 8.5 Hz, 1H), 7.78 (d, J = 8.8 Hz, 1H), 7.47 (s, 1H), 6.86 (s, 1H), 6.64-6.71 (m, 1H), 6.24 (d, J = 16.9 Hz, 1H), 5.75 (d, J = 10.5 Hz, 1H), 4.14 (s, 3H), 3.85 (s, 3H), 3.34-3.35 (m, 1H), 3.10 (brs, 3H), 2.69 (s, 2H), 2.51 (brs, 2H), 2.33-2.49 (m, 1H), 1.42-1.94 (m, 10H). |
| Final Product 180 | C2 | | MS (ESI+) m/z = 515.25 [M + H]+. $^1$H NMR (500 MHz, DMSO-d$_6$) δ 9.92 (s, 1H), 8.83 (s, 1H), 8.65 (s, 2H), 8.34 (s, 1H), 8.11 (s, 1H), 7.88 (d, J = 8.5 Hz, 1H), 7.78 (dd, J = 8.5, 1.0 Hz, 1H), 7.48 (s, 1H), 7.01 (s, 1H), 6.53 (brs, 1H), 6.25 (d, J = 16.7 Hz, 1H), 5.77 (d, J = 10.5 Hz, 1H), 4.13 (s, 3H), 3.86 (s, 3H), 2.89 (brs, 2H), 2.72 (brs, 3H), 2.41-2.45 (m, 4H), 2.20 (s, 3H), 1.01 (s, 3H). |
| Final Product 181 | C28 | | MS (ESI+) m/z = 522.77 [M + H]+. $^1$H NMR (400 MHz, DMSO-d$_6$) δ 9.53 (s, 1H), 8.91 (s, 1H), 8.58 (s, 1H), 8.32 (s, 1H), 8.10 (s, 1H), 7.85 (d, J = 8.4 Hz, 1H), 7.76 (d, J = 8.5 Hz, 1H), 7.53 (s, 1H), 6.95-7.32 (m, 2H), 6.55 (s, 1H), 6.46-6.53 (m, 1H), 6.23 (dd, J = 17.1, 1.8 Hz, 1H), 5.75 (dd, J = 10.2, 2.0 Hz, 1H), 5.14-5.17 (m, 1H), 4.13 (s, 3H), 3.16 (q, J = 7.0 Hz, 2H), 2.47-2.49 (m, 2H), 2.20 (s, 6H). |

TABLE 4-continued

Final Products 19-262

| No. of Final Products | No. of Intermediates | Structure of Final Products | NMR or MS |
|---|---|---|---|
| Final Product 182 | C28 | | MS (ESI⁺) m/z = 592.27 [M + H]⁺. ¹H NMR (400 MHz, DMSO-d₆) δ 9.14 (s, 1H), 9.09 (s, 1H), 8.65 (s, 1H), 8.37 (s, 1H), 8.34 (s, 1H), 8.10 (s, 1H), 7.87 (d, J = 8.4 Hz, 1H), 7.79 (d, J = 8.4, 0.8 Hz, 1H), 7.45 (s, 1H), 6.96-7.33 (m, 2H), 6.61-6.68 (m, 1H), 6.25 (dd, J = 17.2, 1.6 Hz, 1H), 5.77 (d, J = 12.0, 1.6 Hz, 1H), 4.13 (s, 3H), 2.84 (d, J = 4.4 Hz, 4H), 2.63 (s, 4H), 2.45-2.50 (m, 2H), 2.32-2.39 (m, 2H), 2.16 (s, 6H). |
| Final Product 183 | C28 | | MS (ESI⁺) m/z = 565.51 [M + H]⁺. ¹H NMR (400 MHz, DMSO-d₆) δ 9.88 (s, 1H), 9.11 (s, 1H), 8.65 (s, 1H), 8.62 (s, 1H), 8.34 (s, 1H), 8.11 (s, 1H), 7.87 (d, J = 8.5 Hz, 1H), 7.78 (dd, J = 8.8, 1.2 Hz, 1H), 7.42 (s, 1H), 6.94-7.31 (m, 2H), 6.46-6.53 (m, 1H), 6.28 (dd, J = 17.0, 1.6 Hz, 1H), 5.80 (dd, J = 10.4, 1.6 Hz, 1H), 4.13 (s, 3H), 2.85 (t, J = 5.8 Hz, 2H), 2.71 (s, 3H), 2.51-2.55 (m, 6H), 0.96 (t, J = 7.1 Hz, 6H). |
| Final Product 184 | C2 | | MS (ESI⁺) m/z = 582.32 [M + H]⁺. ¹H NMR (500 MHz, DMSO-d₆) δ 9.05 (s, 1H), 8.83 (d, J = 8.9 Hz, 1H), 8.64 (s, 1H), 8.38 (s, 1H), 8.34 (s, 1H), 8.11 (s, 1H), 7.87 (d, J = 8.5 Hz, 1H), 7.79 (d, J = 8.5 Hz, 1H), 7.48 (s, 1H), 6.90 (s, 1H), 6.60-6.66 (m, 1H), 6.23 (dd, J = 17.0, 1.0 Hz, 1H), 5.74 (d, J = 10.8 Hz, 1H), 4.13 (s, 3H), 3.85 (s, 3H), 2.83-2.88 (m, 6H), 2.70 (brs, 4H), 2.18-2.24 (m, 4H), 1.91-1.93 (m, 2H), 1.78 (d, J = 11.4 Hz, 2H), 1.46-1.50 (m, 2H). |
| Final Product 185 | C11 | | MS (ESI⁺) m/z = 579.00 [M + H]⁺. ¹H NMR (500 MHz, DMSO-d₆) δ 9.35 (s, 1H), 9.01 (s, 1H), 8.59 (s, 1H), 8.50 (s, 1H), 8.34 (s, 1H), 8.17 (s, 1H), 8.08 (dd, J = 9.0, 1.5 Hz, 1H), 7.75 (d, J = 8.5 Hz, 1H), 7.01-7.31 (m, 3H), 6.62-6.67 (m, 1H), 6.25 (dd, J = 17.0, 2.0 Hz, 1H), 5.77 (dd, J = 10.0, 1.5 Hz, 1H), 4.20 (t, J = 6.0 Hz, 2H), 4.09 (s, 3H), 2.74 (t, J = 5.5 Hz, 2H), 2.51 (brs, 4H), 2.31 (s, 4H), 2.14 (s, 3H). |
| Final Product 186 | C1 | | MS (ESI⁺) m/z = 515.84 [M + H]⁺. ¹H NMR (500 MHz, DMSO-d₆) δ 9.35 (s, 1H), 8.74 (s, 1H), 8.57 (s, 1H), 8.47 (s, 1H), 8.30 (s, 1H), 8.17 (s, 1H), 8.06 (dd, J = 9.0, 1.5 Hz, 1H), 7.74 (d, J = 9.0 Hz, 1H), 7.25 (s, 1H), 6.92 (s, 1H), 6.50-6.56 (m, 1H), 6.23 (dd, J = 17.0, 2.0 Hz, 1H), 5.73 (dd, J = 10.0, 1.5 Hz, 1H), 4.15 (t, J = 6.0 Hz, 2H), 4.09 (s, 3H), 3.85 (s, 3H), 2.87-2.90 (m, 1H), 2.74 (t, J = 6.0 Hz, 2H), 2.26 (s, 3H), 0.99 (d, J = 6.5 Hz, 6H). |

TABLE 4-continued

Final Products 19-262

| No. of Final Products | No. of Intermediates | Structure of Final Products | NMR or MS |
|---|---|---|---|
| Final Product 187 | C11 | 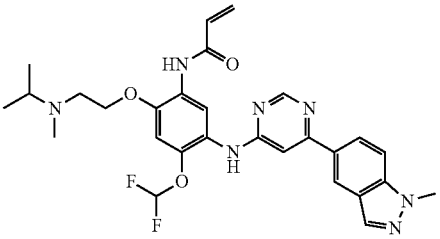 [SMILES: C=CC(=O)Nc1cc(Nc2cc(-c3ccc4c(cnn4C)c3)ncn2)c(OC(F)F)cc1OCCN(C)C(C)C] | MS (ESI⁺) m/z = 551.97 [M + H]⁺. ¹H NMR (400 MHz, DMSO-d₆) δ 9.43 (s, 1H), 8.99 (s, 1H), 8.58 (s, 1H), 8.49 (s, 1H), 8.37 (s, 1H), 8.17 (s, 1H), 8.07 (dd, J = 8.8, 1.6 Hz, 1H), 7.74 (d, J = 8.8 Hz, 1H), 6.96-7.33 (m, 3H), 6.54-6.59 (m, 1H), 6.25 (dd, J = 17.0, 1.8 Hz, 1H), 5.76 (dd, J = 10.0, 1.6 Hz, 1H), 4.13 (t, J = 5.6 Hz, 2H), 4.08 (s, 3H), 2.95-2.78 (m, 1H), 2.74 (t, J = 5.9 Hz, 2H), 2.24 (s, 3H), 0.97 (d, J = 6.5 Hz, 6H). |
| Final Product 188 | C2 | 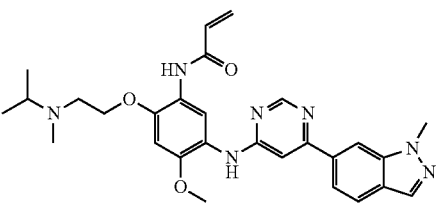 [SMILES: C=CC(=O)Nc1cc(Nc2cc(-c3ccc4cnn(C)c4c3)ncn2)c(OC)cc1OCCN(C)C(C)C] | MS (ESI⁺) m/z = 515.98 [M + H]⁺. ¹H NMR (400 MHz, DMSO-d₆) δ 9.35 (s, 1H), 8.79 (s, 1H), 8.62 (s, 1H), 8.32 (s, 2H), 8.10 (s, 1H), 7.86 (d, J = 8.5 Hz, 1H), 7.76 (dd, J = 8.8, 1.2 Hz, 1H), 7.35 (s, 1H), 6.92 (s, 1H), 6.50-6.57 (m, 1H), 6.22 (dd, J = 17.0, 1.7 Hz, 1H), 5.72 (dd, J = 11.7, 1.6 Hz, 1H), 4.12-4.16 (m, 5H), 3.85 (s, 3H), 2.85-2.88 (m, 1H), 2.72 (t, J = 5.8 Hz, 2H), 2.25 (s, 3H), 0.98 (d, J = 6.5 Hz, 6H). |
| Final Product 189 | C1 | 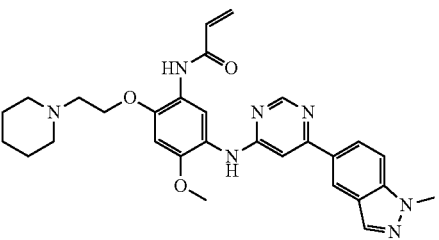 [SMILES: C=CC(=O)Nc1cc(Nc2cc(-c3ccc4c(cnn4C)c3)ncn2)c(OC)cc1OCCN1CCCCC1] | MS (ESI⁺) m/z = 527.76 [M + H]⁺. ¹H NMR (500 MHz, DMSO-d₆) δ 9.24 (s, 1H), 8.73 (s, 1H), 8.57 (s, 1H), 8.47 (s, 1H), 8.26 (s, 1H), 8.17 (s, 1H), 8.06 (dd, J = 8.9, 1.4 Hz, 1H), 7.74 (d, J = 8.9 Hz, 1H), 7.25 (s, 1H), 6.91 (s, 1H), 6.56-6.61 (m, 1H), 6.22 (dd, J = 17.0, 1.7 Hz, 1H), 5.73 (dd, J = 10.3, 1.4 Hz, 1H), 4.21 (t, J = 6.0 Hz, 2H), 4.09 (s, 3H), 3.86 (s, 3H), 2.69 (t, J = 5.8 Hz, 2H), 2.46-2.50 (m, 4H), 1.48-1.53 (m, 4H), 1.38-1.40 (m, 2H). |
| Final Product 190 | C9 | 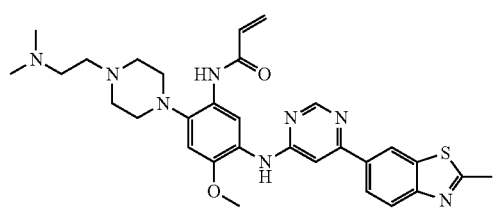 | MS (ESI⁺) m/z = 572.99 [M + H]⁺. ¹H NMR (400 MHz, DMSO-d₆) δ 9.03 (s, 1H), 8.81 (s, 1H), 8.75 (d, J = 1.2 Hz, 1H), 8.61 (s, 1H), 8.31 (s, 1H), 8.11 (dd, J = 8.6, 1.6 Hz, 1H), 8.01 (d, J = 8.6 Hz, 1H), 7.40 (s, 1H), 6.89 (s, 1H), 6.59-6.65 (m, 1H), 6.25 (d, J = 17.1 Hz, 1H), 5.74 (d, J = 10.8 Hz, 1H), 3.85 (s, 3H), 2.86 (d, J = 4.4 Hz, 4H), 2.83 (s, 3H), 2.62 (s, 4H), 2.46 (d, J = 10.4 Hz, 2H), 2.39 (d, J = 7.1 Hz, 2H), 2.16 (s, 6H). |
| Final Product 191 | C9 | 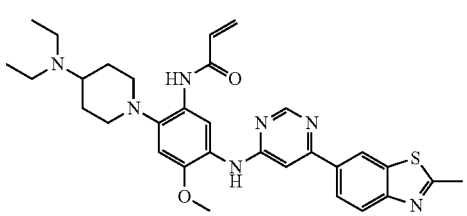 [SMILES: C=CC(=O)Nc1cc(Nc2cc(-c3ccc4nc(C)sc4c3)ncn2)c(OC)cc1N1CCC(N(CC)CC)CC1] | MS (ESI⁺) m/z = 571.64 [M + H]⁺. ¹H NMR (500 MHz, DMSO-d₆) δ 9.03 (s, 1H), 8.81 (s, 1H), 8.75 (d, J = 1.1 Hz, 1H), 8.61 (s, 1H), 8.33 (s, 1H), 8.11 (dd, J = 8.6, 1.5 Hz, 1H), 8.01 (d, J = 8.5 Hz, 1H), 7.38 (s, 1H), 6.85 (d, J = 13.3 Hz, 1H), 6.60-6.69 (m, 1H), 6.26 (d, J = 17.8 Hz, 1H), 5.75 (d, J = 10.9 Hz, 1H), 3.83 (s, 3H), 3.06 (d, J = 10.6 Hz, 2H), 2.83 (s, 3H), 2.65-2.69 (m, 2H), 2.53-2.66 (m, 5H), 1.73-1.74 (m, 4H), 0.99 (t, J = 7.0 Hz, 6H). |

TABLE 4-continued

Final Products 19-262

| No. of Final Products | No. of Intermediates | Structure of Final Products | NMR or MS |
|---|---|---|---|
| Final Product 192 | C12 | | MS (ESI⁺) m/z = 544.86 [M + H]⁺. ¹H NMR (500 MHz, DMSO-d₆) δ 9.02 (s, 1H), 8.96 (s, 1H), 8.59 (s, 1H), 8.46 (d, J = 7.5 Hz, 1H), 8.26 (s, 1H), 8.19 (s, 1H), 7.68 (d, J = 12.0 Hz, 1H), 7.19 (s, 1H), 6.83 (s, 1H), 6.55-6.61 (m, 1H), 6.20 (dd, J = 17.0, 1.5 Hz, 1H), 5.72 (d, J = 8.8 Hz, 1H), 4.05 (s, 3H), 3.83 (s, 3H), 2.87 (d, J = 10.5 Hz, 2H), 2.54 (s, 2H), 2.43 (s, 2H), 2.23 (s, 3H), 1.02 (d, J = 6.0 Hz, 6H). |
| Final Product 193 | C12 | | MS (ESI⁺) m/z = 573.31 [M + H]⁺. ¹H NMR (400 MHz, DMSO-d₆) δ 8.98 (s, 1H), 8.94 (s, 1H), 8.58 (s, 1H), 8.47 (d, J = 7.4 Hz, 1H), 8.29 (s, 1H), 8.19 (d, J = 0.8 Hz, 1H), 7.67 (d, J = 12.3 Hz, 1H), 7.18 (s, 1H), 6.85 (s, 1H), 6.63-6.70 (m, 1H), 6.22 (dd, J = 17.0, 1.7 Hz, 1H), 5.73 (d, J = 11.2 Hz, 1H), 4.04 (s, 3H), 3.81 (s, 3H), 3.05 (d, J = 10.8 Hz, 2H), 2.65-2.72 (m, 2H), 2.53-2.60 (m, 5H), 1.74 (brs, 4H), 0.99 (t, J = 7.1 Hz, 6H). |
| Final Product 194 | C12 | | MS (ESI⁺) m/z = 506.77 [M + H]⁺. ¹H NMR (500 MHz, DMSO-d₆) δ 9.65 (s, 1H), 8.93 (s, 1H), 8.58 (s, 1H), 8.46 (d, J = 7.4 Hz, 1H), 8.30 (s, 1H), 8.19 (s, 1H), 7.67 (d, J = 12.3 Hz, 1H), 7.12 (brs, 1H), 6.93 (s, 1H), 6.44-6.50 (m, 1H), 6.21 (dd, J = 17.0, 1.8 Hz, 1H), 5.73 (dd, J = 10.2, 1.6 Hz, 1H), 4.19 (t, J = 5.6 Hz, 2H), 4.04 (s, 3H), 3.82 (s, 3H), 2.60 (t, J = 5.6 Hz, 2H), 2.26 (s, 6H). |
| Final Product 195 | C12 | | MS (ESI⁺) m/z = 531.30 [M + H]⁺. ¹H NMR (400 MHz, DMSO-d₆) δ 9.29 (s, 1H), 8.96 (s, 1H), 8.60 (s, 1H), 8.46-8.51 (m, 2H), 8.19 (s, 1H), 7.68 (d, J = 12.0 Hz, 1H), 7.23 (s, 1H), 6.97 (s, 1H), 6.54-6.61 (m, 1H), 6.22 (dd, J = 17.2, 1.6 Hz, 1H), 5.73 (dd, J = 11.6, 1.6 Hz, 1H), 4.05 (s, 3H), 3.81 (s, 3H), 3.62 (brs, 1H), 2.58 (s, 3H), 2.53-2.55 (m, 1H), 2.47-2.49 (m, 1H), 2.39-2.43 (m, 2H), 2.22 (s, 3H), 1.90-1.92 (m, 1H), 1.72-1.74 (m, 1H). |
| Final Product 196 | C2 | | MS (ESI⁺) m/z = 529.27 [M + H]⁺. ¹H NMR (400 MHz, DMSO-d₆) δ 9.81 (s, 1H), 8.81 (s, 1H), 8.67 (s, 1H), 8.64 (s, 1H), 8.33 (s, 1H), 8.10 (s, 1H), 7.86 (d, J = 8.4 Hz, 1H), 7.77 (d, J = 8.4 Hz, 1H), 7.44 (s, 1H), 6.99 (s, 1H), 6.35-6.46 (m, 1H), 6.24 (d, J = 16.8 Hz, 1H), 5.76 (d, J = 10.0 Hz, 1H), 4.13 (s, 3H), 3.84 (s, 3H), 2.82 (brs, 3H), 2.73 (s, 3H), 2.44-2.50 (m, 2H), 2.19 (s, 3H), 0.97 (d, J = 6.1 Hz, 6H). |

TABLE 4-continued

Final Products 19-262

| No. of Final Products | No. of Intermediates | Structure of Final Products | NMR or MS |
|---|---|---|---|
| Final Product 197 | C16 | | MS (ESI+) m/z = 547.26 [M + H]+. 1H NMR (500 MHz, DMSO-d6) δ 9.42 (s, 1H), 8.72 (s, 1H), 8.50 (s, 1H), 8.46 (s, 1H), 8.15 (s, 1H), 8.05 (d, J = 8.5 Hz, 1H), 7.73 (d, J = 9.0 Hz, 1H), 6.94 (brs, 1H), 6.56 (s, 1H), 6.46-6.52 (m, 1H), 6.22 (d, J = 17.0 Hz, 1H), 5.72 (d, J = 10.0 Hz, 1H), 4.08 (s, 3H), 3.81 (s, 3H), 3.01 (s, 2H), 2.81 (s, 3H), 2.71-2.76 (m, 1H), 2.51 (brs, 2H), 2.09 (s, 3H), 0.91 (d, J = 6.5 Hz, 6H). |
| Final Product 198 | C17 | | MS (ESI+) m/z = 547.24 [M + H]+. 1H NMR (500 MHz, DMSO-d6) δ 9.46 (s, 1H), 8.79 (s, 1H), 8.54 (s, 1H), 8.30 (s, 1H), 8.10 (s, 1H), 7.84 (d, J = 8.0 Hz, 1H), 7.76 (d, J = 8.5 Hz, 1H), 6.99 (brs, 1H), 6.57 (s, 1H), 6.47-6.53 (m, 1H), 6.22 (d, J = 17.0 Hz, 1H), 5.72 (d, J = 10.5 Hz, 1H), 4.13 (s, 3H), 3.81 (s, 3H), 3.01 (t, J = 6.5 Hz, 2H), 2.81 (s, 3H), 2.70-2.74 (m, 1H), 2.52 (s, 2H), 2.08 (s, 3H), 0.91 (d, J = 6.5 Hz, 6H). |
| Final Product 199 | C28 | | MS (ESI+) m/z = 565.28 [M + H]+. 1H NMR (500 MHz, DMSO-d6) δ 9.98 (s, 1H), 9.19 (s, 1H), 8.67 (s, 1H), 8.64 (s, 1H), 8.35 (s, 1H), 8.11 (s, 1H), 7.87 (d, J = 8.5 Hz, 1H), 7.78 (d, J = 8.5 Hz, 1H), 7.43 (s, 1H), 6.97-7.27 (m, 2H), 6.41-6.46 (m, 1H), 6.28 (d, J = 16.5 Hz, 1H), 5.80 (d, J = 11.0 Hz, 1H), 4.13 (s, 3H) 2.71-2.88 (m, 6H), 2.46 (s, 2H), 2.23 (s, 3H). 0.98 (d, J = 6.0 Hz, 6H). |
| Final Product 200 | C16 | | MS (ESI+) m/z = 533.32 [M + H]+. 1H NMR (500 MHz, DMSO-d6) δ 9.46 (s, 1H), 8.72 (s, 1H), 8.50 (s, 1H), 8.46 (s, 1H), 8.15 (s, 1H), 8.05 (d, J = 8.9 Hz, 1H), 7.73 (d, J = 8.5 Hz, 1H), 6.93 (brs, 1H), 6.57 (s, 1H), 6.46-6.52 (m, 1H), 6.22 (d, J = 17.1 Hz, 1H), 5.73 (d, J = 10.7 Hz, 1H), 4.08 (s, 3H), 3.81 (s, 3H), 3.03 (t, J = 6.9 Hz, 2H), 2.80 (s, 3H), 2.47-2.50 (m, 2H), 2.34 (q, J = 7.0 Hz, 2H), 2.12 (s, 3H), 0.95 (t, J = 7.1 Hz, 3H). |
| Final Product 201 | C17 | | MS (ESI+) m/z = 533.32 [M + H]+. 1H NMR (500 MHz, DMSO-d6) δ 9.50 (s, 1H), 8.80 (s, 1H), 8.55 (s, 1H), 8.31 (s, 1H), 8.10 (s, 1H), 7.85 (d, J = 8.5 Hz, 1H), 7.76 (d, J = 8.5 Hz, 1H), 7.01 (s, 1H), 6.58 (s, 1H), 6.46-6.52 (m, 1H), 6.21 (d, J = 17.0 Hz, 1H), 5.73 (d, J = 11.0 Hz, 1H), 4.14 (s, 3H), 3.81 (s, 3H), 3.04 (t, J = 7.0 Hz, 2H), 2.81 (s, 3H), 2.48 (s, 2H), 2.34 (q, J = 7.0 Hz, 2H), 2.09 (s, 3H), 1.04 (d, J = 7.0 Hz, 3H). |

TABLE 4-continued

Final Products 19-262

| No. of Final Products | No. of Intermediates | Structure of Final Products | NMR or MS |
|---|---|---|---|
| Final Product 202 | C1 | | MS (ESI+) m/z = 583.33 [M + H]+. 1H NMR (500 MHz, DMSO-d6) δ 9.00 (s, 1H), 8.74 (s, 1H), 8.59 (s, 1H), 8.49 (s, 1H), 8.37 (s, 1H), 8.20 (d, J = 26.7 Hz, 1H), 8.07 (d, J = 9.0 Hz, 1H), 7.75 (d, J = 9.0 Hz, 1H), 7.36 (s, 1H), 6.86 (s, 1H), 6.60-6.66 (m, 1H), 6.24 (d, J = 17.0 Hz, 1H), 5.74 (d, J = 10.5 Hz, 1H), 4.08 (s, 3H), 3.81-3.87 (m, 1H), 3.84 (s, 3H), 3.18 (s, 3H), 3.02 (d, J = 11.5 Hz, 2H), 2.62-2.75 (m, 4H), 2.52-2.53 (m, 1H), 2.46-2.48 (m, 1H), 2.09-2.15 (m, 1H), 1.90-2.00 (m, 3H), 1.65-1.69 (m, 3H). |
| Final Product 203 | C2 | | MS (ESI+) m/z = 583.33 [M + H]+. 1H NMR (500 MHz, DMSO-d6) δ 9.02 (s, 1H), 8.81 (s, 1H), 8.64 (s, 1H), 8.39 (s, 1H), 8.34 (s, 1H), 8.10 (s, 1H), 7.87 (d, J = 8.5 Hz, 1H), 7.78 (d, J = 8.0 Hz, 1H), 7.46 (s, 1H), 6.86 (s, 1H), 6.60-6.66 (m, 1H), 6.23 (d, J = 17.0 Hz, 1H), 5.74 (d, J = 10.5 Hz, 1H), 4.13 (s, 3H), 3.85 (s, 4H), 3.18 (s, 3H), 3.02 (d, J = 11.0 Hz, 2H), 2.63-2.75 (m, 4H), 2.52-2.54 (m, 1H), 2.46-2.48 (m, 1H), 2.09-2.20 (m, 1H), 1.90-1.96 (m, 3H), 1.65-1.69 (m, 3H). |
| Final Product 204 | C1 | | MS (ESI+) m/z = 597.36 [M + H]+. 1H NMR (500 MHz, DMSO-d6) δ 9.00 (s, 1H), 8.73 (s, 1H), 8.59 (s, 1H), 8.49 (s, 1H), 8.36 (s, 1H), 8.17 (s, 1H), 8.07 (d, J = 8.5 Hz, 1H), 7.75 (d, J = 9.0 Hz, 1H), 7.36 (s, 1H), 6.84 (s, 1H), 6.60-6.68 (m, 1H), 6.24 (d, J = 17.0 Hz, 1H), 5.74 (d, J = 10.5 Hz, 1H), 4.08 (s, 3H), 3.84 (s, 3H), 3.23 (s, 3H), 3.15-3.20 (m, 1H), 3.06 (d, J = 10.5 Hz, 2H), 2.79-2.81 (m, 2H), 2.67 (t, J = 11.0 Hz, 2H), 2.28-2.34 (m, 1H), 2.26 (t, J = 9.5 Hz, 2H), 1.79-1.86 (m, 6H), 1.38-1.40 (m, 2H). |
| Final Product 205 | C2 | | MS (ESI+) m/z = 597.29 [M + H]+. 1H NMR (500 MHz, DMSO-d6) δ 9.02 (s, 1H), 8.81 (s, 1H), 8.64 (s, 1H), 8.38 (s, 1H), 8.33 (s, 1H), 8.10 (s, 1H), 7.87 (d, J = 8.5 Hz, 1H), 7.78 (d, J = 8.5 Hz, 1H), 7.46 (s, 1H), 6.85 (s, 1H), 6.65-6.70 (m, 1H), 6.24 (d, J = 17.0 Hz, 1H), 5.74 (d, J = 10.0 Hz, 1H), 4.13 (s, 3H), 3.85 (s, 3H), 3.07-3.23 (m, 6H), 2.80 (s, 2H), 2.66 (s, 2H), 2.26-2.36 (m, 3H), 1.78-1.97 (m, 6H), 1.40 (s, 2H). |
| Final Product 206 | C1 | | MS (ESI+) m/z = 569.26 [M + H]+. 1H NMR (400 MHz, DMSO) δ 9.00 (s, 1H), 8.74 (s, 1H), 8.59 (s, 1H), 8.49 (s, 1H), 8.35 (s, 1H), 8.17 (s, 1H), 8.07 (d, J = 8.4 Hz, 1H), 7.75 (d, J = 8.8 Hz, 1H), 7.36 (s, 1H), 6.85 (s, 1H), 6.60-6.67 (m, 1H), 6.23 (d, J = 16.8 Hz, 1H), 5.73 (d, J = 9.2 Hz, 1H), 4.08 (s, 3H), 3.95 (s, 1H), 3.84 (s, 3H), 3.66 (t, J = 5.2 Hz, 2H), 3.50 (s, 2H), 3.16 (s, 3H), 2.80 (s, 2H), 2.65 (t, J = 13.0 Hz, 2H), 2.13 (s, 1H), 1.75 (s, 2H), 1.47 (s, 2H). |

TABLE 4-continued

Final Products 19-262

| No. of Final Products | No. of Intermediates | Structure of Final Products | NMR or MS |
|---|---|---|---|
| Final Product 207 | C2 | | MS (ESI+) m/z = 569.32 [M + H]+. 1H NMR (400 MHz, DMSO-d6) δ 9.01 (s, 1H), 8.80 (s, 1H), 8.63 (s, 1H), 8.37 (s, 1H), 8.33 (s, 1H), 8.10 (s, 1H), 7.86 (d, J = 8.0 Hz, 1H), 7.77 (d, J = 8.4 Hz, 1H), 7.46 (s, 1H), 6.85 (s, 1H), 6.61-6.68 (m, 1H), 6.23 (d, J = 16.8 Hz, 1H), 5.73 (d, J = 10.0 Hz, 1H), 4.13 (s, 3H), 3.95 (s, 1H), 3.85 (s, 3H), 3.50 (s, 3H), 3.16 (s, 2H), 2.98 (s, 2H), 2.76 (s, 2H), 2.65 (t, J = 10.0 Hz, 2H), 2.13 (s, 1H), 1.75 (s, 2H), 1.47 (s, 2H). |
| Final Product 208 | C1 | | MS (ESI+) m/z = 568.37 [M + H]+. 1H NMR (500 MHz, DMSO-d6) δ 9.00 (s, 1H), 8.75 (s, 1H), 8.59 (s, 1H), 8.49 (s, 1H), 8.37 (s, 1H), 8.17 (s, 1H), 8.07 (d, J = 8.9 Hz, 1H), 7.74 (d, J = 8.9 Hz, 1H), 7.37 (s, 1H), 6.85 (s, 1H), 6.64-6.68 (m, 1H), 6.24 (d, J = 17.0 Hz, 1H), 5.73 (d, J = 11.0 Hz, 1H), 4.08 (s, 3H), 3.84-3.89 (m, 5H), 3.28 (t, J = 11.0 Hz, 2H), 3.05 (d, J = 5.0 Hz, 2H), 2.63 (d, J = 11.0 Hz, 2H), 1.76 (d, J = 11.0 Hz, 2H), 1.63 (d, J = 12.0 Hz, 2H), 1.45 (q, J = 11.0 Hz, 2H), 1.34 (s, 1H), 1.17-1.23 (m, 3H). |
| Final Product 209 | C2 | | MS (ESI+) m/z = 568.39 [M + H]+. 1H NMR (500 MHz, DMSO-d6) δ 9.01 (s, 1H), 8.80 (s, 1H), 8.64 (s, 1H), 8.38 (s, 1H), 8.34 (s, 1H), 8.10 (s, 1H), 7.86 (d, J = 8.5 Hz, 1H), 7.78 (d, J = 8.5 Hz, 1H), 7.46 (s, 1H), 6.85 (s, 1H), 6.60-6.64 (m, 1H), 6.24 (d, J = 17.0 Hz, 1H), 5.73 (d, J = 10.5 Hz, 1H), 4.13 (s, 3H), 3.85-3.90 (m, 5H), 3.28 (t, J = 11.0 Hz, 2H), 3.05 (d, J = 10.5 Hz, 2H), 2.63 (t, J = 11.0 Hz, 2H), 1.76 (d, J = 12.0 Hz, 2H), 1.63 (d, J = 12.5 Hz, 2H), 1.46 (q, J = 10.0 Hz, 2H), 1.35 (brs, 1H), 1.18-1.24 (m, 3H). |
| Final Product 210 | C1 | | MS (ESI+) m/z = 624.37 [M + H]+. 1H NMR (400 MHz, DMSO-d6) δ 9.01 (s, 1H), 8.74 (s, 1H), 8.59 (s, 1H), 8.49 (s, 1H), 8.36 (s, 1H), 8.17 (s, 1H), 8.07 (d, J = 8.7 Hz, 1H), 7.75 (d, J = 8.9 Hz, 1H), 7.37 (s, 1H), 6.85 (s, 6.74-6.51 (m, 1H), 6.24 (d, J = 16.9 Hz, 1H), 5.74 (d, J = 10.1 Hz, 1H), 4.53 (s, 2H), 4.42 (s, 2H), 4.08 (s, 3H), 3.84 (s, 3H), 3.37 (brs, 1H), 3.07 (d, J = 9.6 Hz, 2H), 2.67 (t, J = 11.1 Hz, 3H), 2.56 (brs, 3H), 2.27 (brs, 5H), 1.83-1.86 (m, 2H), 1.69-1.72 (m, 2H). |
| Final Product 211 | C2 | | MS (ESI+) m/z = 624.33 [M + H]+. 1H NMR (400 MHz, DMSO-d6) δ 9.02 (s, 1H), 8.81 (s, 1H), 8.63 (s, 1H), 8.38 (s, 1H), 8.33 (s, 1H), 8.10 (s, 1H), 7.87 (d, J = 8.2 Hz, 1H), 7.78 (d, J = 8.3 Hz, 1H), 7.46 (s, 1H), 6.85 (s, 1H), 6.57-6.77 (m, 1H), 6.23 (d, J = 17.0 Hz, 1H), 5.74 (d, J = 10.0 Hz, 1H), 4.53 (brs, 2H), 4.42 (brs, 2H), 4.13 (s, 3H), 3.85 (s, 3H), 3.37 (brs, 1H), 3.07 (d, J = 10.1 Hz, 2H), 2.68 (t, J = 11.0 Hz, 2H), 2.56 (brs, 4H), 2.27 (brs, 5H), 1.83-1.86 (m, 2H), 1.70-1.73 (m, 2H). |

TABLE 4-continued

Final Products 19-262

| No. of Final Products | No. of Intermediates | Structure of Final Products | NMR or MS |
|---|---|---|---|
| Final Product 212 | C1 | 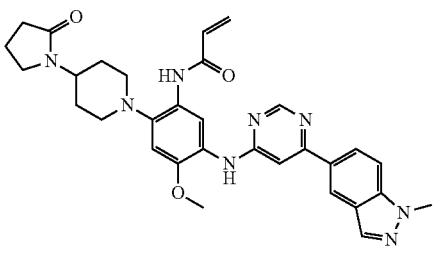 [SMILES: C=CC(=O)Nc1cc(Nc2cc(-c3ccc4c(cnn4C)c3)ncn2)c(OC)cc1N1CCC(N2CCCC2=O)CC1] | MS (ESI+) m/z = 567.35 [M + H]+. 1H NMR (500 MHz, DMSO-d6) δ 9.05 (s, 1H), 8.75 (s, 1H), 8.59 (s, 1H), 8.50 (s, 1H), 8.39 (s, 1H), 8.17 (s, 1H), 8.08 (d, J = 9.0 Hz, 1H), 7.75 (d, J = 8.9 Hz, 1H), 7.38 (s, 1H), 6.90 (s, 1H), 6.66-6.69 (m, 1H), 6.25 (d, J = 17.6 Hz, 1H), 5.75 (d, J = 10.5 Hz, 1H), 4.06 (s, 3H), 3.86-3.91 (m, 1H), 3.85 (s, 3H), 3.39 (t, J = 6.8 Hz, 2H), 3.08 (d, J = 10.9 Hz, 2H), 2.80 (t, J = 11.4 Hz, 2H), 2.25 (t, J = 8.0 Hz, 2H), 1.92-1.98 (m, 4H), 1.62 (d, J = 10.0 Hz, 2H). |
| Final Product 213 | C2 | 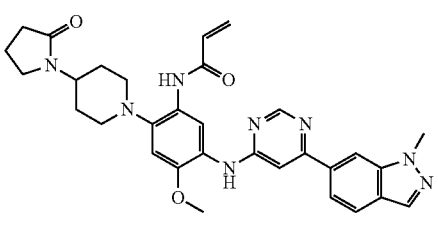 [SMILES: C=CC(=O)Nc1cc(Nc2cc(-c3ccc4cnn(C)c4c3)ncn2)c(OC)cc1N1CCC(N2CCCC2=O)CC1] | MS (ESI+) m/z = 567.36 [M + H]+. 1H NMR (400 MHz, DMSO-d6) δ 9.07 (s, 1H), 8.82 (s, 1H), 8.64 (s, 1H), 8.41 (s, 1H), 8.34 (s, 1H), 8.10 (s, 1H), 7.86 (d, J = 8.0 Hz, 1H), 7.78 (d, J = 8.4 Hz, 1H), 7.48 (s, 1H), 6.91 (s, 1H), 6.67-6.73 (m, 1H), 6.23 (d, J = 17.2 Hz, 1H), 5.74 (d, J = 10.8 Hz, 1H), 4.13 (s, 3H), 3.85-3.91 (m, 4H), 3.39 (s, 2H), 3.07 (d, J = 10.4 Hz, 2H), 2.80 (t, J = 10.4 Hz, 2H), 2.24 (t, J = 7.6 Hz, 2H), 1.95 (s, 4H), 1.62 (d, J = 10.4 Hz, 2H). |
| Final Product 214 | C1 | 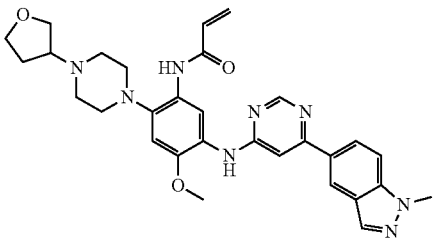 [SMILES: C=CC(=O)Nc1cc(Nc2cc(-c3ccc4c(cnn4C)c3)ncn2)c(OC)cc1N1CCN(C2CCOC2)CC1] | MS (ESI+) m/z = 555.35 [M + H]+. 1H NMR (400 MHz, DMSO-d6) δ 9.06 (s, 1H), 8.76 (s, 1H), 8.59 (s, 1H), 8.49 (s, 1H), 8.36 (s, 1H), 8.17 (s, 1H), 8.07 (d, J = 8.4 Hz, 1H), 7.75 (d, J = 8.8 Hz, 1H), 7.39 (s, 1H), 6.88 (s, 1H), 6.60-6.67 (m, 1H), 6.23 (d, J = 16.8 Hz, 1H), 5.74 (d, J = 10.0 Hz, 1H), 4.08 (s, 3H), 3.80-3.85 (m, 5H), 3.52-3.70 (m, 2H), 2.97 (s, 1H), 2.88 (s, 4H), 2.65 (s, 2H), 2.56 (s, 2H), 2.00-2.01 (m, 1H), 1.78-1.80 (m, 1H). |
| Final Product 215 | C2 | 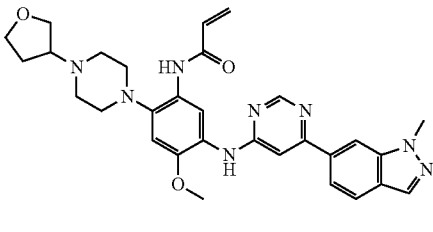 [SMILES: C=CC(=O)Nc1cc(Nc2cc(-c3ccc4cnn(C)c4c3)ncn2)c(OC)cc1N1CCN(C2CCOC2)CC1] | MS (ESI+) m/z = 555.35 [M + H]+. 1H NMR (400 MHz, DMSO-d6) δ 9.07 (s, 1H), 8.82 (s, 1H), 8.64 (s, 1H), 8.38 (s, 1H), 8.33 (s, 1H), 8.10 (s, 1H), 7.86 (d, J = 8.4 Hz, 1H), 7.75 (d, J = 8.0 Hz, 1H), 7.48 (s, 1H), 6.88 (s, 1H), 6.60-6.67 (m, 1H), 6.23 (d, J = 16.8 Hz, 1H), 5.74 (d, J = 10.4 Hz, 1H), 4.13 (s, 3H), 3.85 (s, 3H), 3.81 (d, J = 6.4 Hz, 2H), 3.67 (q, J = 7.6 Hz, 1H), 3.51 (d, J = 6.8 Hz, 1H), 2.97 (s, 1H), 2.88 (s, 4H), 2.65 (s, 2H), 2.57 (s, 2H), 2.01-2.02 (m, 1H), 1.77-1.79 (m, 1H). |
| Final Product 216 | C1 | 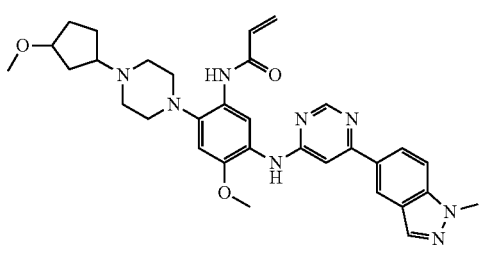 | MS (ESI+) m/z = 583.38 [M + H]+. 1H NMR (400 MHz, DMSO-d6) δ 9.04 (s, 1H), 8.75 (s, 1H), 8.59 (s, 1H), 8.50 (s, 1H), 8.37 (s, 1H), 8.17 (s, 1H), 8.08 (dd, J = 9.2, 1.6 Hz, 1H), 7.75 (d, J = 8.9 Hz, 1H), 7.39 (s, 1H), 6.89 (s, 1H), 6.62-6.68 (m, 1H), 6.23 (d, J = 16.9 Hz, 1H), 5.73 (d, J = 10.7 Hz, 1H), 4.08 (s, 3H), 3.85 (s, 3H), 3.71-3.75 (m, 1H), 3.17 (s, 3H), 2.88 (s, 4H), 2.54-2.60 (m, 5H), 2.16-2.18 (m, 1H), 1.74-1.78 (m, 1H), 1.65-1.68 (m, 2H), 1.42-1.49 (m, 1H), 1.28-1.30 (m, 1H). |

TABLE 4-continued

Final Products 19-262

| No. of Final Products | No. of Intermediates | Structure of Final Products | NMR or MS |
|---|---|---|---|
| Final Product 217 | C2 | | MS (ESI+) m/z = 583.38 [M + H]+. 1H NMR (400 MHz, DMSO-d6) δ 9.06 (s, 1H), 8.82 (s, 1H), 8.64 (s, 1H), 8.38 (s, 1H), 8.34 (s, 1H), 8.10 (s, 1H), 7.87 (d, J = 8.5 Hz, 1H), 7.78 (d, J = 8.4 Hz, 1H), 7.48 (s, 1H), 6.90 (s, 1H), 6.59-6.64 (m, 1H), 6.23 (d, J = 16.9 Hz, 1H), 5.73 (d, J = 10.8 Hz, 1H), 4.13 (s, 3H), 3.86 (s, 3H), 3.81-3.65 (m, 1H), 3.17 (s, 3H), 2.88 (s, 4H), 2.75-2.52 (m, 5H), 2.25-2.12 (m, 1H), 1.75-1.77 (m, 1H), 1.64-1.68 (m, 2H), 1.48-1.51 (m, 1H), 1.30-1.36 (m, 1H). |
| Final Product 218 | C1 | | MS (ESI+) m/z = 541.26 [M + H]+. 1H NMR (400 MHz, DMSO-d6) δ 9.03 (s, 1H), 8.74 (s, 1H), 8.59 (s, 1H), 8.49 (s, 1H), 8.37 (s, 1H), 8.17 (s, 1H), 8.08 (d, J = 8.5 Hz, 1H), 7.75 (d, J = 8.9 Hz, 1H), 7.39 (s, 1H), 6.91 (s, 1H), 6.58-6.65 (m, 1H), 6.23 (d, J = 16.8 Hz, 1H), 5.73 (d, J = 10.2 Hz, 1H), 4.57 (d, J = 6.1 Hz, 2H), 4.48 (s, 2H), 4.08 (s, 3H), 3.86 (s, 3H), 3.51 (brs, 1H), 2.91 (brs, 4H), 2.49-2.41 (m, 4H). |
| Final Product 219 | C2 | | MS (ESI+) m/z = 541.26 [M + H]+. 1H NMR (500 MHz, DMSO-d6) δ 9.06 (s, 1H), 8.82 (s, 1H), 8.64 (s, 1H), 8.39 (s, 1H) 8.34 (s, 1H), 8.10 (s, 1H), 7.87 (d, J = 8.5 Hz, 1H), 7.78 (d, J = 8.5 Hz, 1H), 7.48 (s, 1H), 6.91 (s, 1H), 6.59-6.65 (m, 1H), 6.22 (d, J = 17.2 Hz, 1H), 5.73 (d, J = 10.6 Hz, 1H), 4.58 (t, J = 6.5 Hz, 2H), 4.47 (t, J = 6.1 Hz, 2H), 4.13 (s, 3H), 3.87 (s, 3H), 3.57-3.43 (m, 1H), 2.91 (t, J = 4.2 Hz, 4H), 2.49-2.50 (m, 4H). |
| Final Product 220 | C1 | | MS (ESI+) m/z = 597.42 [M + H]+. 1H NMR (500 MHz, DMSO-d6) δ 9.14 (s, 1H), 8.75 (s, 1H), 8.61 (s, 1H), 8.52 (s, 1H), 8.50 (s, 1H), 8.18 (s, 1H), 8.08 (d, J = 8.5 Hz, 1H), 7.76 (d, J = 9.0 Hz, 1H), 7.42 (s, 1H), 6.94 (s, 1H), 6.61-6.67 (m, 1H), 6.24 (d, J = 17.0 Hz, 1H), 5.73 (d, J = 10.5 Hz, 1H), 4.09 (s, 3H), 3.85 (s, 5H), 3.24 (t, J = 11.5 Hz, 2H), 2.88 (d, J = 10.5 Hz, 2H), 2.65-2.69 (m, 1H), 2.64 (s, 3H), 2.35 (t, J = 11.0 Hz, 1H), 1.99 (t, J = 11.0 Hz, 2H), 1.72 (d, J = 10.4 Hz, 2H), 1.62 (d, J = 12.0 Hz, 2H), 1.52 (q, J = 10.5 Hz, 2H), 1.37 (q, J = 8.5 Hz, 2H). |
| Final Product 221 | C2 | | MS (ESI+) m/z = 597.39 [M + H]+. 1H NMR (500 MHz, DMSO-d6) δ 9.15 (s, 1H), 8.82 (s, 1H), 8.65 (s, 1H), 8.53 (s, 1H), 8.34 (s, 1H), 8.11 (s, 1H), 7.88 (d, J = 8.5 Hz, 1H), 7.79 (d, J = 8.5 Hz, 1H), 7.51 (s, 1H), 6.94 (s, 1H), 6.61-6.65 (m, 1H), 6.23 (d, J = 17.5 Hz, 1H), 5.73 (d, J = 11.0 Hz, 1H), 4.14 (s, 3H), 3.89 (s, 5H), 3.24 (t, J = 11.5 Hz, 2H), 2.88 (d, J = 10.5 Hz, 2H), 2.65-2.73 (m, 1H), 2.64 (s, 3H), 2.36 (brs, 1H), 1.99 (t, J = 11.0 Hz, 2H), 1.72 (d, J = 11.0 Hz, 2H), 1.62 (d, J = 12.0 Hz, 2H), 1.53 (q, J = 10.0 Hz, 2H), 1.37 (q, J = 8.5 Hz, 2H). |

TABLE 4-continued

Final Products 19-262

| No. of Final Products | No. of Intermediates | Structure of Final Products | NMR or MS |
|---|---|---|---|
| Final Product 222 | C1 | | MS (ESI+) m/z = 557.35 [M + H]+. 1H NMR (500 MHz, DMSO-d6) δ 9.23 (s, 1H), 8.75 (s, 1H), 8.60 (s, 2H), 8.50 (s, 1H), 8.17 (s, 1H), 8.08 (d, J = 8.5 Hz, 1H), 7.75 (d, J = 9.0 Hz, 1H), 7.42 (s, 1H), 6.98 (s, 1H), 6.59-6.65 (m, 1H), 6.23 (d, J = 17.0 Hz, 1H), 5.74 (d, J = 10.5 Hz, 1H), 4.09 (s, 3H), 3.84 (s, 3H), 3.62 (s, 1H), 3.39 (t, J = 5.5 Hz, 2H), 3.21 (s, 3H), 2.57-2.60 (m, 6H), 2.46 (s, 3H), 1.87-1.91 (m, 1H), 1.68-1.72 (m, 1H). |
| Final Product 223 | C2 | | MS (ESI+) m/z = 557.37 [M + H]+. 1H NMR (500 MHz, DMSO-d6) δ 9.24 (s, 1H), 8.82 (s, 1H), 8.65 (s, 1H), 8.62 (s, 1H), 8.34 (s, 1H), 8.11 (s, 1H), 7.87 (d, J = 8.5 Hz, 1H), 7.79 (d, J = 8.5 Hz, 1H), 7.51 (s, 1H), 6.98 (s, 1H), 6.60-6.65 (m, 1H), 6.23 (d, J = 17.0 Hz, 1H), 5.74 (d, J = 11.0 Hz, 1H), 4.13 (s, 3H), 3.85 (s, 3H), 3.62 (s, 1H), 3.39 (t, J = 6.0 Hz, 2H), 3.21 (s, 3H), 2.54-2.61 (m, 6H), 2.46-2.50 (m, 3H), 1.70-1.73 (m, 1H), 1.88-1.90 (m, 1H). |
| Final Product 224 | C1 | | MS (ESI+) m/z = 571.33 [M + H]+. 1H NMR (500 MHz, DMSO-d6) δ 9.13 (s, 1H), 8.74 (s, 1H), 8.60 (s, 1H), 8.50 (s, 2H), 8.17 (s, 1H), 8.08 (dd, J = 8.5, 1.0 Hz, 1H), 7.76 (d, J = 9.0 Hz, 1H), 7.42 (s, 1H), 6.93 (s, 1H), 6.63-6.66 (m, 1H), 6.23 (d, J = 17.0 Hz, 1H), 5.72 (d, J = 10.0 Hz, 1H), 4.09 (s, 3H), 3.84 (s, 3H), 3.38 (t, J = 5.5 Hz, 2H), 3.21 (s, 3H), 2.85 (d, J = 11.0 Hz, 2H), 2.64-2.69 (m, 1H), 2.63 (s, 3H), 2.40 (t, J = 6.0 Hz, 2H), 1.85 (t, J = 11.5 Hz, 2H), 1.67 (d, J = 11.0 Hz, 2H), 1.53-1.56 (m, 2H). |
| Final Product 225 | C2 | | MS (ESI+) m/z = 571.31 [M + H]+. 1H NMR (500 MHz, DMSO-d6) δ 9.15 (s, 1H), 8.81 (s, 1H), 8.64 (s, 1H), 8.51 (s, 1H), 8.31 (d, J = 20.8 Hz, 1H), 8.11 (s, 1H), 7.88 (d, J = 8.5 Hz, 1H), 7.78 (d, J = 8.5 Hz, 1H), 7.49 (s, 1H), 6.93 (s, 1H), 6.61-6.64 (m, 1H), 6.23 (d, J = 17.0 Hz, 1H), 5.72 (d, J = 11.0 Hz, 1H), 4.13 (s, 3H), 3.85 (s, 3H), 3.38 (t, J = 6.0 Hz, 2H), 3.21 (s, 3H), 2.85 (d, J = 11.0 Hz, 2H), 2.65-2.70 (m, 1H), 2.64 (s, 3H), 2.40 (t, J = 6.0 Hz, 2H), 1.85 (t, J = 11.0 Hz, 2H), 1.68 (d, J = 10.5 Hz, 2H), 1.54-1.57 (m, 2H). |
| Final Product 226 | C1 | | MS (ESI+) m/z = 541.33 [M + H]+. 1H NMR (500 MHz, DMSO-d6) δ 9.14 (s, 1H), 8.75 (s, 1H), 8.61 (s, 1H), 8.50 (s, 2H), 8.18 (s, 1H), 8.08 (d, J = 8.9 Hz, 1H), 7.76 (d, J = 8.9 Hz, 1H), 7.43 (s, 1H), 6.93 (s, 1H), 6.61-6.66 (m, 1H), 6.24 (d, J = 17.2 Hz, 1H), 5.73 (d, J = 10.6 Hz, 1H), 4.09 (s, 3H), 3.85 (s, 3H), 2.85 (d, J = 11.0 Hz, 2H), 2.68-2.70 (m, 1H), 2.64 (s, 3H), 2.25 (q, J = 7.0 Hz, 2H), 1.68-1.77 (m, 4H), 1.54-1.59 (m, 2H), 0.96 (t, J = 7.1 Hz, 3H). |

TABLE 4-continued

Final Products 19-262

| No. of Final Products | No. of Intermediates | Structure of Final Products | NMR or MS |
|---|---|---|---|
| Final Product 227 | C2 | | MS (ESI+) m/z = 541.28 [M + H]+. 1H NMR (500 MHz, DMSO-d6) δ 9.18 (s, 1H), 8.85 (s, 2H), 8.66 (s, 1H), 8.34 (s, 1H), 8.11 (s, 1H), 7.88 (d, J = 8.5 Hz, 1H), 7.79 (d, J = 8.0 Hz, 1H), 7.54 (s, 1H), 6.99 (s, 1H), 6.65-6.70 (m, 1H), 6.25 (dd, J = 17.0 Hz, 1H), 5.74 (d, J = 10.5 Hz, 1H), 4.14 (s, 3H), 3.87 (s, 3H), 3.44 (brs, 1H), 2.83-3.15 (m, 5H), 2.67 (s, 4H), 1.84-1.94 (m, 4H), 1.23 (s, 3H). |
| Final Product 228 | C3 | | MS (ESI+) m/z = 499.20 [M + H]+. 1H NMR (500 MHz, DMSO-d6) δ 9.04 (s, 1H), 8.97 (s, 1H), 8.87 (s, 1H), 8.49 (d, J = 5.5 Hz, 1H), 8.29 (d, J = 9.0 Hz, 1H), 8.16 (s, 1H), 8.01 (s, 1H), 7.72 (d, J = 8.9 Hz, 1H), 7.49 (d, J = 5.0 Hz, 1H), 6.90 (s, 1H), 6.65-6.71 (m, 1H), 6.33 (d, J = 16.5 Hz, 1H), 5.81 (d, J = 10.5 Hz, 1H), 4.10 (s, 3H), 3.90 (s, 3H), 2.88 (t, J = 4.5 Hz, 4H), 2.56 (brs, 4H), 2.28 (s, 3H). |
| Final Product 229 | C3 | | MS (ESI+) m/z = 527.22 [M + H]+. 1H NMR (500 MHz, DMSO-d6) δ 9.07 (s, 1H), 8.99 (s, 1H), 8.88 (s, 1H), 8.49 (d, J = 5.0 Hz, 1H), 8.29 (d, J = 8.5 Hz, 1H), 8.16 (s, 1H), 8.00 (s, 1H), 7.72 (d, J = 9.0 Hz, 1H), 7.49 (d, J = 5.0 Hz, 1H), 6.87 (s, 1H), 6.64-6.70 (m, 1H), 6.33 (d, J = 17.0 Hz, 1H), 5.81 (d, J = 10.0 Hz, 1H), 4.10 (s, 3H), 3.90 (s, 3H), 2.85 (d, J = 10.5 Hz, 2H), 2.54-2.56 (m, 2H), 2.45 (brs, 2H), 2.24 (s, 3H), 1.04 (d, J = 6.0 Hz, 6H). |
| Final Product 230 | C3 | | MS (ESI+) m/z = 582.23 [M + H]+. 1H NMR (400 MHz, DMSO-d6) δ 9.02 (s, 2H), 8.88 (s, 1H), 8.47-8.48 (d, J = 4.0 Hz, 1H), 8.29 (d, J = 7.2 Hz, 1H), 8.15 (s, 1H), 7.99 (s, 1H), 7.71 (d, J = 7.2 Hz, 1H), 7.48 (d, J = 4.4 Hz, 1H), 6.87 (s, 1H), 6.72-6.77 (m, 1H), 6.33 (d, J = 13.6 Hz, 1H), 5.80 (d, J = 8.0 Hz, 1H), 4.09 (s, 3H), 3.88 (s, 3H), 3.03 (d, J = 8.4 Hz, 2H), 2.69 (t, J = 8.8 Hz, 2H), 2.54 (brs, 4H), 2.29-2.34 (m, 5H), 2.17 (s, 3H), 1.85 (d, J = 8.4 Hz, 2H), 1.70-1.75 (m, 2H). |
| Final Product 231 | C3 | | MS (ESI+) m/z = 527.13 [M + H]+. 1H NMR (500 MHz, DMSO-d6) δ 9.18 (s, 1H), 9.13 (s, 1H), 8.91 (s, 1H), 8.50 (d, J = 5.5 Hz, 1H), 8.31 (d, J = 8.5 Hz, 1H), 8.15 (s, 1H), 8.01 (s, 1H), 7.72 (d, J = 9.0 Hz, 1H), 7.50 (d, J = 5.0 Hz, 1H), 6.96 (s, 1H), 6.67-6.73 (m, 1H), 6.34 (d, J = 17.0 Hz, 1H), 5.80 (d, J = 10.0 Hz, 1H), 4.10 (s, 3H), 3.89 (s, 3H), 2.80 (brs, 2H), 2.72 (brs, 1H), 2.65 (s, 3H), 2.17 (s, 3H), 1.89 (brs, 2H), 1.72 (d, J = 11.5 Hz, 2H), 1.55-1.62 (m, 2H). |

TABLE 4-continued

Final Products 19-262

| No. of Final Products | No. of Intermediates | Structure of Final Products | NMR or MS |
|---|---|---|---|
| Final Product 232 | C3 | | MS (ESI⁺) m/z = 543.17 [M + H]⁺. ¹H NMR (500 MHz, DMSO-d₆) δ 9.05 (s, 1H), 8.98 (s, 1H), 8.87 (s, 1H), 8.48 (d, J = 5.5 Hz, 1H), 8.28 (dd, J = 8.5, 1.0 Hz, 1H), 8.15 (s, 1H), 8.00 (s, 1H), 7.71 (d, J = 9.0 Hz, 1H), 7.48 (d, J = 5.5 Hz, 1H), 6.91 (s, 1H), 6.65-6.71 (m, 1H), 6.33 (d, J = 17.0 Hz, 1H), 5.80 (d, J = 10.0 Hz, 1H), 4.09 (s, 3H), 3.90 (s, 3H), 3.48 (brs, 2H), 3.26 (s, 3H), 2.87 (brs, 4H), 2.51-2.64 (m, 6H). |
| Final Product 233 | C3 | | MS (ESI⁺) m/z = 610.25 [M + H]⁺. ¹H NMR (500 MHz, DMSO-d₆) δ 9.01 (s, 1H), 8.98 (s, 1H), 8.87 (s, 1H), 8.48 (d, J = 5.0 Hz, 1H), 8.29 (d, J = 9.0 Hz, 1H), 8.15 (s, 1H), 7.99 (s, 1H), 7.71 (d, J = 9.0 Hz, 1H), 7.48 (d, J = 5.5 Hz, 1H), 6.86 (s, 1H), 6.72-6.77 (m, 1H), 6.33 (d, J = 17.0 Hz, 1H), 5.80 (d, J = 10.5 Hz, 1H), 4.09 (s, 3H), 3.88 (s, 3H), 3.03 (d, J = 10.5 Hz, 2H), 2.80 (s, 2H), 2.67 (t, J = 11.0 Hz, 2H), 2.50-2.49 (m, 1H), 2.10-2.22 (m, 5H), 1.83-1.97 (m, 4H), 1.69-1.72 (m, 2H), 1.00 (brs, 6H). |
| Final Product 234 | C3 | | yield: 24.03%. MS (ESI⁺) m/z = 610.20 [M + H]⁺. ¹H NMR (500 MHz, DMSO-d₆) δ 9.03 (s, 1H), 8.98 (s, 1H), 8.87 (s, 1H), 8.47 (d, J = 5.0 Hz, 1H), 8.28 (d, J = 9.0 Hz, 1H), 8.15 (s, 1H), 8.00 (s, 1H), 7.71 (d, J = 8.5 Hz, 1H), 7.48 (d, J = 4.5 Hz, 1H), 6.87 (s, 1H), 6.69-6.75 (m, 1H), 6.33 (d, J = 16.5 Hz, 1H), 5.80 (d, J = 10.0 Hz, 1H), 4.09 (s, 3H), 3.88 (s, 3H), 3.41 (brs, 2H), 2.97-3.06 (m, 6H), 2.63-2.70 (m, 6H), 1.85 (brs, 2H), 1.73 (brs, 2H), 1.23-1.27 (m, 6H). |
| Final Product 235 | C3 | | MS (ESI⁺) m/z = 569.20 [M + H]⁺. ¹H NMR (500 MHz, DMSO-d₆) δ 9.05 (s, 1H), 8.98 (s, 1H), 8.87 (s, 1H), 8.48 (d, J = 5.0 Hz, 1H), 8.28 (d, J = 9.0 Hz, 1H), 8.15 (s, 1H), 7.99 (s, 1H), 7.71 (d, J = 9.0 Hz, 1H), 7.47 (d, J = 5.0 Hz, 1H), 6.92 (s, 1H), 6.65-6.71 (m, 1H), 6.32 (d, J = 17.0 Hz, 1H), 5.79 (d, J = 10.0 Hz, 1H), 4.09 (s, 3H), 3.89-3.92 (m, 5H), 3.28-3.30 (m, 2H), 2.87 (s, 4H), 2.70 (s, 4H), 2.42-2.44 (m, 1H), 1.76 (d, J = 12.0 Hz, 2H), 1.41-1.48 (m, 2H). |
| Final Product 236 | C3 | | yield: 34%. MS (ESI⁺) m/z = 597.32 [M + H]⁺. ¹H NMR (400 MHz, DMSO-d₆) δ 9.00 (s, 2H), 8.87 (s, 1H), 8.48 (d, J = 5.2 Hz, 1H), 8.28 (d, J = 8.8, 1.2 Hz, 1H), 8.15 (s, 1H), 7.98 (s, 1H), 7.71 (d, J = 9.2 Hz, 1H), 7.48 (d, J = 5.2 Hz, 1H), 6.87 (s, 1H), 6.70-6.73 (m, 1H), 6.33 (d, J = 16.8 Hz, 1H), 5.80 (d, J = 10.8 Hz, 1H), 4.09 (s, 3H), 3.88 (s, 3H), 3.53-3.57 (m, 2H), 3.04 (d, J = 11.6 Hz, 2H), 2.82 (d, J = 10.4 Hz, 2H), 2.68 (t, J = 10.8 Hz, 2H), 2.20-2.30 (m, 1H), 1.70-1.87 (m, 6H), 1.07 (d, J = 6.4 Hz, 6H). |

TABLE 4-continued

Final Products 19-262

| No. of Final Products | No. of Intermediates | Structure of Final Products | NMR or MS |
|---|---|---|---|
| Final Product 237 | C3 | | MS (ESI+) m/z = 488.15 [M + H]+. 1H NMR (500 MHz, DMSO-d6) δ 9.79 (s, 1H), 8.98 (s, 1H), 8.84 (s, 1H), 8.47 (d, J = 5.5 Hz, 1H), 8.28 (d, J = 9.0 Hz, 1H), 8.14 (s, 1H), 8.01 (s, 1H), 7.71 (d, J = 9.0 Hz, 1H), 7.46 (d, J = 5.0 Hz, 1H), 6.95 (s, 1H), 6.48-6.54 (m, 1H), 6.32 (dd, J = 17.0, 1.5 Hz, 1H), 5.79 (dd, J = 11.5, 1.5 Hz, 1H), 4.18 (t, J = 5.5 Hz, 2H), 4.09 (s, 3H), 3.88 (s, 3H), 2.58 (t, J = 5.0 Hz, 2H), 2.28 (s, 6H). |
| Final Product 238 | C21 | | MS (ESI+) m/z = 529.14 [M + H]+. 1H NMR (500 MHz, DMSO-d6) δ 10.14 (s, 1H), 9.28 (s, 1H), 8.93 (s, 1H), 8.50 (d, J = 5.5 Hz, 1H), 8.28 (dd, J = 9.0, 1.5 Hz, 1H), 8.17 (s, 1H), 8.01 (s, 1H), 7.78 (d, J = 9.0 Hz, 1H), 7.49 (d, J = 5.5 Hz, 1H), 7.04 (s, 1H), 6.51 (brs, 1H), 6.36 (dd, J = 17.0, 1.5 Hz, 1H), 5.83 (dd, J = 10.5, 2.0 Hz, 1H), 5.02-5.08 (m, 1H), 3.90 (s, 3H), 2.92 (brs, 2H), 2.71 (s, 3H), 2.26 (brs, 8H), 1.51 (d, J = 6.5 Hz, 6H). |
| Final Product 239 | C3 | | MS (ESI+) m/z = 529.19 [M + H]+. 1H NMR (500 MHz, DMSO-d6) δ 9.78 (s, 1H), 9.22 (s, 1H), 8.91 (s, 1H), 8.49 (d, J = 5.2 Hz, 1H), 8.30 (d, J = 8.0 Hz, 1H), 8.14 (s, 1H), 8.02 (s, 1H), 7.72 (d, J = 8.8 Hz, 1H), 7.49 (d, J = 5.1 Hz, 1H), 7.00 (s, 1H), 6.53 (s, 1H), 6.34 (dd, J = 16.8, 1.5 Hz, 1H), 5.82 (d, J = 11.0 Hz, 1H), 4.09 (s, 3H), 3.90 (s, 3H), 3.26-2.99 (m, 2H), 2.87 (s, 1H), 2.64-2.70 (m, 3H), 2.46-2.60 (m, 5H), 1.26-1.08 (m, 2H), 0.96 (brs, 4H). |
| Final Product 240 | C29 | | MS (ESI+) m/z = 543.22 [M + H]+. 1H NMR (400 MHz, DMSO-d6) δ 9.78 (s, 1H), 9.23 (s, 1H), 8.91 (s, 1H), 8.49 (d, J = 5.2 Hz, 1H), 8.28 (d, J = 8.8 Hz, 1H), 8.15 (s, 1H), 7.88 (s, 1H), 7.71 (d, J = 8.8 Hz, 1H), 7.45 (d, J = 5.2 Hz, 1H), 7.00 (s, 1H), 6.58 (s, 1H), 6.35 (d, J = 16.9 Hz, 1H), 5.82 (d, J = 11.6 Hz, 1H), 4.48 (q, J = 7.2 Hz, 2H), 3.93 (s, 3H), 3.06 (s, 4H), 2.87 (s, 2H), 2.71 (s, 3H), 2.51-2.60 (m, 2H), 1.43 (t, J = 7.1 Hz, 3H), 1.03-1.07 (m, 6H). |
| Final Product 241 | C3 | | MS (ESI+) m/z = 515.18 [M + H]+. 1H NMR (400 MHz, DMSO-d6) δ 9.93 (s, 1H), 9.23 (s, 1H), 8.90 (s, 1H), 8.49 (d, J = 5.2 Hz, 1H), 8.30 (d, J = 8.8 Hz, 1H), 8.14 (s, 1H), 8.02 (s, 1H), 7.72 (d, J = 8.8 Hz, 1H), 7.49 (d, J = 5.3 Hz, 1H), 7.02 (s, 1H), 6.49-6.53 (m, 1H), 6.35 (d, J = 16.7 Hz, 1H), 5.82 (d, J = 11.7 Hz, 1H), 4.09 (s, 3H), 3.90 (s, 3H), 2.85-2.98 (m, 2H), 2.69 (s, 4H), 2.31-2.49 (m, 3H), 2.21 (brs, 3H), 1.05 (brs, 3H). |

TABLE 4-continued

Final Products 19-262

| No. of Final Products | No. of Intermediates | Structure of Final Products | NMR or MS |
|---|---|---|---|
| Final Product 242 | C30 | | MS (ESI+) m/z = 515.14 [M + H]+. 1H NMR (500 MHz, DMSO-d6) δ 10.14 (s, 1H), 9.33 (s, 1H), 8.96 (s, 1H), 8.50 (d, J = 5.0 Hz, 1H), 8.33 (d, J = 8.5 Hz, 1H), 8.14 (s, 1H), 7.97 (s, 1H), 7.72 (d, J = 8.5 Hz, 1H), 7.51 (d, J = 5.0 Hz, 1H), 7.03 (s, 1H), 6.46-6.48 (m, 1H), 6.36 (d, J = 16.5 Hz, 1H), 5.82 (d, J = 11.0 Hz, 1H), 4.15 (q, J = 7.0 Hz, 2H), 4.09 (s, 3H), 2.90 (s, 2H), 2.69 (s, 3H), 2.23-2.40 (m, 8H), 1.39 (t, J = 6.5 Hz, 3H), |
| Final Product 243 | C22 | | MS (ESI+) m/z = 529.21 [M + H]+. 1H NMR (500 MHz, DMSO-d6) δ 10.18 (s, 1H), 9.36 (s, 1H), 8.97 (s, 1H), 8.50 (d, J = 5.0 Hz, 1H), 8.30 (d, J = 9.0 Hz, 1H), 8.16 (s, 1H), 7.96 (s, 1H), 7.75 (d, J = 9.0 Hz, 1H), 7.50 (d, J = 5.0 Hz, 1H), 7.03 (s, 1H), 6.43-6.49 (m, 1H), 6.36 (d, J = 16.5 Hz, 1H), 5.83 (d, J = 10.0 Hz, 1H), 4.49 (q, J = 7.0 Hz, 2H), 4.15 (q, J = 7.0 Hz, 2H), 2.87 (s, 2H), 2.70 (s, 3H), 2.27 (s, 2H), 2.20 (s, 6H), 1.37-1.44 (m, 6H) |
| Final Product 244 | C3 | | MS (ESI+) m/z = 556.21 [M + H]+. 1H NMR (500 MHz, DMSO-d6) δ 9.38 (s, 1H), 9.12 (s, 1H), 8.90 (s, 1H), 8.49 (d, J = 5.2 Hz, 1H), 8.30 (d, J = 8.9 Hz, 1H), 8.14 (s, 1H), 8.00 (s, 1H), 7.71 (d, J = 8.9 Hz, 1H), 7.49 (d, J = 5.3 Hz, 1H), 6.99 (s, 1H), 6.64-6.69 (m, 1H), 6.34 (dd, J = 17.1, 1.0 Hz, 1H), 5.82 (d, J = 10.7 Hz, 1H), 4.09 (s, 3H), 3.89 (s, 3H), 2.97 (t, J = 6.3 Hz, 2H), 2.69 (s, 3H), 2.35 (brs, 10H), 2.15 (s, 3H). |
| Final Product 245 | C27 | | MS (ESI+) m/z = 592.11 [M + H]+. 1H NMR (400 MHz, DMSO-d6) δ 9.46 (s, 1H), 8.89 (s, 1H), 8.79 (s, 1H), 8.48 (d, J = 5.6 Hz, 1H), 8.45 (s, 1H), 8.26 (d, J = 8.9 Hz, 1H), 8.14 (s, 1H), 7.72 (d, J = 8.9 Hz, 1H), 7.49 (d, J = 5.3 Hz, 1H), 6.94-7.31 (m, 2H), 6.65-6.72 (m, 1H), 6.33 (d, J = 16.9 Hz, 1H), 5.83 (d, J = 11.2 Hz, 1H), 4.09 (s, 3H), 2.97 (t, J = 6.2 Hz, 2H), 2.69 (s, 3H), 2.37-2.39 (m, 10H), 2.16 (s, 3H). |
| Final Product 246 | C3 | | MS (ESI+) m/z = 529.08 [M + H]+. 1H NMR (500 MHz, DMSO-d6) δ 9.48 (s, 1H), 9.17 (s, 1H), 8.90 (s, 1H), 8.49 (d, J = 5.0 Hz, 1H), 8.30 (d, J = 9.0 Hz, 1H), 8.13 (s, 1H), 8.00 (s, 1H), 7.71 (d, J = 9.0 Hz, 1H), 7.49 (d, J = 5.5 Hz, 1H), 6.96 (s, 1H), 6.69-6.75 (m, 1H), 6.33 (d, J = 17.0 Hz, 1H), 5.79 (d, J = 10.5 Hz, 1H), 4.09 (s, 3H), 3.89 (s, 3H), 2.89 (s, 2H), 2.67 (s, 3H), 2.61 (s, 2H), 1.05 (s, 9H). |

TABLE 4-continued

Final Products 19-262

| No. of Final Products | No. of Intermediates | Structure of Final Products | NMR or MS |
|---|---|---|---|
| Final Product 247 | C27 | | yield: 11.30%. MS (ESI$^+$) m/z = 565.22 [M + H]$^+$. $^1$H NMR (500 MHz, DMSO-d$_6$) δ 9.82 (s, 1H), 8.86 (s, 1H), 8.75 (s, 2H), 8.51 (s, 1H), 8.47 (d, J = 5.0 Hz, 1H), 8.24 (d, J = 9.0 Hz, 1H), 8.13 (s, 1H), 7.72 (d, J = 9.0 Hz, 1H), 7.49 (d, J = 5.0 Hz, 1H), 7.01-7.31 (m, 3H), 6.32 (d, J = 17.0 Hz, 1H), 5.81 (d, J = 11.0 Hz, 1H), 4.09 (s, 3H), 3.23 (s, 2H), 3.05 (s, 2H), 2.62 (s, 3H), 1.30 (s, 9H). |
| Final Product 248 | C3 | | MS (ESI$^+$) m/z = 529.21 [M + H]$^+$. $^1$H NMR (500 MHz, DMSO-d$_6$) δ 9.41 (s, 1H), 8.67 (s, 1H), 8.40 (d, J = 5.1 Hz, 1H), 8.21 (d, J = 8.9 Hz, 1H), 8.15 (s, 1H), 7.92 (s, 2H), 7.71 (d, J = 8.8 Hz, 1H), 7.37 (d, J = 5.1 Hz, 1H), 6.48-6.54 (m, 1H), 6.43 (s, 1H), 6.26 (d, J = 17.2 Hz, 1H), 5.74 (d, J = 10.2 Hz, 1H), 4.76 (s, 1H), 4.08 (s, 3H), 3.86 (s, 3H), 3.18 (d, J = 5.6 Hz, 2H), 2.49-2.50 (m, 2H), 2.20 (s, 6H). |
| Final Product 249 | C27 | | MS (ESI$^+$) m/z = 523.29 [M + H]$^+$. $^1$H NMR (400 MHz, DMSO-d$_6$) δ 9.50 (s, 1H), 8.62 (s, 1H), 8.40 (s, 1H), 8.38 (t, J = 5.2 Hz, 1H), 8.19 (s, 1H), 8.16 (s, 1H), 7.73 (s, 1H), 7.70 (s, 1H), 7.37 (d, J = 5.2 Hz, 1H), 6.90-7.27 (m, 1H), 6.53 (s, 1H), 6.47-6.51 (m, 1H), 6.25 (d, J = 17.6 Hz, 1H), 5.76 (d, J = 10.4 Hz, 1H), 5.04 (s, 1H), 4.08 (s ,3H), 3.15 (q, J = 5.6 Hz, 2H), 2.49 (s, 2H), 2.20 (s, 6H). |
| Final Product 250 | C8 | | MS (ESI$^+$) m/z = 559.11 [M + H]$^+$. $^1$H NMR (500 MHz, DMSO-d$_6$) δ 9.49 (s, 1H), 9.04 (s, 1H), 8.89 (s, 1H), 8.86 (s, 1H), 8.63 (s, 1H), 8.31 (s, 1H), 8.19 (s, 1H), 8.17 (s, 1H), 7.43 (s, 1H), 6.89 (s, 1H), 6.60-6.65 (m, 1H), 6.25 (d, J = 17.0 Hz, 1H), 5.74 (d, J = 10.0 Hz, 1H), 3.85 (s, 3H), 2.87 (brs, 4H), 2.62 (brs, 4H), 2.45-2.48 (m, 2H), 2.37 (t, J = 6.0 Hz, 2H), 2.16 (s, 6H). |
| Final Product 251 | C8 | | MS (ESI$^+$) m/z = 490.26 [M + H]$^+$. $^1$H NMR (500 MHz, DMSO-d$_6$) δ 9.48 (s, 1H), 9.46 (s, 1H), 8.86 (s, 1H), 8.70 (s, 1H), 8.57 (s, 1H), 8.13-8.18 (m, 2H), 7.46 (s, 1H), 7.19 (s, 1H), 6.45-6.51 (m, 1H), 6.42 (s, 1H), 6.24 (d, J = 17.0, 1.5 Hz, 1H), 5.72 (d, J = 10.5, 2.0 Hz, 1H), 4.94 (s, 1H), 3.82 (s, 3H), 3.20 (q, J = 6.0 Hz, 2H), 2.49-2.50 (m, 2H), 2.20 (s, 6H). |

TABLE 4-continued

Final Products 19-262

| No. of Final Products | No. of Intermediates | Structure of Final Products | NMR or MS |
|---|---|---|---|
| Final Product 252 | C3 | | MS (ESI+) m/z = 582.34 [M + H]+. 1H NMR (500 MHz, DMSO-d6) δ 9.40 (s, 1H), 9.13 (s, 1H), 8.90 (s, 1H), 8.49 (d, J = 5.5 Hz, 1H), 8.30 (d, J = 8.9 Hz, 1H), 8.14 (s, 1H), 8.00 (s, 1H), 7.71 (d, J = 8.9 Hz, 1H), 7.49 (d, J = 5.2 Hz, 1H), 7.00 (s, 1H), 6.64-6.70 (m, 1H), 6.35 (d, J = 17.0 Hz, 1H), 5.82 (d, J = 10.3 Hz, 1H), 4.09 (s, 3H), 3.89 (s, 3H), 2.97 (t, J = 6.2 Hz, 2H), 2.69 (s, 3H), 2.42-2.50 (m, 4H), 2.32-2.35 (m, 6H), 1.55-1.57 (m, 1H), 0.38 (d, J = 4.5 Hz, 2H), 0.25 (s, 2H). |
| Final Product 253 | C3 | | MS (ESI+) m/z = 610.31 [M + H]+. 1H NMR (500 MHz, DMSO-d6) δ 9.72 (s, 1H), 9.12 (s, 1H), 8.90 (s, 1H), 8.50 (d, J = 5.5 Hz, 1H), 8.31 (d, J = 9.0 Hz, 1H), 8.18 (s, 1H), 7.74 (d, J = 8.5 Hz, 1H), 7.58 (d, J = 5.5 Hz, 1H), 6.90 (s, 1H), 6.69-6.74 (m, 1H), 6.34 (d, J = 17.0 Hz, 1H), 5.81 (d, J = 10.0 Hz, 1H), 4.53 (d, J = 13.0 Hz, 2H), 4.10 (s, 3H), 4.06 (s, 1H), 3.90 (s, 3H), 3.52 (d, J = 9.0 Hz, 2H), 3.46 (t, J = 12.5 Hz, 1H), 3.37 (s, 1H), 3.19 (t, J = 11.5 Hz, 3H), 2.96-3.05 (m, 2H), 2.78 (brs, 2H), 2.35 (s, 5H), 2.13 (d, J = 10.0 Hz, 2H), 2.07 (s, 3H), 1.96-1.99 (m, 2H). |
| Final Product 254 | C3 | | MS (ESI+) m/z = 584.30 [M + H]+. 1H NMR (500 MHz, DMSO-d6) δ 9.34 (s, 1H), 9.10 (s, 1H), 8.90 (s, 1H), 8.49 (d, J = 5.0 Hz, 1H), 8.31 (d, J = 9.0 Hz, 1H), 8.14 (s, 1H), 8.00 (s, 1H), 7.71 (d, J = 8.5 Hz, 1H), 7.49 (d, J = 5.0 Hz, 1H), 6.99 (s, 1H), 6.63-6.69 (m, 1H), 6.36 (d, J = 17.0 Hz, 1H), 5.81 (d, J = 10.5 Hz, 1H), 4.09 (s, 3H), 3.89 (s, 3H), 3.32-3.40 (m, 4H), 3.01 (t, J = 6.5 Hz, 2H), 2.70 (s, 3H), 2.28-2.41 (m, 6H), 1.95 (s, 3H). |
| Final Product 255 | C13 | | MS (ESI+) m/z = 518.21 [M + H]+. 1H NMR (400 MHz, DMSO-d6) δ 10.18 (s, 1H), 9.36 (s, 1H), 9.27 (s, 1H), 8.55 (d, J = 5.2 Hz, 1H), 8.35 (dd, J = 8.6, 1.4 Hz, 1H), 8.03 (s, 1H), 7.98 (s, J = 8.4 Hz, 1H), 7.54 (d, J = 5.2 Hz, 1H), 7.06 (s, 1H), 6.47 (d, J = 5.6 Hz, 2H), 5.84 (t, J = 6.4 Hz, 1H), 3.89 (s, 3H), 2.90 (s, 2H), 2.84 (s, 3H), 2.71 (s, 3H), 2.28-2.33 (m, 2H), 2.24 (s, 6H) |

TABLE 4-continued

Final Products 19-262

| No. of Final Products | No. of Intermediates | Structure of Final Products | NMR or MS |
|---|---|---|---|
| Final Product 256 | C11 | 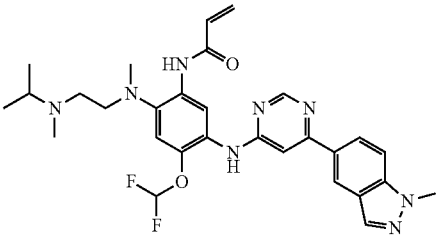 [SMILES: C=CC(=O)Nc1cc(Nc2cc(-c3ccc4c(cnn4C)c3)ncn2)c(OC(F)F)cc1N(C)CCN(C)C(C)C] | MS (ESI⁺) m/z = 565.22 [M + H]⁺. ¹H NMR (400 MHz, DMSO-d₆) δ 9.94 (s, 1H), 9.21 (s, 1H), 8.67 (s, 1H), 8.60 (s, 1H), 8.50 (s, 1H), 8.17 (s, 1H), 8.09 (d, J = 9.2 Hz, 1H), 7.76 (d, J = 8.8 Hz, 1H), 7.32 (d, J = 10.8 Hz, 1H), 6.92-7.29 (m, 2H), 6.40-6.47 (m, 1H), 6.30 (d, J = 17.2 Hz, 1H), 5.82 (d, J = 12.0 Hz, 1H), 4.08 (s, 3H), 2.79-2.87 (m, 3H), 2.71 (s, 3H), 2.44-2.47 (m, 2H), 2.20 (s, 3H), 0.98 (s, d, J = 6.4 Hz, 6H). |
| Final Product 257 | C3 | 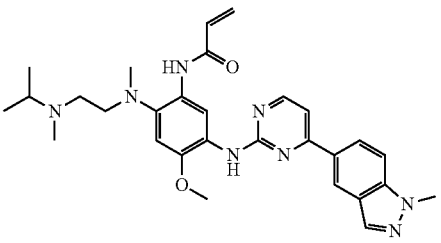 [SMILES: C=CC(=O)Nc1cc(Nc2nccc(-c3ccc4c(cnn4C)c3)n2)c(OC)cc1N(C)CCN(C)C(C)C] | MS (ESI⁺) m/z = 529.27 [M + H]⁺. ¹H NMR (400 MHz, DMSO-d₆) δ 9.84 (s, 2H), 8.83-8.88 (m, 1H), 8.50 (d, J = 5.2 Hz, 1H), 8.30 (d, J = 8.4 Hz, 1H), 8.14 (s, 1H), 8.03 (s, 1H), 7.73 (d, J = 8.8 Hz, 1H), 7.50 (d, J = 5.2 Hz, 1H), 7.05 (brs, 1H), 6.98 (s, 1H), 6.33 (d, J = 16.8 Hz, 1H), 5.81 (d, J = 10.8 Hz, 1H), 4.09 (s, 3H), 3.92 (s, 3H), 3.32-3.47 (m 1H), 2.84-3.05 (m, 2H), 2.62-2.68 (m, 6H), 2.33 (brs, 1H), 2.24 (brs, 1H), 0.98-1.23 (m, 6H). |
| Final Product 258 | C30 | 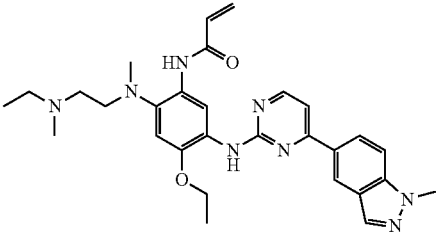 [SMILES: C=CC(=O)Nc1cc(Nc2nccc(-c3ccc4c(cnn4C)c3)n2)c(OCC)cc1N(C)CCN(C)CC] | MS (ESI⁺) m/z = 529.18 [M + H]⁺. ¹H NMR (400 MHz, DMSO-d₆) δ 9.90 (brs, 1H), 9.30 (brs, 1H), 8.93 (s, 1H), 8.50 (d, J = 5.2 Hz, 1H), 8.32 (d, J = 8.8 Hz, 1H), 8.14 (s, 1H), 7.96 (s, 1H), 7.72 (d, J = 8.8 Hz, 1H), 7.51 (d, J = 5.2 Hz, 1H), 7.01 (s, 1H), 6.50-6.55 (m, 1H), 6.37 (d, J = 15.6 Hz, 1H), 5.83 (d, J = 11.6 Hz, 1H), 4.18 (q, J = 6.8 Hz, 2H), 4.09 (s, 3H), 2.89 (brs, 2H), 2.68 (s, 3H), 2.19-2.45 (m, 7H), 1.39 (t, J = 6.8 Hz, 3H), 1.04 (d, J = 6.0 Hz, 3H). |
| Final Product 259 | C27 | 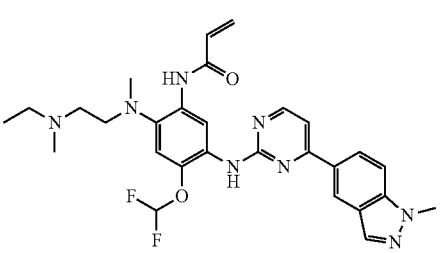 [SMILES: C=CC(=O)Nc1cc(Nc2nccc(-c3ccc4c(cnn4C)c3)n2)c(OC(F)F)cc1N(C)CCN(C)CC] | MS (ESI⁺) m/z = 551.27 [M + H]⁺. ¹H NMR (400 MHz, DMSO-d₆) δ 10.03 (s, 1H), 9.06 (s, 1H), 8.79 (s, 1H), 8.45-8.48 (m, 2H), 8.26 (d, J = 8.8 Hz, 1H), 8.13 (s, 1H), 7.72 (d, J = 8.8 Hz, 1H), 7.49 (d, J = 6.0 Hz, 1H), 6.94-7.31 (m, 2H), 6.47-6.55 (m, 1H), 6.33 (d, J = 16.8 Hz, 1H), 5.83 (d, J = 10.0 Hz, 1H), 4.09 (s, 3H), 2.86 (s, 2H), 2.70 (s, 3H), 2.41 (s, 4H), 2.20 (s, 3H), 1.01-1.04 (m, 3H). |
| Final Product 260 | C27 | 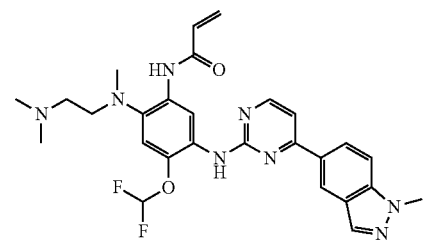 | MS (ESI⁺) m/z = 537.17 [M + H]⁺. ¹H NMR (500 MHz, DMSO-d₆) δ 10.26 (s, 1H), 9.10 (s, 1H), 8.81 (s, 1H), 8.46-8.49 (m, 2H), 8.27 (dd, J = 8.9, 1.3 Hz, 1H), 8.13 (s, 1H), 7.73 (d, J = 8.9 Hz, 1H), 7.50 (d, J = 5.3 Hz, 1H), 6.98-7.28 (m, 2H), 6.44-6.47 (m, 1H), 6.34 (dd, J = 16.9, 1.7 Hz, 1H), 5.85 (dd, J = 10.1, 1.7 Hz, 1H), 4.10 (s, 3H), 2.87 (t, J = 5.2 Hz, 2H), 2.71 (s, 3H), 2.34 (brs, 2H), 2.23 (s, 6H). |

TABLE 4-continued

Final Products 19-262

| No. of Final Products | No. of Intermediates | Structure of Final Products | NMR or MS |
|---|---|---|---|
| Final Product 261 | C31 | | MS (ESI+) m/z = 518.82 [M + H]+. 1H NMR (400 MHz, DMSO-d6) δ 9.50 (s, 1H), 8.58 (s, 1H), 8.41 (s, 1H), 8.33 (d, J = 5.2 Hz, 1H), 8.19 (s, 1H), 8.14 (d, J = 8.7 Hz, 1H), 7.71 (d, J = 8.7 Hz, 1H), 7.32 (d, J = 5.2 Hz, 1H), 6.56 (s, 1H), 6.48-6.53 (m, 1H), 6.24 (d, J = 17.2 Hz, 1H), 5.74 (d, J = 10.8 Hz, 1H), 4.08 (s, 3H), 3.79 (s, 3H), 3.07 (d, J = 10.4 Hz, 2H), 2.78 (s, 3H), 2.49-2.50 (m, 2H), 2.20 (s, 6H). |
| Final Product 262 | C3 | | MS (ESI+) m/z = 555.23 [M + H]+. 1H NMR (500 MHz, DMSO-d6) δ 9.05 (s, 2H), 8.89 (s, 1H), 8.49 (s, 1H), 8.30 (d, J = 7.7 Hz, 1H), 8.16 (s, 1H), 8.01 (s, 1H), 7.72 (d, J = 7.9 Hz, 1H), 7.49 (s, 1H), 6.89 (s, 1H), 6.73-6.75 (m, 1H), 6.35 (d, J = 16.3 Hz, 1H), 5.82 (d, J = 8.7 Hz, 1H), 4.10 (s, 3H), 3.89 (s, 3H), 3.06 (brs 3H), 2.75 (brs, 2H), 2.51-2.54 (m, 4H), 1.80 (brs, 4H), 1.04 (brs, 6H). |

Examples 412-430

Final products with protective groups were prepared by the method of synthesizing the Final Product 18 (EXAMPLE 167) except that the intermediate C and the amines with protective groups which are commercially available or synthesized by EXAMPLES 1-69 were used as the starting materials. Under the protection of argon, the final products with protective groups were deprotected by Pd(ppH$_3$)$_4$/TES with stirring at room temperature with DCM or DCM/MeOH as solvent or were deprotected by acids such as TFA or HCl with stirring at room temperature with DCM as solvent to give Final Products 263-281. (Table 5)

TABLE 5

Final Product 263-281

| | | | |
|---|---|---|---|
| Final Product 263 | C1 | | MS (ESI+) m/z = 515.10 [M + H]+. 1H NMR (500 MHz, DMSO-d6) δ 9.73 (s, 1H), 8.74 (s, 1H), 8.61 (s, 1H), 8.59 (s, 1H), 8.48 (s, 1H), 8.16 (s, 1H), 8.07 (dd, J = 9.0, 1.5 Hz, 1H), 7.74 (d, J = 9.0 Hz, 1H), 7.34 (s, 1H), 6.95 (s, 1H), 6.61-6.67 (m, 1H), 6.24 (dd, J = 17.0, 1.5 Hz, 1H), 5.72 (dd, J = 11.5, 1.5 Hz, 1H), 4.08 (s, 3H), 3.83 (s, 3H), 2.87 (d, J= 5.0 Hz, 2H), 2.63-2.75 (m, 6H), 1.90 (brs, 1H), 1.00 (d, J = 6.0 Hz, 6H). |
| Final Product 264 | C1 | | MS (ESI+) m/z = 513.45 [M + H]+. 1H NMR (500 MHz, DMSO-d6) δ 9.02 (s, 1H), 8.74 (s, 1H), 8.59 (s, 1H), 8.49 (s, 1H), 8.37 (s, 1H), 8.17 (s, 1H), 8.07 (dd, J = 9.0, 1.5 Hz, 1H), 7.75 (d, J = 9.0 Hz, 1H), 7.36 (s, 1H), 6.83 (s, 1H), 6.56-6.62 (m, 1H), 6.22 (d, J = 17.0 Hz, 1H), 5.73 (d, J = 10.5 Hz, 1H), 4.08 (s, 3H), 3.84 (s, 3H), 3.02 (brs, 2H), 2.83-2.85 (d, J = 10.0 Hz, 2H), 2.25 (t, J = 10.0 Hz, 2H), 2.08 (brs, 1H), 0.97 (d, J = 8.5 Hz, 6H). |

TABLE 5-continued

Final Product 263-281

| Final Product 265 | C10 | 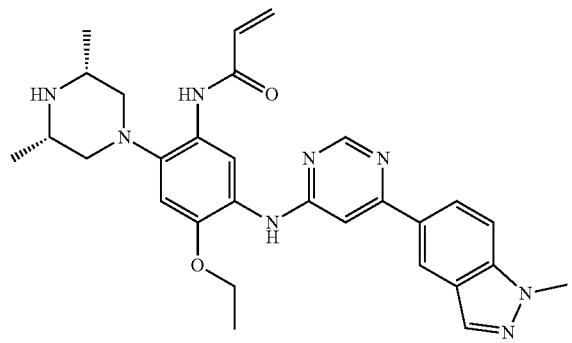 | MS (ESI+) m/z = 527.21 [M + H]+. $^1$H NMR (400 MHz, DMSO-$d_6$) δ 9.02 (s, 1H), 8.64 (s, 1H), 8.60 (s, 1H), 8.51 (s, 1H), 8.34 (s, 1H), 8.17 (s, 1H), 8.09 (dd, J = 8.8, 1.2 Hz, 1H), 7.75 (d, J = 8.9 Hz, 1H), 7.36 (s, 1H), 6.82 (s, 1H), 6.56-6.63 (m, 1H), 6.23 (d, J = 16.8 Hz, 1H), 5.74 (d, J = 10.8 Hz, 1H), 4.15-4.10 (m, 2H), 4.08 (s, 3H), 3.02 (brs, 2H), 2.83 (d, J = 9.6 Hz, 2H), 2.23 (t, J = 10.4 Hz, 2H), 2.07 (brs, 1H), 1.30 (t, J = 7.2 Hz, 3H), 1.00 (d, J = 6.4 Hz, 6H). |
| --- | --- | --- | --- |
| Final Product 266 | C11 | 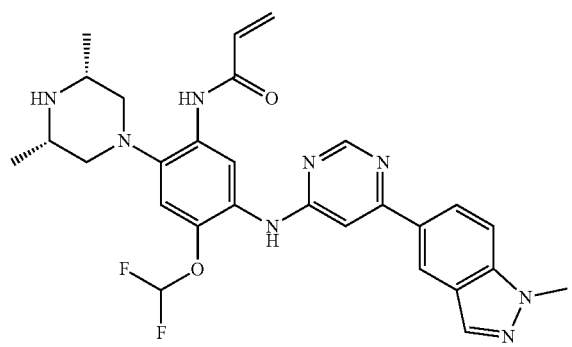 | MS (ESI+) m/z = 549.27 [M + H]+. $^1$H NMR (400 MHz, DMSO-$d_6$) δ 9.14 (s, 1H), 9.02 (s, 1H), 8.60 (s, 1H), 8.50 (s, 1H), 8.38 (s, 1H), 8.17 (s, 1H), 8.08 (dd, J = 8.8, 1.2 Hz, 1H), 7.75 (d, J = 9.2 Hz, 1H), 7.35 (s, 1H), 6.97-7.34 (m, 2H), 6.59-6.66 (m, 1H), 6.24 (dd, J = 17.2, 1.6 Hz, 1H), 5.76 (dd, J = 12.0, 1.6 Hz, 1H), 4.08 (s, 3H), 3.04 (s, 2H), 2.85 (d, J = 9.6 Hz, 2H), 2.20 (t, J = 10.4 Hz, 2H), 2.07 (brs, 1H), 0.97 (d, J = 6.0 Hz, 6H). |
| Final Product 267 | C1 | 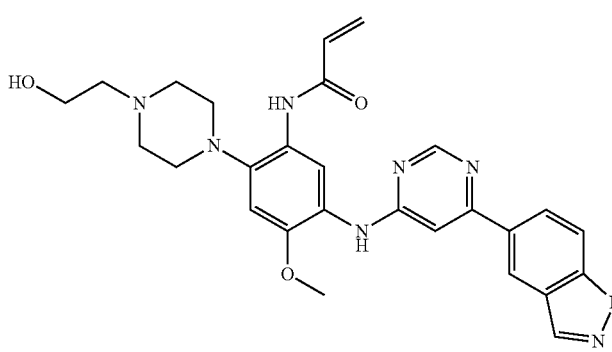 | yield: 36.32%. MS (ESI+) m/z = 529.22 [M + H]+. $^1$H NMR (400 MHz, DMSO-$d_6$) δ 9.03 (s, 1H), 8.75 (s, 1H), 8.59 (s, 1H), 8.49 (s, 1H), 8.35 (s, 1H), 8.17 (s, 1H), 8.08 (d, J = 8.8, 1.2 Hz, 1H), 7.75 (d, J = 9.2 Hz, 1H), 7.38 (s, 1H), 6.88 (s, 1H), 6.58-6.63 (m, 1H), 6.23 (dd, J = 17.2, 1.6 Hz, 1H), 5.74 (d, J = 11.2 Hz, 1H), 4.41 (t, J = 5.2 Hz, 1H), 4.08 (s, 3H), 3.85 (s, 3H), 3.54 (q, J = 6.0 Hz, 2H), 2.87 (t, J = 4.4 Hz, 4H), 2.64 (brs, 4H), 2.46-2.50 (m, 2H). |
| Final Product 268 | C1 | 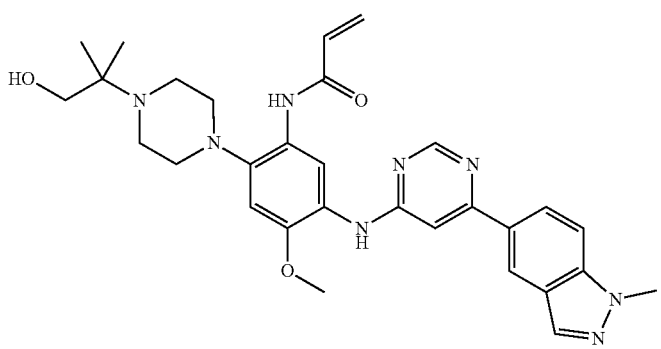 [SMILES: C=CC(=O)Nc1cc(Nc2cc(-c3ccc4c(cnn4C)c3)ncn2)c(OC)cc1N1CCN(C(C)(C)CO)CC1] | MS (ESI+) m/z = 557.29 [M + H]+. $^1$H NMR (500 MHz, DMSO-$d_6$) δ 9.04 (s, 1H), 8.75 (s, 1H), 8.59 (s, 1H), 8.50 (s, 1H), 8.37 (s, 1H), 8.18 (s, 1H), 8.08 (dd, J = 9.0, 1.5 Hz, 1H), 7.76 (d, J = 9.0 Hz, 1H), 7.38 (s, 1H), 6.89 (s, 1H), 6.61-6.66 (m, 1H), 6.24 (dd, J = 17.0, 1.5 Hz, 1H), 5.75 (d, J = 11.2 Hz, 1H), 4.25 (d, J = 5.0 Hz, 1H), 4.09 (s, 3H), 3.85 (s, 3H), 3.33 (s, 2H), 2.86 (d, J = 4.5 Hz, 4H), 2.76 (brs, 4H), 1.00 (s, 6H). |

TABLE 5-continued

Final Product 263-281

| Final Product 269 | C1 | 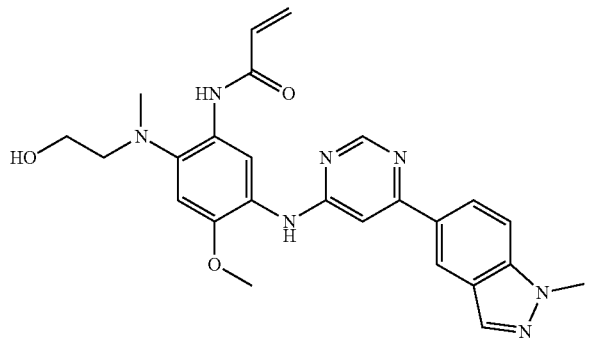 [SMILES: C=CC(=O)Nc1cc(Nc2cc(-c3ccc4c(cnn4C)c3)ncn2)c(OC)cc1N(C)CCO] | MS (ESI+) m/z = 474.23 [M + H]+. <br> $^1$H NMR (500 MHz, DMSO-d$_6$) δ 9.64 (s, 1H), 8.75 (s, 1H), 8.71 (s, 1H), 8.58 (s, 1H), 8.48 (s, 1H), 8.17 (s, 1H), 8.07 (dd, J = 9.0, 1.5 Hz, 1H), 7.75 (d, J = 9.0 Hz, 1H), 7.32 (s, 1H), 6.95 (s, 1H), 6.49-6.55 (m, 1H), 6.25 (dd, J = 17.0, 1.5 Hz, 1H), 5.72 (dd, J = 10.5, 2.0 Hz, 1H), 5.34 (dd, J = 9.5, 4.5 Hz, 1H), 4.08 (s, 3H), 3.84 (s, 3H), 3.61 (q, J = 5.0 Hz, 2H), 2.87 (t, J = 5.0 Hz, 2H), 2.73 (s, 3H). |
|---|---|---|---|
| Final Product 270 | C1 | 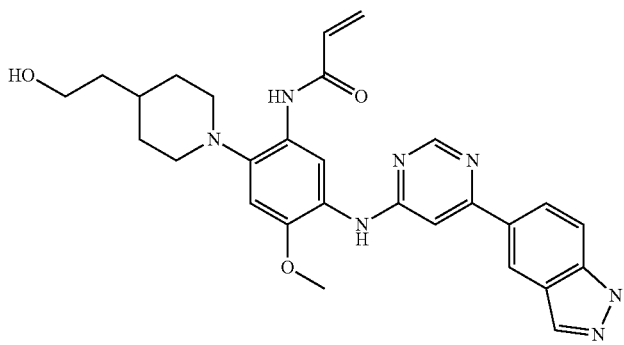 | MS (ESI+) m/z = 528.34 [M + H]+. <br> $^1$H NMR (500 MHz, DMSO-d$_6$) δ 8.99 (s, 1H), 8.74 (s, 1H), 8.59 (s, 1H), 8.49 (s, 1H), 8.35 (s, 1H), 8.17 (s, 1H), 8.07 (dd, J = 8.9, 1.2 Hz, 1H), 7.75 (d, J = 8.9 Hz, 1H), 7.36 (s, 1H), 6.86 (s, 1H), 6.62-6.67 (m, 1H), 6.23 (dd, J = 16.9, 1.0 Hz, 1H), 5.73 (d, J = 10.9 Hz, 1H), 4.37 (t, J = 5.0 Hz, 1H), 4.08 (s, 3H), 3.84 (s, 3H), 3.50 (t, J = 5.5 Hz, 2H), 3.01 (d, J = 11.2 Hz, 2H), 2.65 (t, J = 10.9 Hz, 2H), 1.75 (d, J = 11.1 Hz, 2H), 1.46-1.47 (m, 1H), 1.44 (t, J = 7.0 Hz, 4H). |
| Final Product 271 | C10 | 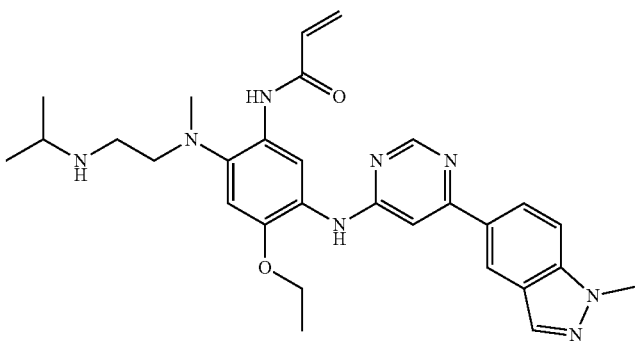 [SMILES: C=CC(=O)Nc1cc(Nc2cc(-c3ccc4c(cnn4C)c3)ncn2)c(OCC)cc1N(C)CCNC(C)C] | MS (ESI+) m/z = 529.23 [M + H]+. <br> $^1$H NMR (400 MHz, DMSO-d$_6$) δ 9.73 (s, 1H), 8.65 (s, 1H), 8.60 (s, 2H), 8.51 (s, 1H), 8.16 (s, 1H), 8.09 (d, J = 8.4 Hz, 1H), 7.74 (d, J = 8.8 Hz, 1H), 7.34 (s, 1H), 6.94 (s, 1H), 6.61-6.67 (m, 1H), 6.25 (d, J = 16.8 Hz, 1H), 5.72 (d, J = 10.4 Hz, 1H), 4.08-4.11 (m, 5H), 2.87 (s, 2H), 2.62-2.74 (m, 6H), 1.94 (brs, 1H), 1.30 (t, J = 6.8 Hz, 3H), 1.01 (d, J = 6.0 Hz, 6H). |
| Final Product 272 | C11 | 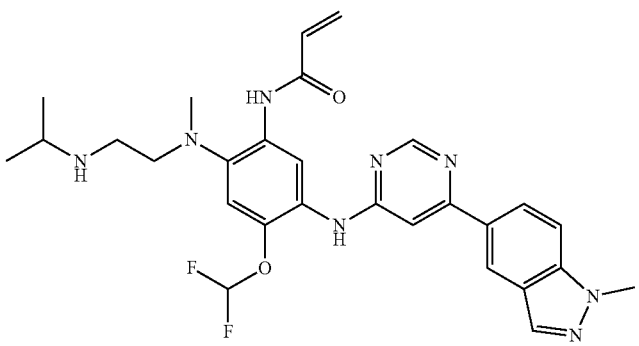 [SMILES: C=CC(=O)Nc1cc(Nc2cc(-c3ccc4c(cnn4C)c3)ncn2)c(OC(F)F)cc1N(C)CCNC(C)C] | MS (ESI+) m/z = 551.18 [M + H]+. <br> $^1$H NMR (400 MHz, DMSO-d$_6$) δ 9.92 (s, 1H), 9.03 (s, 1H), 8.64 (s, 1H), 8.60 (s, 1H), 8.50 (s, 1H), 8.17 (s, 1H), 8.08 (d, J = 9.2 Hz, 1H), 7.75 (d, J = 8.4 Hz, 1H), 7.33 (s, 1H), 6.93-7.31 (m, 2H), 6.64-6.68 (m, 1H), 6.27 (d, J = 16.8 Hz, 1H), 5.77 (d, J = 9.2 Hz, 1H), 4.09 (s, 3H), 2.86 (brs, 2H), 2.66-2.76 (m, 6H), 2.04 (brs, 1H), 1.02 (d, J = 6.0 Hz, 6H). |

TABLE 5-continued

Final Product 263-281

| Final Product 273 | C11 | 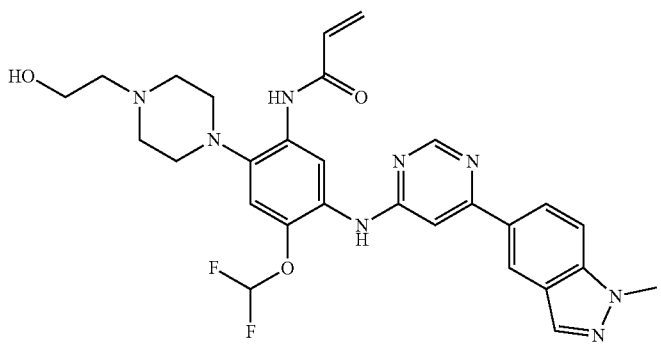 [SMILES: C=CC(=O)Nc1cc(Nc2cc(-c3ccc4c(cnn4C)c3)ncn2)c(OC(F)F)cc1N1CCN(CCO)CC1] | MS (ESI+) m/z = 565.27 [M + H]+.<br>1H NMR (400 MHz, DMSO-d6) δ 9.13 (s, 1H), 9.02 (s, 1H), 8.60 (s, 1H), 8.51 (s, 1H), 8.37 (s, 1H), 8.17 (s, 1H), 8.09 (d, J = 8.8 Hz, 1H), 7.75 (d, J = 8.8 Hz, 1H), 7.36 (s, 1H), 6.96-7.33 (m, 2H), 6.61-6.68 (m, 1H), 6.26 (d, J = 17.2 Hz, 1H), 5.77 (d, J = 10.8 Hz, 1H), 4.40 (t, J = 5.2 Hz, 1H), 4.09 (s, 3H), 3.54 (q, J = 6.0 Hz, 2H), 2.86 (brs, 4H), 2.65 (brs, 4H), 2.46-2.48 (m, 2H). |
|---|---|---|---|
| Final Product 274 | C2 | 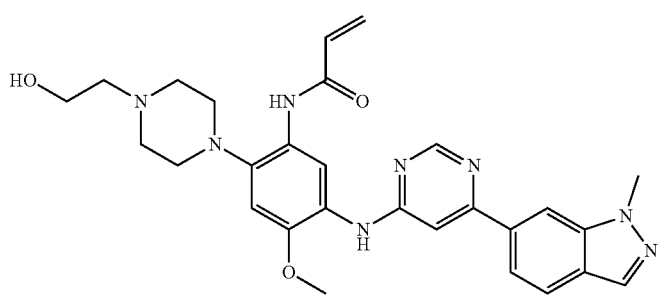 [SMILES: C=CC(=O)Nc1cc(Nc2cc(-c3ccc4cnn(C)c4c3)ncn2)c(OC)cc1N1CCN(CCO)CC1] | MS (ESI+) m/z = 529.31 [M + H]+.<br>1H NMR (400 MHz, DMSO-d6) δ 9.04 (s, 1H), 8.82 (s, 1H), 8.64 (s, 1H), 8.37 (s, 1H), 8.34 (s, 1H), 8.10 (s, 1H), 7.87 (d, J = 8.4 Hz, 1H), 7.78 (d, J = 8.4 Hz, 1H), 7.47 (s, 1H), 6.88 (s, 1H), 6.59-6.66 (m, 1H), 6.23 (d, J = 17.2 Hz, 1H), 5.74 (d, J = 10.8 Hz, 1H), 4.41 (t, J = 5.2 Hz, 1H), 4.13 (s, 3H), 3.86 (s, 3H), 3.54 (q, J = 6.0 Hz, 2H), 2.87 (d, J = 4.4 Hz, 4H), 2.64 (s, 4H), 2.46-2.49 (m, 2H). |
| Final Product 275 | C28 | 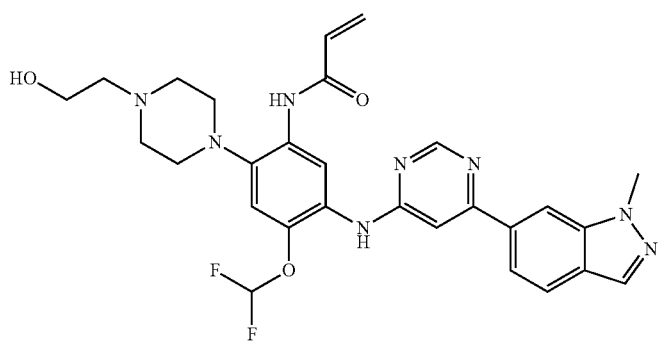 [SMILES: C=CC(=O)Nc1cc(Nc2cc(-c3ccc4cnn(C)c4c3)ncn2)c(OC(F)F)cc1N1CCN(CCO)CC1] | MS (ESI+) m/z = 565.26 [M + H]+.<br>1H NMR (400 MHz, DMSO-d6) δ 9.17 (s, 1H), 9.13 (s, 1H), 8.65 (s, 1H), 8.37 (s, 1H), 8.35 (s, 1H), 8.12 (s, 1H), 7.88 (d, J = 8.5 Hz, 1H), 7.80 (d, J = 8.5 Hz, 1H), 7.46 (s, 1H), 7.01-7.31 (m, 2H), 6.63-6.69 (m, 1H), 6.26 (d, J = 17.4 Hz, 1H), 5.78 (d, J = 10.9 Hz, 1H), 4.42 (t, J = 5.5 Hz, 1H), 4.14 (s, 3H), 3.55 (q, J = 6.0 Hz, 2H), 2.86 (brs, 4H), 2.65 (brs, 4H), 2.48 (d, J = 6.2 Hz, 2H). |
| Final Product 276 | C2 | 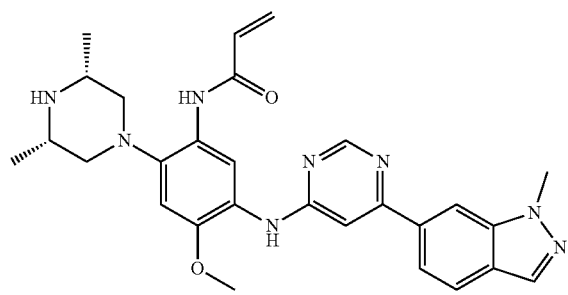 [SMILES: C=CC(=O)Nc1cc(Nc2cc(-c3ccc4cnn(C)c4c3)ncn2)c(OC)cc1N1C[C@@H](C)N[C@@H](C)C1] | MS (ESI+) m/z = 513.24 [M + H]+.<br>1H NMR (400 MHz, DMSO-d6) δ 9.06 (s, 1H), 8.83 (s, 1H), 8.65 (s, 1H), 8.41 (s, 1H), 8.35 (s, 1H), 8.12 (s, 1H), 7.89 (d, J = 8.5 Hz, 1H), 7.79 (d, J = 8.5 Hz, 1H), 7.48 (s, 1H), 6.85 (s, 1H), 6.60-6.66 (m, 1H), 6.24 (d, J = 17.0 Hz, 1H), 5.76 (d, J = 10.9 Hz, 1H), 4.15 (s, 3H), 3.87 (s, 3H), 3.04 (s, 2H), 2.86 (d, J = 10.2 Hz, 2H), 2.27 (t, J = 10.6 Hz, 2H), 0.99 (d, J = 6.3Hz, 6H). |
| Final Product 277 | C28 | 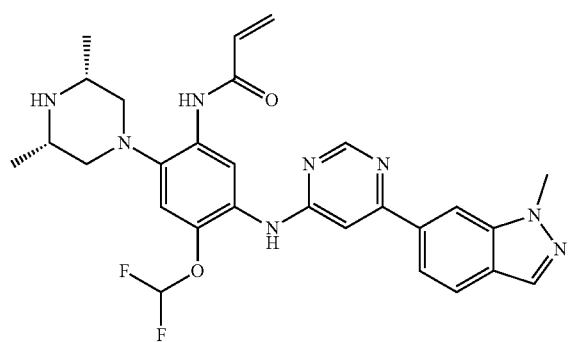 [SMILES: C=CC(=O)Nc1cc(Nc2cc(-c3ccc4cnn(C)c4c3)ncn2)c(OC(F)F)cc1N1C[C@@H](C)N[C@@H](C)C1] | MS (ESI+) m/z = 549.31 [M + H]+.<br>1H NMR (400 MHz, DMSO-d6) δ 9.15 (s, 1H), 9.11 (s, 1H), 8.65 (s, 1H), 8.39 (s, 1H), 8.34 (s, 1H), 8.11 (s, 1H), 7.88 (d, J = 8.8 Hz, 1H), 7.78 (dd, J = 8.5, 0.8 Hz, 1H), 7.44 (s, 1H), 7.35-6.98 (m, 2H), 6.59-6.66 (m, 1H), 6.25 (dd, J = 17.0, 1.6 Hz, 1H), 5.78 (d, J = 11.7 Hz, 1H), 4.13 (s, 3H), 3.01-3.07 (m, 2H), 2.86 (d, J = 9.7 Hz, 2H), 2.19 (t, J = 10.5 Hz, 2H), 2.10 (s, 1H), 0.97 (d, J = 6.3 Hz, 6H). |

TABLE 5-continued

Final Product 263-281

| Final Product 278 | C3 | 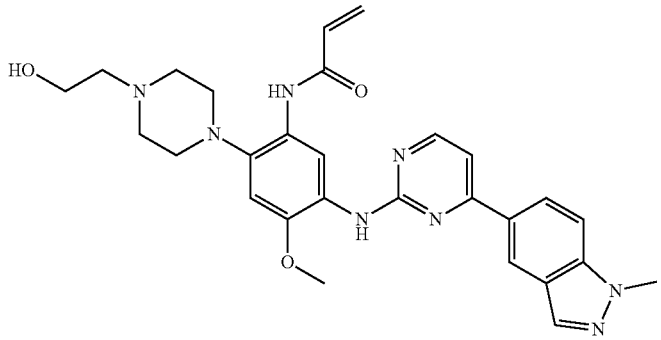 [SMILES: C=CC(=O)Nc1cc(Nc2nccc(-c3ccc4c(cnn4C)c3)n2)c(OC)cc1N1CCN(CCO)CC1] | MS (ESI+) m/z = 529.16 [M + H]+. $^1$H NMR (500 MHz, DMSO-$d_6$) δ 9.05 (s, 1H), 8.97 (s, 1H), 8.87 (s, 1H), 8.48 (d, J = 4.0 Hz, 1H), 8.29 (d, J = 8.1 Hz, 1H), 8.15 (s, 1H), 8.00 (s, 1H), 7.71 (d, J = 8.3 Hz, 1H), 7.49 (d, J = 3.5 Hz, 1H), 6.91 (s, 1H), 6.65-6.70 (m, 1H), 6.32 (d, J = 16.6 Hz, 1H), 5.80 (d, J = 9.4 Hz, 1H), 4.45 (s, 1H), 4.09 (s, 3H), 3.89 (s, 3H), 3.54 (brs, 4H), 2.86 (brs, 4H), 2.64 (brs, 4H). |
| --- | --- | --- | --- |
| Final Product 279 | C3 | 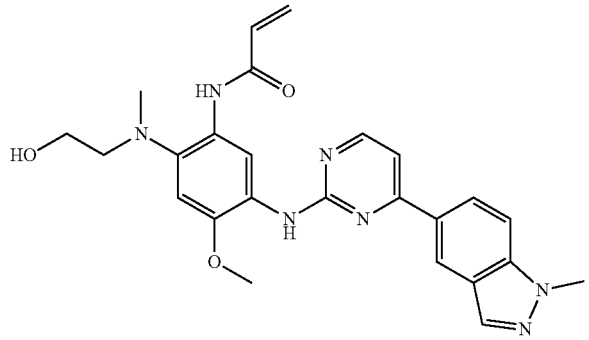 | yield: 73%. MS (ESI+) m/z = 513.24 [M + H]+. $^1$H NMR (500 MHz, DMSO-$d_6$) δ 9.64 (s, 1H), 9.31 (s, 1H), 8.92 (s, 1H), 8.48 (d, J = 5.0 Hz, 1H), 8.31 (d, J = 9.0 Hz, 1H), 8.13 (s, 1H), 8.00 (s, 1H), 7.72 (d, J = 8.5 Hz, 1H), 7.48 (d, J = 5.0 Hz, 1H), 6.97 (s, 1H), 6.56-6.62 (m, 1H), 6.34 (d, J = 16.5 Hz, 1H), 5.78 (d, J = 10.5 Hz, 1H), 5.27 (s, 1H), 4.09 (s, 3H), 3.88 (s, 3H), 3.59 (d, J = 4.5 Hz, 2H), 2.86 (d, J = 4.0 Hz, 2H), 2.72 (s, 3H). |
| Final Product 280 | C3 | 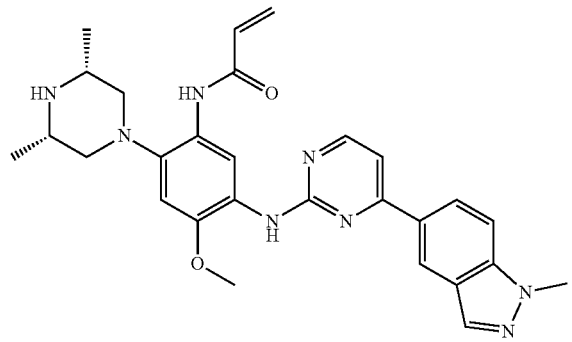 | MS (ESI+) m/z = 513.30 [M + H]+. $^1$H NMR (400 MHz, DMSO-$d_6$) δ 9.05 (s, 1H), 9.01 (s, 1H), 8.88 (s, 1H), 8.48 (d, J = 5.2 Hz, 1H), 8.30 (d, J = 8.0 Hz, 1H), 8.15 (s, 1H), 7.99 (s, 1H), 7.73 (d, J = 8.8 Hz, 1H), 7.49 (d, J = 5.2 Hz, 1H), 6.86 (s, 1H), 6.62-6.69 (m, 1H), 6.34 (d, J = 17.6 Hz, 1H), 5.81 (d, J = 10.8 Hz, 1H), 4.09 (s, 3H), 3.89 (s, 3H), 3.03 (brs, 2H), 2.83 (d, J = 10.0 Hz, 2H), 2.26 (t, J = 10.4 Hz, 2H), 2.07 (brs, 1H), 0.98 (d, J = 6.4 Hz, 6H). |
| Final Product 281 | C3 | 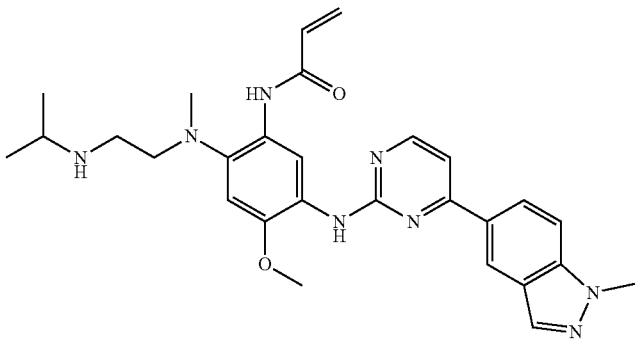 [SMILES: C=CC(=O)Nc1cc(Nc2nccc(-c3ccc4c(cnn4C)c3)n2)c(OC)cc1N(C)CCNC(C)C] | yield: 19.41%. MS (ESI+) m/z = 515.22 [M + H]+. $^1$H NMR (400 MHz, DMSO-$d_6$) δ 9.73 (s, 1H), 9.22 (s, 1H), 8.91 (s, 1H), 8.48 (s, 1H), 8.31 (s, 1H), 8.13 (s, 1H), 8.00 (s, 1H), 7.71 (d, J = 4.0 Hz, 1H), 7.48 (s, 1H), 6.97 (s, 1H), 6.70-6.80 (m, 1H), 6.32 (d, J = 15.6 Hz, 1H), 5.79 (s, 1H), 4.09 (s, 3H), 3.88 (s, 3H), 2.88 (s, 2H), 2.61-2.68 (m, 6H), 1.90 (brs, 1H), 1.01 (s, 6H). |

EXAMPLE 431

Preparation of Final Product 282

N-(2-(4-methylpiperazine-1-yl)-4-ethyl-5-{[6-(1-methyl-1H-indole-5-yl)pyrimidine-4-yl]amino}phenyl)acrylamide (Final Product 282)

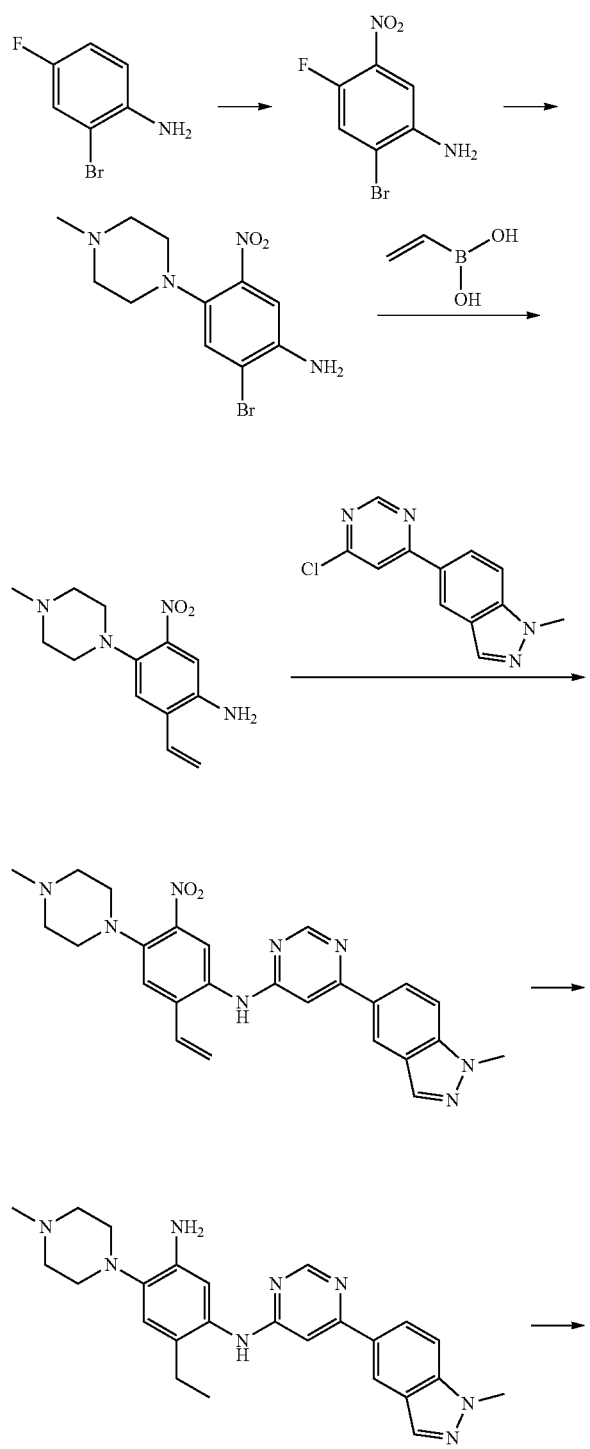

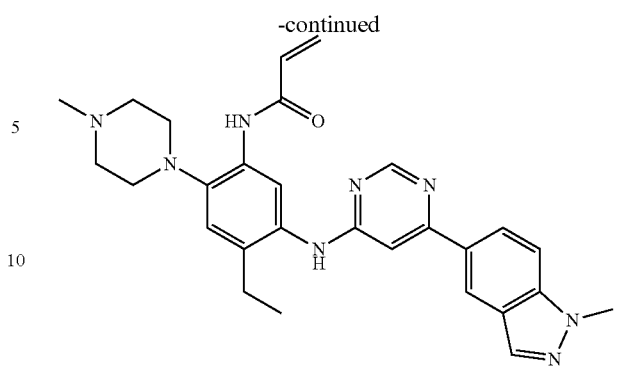

Final Product 282

Step 1: 2-bromo-4-fluoro-5-nitroaniline

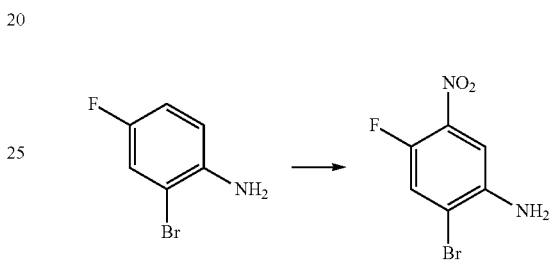

2-bromo-4-fluoroaniline (10 g, 52.9 mmol) and concentrated sulfuric acid (100 mL) were added to a 250 mL single-necked bottle in order, stirred at 30° C. for 1 h. The mixture was cooled to −5~−10° C., potassium nitrate (5.61 g, 55.5 mmol) was added thereinto in batches, after the addition completed, reacted at 0° C. for 2 h, when the materials reacted completely, the reaction mixture was poured into cold 50% aqueous sodium hydroxide solution (pH>7) and filtered, the filtrate was concentrated under reduced pressure to give a crude product. The crude product was purified by column chromatography with PE/EA=10/1 as eluent, the product was collected and concentrated under reduced pressure to give a 6.0 g of pale yellow solid with a yield of 48.8%.

Step 2: 2-bromo-4-(4-methylpiperazine-1-yl)-5-nitroaniline

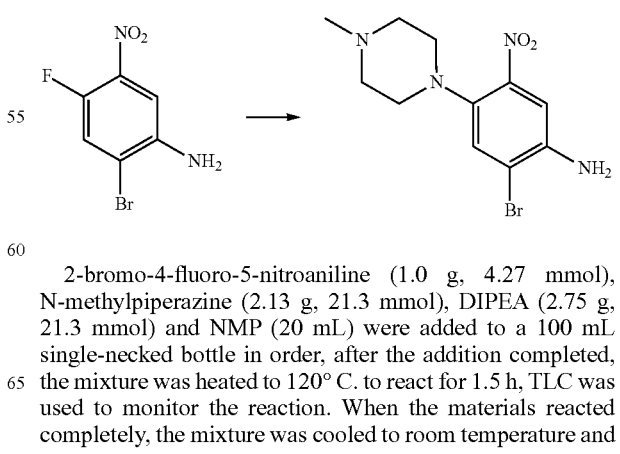

2-bromo-4-fluoro-5-nitroaniline (1.0 g, 4.27 mmol), N-methylpiperazine (2.13 g, 21.3 mmol), DIPEA (2.75 g, 21.3 mmol) and NMP (20 mL) were added to a 100 mL single-necked bottle in order, after the addition completed, the mixture was heated to 120° C. to react for 1.5 h, TLC was used to monitor the reaction. When the materials reacted completely, the mixture was cooled to room temperature and then poured into 100 mL water, the aqueous phase was extracted with ethyl acetate (100 mL×2) twice, the organic phases were combined and concentrated under reduced pressure to give a crude product. The crude product was purified by column chromatography with DCM/MeOH=50/1 as eluent, the product was collected and concentrated under reduced pressure to give a 1.4 g of pale red solid with a yield of 104.4%.

Step 3: 4-(4-methylpiperazine-1-yl)-5-nitro-2-vinylaniline

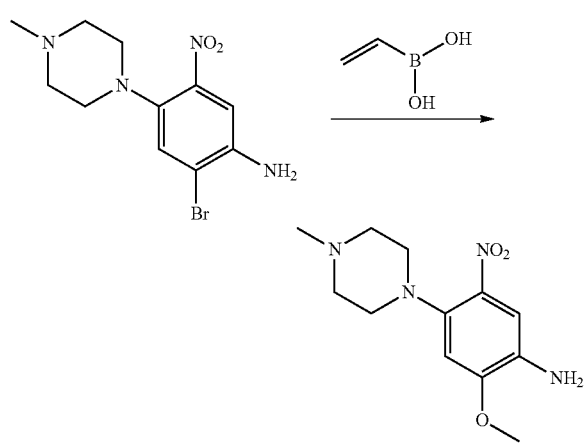

2-bromo-4-(4-methylpiperazine-1-yl)-5-nitroaniline (1.3 g, 4.14 mmol), vinylboronic acid (956 mg, 6.21 mmol), palladium acetate (278 mg, 1.24 mmol), triphenylphosphine (542 mg, 2.07 mmol), cesium carbonate (13.5 g, 41.4 mmol), toluene (40 mL) and water (10 mL) were added to a 100 mL single-necked bottle in order under the protection of argon. When the addition completed, the mixture was heated to 100° C. to react for 2-3 h. After the materials reacted completely, the mixture was cooled to room temperature, and then 50 mL water was added thereinto, the aqueous phase was extracted with ethyl acetate (100 mL×2) twice, the organic phases were combined and concentrated under reduced pressure to give a crude product. The crude product was purified by column chromatography with DCM/MeOH=50/1 as eluent, the product was collected and concentrated under reduced pressure to give a 490 mg of pale red oil with a yield of 45.4%.

Step 4: (1-methyl-1H-indole-5-yl)-N-(4-(4-methylpiperazine-1-yl)-5-nitro-2-vinylphenyl)pyrimidine-4-amine

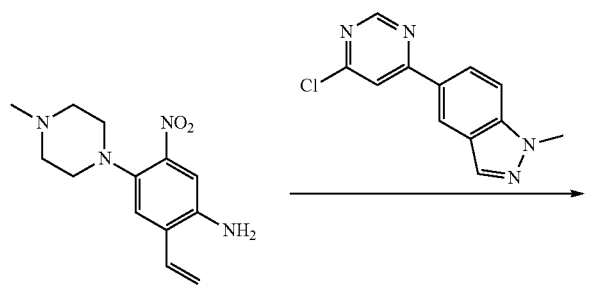

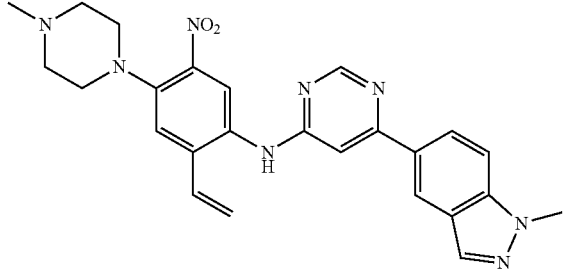

The compound was prepared by the method of EXAMPLE 150 except that 4-(4-methylpiperazine-1-yl)-5-nitro-2-vinylaniline and the intermediate A1 were used as the starting materials to give a 460 mg of pale red solid with a yield of 55.7%.

Step 5: 6-ethyl-N1-(6-(1-methyl-1H-indole-5-yl) pyrimidine-4-yl)-4-(4-methyl-piperazine-1-yl)phenyl-1,3-diamine

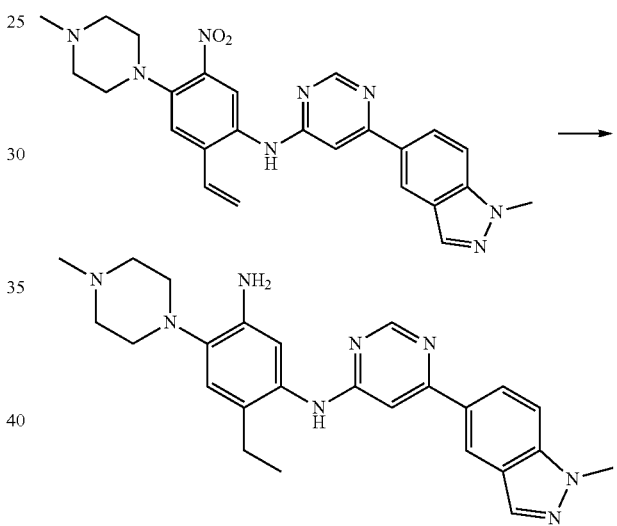

The compound was prepared by the method of the step 2 of EXAMPLE 167 except that (1-methyl-1H-indole-5-yl)-N-(4-(4-methylpiperazine-1-yl)-5-nitro-2-vinylphenyl) pyrimidine-4-amine was used as the starting material to give a 120 mg of pale red solid with a yield of 58.4%.

Step 6: N-(2-(4-methylpiperazine-1-yl)-4-ethyl-5-{[6-(1-methyl-1H-indole-5-yl) pyrimidine-4-yl] amino}phenyl)acrylamide

283

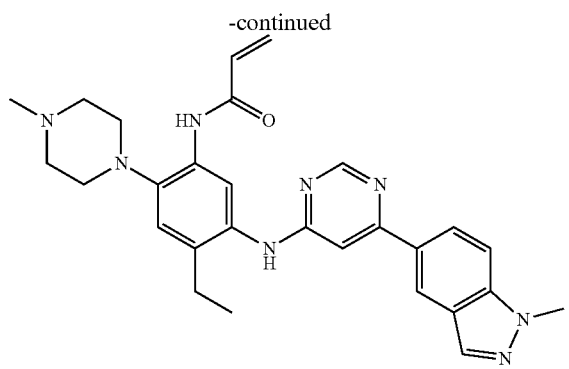

Final Product 282

The compound was prepared by the method of the step 3 of EXAMPLE 167 except that 6-ethyl-N1-(6-(1-methyl-1H-indole-5-yl)pyrimidine-4-yl)-4-(4-methylpiperazine-1-yl)phenyl-1,3-diamine was used as the starting material to give a 40 mg of pale yellow solid with a yield 21.1%.

MS (ESI$^+$) m/z=497.25[M+H]$^+$. $^1$H NMR (400 MHz, DMSO-d$_6$) δ 9.05 (s, 1H), 8.96 (s, 1H), 8.53 (s, 1H), 8.47 (s, 1H), 8.15 (s, 1H), 8.05 (d, J=8.8 Hz, 1H), 7.96 (s, 1H), 7.73 (d, J=8.8 Hz, 1H), 7.09 (d, J=9.2 Hz, 2H), 6.60-6.67 (m, 1H), 6.24 (d, J=16.8 Hz, 1H), 5.75 (d, J=10.8 Hz, 1H), 4.07 (s, 3H), 2.86 (s, 4H), 2.61-2.70 (m, 6H), 2.26 (s, 3H), 1.10 (t, J=7.6 Hz, 3H).

EXAMPLE 432

Preparation of Final Product 283

N-(2-(4-morpholinopiperidine-1-yl)-4-ethyl-5{[6-(1-methyl-1H-indole-5-yl)pyrimidine-4-yl]amino}phenyl)acrylamide (Final Product 283)

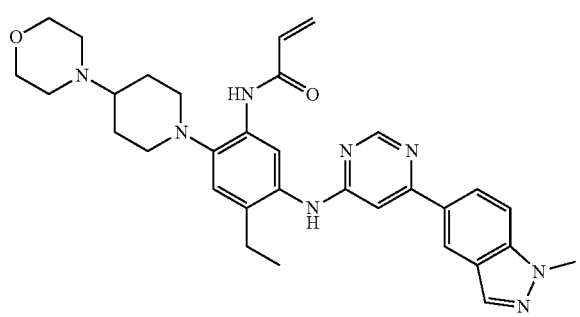 [SMILES: C=CC(=O)Nc1cc(Nc2cc(-c3ccc4c(cnn4C)c3)ncn2)c(CC)cc1N1CCC(N2CCOCC2)CC1]

The compound was prepared by the method of synthesizing Final Product 282 except that 2-bromo-4-fluoro-5-nitroaniline was used as the starting material.

MS (ESI$^+$) m/z=567.26[M+H]$^+$. $^1$H NMR (400 MHz, DMSO-d$_6$) δ 9.04 (s, 1H), 8.95 (s, 1H), 8.54 (s, 1H), 8.47 (s, 1H), 8.15 (d, J=0.4 Hz, 1H), 8.06 (dd, J=1.2, 8.4 Hz, 1H), 8.00 (s, 1H), 7.73 (d, J=6.8 Hz, 1H), 7.10 (s, 1H), 7.06 (s, 1H), 6.67-6.73 (m, 1H), 6.25 (dd, J=1.6, 13.6 Hz, 1H), 5.75 (dd, J=1.2, 9.6 Hz, 1H), 4.08 (s, 3H), 3.60 (s, 4H), 3.05 (s, 4H), 2.67 (t, J=9.2 Hz, 2H), 2.57-2.60 (m, 2H), 2.57 (s, 2H), 2.27 (t, J=8.8 Hz, 1H), 1.88 (d, J=8.4 Hz, 2H), 1.70-1.76 (m, 2H), 1.10 (t, J=6.0 Hz, 3H).

EXAMPLE 433

Preparation of Final Product 284

N-(2-(4-(3-(dimethylamino)pyrrolidine-1-yl)-4-methoxy-5{[6-(1-methyl-1H-indole-5-yl) pyrimidine-4-yl]amino}phenyl)acrylamide (Final Product 284)

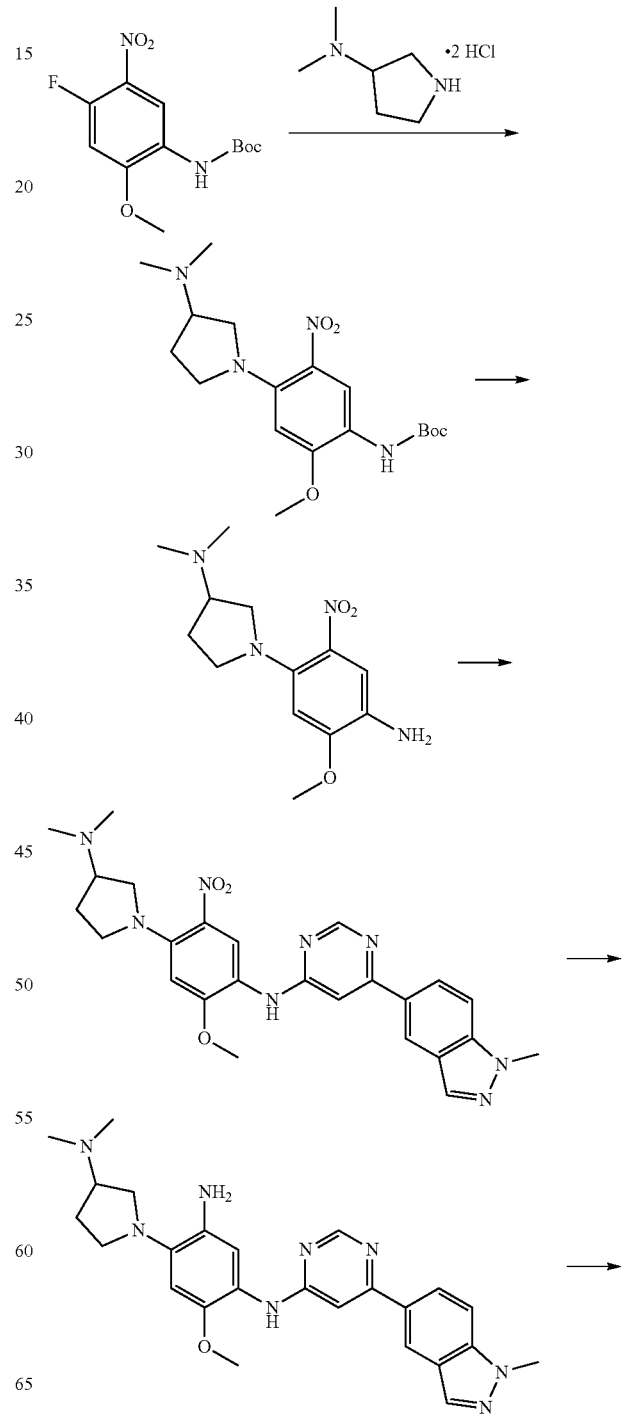

285

-continued

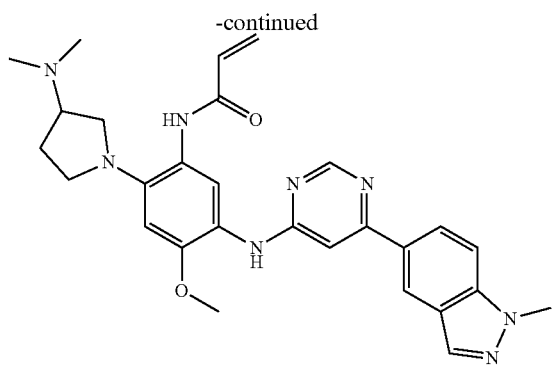

Final Product 284

Step 1: tert-butyl 4-(3-(dimethyamino)pyrrolidine-1-yl)-2-methoxy-5-nitrophenyl) carbamate

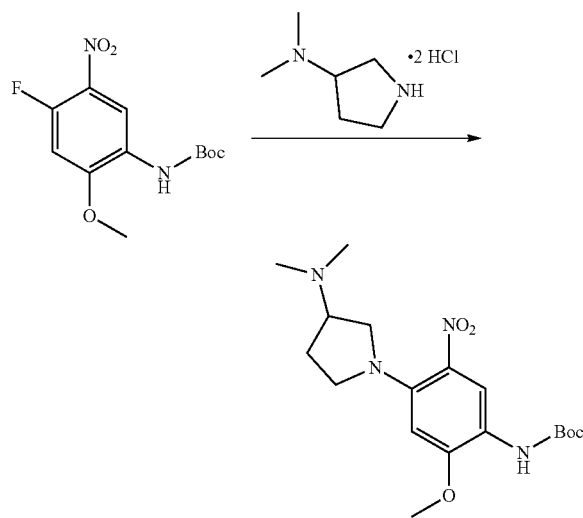

The compound was prepared by the method of the step 2 of EXAMPLE 113 except that tert-butyl (4-fluoro-2-methoxy-5-nitrophenyl) carbamate and 3-(dimethyamino) pyrrolidine dihydrochloride were used as the starting materials.

Step 2: 1-(4-amino-5-methoxy-2-nitrophenyl)-N,N-dimethyl-pyrrolidine-3-amine

286

-continued

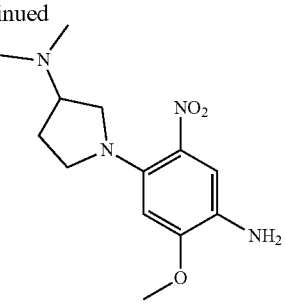

Tert-butyl 4-(3-(dimethyamino)pyrrolidine-1-yl)-2-methoxy-5-nitrophenyl)carbamate (210 mg, 1.91 mmol), DCM (10 mL) and trifluoroacetic acid (4 mL) were added to a 100 mL single-necked bottle in order, stirred at room temperature for 30 min. After the materials reacted completely, the pH of the reaction mixture was adjusted with saturated sodium bicarbonate solution to alkaline, and then extracted with dichloromethane (30 mL×3) for three times, the organic phases were combined, washed with saturated brine (30 mL×2) twice, dried with anhydrous sodium sulfate for 30 min, and filtered, the filtrate was concentrated under reduced pressure, the residue was purified by column chromatography with DCM/CH$_3$OH=30/1 as eluent, the product was collected and concentrated under reduced pressure to give a 110 mg of red oil.

Step 3: N-(4-(3-(dimethylamino)pyrrolidine-1-yl)-2-methoxy-5-nitrophenyl)-6-(1-methyl-1H-indole-5-yl)pyrimidine-4-amine

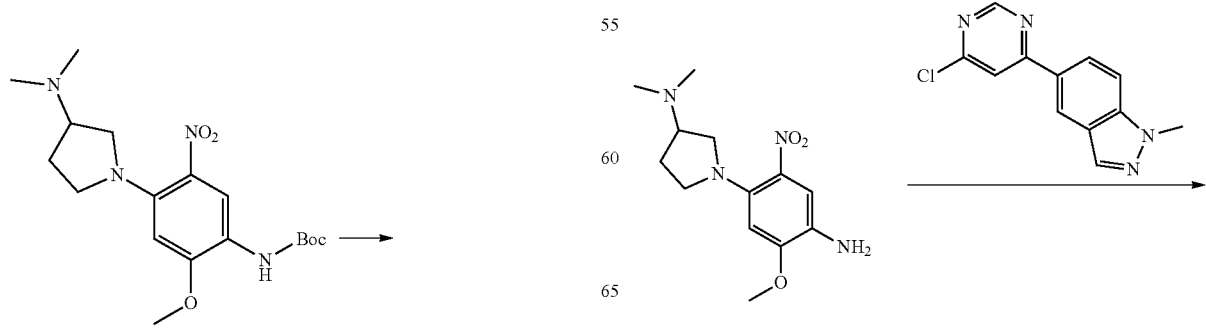

-continued

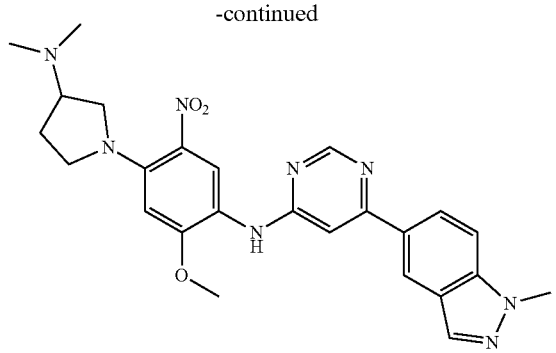

The compound was prepared by the method of EXAMPLE 150 except that 1-(4-amino-5-methoxy-2-nitrophenyl)-N,N-dimethylpyrrolidine-3-amine and the intermediate A1 were used as the starting materials.

Step 4: (3-(dimethylamino)pyrrolidine-1-yl)-6-methoxy-N1-6-(1-methyl-1H-indole-5-yl)pyrimidine-4-yl)benzene-1,3-diamine

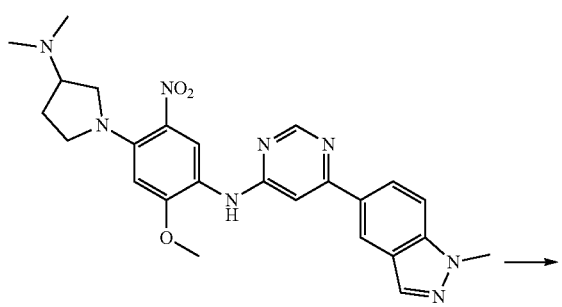

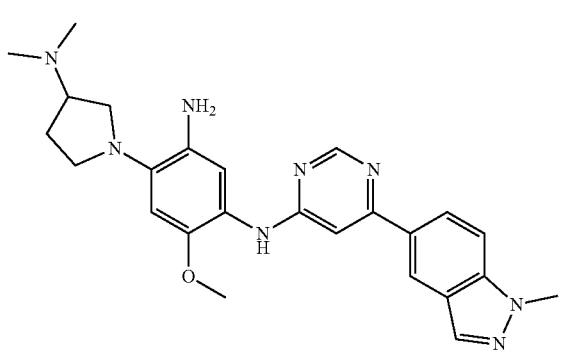

The compound was prepared by the method of the step 2 of EXAMPLE 167 except that N-(4-(3-(dimethylamino)pyrrolidine-1-yl)-2-methoxy-5-nitrophenyl) 6-(1-methyl-1H-indole-5-yl)pyrimidine-4-amine was used as the starting material.

Step 5: N-(2-(4-(3-(dimethylamino)pyrrolidine-1-yl)-4-methoxy-5{[6-(1-methyl-1H-indole-5-yl)pyrimidine-4-yl]amino}phenyl)acrylamide

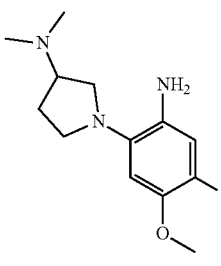

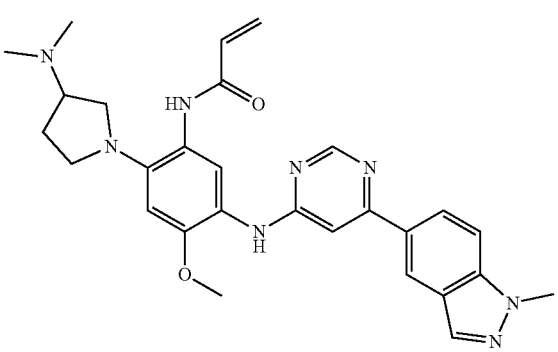

Final Product 284

The compound was prepared by the method of the step 3 of EXAMPLE 167 except that (3-(dimethylamino)pyrrolidine-1-yl)-6-methoxy-N1-6-(1-methyl-1H-indole-5-yl)pyrimidine-4-yl)benzene-1,3-diamine was used as the starting material.

MS (ESI$^+$) m/z=513.23[M+H]$^+$. $^1$H NMR (500 MHz, DMSO-d$_6$) δ 9.41 (s, 1H), 8.64 (s, 1H), 8.55 (s, 1H), 8.46 (s, 1H), 8.16 (s, 1H), 8.06 (d, J=9.0 Hz, 1H), 7.73 (d, J=9.0 Hz, 1H), 7.60 (s, 1H), 7.22 (s, 1H), 6.46-6.52 (m, 2H), 6.21 (d, J=18.0 Hz, 1H), 5.70 (d, J=10.0 Hz, 1H), 4.08 (s, 3H), 3.84 (s, 3H), 3.36-3.41 (m, 1H), 3.20-3.28 (m, 3H), 2.66 (d, J=25.6 Hz, 1H), 2.24 (d, J=65.3 Hz, 6H), 2.08 (d, J=5.1 Hz, 1H), 1.72 (m, 1H).

Examples 434-439

The Final Products 285-290 were prepared by the method of synthesizing the Final Product 284 except that the intermediate A and nitroanilines prepared by EXAMPLES 83-90 were used as the starting materials. (Table 6)

TABLE 6

Final Products 285-290

| Final Product 285 | A15 | 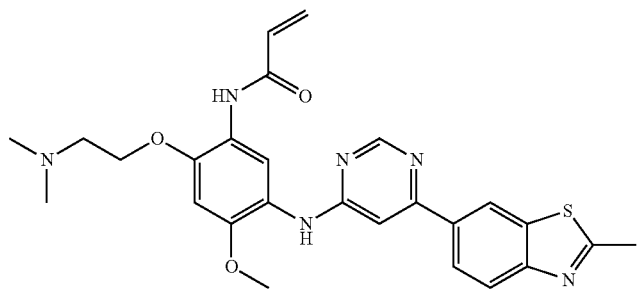 | MS (ESI+) m/z = 505.22 [M + H]+. <br> 1H NMR (500 MHz, DMSO-d6) δ 9.69 (s, 1H), 8.82 (s, 1H), 8.74 8.74 (s, 1H), 8.60 (s, 1H), 8.33 (s, 1H), 8.10 (d, J = 8.6 Hz, 1H), 8.00 (d, J = 8.5 Hz, 1H), 7.29 (s, 1H), 6.94 (s, 1H), 6.45-6.51 (m, 1H), 6.24 (d, J = 17.0 Hz, 1H), 5.74 (d, J = 10.4 Hz, 1H), 4.19 (t, J = 5.6 Hz, 2H), 3.84 (s, 3H), 2.83 (s, 3H), 2.60 (t, J = 5.6 Hz, 2H), 2.27 (s, 6H). |
|---|---|---|---|
| Final Product 286 | A1 | 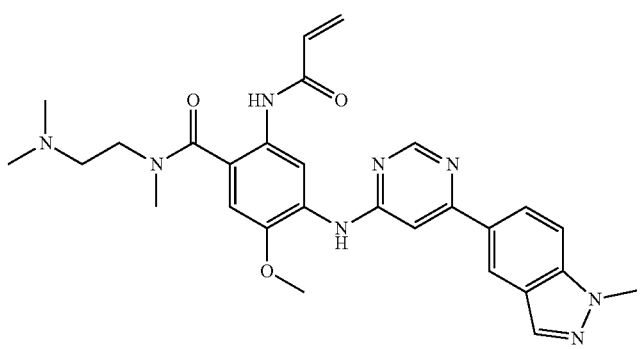 | MS (ESI+) m/z = 529.17 [M + H]+. <br> 1H NMR (500 MHz, DMSO-d6) δ 9.62 (s, 1H), 8.92 (s, 1H), 8.71 (s, 1H), 8.54 (s, 1H), 8.43 (s, 1H), 8.20 (s, 1H), 8.11 (d, J = 9.0, 1.0 Hz, 1H), 7.79 (d, J = 9.0 Hz, 1H), 7.67 (d, J = 20.5 Hz, 1H), 6.95 (s, 1H), 6.51-6.38 (m, 1H), 6.22 (dd, J = 17.0, 2.0 Hz, 1H), 5.73 (dd, J = 10.5, 1.5 Hz, 1H), 4.10 (s, 3H), 3.91 (s, 3H), 3.49 (m 1H), 3.23 (s, 1H), 2.86-2.91 (m, 3H), 2.34-2.43 (m, 2H), 2.20 (s, 3H), 1.99 (s, 3H). |
| Final Product 287 | A1 | 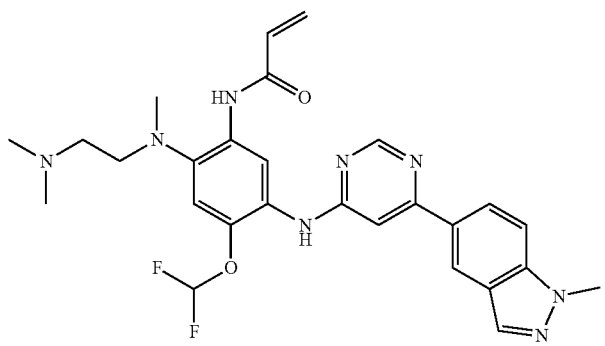 | MS (ESI+) m/z = 537.15 [M + H]+. <br> 1H NMR (500 MHz, DMSO-d6) δ 10.24 (s, 1H), 9.05 (s, 1H), 8.71 (s, 1H), 8.61 (s, 1H), 8.51 (s, 1H), 8.18 (s, 1H), 8.09 (dd, J = 9.0, 1.5 Hz, 1H), 7.76 (d, J = 9.0 Hz, 1H), 7.36 (s, 1H), 6.98-7.27 (m, 2H), 6.40-6.45 (m, 1H), 6.28 (dd, J = 17.0, 2.0 Hz, 1H), 5.80 (dd, J = 10.0, 1.5 Hz, 1H), 4.09 (s, 3H), 2.86 (t, J = 5.5 Hz, 2H), 2.71 (s, 3H), 2.36 (s, 2H), 2.22 (s, 6H). |
| Final Product 288 | A1 | 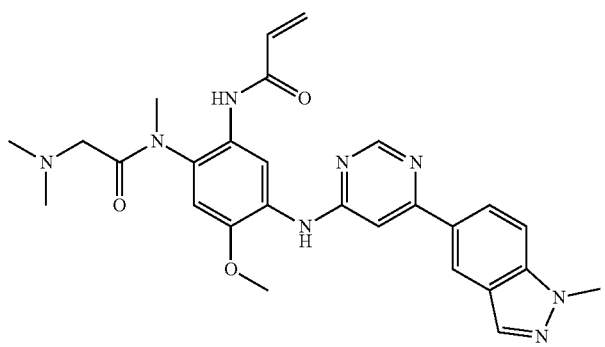 | MS (ESI+) m/z = 514.90 [M + H]+. <br> 1H NMR (400 MHz, DMSO-d6) δ 9.55 (s, 1H), 8.87 (s, 1H), 8.69 (s, 1H), 8.53 (s, 1H), 8.51 (s, 1H), 8.18 (s, 1H), 8.10 (d, J = 8.9 Hz, 1H), 7.77 (d, J = 8.8 Hz, 1H), 7.65 (s, 1H), 7.10 (s, 1H), 6.48-6.55 (m, 1H), 6.23 (d, J = 17.1 Hz, 1H), 5.75 (d, J = 10.5 Hz, 1H), 4.09 (s, 3H), 3.90 (s, 3H), 3.06 (s, 3H), 2.83 (q, J = 15.1 Hz, 2H), 2.15 (s, 6H). |

TABLE 6-continued

Final Products 285-290

Final Product 289  A1  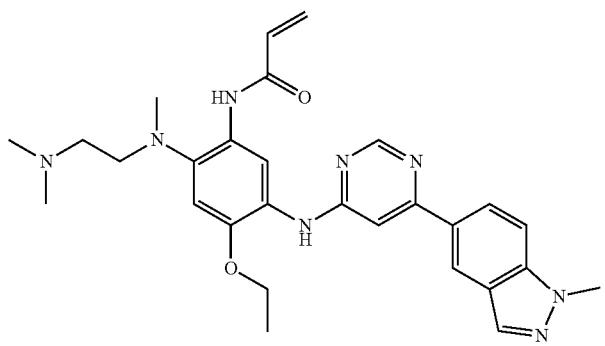  MS (ESI⁺) m/z = 515.16 [M + H]⁺.
¹H NMR (400 MHz, DMSO-d₆) δ
10.11 (s, 1H), 8.66 (s, 2H), 8.61
(s, 1H), 8.52 (s, 1H), 8.17
(s, 1H), 8.10 (dd, J = 7.2, 1.2
Hz, 1H), 7.75 (d, J = 7.2 Hz, 1H),
7.38 (s, 1H), 7.01 (s, 1H),
6.38-6.43 (m, 1H), 6.25 (dd, J =
13.6, 1.2 Hz, 1H), 5.75 (d,
J = 10.4, 1.2 Hz, 1H), 4.12 (t, J =
5.6 Hz, 2H), 4.09 (s, 3H),
2.88 (s, 2H), 2.71 (s, 3H), 2.33
(s, 2H), 2.22 (s, 6H), 1.31
(t, J = 5.6 Hz, 3H).

Final Product 290  A3  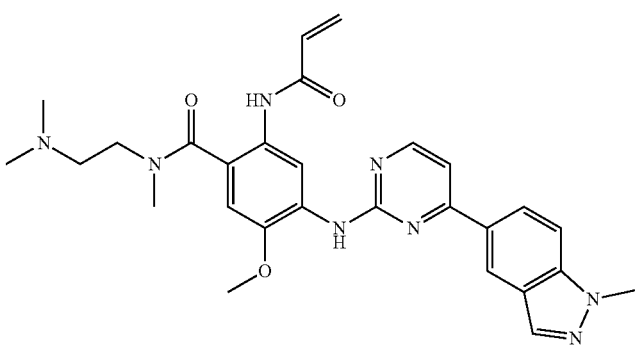  MS (ESI⁺) m/z = 529.14 [M + H]⁺.
¹H NMR (500 MHz, DMSO-d₆) δ
9.60 (s, 1H), 8.80-8.85 (m, 2H),
8.57 (s, 1H), 8.29 (dd, J = 9.0,
1.0 Hz, 1H), 8.15 (d, J = 5.0 Hz,
2H), 7.73 (d, J = 9.0 Hz, 1H),
7.58 (d, J = 5.5 Hz, 1H), 6.96 (s,
1H), 6.50-6.55 (m, 1H), 6.31
(dd, J = 17.0, 1.5 Hz, 1H), 5.80
(d, J = 10.0 Hz, 1H), 4.09 (s, 3H),
3.95 (s, 3H), 3.52 (m, 1H),
3.26 (s, 1H), 2.87-2.97 (m, 3H),
2.36-2.46 (m, 2H), 2.21 (s, 3H),
1.99 (s, 3H).

EXAMPLE 440

Preparation of Final Product 291

N-(4-cyclopropoxy-2-((2-(dimethyamino)ethyl)(methyl)amino)-5-((6-(1-methyl-1H-indole-5-yl)pyrimidine-4-yl)amino)phenyl)acrylamide (Final Product 291)

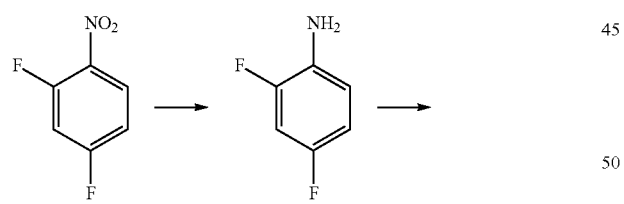

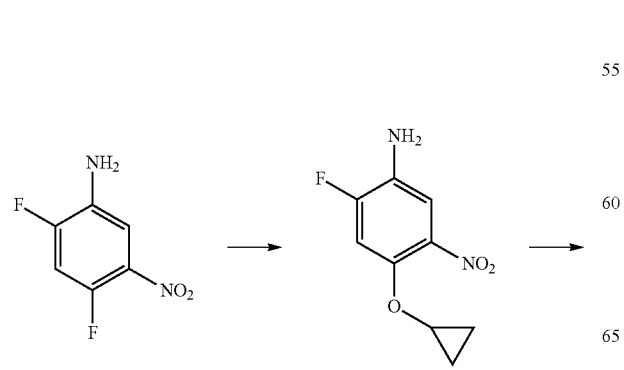

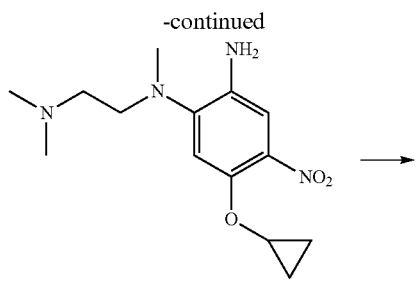

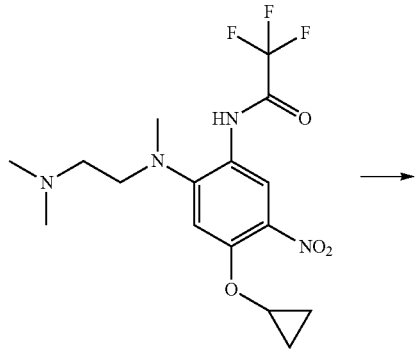

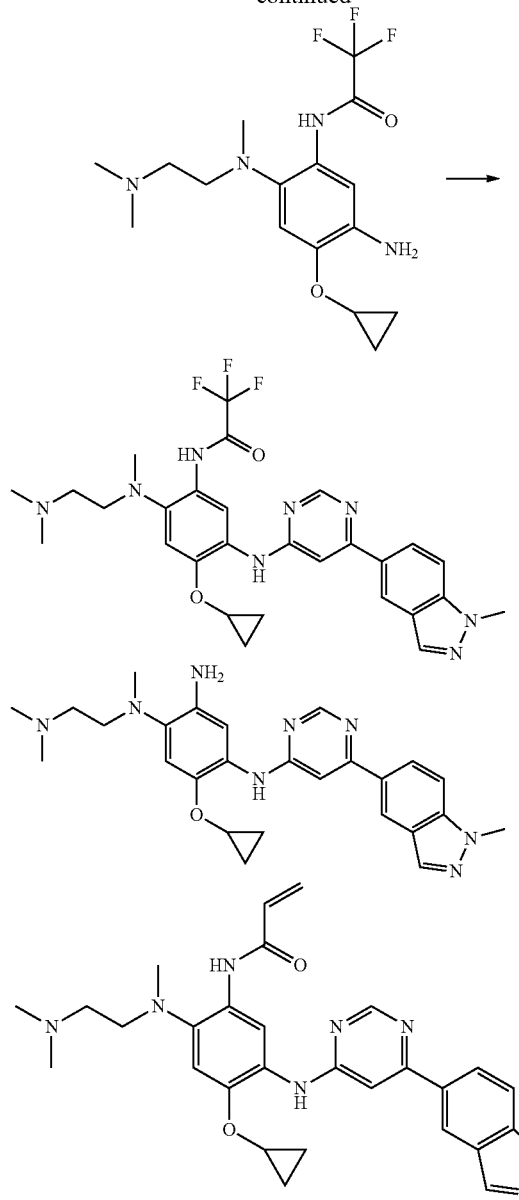

Final Product 291

Step 1: 2,4-difluoroaniline

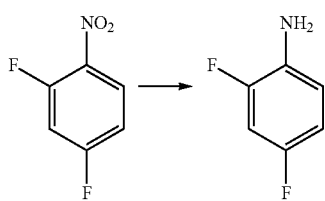 [SMILES: O=[N+]([O-])c1ccc(F)cc1F ; Nc1ccc(F)cc1F]

2,4-difluoronitrobenzene (1 g), methanol (10 mL) and Pd/C (100 mg) were added to a 100 mL single-necked bottle in order, substituted with hydrogen for three times, the mixture was reacted with stirring at room temperature for 2-3 h, then filtered, the filtrate was concentrated under reduced pressure to give a 810 mg of product.

Step 2: 2,4-difluoro-5-nitroaniline

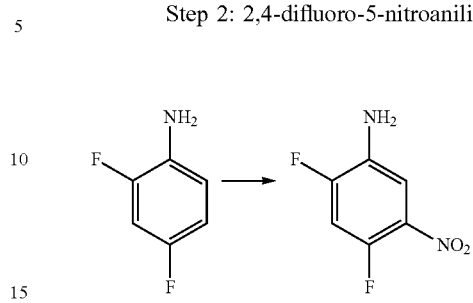

2,4-difluoroaniline (630 mg, 4.88 mmol) and concentrated sulfuric acid (10 mL) were added to a 100 mL three-necked bottle, the mixture was cooled to 0-5° C. in an ice-water bath. Potassium nitrate (542 mg, 1.1 eq) was added thereinto in batches slowly, the mixture was reacted at the same temperature for 1-2 h. The reaction mixture was added to water (200 mL) dropwise slowly, and then the pH was adjust to neutral with sodium carbonate, extracted with ethyl acetate (50 mL×3) for three times, the organic phases were combined, washed with saturated brine twice, dried with anhydrous sodium sulfate for 30 min, and filtered, the filtrate was concentrated under reduced pressure to give a 750 mg of product.

Step 3: 4-cyclopropoxy-2-fluoro-5-nitroaniline

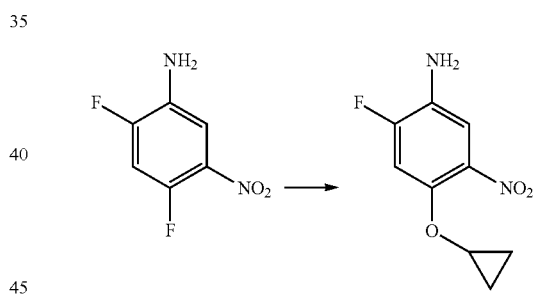

2,4-difluoro-5-nitroaniline (650 mg) and DMF (20 mL) were added to a 100 mL three-necked bottle, the mixture was cooled to 0-5° C. in an ice-water bath, cyclopropanol (216.8 mg, 1 eq) was added thereinto. Sodium tert-butoxide (466 mg, 1.3 eq) was added thereinto in batches slowly, the mixture was reacted at the same temperature for 1-2 h. The reaction mixture was poured into water (100 mL), extracted with ethyl acetate (50 mL×3) for three times, the organic phases were combined, washed with saturated brine twice, dried with anhydrous sodium sulfate for 30 min, and filtered, the filtrate was concentrated under reduced pressure to give a crude product, the crude product was purified by column chromatography with PE/EA=10/1 as eluent, the product was collected and concentrated under reduced pressure to give 392 mg.

Step 4: 5-cyclopropoxy-N1-(2-(dimethylamino) ethyl)-N1-methyl-4-nitrophenyl-1,2-diamine

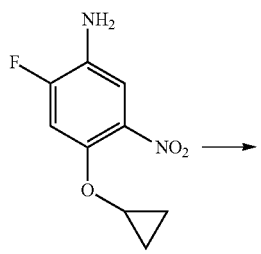

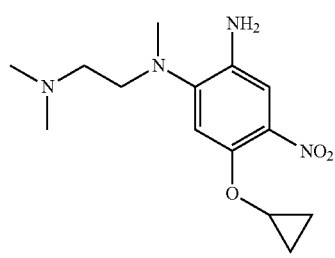

4-cyclopropoxy-2-fluoro-5-nitroaniline (300 mg), DMF (5 mL), N1,N2,N3-trimethyl ethylenediamine (433 mg, 3 eq) and DIPEA (548 mg, 3 eq) were added to a 100 mL three-necked bottle in order, the mixture was dissolved with stirring, heated to 50-60° C. in an oil bath to react with stirring for 6-7 h. After the reaction completed, the mixture was cooled to room temperature naturally, water (50 mL) was added, the reaction mixture was extracted with ethyl acetate (50 mL×3) for three times, the organic phases were combined, washed with saturated brine twice, dried with anhydrous sodium sulfate for 30 min, and filtered, the filtrate was concentrated under reduced pressure to give a crude product, the crude product was accordingly purified by column chromatography with DCM/MeOH=20/1 as eluent, the product was collected and concentrated under reduced pressure to give 292 mg.

Step 5: N-(4-cyclopropoxy-2-((2-(dimethylamino) ethyl)(methyl)amino)-5-nitro phenyl)-2,2,2-trifluoroacetamide

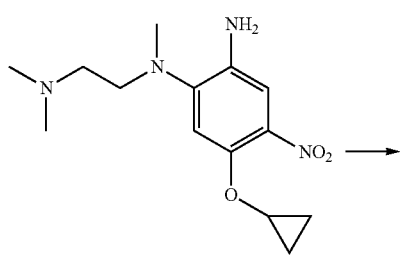

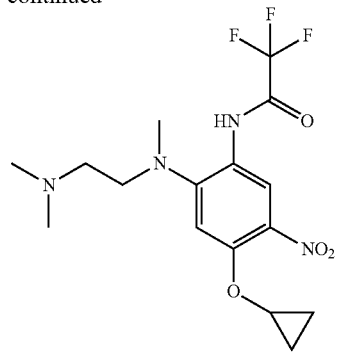

5-cyclopropoxy N1-(2-(dimethylamino)ethyl)-N1-methyl-4-nitrophenyl-1,2-diamine (310 mg) and ethyl acetate (25 mL) were added to a 100 mL three-necked bottle, trifluoroacetic anhydride (243 mg, 1.1 eq) in ethyl acetate (0.5 mL) was added dropwise thereinto with stirring at room temperature, after the addition completed, the mixture was reacted with stirring at room temperature for 1 h. Water (50 mL) was added thereinto, the mixture was extracted with ethyl acetate (30 mL×3) for three times, the organic phases were combined, washed with saturated brine twice, dried with anhydrous sodium sulfate for 30 min, and filtered, the filtrate was concentrated under reduced pressure to give 300 mg of product.

Step 6: N-(5-amino-4-cyclopropyl-2-((2-(dimethylamino)ethyl)(methyl)amino) phenyl)-2,2,2-trifluoroacetamide

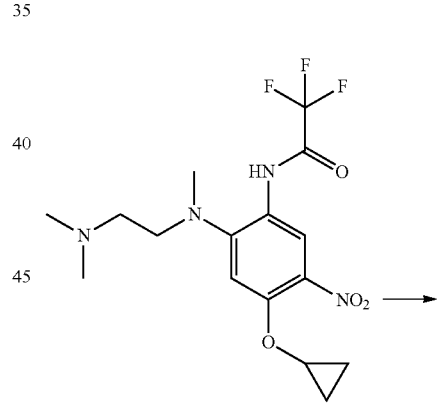

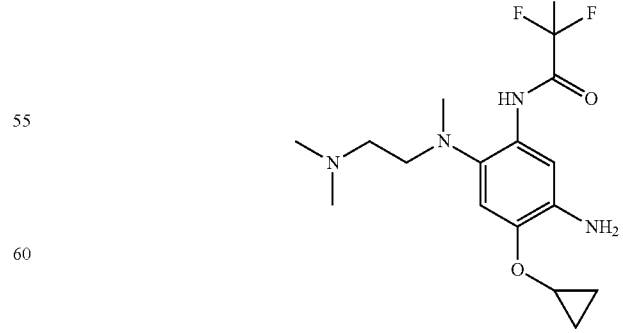

N-(4-cyclopropoxy-2-((2-(dimethylamino)ethyl)(methyl) amino)-5-nitrophenyl)-2,2,2-trifluoro-acetamide (300 mg), methanol (10 mL) and Pd/C (30 mg) were added to a 100 mL single-necked bottle in order, substituted with hydrogen for three times, the mixture was reacted at room temperature for 2-3 h. Filtered, the filtrate was concentrated under reduced pressure to give a 300 mg of oily product.

Step 7: N-(4-cyclopropoxy-2-((2-(dimethylamino)ethyl)(methyl)amino)-5-((6-(1-methyl-1H-indole-5-yl)pyrimidine-4-yl)amino)phenyl)-2,2,2-trifluoroacetamide

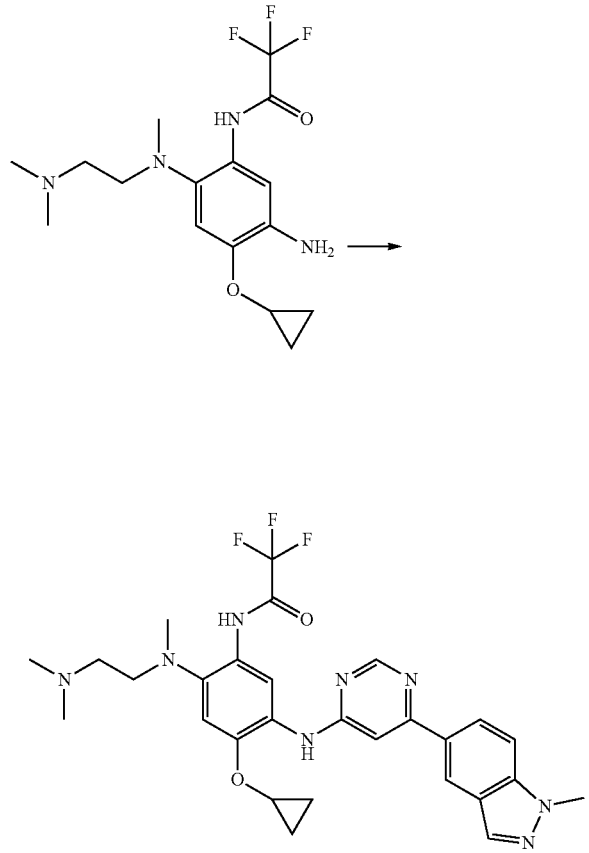

N-(5-amino-4-cyclopropyl-2-((2-(dimethylamino)ethyl)(methyl)amino)phenyl)-2,2,2-trifluoroacetamide (80 mg), the intermediate A1 (54 mg, 1 eq), cesium carbonate (144 mg, 2 eq), Xantphos (26 mg, 0.2 eq), toluene (10 mL) and Pd$_2$(dba)$_3$ (20 mg, 0.1 eq) were added to a 100 mL three-necked bottle in order under the protection of argon, the mixture was heated to 90-95° C. in an oil bath, and reacted with stirring for 8-10 h. After being cooled to room temperature, the reaction mixture was concentrated under reduced pressure to give a crude product, the crude product was accordingly purified by column chromatography with DCM/MeOH=10/1 as eluent, the product was collected and concentrated under reduced pressure to give 80 mg.

Step 8: 5-cyclopropoxy-N1-2-(dimethylamino)ethyl)-N1-methyl-N4-(6-(1-methyl-1H-indole-5-yl)pyrimidine-4-yl)phenyl-1,2,4-triamine

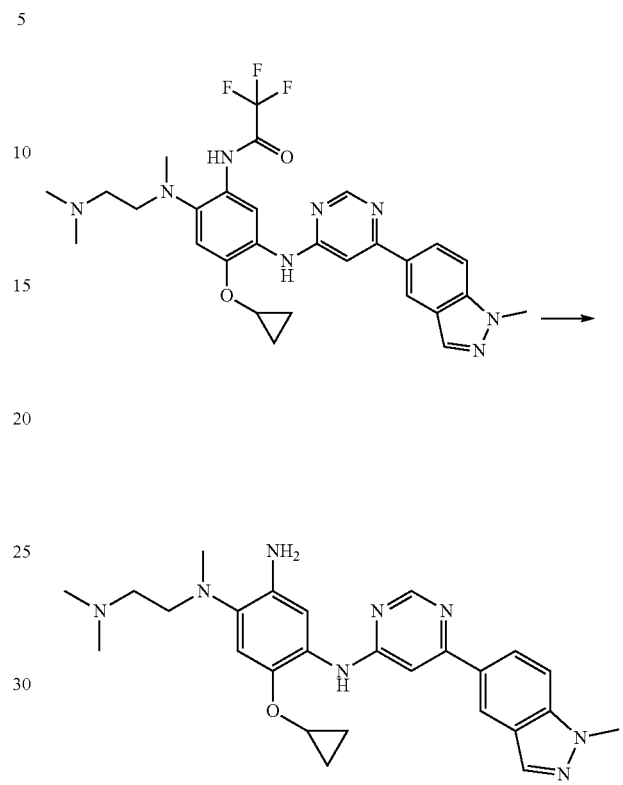

N-(4-cyclopropoxy-2-((2-(dimethylamino)ethyl)(methyl)amino)-5-((6-(1-methyl-1H-indole-5-yl)pyrimidine-4-yl)amino)phenyl)-2,2,2-trifluoroacetamide (80 mg) and ethanol/water=1/1 in 1N piperidine (8 mL) were added to a 100 mL single-necked bottle, the mixture was reacted with stirring at room temperature for 8-10 h. Water (30 mL) and ethyl acetate (30 mL) were added thereinto, then separated organic phase, the aqueous phase was extracted with ethyl acetate twice, the organic phases were combined, dried with anhydrous sodium sulfate for 30 min, and filtered, the filtrate was concentrated under reduced pressure to give a crude product, the crude product was purified by column chromatography with DCM/MeOH=10/1 as eluent, the product was collected and concentrated under reduced pressure to give 50 mg.

Step 9: N-(4-cyclopropoxy-2-((2-(dimethyamino)ethyl)(methyl)amino)-5-((6-(1-methyl-1H-indole-5-yl)pyrimidine-4-yl)amino)phenyl)acrylamide

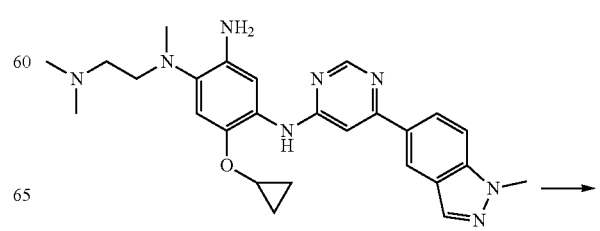

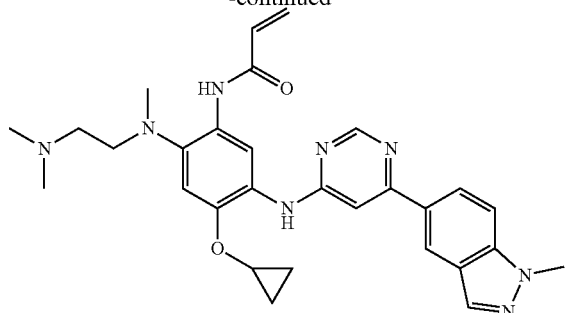

The Final Product 291 was prepared by the method of the step 3 of EXAMPLE 167 except that 5-cyclopropoxy N1-2-(dimethylamino)ethyl)-N1-methyl-N4-(6-(1-methyl-1H-indole-5-yl)pyrimidine-4-yl)phenyl-1,2,4-triamine was used as the starting material.

MS (ESI+) m/z=527.06 [M+H]+. 1H NMR (500 MHz, DMSO-d6) δ 9.25 (s, 1H), 9.19 (s, 1H), 8.61 (s, 1H), 8.53 (s, 1H), 8.41 (s, 1H), 8.16 (s, 1H), 8.12 (dd, J=8.9, 1.0 Hz, 1H), 7.75 (d, J=8.9 Hz, 1H), 7.30 (s, 1H), 7.18 (s, 1H), 6.62-6.68 (m, 1H), 6.23 (dd, J=17.0, 1.5 Hz, 1H), 5.71 (dd, J=12.0, 1.5 Hz, 1H), 4.08 (s, 3H), 3.93-3.96 (m, 1H), 2.98 (s, 2H), 2.71 (s, 3H), 2.36-2.49 (m, 2H), 2.20 (brs, 6H), 0.76-0.82 (m, 4H).

EXAMPLE 441

Preparation of Final Product 292

N-(4-cyclopropoxy-2-((2-(dimethyamino)ethyl)(methyl)amino)-5-((4-(1-methyl-1H-indole-5-yl)pyrimidine-2-yl)amino)phenyl)acrylamide (Final Product 292)

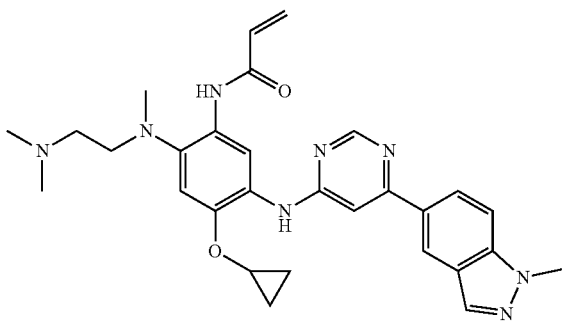

The Final Product 292 was prepared by the method of preparing Final Product 291 except that 2,4-difluoroaniline and intermediate A3 were used as the starting materials.

MS (ESI+) m/z=527.26 [M+H]+. 1H NMR (400 MHz, DMSO-d6) δ 9.15-9.19 (m, 3H), 8.85 (s, 1H), 8.48 (d, J=5.0 Hz, 1H), 8.30 (d, J=8.8 Hz, 1H), 8.12 (s, 1H), 7.71 (d, J=8.9 Hz, 1H), 7.44 (d, J=5.0 Hz, 1H), 7.26 (s, 1H), 6.68-6.75 (m, 1H), 6.32 (d, J=17.1 Hz, 1H), 5.78 (d, J=10.0 Hz, 1H), 4.09 (s, 3H), 3.93 (brs, 1H), 2.93 (t, J=6.0 Hz, 2H), 2.71 (s, 3H), 2.35 (t, J=5.6 Hz, 2H), 2.18 (s, 6H), 0.76-0.80 (m, 4H).

EXAMPLE 442

Preparation of Final Product 293

N-(2-((1-acetylpiperidine-4-yl)(methyl)amino)-4-methoxy-5-((6-(1-methyl-1H-indole-5-yl)pyrimidine-4-yl)amino)phenyl)acrylamide (Final Product 293)

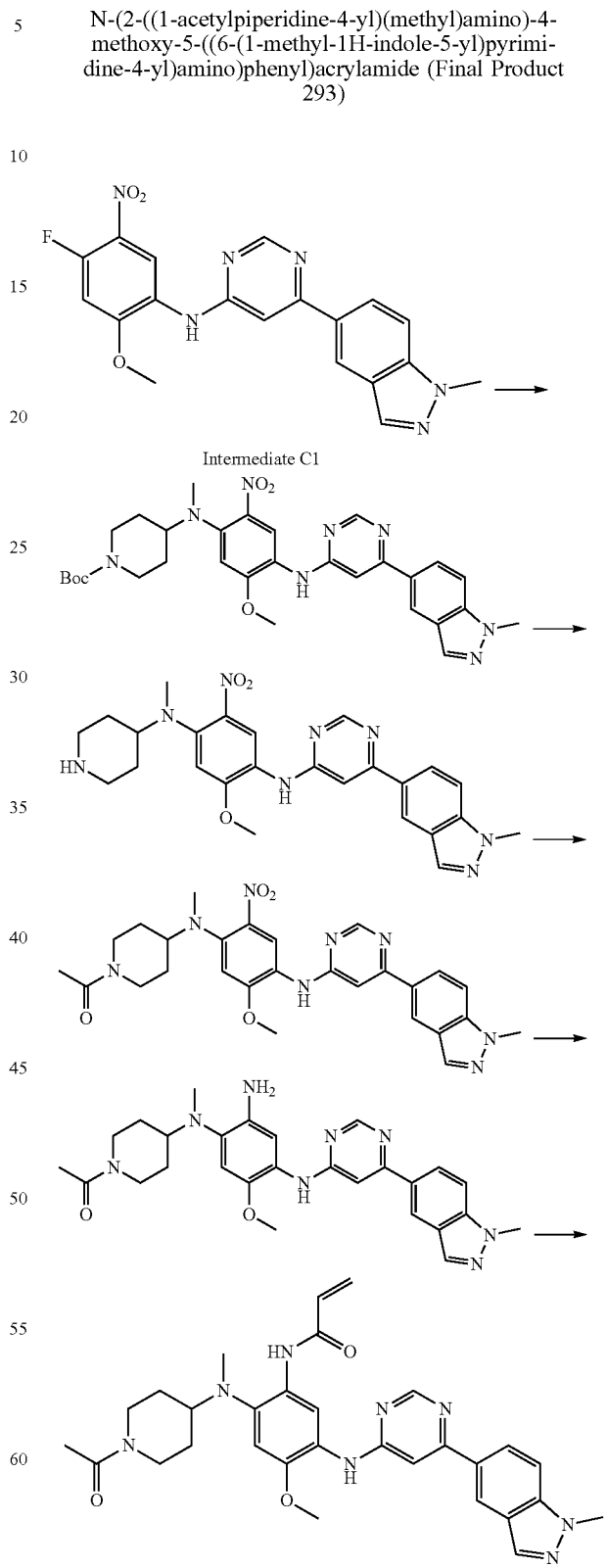

Final Product 293

Step 1: tert-butyl ((5-methoxy-4-((6-(1-methyl-1H-indole-5-yl) pyrimidine-4-yl)amino-2-nitrophenyl) (methyl)amino)piperidine-1-carboxylate

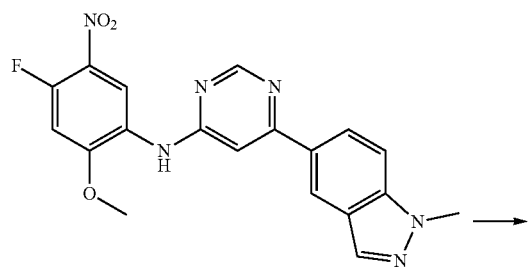

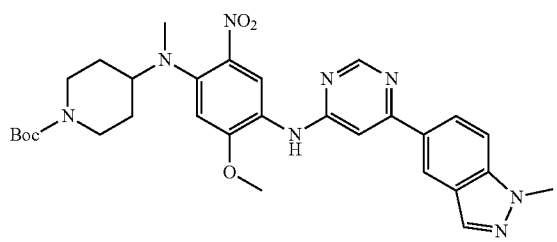

Intermediate C1 (300 mg, 0.76 mmol), potassium carbonate (726 mg, 9 eq), 1-tert-butyloxycarbonyl-4-methyanimopiperidine (489 mg, 3 eq), potassium iodide (758 mg, 6 eq) and DMF (20 mL) were added to a 100 mL three-necked bottle, the mixture was heated to 50-60° C. in an oil bath and reacted with stirring for 3 days, then cooled to room temperature, water (20 mL) and DCM (20 mL) were added separation, then separated organic phase, the aqueous phase was extracted with DCM (30 mL×4) for four times, the organic phases were combined, washed by saturated brine (30 mL×3) for three times, dried with anhydrous sodium sulfate for 30 min, and filtered, the filtrate was concentrated under reduced pressure to give a crude product, the crude product was purified by column chromatography with DCM/MeOH=50/1 as eluent, the product was collected and concentrated under reduced pressure to give a 340 mg of red solid.

Step 2: 2-methoxy-N4-methyl-N1-(6-(1-methyl-1H-indole-5-yl)pyrimidine-4-yl)-5-nitro-N4-(piperidine-4-yl)-phenyl-1,4-diamine

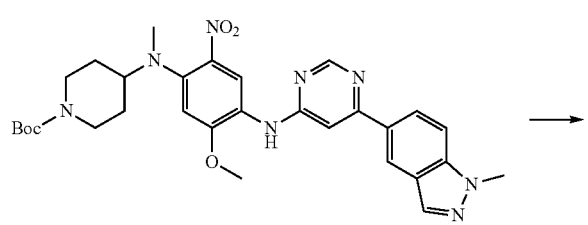

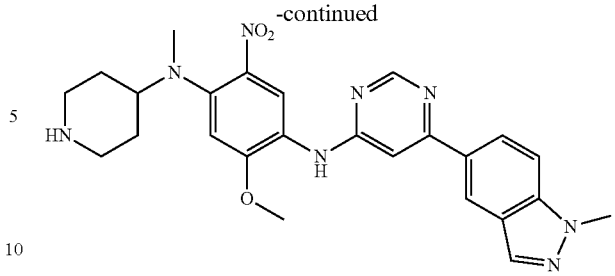

Tert-butyl ((5-methoxy-4-((6-(1-methyl-1H-indole-5-yl) pyrimidine-4-yl)amino-2-nitrophenyl) (methyl)amino)piperidine-1-carboxylate (340 mg, 0.6 mmol) and DCM (5 mL) were added to a 100 mL single-necked bottle, after the materials dissolved with stirring, trifluoroacetic acid (4 mL) was added dropwise thereinto, after the addition completed, the mixture was react with stirring at room temperature. TLC was used to monitor the reaction, when the reaction completed, the reaction mixture was concentrated, adjust with saturated sodium bicarbonate solution to have pH=9, then the mixture was extracted with DCM (30 mL×3) for three times, the organic phases were combined, dried with anhydrous sodium sulfate for 30 min, and filtered under reduced pressure, the filtrate was concentrated under reduced pressure to give a crude product, the crude product was purified by column chromatography with DCM/MeOH=10/1 as eluent, the product was collected and concentrated under reduced pressure to give 120 mg.

Step 3: 1-(4-((5-methoxy-4-((6-(1-methyl-1H-indole-5-yl)pyrimidine-4-yl)amino-2-nitrophenyl) (methyl)amino)piperidine-1-yl)ethanone

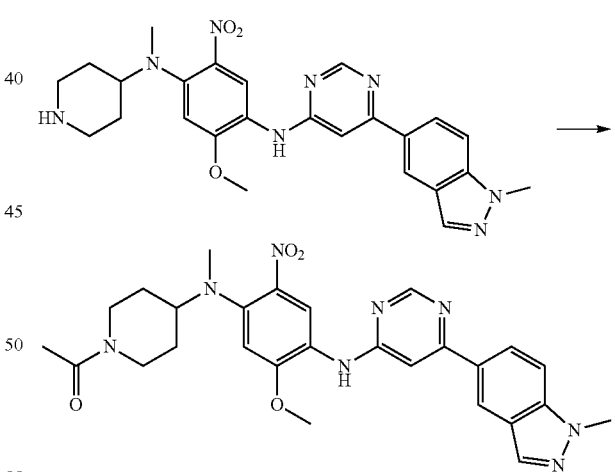

2-methoxy-N4-methyl-N1-(6-(1-methyl-1H-indole-5-yl) pyrimidine-4-yl)-5-nitro-N4-(piperidine-4-yl)-phenyl-1,4-diamine (120 mg, 0.25 mmol), triethylamine (50 mg, 2 eq) and DCM (15 mL) were added to a 100 mL three-necked bottle, the mixture were stirred to dissolve. The mixture was cooled to 0-5° C., acetic anhydride (30 mg, 1.2 eq) was added dropwise to the reaction mixture, after the addition completed, the mixture was warmed to room temperature and stirred. TLC was used to monitor the reaction, when the reaction completed, water (20 mL) and ethyl acetate (30 mL) were added separation, then separated the organic phase, the aqueous phase was extracted with ethyl acetate (30 mL×3) for three times, the organic phases were combined, washed with saturated brine (30 mL×2) twice, dried with anhydrous sodium sulfate for 30 min, and filtered, the filtrate was concentrated under reduced pressure to give a 100 mg of crude product.

Steps 4-5: N-(2-((1-acetylpiperidine-4-yl)(methyl) amino)-4-methoxy-5-((6-(1-methyl-1H-indole-5-yl) pyrimidine-4-yl)amino)phenyl)acrylamide



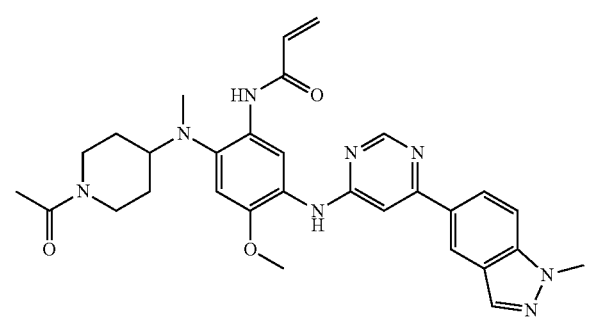

Final Product 293 was prepared by the method of the steps 2-3 of EXAMPLE 167 except that 1-(4-((5-methoxy-4-((6-(1-methyl-1H-indole-5-yl)pyrimidine-4-yl)amino-2-nitrophenyl)(methyl)amino)piperidine-1-yl)ethanone was used as the starting material.

MS (ESI$^+$) m/z=555.30 [M+H]$^+$. $^1$H NMR (400 MHz, DMSO-d$_6$) δ 9.14 (s, 1H), 8.75 (s, 1H), 8.61 (s, 1H), 8.55 (s, 1H), 8.50 (s, 1H), 8.18 (s, 1H), 8.09 (dd, J=8.8, 1.2 Hz, 1H), 7.77 (d, J=9.2 Hz, 1H), 7.43 (s, 1H), 6.95 (s, 1H), 6.61-6.68 (m, 1H), 6.26 (dd, J=16.8, 1.2 Hz, 1H), 5.74 (d, J=11.6 Hz, 1H), 4.38 (d, J=12.8 Hz, 1H), 4.09 (s, 3H), 3.85 (s, 3H), 3.79-3.84 (m, 1H), 2.92-2.97 (m, 2H), 2.63 (s, 2H), 2.44-2.48 (m, 2H), 1.98 (s, 3H), 1.74-1.78 (m, 2H), 1.37-1.50 (m, 2H).

EXAMPLE 443

Preparation of Final Product 294

N-(2-(4-metheylpiperazine-1-yl)methyl)-4-methoxy-5-{[6-(1-methyl-1H-indole-5-yl)pyrimidine-4-yl] amino}phenyl)acrylamide (Final Product 294)

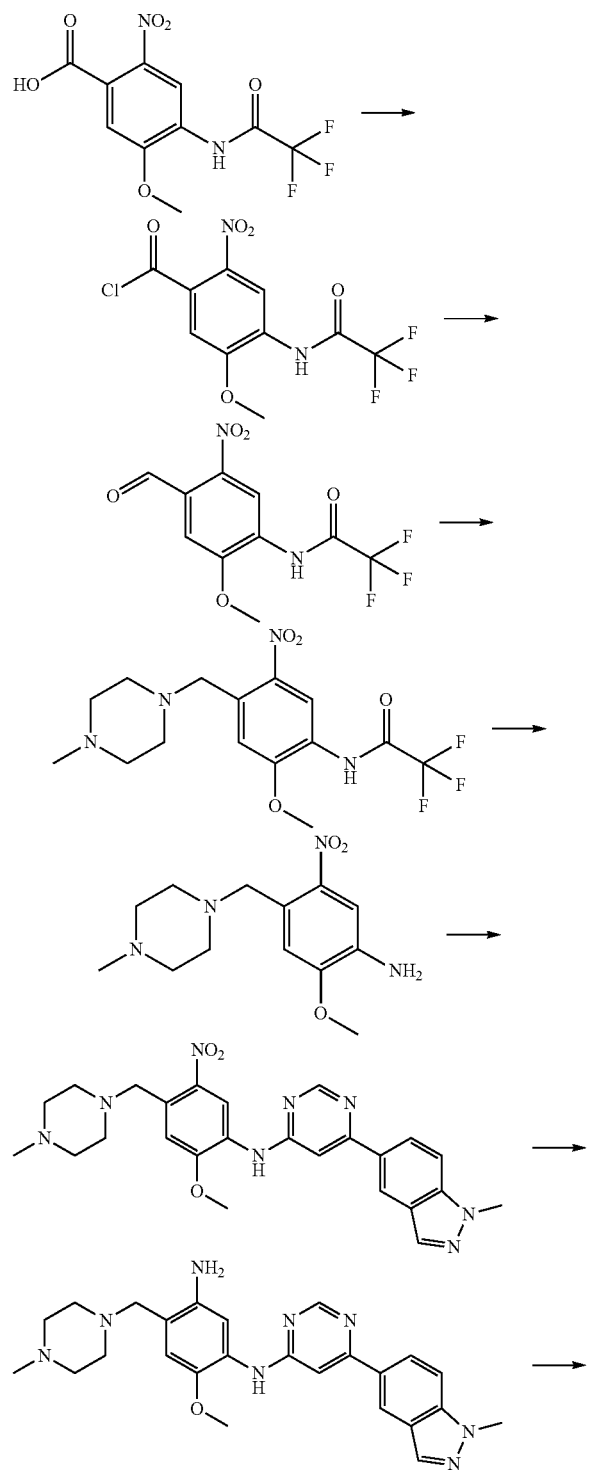

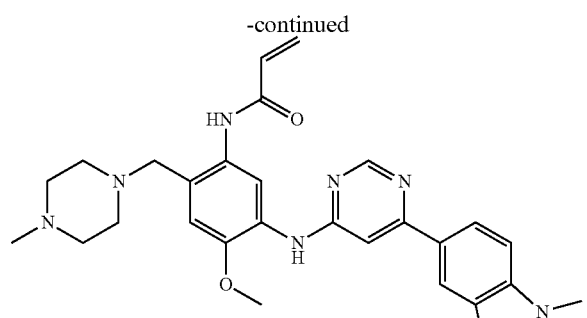

Final Product 294

Step 1: 2,2,2-trifluoro-N-(4-formyl-2-methoxy-5-nitrophenyl)acetamide

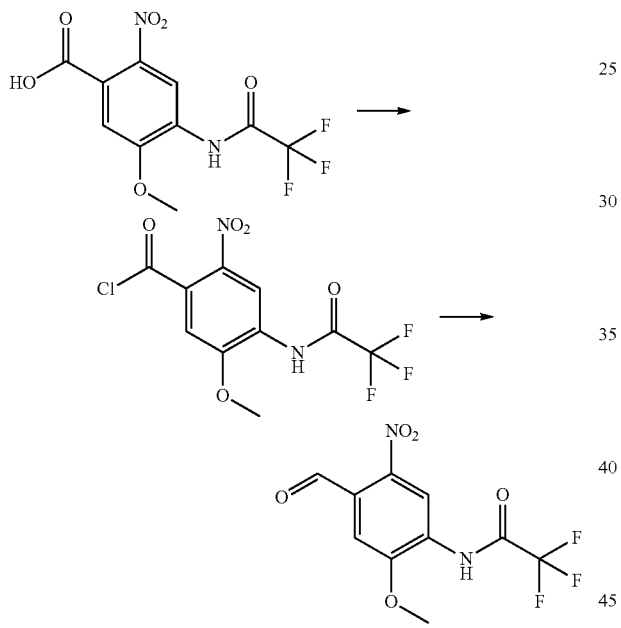

5-methoxy-2-nitro-4-(2,2,2-trifluoroacetamido)benzoic acid (1 g, 3.24 mmol), DCM (10 mL) and 2 drops of DMF were added to a 100 mL three-necked bottle under the protection of argon, acyl chloride (824 mg, 2 eq) in DCM (1 mL) was added dropwise thereinto with stirring at room temperature, the mixture was stirred at the same temperature for 1 h until the reaction mixture became clear. The reaction mixture was transferred to a 100 mL single-necked bottle and concentrated under reduced pressure till one third left, 20 mL toluene was added thereinto, concentrated under reduced pressure at room temperature. The residue was transferred to the previous 100 mL three-necked bottle under the protection of argon, cooled to 0-5° C., tetratriphenylphosphine (374 mg) was added thereinto, then tributyltin hydride (1400 mg) was added thereinto dropwise slowly for about 30 min, after the addition completed, the mixture was reacted at 0-5° C. with stirring for 2 h, then warmed to room temperature to react overnight. After the reaction completed, the reaction mixture was concentrated under reduced pressure, the residue was purified by column chromatography with PE/EA=5/1 as eluent, the product was collected and concentrated under reduced pressure to give 446 mg with a yield of 47%.

Step 2: 2-methoxy-4-((4-methylpiperazine-1-yl)methyl)-5-nitroaniline

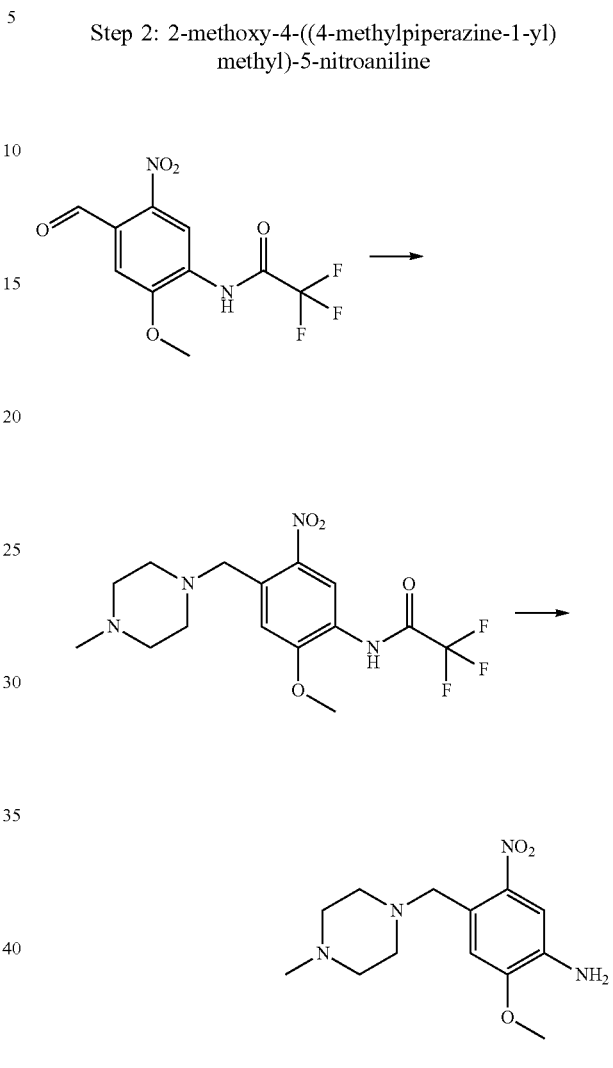

2,2,2-trifluoro-N-(4-formyl-2-methoxy-5-nitrophenyl)acetamide (100 mg, 0.34 mmol), methanol (5 mL), 1-2 drops of acetic acid and N-methylpiperazine (34 mg, 0.34 mmol) were added to a 100 mL three-necked bottle in order. The mixture was stirred at room temperature, sodium cyanoborohydride (64 mg, 1.0 mmol) was added thereinto in batches for about 10 min, after the addition completed, the mixture was stirred at room temperature for about 6-7 h. When the reaction completed, 1 N aqueous sodium hydroxide was added and stirred at room temperature, TLC was used to monitor the reaction, when the reaction completed, 20 mL water (20 mL) and ethyl acetate (20 mL) were added thereinto, stirred for 5 min, separated organic phase, the aqueous phase was extracted with ethyl acetate (20 mL×2) twice, the organic phases were combined, washed with saturated brine twice, dried with anhydrous sodium sulfate for 30 min, concentrated under reduced pressure to give a crude product, the crude product was purified by column chromatography with gradient eluent of DCM/MeOH=50/1-10/1, the product was collected and concentrated under reduced pressure to give a 30 mg.

Step 3: N-(2-methoxy-4-((4-methylpiperazine-1-yl)-5-nitrophenyl)-6-(1-methyl-1H-indole-5-yl)pyrimidine-4-amine

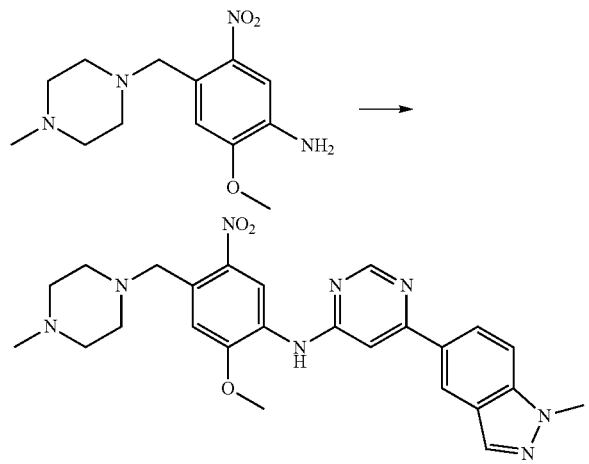

The compound was prepared by the method of EXAMPLE 150 except that 2-methoxy-4-((4-methylpiperazine-1-yl)methyl)-5-nitroaniline and intermediate A1 were used as the starting materials.

Steps 4-5: N-(2-(4-metheylpiperazine-1-yl)methyl)-4-methoxy-5-{[6-(1-methyl-1H-indole-5-yl)pyrimidine-4-yl]amino}phenyl)acrylamide

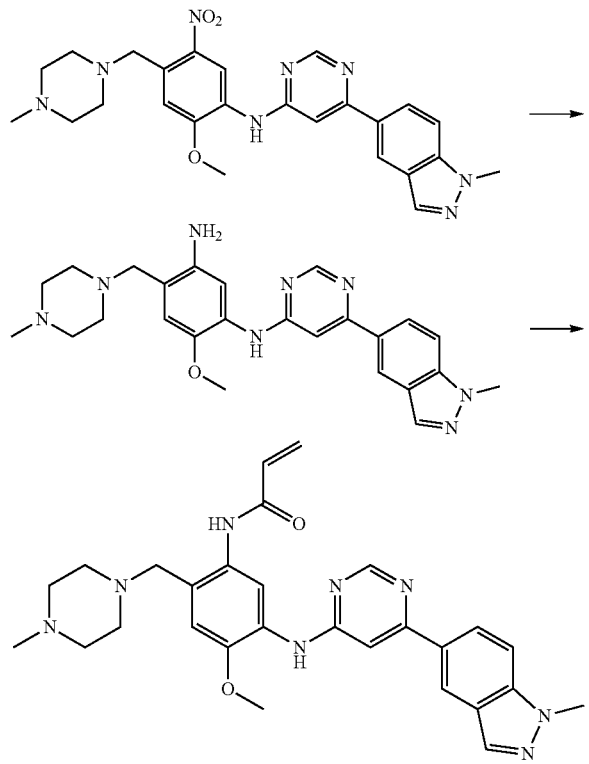

Final Product 294

The compound was prepared by the method of the steps 2-3 of EXAMPLE 167 except that N-(2-methoxy-4-((4-methylpiperazine-1-yl)methyl)-5-nitrophenyl)-6-(1-methyl-1H-indole-5-yl)pyrimidine-4-amine was used as the starting material.

MS (ESI⁺) m/z=513.16 [M+H]⁻. ¹H NMR (500 MHz, DMSO-d₆) δ 10.62 (s, H), =0.5 Hz, 1H), 8.08 (dd, J=1.5, 9.0 Hz, 1H), 7.76 (d, J=9.0 Hz, 1H), 7.48 (s, 1H), 7.01 (s, 1H), 6.30-6.36 (m, 1H), 6.23 (dd, J=2.0, 17.0 1H), 5.79 (dd, J=1.5, 10.0 Hz, 1H), 4.09 (s, 3H), 3.84 (s, 3H), 3.59 (s, 2H), 2.30-2.50 (m, 8H), 2.19 (s, 3H).

EXAMPLE 444

Preparation of Final Product 295

(E)-4-(dimethylamino)-N-(2-acetyl-4-methoxy-5-nitrophenyl)-6-(1-methyl-H-indol-5-yl)pyrimidine-4-yl)amino)phenyl)but-2-enamide (Final Product 295)

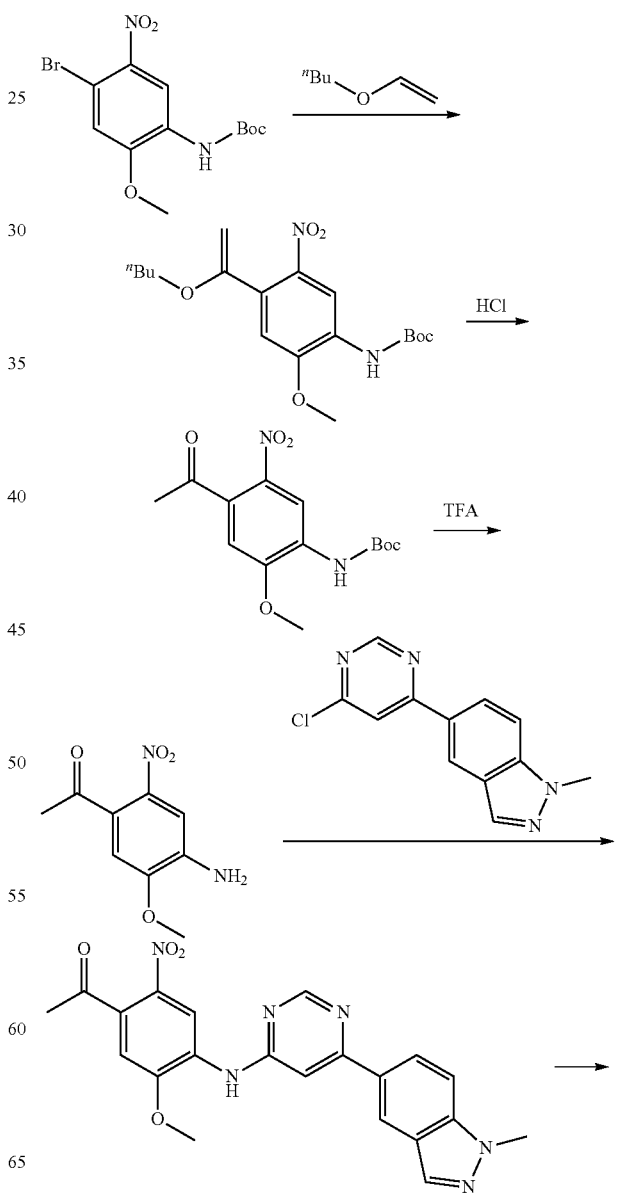

-continued

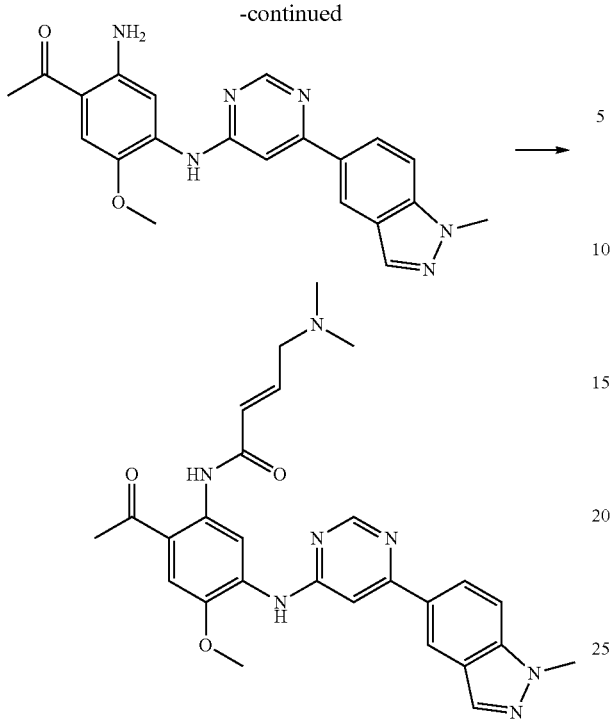

Final Product 295

Step 1: tert-butyl (4-(1-butoxyvinyl)-2-methoxy-5-nitrophenyl)carbamate

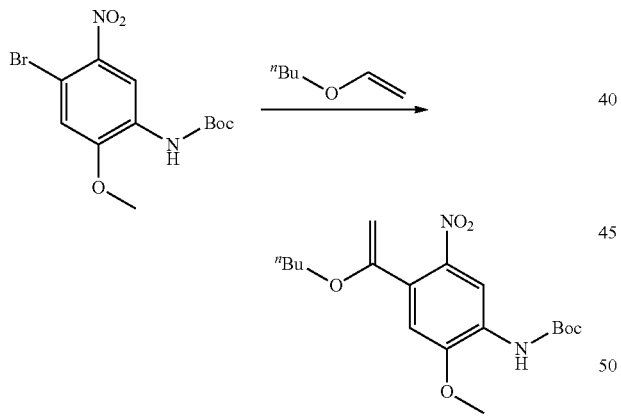

Tert-butyl (4-bromo-2-methoxy-5-nitrophenyl)carbamate (1.4 g, 4.04 mmol), 1-(ethenyloxy) butane (4.04 g, 40.4 mmol), trimethylamine (531.2 mg, 5.26 mmol), n-butanol (60 mL) and Pd(PPh$_3$)$_4$ (468 mg, 0.404 mmol) were added to a 100 mL single-necked bottle in order under the protection of argon. The mixture was heated to 110° C. to react for 12 h, and cooled to room temperature and water (50 mL) was added, the reaction mixture was extracted with ethyl acetate (50 mL×3) for three times, the organic phases were combined and concentrated to give a crude product. The crude product was purified by column chromatography with PE/EA=100/1 as eluent, the product was collected and concentrated under reduced pressure to give a 1.4 g of pale yellow oil with a yield of 94.6%.

Step 2: tert-butyl (4-acetyl-2-methoxy-5-nitrophenyl)carbamate

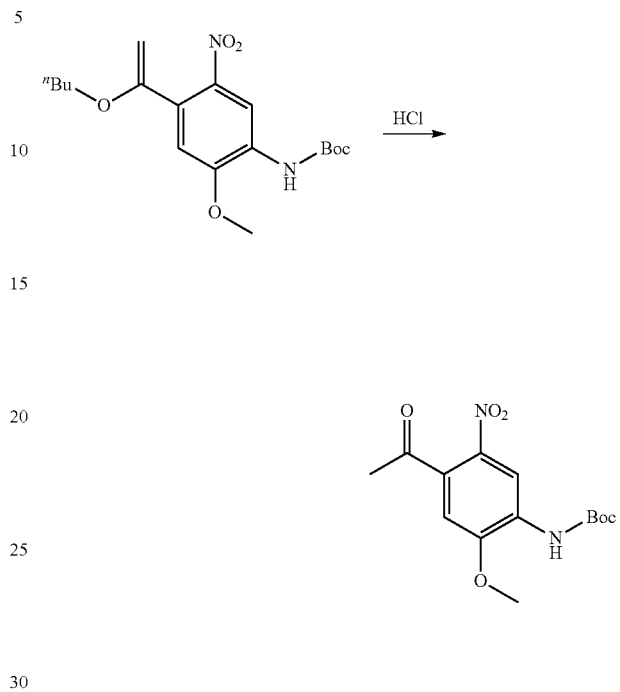

Tert-butyl (4-(1-butoxyvinyl)-2-methoxy-5-nitrophenyl) carbamate (1.4 g, 3.8 mmol), tetrahydrofuran (30 mL) and 3N HCl (12 mL) were sequentially added to a 100 mL single-necked bottle, the mixture was stirred at room temperature to react for 1 h. After the starting materials were reacted completely, saturated sodium carbonate was added to adjust the pH to >7, extracted with ethyl acetate (50 mL×3) for three times, the organic phases were combined and concentrated to give 1.0 g of pale yellow oil with a yield of 84.7%.

Step 3: 1-(4-amino-5-methoxy-2-nitrophenyl)ethan-1-one

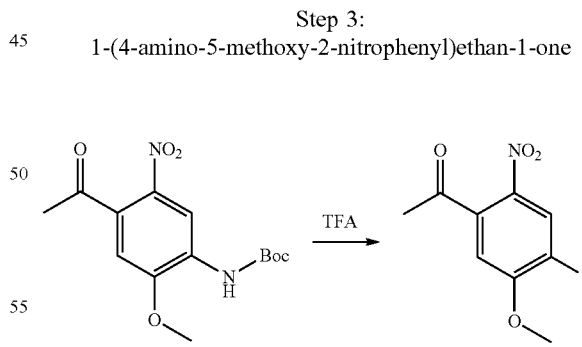

Tert-butyl (4-acetyl-2-methoxy-5-nitrophenyl)carbamate (1.0 g, 3.22 mmol), dichloromethane (20 mL) and trifluoroacetic acid (8 mL) were added to a 100 mL single-necked bottle in order. The mixture was reacted at room temperature for 1 h, then 60 mL saturated sodium carbonate was added to adjust the pH to >7, the aqueous phase was extracted with dichloromethane (50 mL×2) twice, the organic phases were combined and concentrated to give 520 mg pale yellow oil with a yield of 76.8%.

Step 4: 1-(5-methoxy-4-((6-(1-methyl-1H-indole-5-yl)pyrimidine-4-yl)amino)-2-nitrophenyl)ethan-1-one

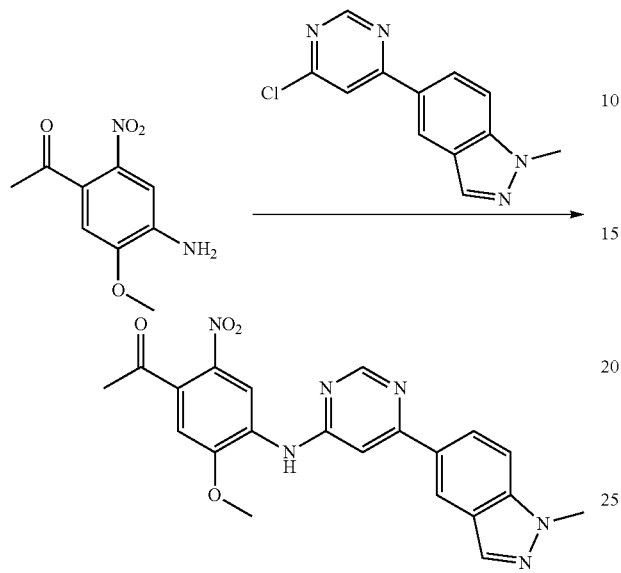

The compound was prepared by the method of EXAMPLE 150 except that 1-(4-amino-5-methoxy-2-nitrophenyl)ethan-1-one (162 mg, 0.771 mmol) and intermediate A1 were used as the starting materials and DME was used as the solvent.

Step 5: 1-(2-amino-5-methoxy-4-((6-(1-methyl-1H-indole-5-yl)pyrimidine-4-yl) amino)phenyl)ethan-1-one

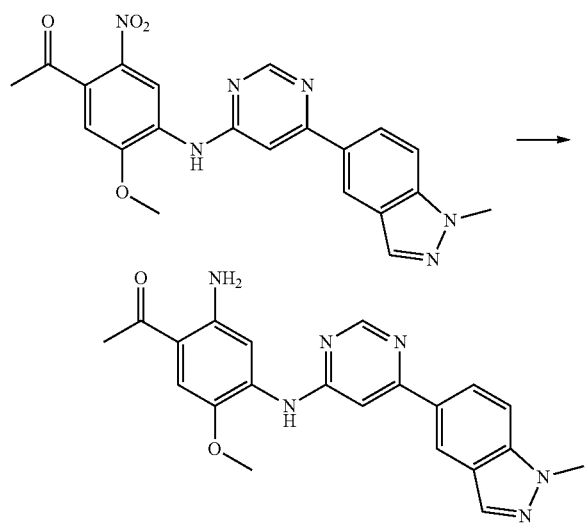

1-(5-methoxy-4-((6-(1-methyl-1H-indole-5-yl)pyrimidine-4-yl)amino)-2-nitrophenyl) ethan-1-one (100 mg, 0.24 mmol), tetrahydrofuran/dichloromethane=1/1 (20 mL) and Pd/C (10 mg) were added to a 100 mL single-necked bottle in order. The mixture was stirred under the pressure of hydrogen at room temperature for 10 h. Then the reaction mixture was filtered, the filtrate was concentrated under reduced pressure to give a 70 mg of pale yellow solid with a yield of 75.4%.

Step 6: (E)-4-(dimethylamino)-N-(2-acetyl-4-methoxy-5-((6-(1-methyl-1H-indol-5-yl)pyrimidine-4-yl)amino)phenyl)but-2-enamide

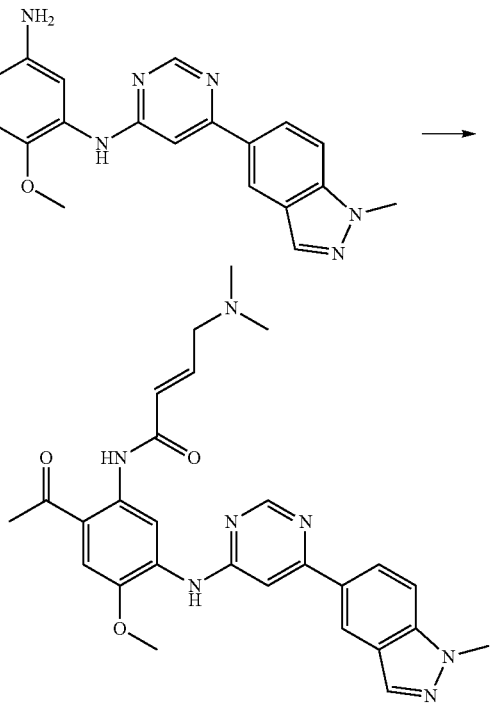

Final Product 295

Trans-4-dimethylaminocrotonic acid hydrochloride (220 mg, 1.70 mmol), acetonitrile (3 mL) and one drop of DMF were added to a 100 mL single-necked bottle in order, and then acyl chloride (600 mg, 4.76 mmol) was added dropwise at room temperature, after the addition completed, the mixture was heated to 45° C. to react for 0.5-1 h, after the materials were reacted completely, the mixture was concentrated under reduced pressure to give 200 mg black oil.

1-(2-amino-5-methoxy-4-((6-(1-methyl-1H-indole-5-yl)pyrimidine-4-yl)amino)phenyl)ethan-1-one (70 mg, 0.18 mmol) and dichloromethane (10 mL) were added to a 100 mL single-necked bottle in order, then the mixture was cooled to 0-5° C., (E)-4-(dimethylamino)but-2-enamide (80.7 mg, 0.549 mmol) in acetonitrile (2 mL) was added dropwise thereinto. After the addition completed, the mixture was reacted at room temperature for 30 min, then 30 mL saturated sodium bicarbonate solution was added, the aqueous phase was extracted with dichloromethane (50 mL×3) for three times, the organic phases were combined and concentrated under reduced pressure to give a crude product. The crude product was purified by preparative thin layer chromatography to give 6 mg of pale yellow solid with a yield of 7%.

MS (ESI⁺) m/z=500.12[M+H]⁺. ¹H NMR (500 MHz, DMSO-d₆) δ 11.54 (s, 1H), 9.51 (s, 1H), 9.12 (s, 1H), 8.79 (s, 1H), 8.55 (s, 1H), 8.20 (s, 1H), 8.12 (d, J=8.5 Hz, 1H), 7.85 (s, 1H), 7.79 (d, J=8.5 Hz, 1H), 7.52 (s, 1H), 6.74-6.80 (m, 1H), 6.21 (d, J=15.5 Hz, 1H), 4.10 (s, 3H), 3.99 (s, 3H), 3.10 (d, J=11.0 Hz, 2H), 2.64 (s, 3H), 2.20 (s, 6H).
EXAMPLE 445
Preparation of Final Product 296
The method of EXAMPLE 92 in CN102083800A was used for preparing the known compound (Final Product 296) disclosed by the present application (see Table 7).
TABLE 7
Compounds as EGFR Kinase Inhibitor (Final Products)
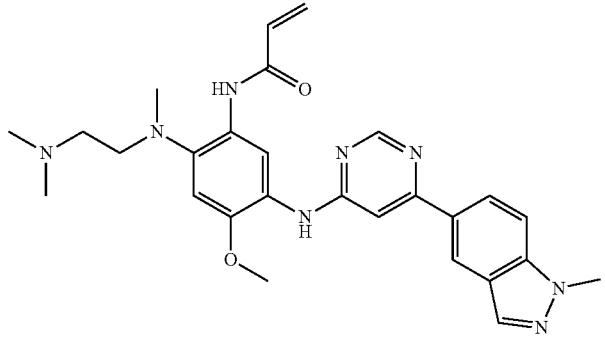
1
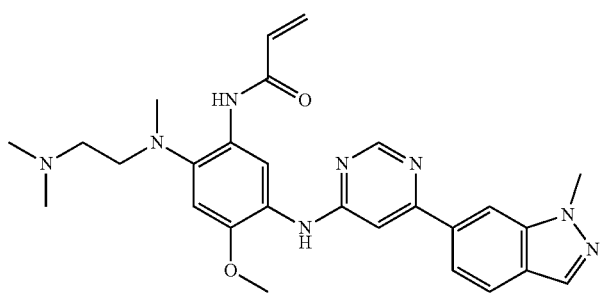 [SMILES: C=CC(=O)Nc1cc(Nc2cc(-c3ccc4cnn(C)c4c3)ncn2)c(OC)cc1N(C)CCN(C)C]
2
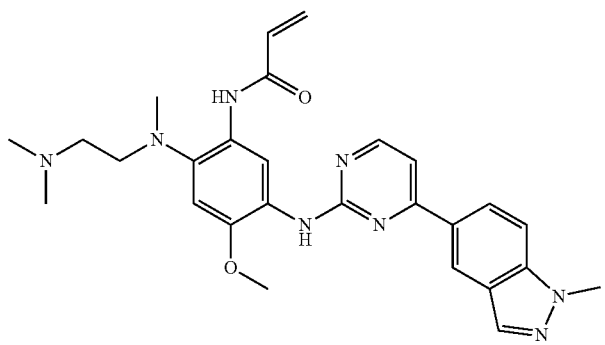
3
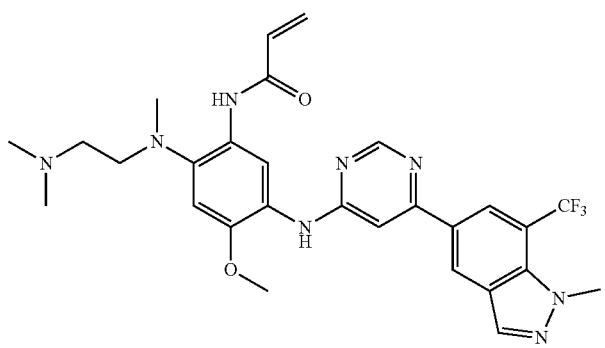
4

TABLE 7-continued
Compounds as EGFR Kinase Inhibitor (Final Products)
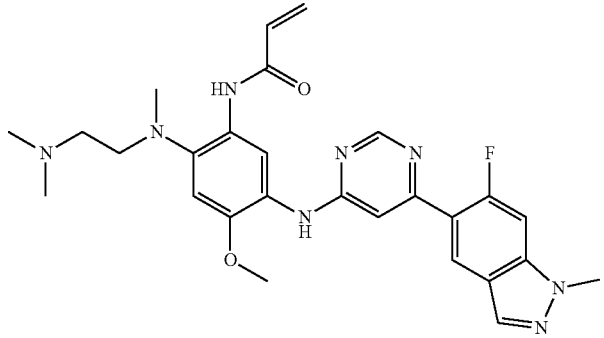
5
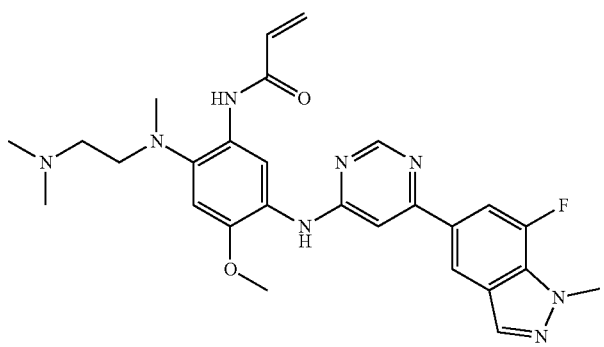
6
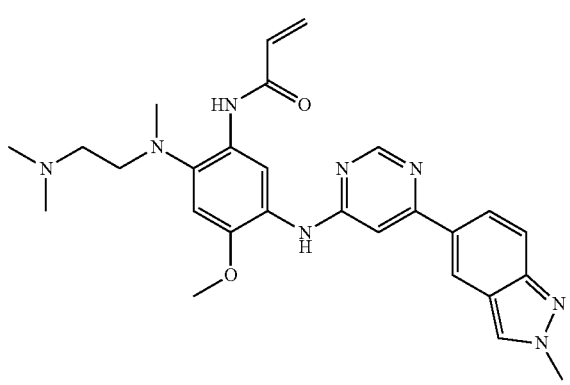
7
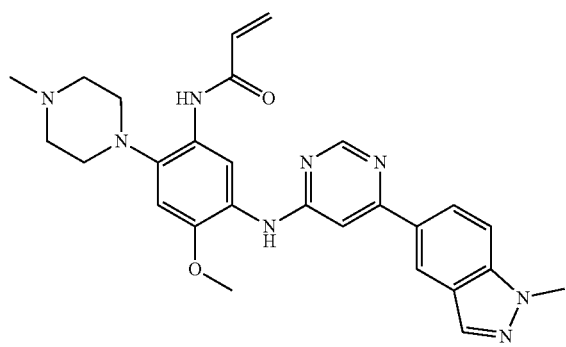
8

TABLE 7-continued
Compounds as EGFR Kinase Inhibitor (Final Products)
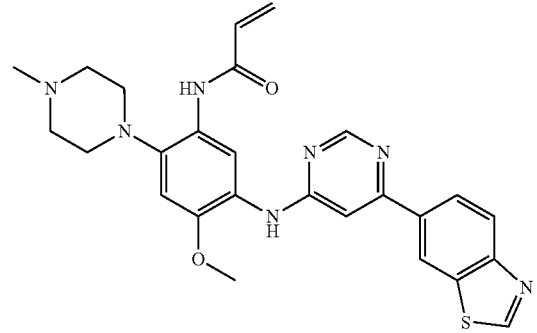 [SMILES: C=CC(=O)Nc1cc(Nc2cc(-c3ccc4ncsc4c3)ncn2)c(OC)cc1N1CCN(C)CC1]
9
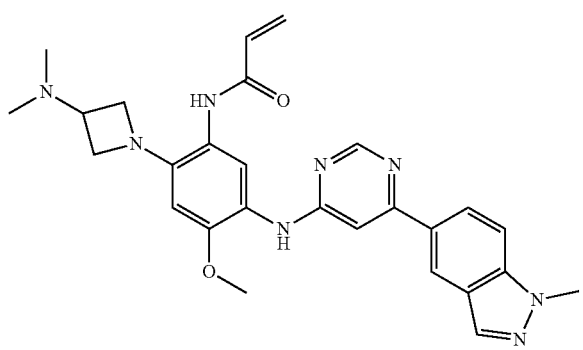
10
11
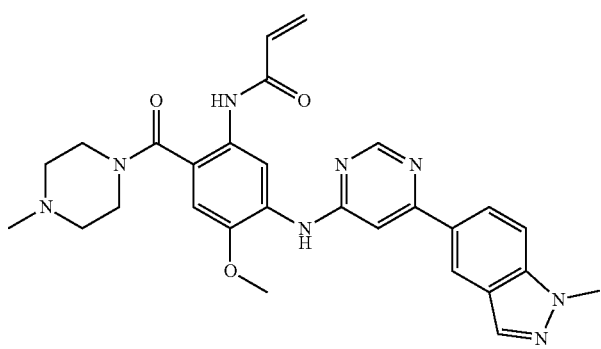
12

TABLE 7-continued
Compounds as EGFR Kinase Inhibitor (Final Products)
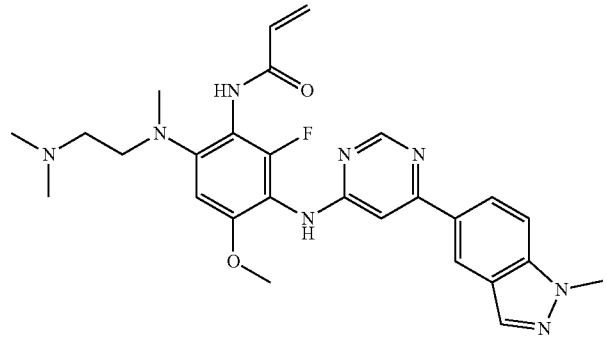
13
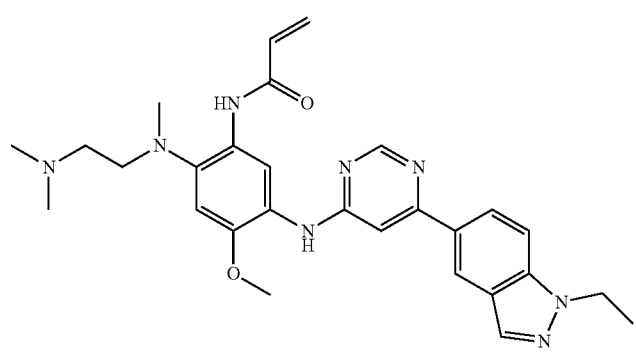 [SMILES: C=CC(=O)Nc1cc(Nc2cc(-c3ccc4c(cnn4CC)c3)ncn2)c(OC)cc1N(C)CCN(C)C]
14
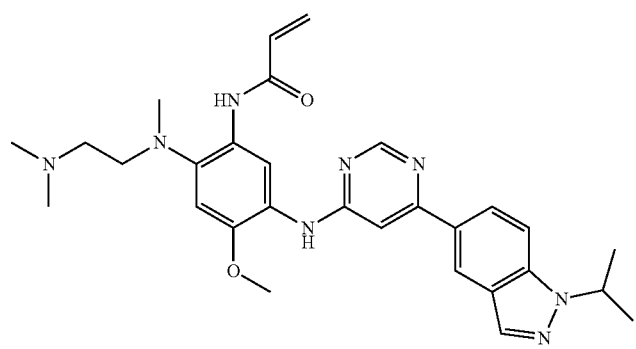 [SMILES: C=CC(=O)Nc1cc(Nc2cc(-c3ccc4c(cnn4C(C)C)c3)ncn2)c(OC)cc1N(C)CCN(C)C]
15
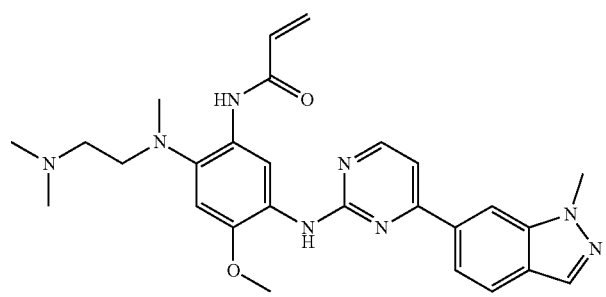 [SMILES: C=CC(=O)Nc1cc(Nc2nccc(-c3ccc4cnn(C)c4c3)n2)c(OC)cc1N(C)CCN(C)C]
16

TABLE 7-continued
Compounds as EGFR Kinase Inhibitor (Final Products)
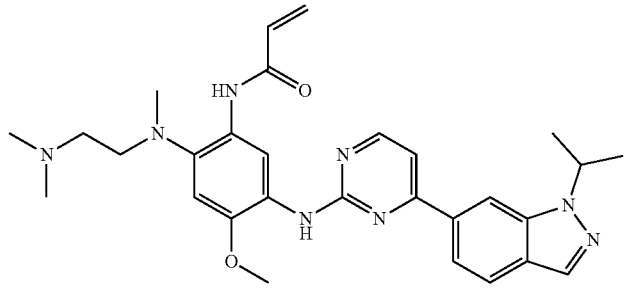 [SMILES: C=CC(=O)Nc1cc(Nc2nccc(-c3ccc4cnn(C(C)C)c4c3)n2)c(OC)cc1N(C)CCN(C)C]
17
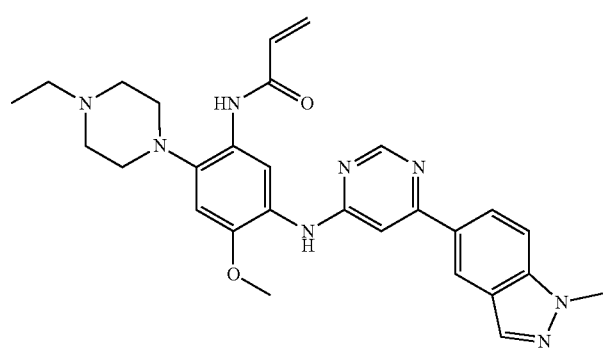 [SMILES: C=CC(=O)Nc1cc(Nc2cc(-c3ccc4c(cnn4C)c3)ncn2)c(OC)cc1N1CCN(CC)CC1]
18
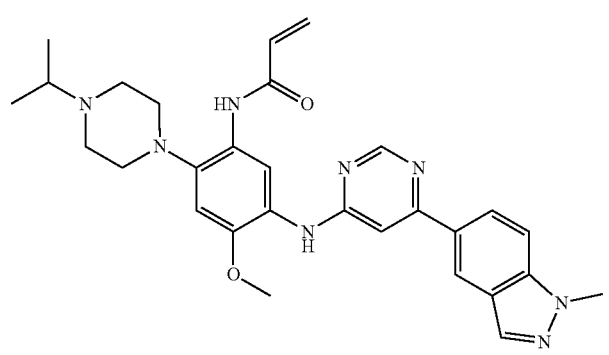 [SMILES: C=CC(=O)Nc1cc(Nc2cc(-c3ccc4c(cnn4C)c3)ncn2)c(OC)cc1N1CCN(C(C)C)CC1]
19
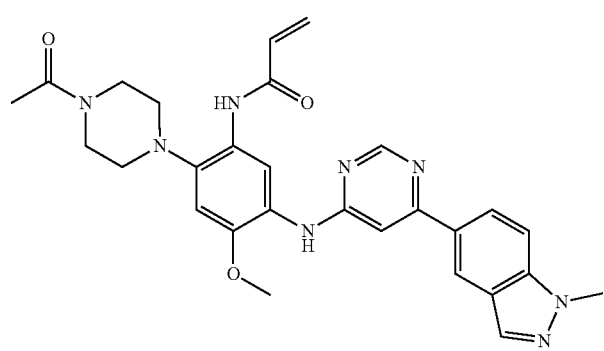 [SMILES: C=CC(=O)Nc1cc(Nc2cc(-c3ccc4c(cnn4C)c3)ncn2)c(OC)cc1N1CCN(C(C)=O)CC1]
20

TABLE 7-continued
Compounds as EGFR Kinase Inhibitor (Final Products)
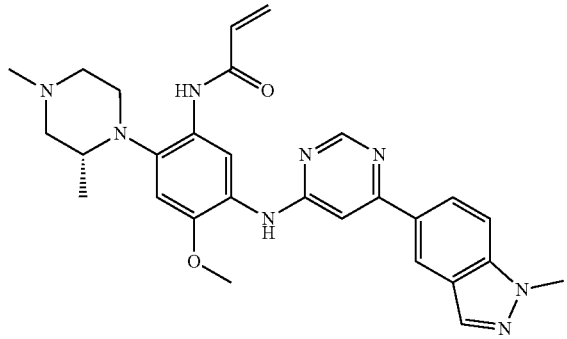
21
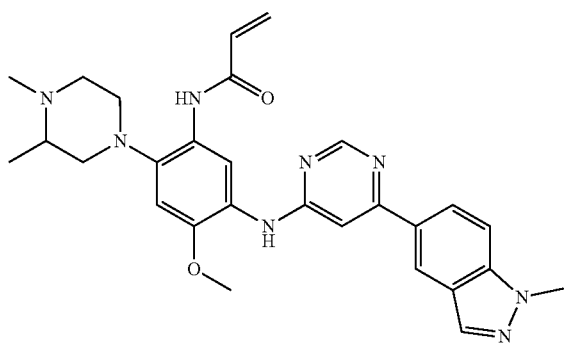
22
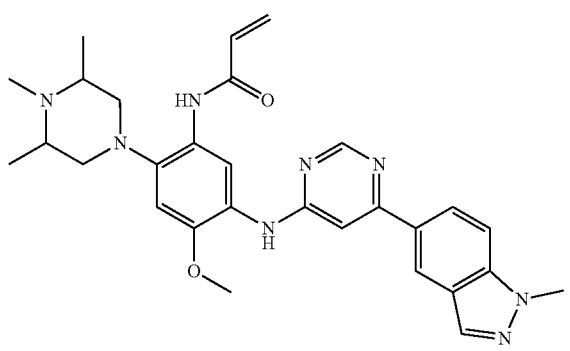
23
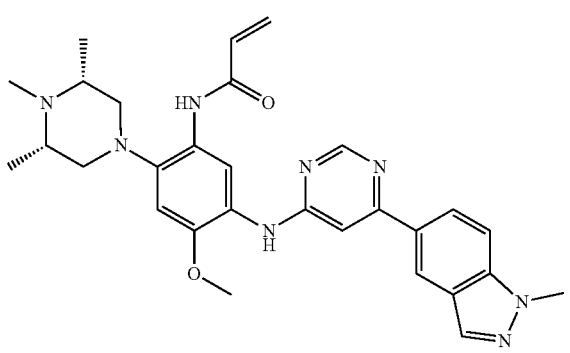
24

TABLE 7-continued
Compounds as EGFR Kinase Inhibitor (Final Products)
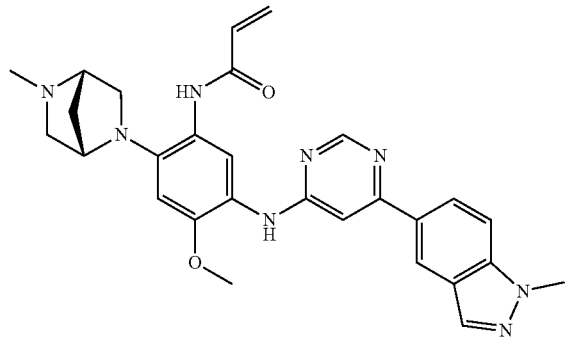
25
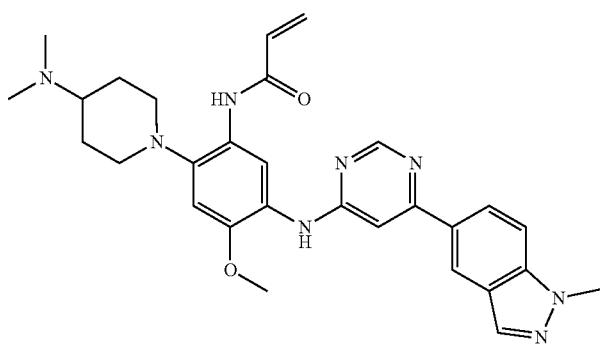
26
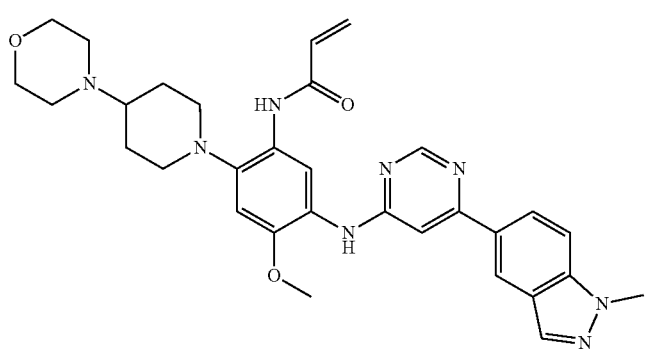 [SMILES: C=CC(=O)Nc1cc(Nc2cc(-c3ccc4c(cnn4C)c3)ncn2)c(OC)cc1N1CCC(N2CCOCC2)CC1]
27
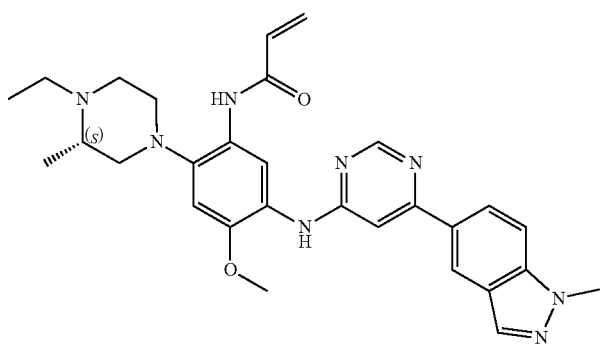
28

TABLE 7-continued
Compounds as EGFR Kinase Inhibitor (Final Products)
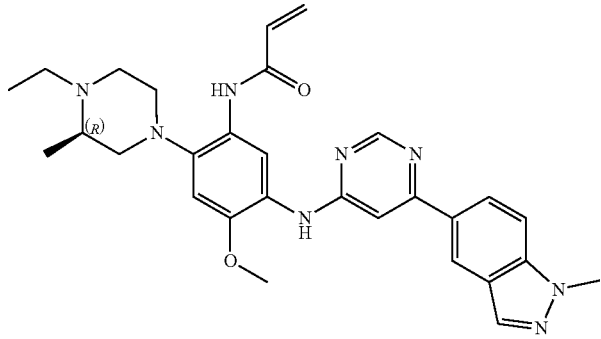
29
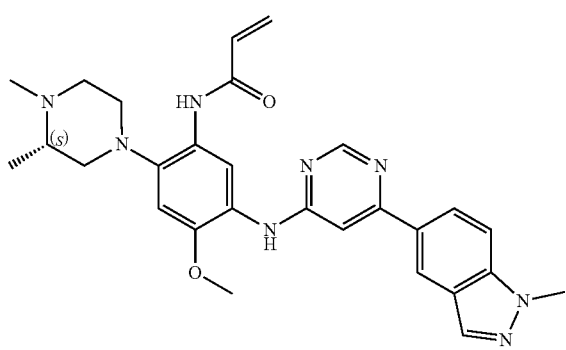
30
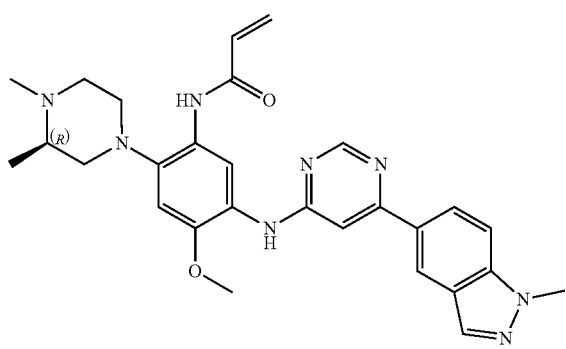
31
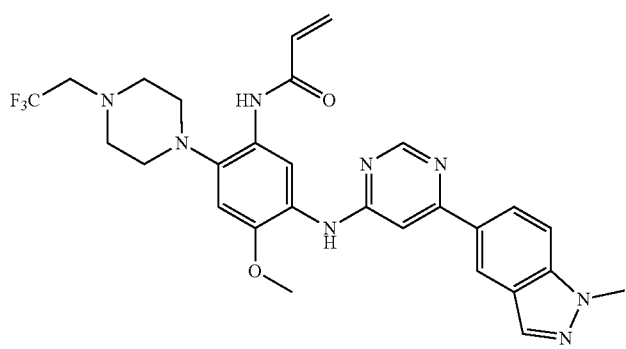 [SMILES: C=CC(=O)Nc1cc(Nc2cc(-c3ccc4c(cnn4C)c3)ncn2)c(OC)cc1N1CCN(CC(F)(F)F)CC1]
32

TABLE 7-continued
Compounds as EGFR Kinase Inhibitor (Final Products)
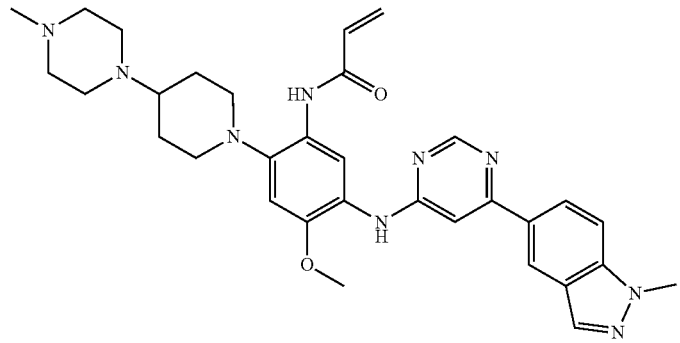
33
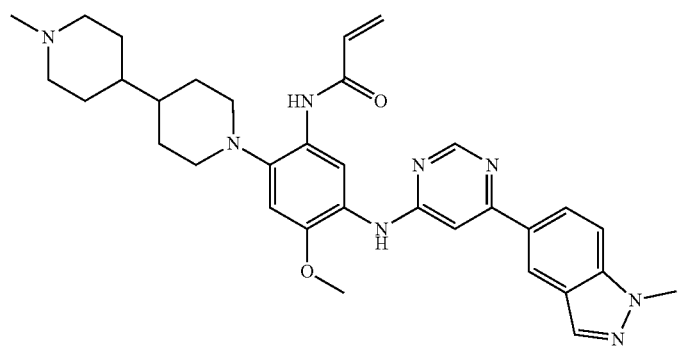
34
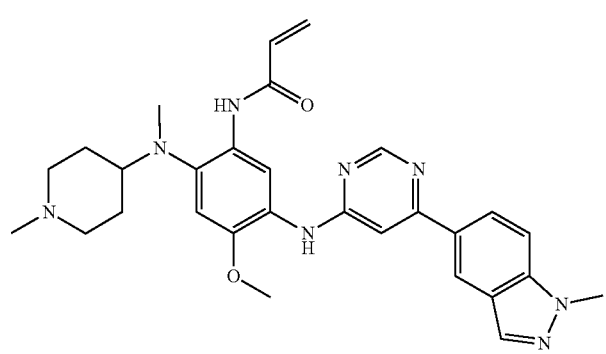
35
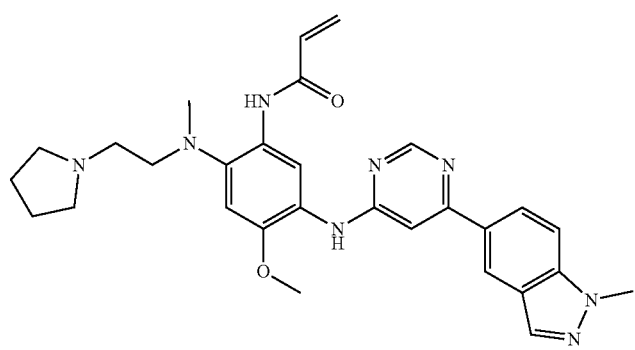 [SMILES: C=CC(=O)Nc1cc(Nc2cc(-c3ccc4c(cnn4C)c3)ncn2)c(OC)cc1N(C)CCN1CCCC1]
36

TABLE 7-continued
Compounds as EGFR Kinase Inhibitor (Final Products)
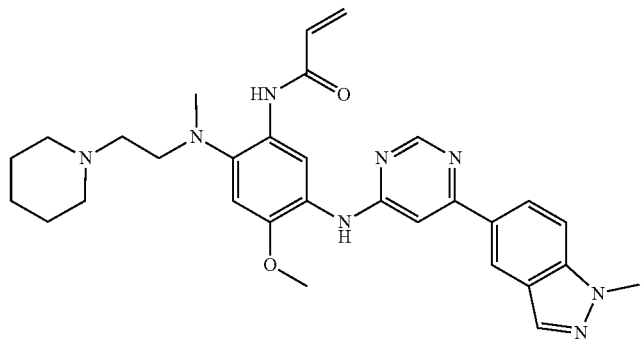 [SMILES: C=CC(=O)Nc1cc(Nc2cc(-c3ccc4c(cnn4C)c3)ncn2)c(OC)cc1N(C)CCN1CCCCC1]
37
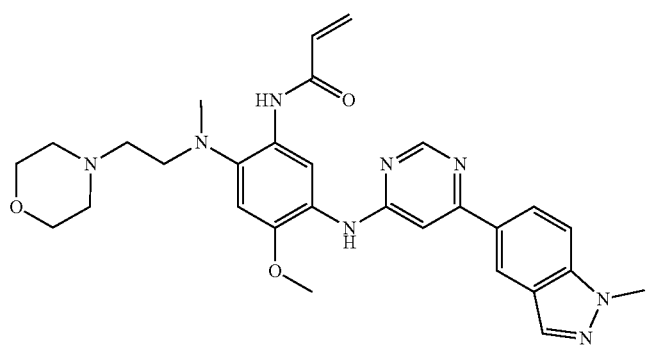 [SMILES: C=CC(=O)Nc1cc(Nc2cc(-c3ccc4c(cnn4C)c3)ncn2)c(OC)cc1N(C)CCN1CCOCC1]
38
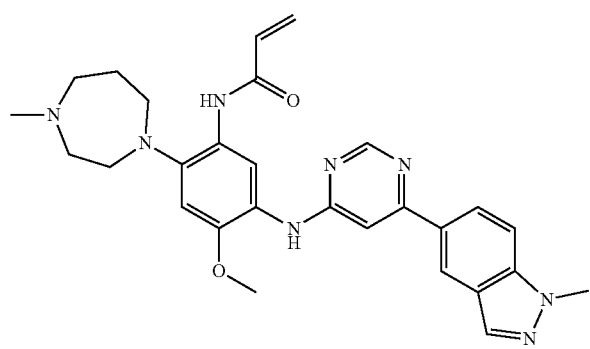
39
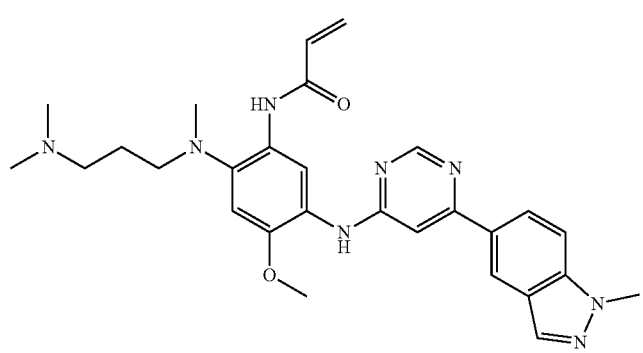
40

TABLE 7-continued
Compounds as EGFR Kinase Inhibitor (Final Products)
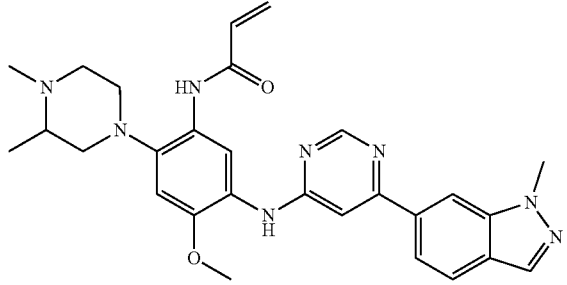 [SMILES: C=CC(=O)Nc1cc(Nc2cc(-c3ccc4cnn(C)c4c3)ncn2)c(OC)cc1N1CCN(C)C(C)C1]
41
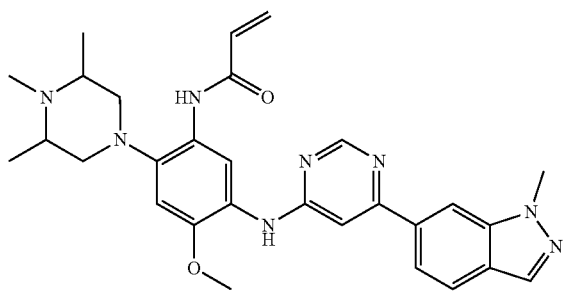
42
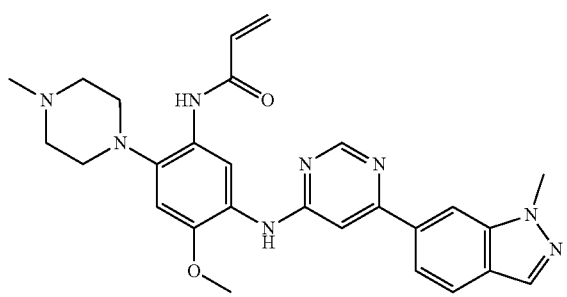 [SMILES: C=CC(=O)Nc1cc(Nc2cc(-c3ccc4cnn(C)c4c3)ncn2)c(OC)cc1N1CCN(C)CC1]
43
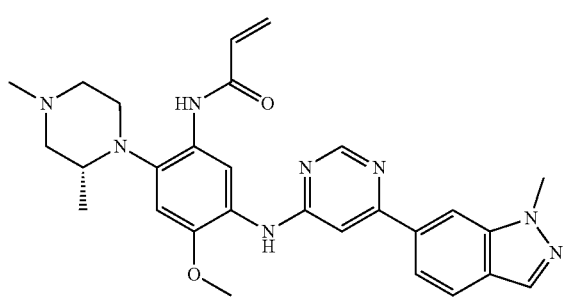 [SMILES: C=CC(=O)Nc1cc(Nc2cc(-c3ccc4cnn(C)c4c3)ncn2)c(OC)cc1N1CCN(C)C[C@H]1C]
44
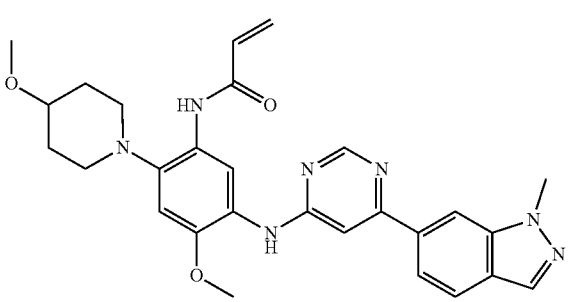 [SMILES: C=CC(=O)Nc1cc(Nc2cc(-c3ccc4cnn(C)c4c3)ncn2)c(OC)cc1N1CCC(OC)CC1]
45

TABLE 7-continued
Compounds as EGFR Kinase Inhibitor (Final Products)
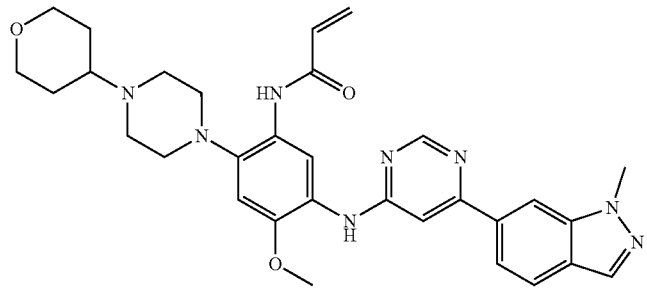
46
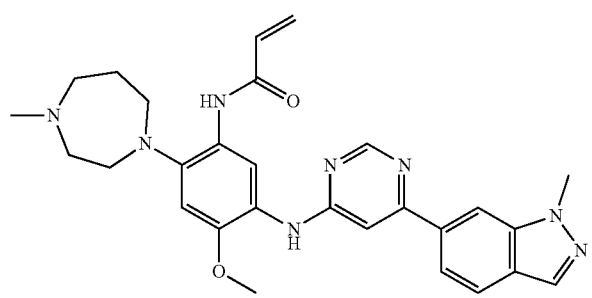 [SMILES: C=CC(=O)Nc1cc(Nc2cc(-c3ccc4cnn(C)c4c3)ncn2)c(OC)cc1N1CCCN(C)CC1]
47
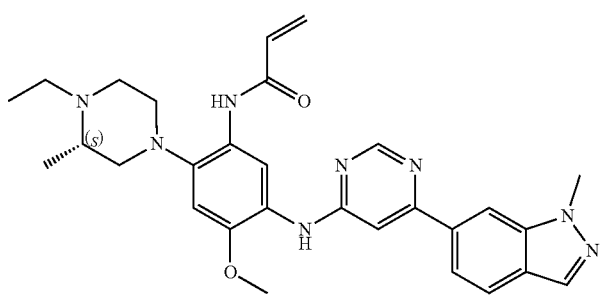
48
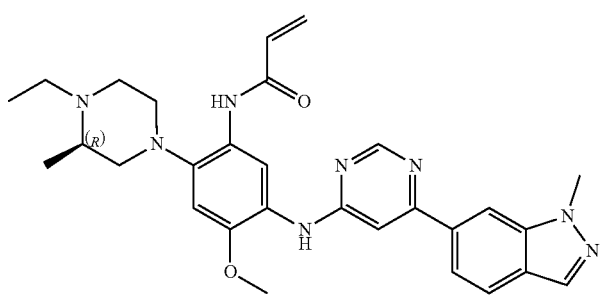
49
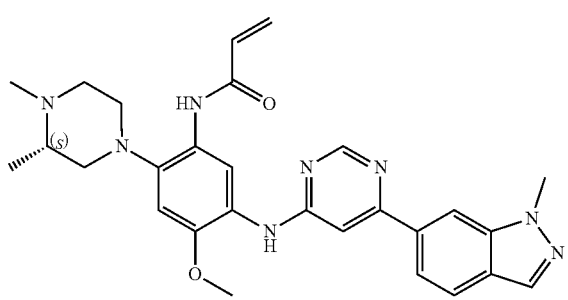
50

TABLE 7-continued
Compounds as EGFR Kinase Inhibitor (Final Products)
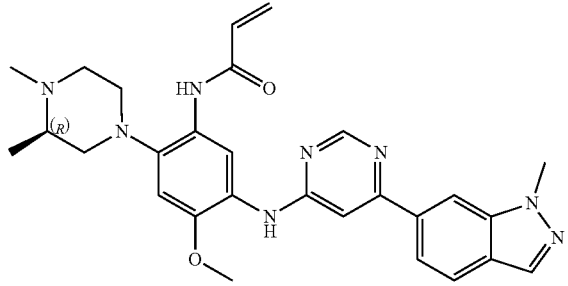
51
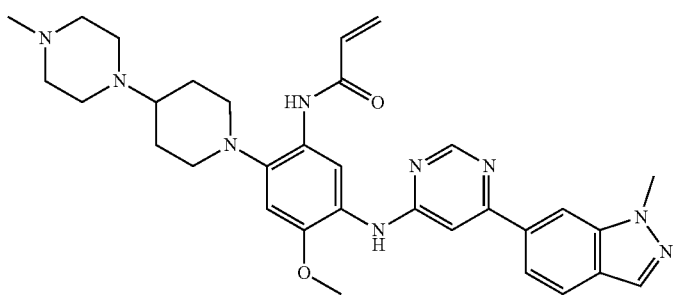 [SMILES: C=CC(=O)Nc1cc(Nc2cc(-c3ccc4cnn(C)c4c3)ncn2)c(OC)cc1N1CCC(N2CCN(C)CC2)CC1]
52
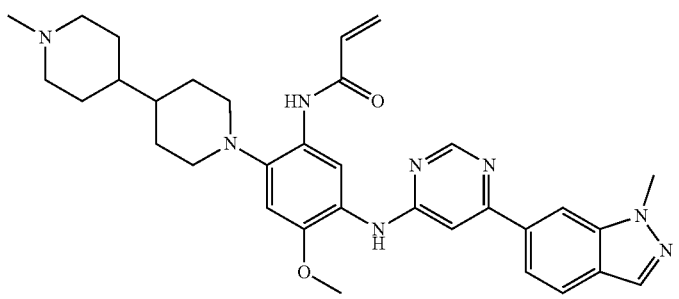 [SMILES: C=CC(=O)Nc1cc(Nc2cc(-c3ccc4cnn(C)c4c3)ncn2)c(OC)cc1N1CCC(C2CCN(C)CC2)CC1]
53
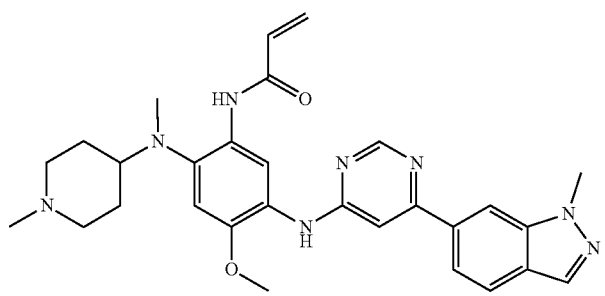 [SMILES: C=CC(=O)Nc1cc(Nc2cc(-c3ccc4cnn(C)c4c3)ncn2)c(OC)cc1N(C)C1CCN(C)CC1]
54
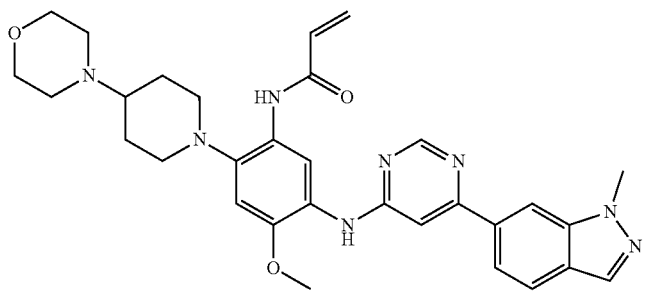 [SMILES: C=CC(=O)Nc1cc(Nc2cc(-c3ccc4cnn(C)c4c3)ncn2)c(OC)cc1N1CCC(N2CCOCC2)CC1]
55

TABLE 7-continued
Compounds as EGFR Kinase Inhibitor (Final Products)
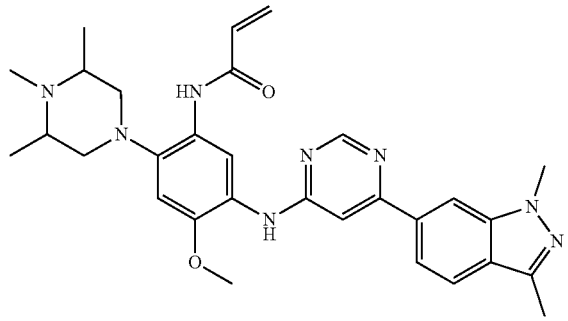 [SMILES: C=CC(=O)Nc1cc(Nc2cc(-c3ccc4c(C)nn(C)c4c3)ncn2)c(OC)cc1N1CC(C)N(C)C(C)C1]
56
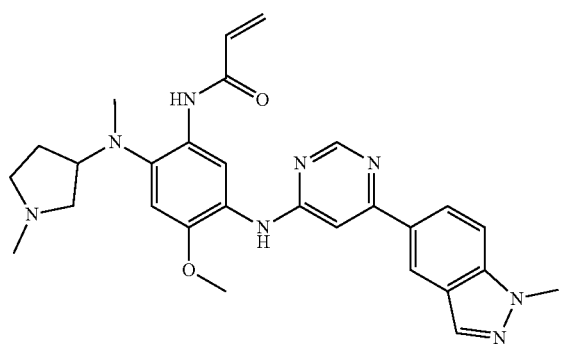 [SMILES: C=CC(=O)Nc1cc(Nc2cc(-c3ccc4c(cnn4C)c3)ncn2)c(OC)cc1N(C)C1CCN(C)C1]
57
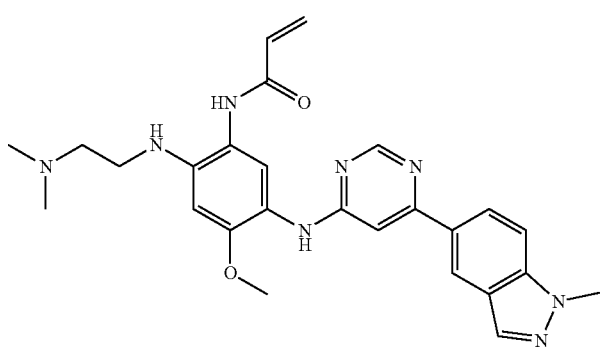
58
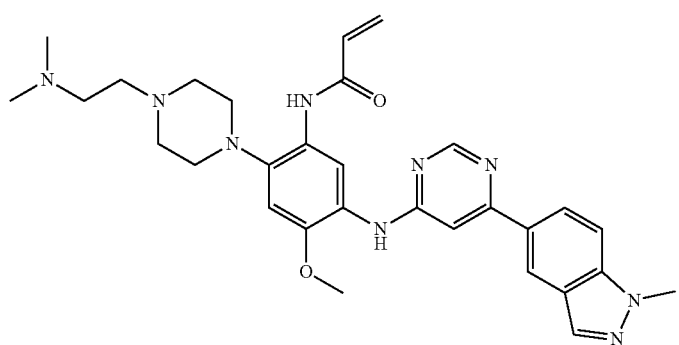
59

TABLE 7-continued
Compounds as EGFR Kinase Inhibitor (Final Products)
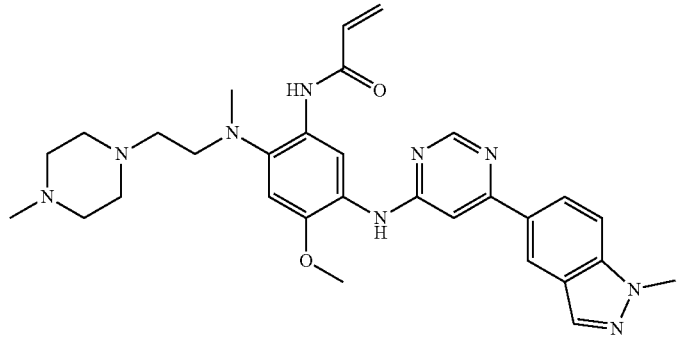
60
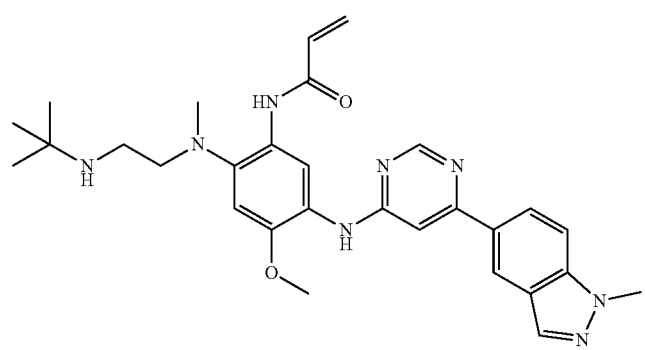 [SMILES: C=CC(=O)Nc1cc(Nc2cc(-c3ccc4c(cnn4C)c3)ncn2)c(OC)cc1N(C)CCNC(C)(C)C]
61
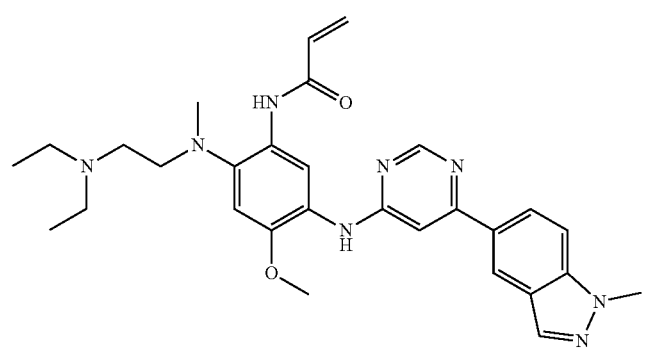 [SMILES: C=CC(=O)Nc1cc(Nc2cc(-c3ccc4c(cnn4C)c3)ncn2)c(OC)cc1N(C)CCN(CC)CC]
62
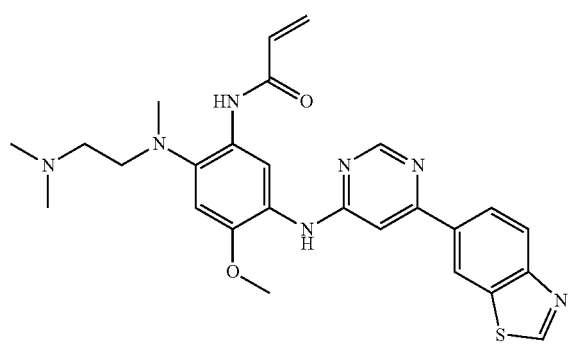 [SMILES: C=CC(=O)Nc1cc(Nc2cc(-c3ccc4ncsc4c3)ncn2)c(OC)cc1N(C)CCN(C)C]
63

TABLE 7-continued
Compounds as EGFR Kinase Inhibitor (Final Products)
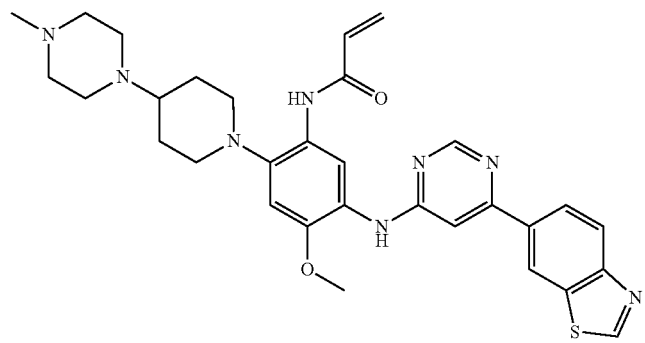 [SMILES: C=CC(=O)Nc1cc(Nc2cc(-c3ccc4ncsc4c3)ncn2)c(OC)cc1N1CCC(N2CCN(C)CC2)CC1]
64
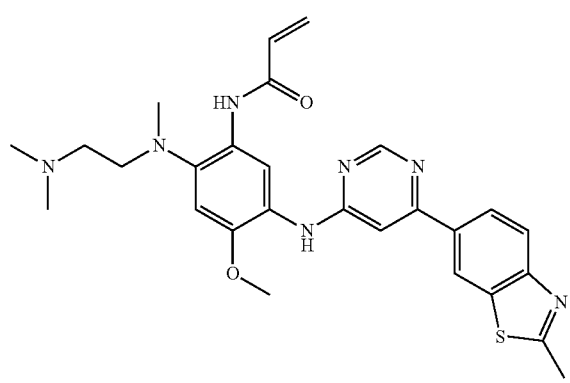
65
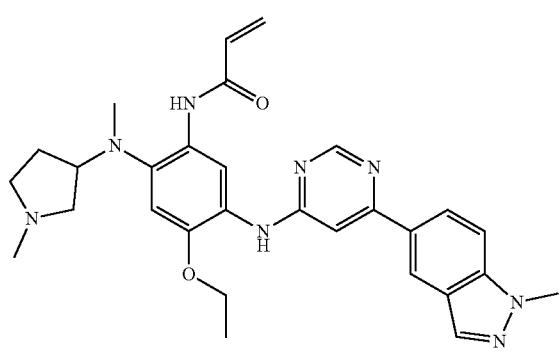 [SMILES: C=CC(=O)Nc1cc(Nc2cc(-c3ccc4c(cnn4C)c3)ncn2)c(OCC)cc1N(C)C1CCN(C)C1]
66
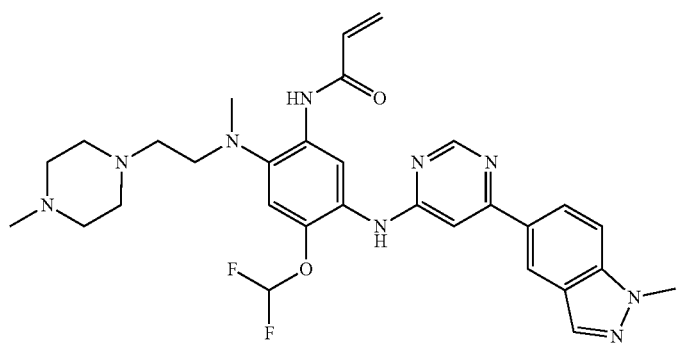
67

TABLE 7-continued
Compounds as EGFR Kinase Inhibitor (Final Products)
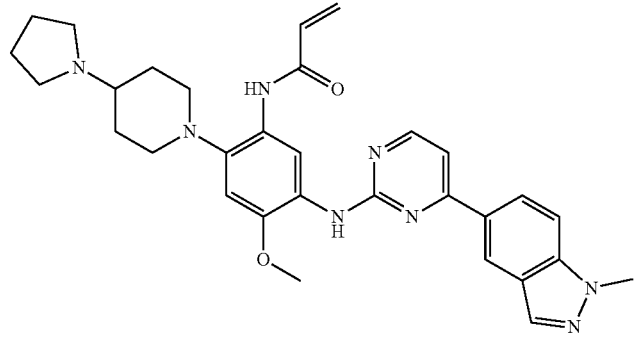 [SMILES: C=CC(=O)Nc1cc(Nc2nccc(-c3ccc4c(cnn4C)c3)n2)c(OC)cc1N1CCC(N2CCCC2)CC1]
68
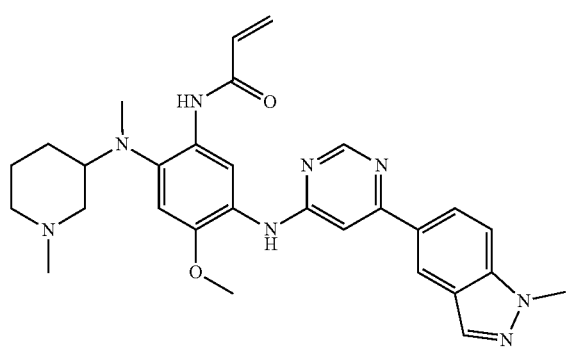 [SMILES: C=CC(=O)Nc1cc(Nc2cc(-c3ccc4c(cnn4C)c3)ncn2)c(OC)cc1N(C)C1CCCN(C)C1]
69
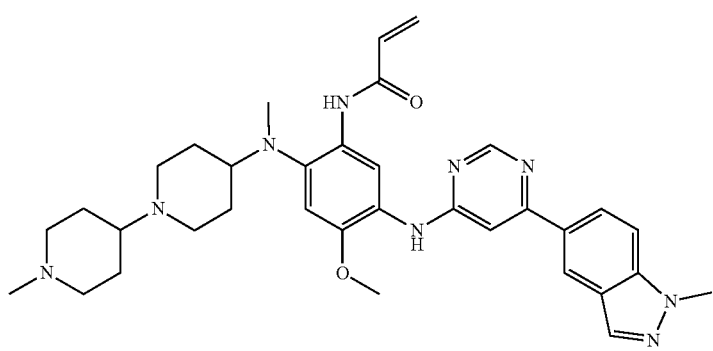
70
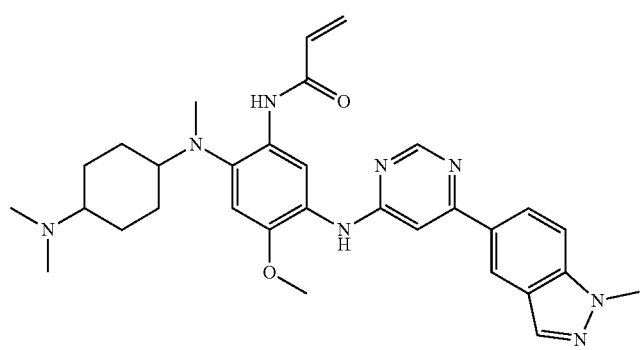
71

TABLE 7-continued
Compounds as EGFR Kinase Inhibitor (Final Products)
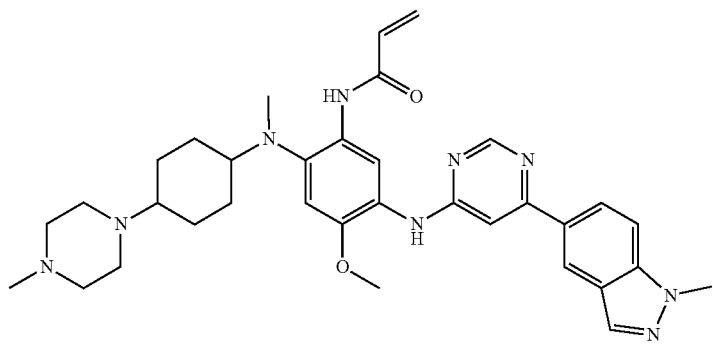
72
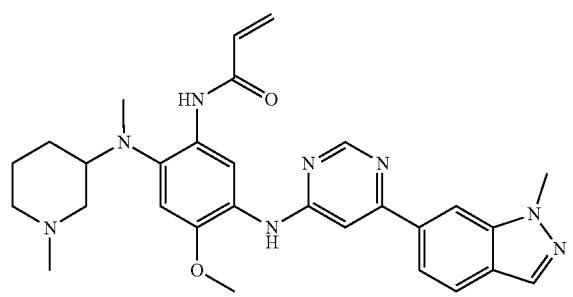 [SMILES: C=CC(=O)Nc1cc(Nc2cc(-c3ccc4cnn(C)c4c3)ncn2)c(OC)cc1N(C)C1CCCN(C)C1]
73
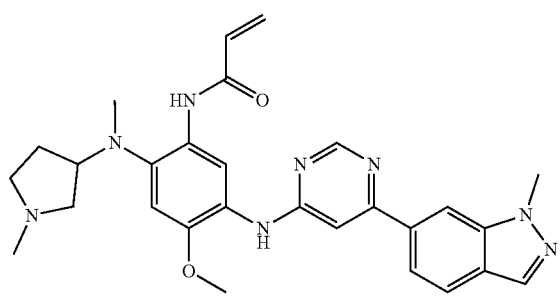 [SMILES: C=CC(=O)Nc1cc(Nc2cc(-c3ccc4cnn(C)c4c3)ncn2)c(OC)cc1N(C)C1CCN(C)C1]
74
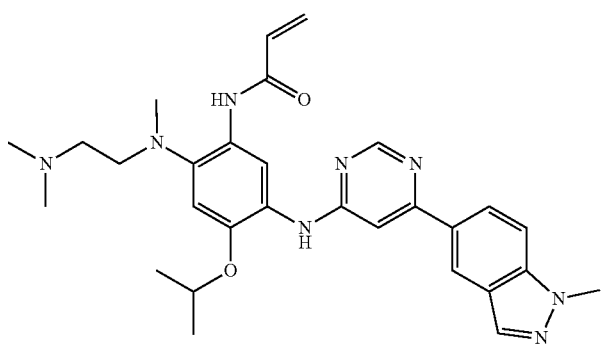
75

TABLE 7-continued
Compounds as EGFR Kinase Inhibitor (Final Products)
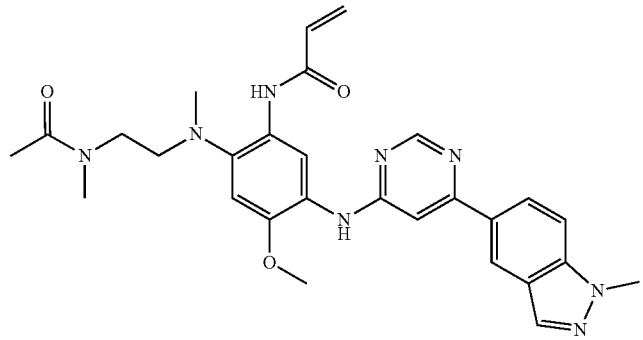 [SMILES: C=CC(=O)Nc1cc(Nc2cc(-c3ccc4c(cnn4C)c3)ncn2)c(OC)cc1N(C)CCN(C)C(C)=O]
76
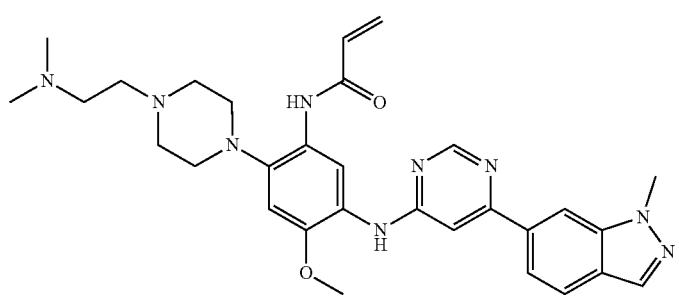 [SMILES: C=CC(=O)Nc1cc(Nc2cc(-c3ccc4cnn(C)c4c3)ncn2)c(OC)cc1N1CCN(CCN(C)C)CC1]
77
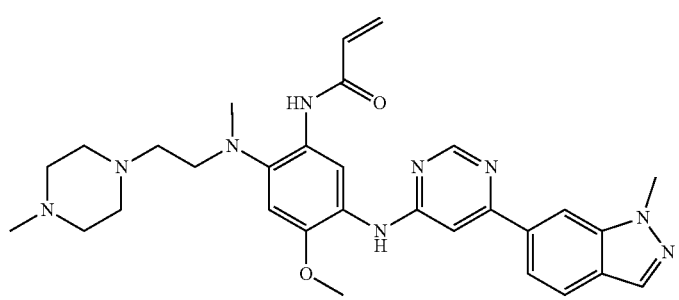 [SMILES: C=CC(=O)Nc1cc(Nc2cc(-c3ccc4cnn(C)c4c3)ncn2)c(OC)cc1N(C)CCN1CCN(C)CC1]
78
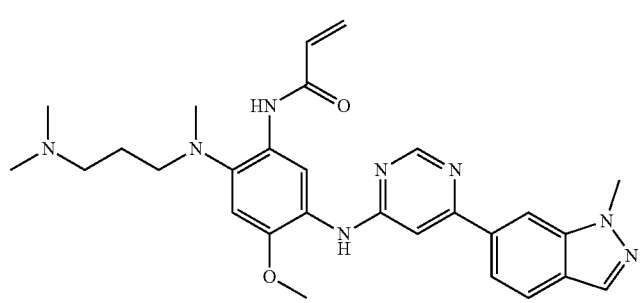 [SMILES: C=CC(=O)Nc1cc(Nc2cc(-c3ccc4cnn(C)c4c3)ncn2)c(OC)cc1N(C)CCCN(C)C]
79
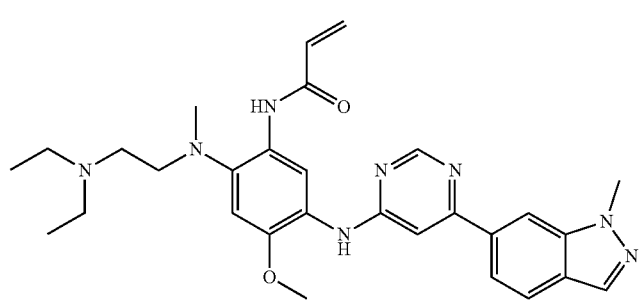 [SMILES: C=CC(=O)Nc1cc(Nc2cc(-c3ccc4cnn(C)c4c3)ncn2)c(OC)cc1N(C)CCN(CC)CC]
80

TABLE 7-continued
Compounds as EGFR Kinase Inhibitor (Final Products)
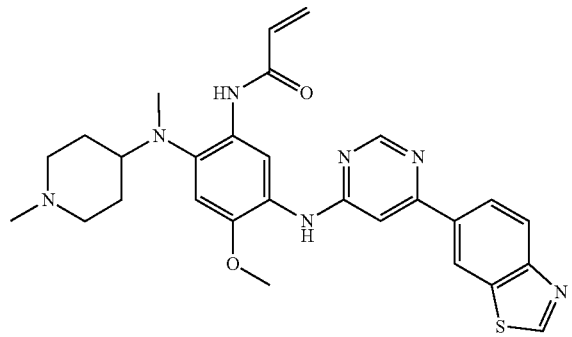 [SMILES: C=CC(=O)Nc1cc(Nc2cc(-c3ccc4ncsc4c3)ncn2)c(OC)cc1N(C)C1CCN(C)CC1]
81
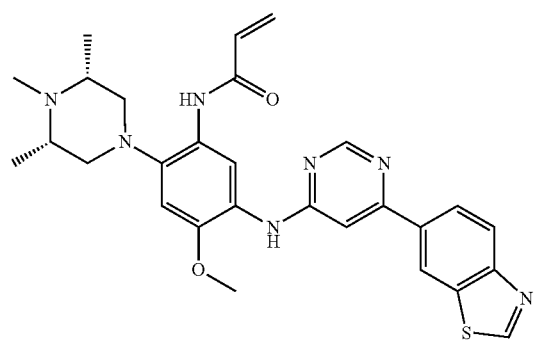 [SMILES: C=CC(=O)Nc1cc(Nc2cc(-c3ccc4ncsc4c3)ncn2)c(OC)cc1N1C[C@@H](C)N(C)[C@@H](C)C1]
82
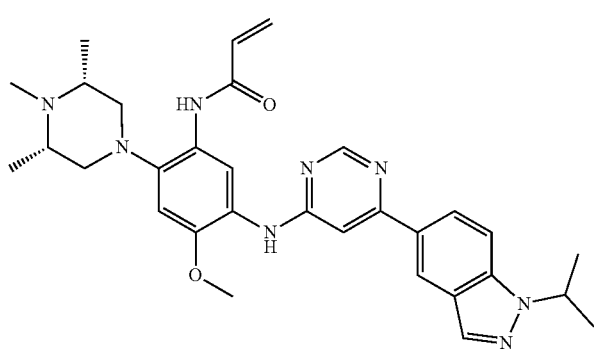 [SMILES: C=CC(=O)Nc1cc(Nc2cc(-c3ccc4c(cnn4C(C)C)c3)ncn2)c(OC)cc1N1C[C@@H](C)N(C)[C@@H](C)C1]
83
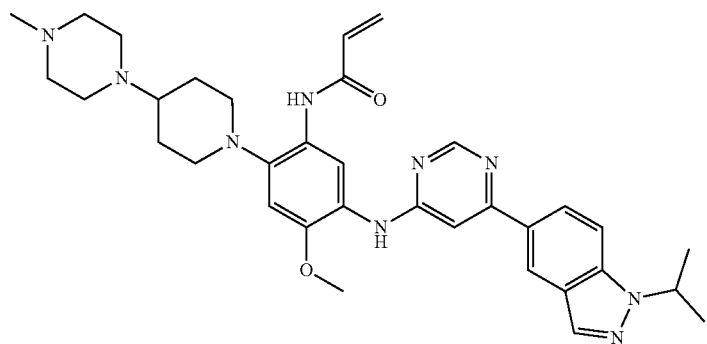 [SMILES: C=CC(=O)Nc1cc(Nc2cc(-c3ccc4c(cnn4C(C)C)c3)ncn2)c(OC)cc1N1CCC(N2CCN(C)CC2)CC1]
84

TABLE 7-continued
Compounds as EGFR Kinase Inhibitor (Final Products)
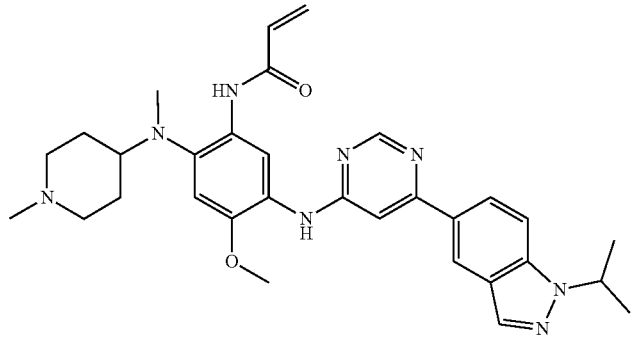 [SMILES: C=CC(=O)Nc1cc(Nc2cc(-c3ccc4c(cnn4C(C)C)c3)ncn2)c(OC)cc1N(C)C1CCN(C)CC1]
85
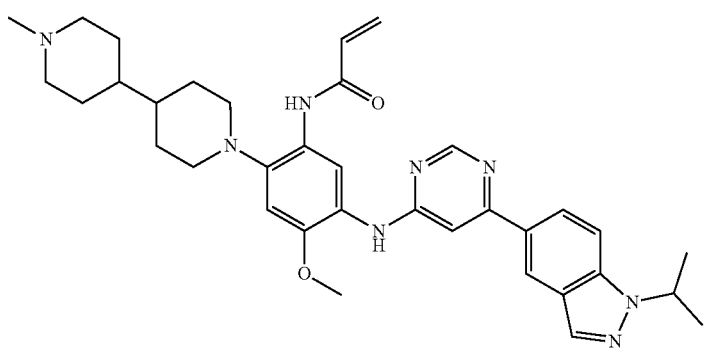 [SMILES: C=CC(=O)Nc1cc(Nc2cc(-c3ccc4c(cnn4C(C)C)c3)ncn2)c(OC)cc1N1CCC(C2CCN(C)CC2)CC1]
86
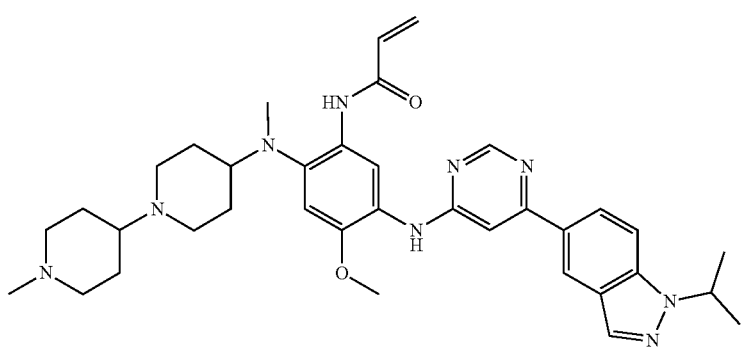 [SMILES: C=CC(=O)Nc1cc(Nc2cc(-c3ccc4c(cnn4C(C)C)c3)ncn2)c(OC)cc1N(C)C1CCN(C2CCN(C)CC2)CC1]
87
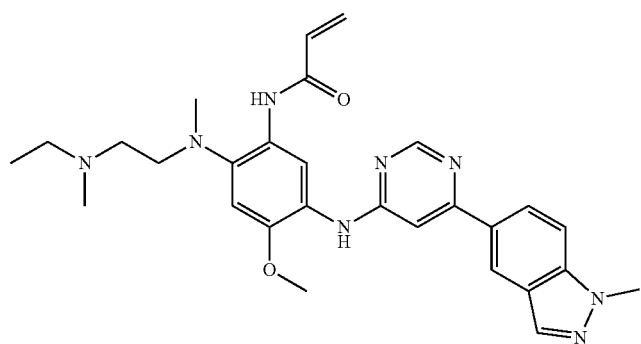 [SMILES: C=CC(=O)Nc1cc(Nc2cc(-c3ccc4c(cnn4C)c3)ncn2)c(OC)cc1N(C)CCN(C)CC]
88

TABLE 7-continued
Compounds as EGFR Kinase Inhibitor (Final Products)
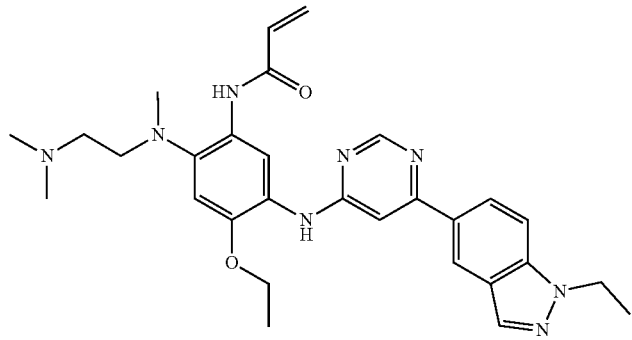 [SMILES: C=CC(=O)Nc1cc(Nc2cc(-c3ccc4c(cnn4CC)c3)ncn2)c(OCC)cc1N(C)CCN(C)C]
89
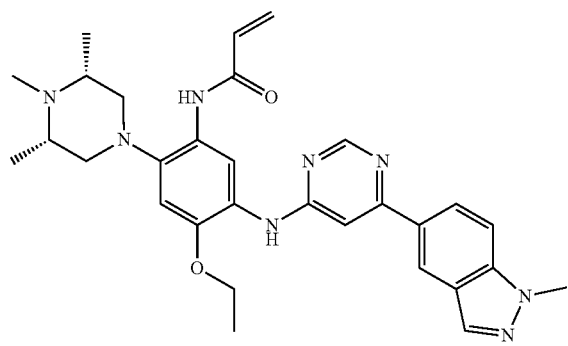
90
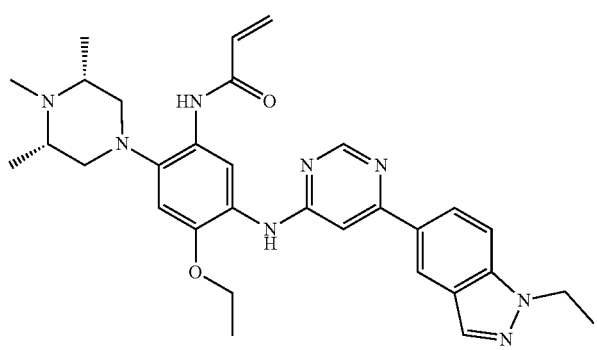 [SMILES: C=CC(=O)Nc1cc(Nc2cc(-c3ccc4c(cnn4CC)c3)ncn2)c(OCC)cc1N1C[C@@H](C)N(C)[C@@H](C)C1]
91
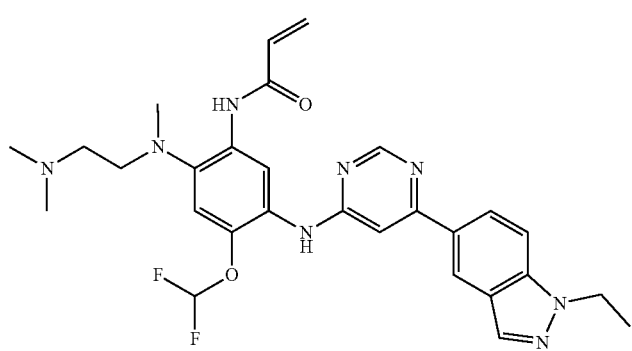 [SMILES: C=CC(=O)Nc1cc(Nc2cc(-c3ccc4c(cnn4CC)c3)ncn2)c(OC(F)F)cc1N(C)CCN(C)C]
92

TABLE 7-continued
Compounds as EGFR Kinase Inhibitor (Final Products)
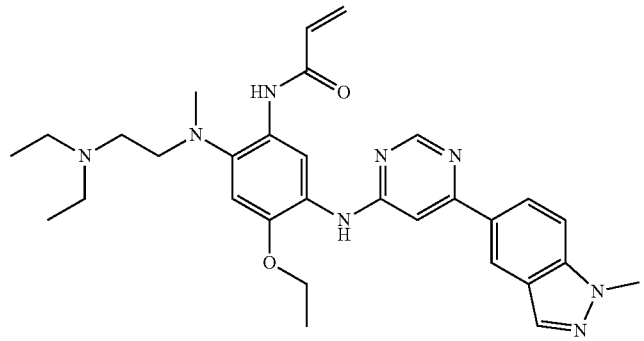 [SMILES: C=CC(=O)Nc1cc(Nc2cc(-c3ccc4c(cnn4C)c3)ncn2)c(OCC)cc1N(C)CCN(CC)CC]
93
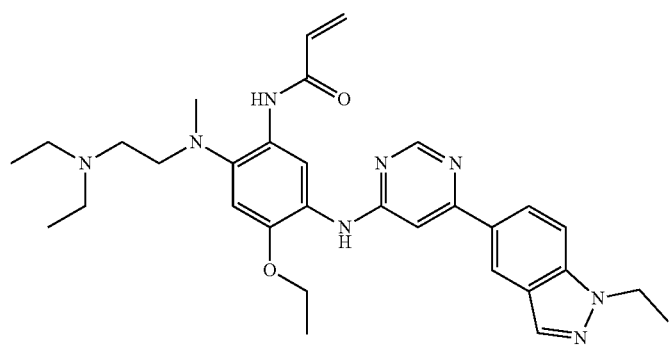 [SMILES: C=CC(=O)Nc1cc(Nc2cc(-c3ccc4c(cnn4CC)c3)ncn2)c(OCC)cc1N(C)CCN(CC)CC]
94
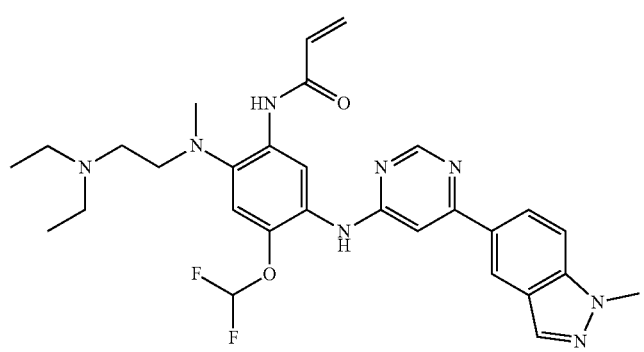 [SMILES: C=CC(=O)Nc1cc(Nc2cc(-c3ccc4c(cnn4C)c3)ncn2)c(OC(F)F)cc1N(C)CCN(CC)CC]
95
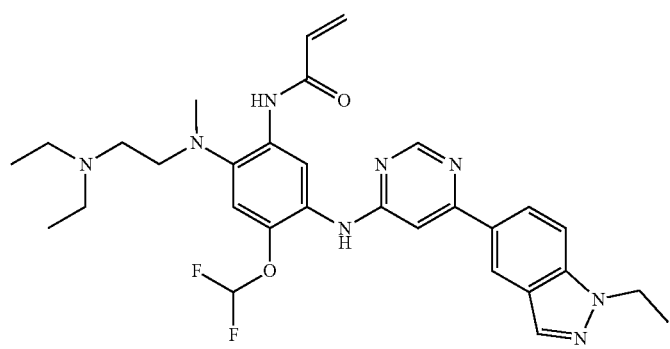 [SMILES: C=CC(=O)Nc1cc(Nc2cc(-c3ccc4c(cnn4CC)c3)ncn2)c(OC(F)F)cc1N(C)CCN(CC)CC]
96

TABLE 7-continued
Compounds as EGFR Kinase Inhibitor (Final Products)
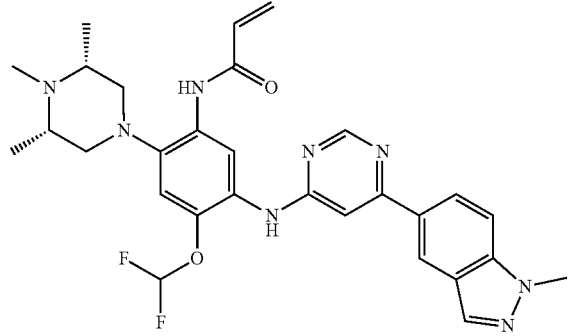
97
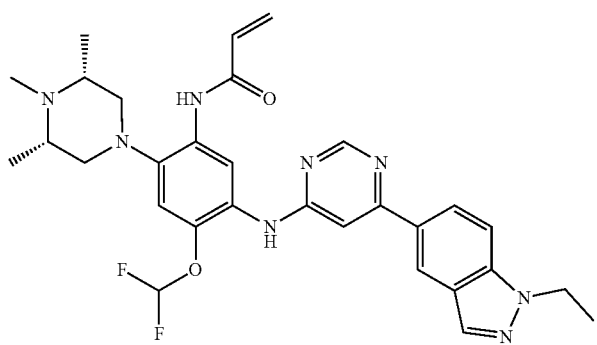 [SMILES: C=CC(=O)Nc1cc(Nc2cc(-c3ccc4c(cnn4CC)c3)ncn2)c(OC(F)F)cc1N1C[C@@H](C)N(C)[C@@H](C)C1]
98
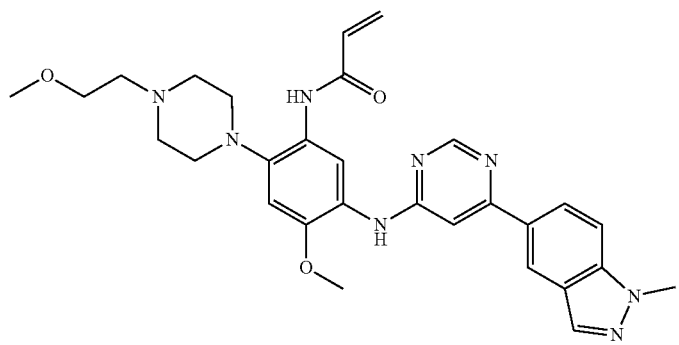
99
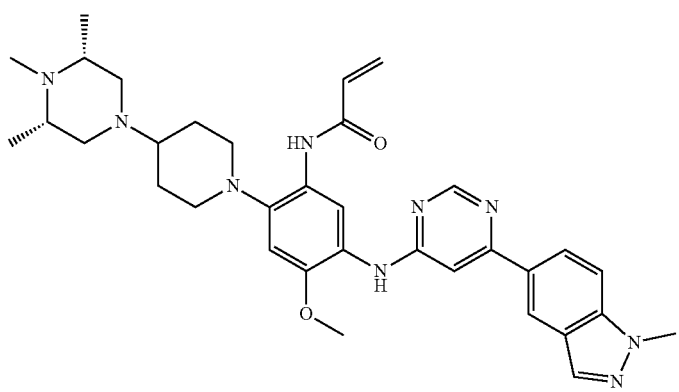
100

TABLE 7-continued
Compounds as EGFR Kinase Inhibitor (Final Products)
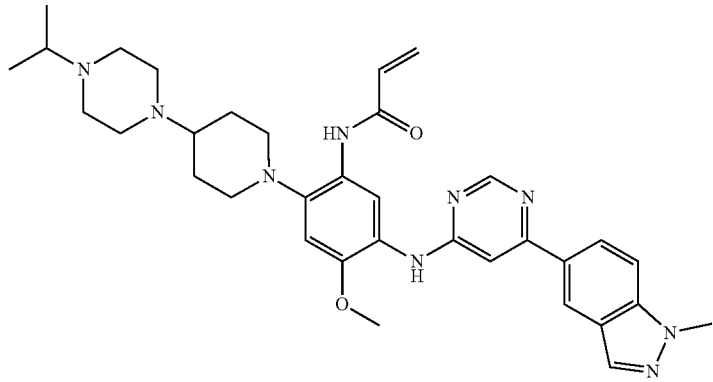 [SMILES: C=CC(=O)Nc1cc(Nc2cc(-c3ccc4c(cnn4C)c3)ncn2)c(OC)cc1N1CCC(N2CCN(C(C)C)CC2)CC1]
101
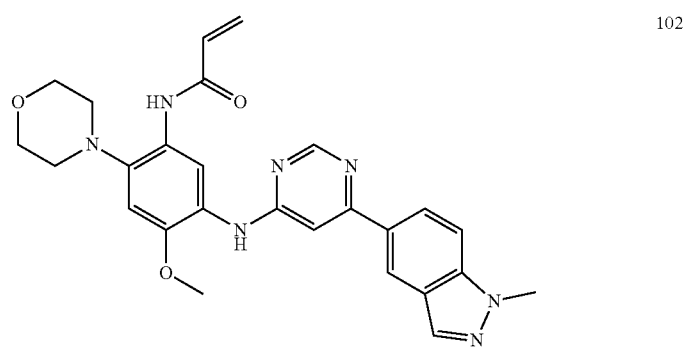
102
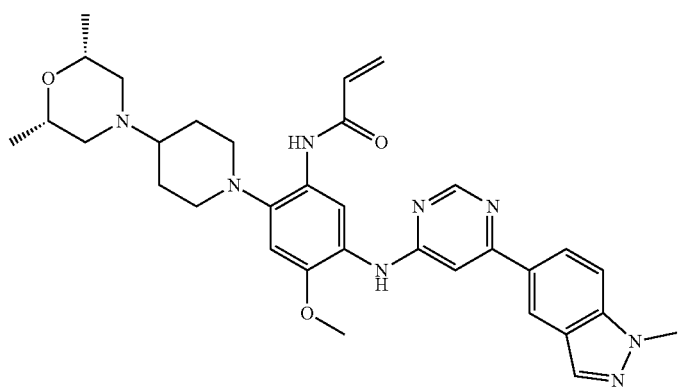
103
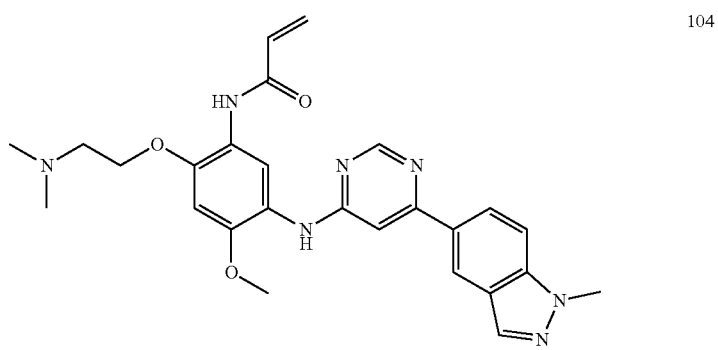
104

TABLE 7-continued
Compounds as EGFR Kinase Inhibitor (Final Products)
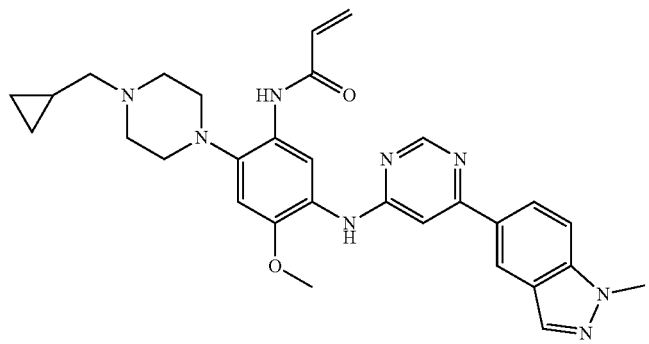 [SMILES: C=CC(=O)Nc1cc(Nc2cc(-c3ccc4c(cnn4C)c3)ncn2)c(OC)cc1N1CCN(CC2CC2)CC1]
105
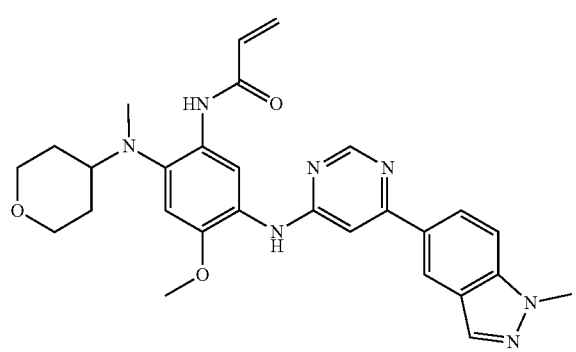 [SMILES: C=CC(=O)Nc1cc(Nc2cc(-c3ccc4c(cnn4C)c3)ncn2)c(OC)cc1N(C)C1CCOCC1]
106
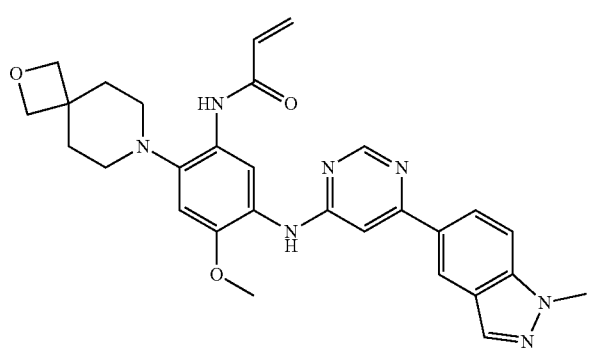 [SMILES: C=CC(=O)Nc1cc(Nc2cc(-c3ccc4c(cnn4C)c3)ncn2)c(OC)cc1N1CCC2(CC1)COC2]
107
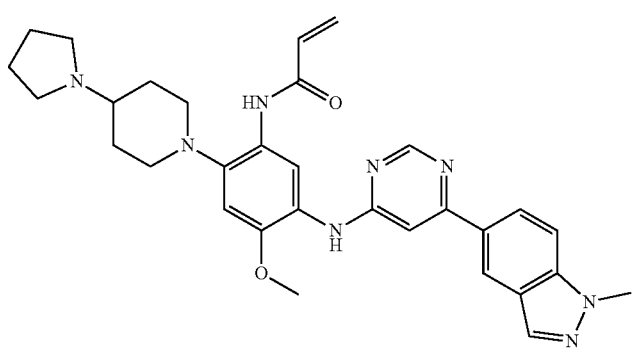 [SMILES: C=CC(=O)Nc1cc(Nc2cc(-c3ccc4c(cnn4C)c3)ncn2)c(OC)cc1N1CCC(N2CCCC2)CC1]
108

TABLE 7-continued
Compounds as EGFR Kinase Inhibitor (Final Products)
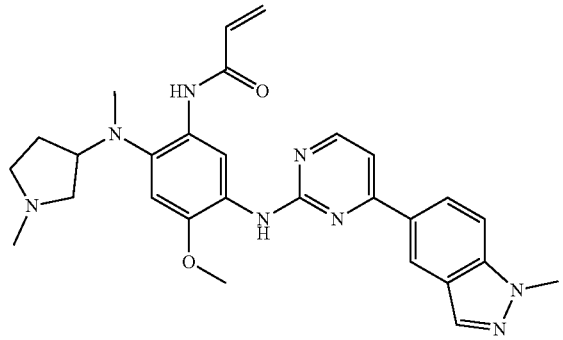 [SMILES: C=CC(=O)Nc1cc(Nc2nccc(-c3ccc4c(cnn4C)c3)n2)c(OC)cc1N(C)C1CCN(C)C1]
109
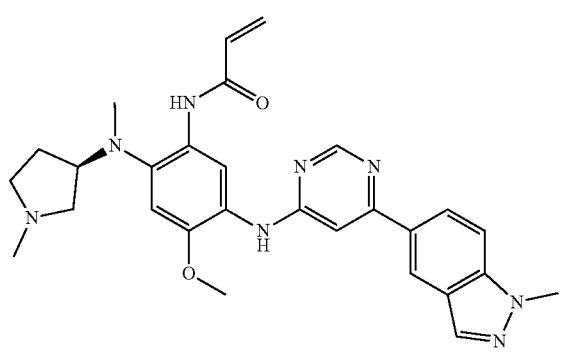 [SMILES: C=CC(=O)Nc1cc(Nc2cc(-c3ccc4c(cnn4C)c3)ncn2)c(OC)cc1N(C)[C@@H]1CCN(C)C1]
110
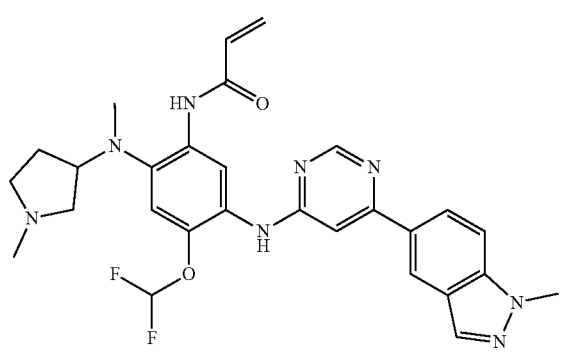 [SMILES: C=CC(=O)Nc1cc(Nc2cc(-c3ccc4c(cnn4C)c3)ncn2)c(OC(F)F)cc1N(C)C1CCN(C)C1]
111
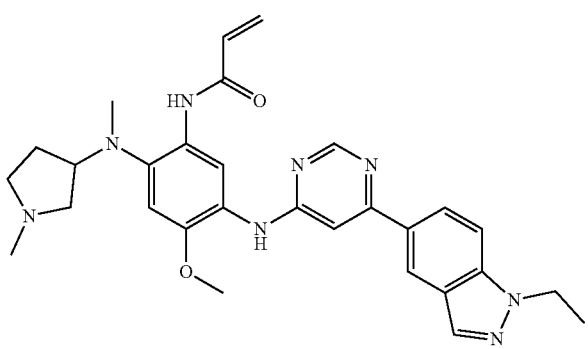 [SMILES: C=CC(=O)Nc1cc(Nc2cc(-c3ccc4c(cnn4CC)c3)ncn2)c(OC)cc1N(C)C1CCN(C)C1]
112

TABLE 7-continued
Compounds as EGFR Kinase Inhibitor (Final Products)
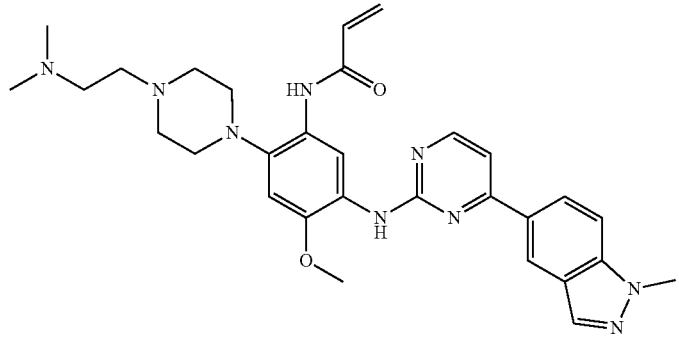
113
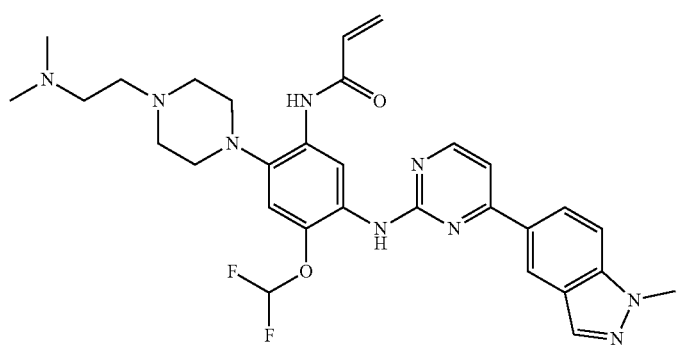
114
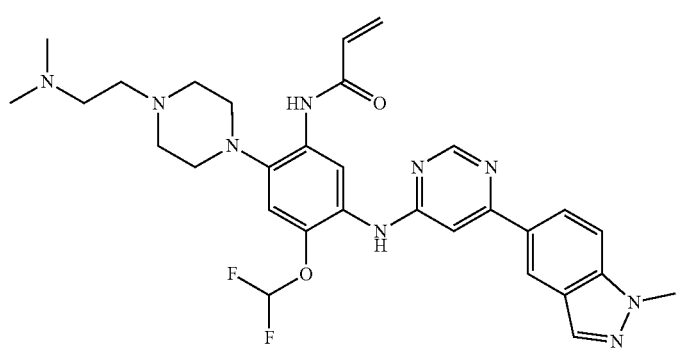
115
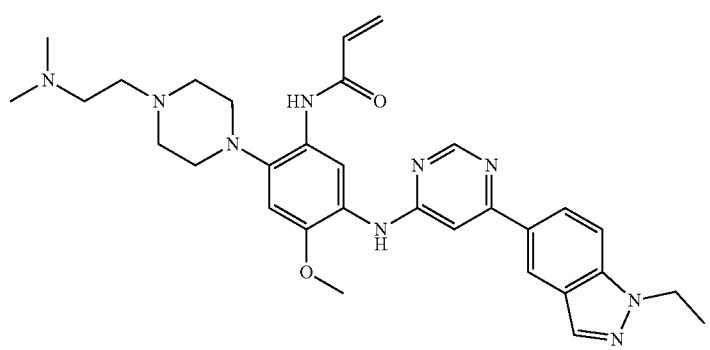 [SMILES: C=CC(=O)Nc1cc(Nc2cc(-c3ccc4c(cnn4CC)c3)ncn2)c(OC)cc1N1CCN(CCN(C)C)CC1]
116

TABLE 7-continued
Compounds as EGFR Kinase Inhibitor (Final Products)
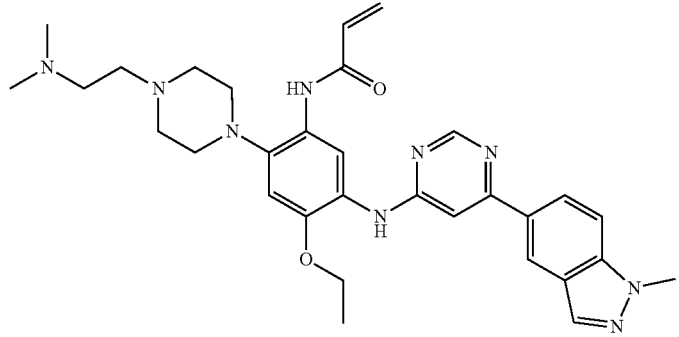
117
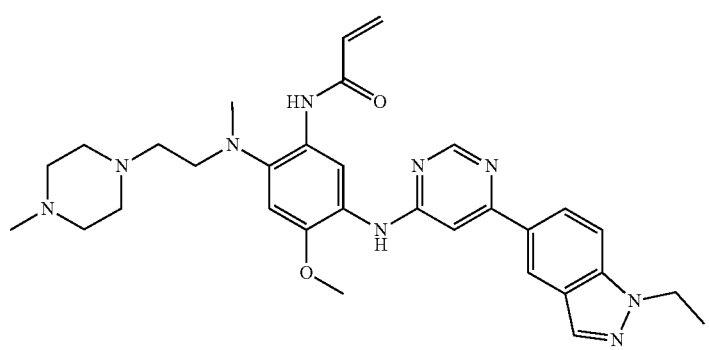 [SMILES: C=CC(=O)Nc1cc(Nc2cc(-c3ccc4c(cnn4CC)c3)ncn2)c(OC)cc1N(C)CCN1CCN(C)CC1]
118
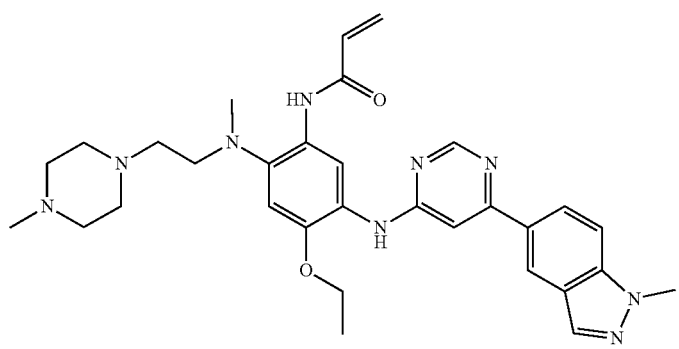
119
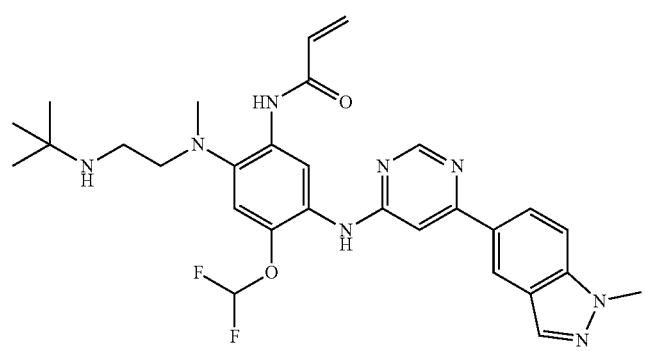 [SMILES: C=CC(=O)Nc1cc(Nc2cc(-c3ccc4c(cnn4C)c3)ncn2)c(OC(F)F)cc1N(C)CCNC(C)(C)C]
120

TABLE 7-continued
Compounds as EGFR Kinase Inhibitor (Final Products)
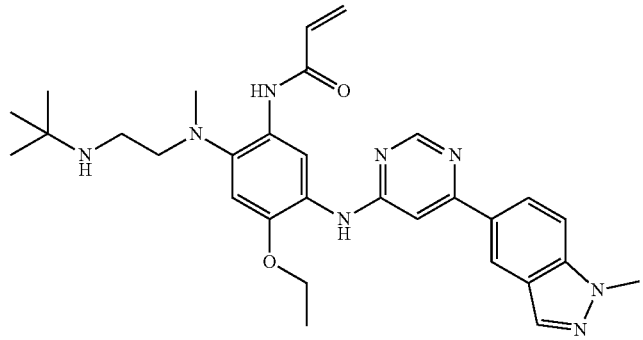 [SMILES: C=CC(=O)Nc1cc(Nc2cc(-c3ccc4c(cnn4C)c3)ncn2)c(OCC)cc1N(C)CCNC(C)(C)C]
121
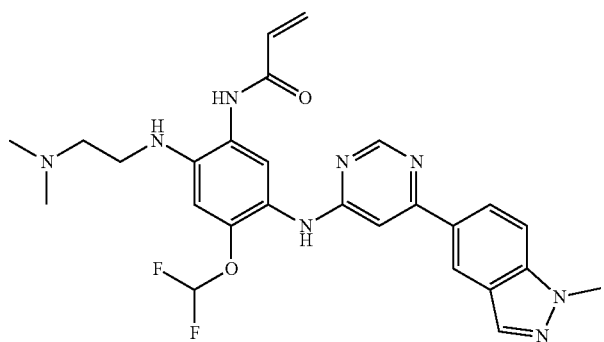
122
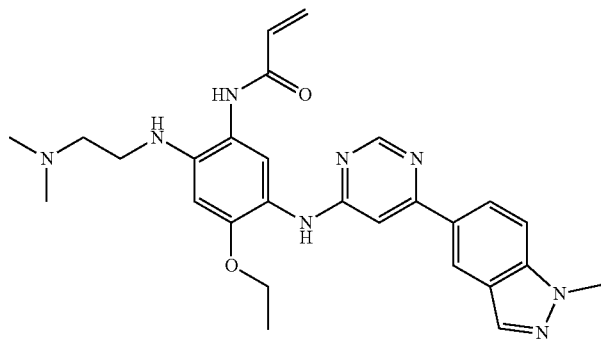
123
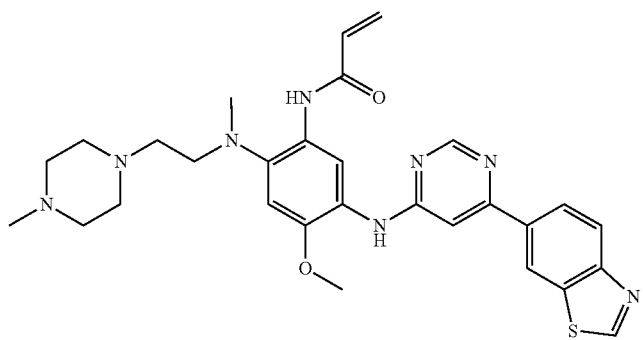 [SMILES: C=CC(=O)Nc1cc(Nc2cc(-c3ccc4ncsc4c3)ncn2)c(OC)cc1N(C)CCN1CCN(C)CC1]
124

TABLE 7-continued
Compounds as EGFR Kinase Inhibitor (Final Products)
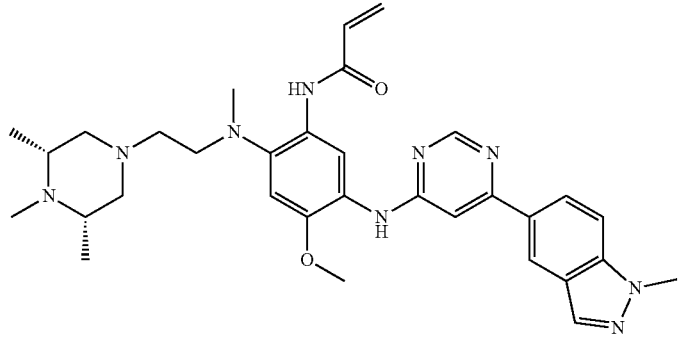
125
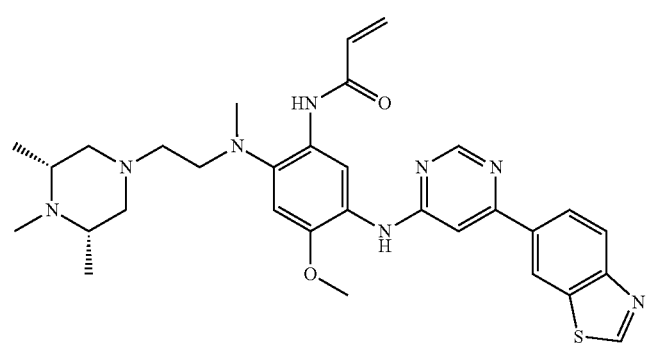 [SMILES: C=CC(=O)Nc1cc(Nc2cc(-c3ccc4ncsc4c3)ncn2)c(OC)cc1N(C)CCN1C[C@@H](C)N(C)[C@@H](C)C1]
126
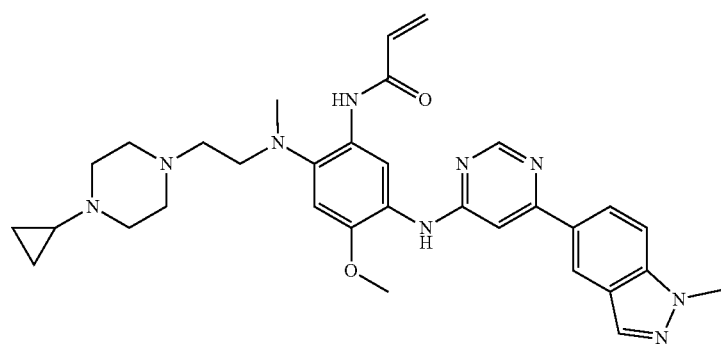 [SMILES: C=CC(=O)Nc1cc(Nc2cc(-c3ccc4c(cnn4C)c3)ncn2)c(OC)cc1N(C)CCN1CCN(C2CC2)CC1]
127
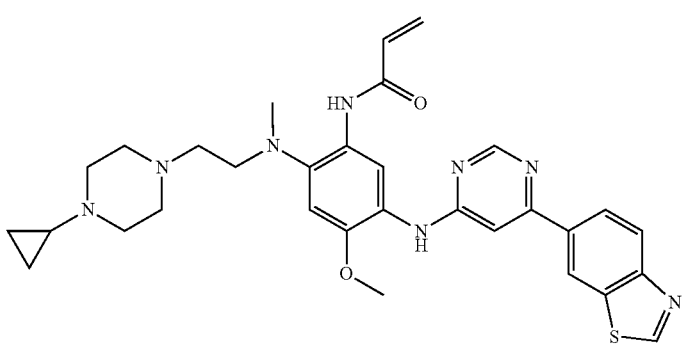 [SMILES: C=CC(=O)Nc1cc(Nc2cc(-c3ccc4ncsc4c3)ncn2)c(OC)cc1N(C)CCN1CCN(C2CC2)CC1]
128

TABLE 7-continued
Compounds as EGFR Kinase Inhibitor (Final Products)
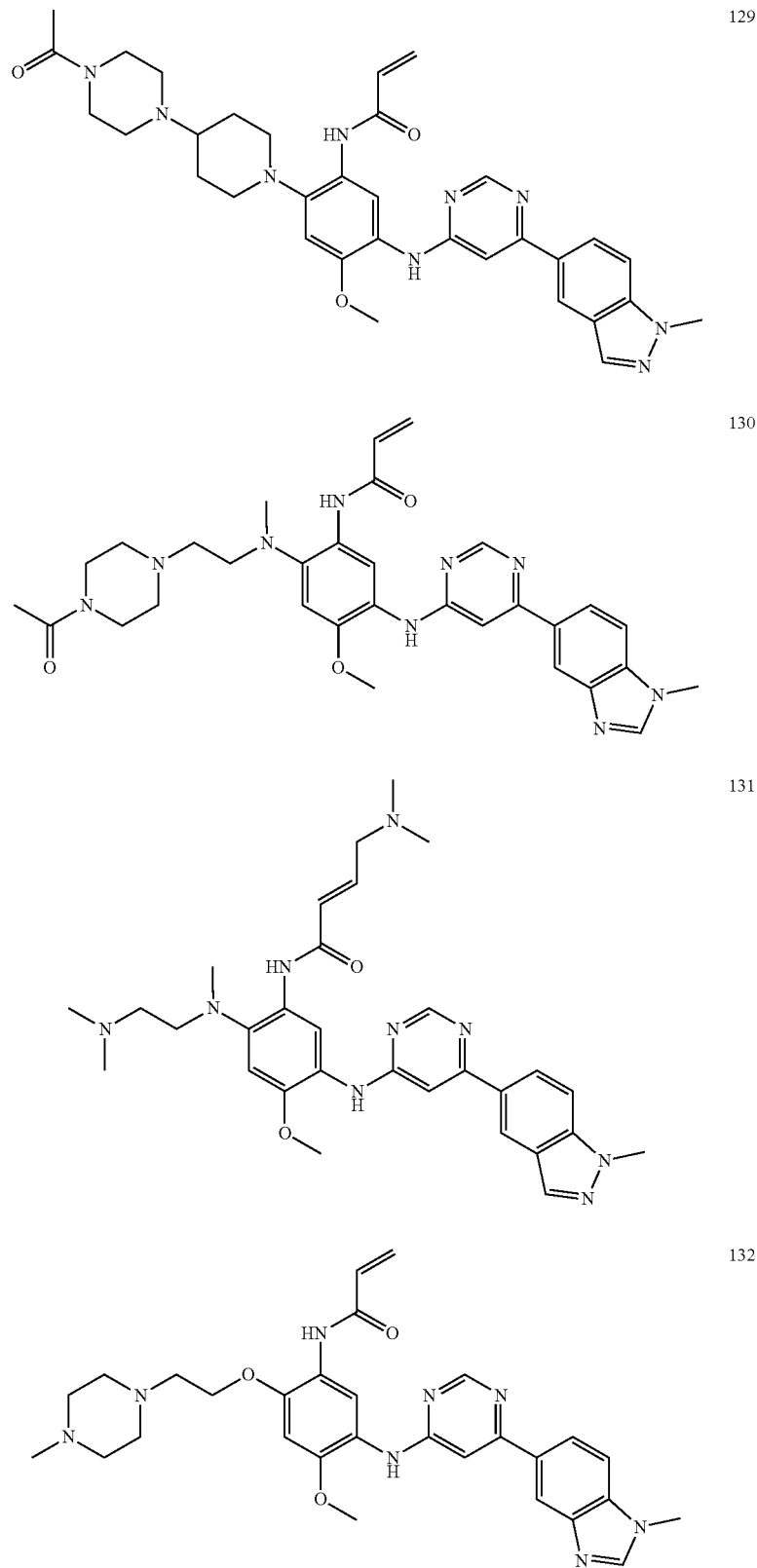

TABLE 7-continued
Compounds as EGFR Kinase Inhibitor (Final Products)
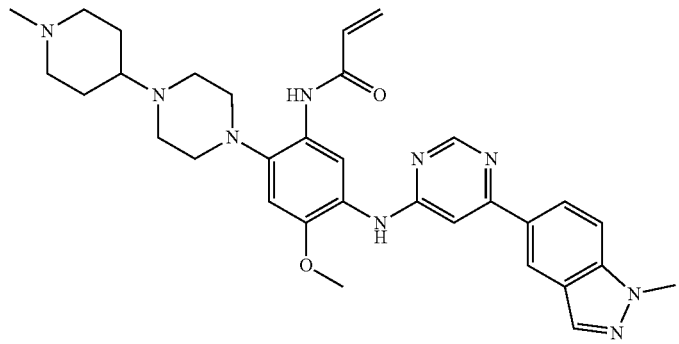
133
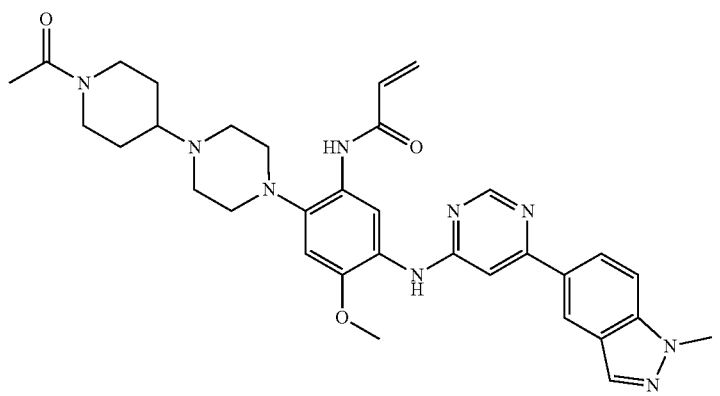 [SMILES: C=CC(=O)Nc1cc(Nc2cc(-c3ccc4c(cnn4C)c3)ncn2)c(OC)cc1N1CCN(C2CCN(C(C)=O)CC2)CC1]
134
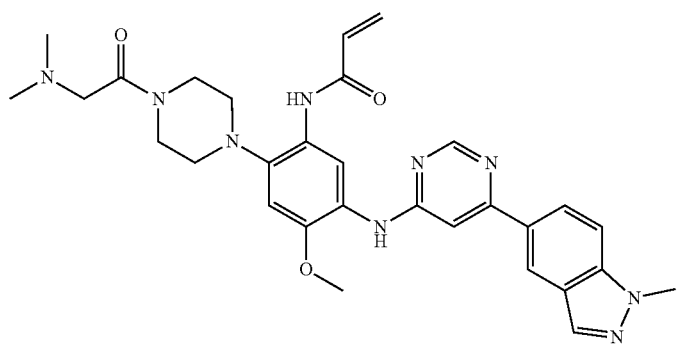
135
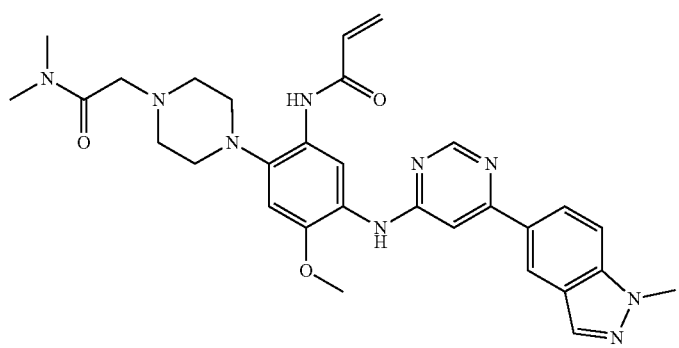
136

TABLE 7-continued
Compounds as EGFR Kinase Inhibitor (Final Products)
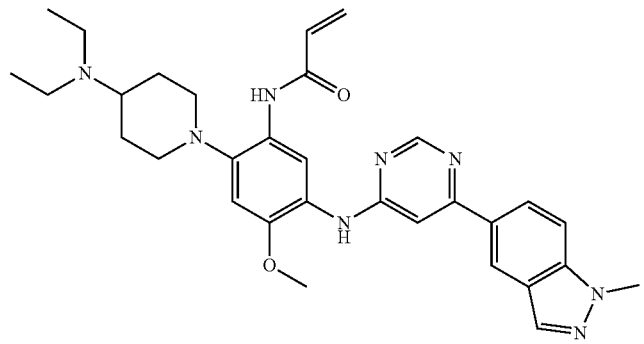 [SMILES: C=CC(=O)Nc1cc(Nc2cc(-c3ccc4c(cnn4C)c3)ncn2)c(OC)cc1N1CCC(N(CC)CC)CC1]
137
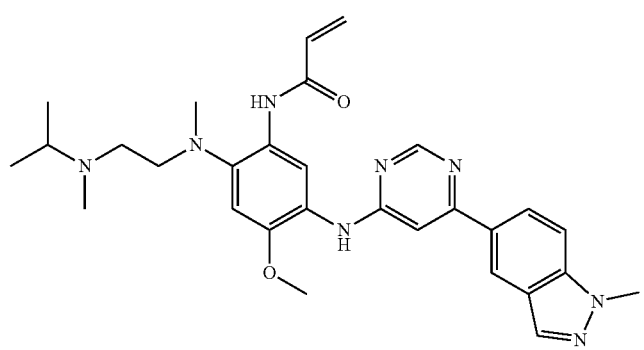 [SMILES: C=CC(=O)Nc1cc(Nc2cc(-c3ccc4c(cnn4C)c3)ncn2)c(OC)cc1N(C)CCN(C)C(C)C]
138
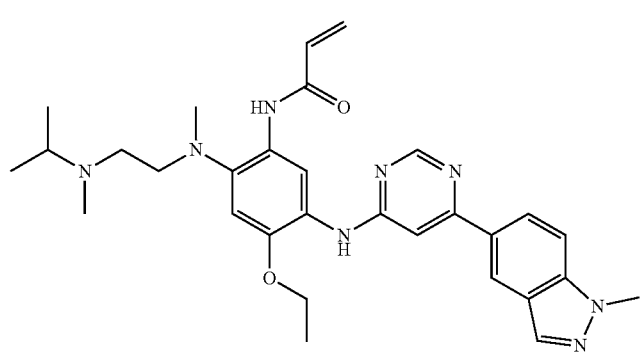 [SMILES: C=CC(=O)Nc1cc(Nc2cc(-c3ccc4c(cnn4C)c3)ncn2)c(OCC)cc1N(C)CCN(C)C(C)C]
139
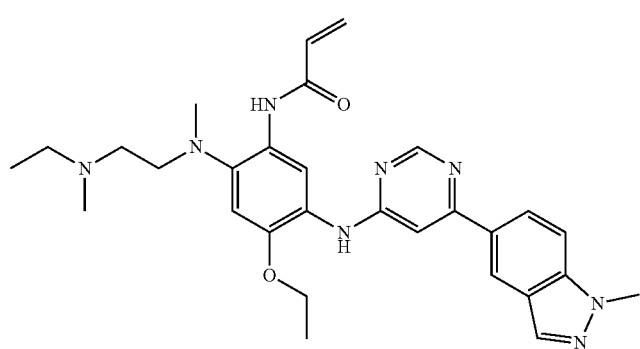 [SMILES: C=CC(=O)Nc1cc(Nc2cc(-c3ccc4c(cnn4C)c3)ncn2)c(OCC)cc1N(C)CCN(C)CC]
140

TABLE 7-continued
Compounds as EGFR Kinase Inhibitor (Final Products)
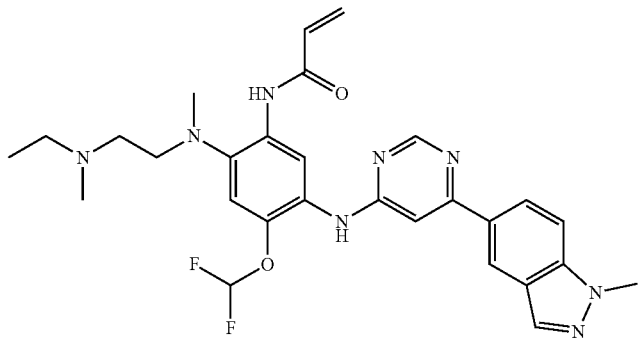 [SMILES: C=CC(=O)Nc1cc(Nc2cc(-c3ccc4c(cnn4C)c3)ncn2)c(OC(F)F)cc1N(C)CCN(C)CC]
141
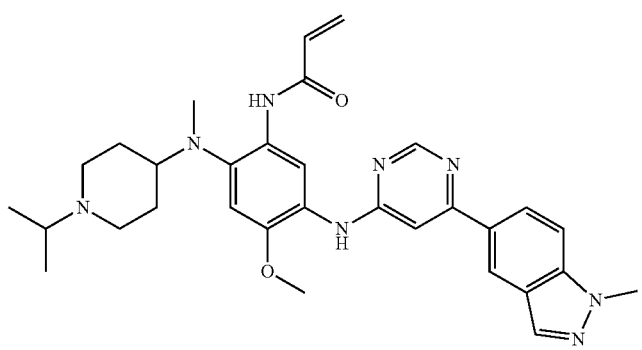 [SMILES: C=CC(=O)Nc1cc(Nc2cc(-c3ccc4c(cnn4C)c3)ncn2)c(OC)cc1N(C)C1CCN(C(C)C)CC1]
142
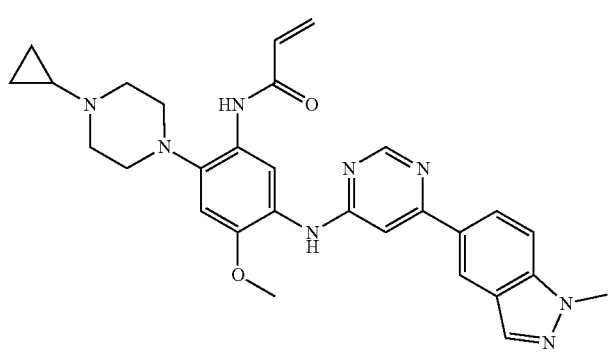 [SMILES: C=CC(=O)Nc1cc(Nc2cc(-c3ccc4c(cnn4C)c3)ncn2)c(OC)cc1N1CCN(C2CC2)CC1]
143
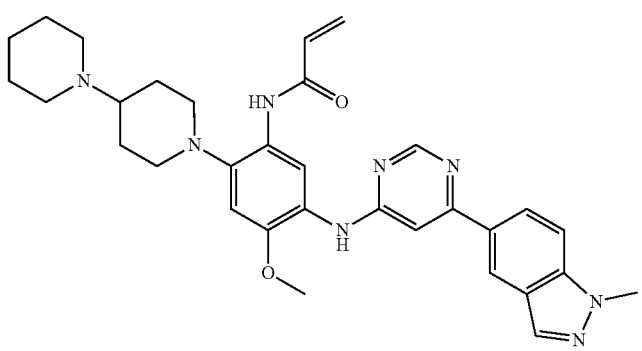 [SMILES: C=CC(=O)Nc1cc(Nc2cc(-c3ccc4c(cnn4C)c3)ncn2)c(OC)cc1N1CCC(N2CCCCC2)CC1]
144

TABLE 7-continued
Compounds as EGFR Kinase Inhibitor (Final Products)
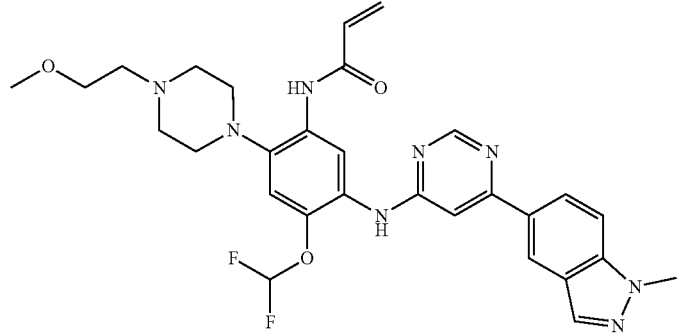
145
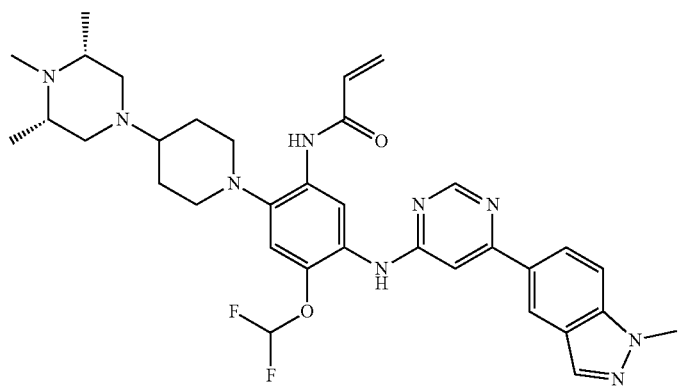
146
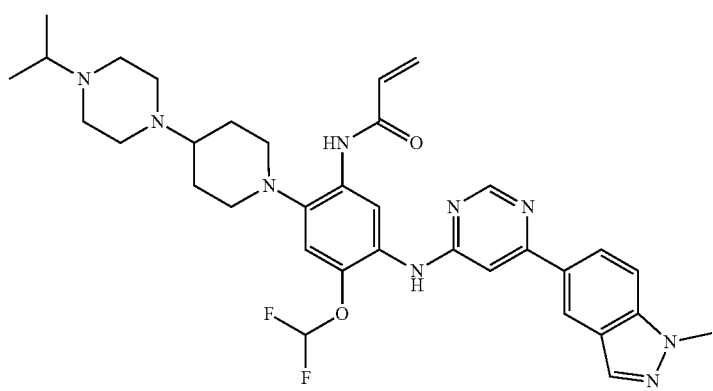 [SMILES: C=CC(=O)Nc1cc(Nc2cc(-c3ccc4c(cnn4C)c3)ncn2)c(OC(F)F)cc1N1CCC(N2CCN(C(C)C)CC2)CC1]
147
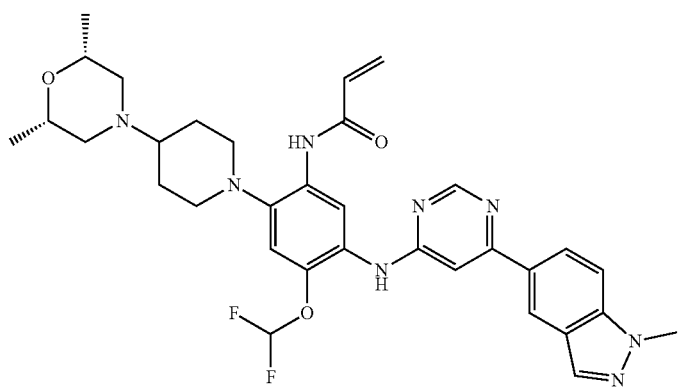
148

TABLE 7-continued
Compounds as EGFR Kinase Inhibitor (Final Products)
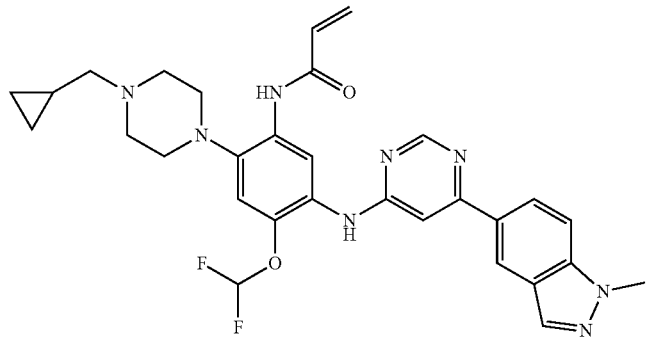 [SMILES: C=CC(=O)Nc1cc(Nc2cc(-c3ccc4c(cnn4C)c3)ncn2)c(OC(F)F)cc1N1CCN(CC2CC2)CC1]
149
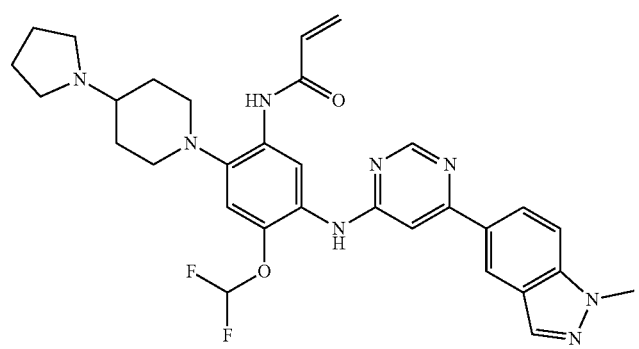 [SMILES: C=CC(=O)Nc1cc(Nc2cc(-c3ccc4c(cnn4C)c3)ncn2)c(OC(F)F)cc1N1CCC(N2CCCC2)CC1]
150
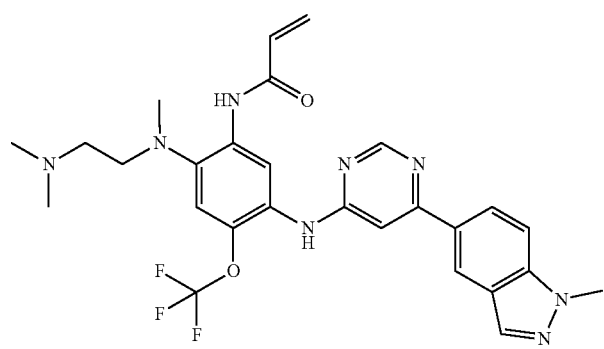
151
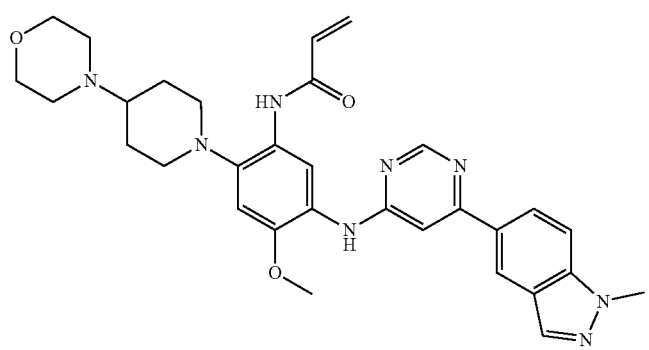 [SMILES: C=CC(=O)Nc1cc(Nc2cc(-c3ccc4c(cnn4C)c3)ncn2)c(OC)cc1N1CCC(N2CCOCC2)CC1]
152

TABLE 7-continued
Compounds as EGFR Kinase Inhibitor (Final Products)
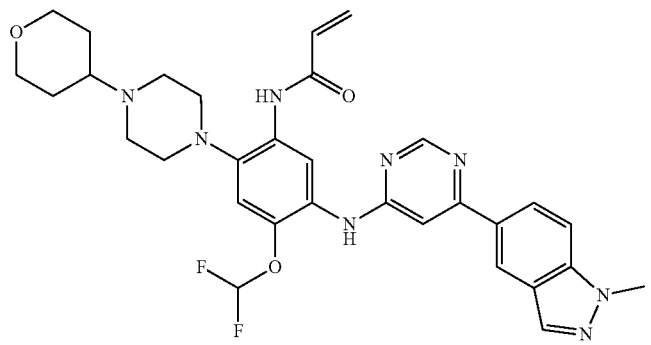 [SMILES: C=CC(=O)Nc1cc(Nc2cc(-c3ccc4c(cnn4C)c3)ncn2)c(OC(F)F)cc1N1CCN(C2CCOCC2)CC1]
153
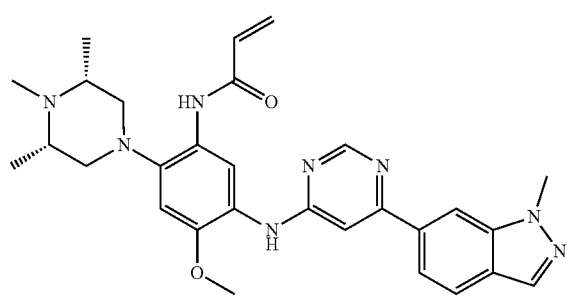 [SMILES: C=CC(=O)Nc1cc(Nc2cc(-c3ccc4cnn(C)c4c3)ncn2)c(OC)cc1N1C[C@@H](C)N(C)[C@@H](C)C1]
154
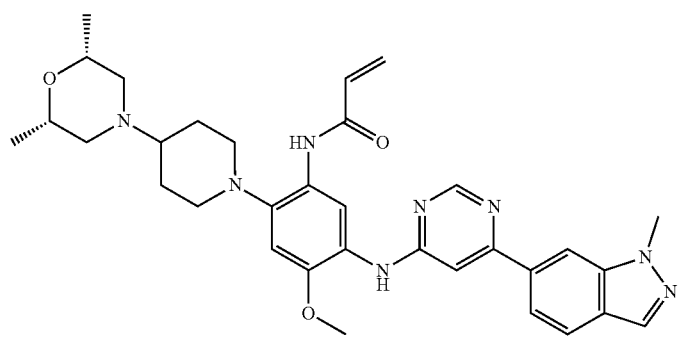 [SMILES: C=CC(=O)Nc1cc(Nc2cc(-c3ccc4cnn(C)c4c3)ncn2)c(OC)cc1N1CCC(N2C[C@@H](C)O[C@@H](C)C2)CC1]
155
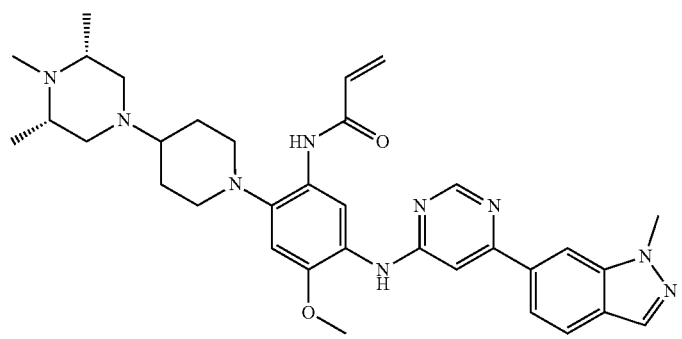 [SMILES: C=CC(=O)Nc1cc(Nc2cc(-c3ccc4cnn(C)c4c3)ncn2)c(OC)cc1N1CCC(N2C[C@@H](C)N(C)[C@@H](C)C2)CC1]
156

TABLE 7-continued
Compounds as EGFR Kinase Inhibitor (Final Products)
157
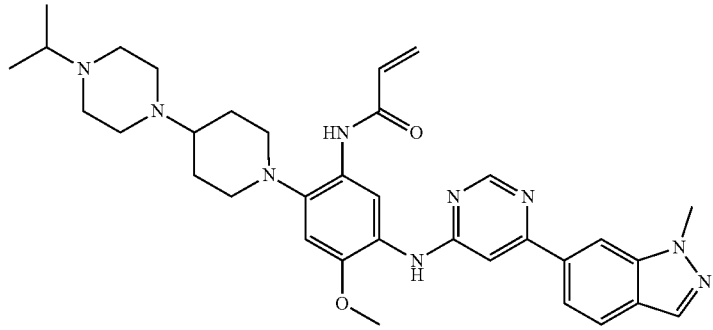 [SMILES: C=CC(=O)Nc1cc(Nc2cc(-c3ccc4cnn(C)c4c3)ncn2)c(OC)cc1N1CCC(N2CCN(C(C)C)CC2)CC1]
158
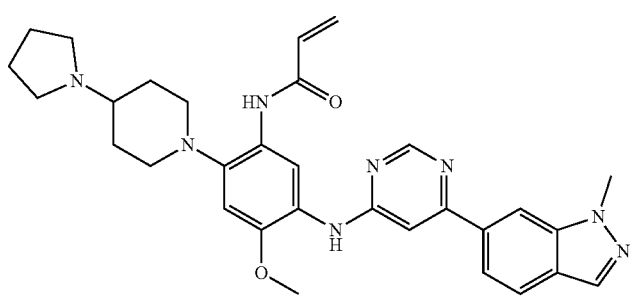 [SMILES: C=CC(=O)Nc1cc(Nc2cc(-c3ccc4cnn(C)c4c3)ncn2)c(OC)cc1N1CCC(N2CCCC2)CC1]
159
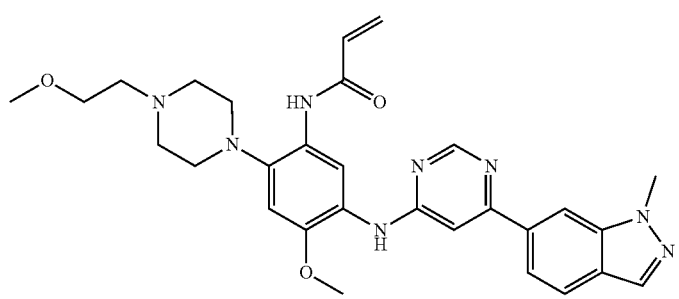 [SMILES: C=CC(=O)Nc1cc(Nc2cc(-c3ccc4cnn(C)c4c3)ncn2)c(OC)cc1N1CCN(CCOC)CC1]
160
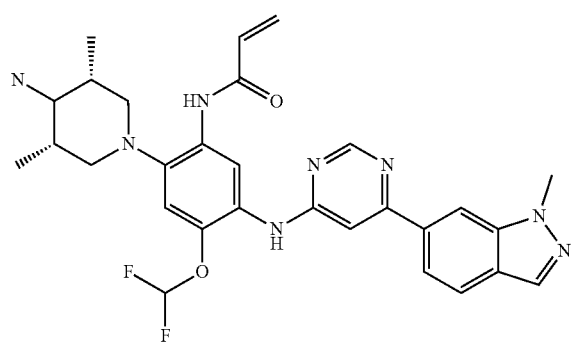 [SMILES: C=CC(=O)Nc1cc(Nc2cc(-c3ccc4cnn(C)c4c3)ncn2)c(OC(F)F)cc1N1C[C@@H](C)C(N)[C@@H](C)C1]
161
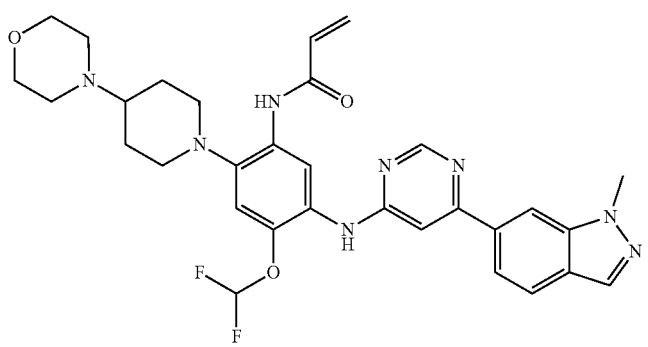 [SMILES: C=CC(=O)Nc1cc(Nc2cc(-c3ccc4cnn(C)c4c3)ncn2)c(OC(F)F)cc1N1CCC(N2CCOCC2)CC1]

TABLE 7-continued
Compounds as EGFR Kinase Inhibitor (Final Products)
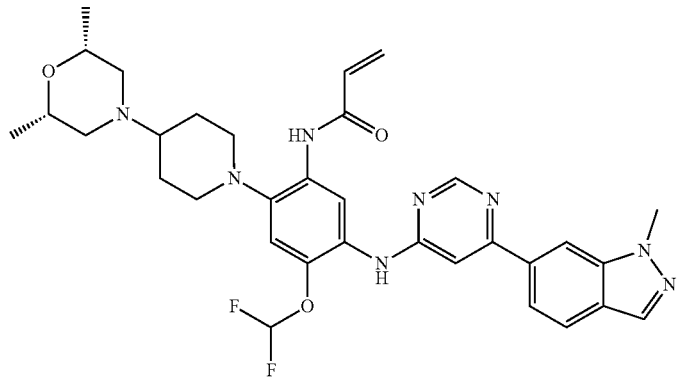 [SMILES: C=CC(=O)Nc1cc(Nc2cc(-c3ccc4cnn(C)c4c3)ncn2)c(OC(F)F)cc1N1CCC(N2C[C@@H](C)O[C@@H](C)C2)CC1]
162
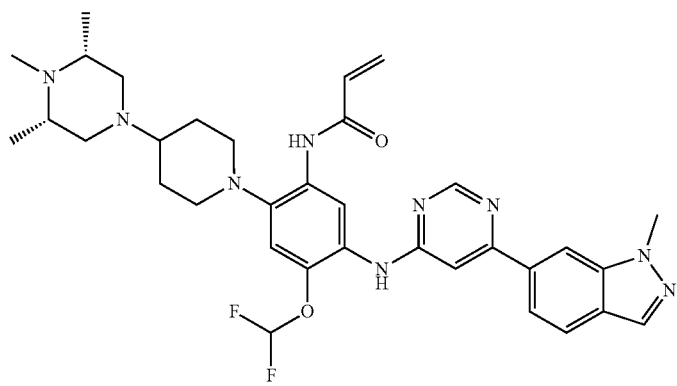 [SMILES: C=CC(=O)Nc1cc(Nc2cc(-c3ccc4cnn(C)c4c3)ncn2)c(OC(F)F)cc1N1CCC(N2C[C@@H](C)N(C)[C@@H](C)C2)CC1]
163
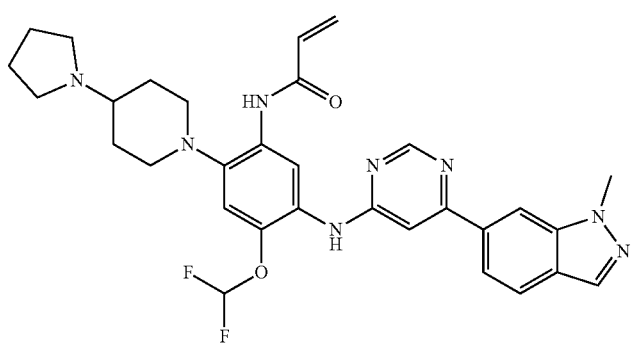 [SMILES: C=CC(=O)Nc1cc(Nc2cc(-c3ccc4cnn(C)c4c3)ncn2)c(OC(F)F)cc1N1CCC(N2CCCC2)CC1]
164
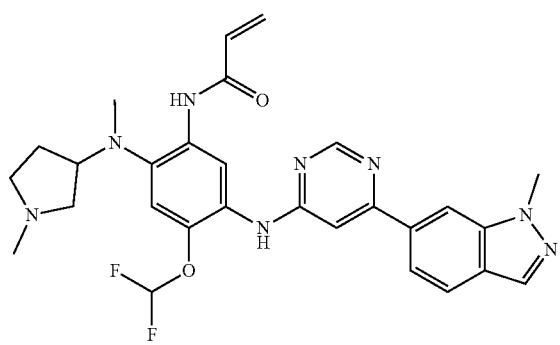 [SMILES: C=CC(=O)Nc1cc(Nc2cc(-c3ccc4cnn(C)c4c3)ncn2)c(OC(F)F)cc1N(C)C1CCN(C)C1]
165

TABLE 7-continued
Compounds as EGFR Kinase Inhibitor (Final Products)
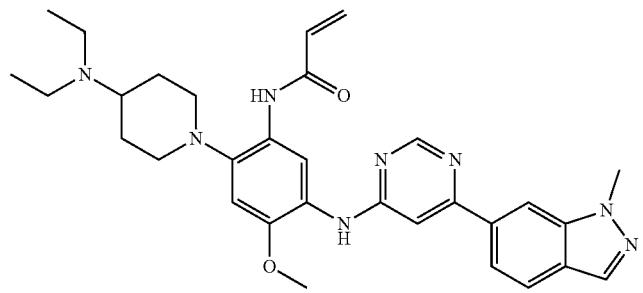 [SMILES: C=CC(=O)Nc1cc(Nc2cc(-c3ccc4cnn(C)c4c3)ncn2)c(OC)cc1N1CCC(N(CC)CC)CC1]
166
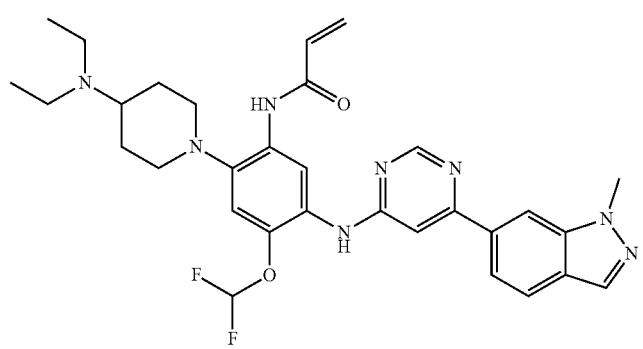 [SMILES: C=CC(=O)Nc1cc(Nc2cc(-c3ccc4cnn(C)c4c3)ncn2)c(OC(F)F)cc1N1CCC(N(CC)CC)CC1]
167
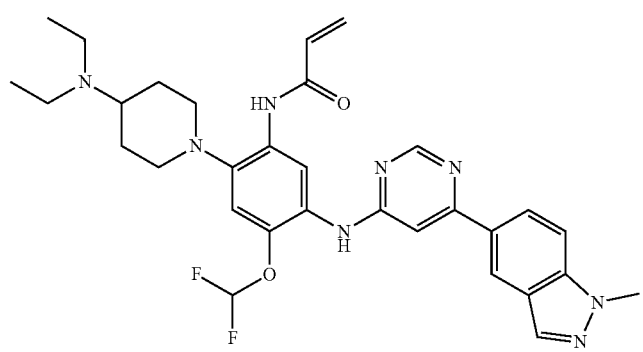 [SMILES: C=CC(=O)Nc1cc(Nc2cc(-c3ccc4c(cnn4C)c3)ncn2)c(OC(F)F)cc1N1CCC(N(CC)CC)CC1]
168
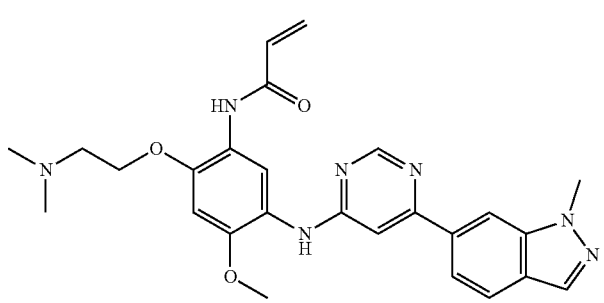 [SMILES: C=CC(=O)Nc1cc(Nc2cc(-c3ccc4cnn(C)c4c3)ncn2)c(OC)cc1OCCN(C)C]
169

TABLE 7-continued
Compounds as EGFR Kinase Inhibitor (Final Products)
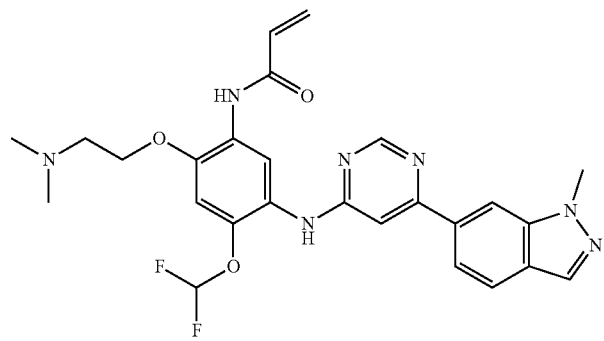 [SMILES: C=CC(=O)Nc1cc(Nc2cc(-c3ccc4cnn(C)c4c3)ncn2)c(OC(F)F)cc1OCCN(C)C]
170
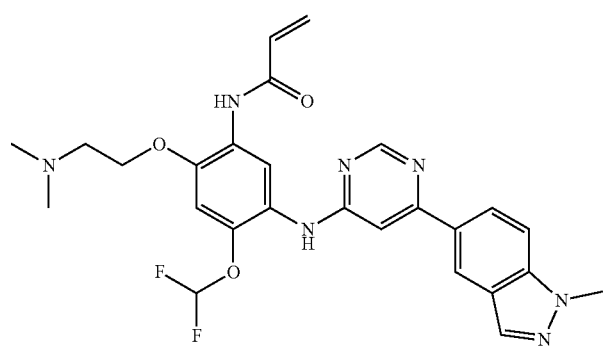
171
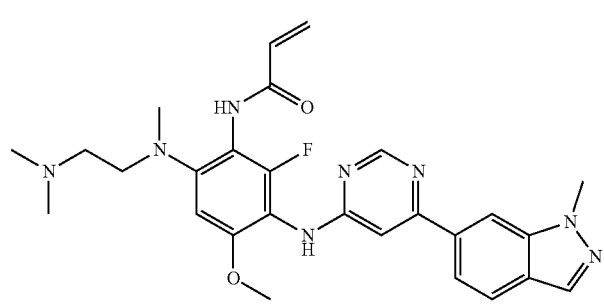 [SMILES: C=CC(=O)Nc1c(N(C)CCN(C)C)cc(OC)c(Nc2cc(-c3ccc4cnn(C)c4c3)ncn2)c1F]
172
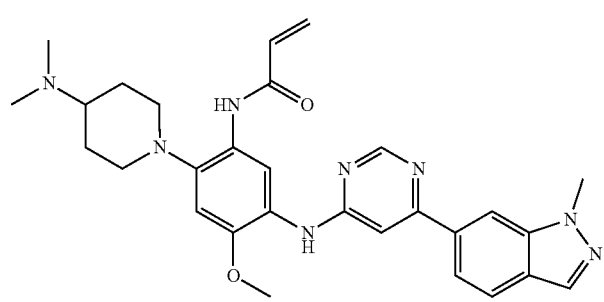 [SMILES: C=CC(=O)Nc1cc(Nc2cc(-c3ccc4cnn(C)c4c3)ncn2)c(OC)cc1N1CCC(N(C)C)CC1]
173
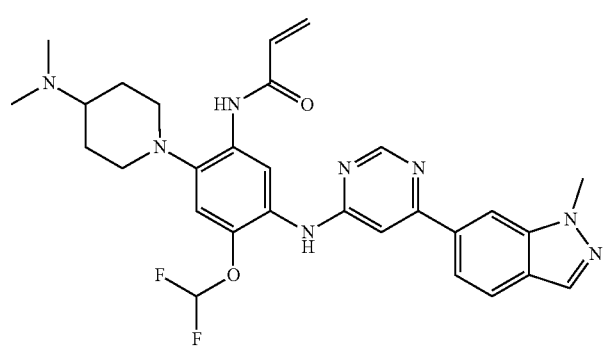 [SMILES: C=CC(=O)Nc1cc(Nc2cc(-c3ccc4cnn(C)c4c3)ncn2)c(OC(F)F)cc1N1CCC(N(C)C)CC1]
174

TABLE 7-continued
Compounds as EGFR Kinase Inhibitor (Final Products)
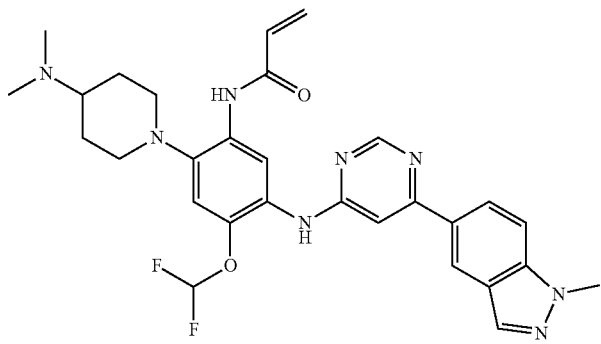
175
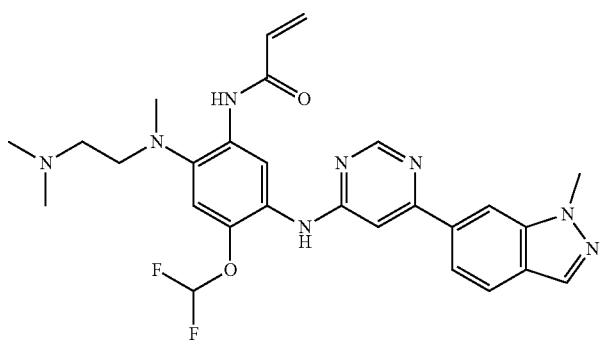 [SMILES: C=CC(=O)Nc1cc(Nc2cc(-c3ccc4cnn(C)c4c3)ncn2)c(OC(F)F)cc1N(C)CCN(C)C]
176
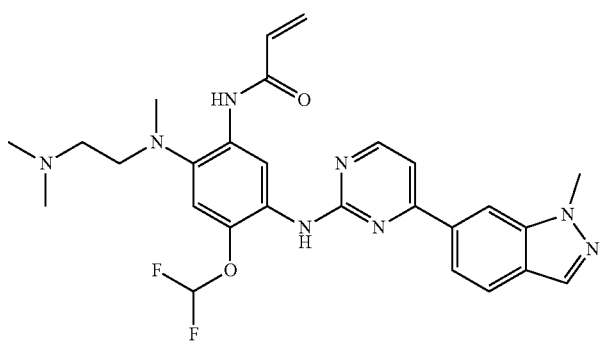 [SMILES: C=CC(=O)Nc1cc(Nc2nccc(-c3ccc4cnn(C)c4c3)n2)c(OC(F)F)cc1N(C)CCN(C)C]
177
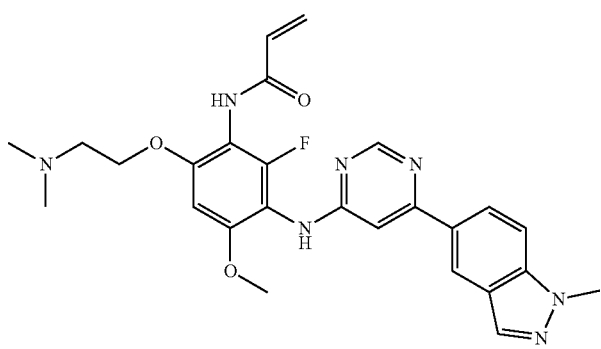
178

TABLE 7-continued
Compounds as EGFR Kinase Inhibitor (Final Products)
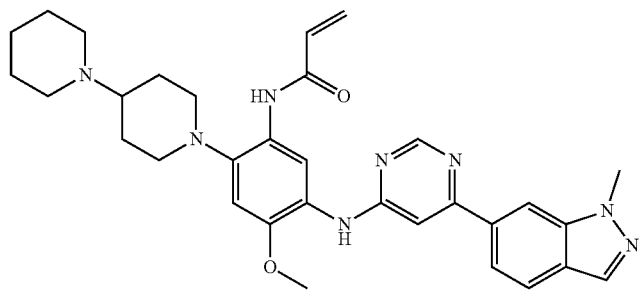 [SMILES: C=CC(=O)Nc1cc(Nc2cc(-c3ccc4cnn(C)c4c3)ncn2)c(OC)cc1N1CCC(N2CCCCC2)CC1]
179
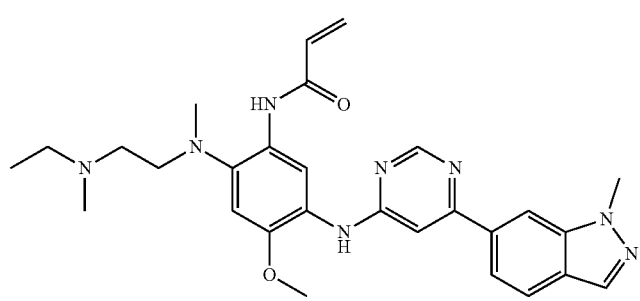 [SMILES: C=CC(=O)Nc1cc(Nc2cc(-c3ccc4cnn(C)c4c3)ncn2)c(OC)cc1N(C)CCN(C)CC]
180
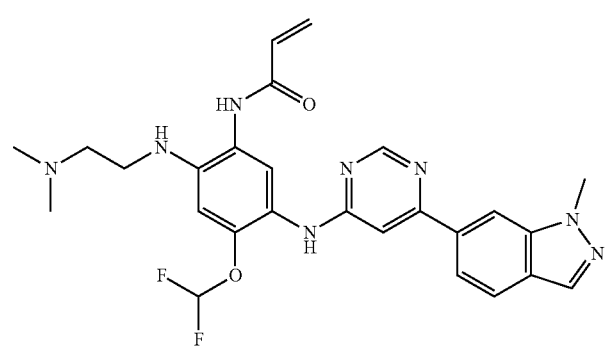 [SMILES: C=CC(=O)Nc1cc(Nc2cc(-c3ccc4cnn(C)c4c3)ncn2)c(OC(F)F)cc1NCCN(C)C]
181
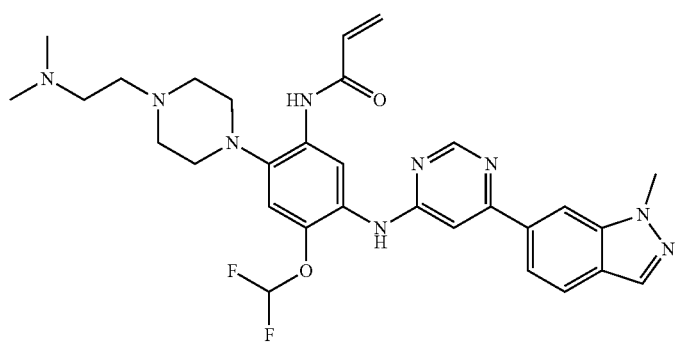 [SMILES: C=CC(=O)Nc1cc(Nc2cc(-c3ccc4cnn(C)c4c3)ncn2)c(OC(F)F)cc1N1CCN(CCN(C)C)CC1]
182
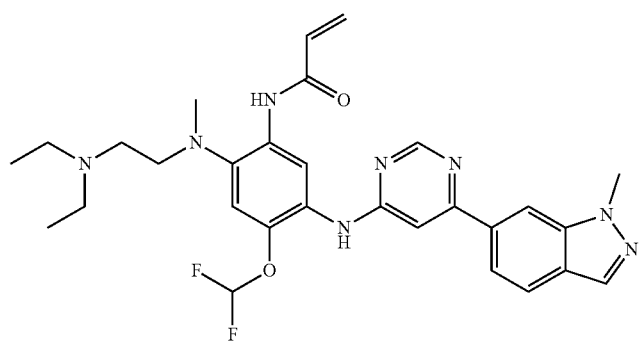 [SMILES: C=CC(=O)Nc1cc(Nc2cc(-c3ccc4cnn(C)c4c3)ncn2)c(OC(F)F)cc1N(C)CCN(CC)CC]
183

TABLE 7-continued
Compounds as EGFR Kinase Inhibitor (Final Products)
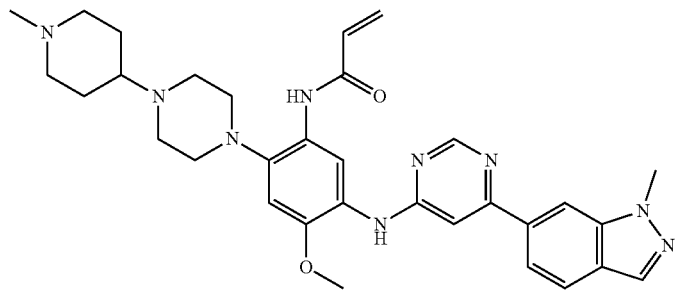 [SMILES: C=CC(=O)Nc1cc(Nc2cc(-c3ccc4cnn(C)c4c3)ncn2)c(OC)cc1N1CCN(C2CCN(C)CC2)CC1]
184
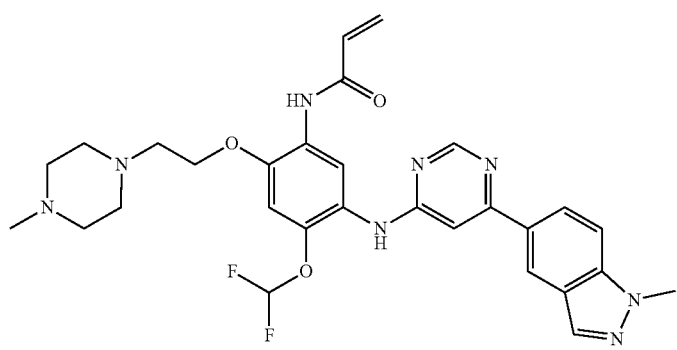
185
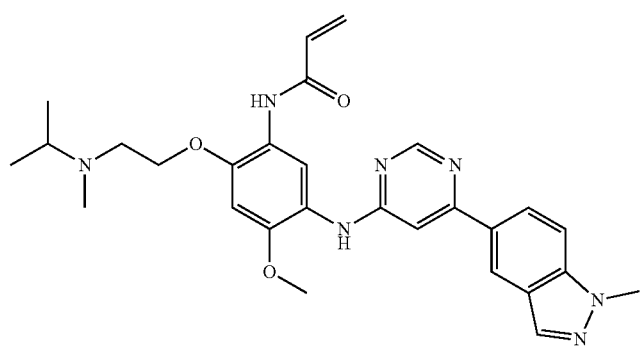 [SMILES: C=CC(=O)Nc1cc(Nc2cc(-c3ccc4c(cnn4C)c3)ncn2)c(OC)cc1OCCN(C)C(C)C]
186
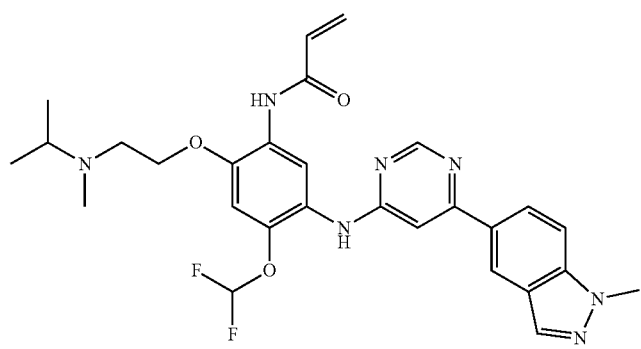 [SMILES: C=CC(=O)Nc1cc(Nc2cc(-c3ccc4c(cnn4C)c3)ncn2)c(OC(F)F)cc1OCCN(C)C(C)C]
187

TABLE 7-continued
Compounds as EGFR Kinase Inhibitor (Final Products)
188
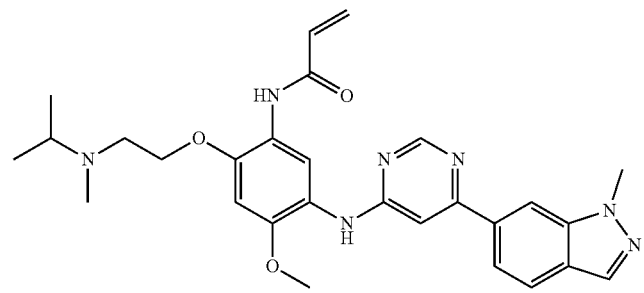 [SMILES: C=CC(=O)Nc1cc(Nc2cc(-c3ccc4cnn(C)c4c3)ncn2)c(OC)cc1OCCN(C)C(C)C]
189
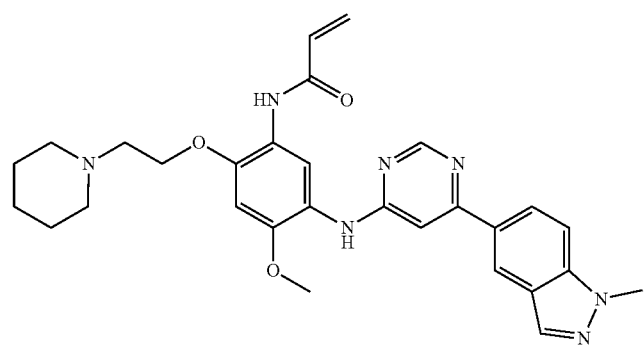 [SMILES: C=CC(=O)Nc1cc(Nc2cc(-c3ccc4c(cnn4C)c3)ncn2)c(OC)cc1OCCN1CCCCC1]
190
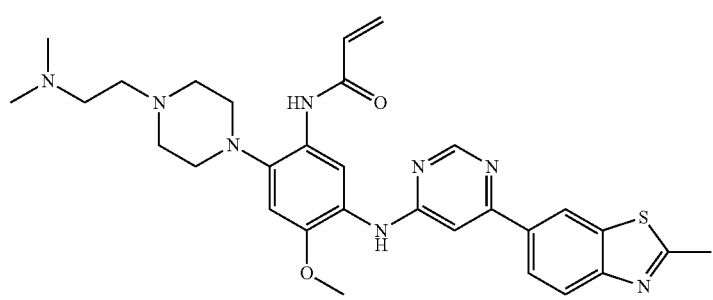
191
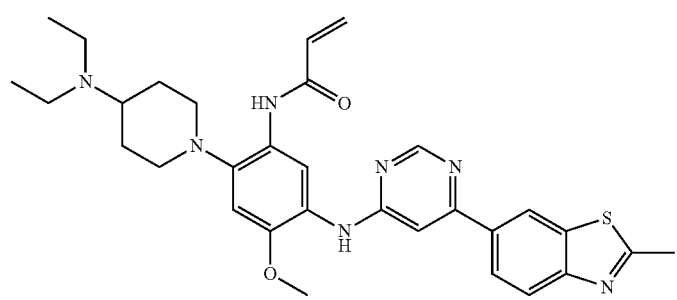 [SMILES: C=CC(=O)Nc1cc(Nc2cc(-c3ccc4nc(C)sc4c3)ncn2)c(OC)cc1N1CCC(N(CC)CC)CC1]
192
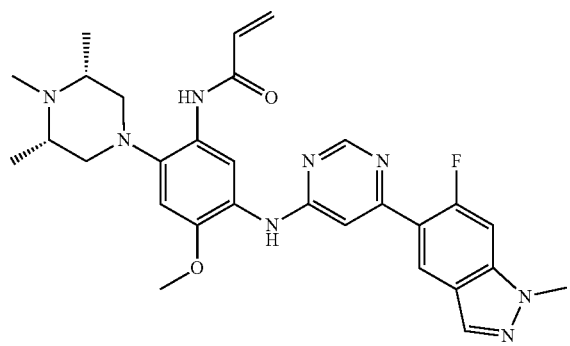

TABLE 7-continued
Compounds as EGFR Kinase Inhibitor (Final Products)
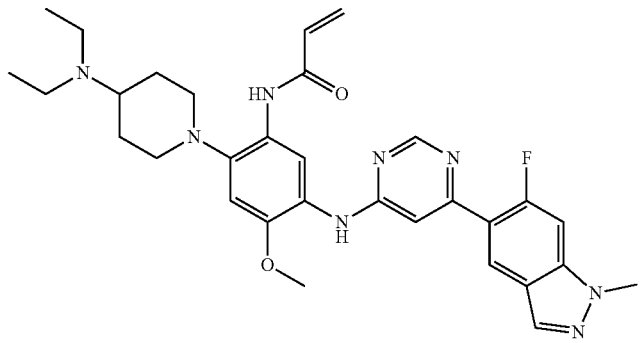 [SMILES: C=CC(=O)Nc1cc(Nc2cc(-c3cc4cnn(C)c4cc3F)ncn2)c(OC)cc1N1CCC(N(CC)CC)CC1]
193
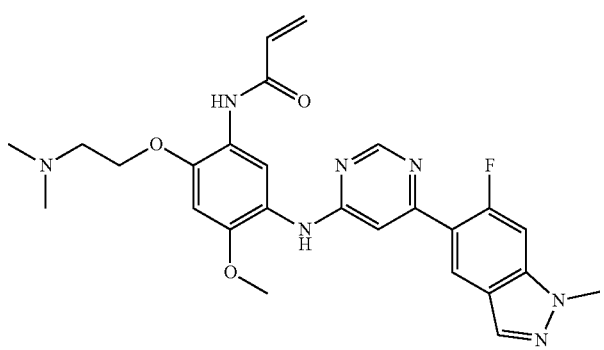
194
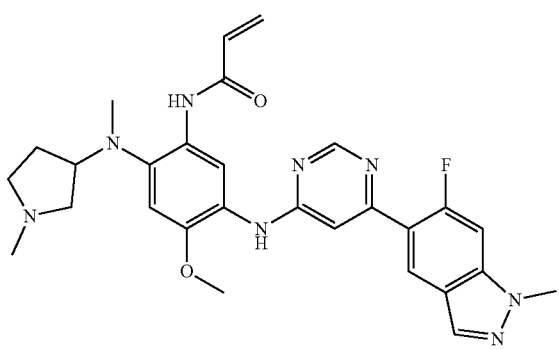 [SMILES: C=CC(=O)Nc1cc(Nc2cc(-c3cc4cnn(C)c4cc3F)ncn2)c(OC)cc1N(C)C1CCN(C)C1]
195
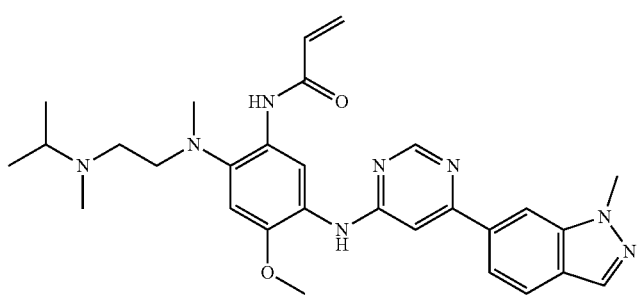 [SMILES: C=CC(=O)Nc1cc(Nc2cc(-c3ccc4cnn(C)c4c3)ncn2)c(OC)cc1N(C)CCN(C)C(C)C]
196

TABLE 7-continued
Compounds as EGFR Kinase Inhibitor (Final Products)
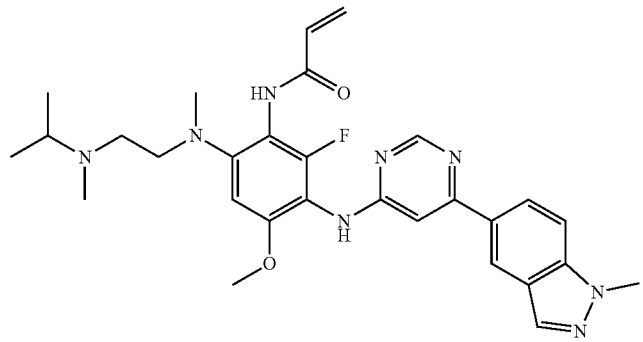 [SMILES: C=CC(=O)Nc1c(N(C)CCN(C)C(C)C)cc(OC)c(Nc2cc(-c3ccc4c(cnn4C)c3)ncn2)c1F]
197
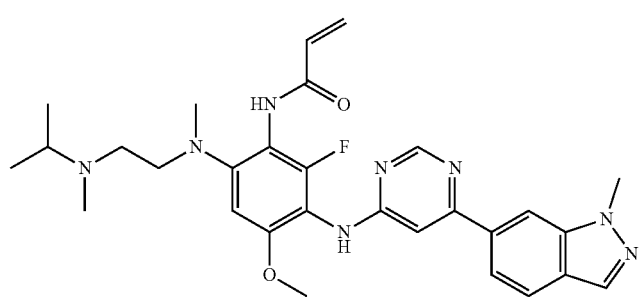 [SMILES: C=CC(=O)Nc1c(N(C)CCN(C)C(C)C)cc(OC)c(Nc2cc(-c3ccc4cnn(C)c4c3)ncn2)c1F]
198
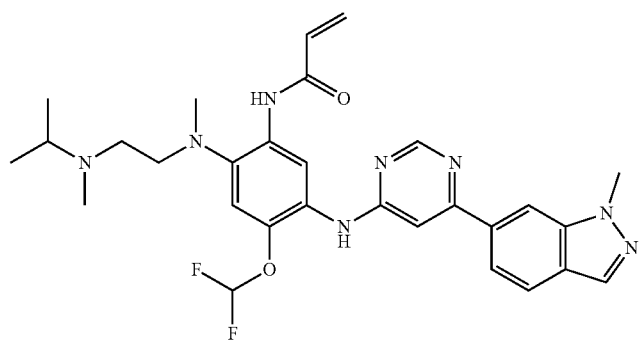 [SMILES: C=CC(=O)Nc1cc(Nc2cc(-c3ccc4cnn(C)c4c3)ncn2)c(OC(F)F)cc1N(C)CCN(C)C(C)C]
199
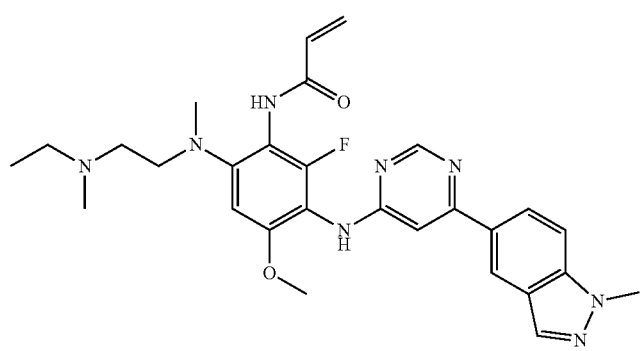 [SMILES: C=CC(=O)Nc1c(N(C)CCN(C)CC)cc(OC)c(Nc2cc(-c3ccc4c(cnn4C)c3)ncn2)c1F]
200

TABLE 7-continued
Compounds as EGFR Kinase Inhibitor (Final Products)
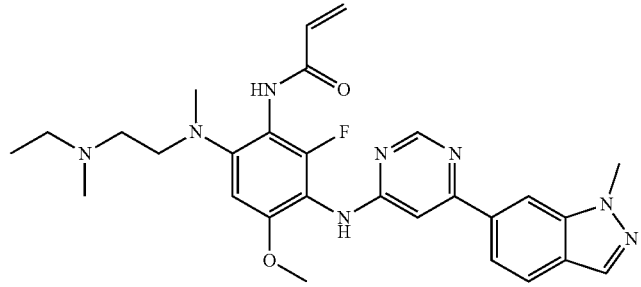 [SMILES: C=CC(=O)Nc1c(N(C)CCN(C)CC)cc(OC)c(Nc2cc(-c3ccc4cnn(C)c4c3)ncn2)c1F]
201
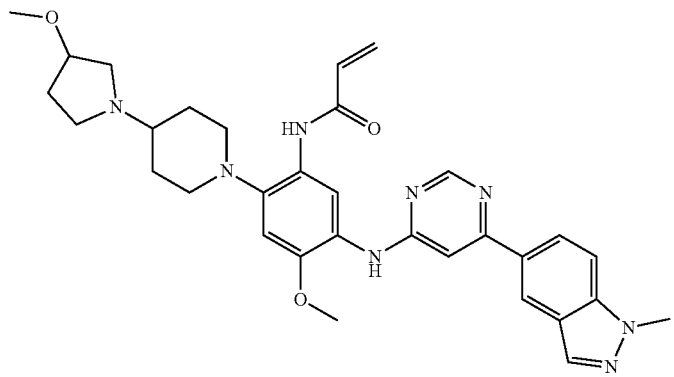
202
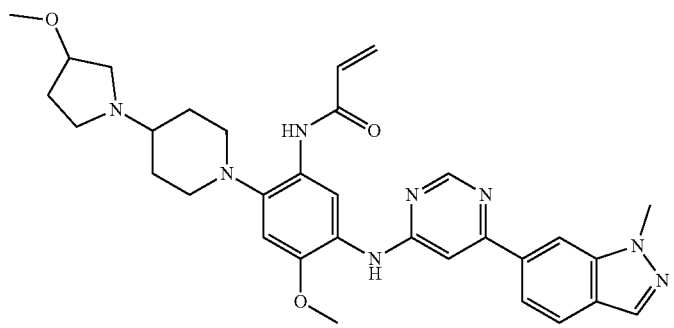 [SMILES: C=CC(=O)Nc1cc(Nc2cc(-c3ccc4cnn(C)c4c3)ncn2)c(OC)cc1N1CCC(N2CCC(OC)C2)CC1]
203
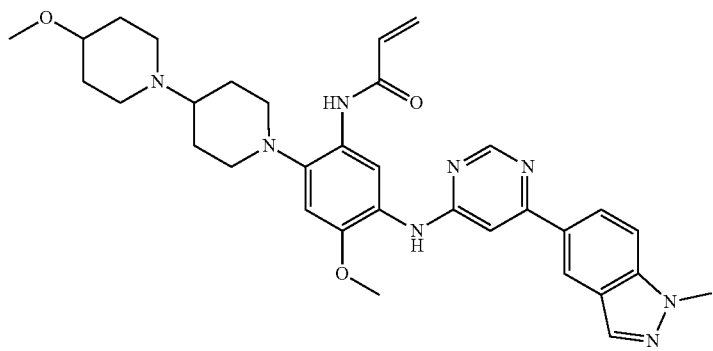
204

TABLE 7-continued
Compounds as EGFR Kinase Inhibitor (Final Products)
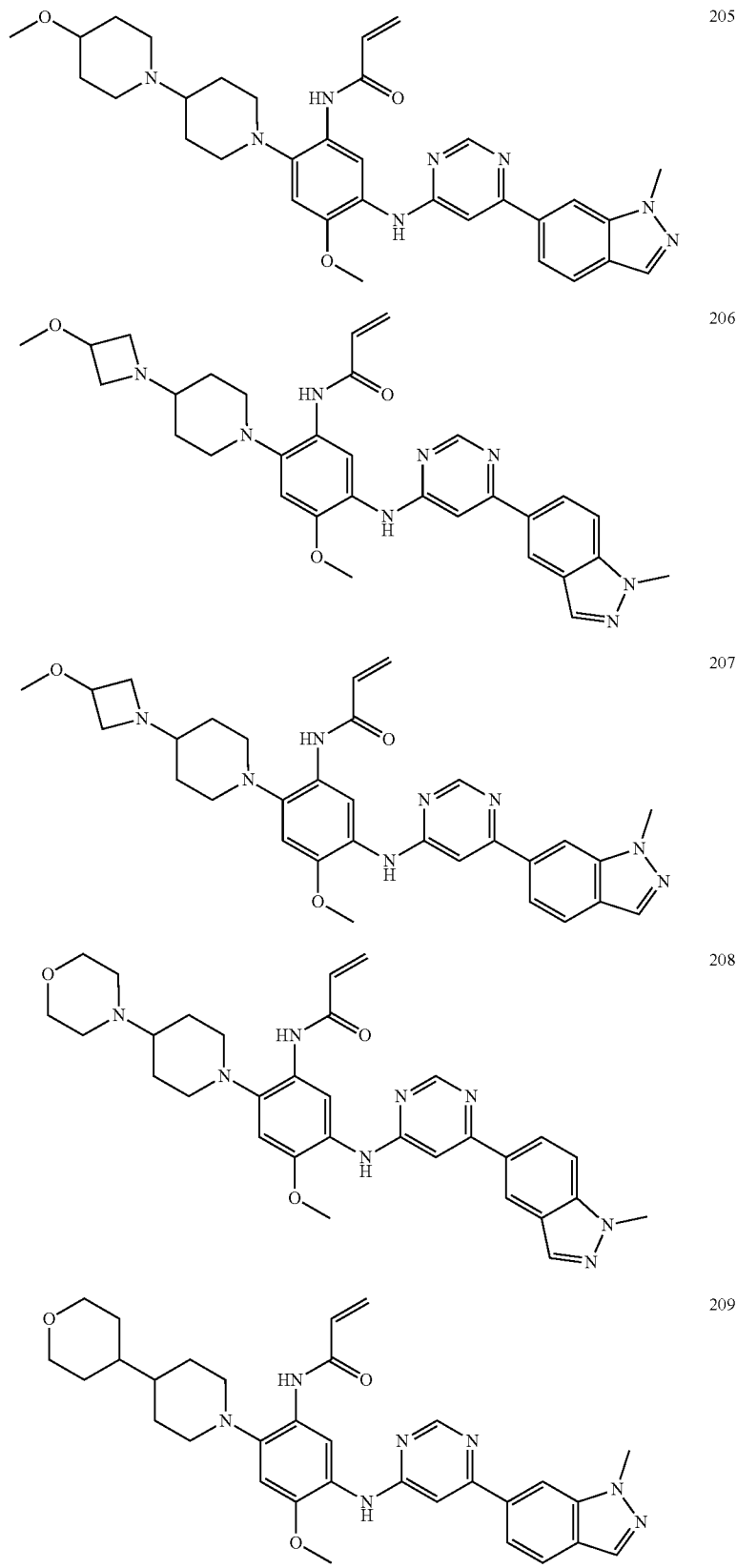
205
206
207
208
209

TABLE 7-continued
Compounds as EGFR Kinase Inhibitor (Final Products)
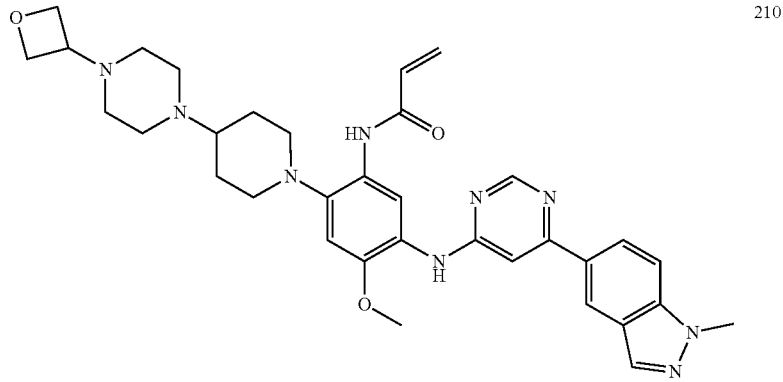
210
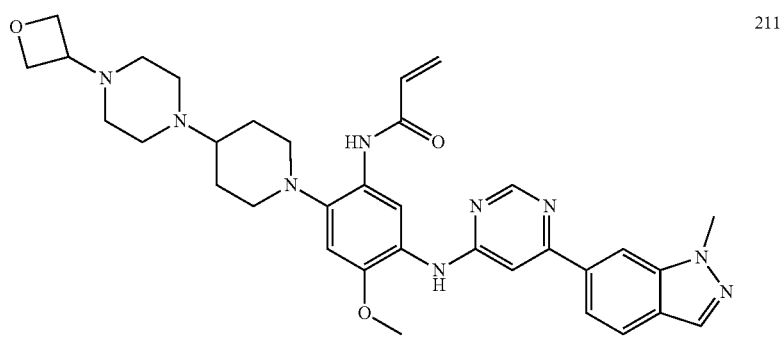
211
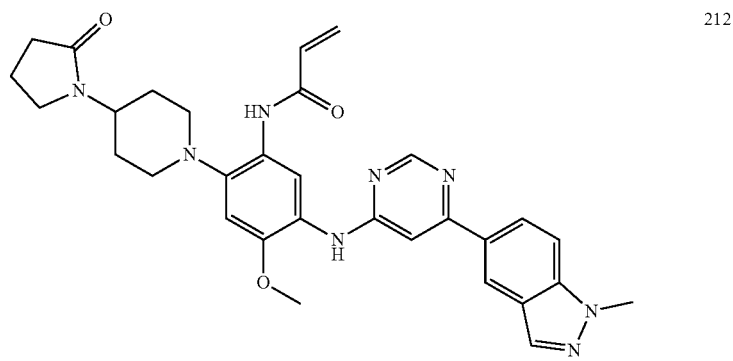
212
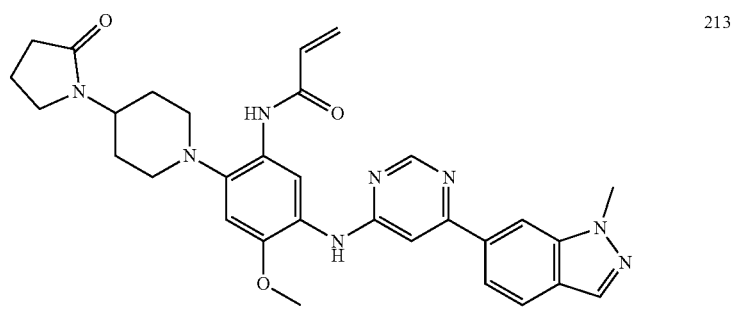
213

TABLE 7-continued
Compounds as EGFR Kinase Inhibitor (Final Products)
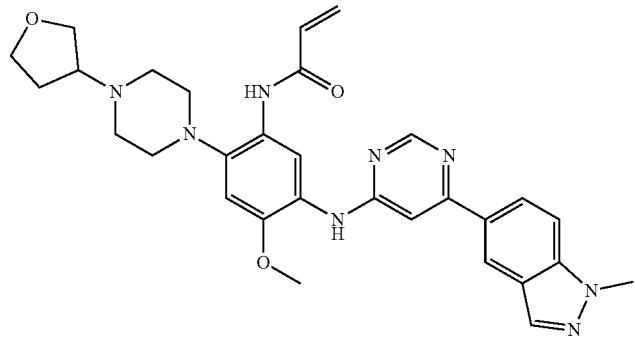 [SMILES: C=CC(=O)Nc1cc(Nc2cc(-c3ccc4c(cnn4C)c3)ncn2)c(OC)cc1N1CCN(C2CCOC2)CC1]
214
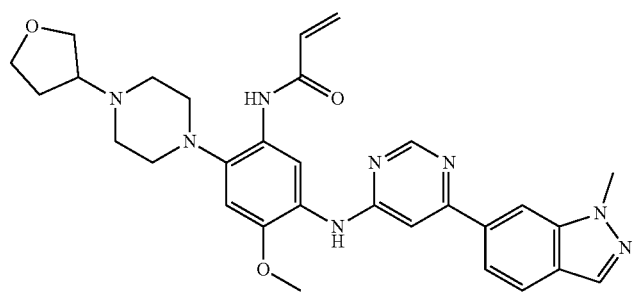 [SMILES: C=CC(=O)Nc1cc(Nc2cc(-c3ccc4cnn(C)c4c3)ncn2)c(OC)cc1N1CCN(C2CCOC2)CC1]
215
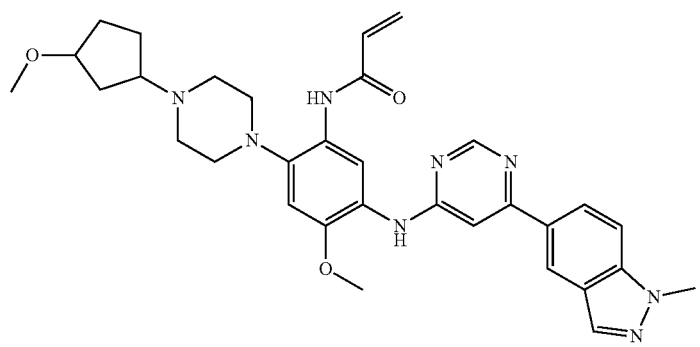
216
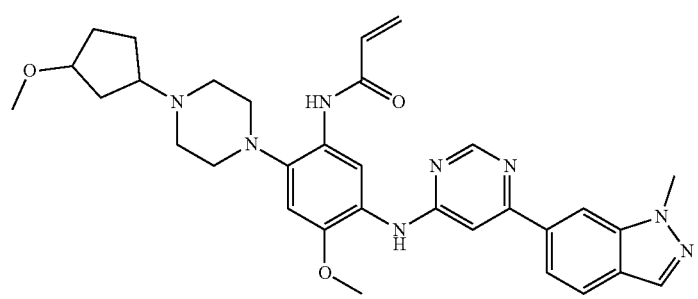 [SMILES: C=CC(=O)Nc1cc(Nc2cc(-c3ccc4cnn(C)c4c3)ncn2)c(OC)cc1N1CCN(C2CCC(OC)C2)CC1]
217

TABLE 7-continued
Compounds as EGFR Kinase Inhibitor (Final Products)
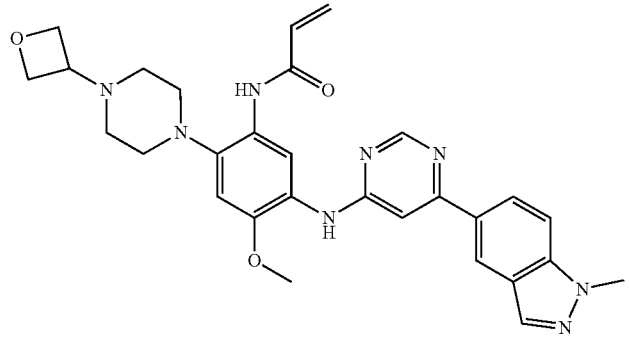 [SMILES: C=CC(=O)Nc1cc(Nc2cc(-c3ccc4c(cnn4C)c3)ncn2)c(OC)cc1N1CCN(C2COC2)CC1]
218
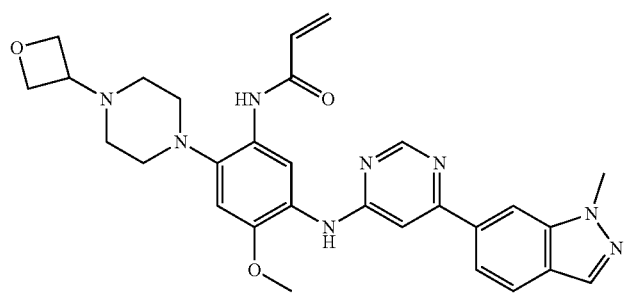 [SMILES: C=CC(=O)Nc1cc(Nc2cc(-c3ccc4cnn(C)c4c3)ncn2)c(OC)cc1N1CCN(C2COC2)CC1]
219
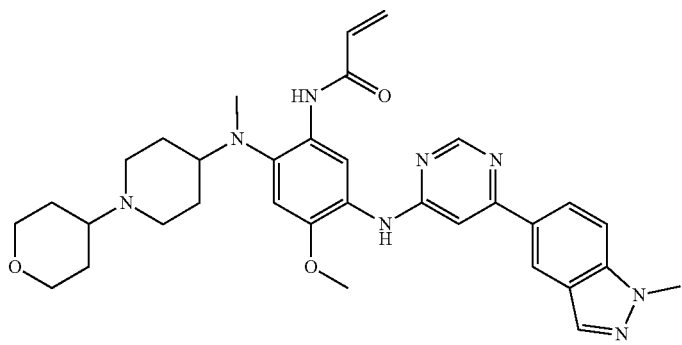 [SMILES: C=CC(=O)Nc1cc(Nc2cc(-c3ccc4c(cnn4C)c3)ncn2)c(OC)cc1N(C)C1CCN(C2CCOCC2)CC1]
220
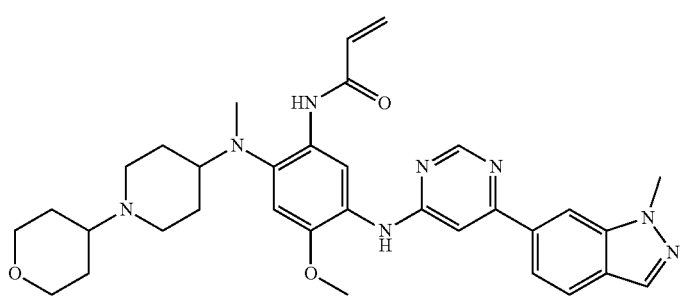 [SMILES: C=CC(=O)Nc1cc(Nc2cc(-c3ccc4cnn(C)c4c3)ncn2)c(OC)cc1N(C)C1CCN(C2CCOCC2)CC1]
221

TABLE 7-continued
Compounds as EGFR Kinase Inhibitor (Final Products)
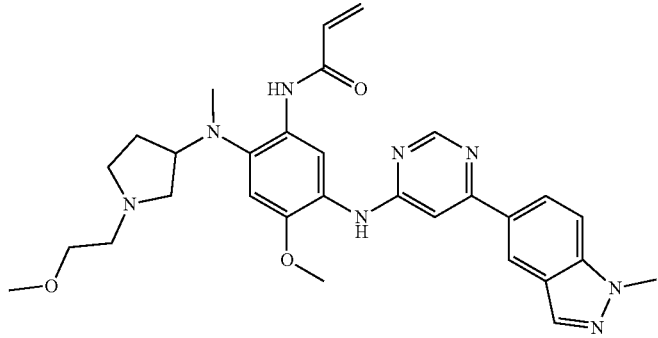
222
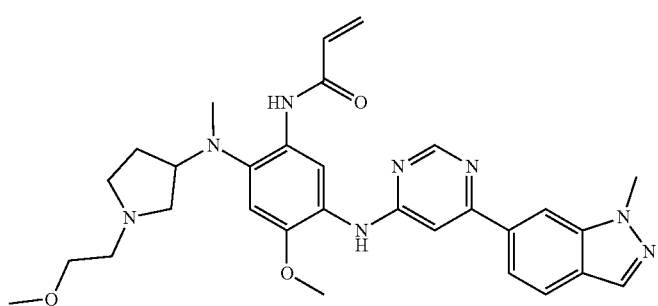 [SMILES: C=CC(=O)Nc1cc(Nc2cc(-c3ccc4cnn(C)c4c3)ncn2)c(OC)cc1N(C)C1CCN(CCOC)C1]
223
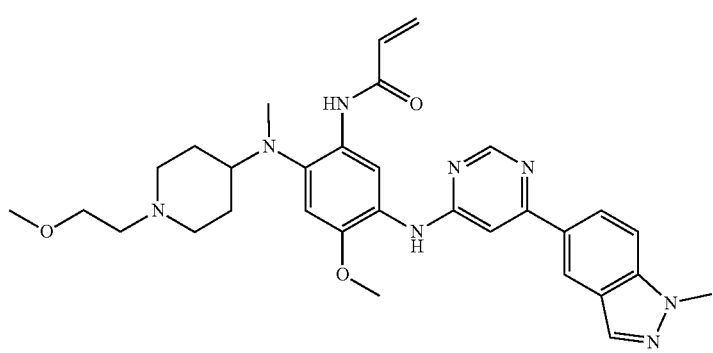
224
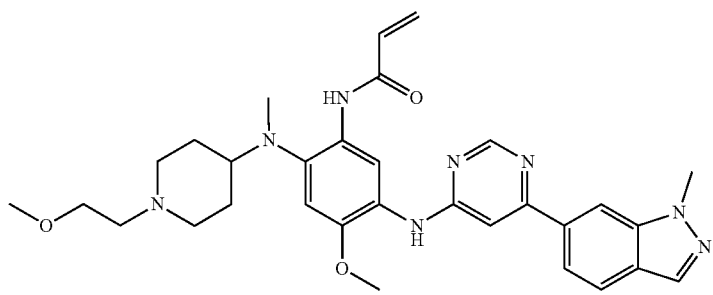 [SMILES: C=CC(=O)Nc1cc(Nc2cc(-c3ccc4cnn(C)c4c3)ncn2)c(OC)cc1N(C)C1CCN(CCOC)CC1]
225

TABLE 7-continued
Compounds as EGFR Kinase Inhibitor (Final Products)
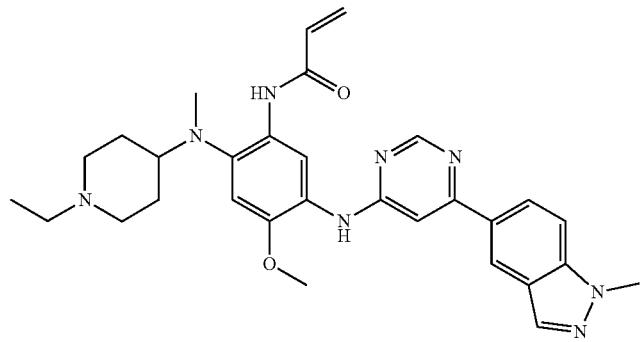 [SMILES: C=CC(=O)Nc1cc(Nc2cc(-c3ccc4c(cnn4C)c3)ncn2)c(OC)cc1N(C)C1CCN(CC)CC1]
226
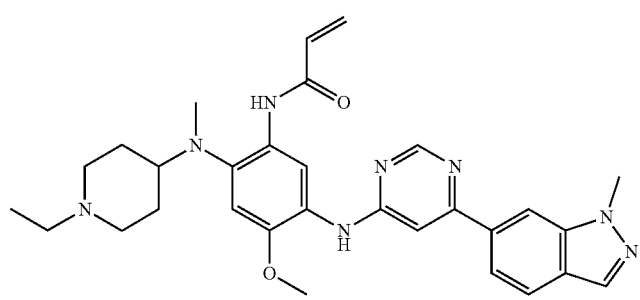 [SMILES: C=CC(=O)Nc1cc(Nc2cc(-c3ccc4cnn(C)c4c3)ncn2)c(OC)cc1N(C)C1CCN(CC)CC1]
227
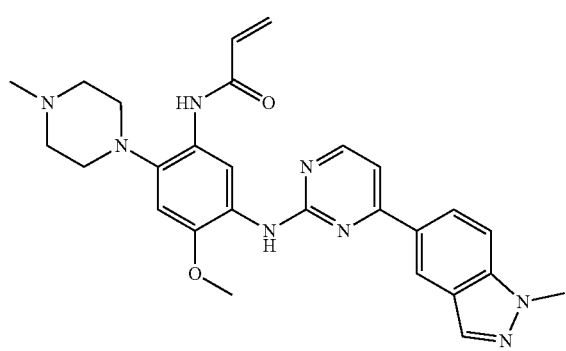
228
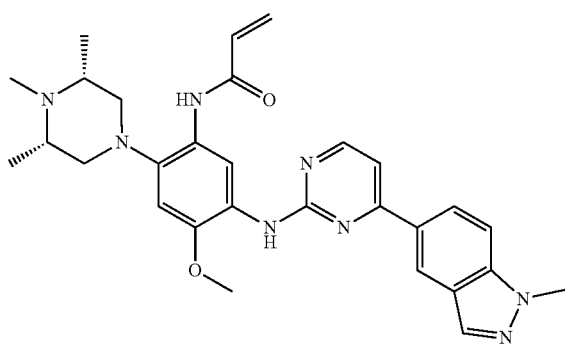
229

423
TABLE 7-continued
Compounds as EGFR Kinase Inhibitor (Final Products)
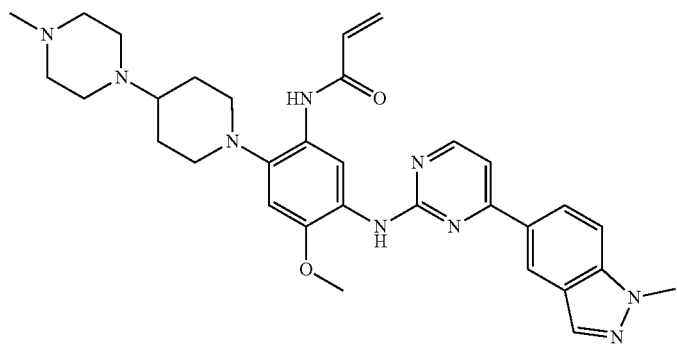
230
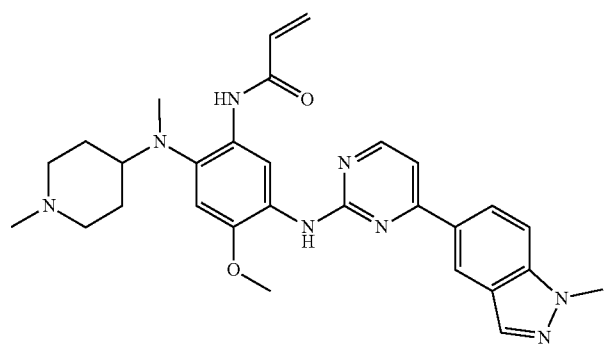
231
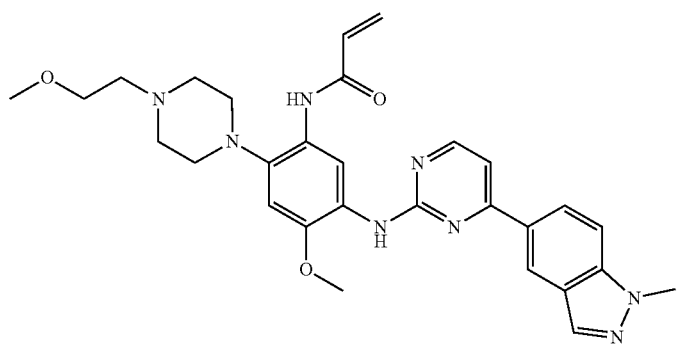
232
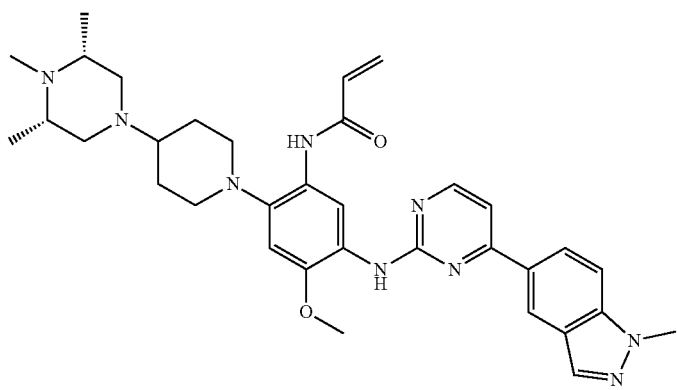
233

TABLE 7-continued
Compounds as EGFR Kinase Inhibitor (Final Products)
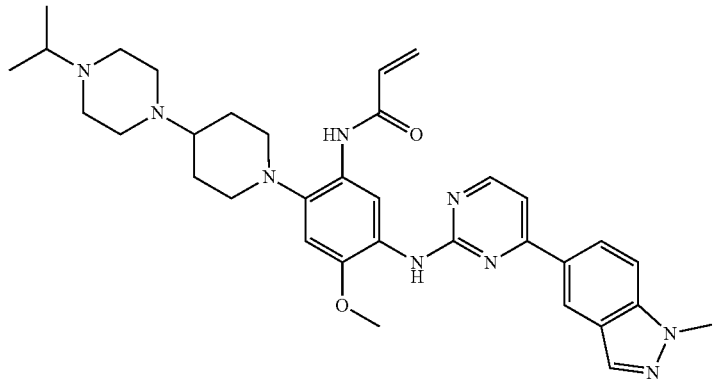 [SMILES: C=CC(=O)Nc1cc(Nc2nccc(-c3ccc4c(cnn4C)c3)n2)c(OC)cc1N1CCC(N2CCN(C(C)C)CC2)CC1]
234
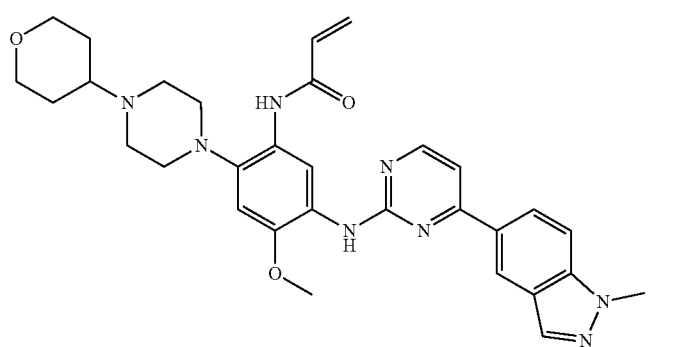 [SMILES: C=CC(=O)Nc1cc(Nc2nccc(-c3ccc4c(cnn4C)c3)n2)c(OC)cc1N1CCN(C2CCOCC2)CC1]
235
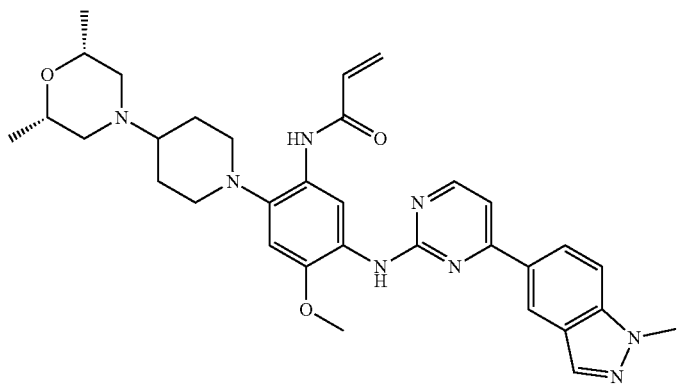
236
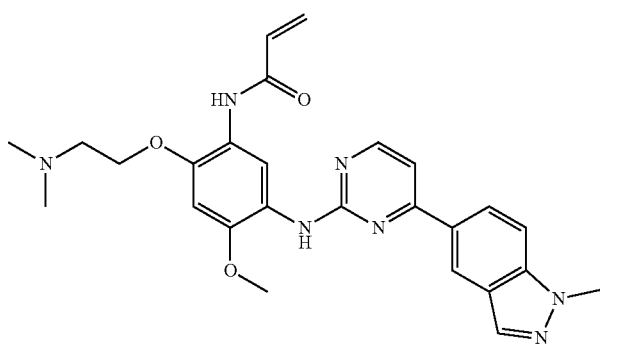
237

TABLE 7-continued
Compounds as EGFR Kinase Inhibitor (Final Products)
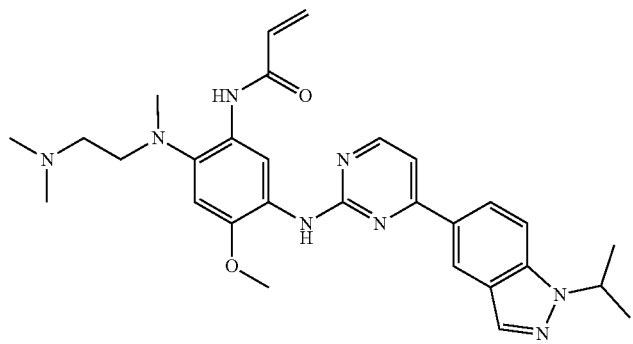 [SMILES: C=CC(=O)Nc1cc(Nc2nccc(-c3ccc4c(cnn4C(C)C)c3)n2)c(OC)cc1N(C)CCN(C)C]
238
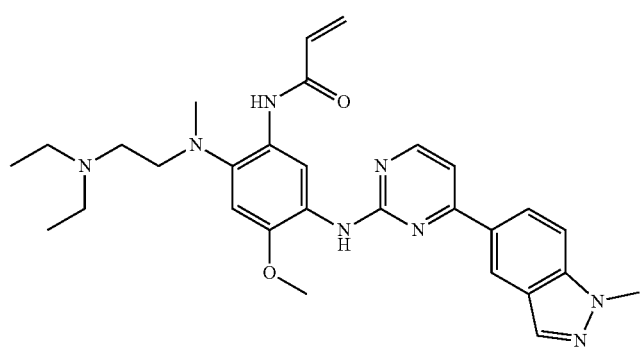 [SMILES: C=CC(=O)Nc1cc(Nc2nccc(-c3ccc4c(cnn4C)c3)n2)c(OC)cc1N(C)CCN(CC)CC]
239
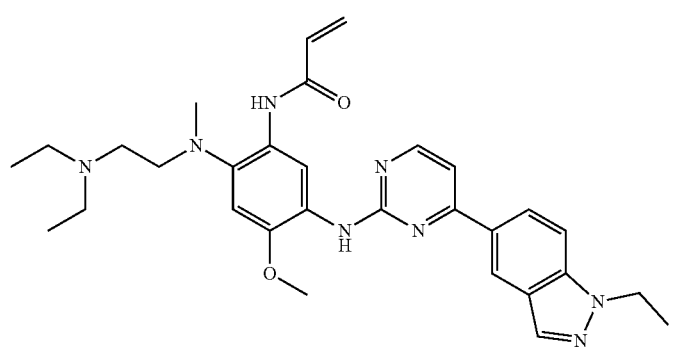 [SMILES: C=CC(=O)Nc1cc(Nc2nccc(-c3ccc4c(cnn4CC)c3)n2)c(OC)cc1N(C)CCN(CC)CC]
240
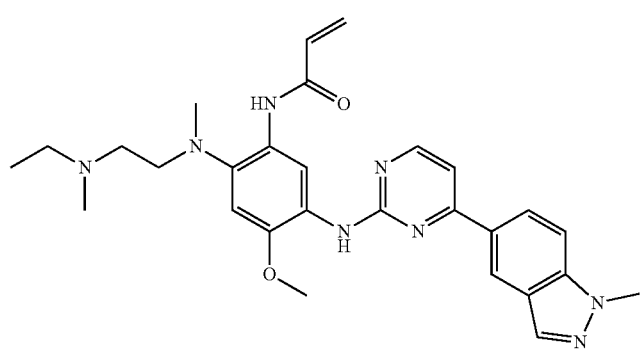 [SMILES: C=CC(=O)Nc1cc(Nc2nccc(-c3ccc4c(cnn4C)c3)n2)c(OC)cc1N(C)CCN(C)CC]
241

TABLE 7-continued
Compounds as EGFR Kinase Inhibitor (Final Products)
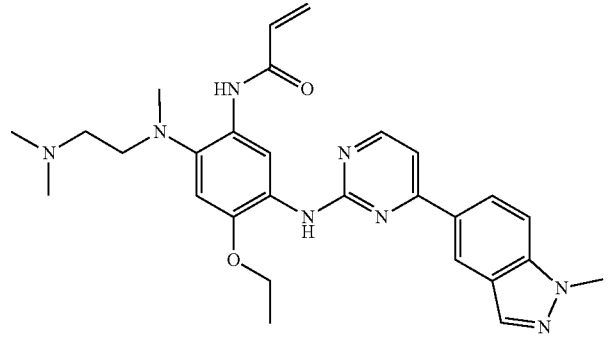
242
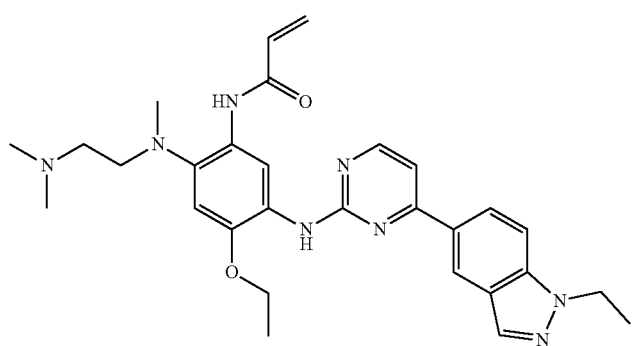 [SMILES: C=CC(=O)Nc1cc(Nc2nccc(-c3ccc4c(cnn4CC)c3)n2)c(OCC)cc1N(C)CCN(C)C]
243
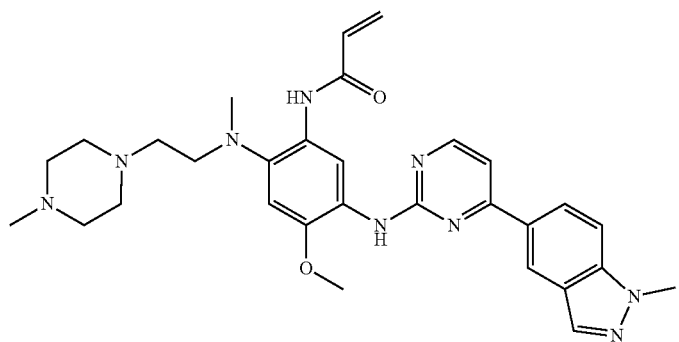
244
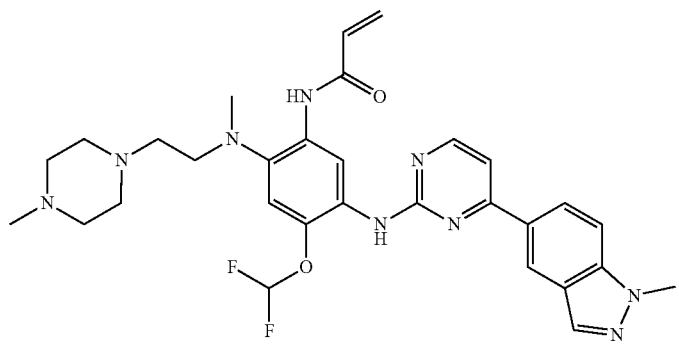
245

TABLE 7-continued
Compounds as EGFR Kinase Inhibitor (Final Products)
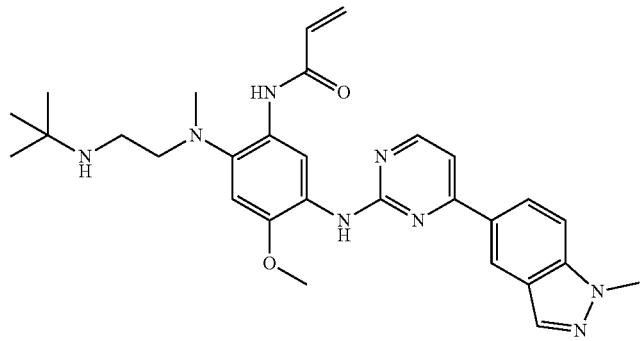 [SMILES: C=CC(=O)Nc1cc(Nc2nccc(-c3ccc4c(cnn4C)c3)n2)c(OC)cc1N(C)CCNC(C)(C)C]
246
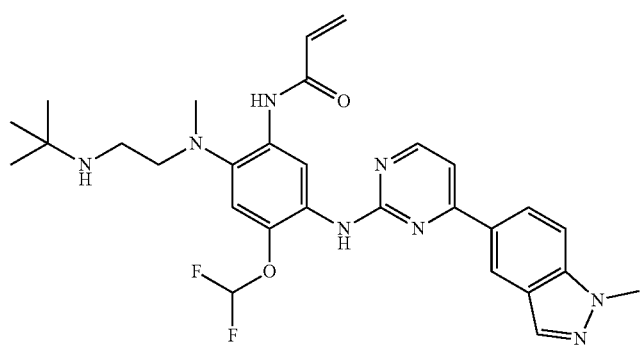 [SMILES: C=CC(=O)Nc1cc(Nc2nccc(-c3ccc4c(cnn4C)c3)n2)c(OC(F)F)cc1N(C)CCNC(C)(C)C]
247
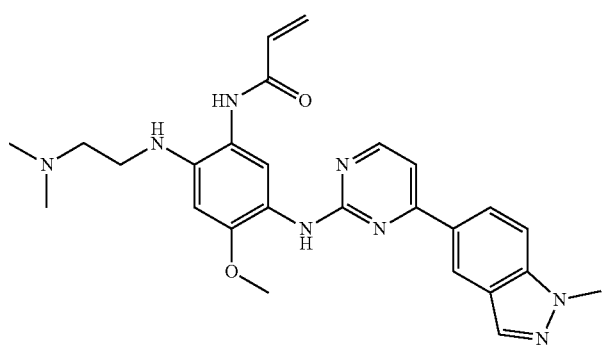
248
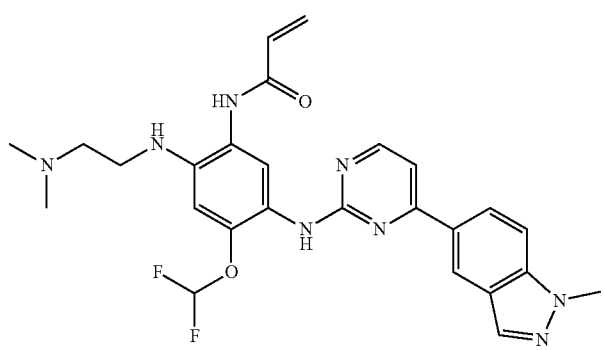
249

TABLE 7-continued
Compounds as EGFR Kinase Inhibitor (Final Products)
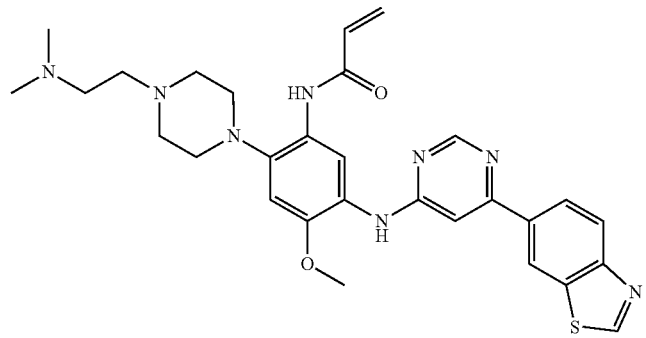 [SMILES: C=CC(=O)Nc1cc(Nc2cc(-c3ccc4ncsc4c3)ncn2)c(OC)cc1N1CCN(CCN(C)C)CC1]
250
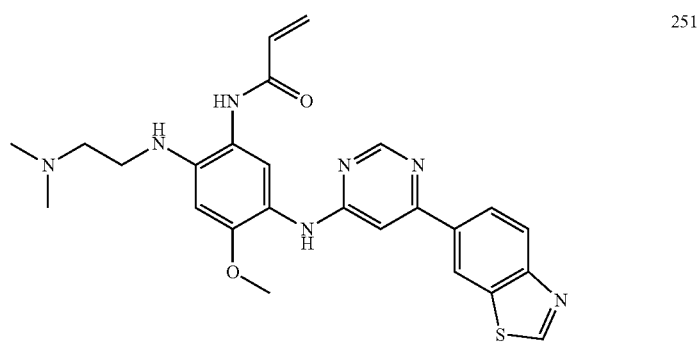
251
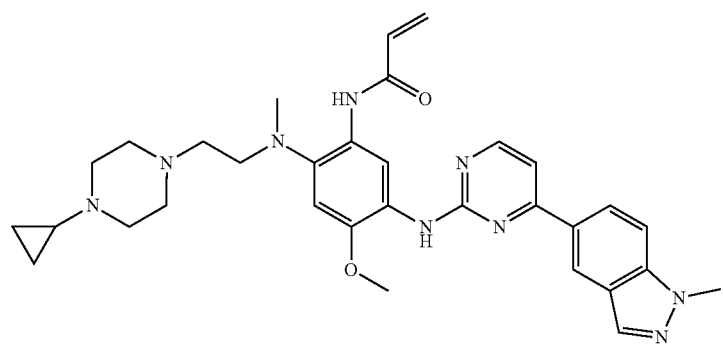 [SMILES: C=CC(=O)Nc1cc(Nc2nccc(-c3ccc4c(cnn4C)c3)n2)c(OC)cc1N(C)CCN1CCN(C2CC2)CC1]
252
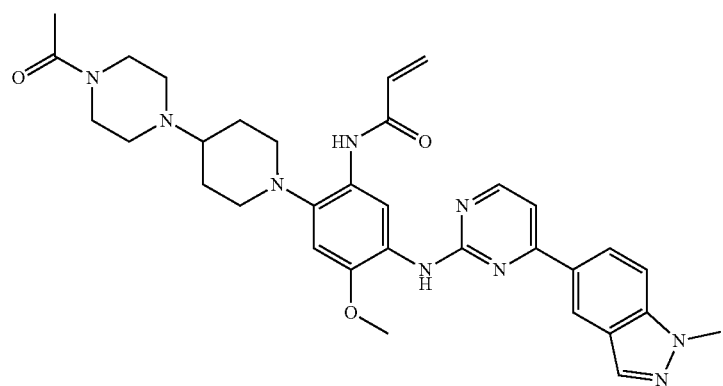 [SMILES: C=CC(=O)Nc1cc(Nc2nccc(-c3ccc4c(cnn4C)c3)n2)c(OC)cc1N1CCC(N2CCN(C(C)=O)CC2)CC1]
253

TABLE 7-continued
Compounds as EGFR Kinase Inhibitor (Final Products)
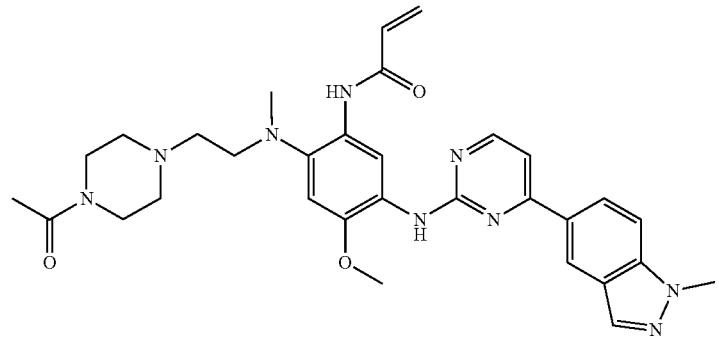 [SMILES: C=CC(=O)Nc1cc(Nc2nccc(-c3ccc4c(cnn4C)c3)n2)c(OC)cc1N(C)CCN1CCN(C(C)=O)CC1]
254
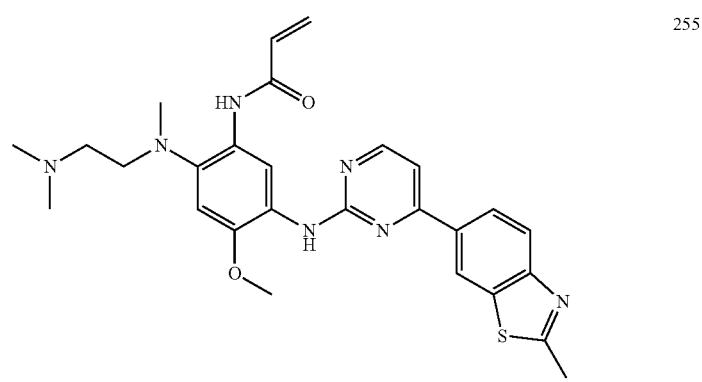
255
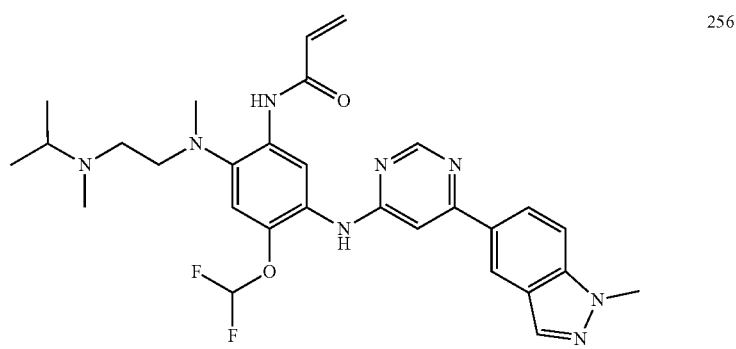
256
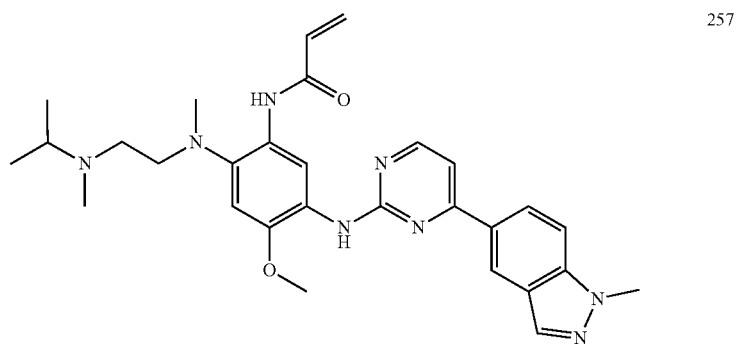
257

TABLE 7-continued
Compounds as EGFR Kinase Inhibitor (Final Products)
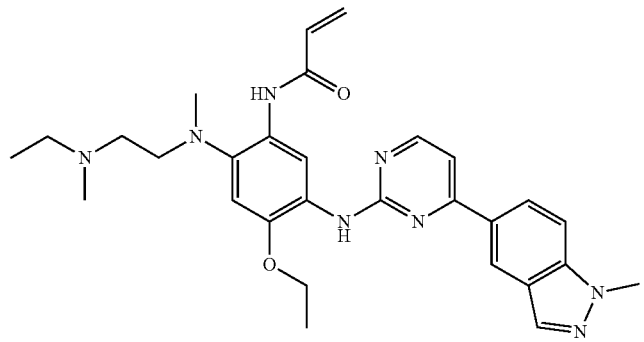
258
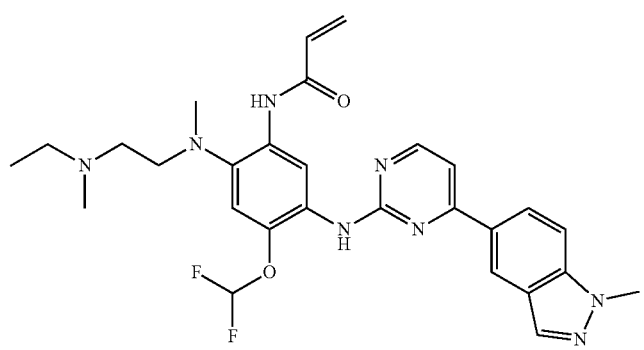 [SMILES: C=CC(=O)Nc1cc(Nc2nccc(-c3ccc4c(cnn4C)c3)n2)c(OC(F)F)cc1N(C)CCN(C)CC]
259
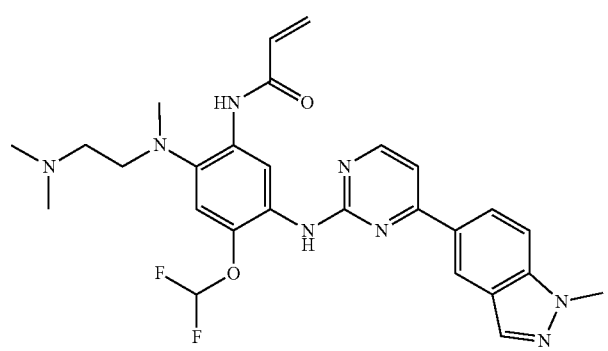
260
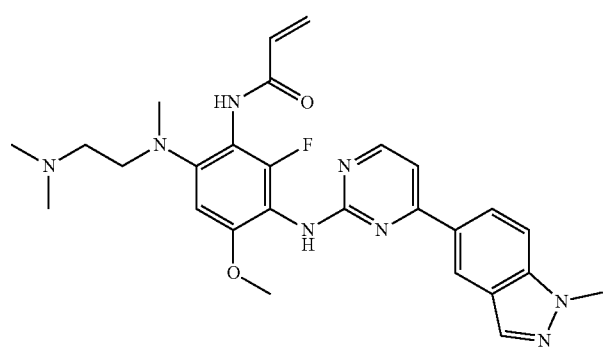
261

TABLE 7-continued
Compounds as EGFR Kinase Inhibitor (Final Products)
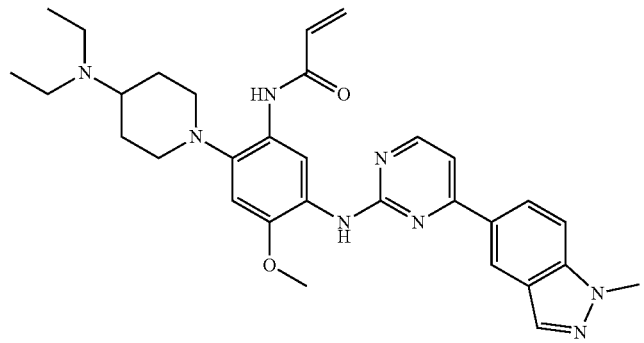 [SMILES: C=CC(=O)Nc1cc(Nc2nccc(-c3ccc4c(cnn4C)c3)n2)c(OC)cc1N1CCC(N(CC)CC)CC1]
262
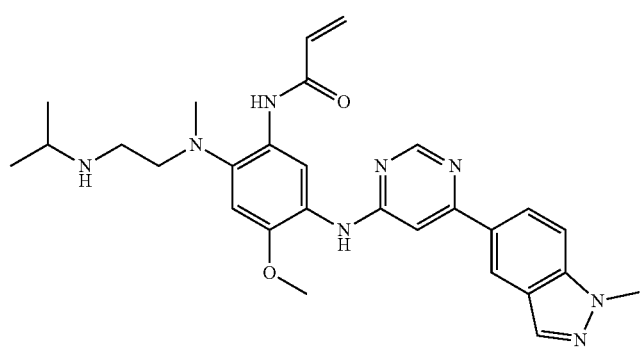 [SMILES: C=CC(=O)Nc1cc(Nc2cc(-c3ccc4c(cnn4C)c3)ncn2)c(OC)cc1N(C)CCNC(C)C]
263
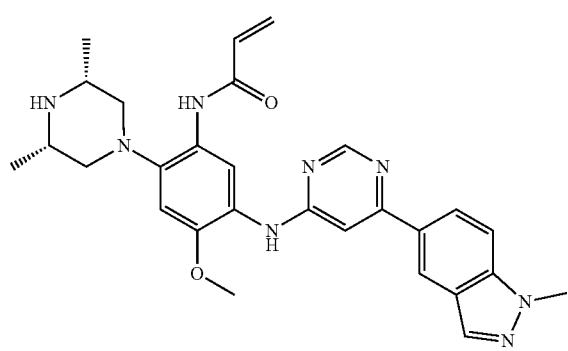
264
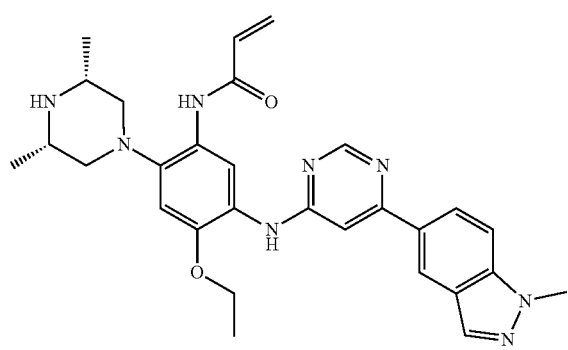
265

441
442
TABLE 7-continued
Compounds as EGFR Kinase Inhibitor (Final Products)
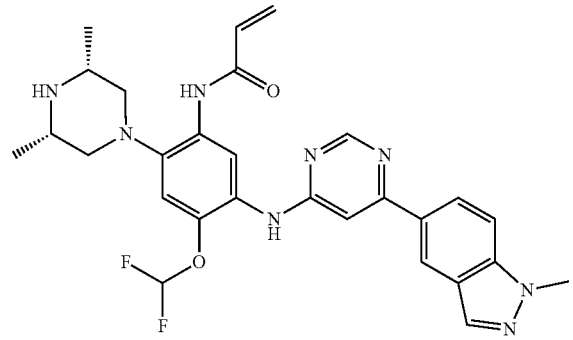
266
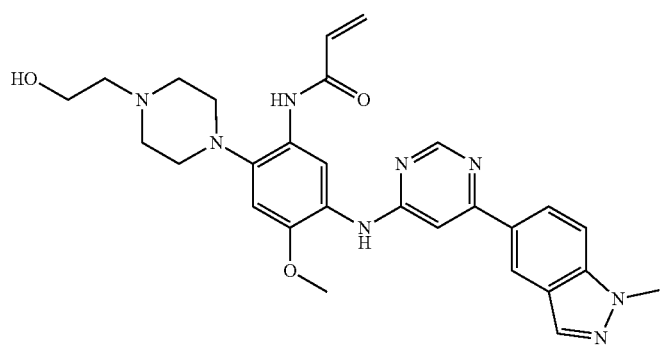 [SMILES: C=CC(=O)Nc1cc(Nc2cc(-c3ccc4c(cnn4C)c3)ncn2)c(OC)cc1N1CCN(CCO)CC1]
267
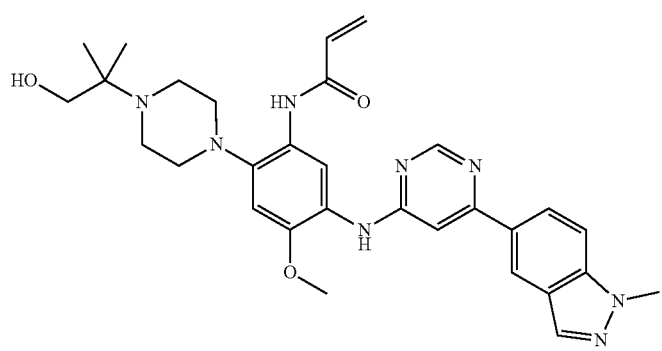 [SMILES: C=CC(=O)Nc1cc(Nc2cc(-c3ccc4c(cnn4C)c3)ncn2)c(OC)cc1N1CCN(C(C)(C)CO)CC1]
268
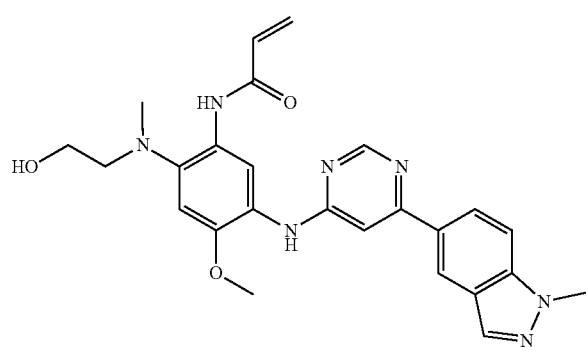 [SMILES: C=CC(=O)Nc1cc(Nc2cc(-c3ccc4c(cnn4C)c3)ncn2)c(OC)cc1N(C)CCO]
269

TABLE 7-continued
Compounds as EGFR Kinase Inhibitor (Final Products)
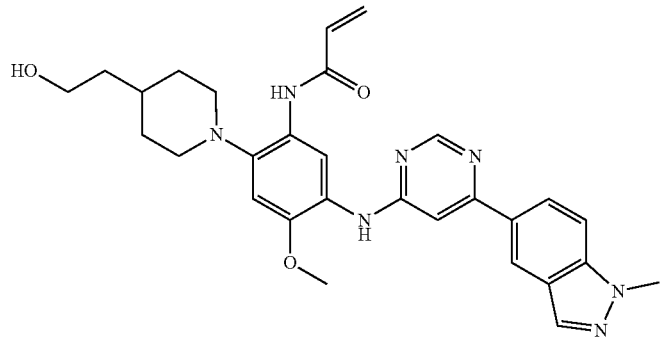 [SMILES: C=CC(=O)Nc1cc(Nc2cc(-c3ccc4c(cnn4C)c3)ncn2)c(OC)cc1N1CCC(CCO)CC1]
270
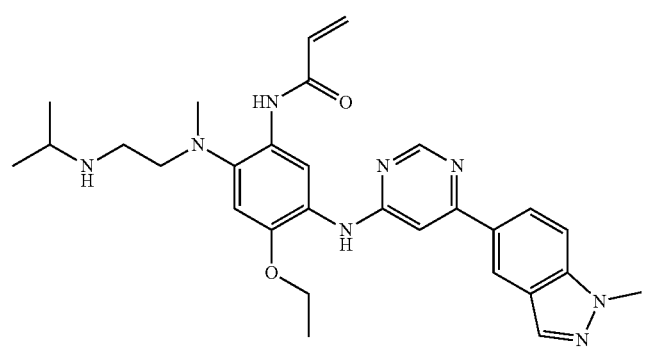 [SMILES: C=CC(=O)Nc1cc(Nc2cc(-c3ccc4c(cnn4C)c3)ncn2)c(OCC)cc1N(C)CCNC(C)C]
271
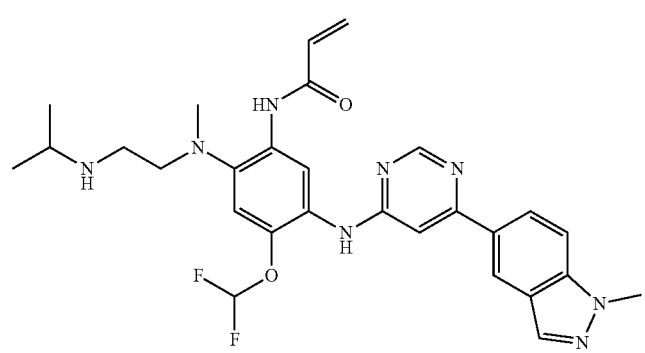 [SMILES: C=CC(=O)Nc1cc(Nc2cc(-c3ccc4c(cnn4C)c3)ncn2)c(OC(F)F)cc1N(C)CCNC(C)C]
272
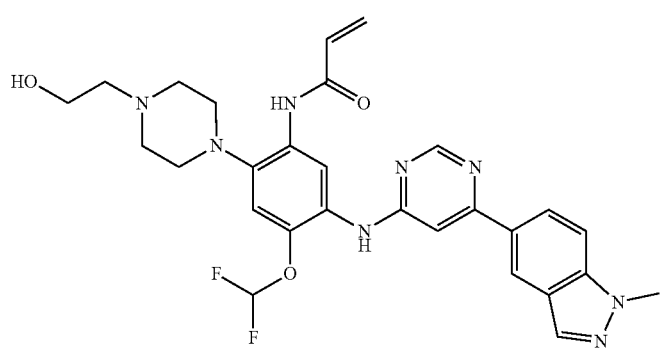 [SMILES: C=CC(=O)Nc1cc(Nc2cc(-c3ccc4c(cnn4C)c3)ncn2)c(OC(F)F)cc1N1CCN(CCO)CC1]
273

TABLE 7-continued
Compounds as EGFR Kinase Inhibitor (Final Products)
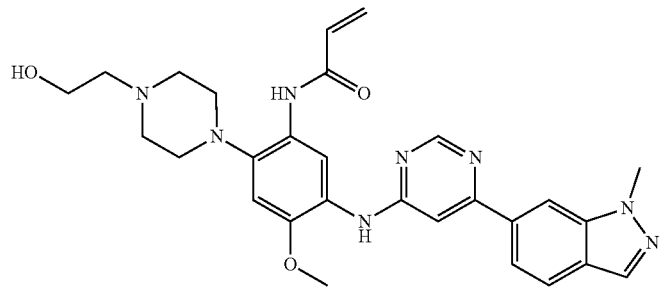 [SMILES: C=CC(=O)Nc1cc(Nc2cc(-c3ccc4cnn(C)c4c3)ncn2)c(OC)cc1N1CCN(CCO)CC1]
274
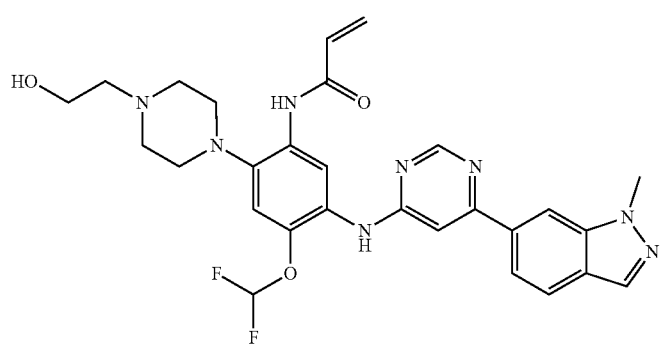 [SMILES: C=CC(=O)Nc1cc(Nc2cc(-c3ccc4cnn(C)c4c3)ncn2)c(OC(F)F)cc1N1CCN(CCO)CC1]
275
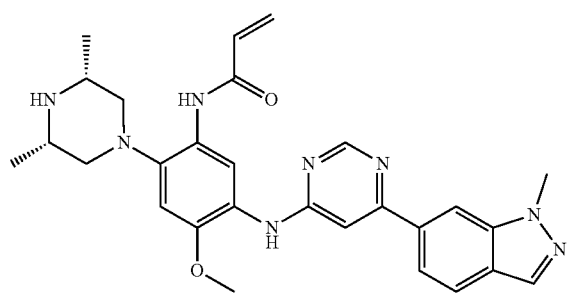 [SMILES: C=CC(=O)Nc1cc(Nc2cc(-c3ccc4cnn(C)c4c3)ncn2)c(OC)cc1N1C[C@@H](C)N[C@@H](C)C1]
276
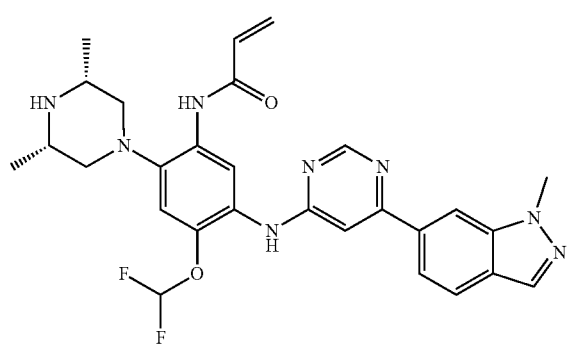 [SMILES: C=CC(=O)Nc1cc(Nc2cc(-c3ccc4cnn(C)c4c3)ncn2)c(OC(F)F)cc1N1C[C@@H](C)N[C@@H](C)C1]
277
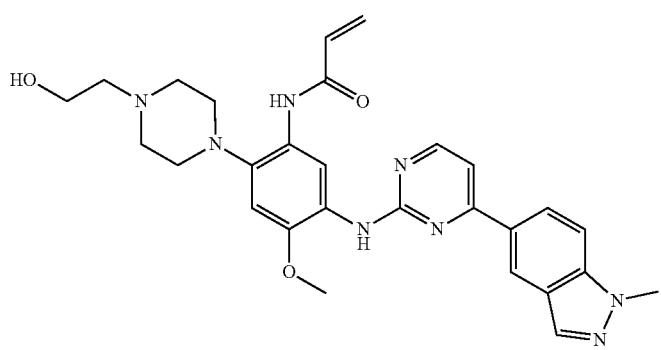 [SMILES: C=CC(=O)Nc1cc(Nc2nccc(-c3ccc4c(cnn4C)c3)n2)c(OC)cc1N1CCN(CCO)CC1]
278

TABLE 7-continued
Compounds as EGFR Kinase Inhibitor (Final Products)
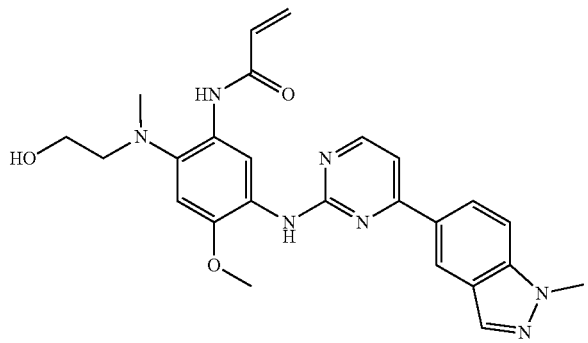
279
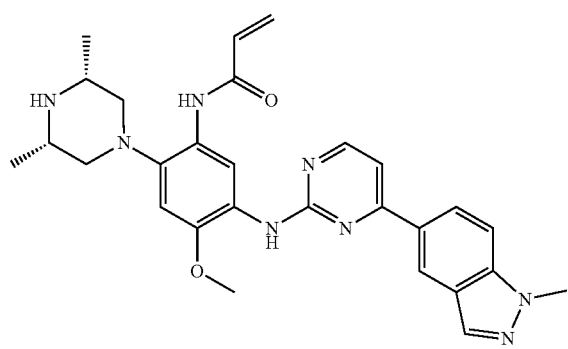
280
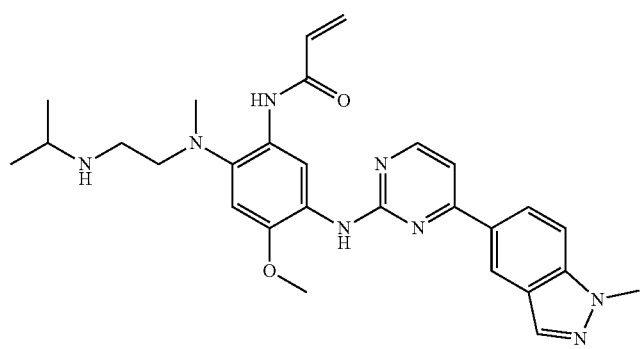 [SMILES: C=CC(=O)Nc1cc(Nc2nccc(-c3ccc4c(cnn4C)c3)n2)c(OC)cc1N(C)CCNC(C)C]
281
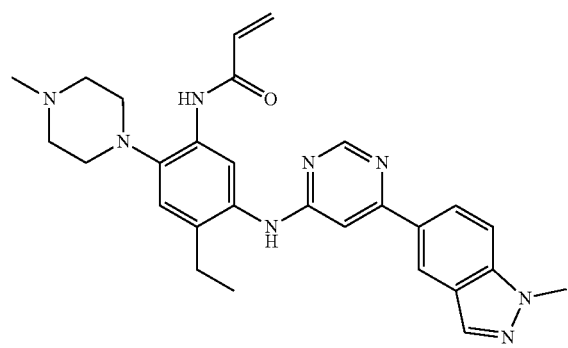
282

TABLE 7-continued
Compounds as EGFR Kinase Inhibitor (Final Products)
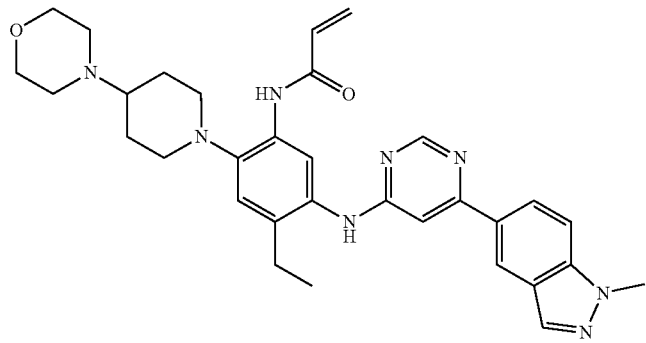 [SMILES: C=CC(=O)Nc1cc(Nc2cc(-c3ccc4c(cnn4C)c3)ncn2)c(CC)cc1N1CCC(N2CCOCC2)CC1]
283
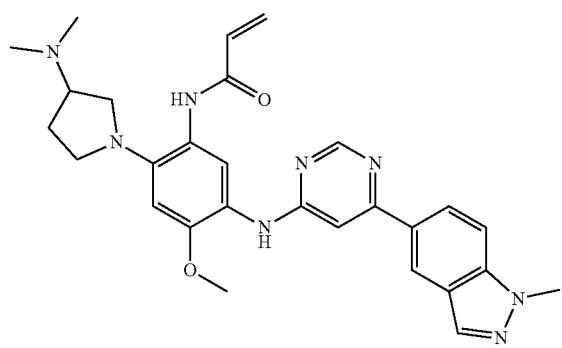
284
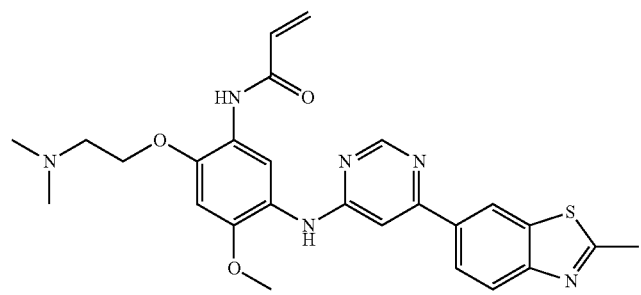
285
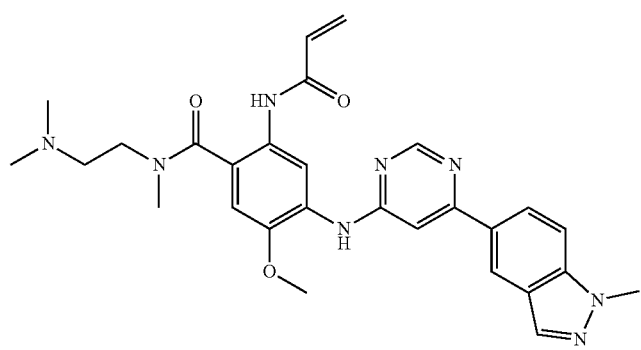
286

TABLE 7-continued
Compounds as EGFR Kinase Inhibitor (Final Products)
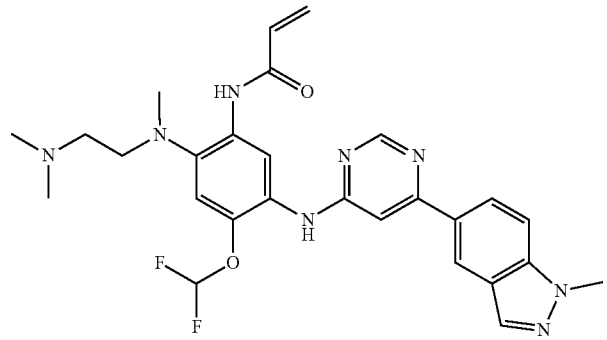
287
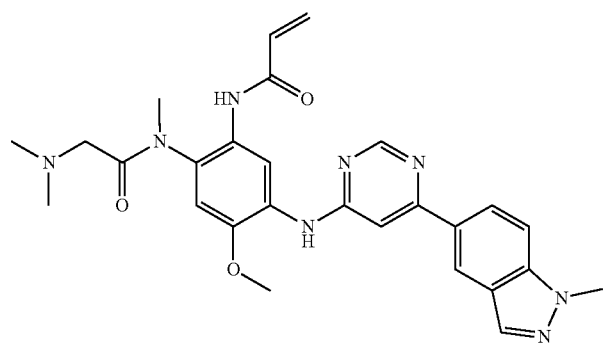
288
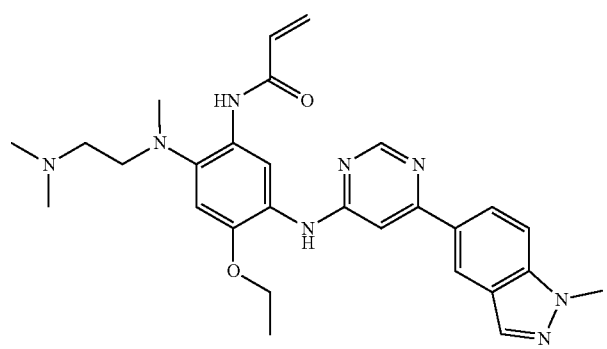
289
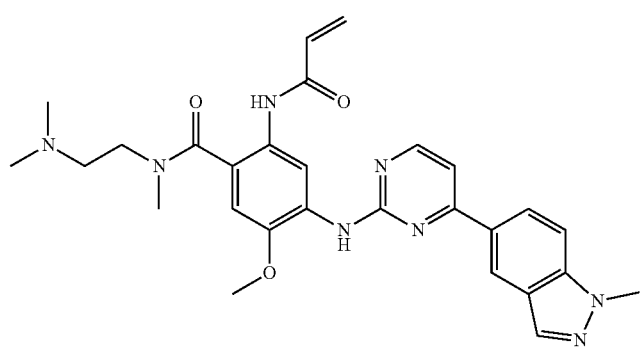
290

TABLE 7-continued
Compounds as EGFR Kinase Inhibitor (Final Products)
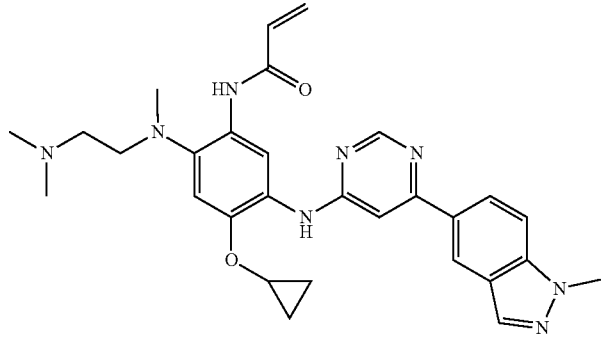
291
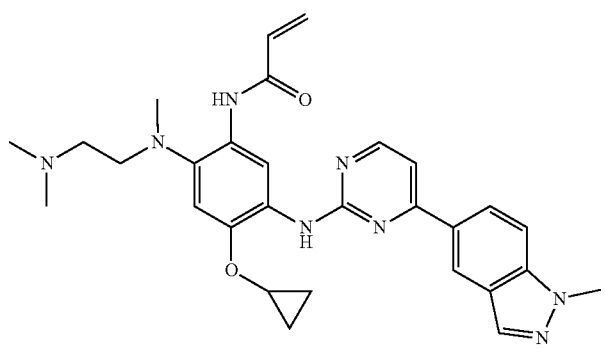
292
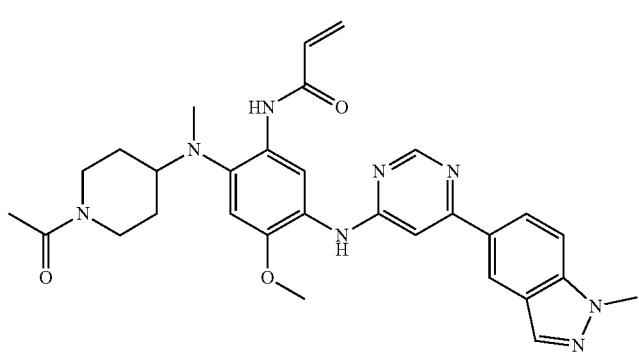 [SMILES: C=CC(=O)Nc1cc(Nc2cc(-c3ccc4c(cnn4C)c3)ncn2)c(OC)cc1N(C)C1CCN(C(C)=O)CC1]
293
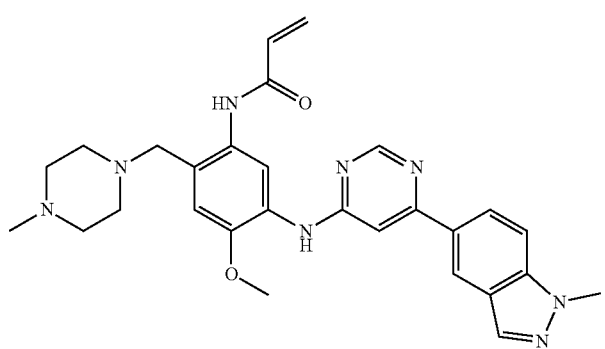
294

TABLE 7-continued

Compounds as EGFR Kinase Inhibitor (Final Products)

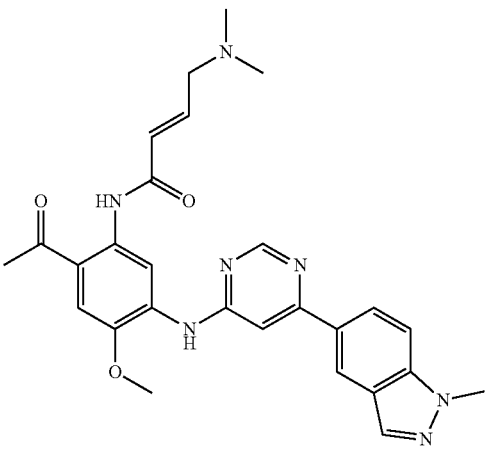 [SMILES: COc1cc(C(C)=O)c(NC(=O)/C=C/CN(C)C)cc1Nc1cc(-c2ccc3c(cnn3C)c2)ncn1]

295

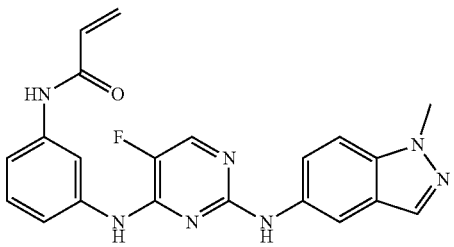 [SMILES: C=CC(=O)Nc1cccc(Nc2nc(Nc3ccc4c(cnn4C)c3)ncc2F)c1]

296

EXAMPLE 446

Cell Proliferation Inhibition Experiment

In this EXAMPLE, the celltiter-Glo (CTG) method was used to evaluate the inhibition effect of the above-prepared compounds on proliferation in three cancer cell lines NCI-H1975, PC-9 and A-431, the 50% inhibitory concentration ($IC_{50}$) was calculated.

1. Experimental Design

Compounds were tested in the selected cell lines, and solvent is set as control, nine concentrations were detected with three parallel wells for each concentration.

2. Reagents and Materials
  1) fetal bovine serum FBS (GIBCO, Cat #10099-141)
  2) CellTiter-Glo® Luminescent Cell Viability Assay (Promega, Cat #G7572)
  3) 96-well plate with flat clear bottom, black wall plates (Corning®, Cat #3340)

3. Instruments

EnVision multi-labelled microporous plate detector, PerkinElmer, 2104-0010A; $CO_2$ incubator, Thermo Scientific, Model 3100 Series;

Biosafety cabinet, Thermo Scientific, Model 1300 Series A2;

Inverted microscope, Olympus, CKX41SF;
Refrigerator, SIEMENS, KK25E76TI.

4. Experimental Method

The first day: Incubation and plant of cells
  1) Cells in logarithmic growth phase were harvested and counted by cell counter. Cell viability was detected by trypan blue exclusion assay to ensure that the viability of each cell line was above 90%.
  2) Cell concentration was adjusted by diluting complete culture medium, and 90 μL cell suspension was added to a 96-well plate (T0 plate and drug plate to be tested) to make the cell density reach the specified concentration.
  3) Cells in 96-well plate were incubated overnight at condition of 37° C., 5% $CO_2$ and 95% humidity.

The second day: Reading T0 plate
  1) 10 μL culture medium was added to T0 plate.
  2) CTG reagent was melt, while the cell plate was balanced to room temperature for 30 minutes.
  3) The same volume of CTG solution was added to each well.
  4) The cell plate was vibrated for 2 minutes on an orbital shaker to lyze the cells.
  5) The cell plate was placed at room temperature for 10 minutes to stabilize the cold light signal.
  6) The cold light value was read with EnVision.

Drug Addition
  1) Drug dilution. The compounds to be tested were dissolved and packaged, then a gradient elution was performed to obtain a solution diluted 10 times.
  2) Drug addition. 10 L drug solution was added into each well of the 96-well plate, which was inoculated cells, three parallel wells were set for each cell concentration. The highest concentration of the compounds to be tested on A-431 was 30 μM, nine concentrations was set with 3 times dilution; while the highest concentration on NCI-H1975 and PC-9 was 1.111 μM, 9 concentrations was set with 3 times dilution.
  3) Culture. Cells in 96-well plates in which drugs have been added were cultured at condition of 37° C., 5% $CO_2$ and 95% humidity for 3 days, and then CTG assay was performed respectively.

The third day: reading plate at the terminal
  1) CTG reagent was melt, while the cell plate was balanced to room temperature for 30 minutes.

2) The same volume of CTG solution was added to each well.
3) The cell plate was vibrated for 2 minutes on an orbital shaker to lyze the cells.
4) The cell plate was placed at room temperature for 10 minutes to stabilize the cold light signal.
5) The cold light value was read with EnVision 5. Data Processing Data were analyzed using GraphPad Prism 5.0 software, and non-linear S curve regression was used for fitting the data to give a dose-effect curve, $IC_{50}$ value was calculated accordingly.

Cell Survival Rate (%)=($Lum_{drugs}$−$Lum_{control}$)/($Lum_{cell}$−$Lum_{control}$)×100%.

6. Experimental Results

TABLE 8

$IC_{50}$ of Compounds in Cell Lines NCI-H1975, PC-9 and A-431

| Final Product | NCI-H1975 $IC_{50}$ (nM) | PC-9 $IC_{50}$ (nM) | A-431 $IC_{50}$ (nM) | A-431/ NCI-H1975 Selectivity |
|---|---|---|---|---|
| 1 | 4.7 | 5.6 | 890.4 | 187.8 |
| 2 | 6.6 | 4.4 | 362.3 | 85.8 |
| 3 | 4.1 | 7.9 | 491.2 | 120.3 |
| 4 | 15.1 | 10.1 | 514.4 | 34.0 |
| 5 | 5.6 | 3.9 | 302.2 | 53.9 |
| 6 | 32.1 | 19.4 | 1720.1 | 53.7 |
| 7 | 11.1 | 10.7 | 129.3 | 11.6 |
| 8 | 3.5 | 27.3 | 872.5 | 251.1 |
| 9 | 52.6 | 36.2 | 766.8 | 14.6 |
| 10 | 47.3 | 27.7 | 1987.0 | 42.0 |
| 11 | 67.4 | 21.8 | 2139.9 | 31.7 |
| 12 | 53.1 | 56.9 | 4126.3 | 77.7 |
| 13 | 1.8 | 8.6 | 769.7 | 427.6 |
| 14 | 6.1 | 5.9 | 1146.8 | 188.0 |
| 15 | 21.6 | 12.7 | 1289.5 | 59.7 |
| 16 | 57.0 | 40.5 | 1546.3 | 27.1 |
| 17 | 22.2 | 16.9 | 1246.8 | 56.2 |
| 18 | 11.1 | 8.9 | 983.0 | 88.8 |
| 19 | 18.1 | 10.7 | 850.0 | 47.0 |
| 20 | 46.1 | 24.9 | 1565.2 | 33.9 |
| 21 | 46.4 | 29.6 | 2766.8 | 59.7 |
| 22 | 18.1 | 13.4 | 1055.8 | 58.3 |
| 23 | 13.7 | 9.0 | 617.3 | 45.0 |
| 24 | 11.8 | 8.1 | 1061.3 | 90.1 |
| 25 | 54.7 | 67.8 | 736.4 | 13.5 |
| 26 | 10.4 | 9.1 | 216.2 | 20.7 |
| 27 | 14.2 | 21.6 | 387.0 | 27.2 |
| 28 | 32.3 | 19.6 | 1427.4 | 44.2 |
| 29 | 55.7 | 79.9 | 1812.9 | 32.6 |
| 30 | 32.4 | 24.7 | 1353.4 | 41.8 |
| 31 | 52.7 | 45.6 | 1576.2 | 29.9 |
| 32 | 186.1 | 10.9 | 9327.6 | 50.1 |
| 33 | 5.6 | 8.2 | 812.8 | 145.7 |
| 34 | 26.3 | 10.7 | 1947.0 | 74.1 |
| 35 | 13.2 | 16.4 | 1593.8 | 120.8 |
| 36 | 31.4 | 22.0 | 1011.8 | 32.3 |
| 37 | 67.5 | 79.8 | 1724.7 | 25.5 |
| 38 | 75.9 | 89.7 | 3312.7 | 43.7 |
| 39 | 24.5 | 25.7 | 973.3 | 39.6 |
| 40 | 57.0 | 46.1 | 1965.0 | 34.5 |
| 41 | 20.4 | 10.6 | 611.8 | 30.0 |
| 42 | 25.8 | 34.6 | 686.4 | 26.6 |
| 43 | 29.8 | 16.7 | 1140.0 | 38.3 |
| 44 | 101.6 | 32.8 | 1597.6 | 15.7 |
| 45 | 136.9 | 23.6 | 2606.3 | 19.0 |
| 46 | 82.8 | 32.7 | 1251.2 | 15.1 |
| 47 | 49.0 | 34.0 | 670.9 | 13.7 |
| 48 | 67.2 | 49.7 | 1390.4 | 20.7 |
| 49 | 85.6 | 88.0 | 1471.8 | 17.2 |
| 50 | 59.2 | 47.5 | 1077.5 | 18.2 |
| 51 | 69.4 | 59.8 | 1446.7 | 20.8 |
| 52 | 41.7 | 39.0 | 614.9 | 14.7 |
| 53 | 151.2 | 67.9 | 1249.7 | 8.3 |
| 54 | 111.1 | 88.2 | 1309.7 | 11.8 |
| 55 | 32.2 | 3.6 | 585.9 | 18.2 |
| 56 | 112.8 | 56.7 | 1225.6 | 10.9 |
| 57 | 13.3 | 10.7 | 1422.3 | 107.3 |
| 58 | 8.8 | 6.9 | 1129.1 | 128.8 |
| 59 | 10.0 | 8.9 | 1265.1 | 126.1 |
| 60 | 10.6 | 9.6 | 2301.1 | 217.0 |
| 61 | 17.8 | 9.4 | 1618.2 | 91.0 |
| 62 | 33.5 | 15.7 | 1171.5 | 35.0 |
| 63 | 4.1 | 6.5 | 540.3 | 130.7 |
| 64 | 13.1 | 5.4 | 689.5 | 52.6 |
| 65 | 10.9 | 12.0 | 764.7 | 70.2 |
| 66 | 8.1 | 8.5 | 778.9 | 96.2 |
| 67 | 14.6 | 15.0 | 890.9 | 61.0 |
| 68 | 14.7 | 15.3 | 921.4 | 62.7 |
| 69 | 13.4 | 10.4 | 1827.2 | 136.8 |
| 70 | 17.6 | 14.7 | 1162.8 | 66.1 |
| 71 | 33.1 | 27.8 | 2559.6 | 77.3 |
| 72 | 45.2 | 29.7 | 1904.5 | 42.1 |
| 73 | 65.3 | 50.4 | 1025.4 | 15.7 |
| 74 | 31.9 | 10.6 | 1149.8 | 36.0 |
| 75 | 24.3 | 13.6 | 1500.3 | 61.7 |
| 76 | 87.3 | 57.9 | 9450.5 | 108.3 |
| 77 | 34.5 | 16.4 | 1154.9 | 33.5 |
| 78 | 61.8 | 47.8 | 1029.6 | 16.7 |
| 79 | 73.6 | 67.9 | 1104.5 | 15 |
| 80 | 43.0 | 35.9 | 586.2 | 13.6 |
| 81 | 28.7 | 26.4 | 1379.8 | 48.1 |
| 82 | 24.0 | 29.6 | 1094.2 | 45.6 |
| 83 | 67.2 | 77.9 | 1516.6 | 22.6 |
| 84 | 34.4 | 27.5 | 987.9 | 28.7 |
| 85 | 72.3 | 56.7 | 1835.8 | 25.4 |
| 86 | 91.6 | 76.4 | 1776.0 | 19.4 |
| 87 | 113.6 | 77.6 | 1958.0 | 17.2 |
| 88 | 6.1 | 7.2 | 987.2 | 161.8 |
| 89 | 19.9 | 14.8 | 954.3 | 48.0 |
| 90 | 26.5 | 15.5 | 1754.3 | 66.2 |
| 91 | 62.2 | 47.2 | 1322.8 | 21.3 |
| 92 | 9.3 | 13.1 | 763.9 | 82.1 |
| 93 | 20.5 | 18.5 | 854.2 | 41.7 |
| 94 | 47.8 | 55.7 | 2038.2 | 42.6 |
| 95 | 6.7 | 12.2 | 997.4 | 148.9 |
| 96 | 13.7 | 10.8 | 945.3 | 69 |
| 97 | 33.1 | 22.6 | 798.4 | 24.1 |
| 98 | 83.5 | 31.7 | 1064.3 | 12.7 |
| 99 | 9.8 | 43.2 | 886.4 | 90.4 |
| 100 | 5.7 | 15.3 | 653.7 | 114.7 |
| 101 | 7.3 | 19.5 | 632.7 | 86.7 |
| 102 | 14.1 | 12.5 | 986.4 | 70.0 |
| 103 | 8.0 | 19.2 | 648.2 | 81.0 |
| 104 | 6.0 | 14.2 | 543.6 | 90.6 |
| 105 | 14.6 | 17.9 | 778.3 | 53.3 |
| 106 | 96.9 | NT | 2017.4 | 20.8 |
| 107 | 16.5 | 17.8 | 1290.3 | 78.2 |
| 108 | 3.2 | 5.7 | 567.2 | 177.3 |
| 109 | 32.3 | 35.0 | 1432.7 | 44.4 |
| 110 | 8.0 | 6.9 | 598.6 | 74.8 |
| 111 | 18.0 | 16.8 | 947.7 | 52.7 |
| 112 | 9.0 | 9.7 | 654.1 | 72.7 |
| 113 | 56.6 | 45.6 | 1356.9 | 24.0 |
| 114 | 31.5 | 32.7 | 1477.9 | 46.9 |
| 115 | 5.3 | 9.0 | 532.8 | 100.5 |
| 116 | 9.1 | 8.2 | 654.2 | 71.9 |
| 117 | 11.3 | 11.2 | 678.9 | 60.1 |
| 118 | 19.9 | 23.6 | 1057.8 | 53.2 |
| 119 | 23.1 | 17.8 | 1247.9 | 54.0 |
| 120 | 8.2 | 6.7 | 598.2 | 73.0 |
| 121 | 40.2 | 31.1 | 2314.7 | 57.6 |
| 122 | 5.2 | 11.6 | 579.6 | 111.5 |
| 123 | 13.7 | 15.5 | 698.3 | 51.0 |
| 124 | 35.2 | 32.3 | 1466.8 | 41.7 |
| 125 | 32.1 | 22.1 | 1577.9 | 49.2 |
| 126 | 85.0 | 64.1 | 2011.7 | 23.7 |
| 127 | 45.1 | 163.2 | 2301.2 | 51.0 |

TABLE 8-continued

IC$_{50}$ of Compounds in Cell Lines NCI-H1975, PC-9 and A-431

| Final Product | NCI-H1975 IC$_{50}$ (nM) | PC-9 IC$_{50}$ (nM) | A-431 IC$_{50}$ (nM) | A-431/ NCI-H1975 Selectivity |
|---|---|---|---|---|
| 128 | 103.4 | 70.7 | 1369.7 | 13.2 |
| 129 | 8.0 | 13.1 | 746.2 | 93.3 |
| 130 | 56.6 | 43.2 | 2314.7 | 40.9 |
| 131 | 9.6 | 14.8 | 578.3 | 60.2 |
| 132 | 42.3 | 118.3 | 2044.6 | 48.3 |
| 133 | 9.9 | 10.7 | 598.3 | 60.4 |
| 134 | 33.8 | 31.1 | 1432.7 | 42.4 |
| 135 | 15.4 | 17.7 | 756.4 | 49.1 |
| 136 | 56.2 | 45.6 | 2302.7 | 41.1 |
| 137 | 4.8 | 7.6 | 597.4 | 124.5 |
| 138 | 16.8 | 12.3 | 945.8 | 56.3 |
| 139 | 43.1 | 57.9 | 1156.0 | 26.8 |
| 140 | 11.7 | 13.8 | 987.3 | 84.4 |
| 141 | 8.4 | 23.1 | 539.4 | 64.2 |
| 142 | 24.5 | 32.6 | 967.9 | 39.5 |
| 143 | 51.6 | 23.5 | 988.2 | 19.2 |
| 144 | 6.8 | 16.4 | 572.1 | 84.1 |
| 145 | 37.1 | 33.7 | 1456.2 | 39.3 |
| 146 | 10.2 | 14.9 | 800.3 | 78.5 |
| 147 | 18.4 | 24.7 | 978.3 | 53.2 |
| 148 | 28.7 | 31.9 | 1346.7 | 46.9 |
| 149 | 28.4 | 674.2 | 1368.9 | 48.2 |
| 150 | 5.3 | 19.3 | 543.1 | 102.5 |
| 151 | 58.9 | 79.9 | 2045.7 | 34.7 |
| 152 | 23.6 | 43.2 | 1966.7 | 83.3 |
| 153 | 25.0 | 35.1 | 1324.5 | 53.0 |
| 154 | 34.7 | 36.4 | 1400.3 | 40.4 |
| 155 | 13.6 | 6.0 | 873.5 | 64.2 |
| 156 | 25.1 | 2.7 | 1243.7 | 49.5 |
| 157 | 32.7 | 11.0 | 1654.3 | 50.6 |
| 158 | 9.4 | 4.9 | 680.3 | 72.4 |
| 159 | 31.9 | 27.9 | 1534.7 | 48.1 |
| 160 | 39.2 | 32.7 | 2078.3 | 53.0 |
| 161 | 17.4 | 19.9 | 1032.4 | 59.3 |
| 162 | 16.8 | 18.9 | 762.8 | 45.4 |
| 163 | 18.5 | 13.8 | 834.4 | 45.1 |
| 164 | 12.6 | 23.2 | 590.7 | 46.9 |
| 165 | 50.0 | 40.7 | 2647.8 | 53.0 |
| 166 | 16.0 | 8.9 | 986.2 | 61.6 |
| 167 | 16.5 | 17.1 | 1046.7 | 63.4 |
| 168 | 6.8 | 21.5 | 584.1 | 85.9 |
| 169 | 34.3 | 11.4 | 1643.8 | 47.9 |
| 170 | 37.4 | 28.0 | 1648.9 | 44.1 |
| 171 | 26.2 | 38.0 | 743.3 | 28.4 |
| 172 | 18.6 | 16.3 | 953.6 | 51.3 |
| 173 | 22.7 | 7.3 | 1054.8 | 46.5 |
| 174 | 23.5 | 15.4 | 1325.7 | 56.4 |
| 175 | 8.1 | 26.0 | 793.4 | 98.0 |
| 176 | 21.2 | 4.8 | 1078.3 | 50.9 |
| 177 | 19.0 | 23.5 | 1468.4 | 77.3 |
| 178 | 42.9 | 34.6 | 2001.4 | 46.7 |
| 179 | 16.2 | 2.9 | 983.7 | 60.7 |
| 180 | 25.1 | 3.8 | 893.5 | 35.6 |
| 181 | 45.8 | 21.4 | 1679.4 | 36.7 |
| 182 | 53.3 | 55.9 | 1735.6 | 32.6 |
| 183 | 40.4 | 69.8 | 984.3 | 24.4 |
| 184 | 49.5 | 32.6 | 1056.2 | 21.3 |
| 185 | 53.8 | 43.7 | 2031.7 | 37.8 |
| 186 | 76.1 | 50.2 | 2567.8 | 33.7 |
| 187 | 53.0 | 46.8 | 2407.2 | 45.4 |
| 188 | 113.8 | 55.9 | 2789.3 | 24.5 |
| 189 | 108.6 | 24.1 | 2643.8 | 24.3 |
| 190 | 107.7 | 24.7 | 2077.1 | 19.3 |
| 191 | 91.8 | 56.4 | 1760.9 | 19.2 |
| 192 | 47.0 | 33.0 | 1843.9 | 39.2 |
| 193 | 52.8 | 30.9 | 1479.3 | 28.0 |
| 194 | 75.2 | 45.8 | 1637.9 | 21.8 |
| 195 | 20.4 | 19.5 | 1437.6 | 70.5 |
| 196 | 36.4 | 20.7 | 2017.3 | 55.4 |
| 197 | 20.7 | 13.4 | 1347.9 | 65.1 |
| 198 | 77.1 | 65.8 | 2344.7 | 30.4 |
| 199 | 37.8 | 24.7 | 1977.8 | 52.3 |
| 200 | 14.2 | 27.0 | 983.5 | 69.3 |
| 201 | 24.5 | 21.1 | 1344.7 | 54.9 |
| 202 | 10.7 | 12.7 | 798.3 | 74.6 |
| 203 | 8.1 | 7.2 | 982.1 | 121.2 |
| 204 | 15.7 | 15.8 | 890.7 | 56.7 |
| 205 | 13.0 | 7.6 | 884.7 | 68.1 |
| 206 | 8.1 | 12.1 | 773.0 | 95.4 |
| 207 | 10.2 | 5.6 | 894.8 | 87.7 |
| 208 | 20.0 | 10.7 | 1097.4 | 54.8 |
| 209 | 24.7 | 12.0 | 1623.9 | 65.7 |
| 210 | 10.4 | 11.7 | 983.0 | 94.5 |
| 211 | 11.3 | 7.4 | 1035.2 | 91.6 |
| 212 | 71.8 | 54.7 | 2033.5 | 28.3 |
| 213 | 74.9 | 55.6 | 2055.8 | 27.4 |
| 214 | 19.7 | 16.7 | 1529.0 | 77.6 |
| 215 | 18.4 | 15.4 | 1437.7 | 78.1 |
| 216 | 13.6 | 12.8 | 1224.2 | 90.0 |
| 217 | 16.9 | 13.6 | 1399.0 | 82.8 |
| 218 | 21.2 | 9.2 | 1834.9 | 86.6 |
| 219 | 49.4 | 45.9 | 2508.3 | 50.8 |
| 220 | 60.7 | 55.4 | 2433.6 | 40.1 |
| 221 | 70.3 | 96.0 | 2438.9 | 34.7 |
| 222 | 13.6 | 20.7 | 983.2 | 72.3 |
| 223 | 40.5 | 40.6 | 2322.7 | 57.4 |
| 224 | 15.8 | 27.1 | 1094.3 | 69.3 |
| 225 | 75.1 | 67.2 | 2468.9 | 32.9 |
| 226 | 68.2 | 54.6 | 2388.4 | 35.0 |
| 227 | 79.6 | 90.7 | 2437.8 | 30.6 |
| 228 | 65.7 | 35.7 | 1580.1 | 24.1 |
| 229 | 93.8 | 68.1 | 1624.6 | 17.3 |
| 230 | 68.2 | 59.4 | 1983.3 | 29.1 |
| 231 | 96.8 | 76.5 | 1727.4 | 17.8 |
| 232 | 90.2 | 82.7 | 2563.3 | 28.4 |
| 233 | 71.4 | 54.9 | 2437.2 | 34.1 |
| 234 | 80.1 | 32.7 | 2455.8 | 30.7 |
| 235 | 94.0 | 24.9 | 2399.4 | 25.5 |
| 236 | 60.0 | 38.7 | 2079.4 | 34.7 |
| 237 | 21.7 | 44.5 | 1824.6 | 84.1 |
| 238 | 51.6 | 99.4 | 1939.2 | 37.6 |
| 239 | 33.0 | 67.9 | 1577.9 | 47.8 |
| 240 | 62.0 | 110.4 | 2978.3 | 48.0 |
| 241 | 22.9 | 210.6 | 1037.4 | 45.3 |
| 242 | 26.7 | 28.1 | 1200.3 | 45.0 |
| 243 | 42.9 | 65.4 | 2178.3 | 50.8 |
| 244 | 59.7 | 84.7 | 2400.3 | 40.2 |
| 245 | 61.6 | 70.7 | 2378.3 | 38.6 |
| 246 | 89.7 | 67.2 | 2298.0 | 25.6 |
| 247 | 37.1 | 37.4 | 2988.3 | 80.5 |
| 248 | 13.3 | 27.7 | 2849.6 | 214.3 |
| 249 | 8.6 | 61.0 | 943.1 | 109.7 |
| 250 | 12.5 | 12.7 | 1023.6 | 81.9 |
| 251 | 12.5 | 7.0 | 1102.3 | 88.2 |
| 252 | 187.5 | 25.5 | 2993.6 | 16.0 |
| 253 | 62.2 | 32.1 | 2489.3 | 40.0 |
| 254 | 131.9 | 30.9 | 2274.4 | 17.2 |
| 255 | 46.4 | 30.0 | 2013.4 | 43.4 |
| 256 | 9.6 | 19.2 | 992.1 | 103.3 |
| 257 | 58.6 | 42.7 | 2067.4 | 35.3 |
| 258 | 51.6 | 32.4 | 2946.3 | 57.1 |
| 259 | 14.9 | 19.9 | 1528.3 | 102.6 |
| 260 | 12.8 | 20.1 | 1324.6 | 103.5 |
| 261 | 37.0 | 40.8 | 2100.4 | 56.8 |
| 262 | 123.5 | 52.7 | 2978.3 | 24.1 |
| 263 | 9.1 | 18.5 | 1200.5 | 131.9 |
| 264 | 5.5 | 22.1 | 923.5 | 167.9 |
| 265 | 20.6 | 34.7 | 1624.7 | 78.9 |
| 266 | 10.1 | 24.8 | 938.2 | 92.9 |
| 267 | 16.1 | 29.3 | 1036.8 | 64.4 |
| 268 | 27.1 | 15.6 | 1700.2 | 62.7 |
| 269 | 21.6 | 16.3 | 1573.9 | 72.9 |
| 270 | 44.4 | 54.6 | 2403.2 | 54.1 |
| 271 | 25.2 | 77.7 | 2391.0 | 94.9 |
| 272 | 5.6 | 13.9 | 987.2 | 176.3 |
| 273 | 53.3 | 79.8 | 2678.3 | 50.2 |
| 274 | 47.0 | 56.7 | 2038.9 | 43.4 |
| 275 | 136.0 | 43.2 | 3302.1 | 24.3 |

TABLE 8-continued

IC$_{50}$ of Compounds in Cell Lines NCI-H1975, PC-9 and A-431

| Final Product | NCI-H1975 IC$_{50}$ (nM) | PC-9 IC$_{50}$ (nM) | A-431 IC$_{50}$ (nM) | A-431/ NCI-H1975 Selectivity |
|---|---|---|---|---|
| 276 | 32.4 | 13.0 | 2108.3 | 65.1 |
| 277 | 52.9 | 21.9 | 2006.6 | 37.9 |
| 278 | 117.1 | 40.9 | 2478.9 | 21.2 |
| 279 | 25.7 | 21.4 | 2899.1 | 112.8 |
| 280 | 99.4 | 87.4 | 3217.6 | 32.4 |
| 281 | 72.0 | 67.9 | 3327.8 | 46.2 |
| 282 | 22.7 | 32.7 | 1370.3 | 60.4 |
| 283 | 37.3 | 46.9 | 1519.7 | 40.8 |
| 284 | 26.3 | 13.4 | 670.2 | 25.5 |
| 285 | 40.6 | 23.1 | 632.7 | 15.6 |
| 286 | 40.1 | 30.9 | 803.6 | 20.0 |
| 287 | 4.0 | 9.2 | 611.8 | 152.9 |
| 288 | 98.2 | 76.7 | 1924.5 | 19.6 |
| 289 | 12.2 | 24.1 | 1037.9 | 85.1 |
| 290 | 30.8 | 36.5 | 1629.3 | 52.9 |
| 291 | 89.5 | 54.3 | 2734.5 | 30.6 |
| 292 | 90.4 | 64.7 | 2978.4 | 32.9 |
| 293 | 79.6 | 54.2 | 2733.8 | 34.3 |
| 294 | 71.3 | 44.9 | 4581.8 | 64.2 |
| 295 | 32.5 | 27.9 | 3769.4 | 116.0 |
| known compound 296 | 90.7 | 121 | 1442.6 | 15.9 |

Note:
NC = not calculated;
NT = not tested.
Conclusion: The final products in the EXAMPLES of the present invention showed very strong inhibitory effects on EGFR mutant NCI-H1975 cells, but low inhibitory effects on wild type A-431 cells. Moreover they showed good selectivity on wild type/mutant cells.

EXAMPLE 447

P-gp Substrate Evaluation Experiment

1. Experimental Design
Cell Culture
1) High glucose DMEM medium containing L-glutamine was used and 10% fetal bovine serum, 0.1 mg/mL streptomycin and 0.6 mg/mL penicillin were added.
2) MDCKII-MDR1 was cultured in a T-75 cell culture bottle. The incubator was set at the condition of 37° C., 5% CO$_2$ and 95% relative humidity. Cells could be inoculated in Transwell when the cell confluence reached 70-90%.
3) Before cell plant, 50 µL cell culture medium was added to each well in the upper chamber of the Transwell, and 25 mL cell culture medium was added to the lower chamber of the Transwell. After being incubated in a 37° C., 5% CO$_2$ incubator for 1 hour, the culture plate can be used to inoculate cells.
4) the cells was gently washed by PBS (5 mL), and then the PBS was discarded, 1.5 mL trypsogen containing EDTA was added thereinto to incubate at 37° C. for 5 to 10 minutes until the cells completely detached. Serum-containing medium was added to terminate the digestion process.
5) Cell suspension was transferred to a round-bottom centrifugal tube and centrifuged for 10 minutes at 120×g.
6) Cells were resuspended in medium with a final concentration of 1.56×10$^6$ cells/mL.
Inoculation of MDCKII-MDR1 Cells
1) Cell suspension was added to the upper chamber of the 96-well Transwell plate with 50 mL each well, and the final inoculation density was 5.45×10$^5$ cells/cm$^2$.
2) The medium was changed 48 hours after inoculation, the culture was carried out for 4-7 days, and the medium was changed every other day.
Evaluation of Cell Monolayer Integrity
1) After 4-7 days of culture, MDCKII-MDR1 and MDKII should merge and differentiate completely. At this time, they could be applied to penetration test.
2) The resistance of cell monolayer was measured by a resistance meter (Millipore, USA) and the resistance of each well was recorded.
3) After finishing the detection, the Transwell plate was put back into the incubator.
4) Resistance value was calculated:

Resistance measured (ohms)×layer area (cm$^2$)=TEER value (ohm·cm$^2$)

If TEER value was less than 42 ohms·cm$^2$, the well can not be used for penetration testing.
Drug Penetration Test
1) The MDCKII-MDR1 Transwell plate was taken out from the incubator. The cell monolayer was rinsed with HBSS buffer (25 mM HEPES, pH 7.4) twice and incubated for 30 minutes at 37° C.
2) The transport rate of compounds from the top to the bottom was determined. 100 µL HBSS buffer (25 mM HEPES, pH 7.4) containing TA or control drug was added to each well in the upper chamber (top), and 300 µL HBSS buffer (25 mM HEPES, pH 7.4) was added to each well in the lower chamber (bottom).
3) The transport rate of compounds from the bottom to the top was determined. 100 µL HBSS buffer (25 mM HEPES, pH 7.4) was added to each well in the upper chamber (top), and 300 µL HBSS buffer (25 mM HEPES, pH 7.4) containing TA or control drug was added to each well in the lower chamber (bottom).
4) The upper and lower transporters were combined and incubated for 2 hours at 37° C.
5) After finishing the incubation, 80 µL of sample was taken respectively from each well in the upper and the lower chamber of the Transwell plate and added to a new sample tube. three times volume of acetonitrile containing internal standard (200 nM alprazolam, 200 nM labellol, 200 nM diclofenac acid and 100 nM toluene sulfonylurea) was added into the sample tube, after vortexing for 5 minutes, the tube was centrifuged at 4,000 g for 15 minutes. 70 µL supernatant was drawn, diluted with equal volume of water and then subjected to LC-MS/MS analysis. All samples were prepared in three parallel ways.
6) The cell monolayer integrity after 2-hour incubation was evaluated by leakage of fluorescent yellow, HBSS (25 mM HEPES, pH 7.4) was used to dilute the stock solution of fluorescent yellow till the final concentration was 100 µM. 100 µL fluorescent yellow solution was added to each well in the upper chamber of the Transwell plate and 300 µL HBSS (25 mM HEPES, pH 7.4) was added to each well in the lower chamber of the Transwell plate. After incubation at 37° C. for 30 minutes, 80 µL solution was drawn respectively from each well in the upper and lower chamber to a new 96-well plate. The fluorescence was determined at 485 nm as excitation wavelength and 530 nm as emission wavelength by using a microplate reader.

2. Data Processing
Data calculation was carried out through Excel, the apparent permeability index ($P_{app}$, cm/s) of compounds was calculated through the formula shown as follow:

apparent permeability index =

$$\frac{\frac{\text{volumn of solution from receiving terminal}}{\text{membrane area} \times \text{incubation time}} \times \frac{\text{concentration of drugs from receiving terminal}}{\text{inital concentration of drugs from providing terminal}}$$

wherein, the membrane area in the formula is the membrane area of Transwell-96 plate (0.143 cm$^2$); the unit of incubation time is second (s).

Efflux ratio was calculated through the formula shown as follow:

$$\text{Efflux Ratio} = \frac{\text{apparent permeability index from bottom to top}}{\text{apparent permeability index from top to bottom}}$$

TABLE 9

Efflux Ratio of Compounds to be tested

| Final Product | ER (Efflux Ratio) |
|---|---|
| 1 | 4.04 |
| 2 | 2.19 |
| 3 | 5.87 |
| 5 | 12.2 |
| 8 | 3.14 |
| 13 | 31.23 |
| 23 | 4.28 |
| 24 | 1.05 |
| 26 | 5.79 |
| 27 | 1.67 |
| 33 | 7.70 |
| 34 | 6.12 |
| 35 | 9.19 |
| 42 | 3.69 |
| 55 | 2.71 |
| 57 | 5.30 |
| 58 | 49.19 |
| 59 | 46.97 |
| 60 | 6.49 |
| 61 | 22.12 |
| 62 | 2.44 |
| 68 | 8.98 |
| 70 | 41.43 |
| 99 | 1.54 |
| 100 | 20.01 |
| 101 | 15.09 |
| 103 | 2.28 |
| 104 | 3.12 |
| 108 | 18.09 |
| 110 | 7.28 |
| 115 | 41.93 |
| 116 | 67.93 |
| 129 | 55.66 |
| 131 | 51.68 |
| 135 | 55.84 |
| 137 | 7.83 |
| 138 | 2.17 |
| 144 | 11.57 |
| 154 | 1.25 |
| 155 | 0.93 |
| 158 | 15.27 |
| 159 | 1.12 |
| 164 | 34.38 |
| 166 | 11.69 |
| 167 | 29.86 |
| 168 | 23.14 |
| 172 | 43.87 |
| 173 | 32.19 |
| 176 | 3.98 |
| 179 | 17.13 |
| 180 | 3.07 |

TABLE 9-continued

Efflux Ratio of Compounds to be tested

| Final Product | ER (Efflux Ratio) |
|---|---|
| 200 | 65.23 |
| 203 | 6.51 |
| 205 | 4.29 |
| 206 | 5.87 |
| 210 | 11.40 |
| 211 | 8.33 |
| 250 | 15.79 |
| 251 | 42.64 |
| 264 | 15.50 |
| 267 | 14.64 |

The invention claimed is:

1. A compound shown in Formula I or a pharmaceutically acceptable salt, stereoisomer, prodrug or solvate thereof

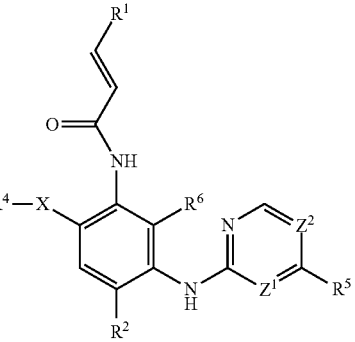

I wherein, in Formula I,
R$^1$ is hydrogen or

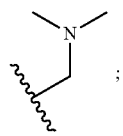

;

R$^2$ is C$_{1-6}$ alkyl or OR$^8$, R$^8$ is hydrogen, C$_{1-8}$ alkyl, halogenated C$_{1-8}$ alkyl, C$_{3-8}$ cycloalkyl, halogenated C$_{3-8}$ cycloalkyl, C$_{3-7}$ cycloalkyl-C$_{1-6}$ alkyl, substituted or unsubstituted 4-7 membered heterocyclyl containing 1-2 heteroatoms selected from N, O and S, or substituted or unsubstituted 4-7 membered heterocyclyl-C$_{1-8}$ alkyl containing 1-2 heteroatoms selected from N, O and S;

X is a chemical bond, O, S, CO, NR$^3$ or CR$^3$, wherein R$^3$ is hydrogen, C$_{1-6}$ alkyl, halogenated C$_{1-6}$ alkyl, C$_{3-8}$ cycloalkyl, halogenated C$_{3-8}$ cycloalkyl, C$_{1-6}$ alkoxy-C$_{1-6}$ alkyl, C$_{1-8}$ alkyl-CO or 4-6 membered heterocyclyl;

R$^4$ is C$_{1-6}$ alkyl, C$_{3-6}$ cycloalkyl, 4-7 membered heterocyclyl or 4-7 membered bicyclo-bridged heterocyclyl, the C$_{1-6}$ alkyl, C$_{3-6}$ cycloalkyl, 4-7 membered heterocyclyl or 4-7 membered bicyclo-bridged heterocyclyl can be optionally substituted by 1-3 substituents independently selected from the group consisting of: C$_{1-6}$ alkyl, halogenated C$_{1-6}$ alkyl, C$_{1-6}$ alkoxy, halogenated C$_{1-6}$ alkoxy, C$_{3-6}$ cycloalkyl, halogenated C$_{3-6}$ cycloalkyl, C$_{3-6}$ cycloalkoxy, halogenated C$_{3-6}$ cycloalkoxy, $C_{1-6}$ alkoxy-$C_{1-6}$ alkyl, hydroxy-$C_{1-6}$ alkyl, amino-$C_{1-6}$ alkyl, $C_{1-6}$ alkyl-amino-$C_{1-6}$ alkyl, halogen, hydroxyl, cyano, cyano-$C_{1-8}$ alkyl, amino, $C_{1-6}$ alkyl-amino, di($C_{1-6}$ alkyl)-amino, $C_{3-6}$ cycloalkyl-amino, $C_{1-6}$ alkylcarbonyl, $C_{1-6}$ alkyl-amino-acyl, di($C_{1-6}$ alkyl)-amino-acyl, $C_{3-6}$ cycloalkyl-amino-acyl, $C_{1-6}$ acyl-amino, substituted or unsubstituted heterocyclyl, and substituted or unsubstituted heterocyclyl-alkyl, wherein the substituent can optionally form a ring together with the carbon atom to which they are linked; $R^5$ is a fused ring formed by two rings selected from:

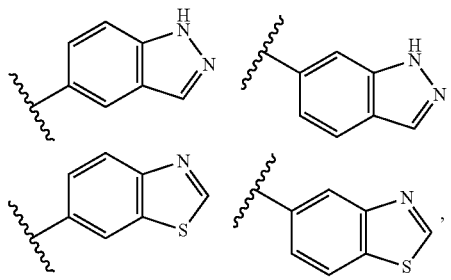

the fused ring is optionally substituted by 1-3 substituents independently selected from the group consisting of: $C_{1-6}$ alkyl, halogenated $C_{1-6}$ alkyl, $C_{1-6}$ alkoxy, halogenated $C_{1-6}$ alkoxy, $C_{3-6}$ cycloalkyl, halogenated $C_{3-6}$ cycloalkyl, $C_{3-6}$ cycloalkoxy, halogenated $C_{3-6}$ cycloalkoxy, $C_{1-6}$ alkoxy-$C_{1-6}$ alkyl, hydroxyl-$C_{1-6}$ alkyl, amino-$C_{1-6}$ alkyl, $C_{1-6}$ alkyl-amino-$C_{1-6}$ alkyl, halogen, hydroxyl, cyano, cyano-$C_{1-8}$ alkyl, amino, $C_{1-6}$ alkyl-amino, di($C_{1-6}$ alkyl)-amino, $C_{3-6}$ cycloalkyl-amino, $C_{1-6}$ alkyl-amino-acyl, di($C_{1-6}$ alkyl)-amino-acyl, $C_{3-6}$ cycloalkyl-amino-acyl, $C_{1-6}$ acyl-amino, substituted or unsubstituted heterocyclyl, and substituted or unsubstituted heterocyclyl-alkyl, wherein the substituent can optionally form a ring together with the carbon atom to which they are linked;
$R^6$ is hydrogen, halogen, hydroxyl, cyano, $C_{1-3}$ alkyl, halogenated $C_{1-3}$ alkyl $C_{3-6}$ cycloalkyl, halogenated $C_{3-6}$ cycloalkyl, $C_{1-3}$ alkoxy, halogenated $C_{1-3}$ alkoxy, $C_{3-6}$ cycloalkoxy, or halogenated $C_{3-6}$ cycloalkoxy;
$Z^1$ is C—$R^7$, $Z^2$ is N, or $Z^1$ is N, $Z^2$ is C—$R^7$, wherein $R^7$ is hydrogen, halogen, cyano, $C_{1-3}$ alkyl, halogenated $C_{1-3}$ alkyl, $C_{3-6}$ cycloalkyl, or halogenated $C_{3-6}$ cycloalkyl.

2. The compound or a pharmaceutically acceptable salt, stereoisomer, prodrug or solvate thereof according to claim 1, wherein, in Formula I, $R^2$ is $OR^8$, wherein $R^8$ is $C_{1-5}$ alkyl, halogenated $C_{1-5}$ alkyl, $C_{3-7}$ cycloalkyl, halogenated $C_{3-7}$ cycloalkyl or $C_{3-7}$ cycloalkyl-methyl.

3. The compound or a pharmaceutically acceptable salt, stereoisomer, prodrug or solvate thereof according to claim 1, wherein, in Formula I, X is a chemical bond or $NR^3$, wherein $R^3$ is hydrogen, methyl, ethyl, and methoxyethyl.

4. The compound or a pharmaceutically acceptable salt, stereoisomer, prodrug or solvate thereof according to claim 1, wherein, in Formula I, $R^4$ is $C_{1-3}$ alkyl, $C_{3-6}$ cycloalkyl, 4-7 membered heterocyclyl or 4-7 membered bicyclo-bridged heterocyclyl containing 1-2 heteroatoms selected from the group consisting of: N, O and S, the $C_{1-3}$ alkyl, $C_{3-6}$ cycloalkyl, 4-7 membered heterocyclyl or 4-7 membered bicyclo-bridged heterocyclyl can be optionally substituted by 1-3 substituents independently selected from the group consisting of: $C_{1-6}$ alkyl, halogenated $C_{1-6}$ alkyl, $C_{1-6}$ alkoxy, halogenated $C_{1-6}$ alkoxy, $C_{3-6}$ cycloalkyl, halogenated $C_{3-6}$ cycloalkyl, $C_{3-6}$ cycloalkoxy, halogenated $C_{3-6}$ cycloalkoxy, $C_{1-6}$ alkoxy-$C_{1-6}$ alkyl, hydroxyl-$C_{1-6}$ alkyl, amino-$C_{1-6}$ alkyl, $C_{1-6}$ alkyl-amino-$C_{1-6}$ alkyl, halogen, hydroxyl, cyano, cyano-$C_{1-8}$ alkyl, amino, $C_{1-6}$ alkyl-amino, di($C_{1-6}$ alkyl)-amino, $C_{3-6}$ cycloalkyl-amino, $C_{1-6}$ alkylcarbonyl, $C_{1-6}$ alkyl-amino-acyl, di($C_{1-6}$ alkyl)-amino-acyl, $C_{3-6}$ cycloalkyl-amino-acyl, $C_{1-6}$ acyl-amino, and substituted or unsubstituted 4-7 membered heterocyclyl.

5. The compound or a pharmaceutically acceptable salt, stereoisomer, prodrug or solvate thereof according to claim 1, wherein, in Formula I $R^5$ is selected from the group consisting of:

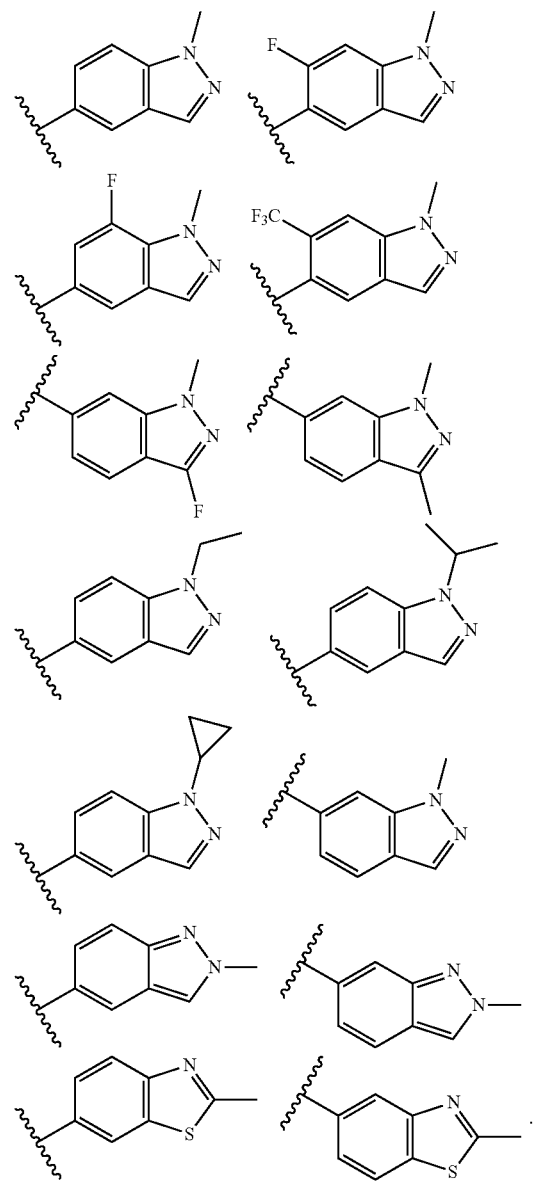

6. The compound or a pharmaceutically acceptable salt, stereoisomer, prodrug or solvate thereof according to claim 1, wherein, in Formula I, $R^6$ is hydrogen, halogen, hydroxyl, cyano, $C_{1-3}$ alkyl, halogenated $C_{1-3}$ alkyl, $C_{1-3}$ alkoxy, or halogenated $C_{1-3}$ alkoxy.

7. The compound or a pharmaceutically acceptable salt, stereoisomer, prodrug or solvate thereof according to claim 1, wherein, in Formula I, $R^1$ is hydrogen;

$R^2$ is $OR^8$, wherein $R^8$ is $C_{1-5}$ alkyl, halogenated $C_{1-5}$ alkyl, $C_{3-7}$ cycloalkyl, halogenated $C_{3-7}$ cycloalkyl or $C_{3-7}$ cycloalkyl-methyl;

X is a chemical bond or $NR^3$, wherein $R^3$ is hydrogen, methyl, ethyl, or methoxyethyl;

$R^4$ is $C_{1-3}$ alkyl, $C_{3-6}$ cycloalkyl, 4-7 membered heterocyclyl or 4-7 membered bicyclo-bridged heterocyclyl containing 1-2 heteroatoms selected from the group consisting of: N, O and S, the $C_{1-3}$ alkyl, $C_{3-6}$ cycloalkyl, 4-7 membered heterocyclyl or 4-7 membered bicyclo-bridged heterocyclyl can be optionally substituted by 1-3 substituents independently selected from the group consisting of: $C_{1-6}$ alkyl, halogenated $C_{1-6}$ alkyl, $C_{1-6}$ alkoxy; halogenated $C_{1-6}$ alkoxy, $C_{3-6}$ cycloalkyl, halogenated $C_{3-6}$ cycloalkyl, $C_{3-6}$ cycloalkoxy, halogenated $C_{3-6}$ cycloalkoxy, $C_{1-6}$ alkoxy-$C_{1-6}$, alkyl, hydroxyl-$C_{1-6}$ alkyl, amino-$C_{1-6}$ alkyl, $C_{1-6}$ alkyl-amino-$C_{1-6}$ alkyl, halogen, hydroxyl, cyano, cyano-$C_{1-8}$ alkyl, amino, $C_{1-6}$ alkyl-amino, di($C_{1-6}$ alkyl)-amino, $C_{3-6}$ cycloalkyl-amino, $C_{1-6}$ alkylcarbonyl, $C_{1-6}$ alkyl-amino-acyl, di($C_{1-6}$ alkyl)-amino-acyl, $C_{3-6}$ cycloalkyl-amino-acyl, $C_{1-6}$ acyl-amino, and substituted or unsubstituted 4-7 membered heterocyclyl;

$R^5$ is a fused ring formed by two rings and selected from:

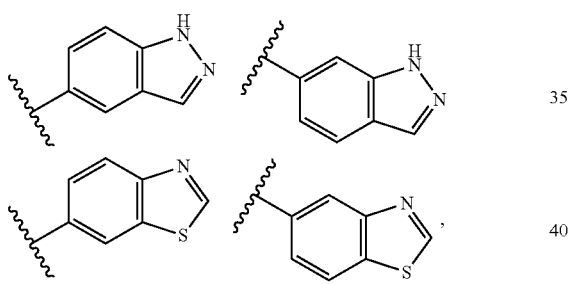

wherein the fused ring is optionally substituted by 1-3 substituents independently selected from the group consisting of: $C_{1-6}$ alkyl, halogenated $C_{1-6}$ alkyl, $C_{1-6}$ alkoxy, halogenated $C_{1-6}$ alkoxy, $C_{3-6}$ cycloalkyl, halogenated $C_{3-6}$ cycloalkyl, $C_{3-6}$ cycloalkoxy, halogenated $C_{3-6}$ cycloalkoxy, $C_{1-6}$ alkoxy-$C_{1-6}$ alkyl, hydroxyl-$C_{1-6}$, alkyl, amino-$C_{1-6}$ alkyl, $C_{1-6}$ alkyl-amino-$C_{1-6}$ alkyl, halogen, hydroxyl, cyano, cyano-$C_{1-8}$ alkyl, amino, $C_{1-6}$ alkyl-amino, di($C_{1-6}$ alkyl)-amino, $C_{3-6}$ cycloalkyl-amino, $C_{1-6}$ alkyl-amino-acyl; di($C_{1-6}$ alkyl)-amino-acyl; $C_{3-6}$ cycloalkyl-amino-acyl, $C_{1-6}$ acyl-amino, substituted or unsubstituted heterocyclyl, and substituted or unsubstituted heterocyclyl-alkyl, wherein the substituent can optionally form a ring together with the carbon atom to which they are linked;

$R^6$ is hydrogen, halogen; hydroxyl, cyano, $C_{1-3}$ alkyl, halogenated $C_{1-3}$ alkyl, $C_{1-3}$ alkoxy, and halogenated $C_{1-3}$ alkoxy;

$Z^1$ is C—$R^7$, $Z^2$ is N, or $Z^1$ is N, $Z^2$ is C—$R^7$, wherein $R^7$ is hydrogen.

8. A method for preparing the compound according to claim 1, comprising the following steps: reacting compound 1 with compound M to form compound 2 in the presence of base, after that reacting the compound 2 with compound 3 to give the compound shown in Formula I in the presence of acid;

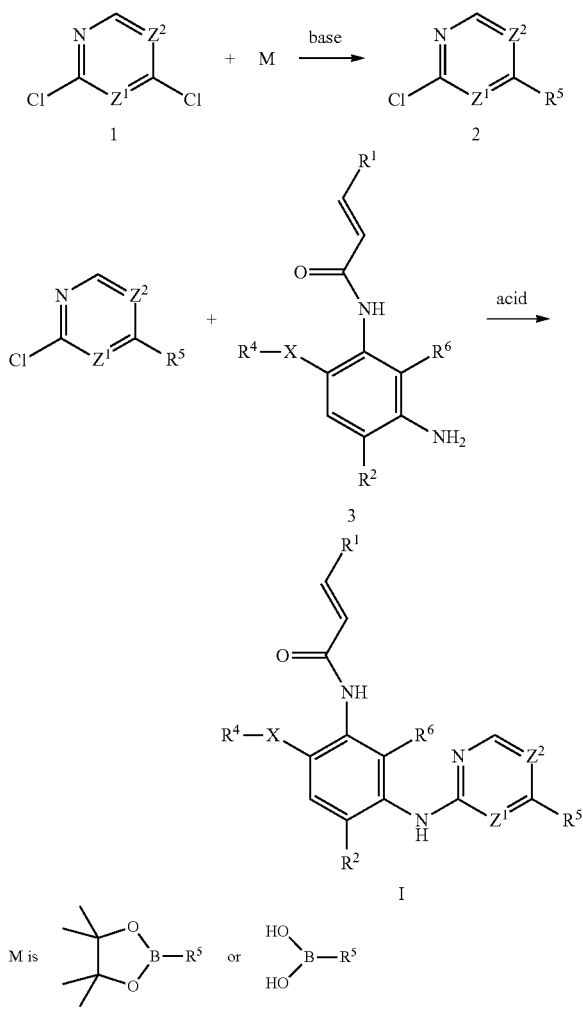

wherein $R^1$, $R^2$, $R^4$, $R^5$, $R^6$, X, $Z^1$ and $Z^2$ are as defined in claim 1, or, the method for preparing the compound shown in Formula I comprising the following steps:

(1) reacting compound 1 with compound M to supply compound 2 in the presence of base;

(2) reacting the compound 2 with compound 4 to form compound 5 in the presence of acid;

(3) reacting the compound 5 with $R^4$—X—H to give compound 6 in the presence of base;

(4) reducing the compound 6 to provide compound 7;

(5) reacting the compound 7 with compound 8 to form the compound shown in Formula I;

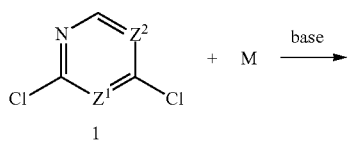

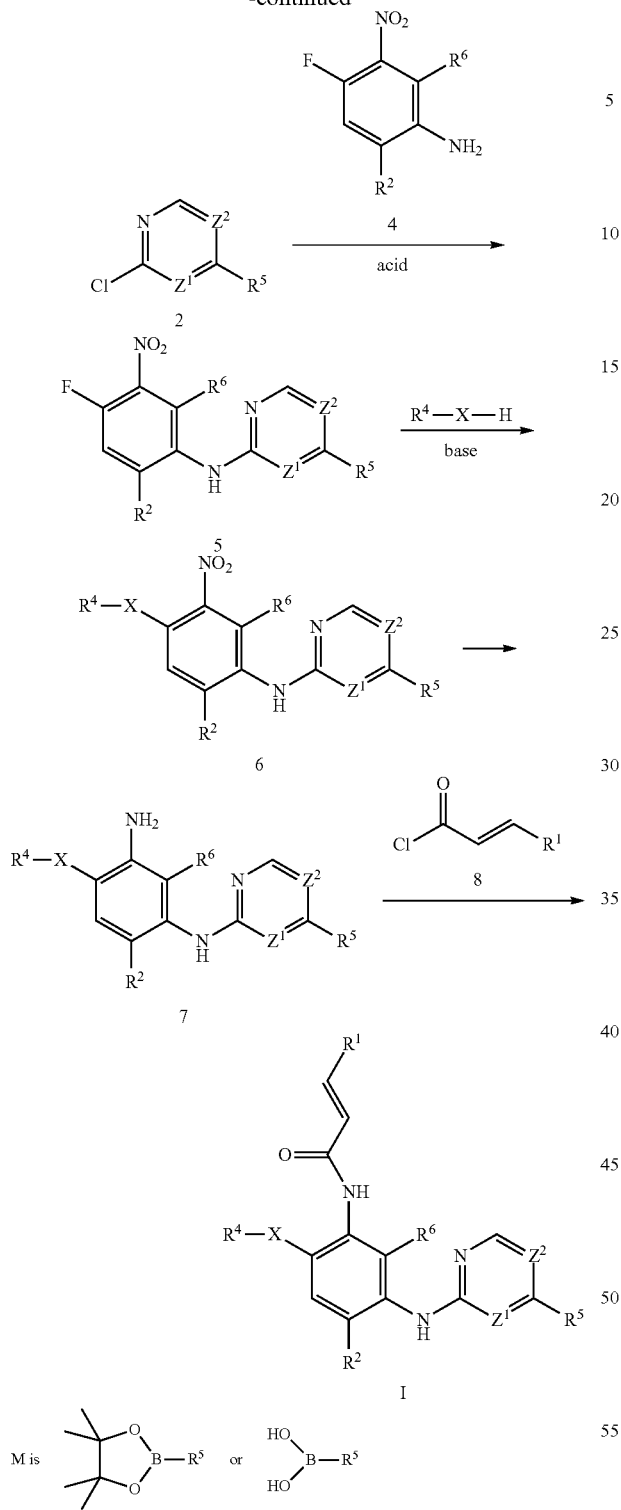

wherein R¹, R², R⁴, R⁵, R⁶, X, Z¹ and Z² are as defined in claim 1.

9. A pharmaceutical composition comprising the compound or a pharmaceutically acceptable salt, stereoisomer, prodrug or solvate thereof according to claim 1 and pharmaceutically acceptable carriers or excipients.

10. A method of treating tumors in a subject comprising administering to the subject a therapeutically effective amount of the compound or a pharmaceutically acceptable salt, stereoisomer, prodrug or solvate thereof according to claim 1 or the pharmaceutical composition.

11. The compound or a pharmaceutically acceptable salt, stereoisomer, prodrug or solvate thereof according to claim 1, wherein, in Formula I, R² is OR⁸, R⁸ methyl, ethyl, n-propyl, isopropyl, cyclopropyl, difluoromethyl, trifluoromethyl, cyclobutyl, and cyclopropylmethyl.

12. The compound or a pharmaceutically acceptable salt, stereoisomer, prodrug or solvate thereof according to claim 1, wherein, in Formula I, R⁴ is selected from the group consisting of:

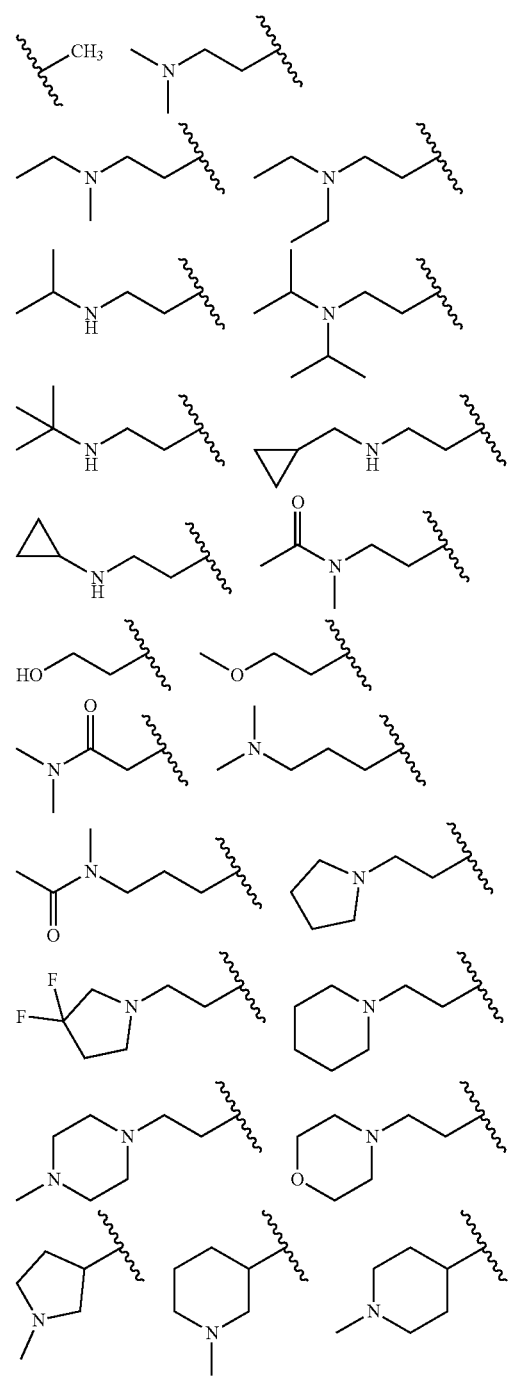

471
-continued
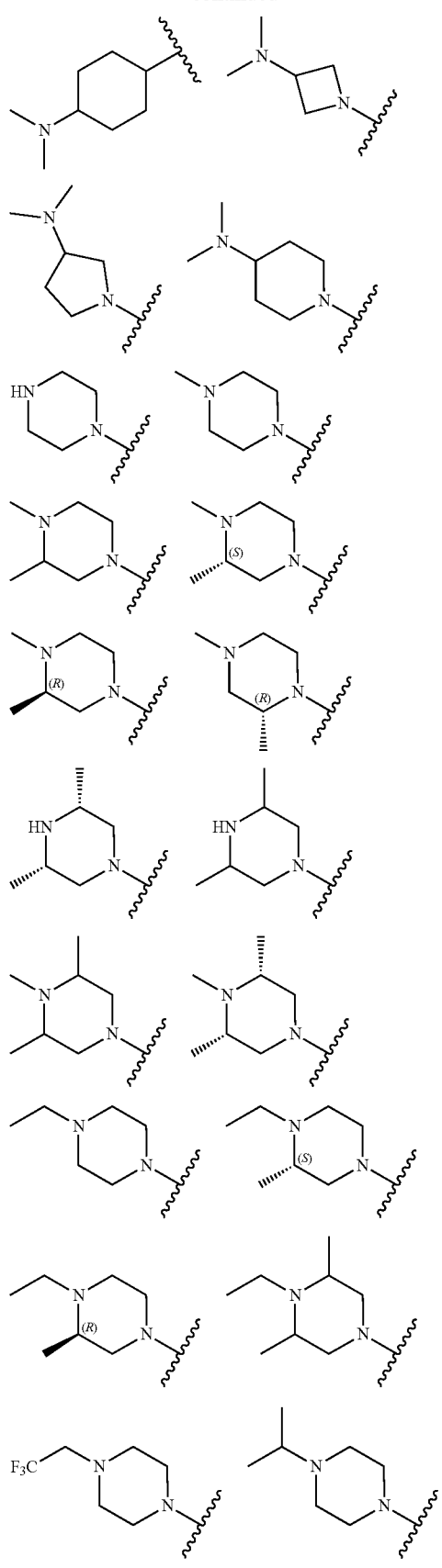
472
-continued
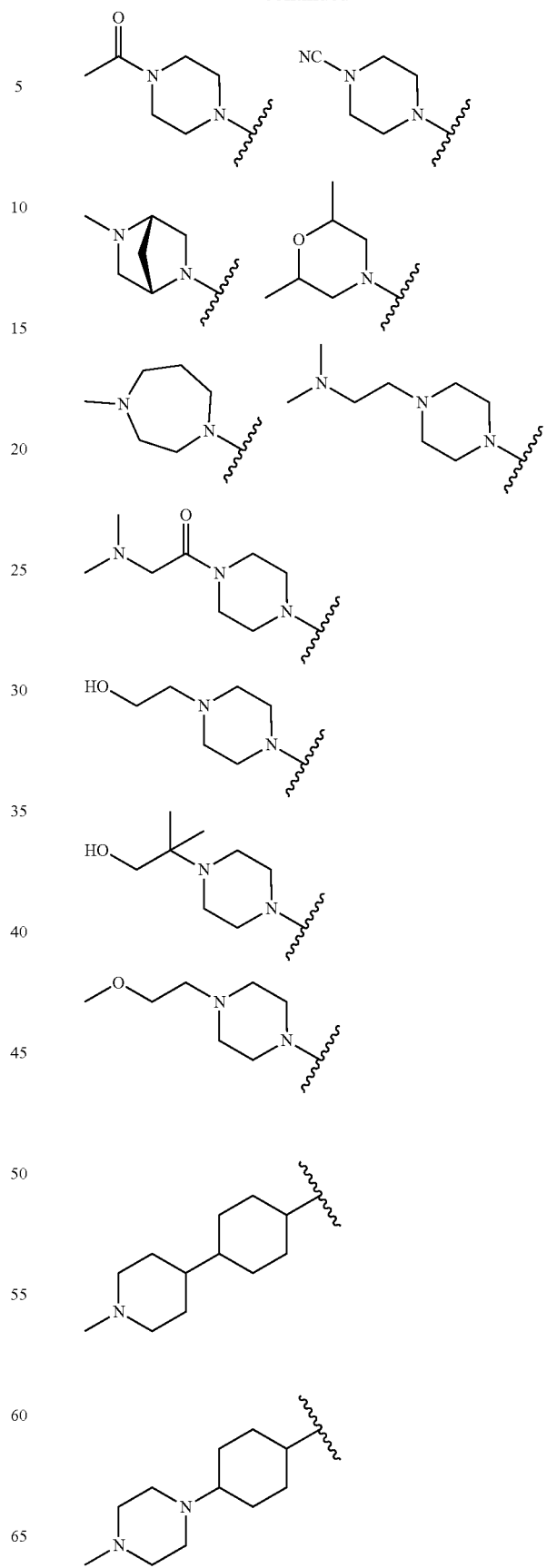

473
-continued
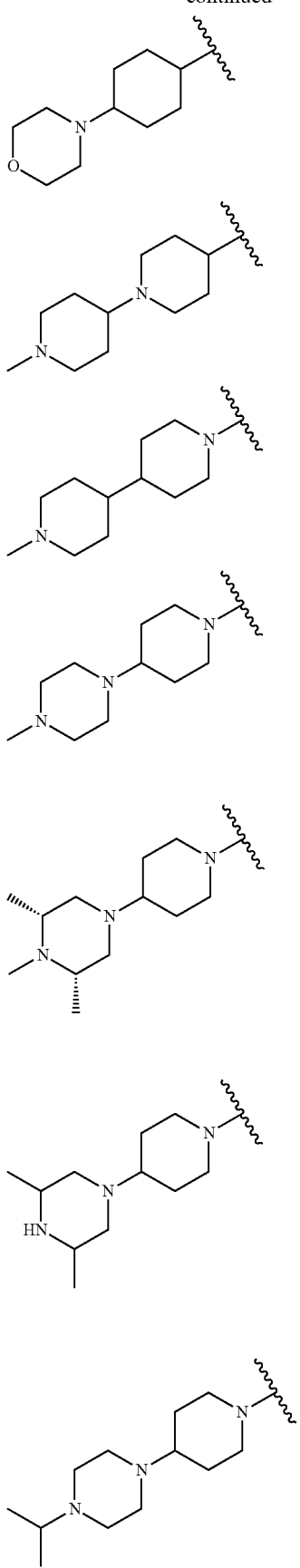
474
-continued
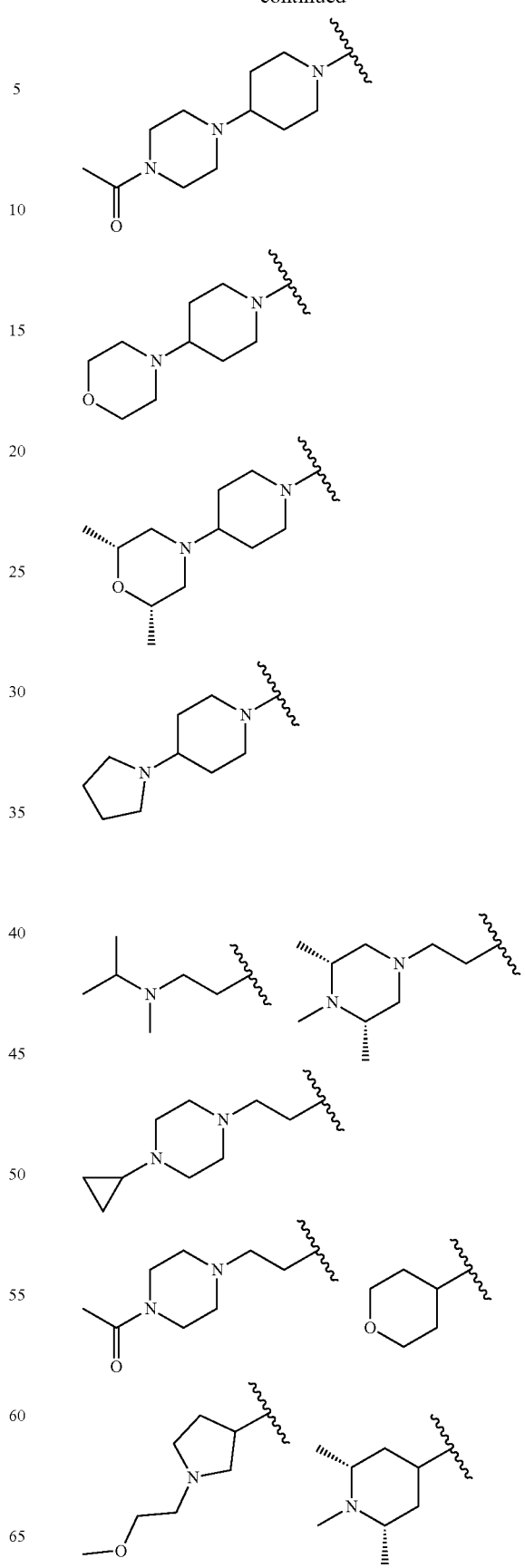

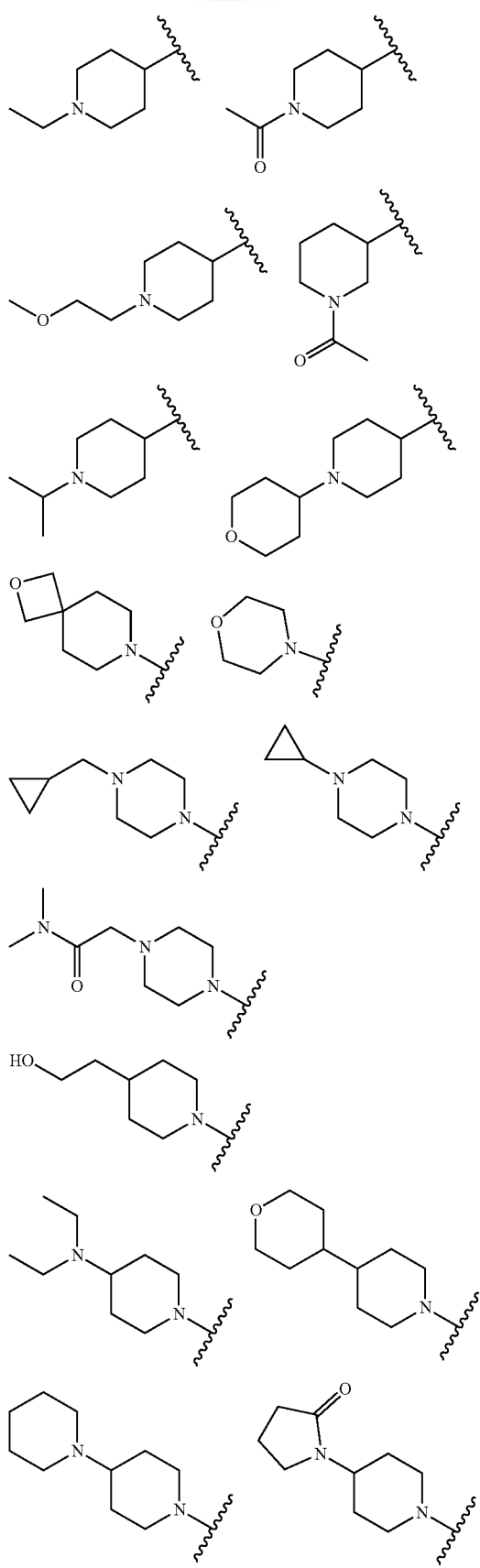
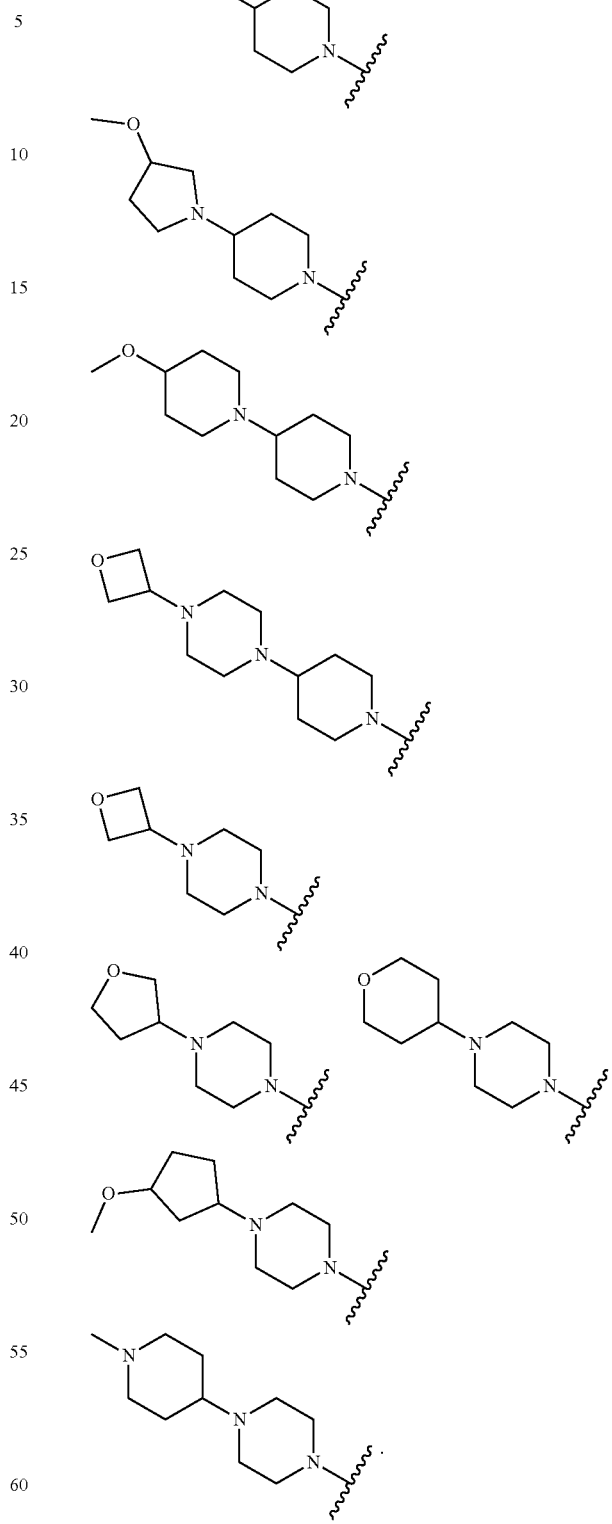
13. The compound or a pharmaceutically acceptable salt, stereoisomer, prodrug or solvate thereof according to claim 1, wherein, in Formula I $Z^1$ is C—$R^7$, $Z^2$ is N, or $Z^1$ is N, $Z^2$ is C—$R^7$, wherein $R^7$ is hydrogen.

14. The compound or a pharmaceutically acceptable salt, stereoisomer, prodrug or solvate thereof according to claim 1, wherein, in Formula I, $R^1$ is hydrogen;

$R^2$ is $OR^8$, $R^8$ is methyl, ethyl, n-propyl, isopropyl, cyclopropyl, difluoromethyl, trifluoromethyl, cyclobutyl, and cyclopropylmethyl;

X is a chemical bond or $NR^3$, wherein $R^3$ is hydrogen, methyl, ethyl, and methoxyethyl;

$R^4$ is selected from the group consisting of:

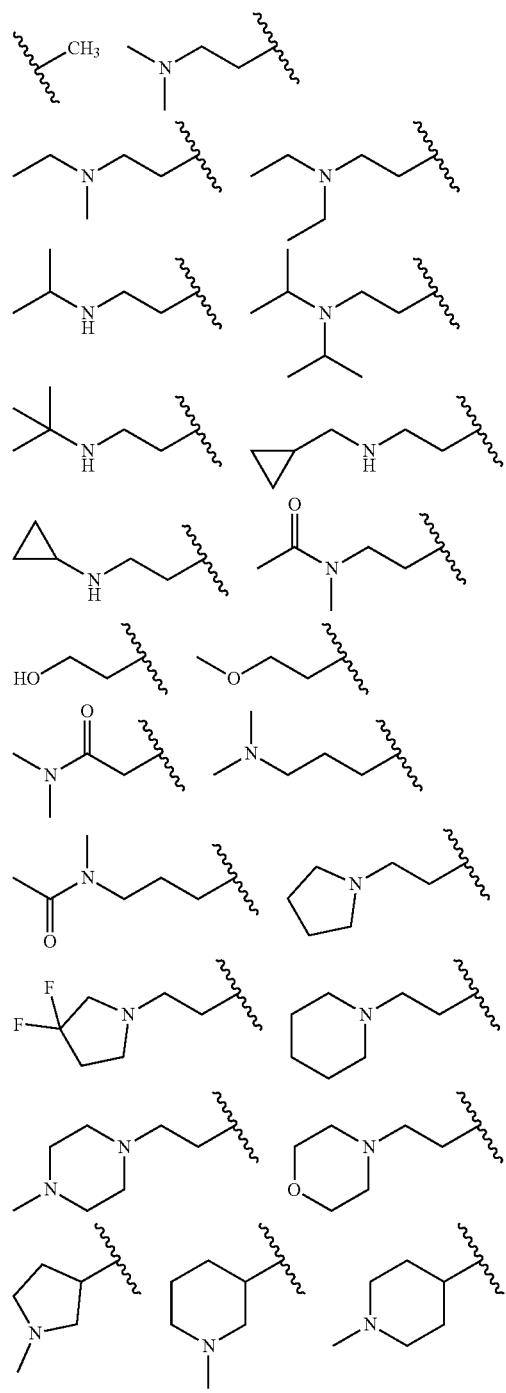

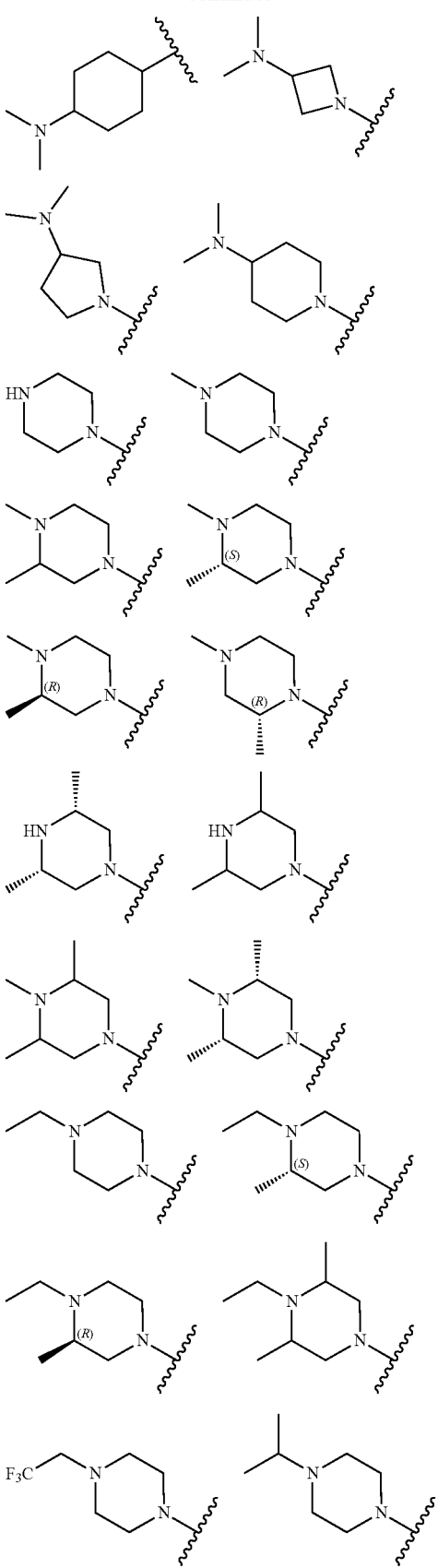

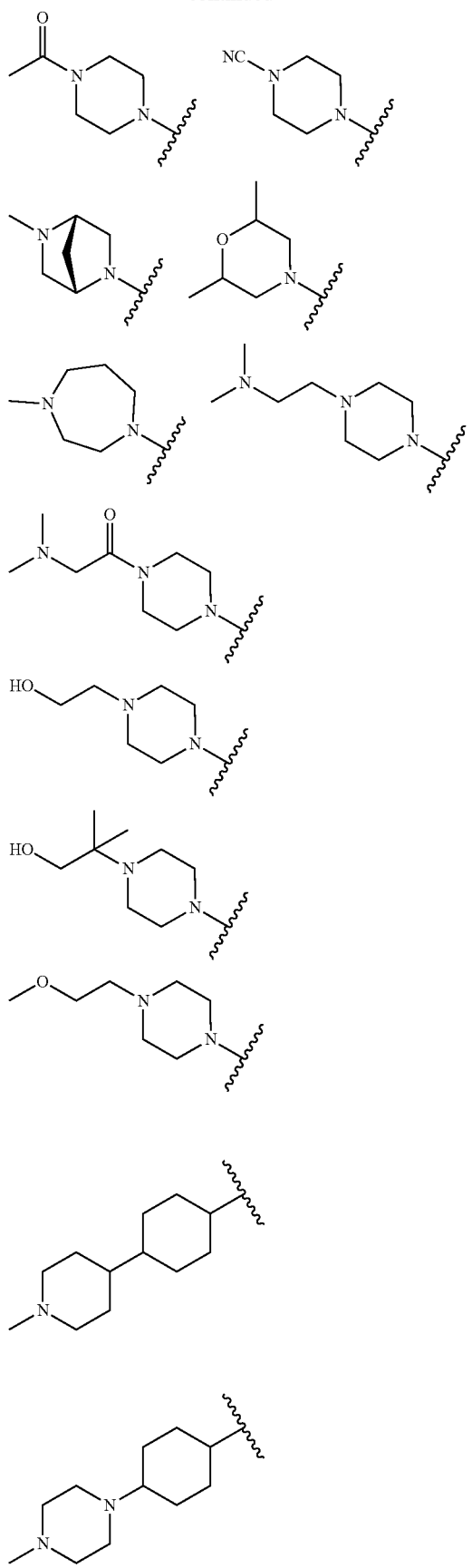
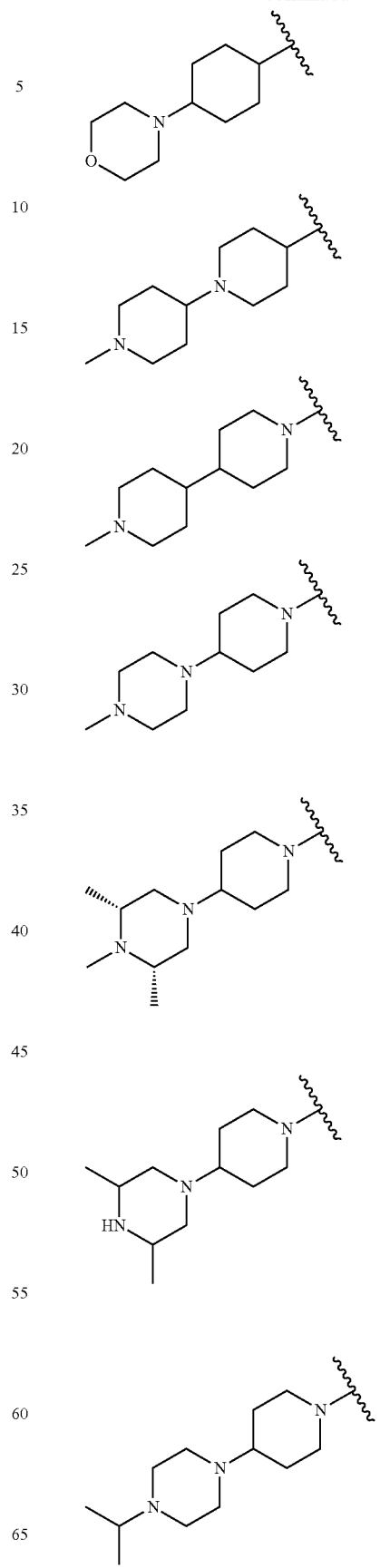

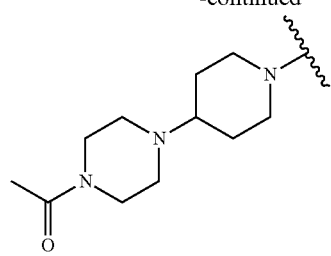
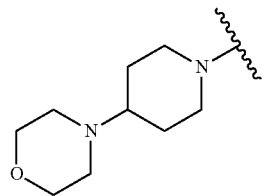
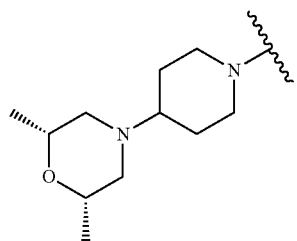
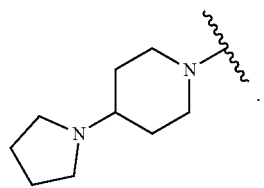
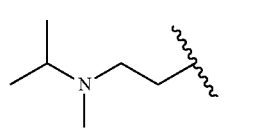
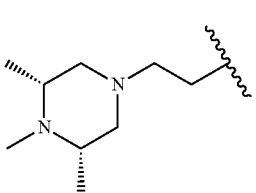
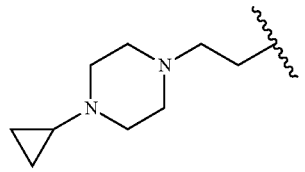
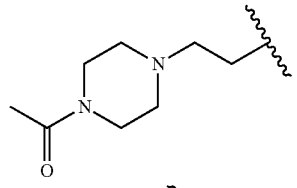
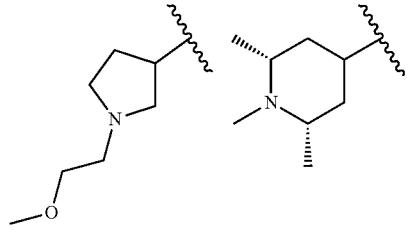
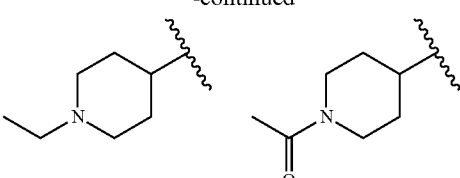
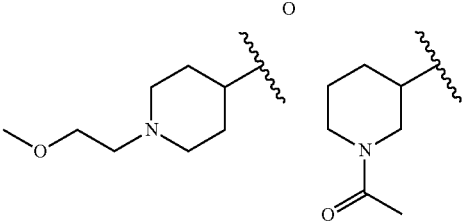
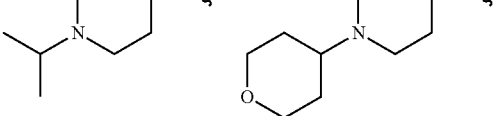
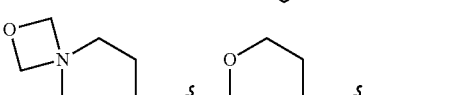
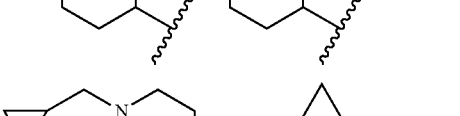
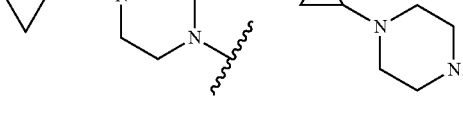
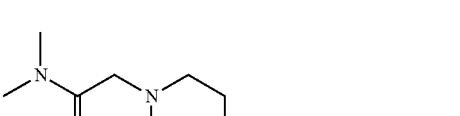
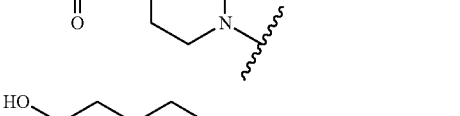
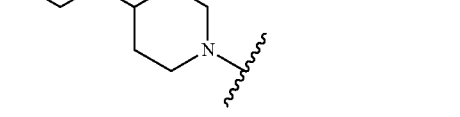
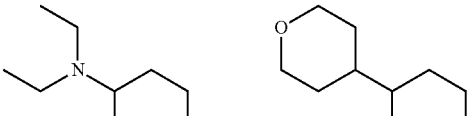
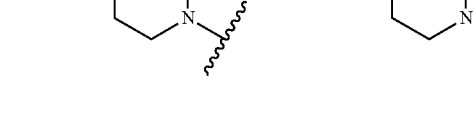

483
-continued

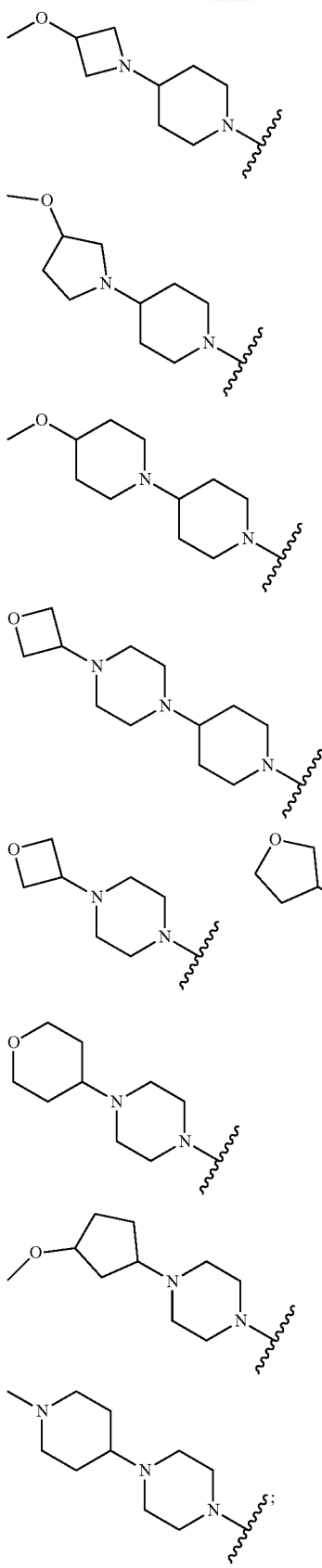

484

R⁵ is selected from the group consisting of:

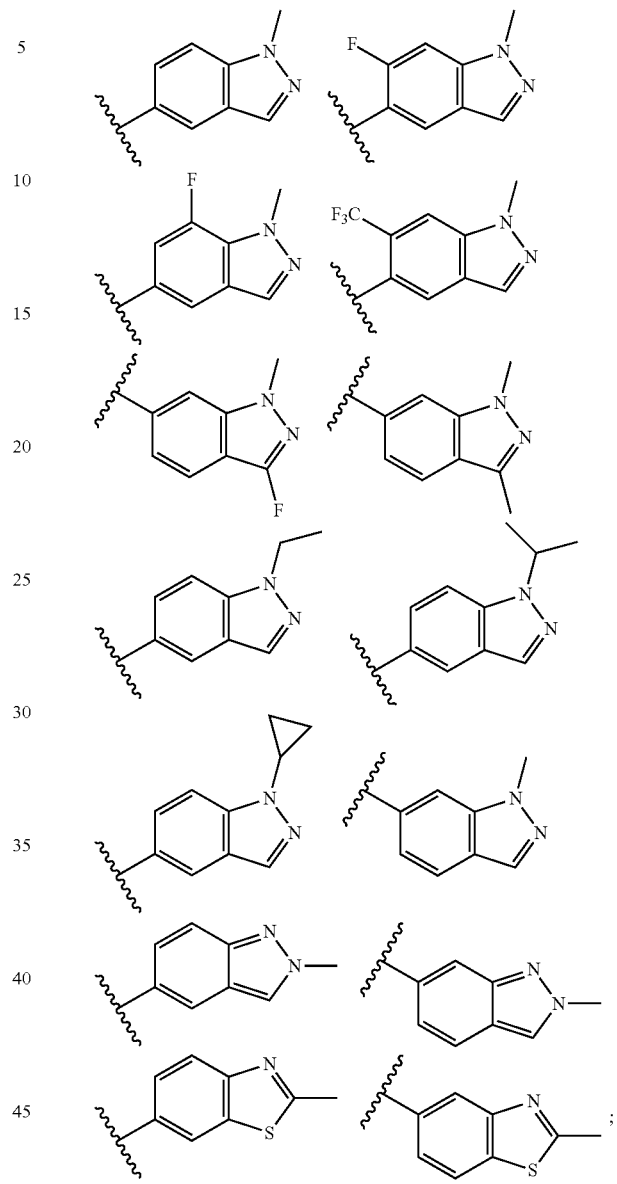

R⁶ is hydrogen and halogen;
Z¹ is C—R⁷, Z² is N, or Z¹ is N, Z² is C—R⁷, wherein R⁷ is hydrogen.

15. The compound or a pharmaceutically acceptable salt, stereoisomer, prodrug or solvate thereof according to claim 1, wherein, in Formula I,
R¹ is hydrogen;
R² is OR⁸, R⁸ is methyl, ethyl, and difluoromethyl;
X is a chemical bond or NR³, wherein R³ is hydrogen; $C_{1-6}$ alkyl;
R⁴ is selected from the group consisting of:

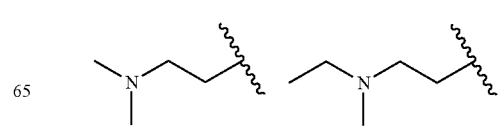

485
-continued
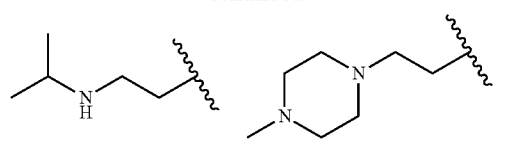
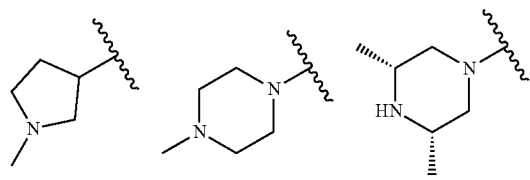
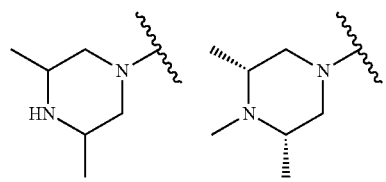
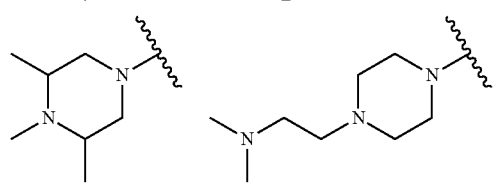
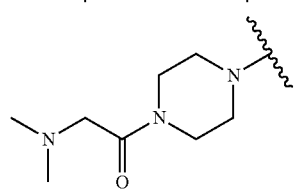
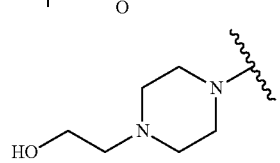
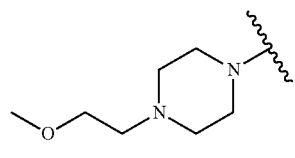
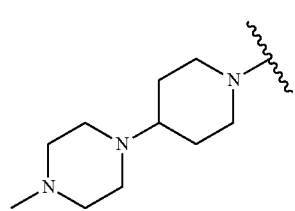
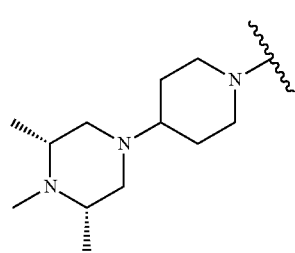
486
-continued
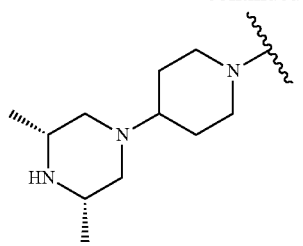
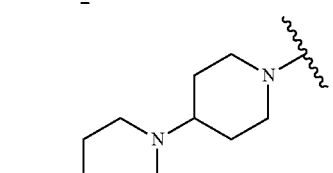
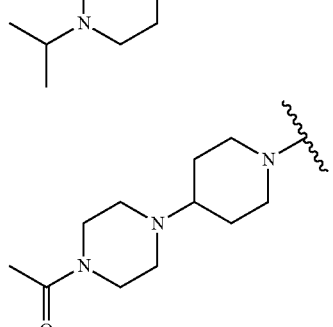
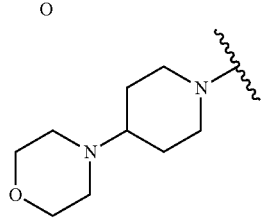
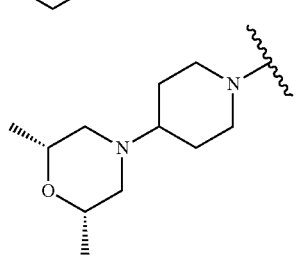
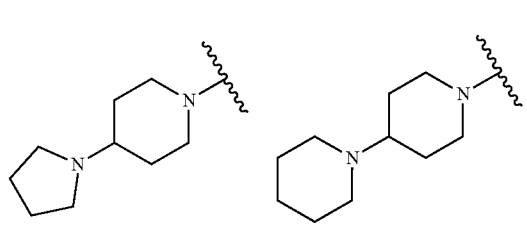
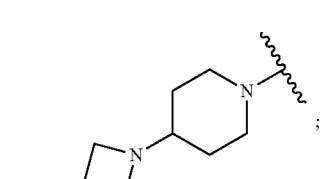

R[5] is selected from the group consisting of:
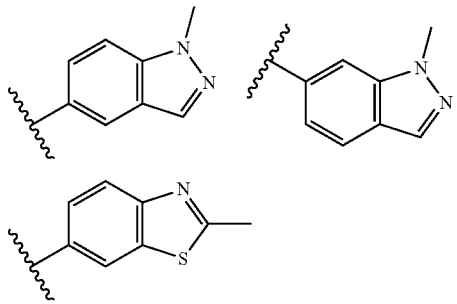
R[6] is hydrogen or halogen;
Z[1] is C—R[7], Z[2] is N, or Z[1] is N, Z[2] is C—R[7], wherein R[7] is hydrogen.
16. The compound or a pharmaceutically acceptable salt, stereoisomer, prodrug or solvate thereof according to claim 1, wherein, the compound shown in Formula I is selected from the following compounds:
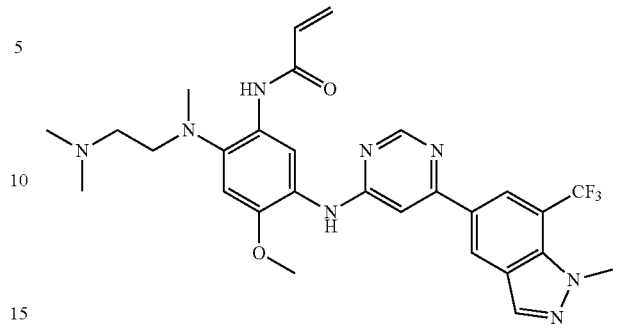
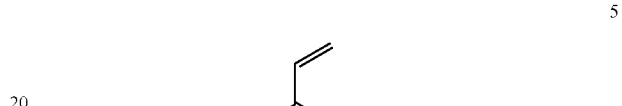
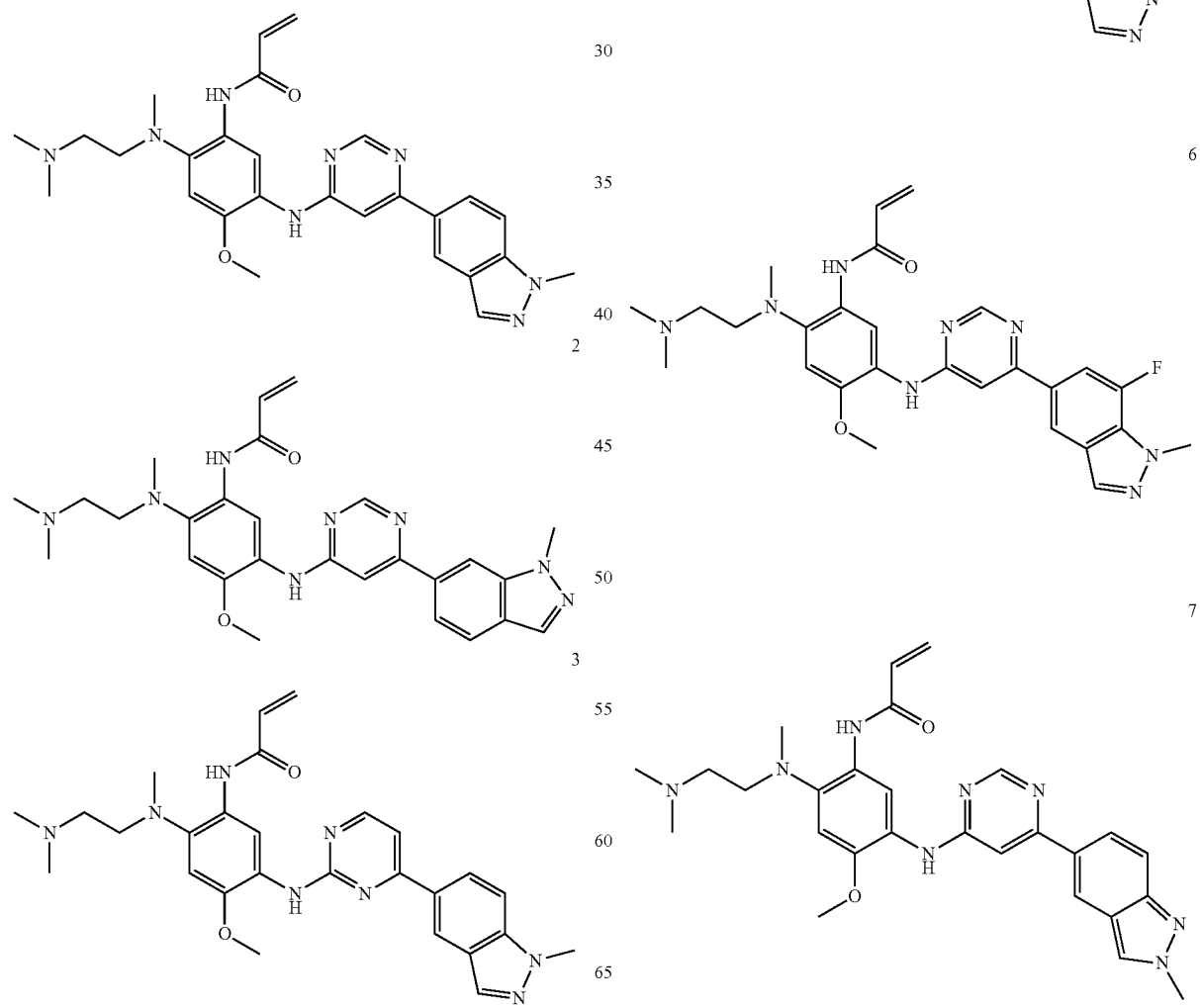

8
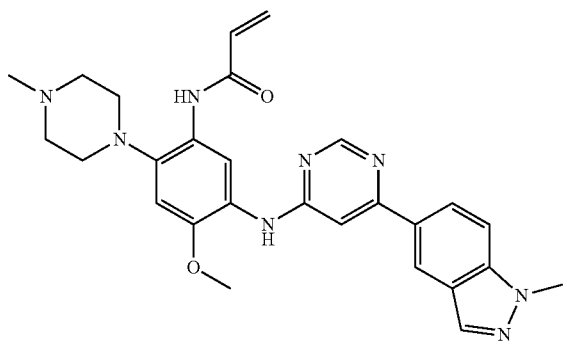
9
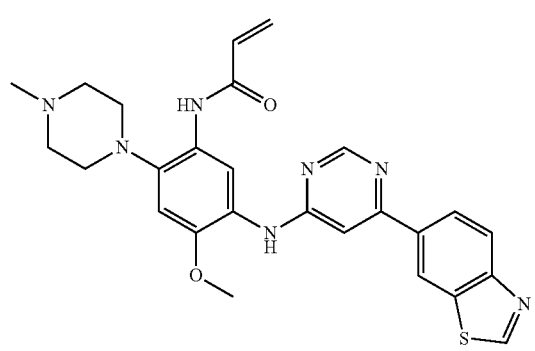
10
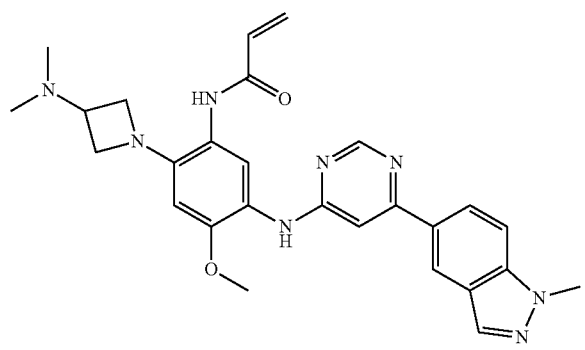
11
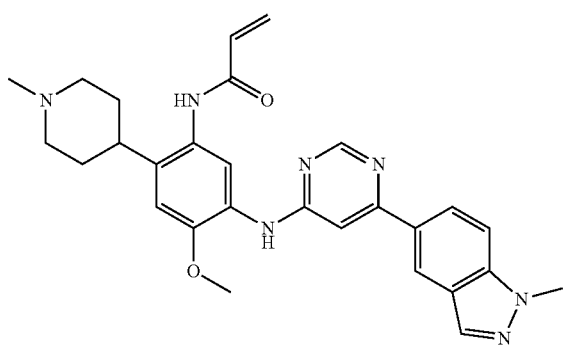
12
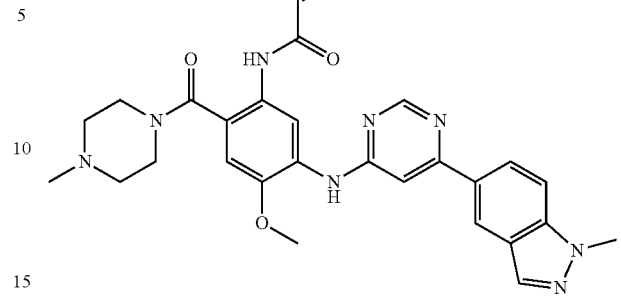
13
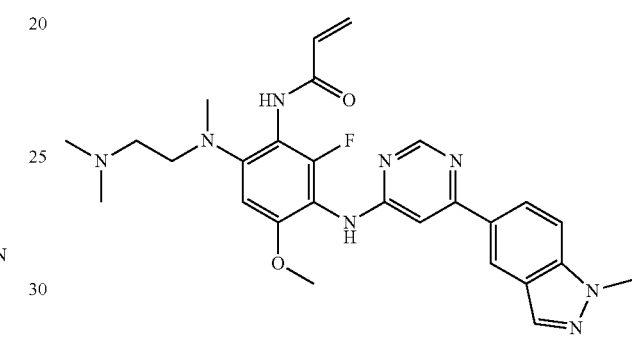
14
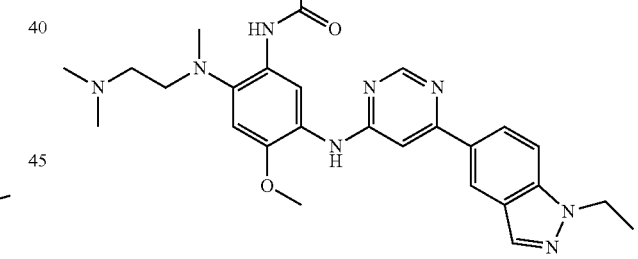
15
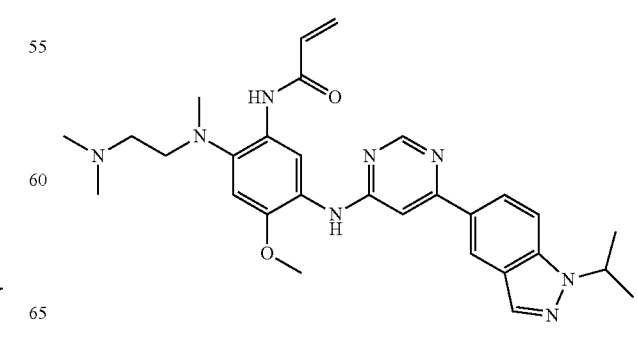

491
-continued
16
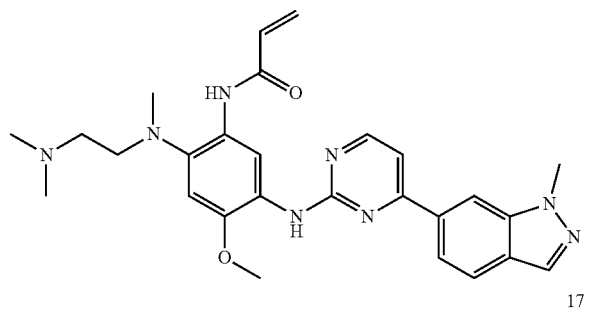
17
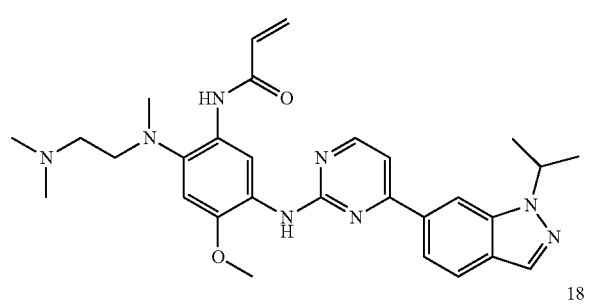
18
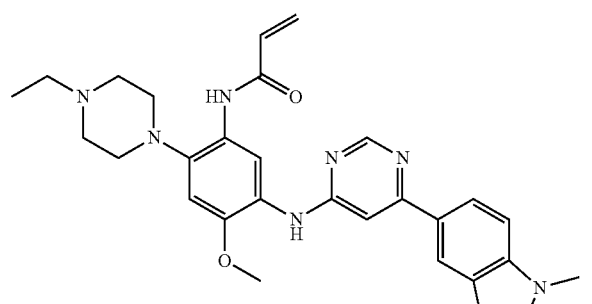
19
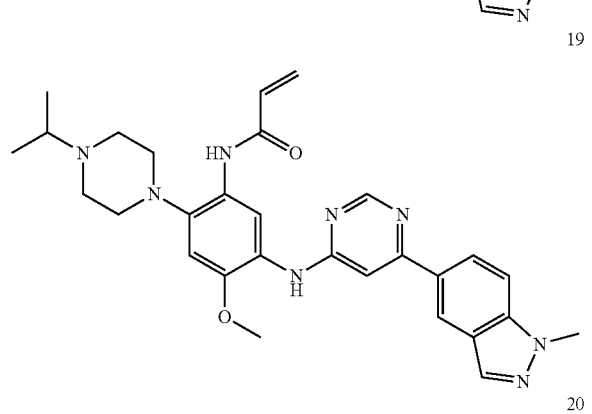
20
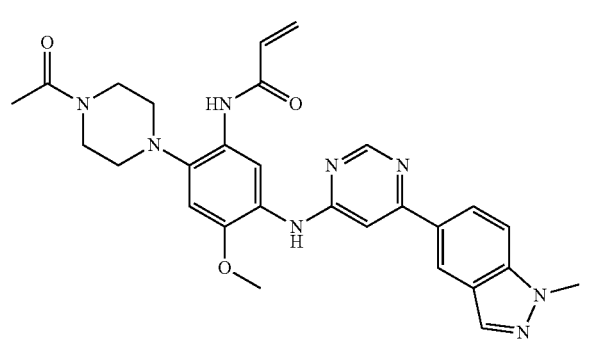
492
-continued
21
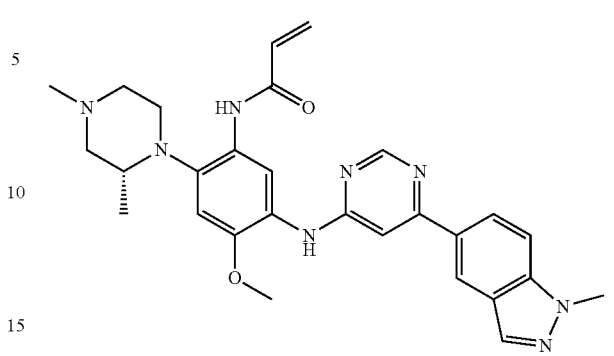
22
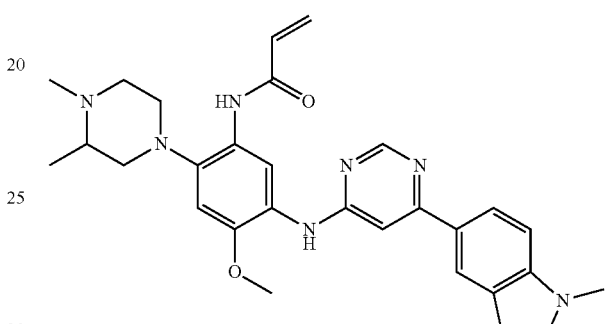
23
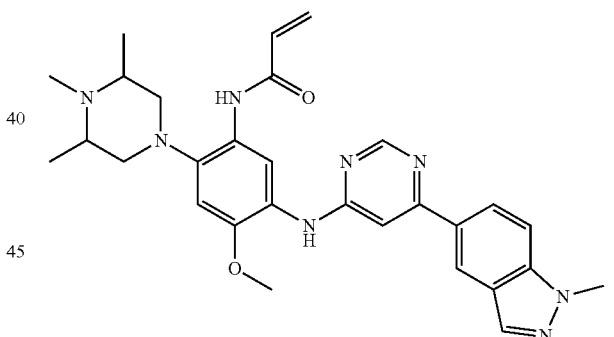
24
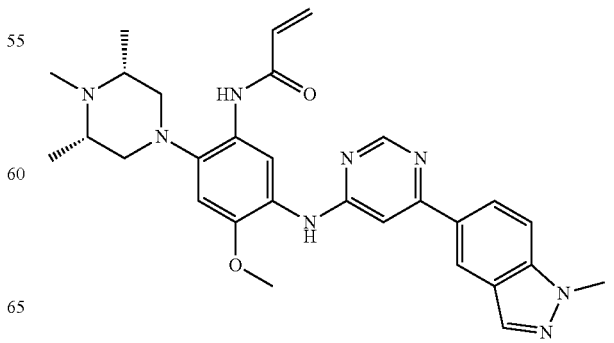

493
25
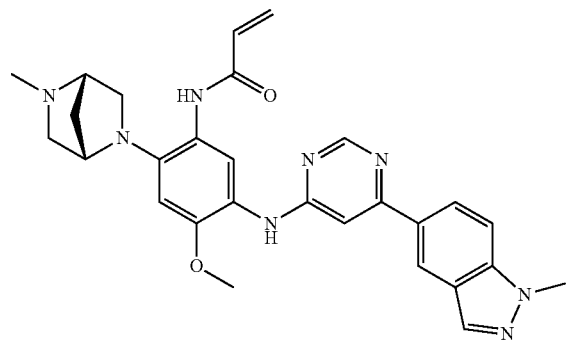
26
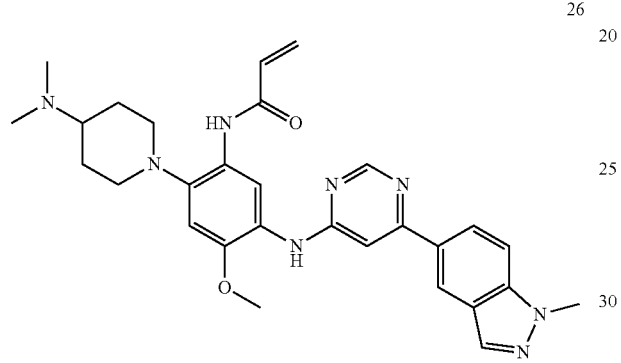
27
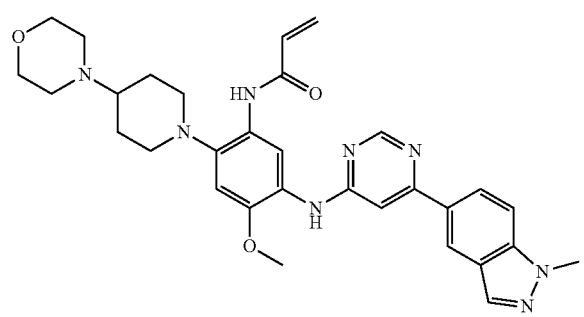
28
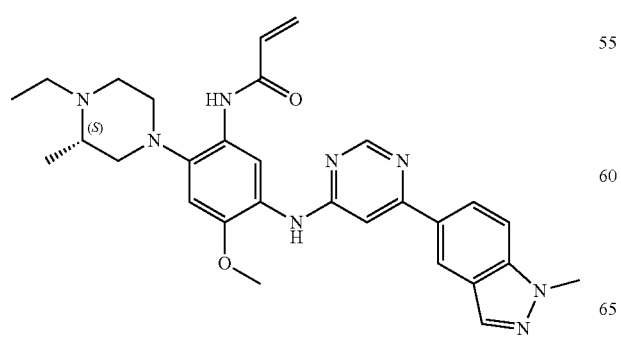
494
29
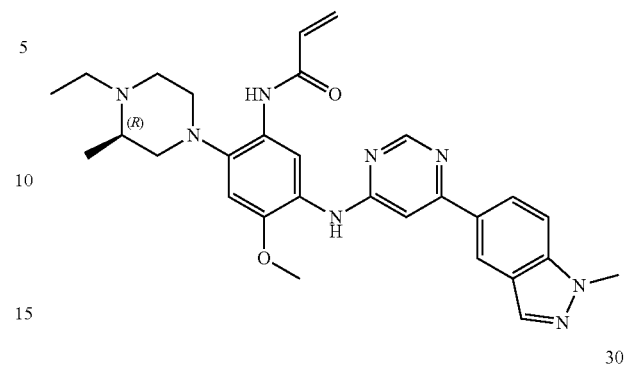
30
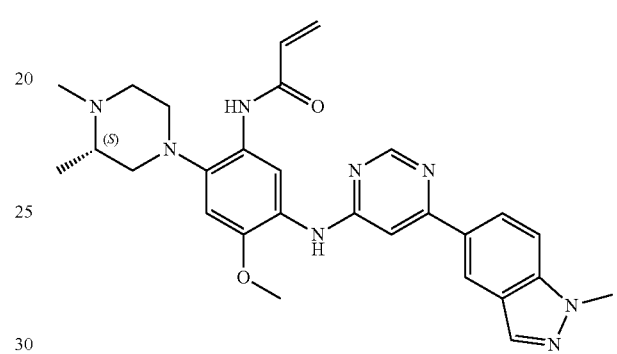
31
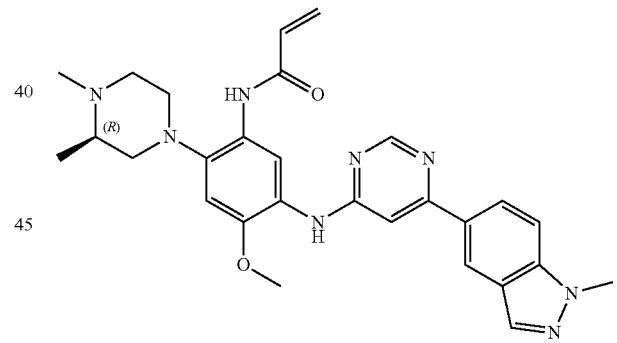
32
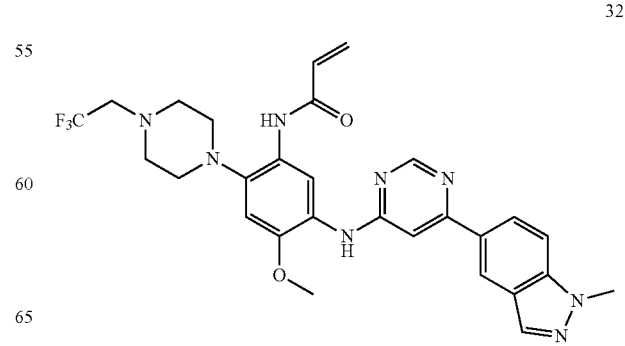

33
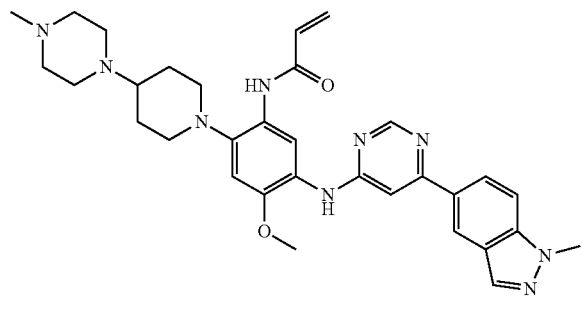
37
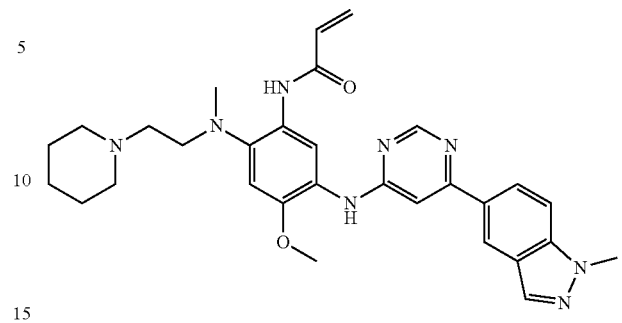
34
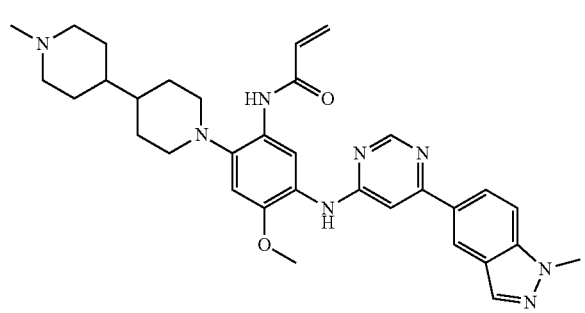
38
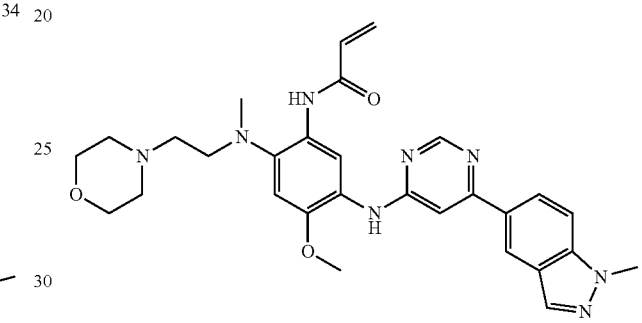
35
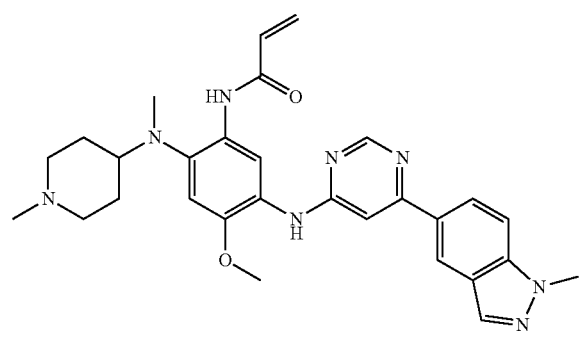
39
39
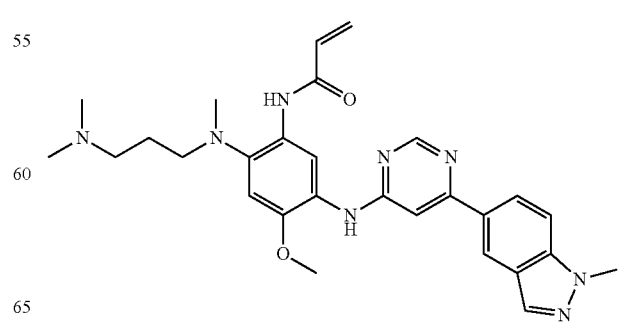
36
40

41
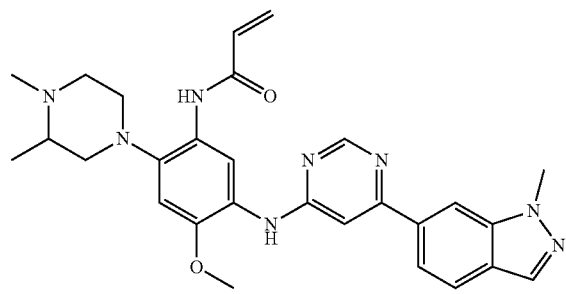
42
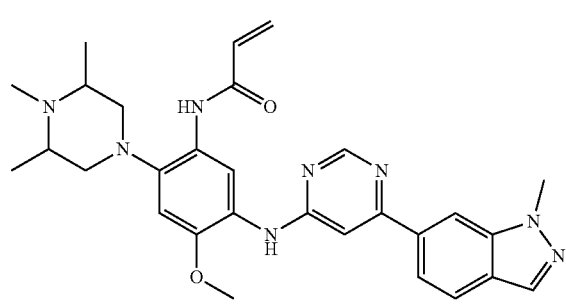
43
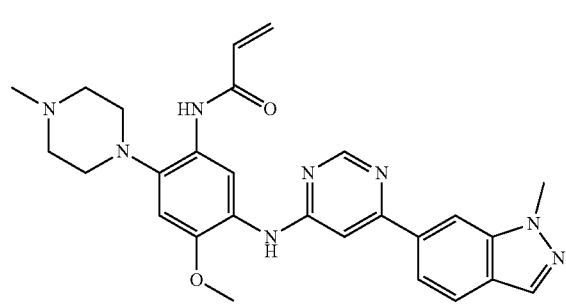
44
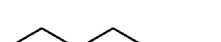
45
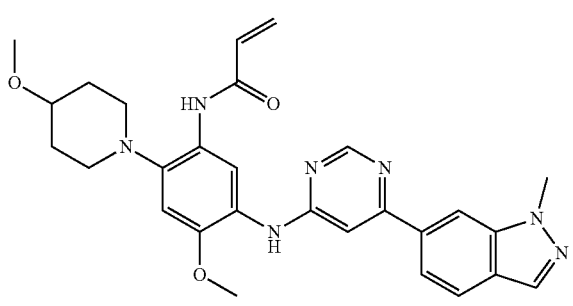
46
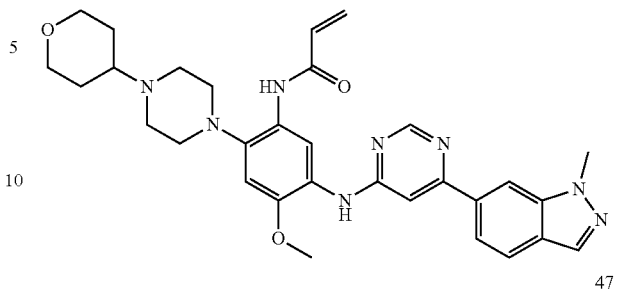
47
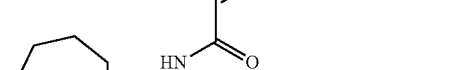
48
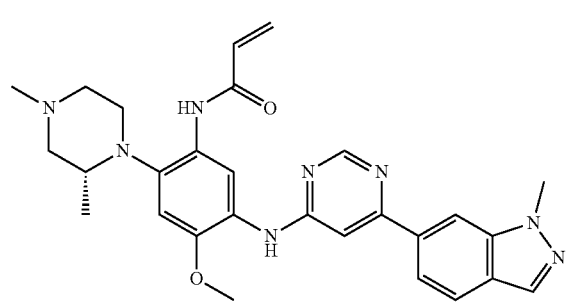
49
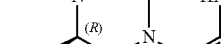
50

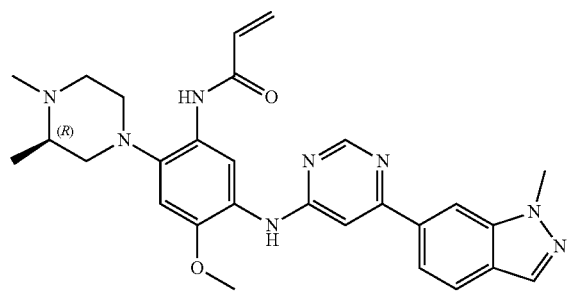
51
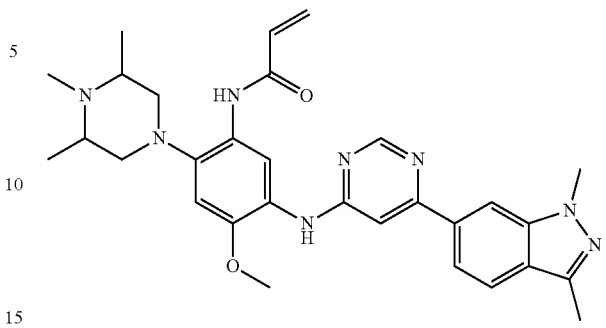
56
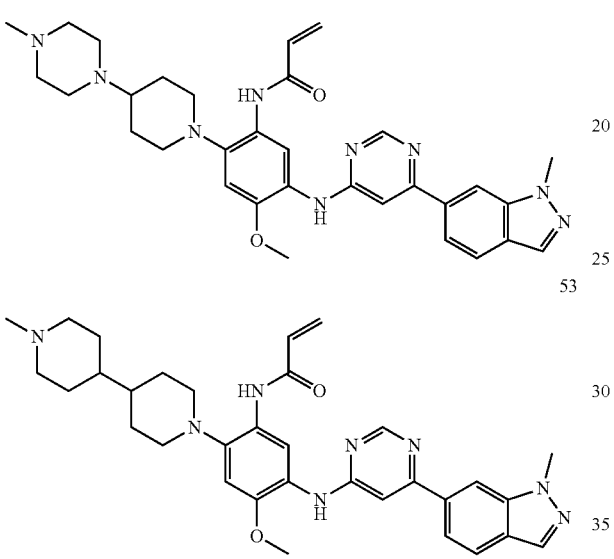
52
53
54
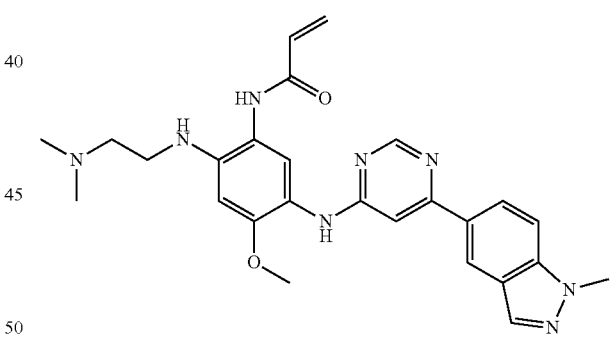
57
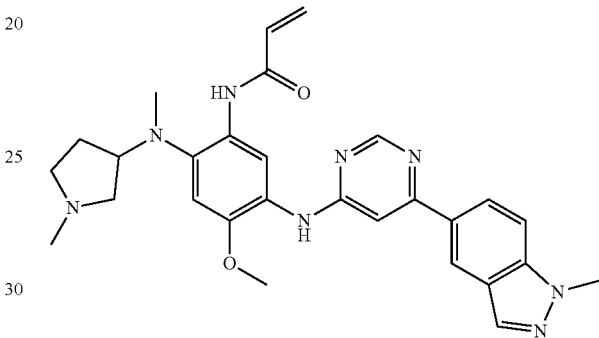
58
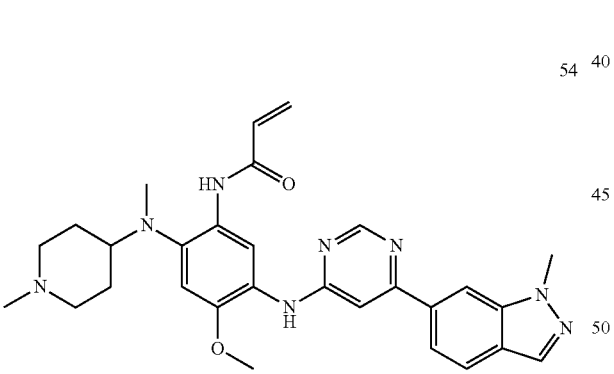
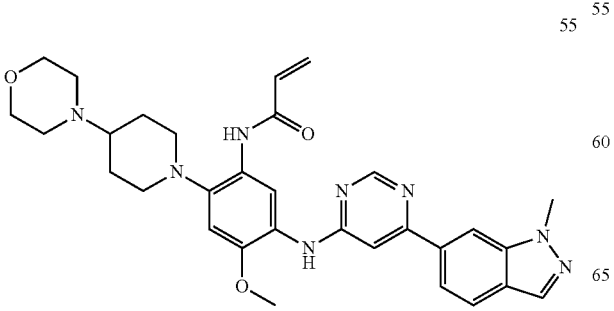
55
59

501
60
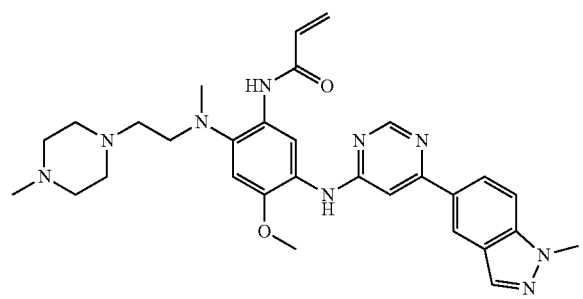
61
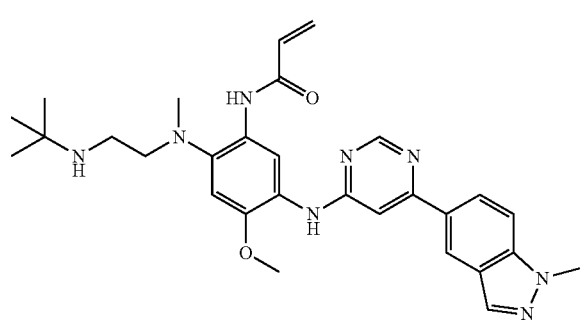
62
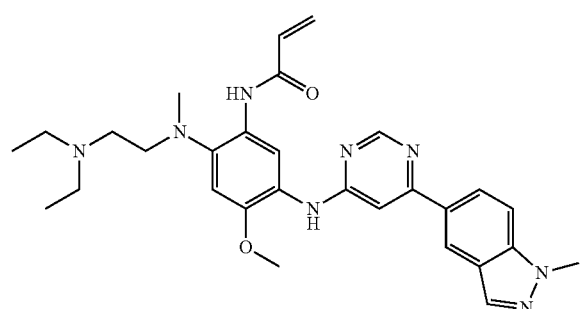
63
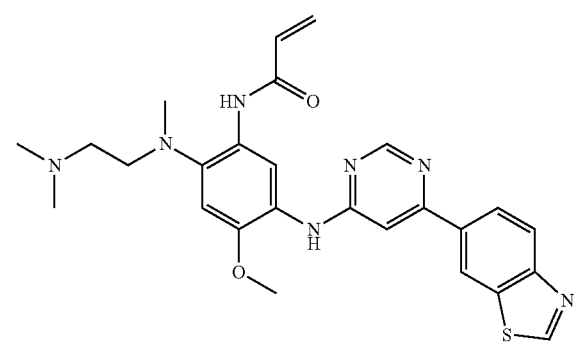
502
64
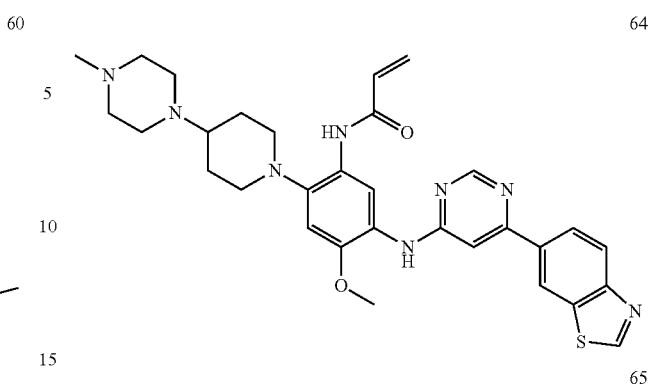
65
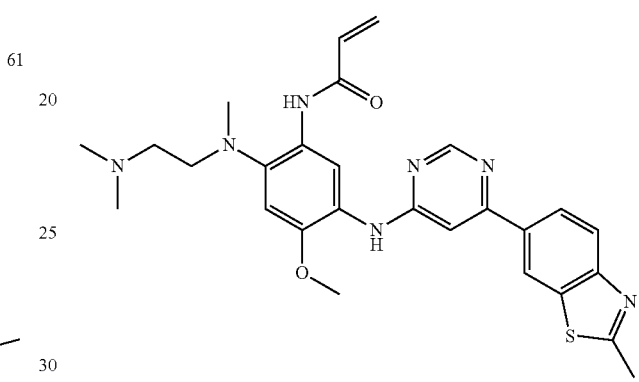
66
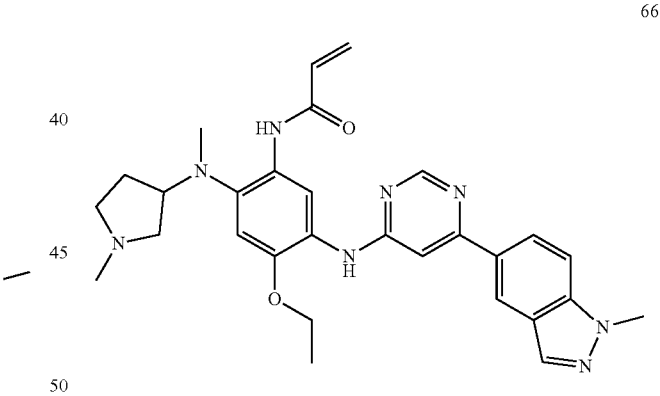
67
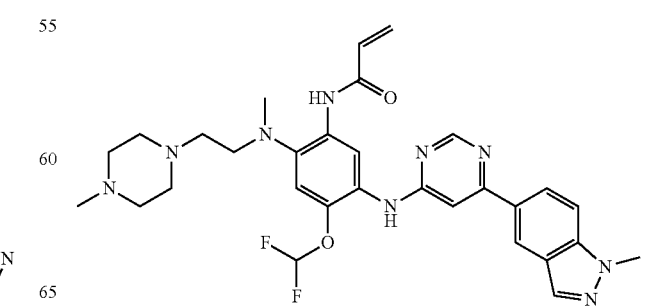

68
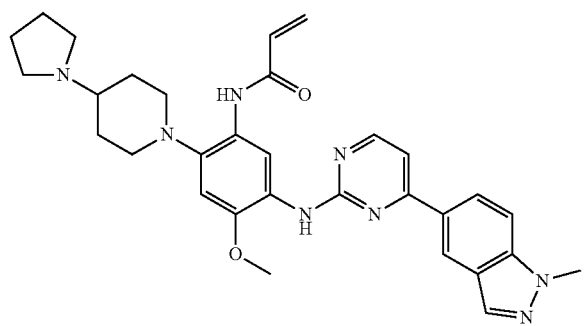
69
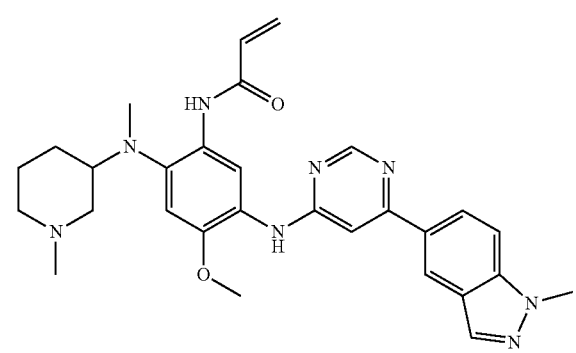
70
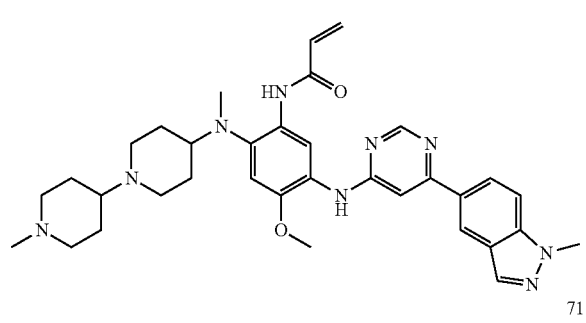
71
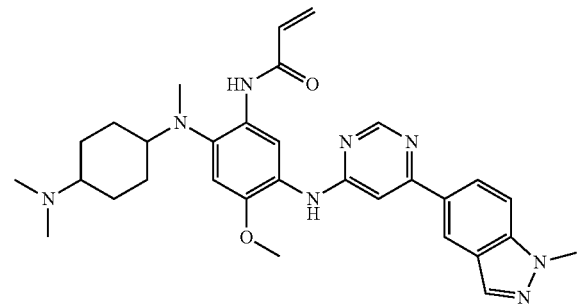
72
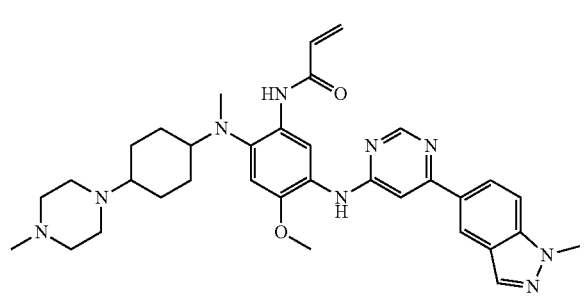
73
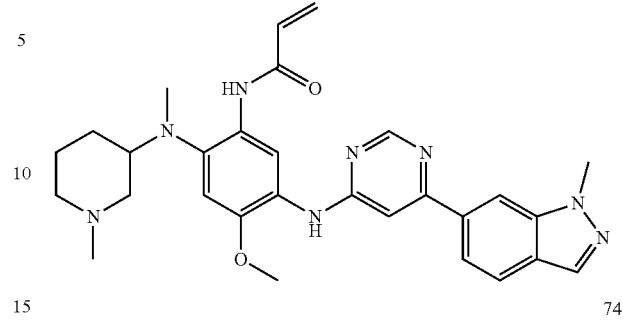
74
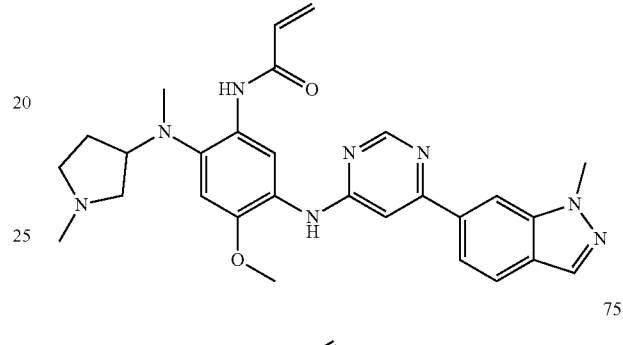
75
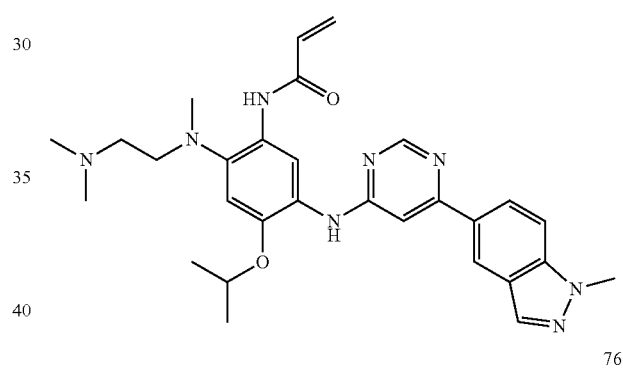
76
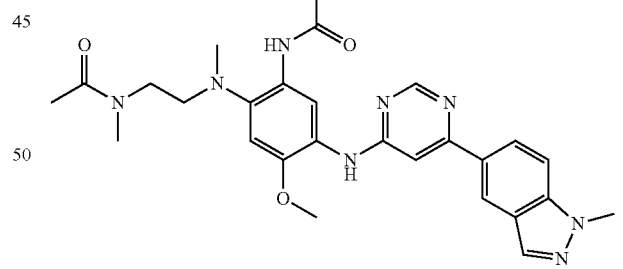
77
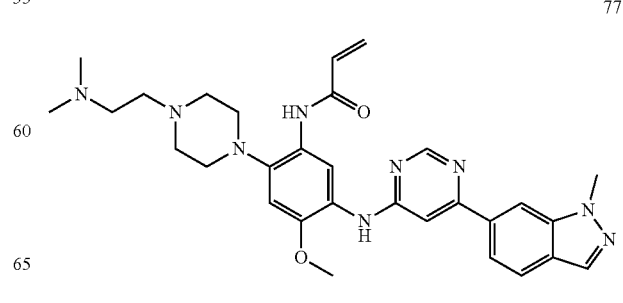

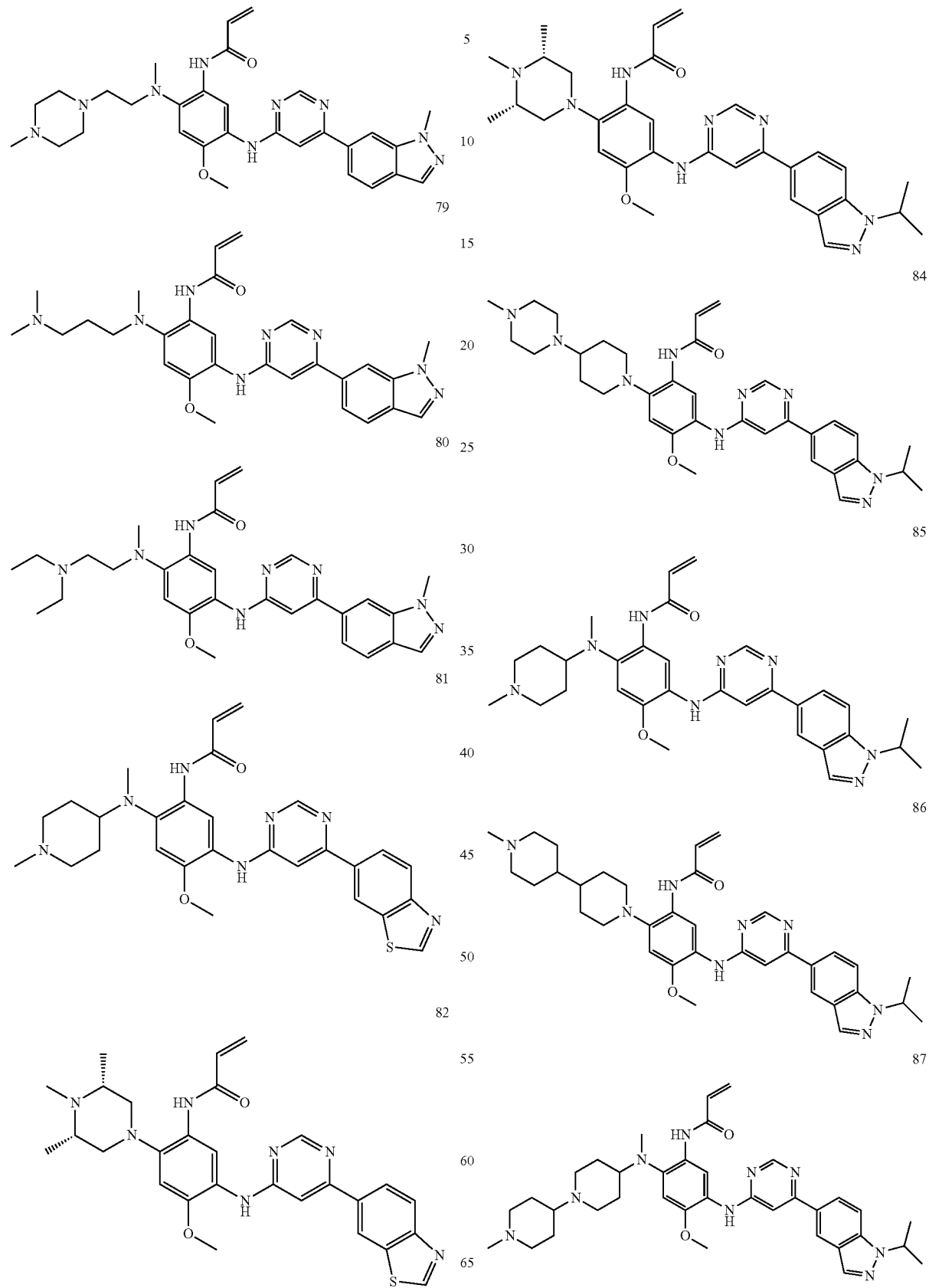

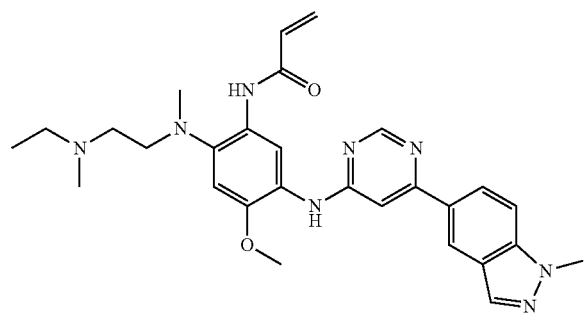
88
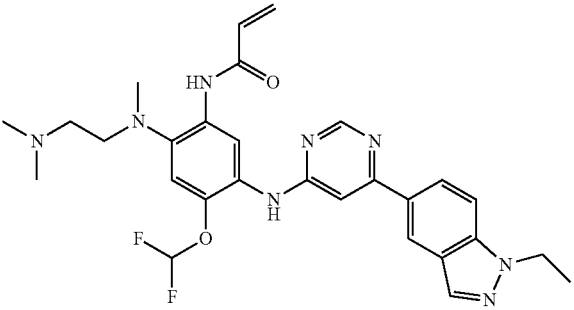
92
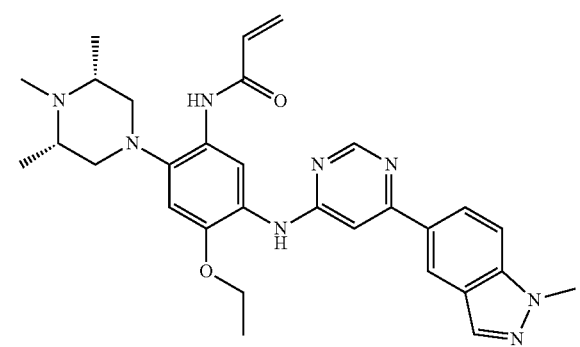
89
90
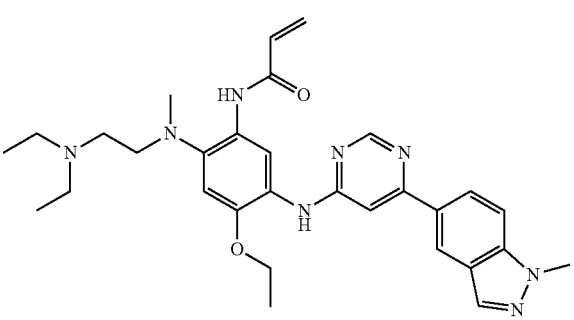
93
94
95
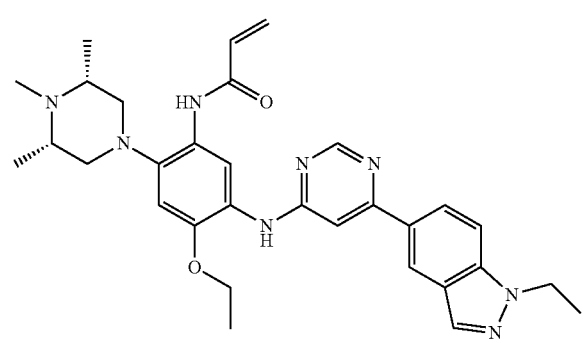
91
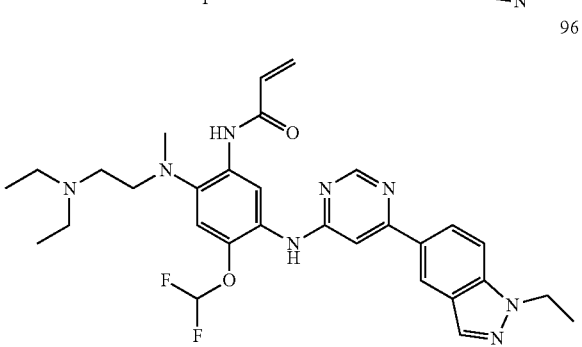
96

97
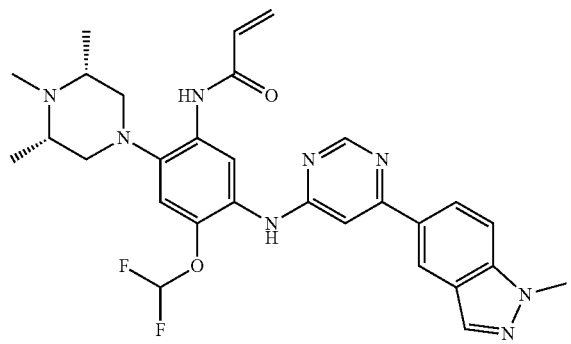
98
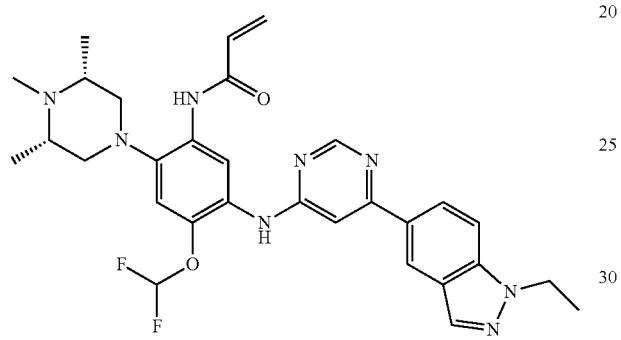
99
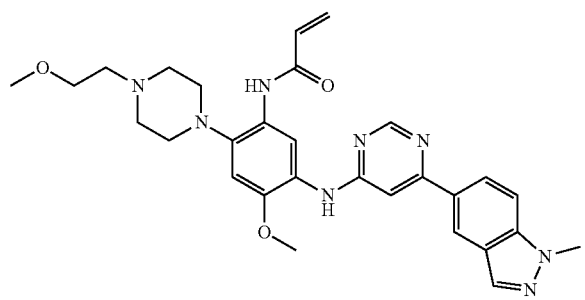
100
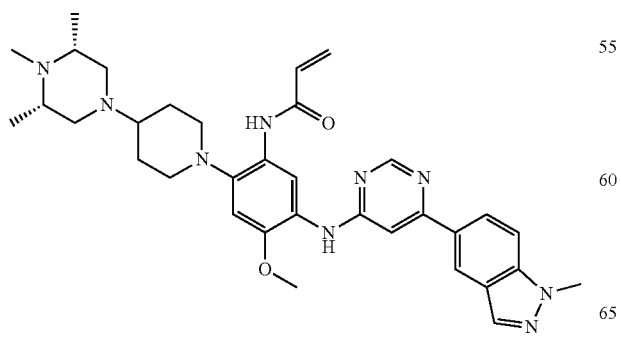
101
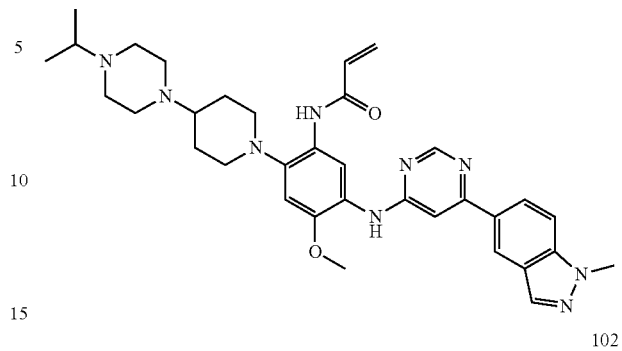
102
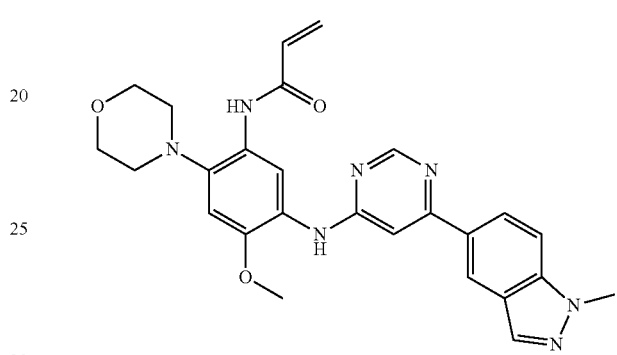
103
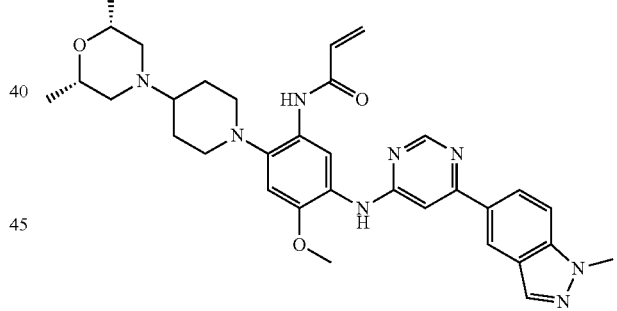
104
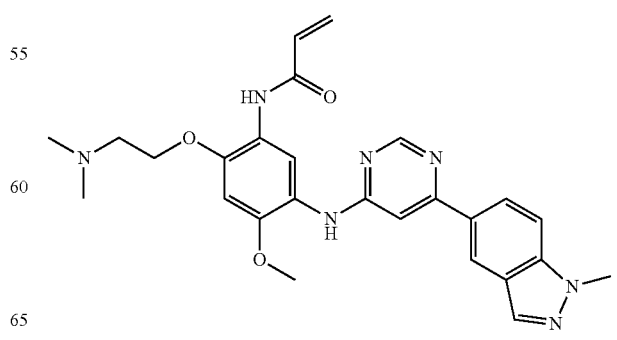

105
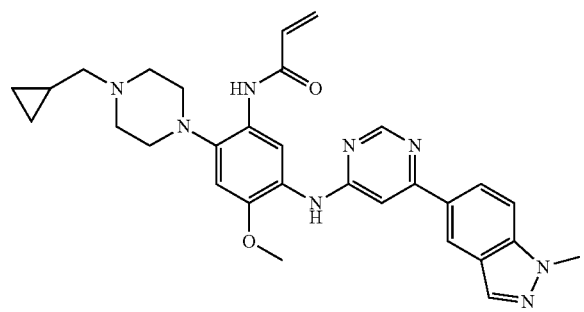
109
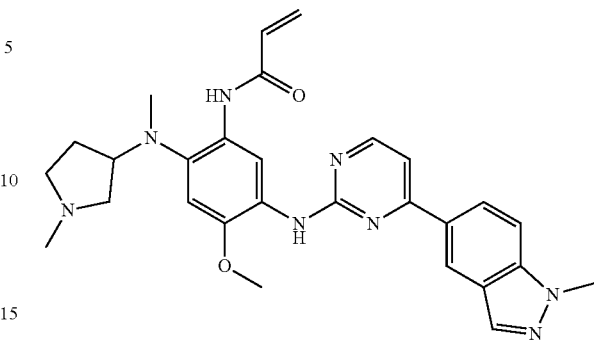
106
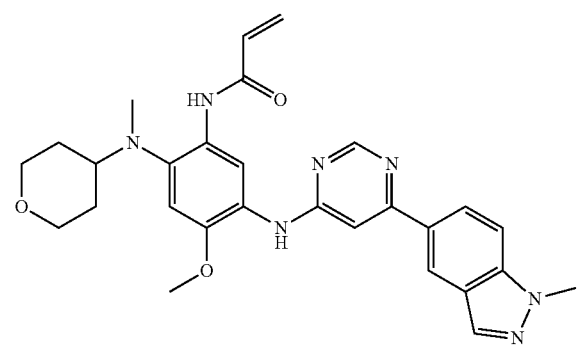
110
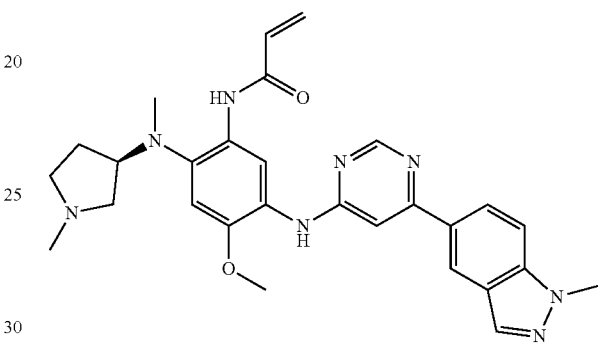
107
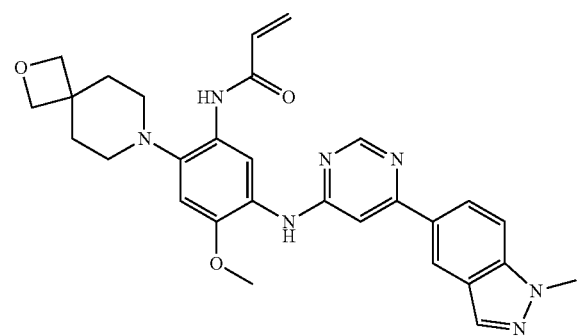
111
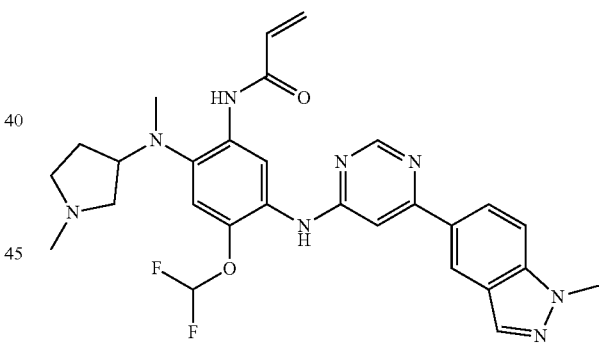
108
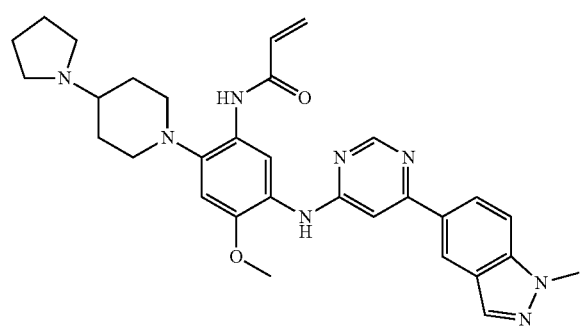
112
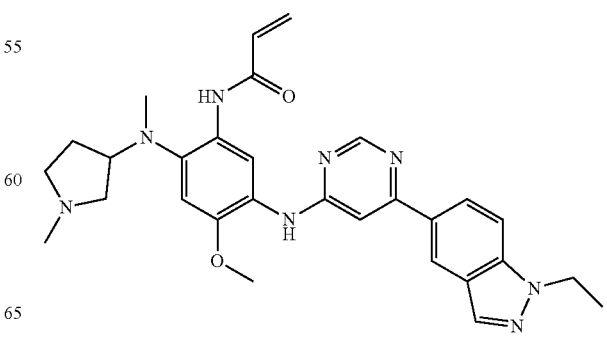

113
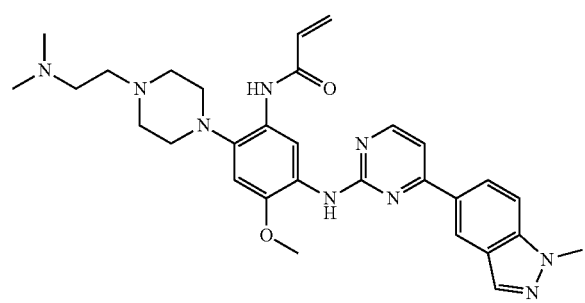
114
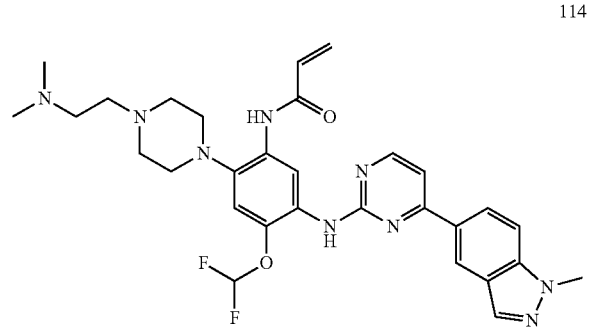
115
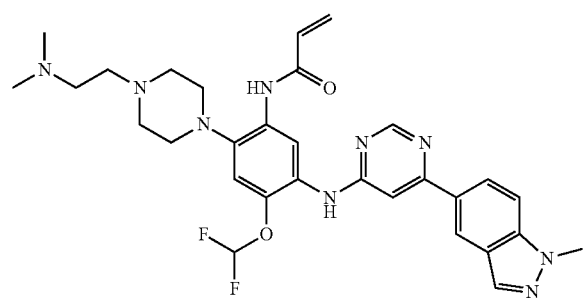
116
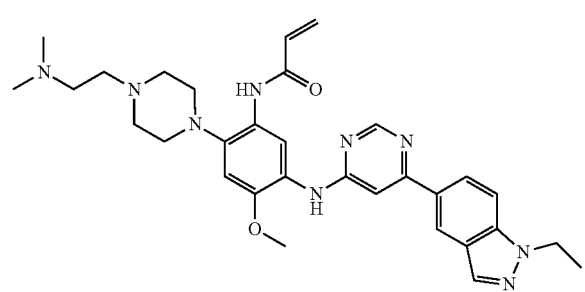
117
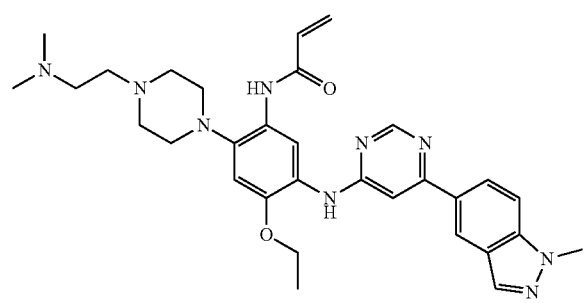
118
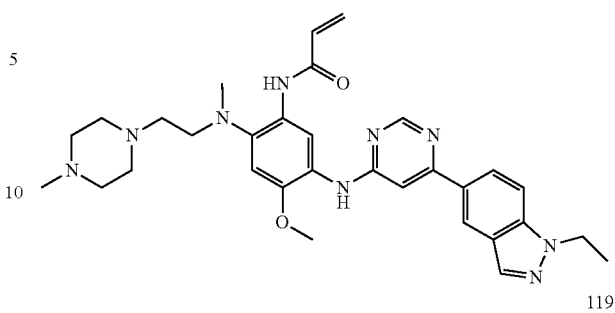
119
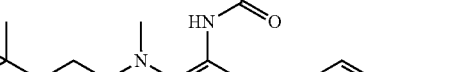
120
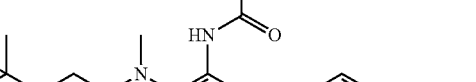
121
122

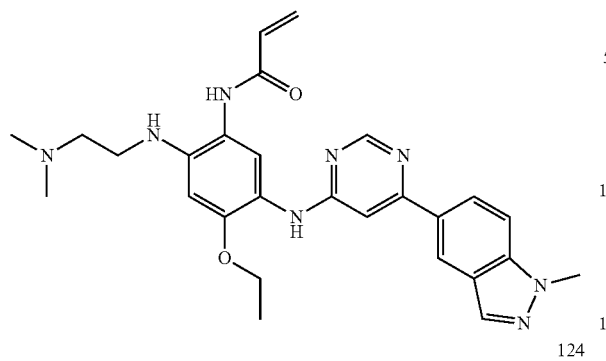
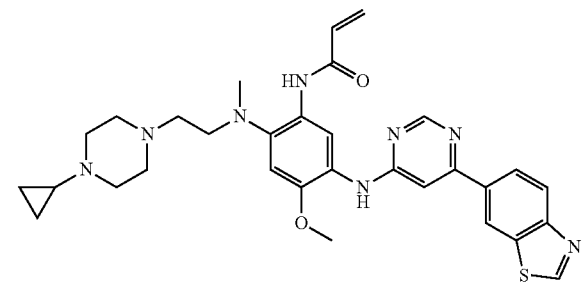
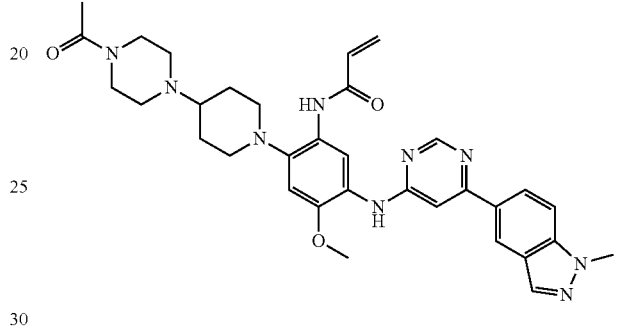
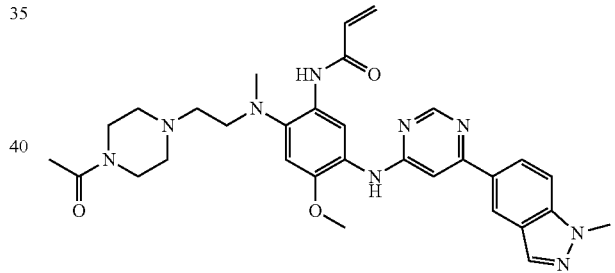
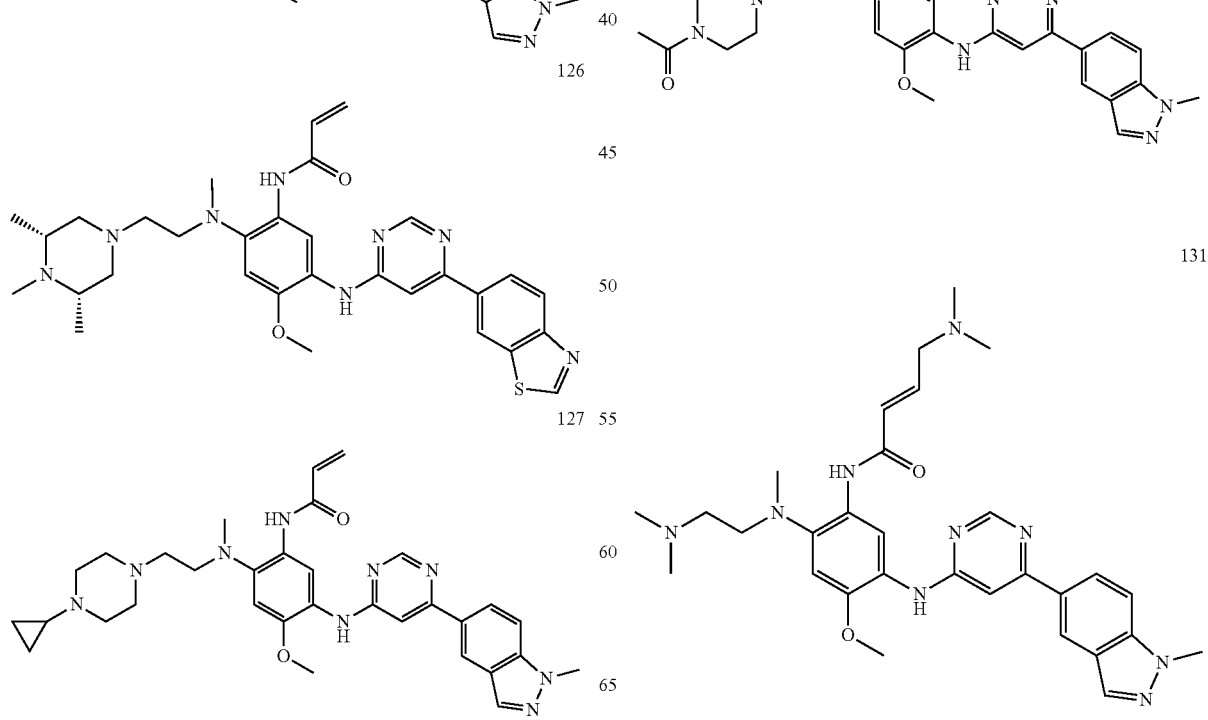

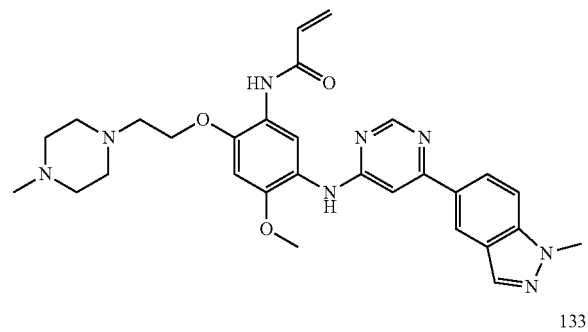
132
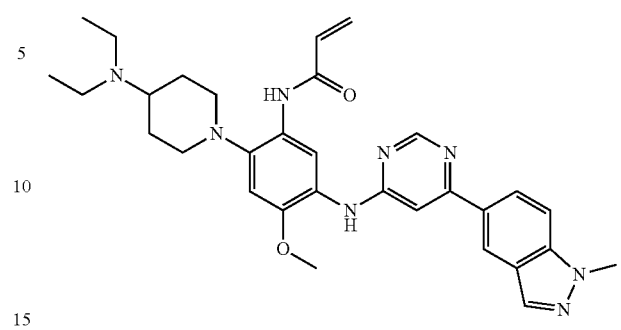
137
133
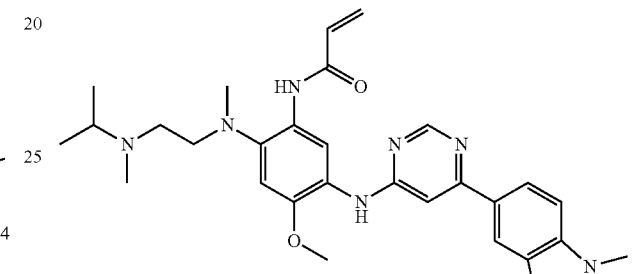
138
134
139
135
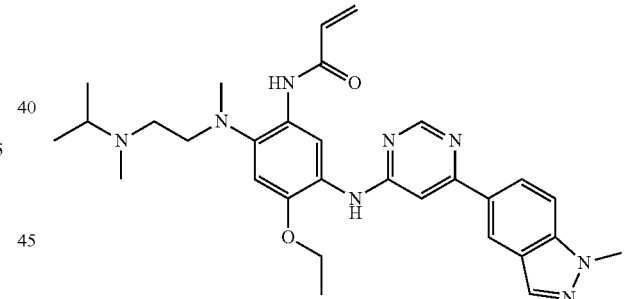
140
136
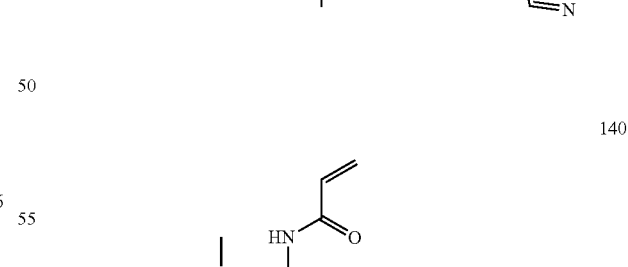
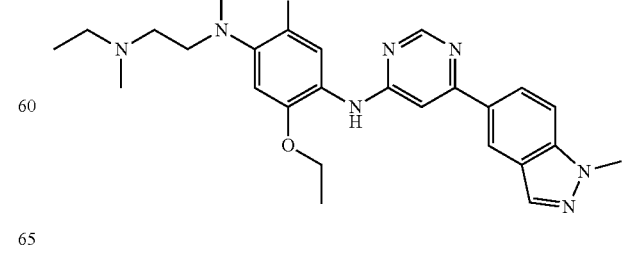

141
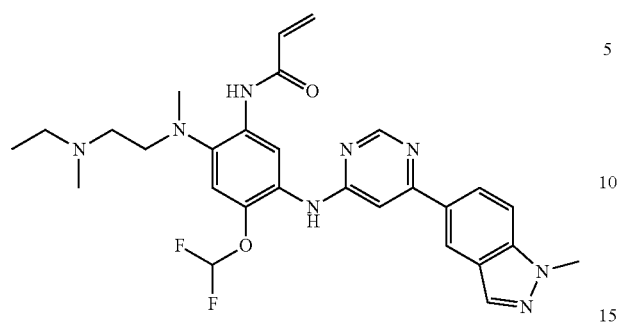
145
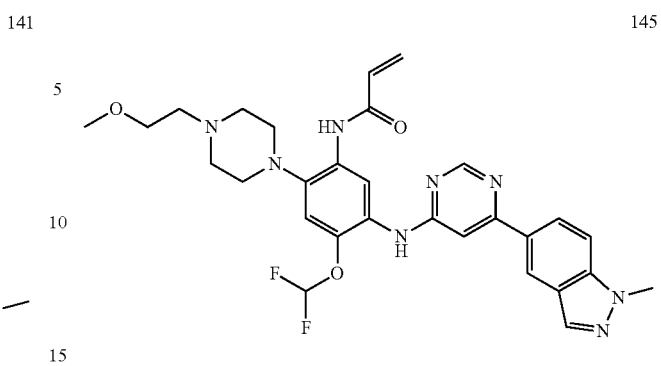
142
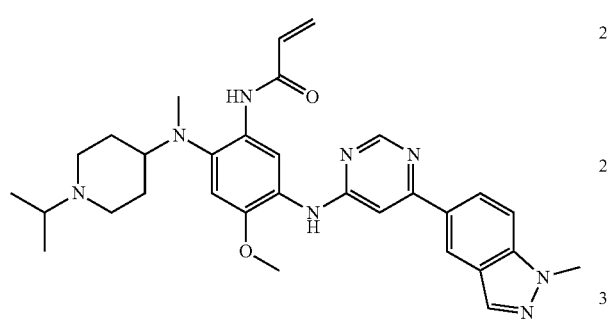
146
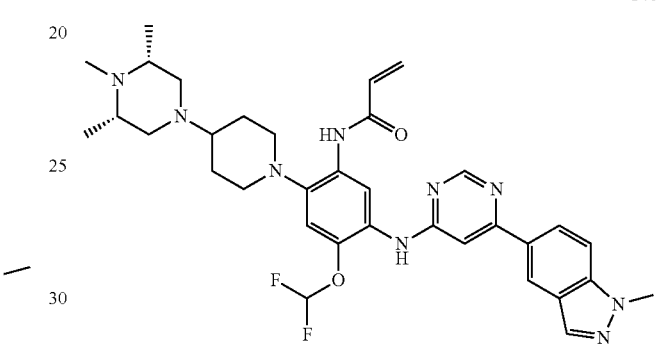
143
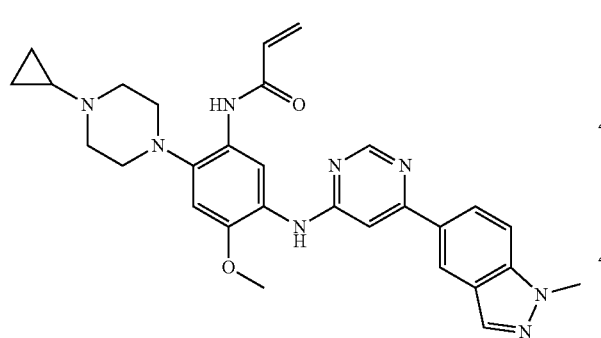
147
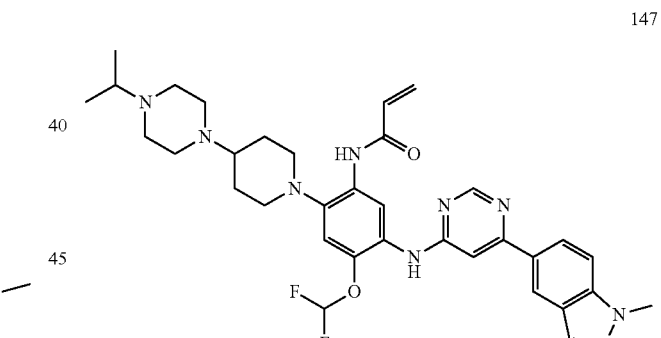
144
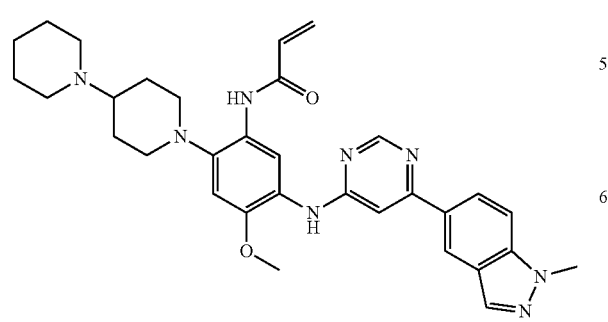
148
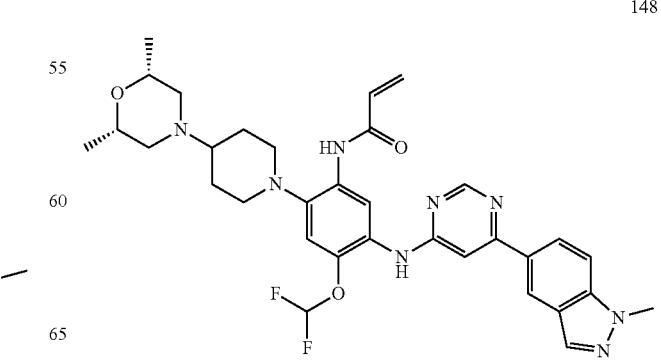

-continued
149
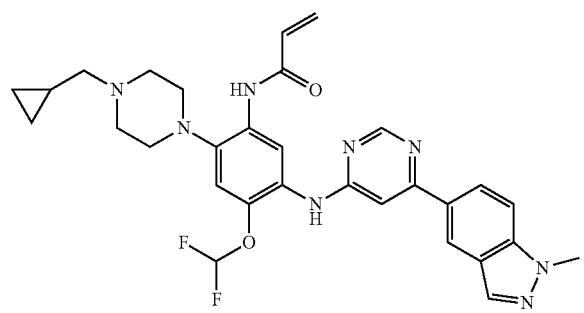
150
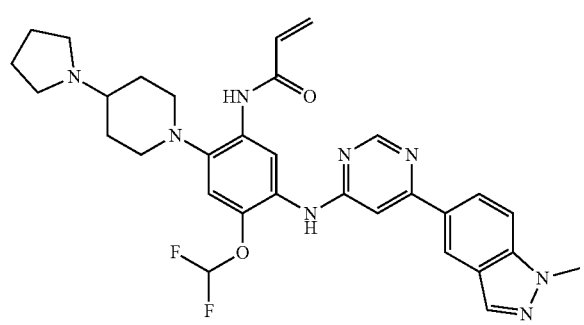
151
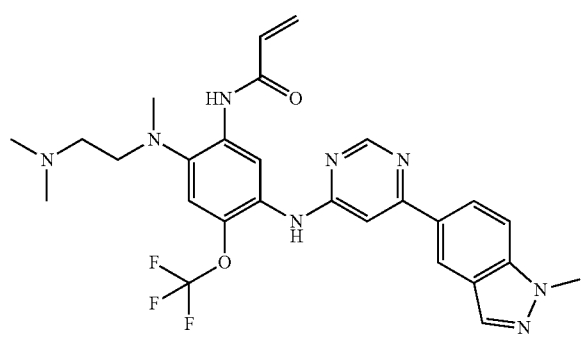
152
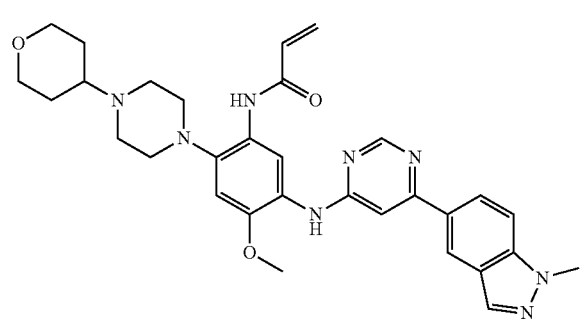
-continued
153
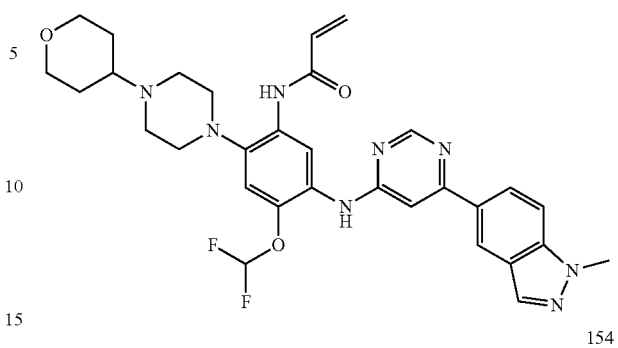
154
155
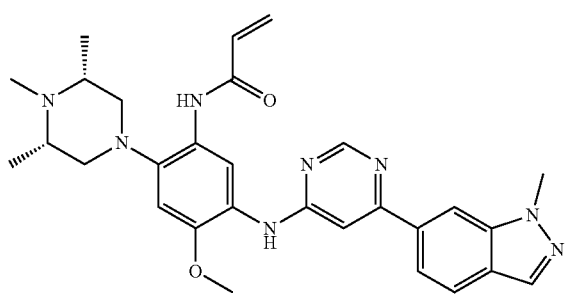
156
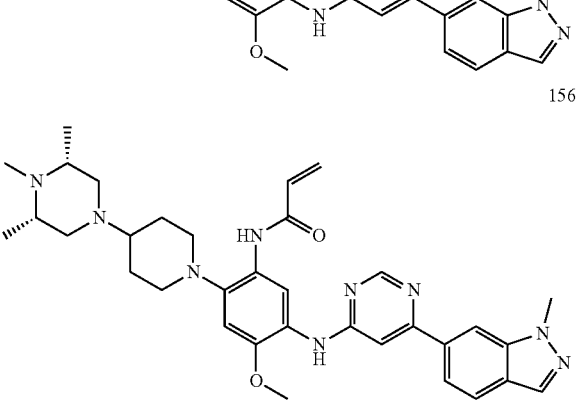
157
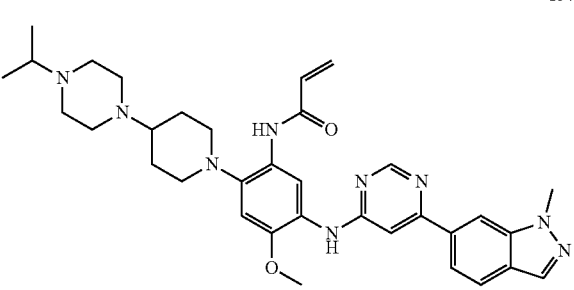

523
-continued
158
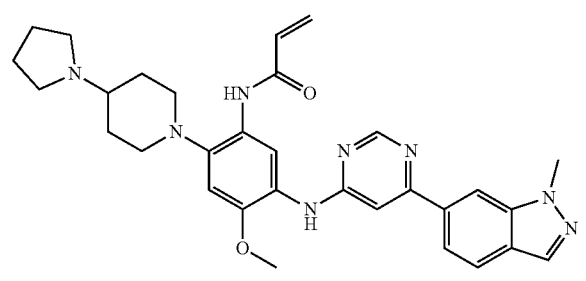
159
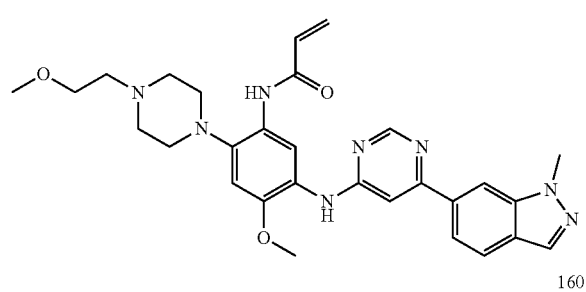
160
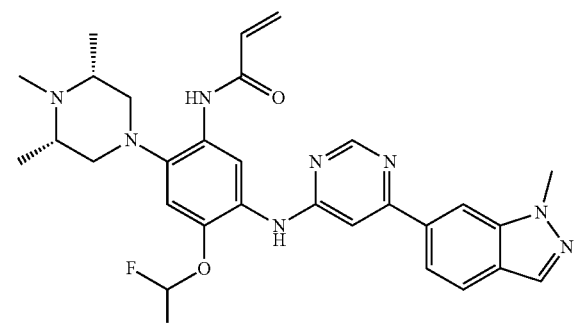
161
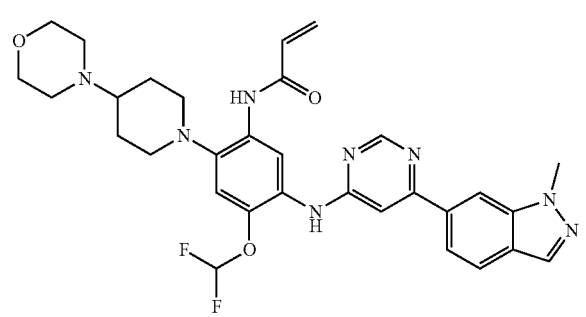
162
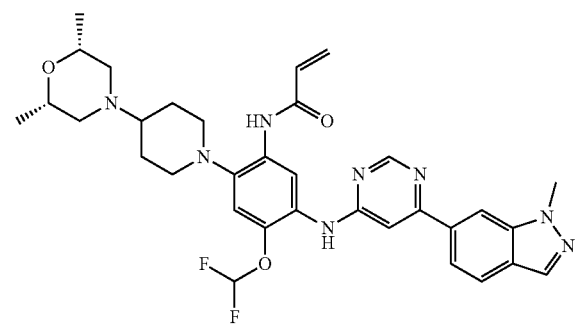
524
-continued
163
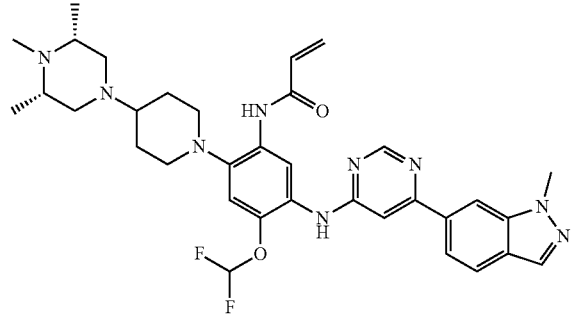
164
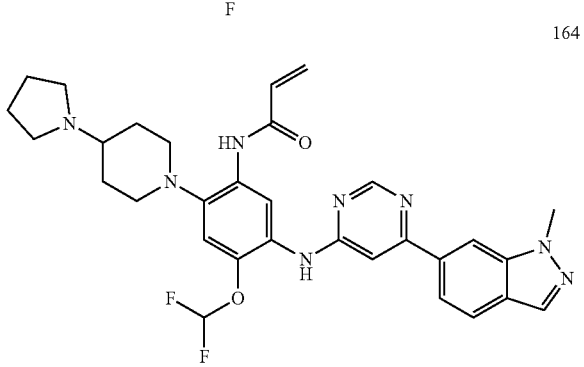
165
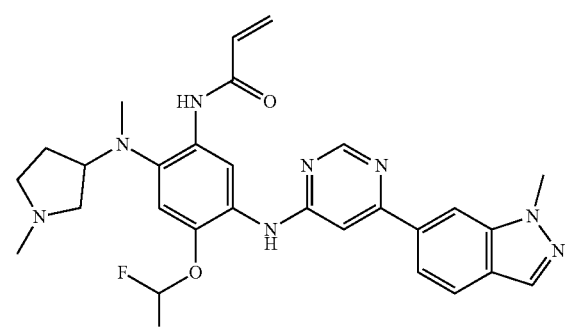
166
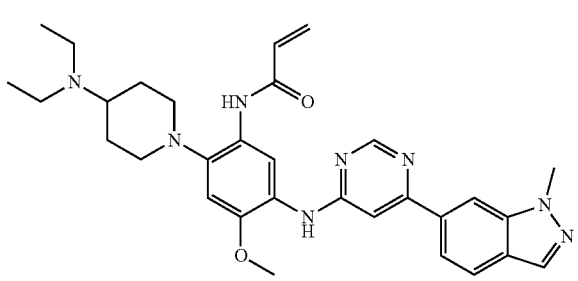
167
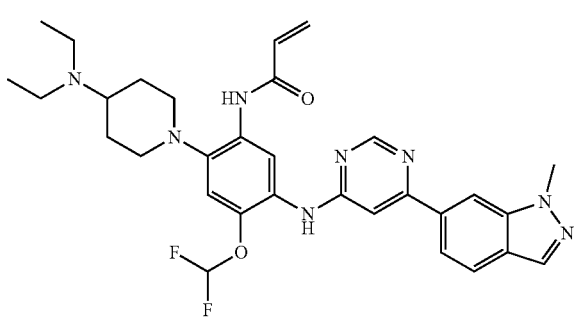

168
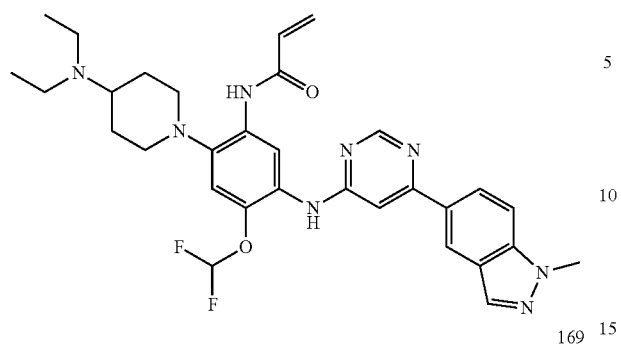
169
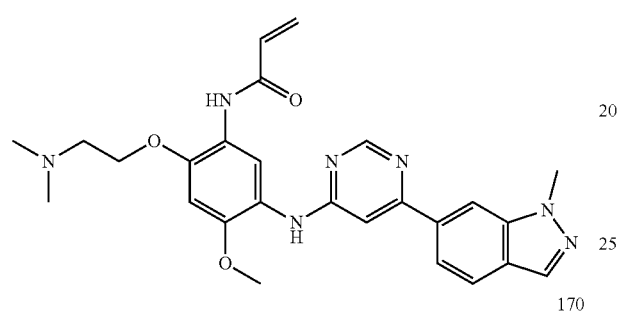
170
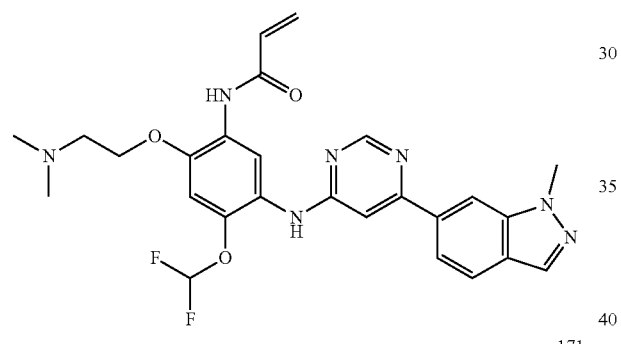
171
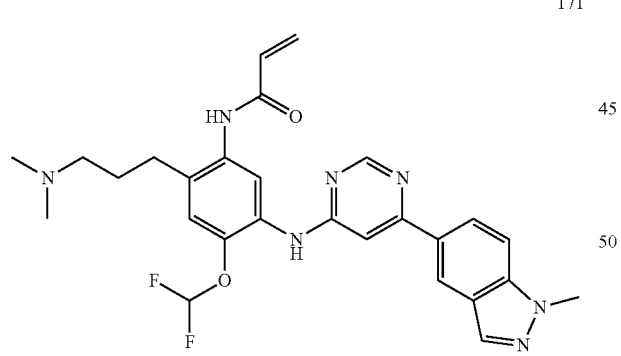
172
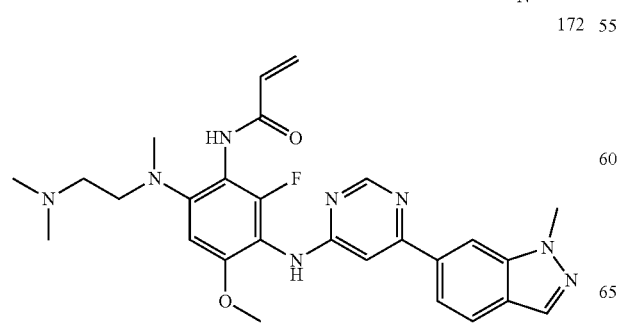
173
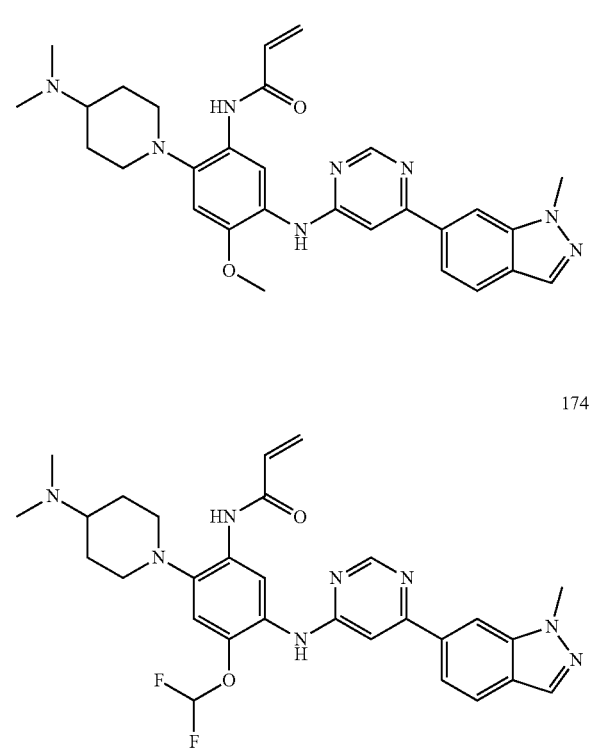
174
175
176
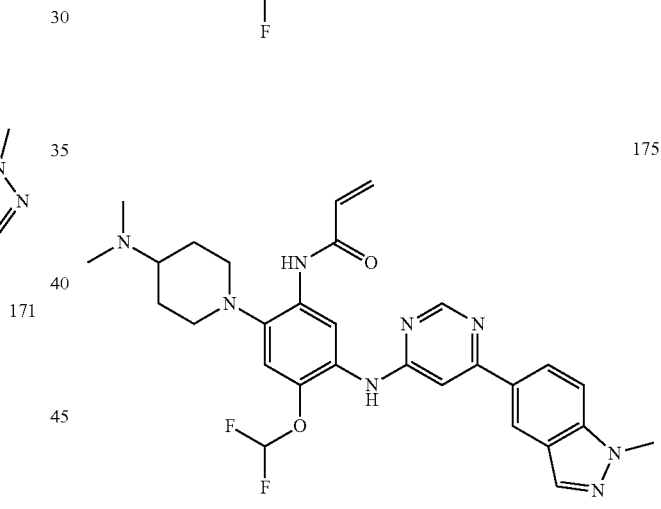
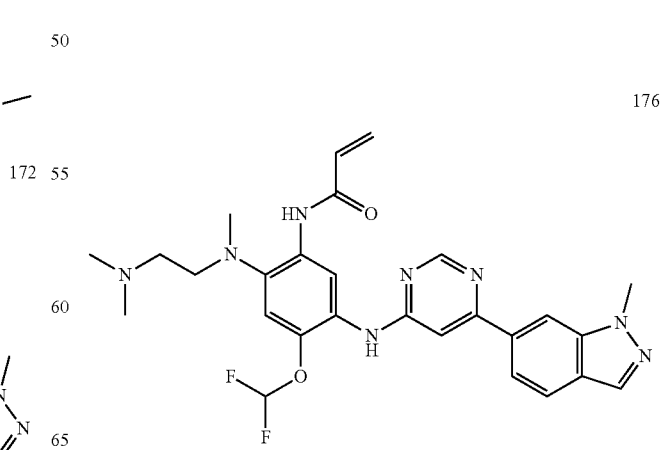

177
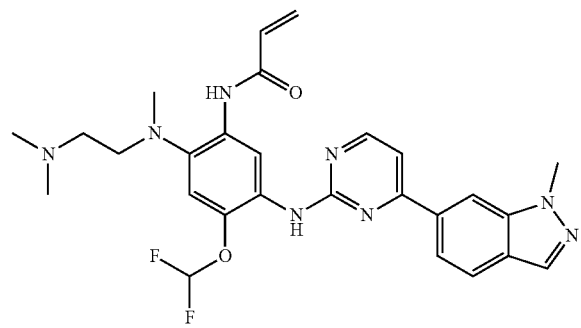
178
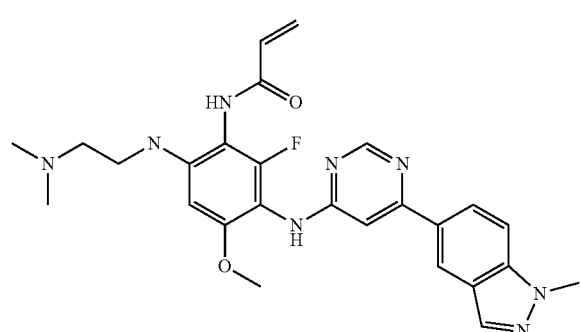
179
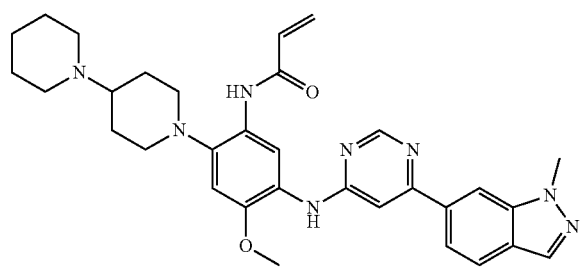
180
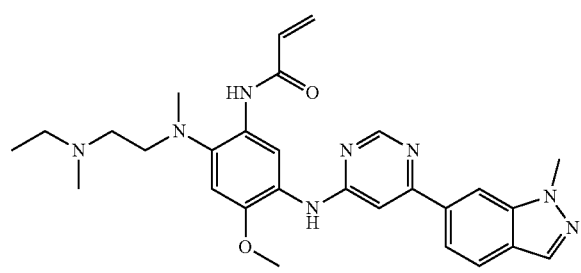
181
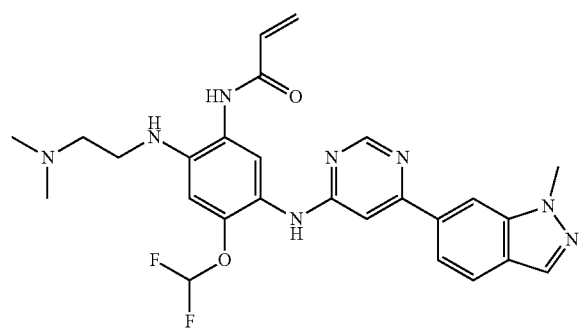
182
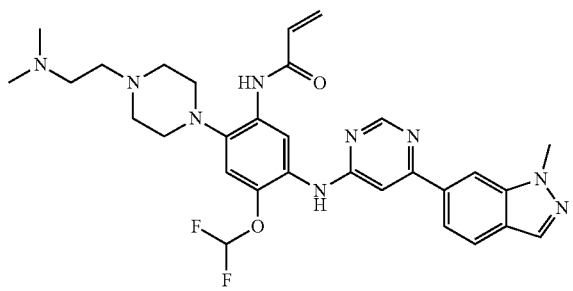
183
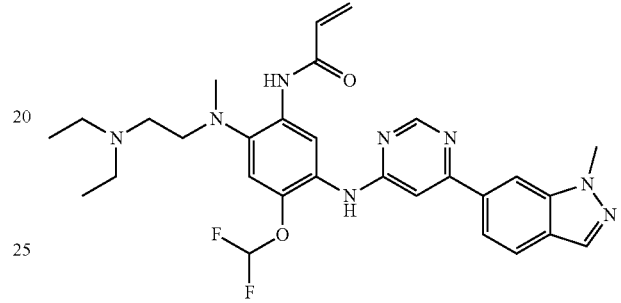
184
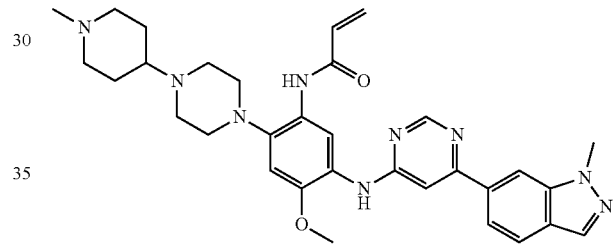
185
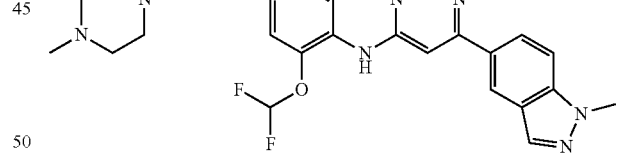
186
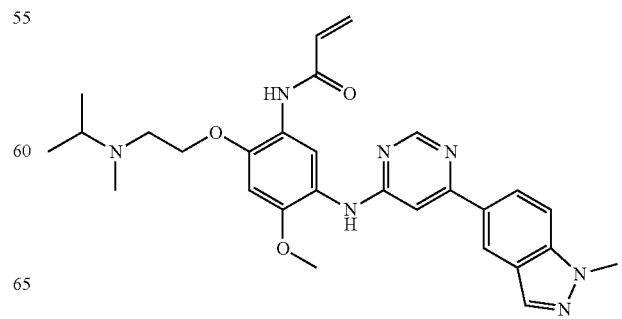

187
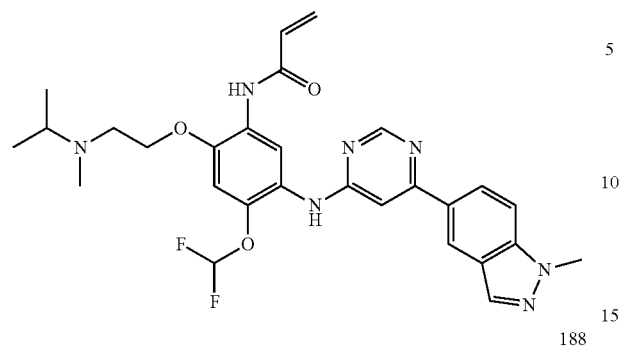
192
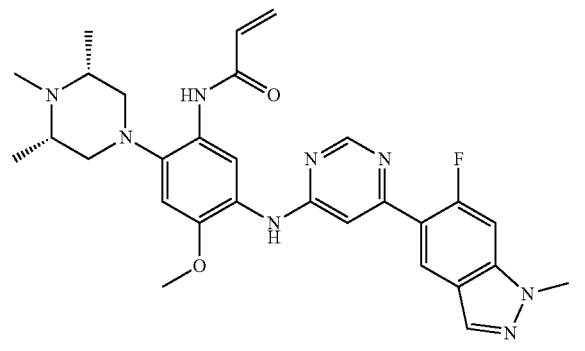
188
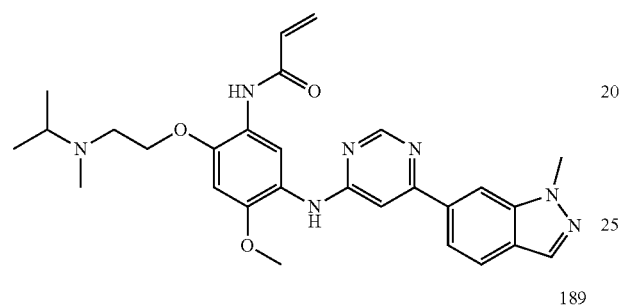
193
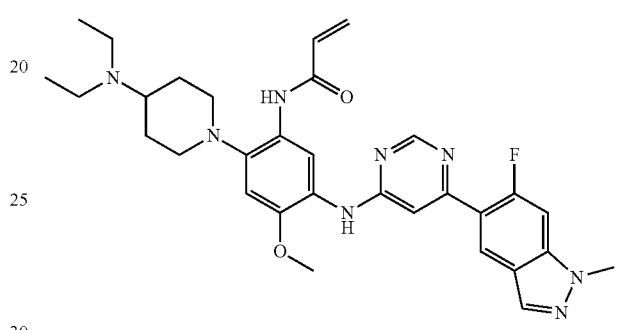
189
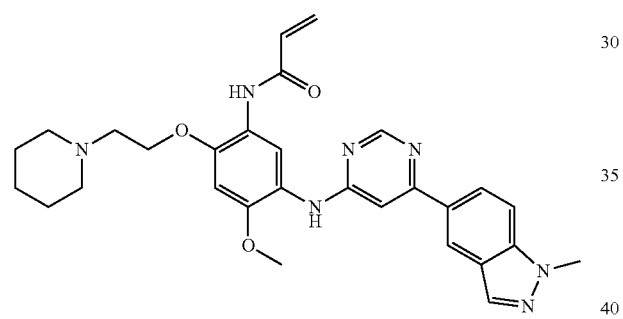
194
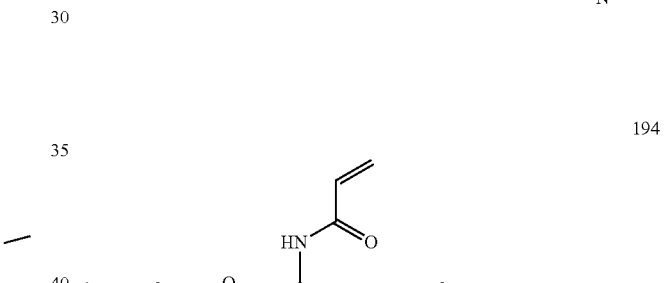
190
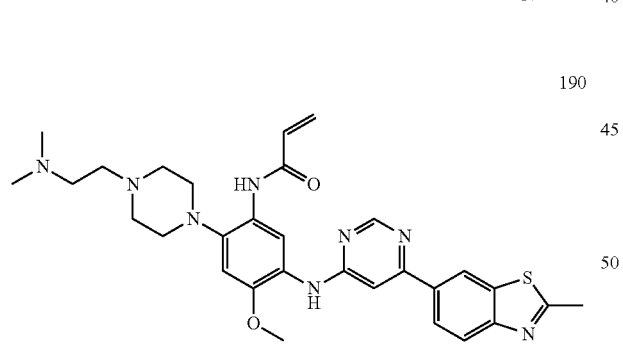
195
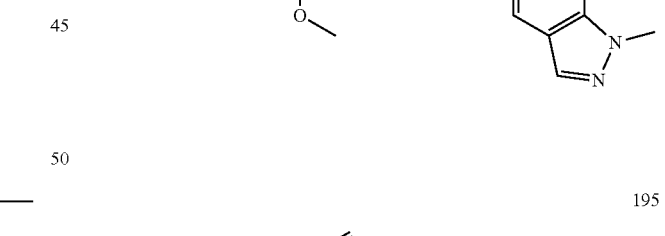
191
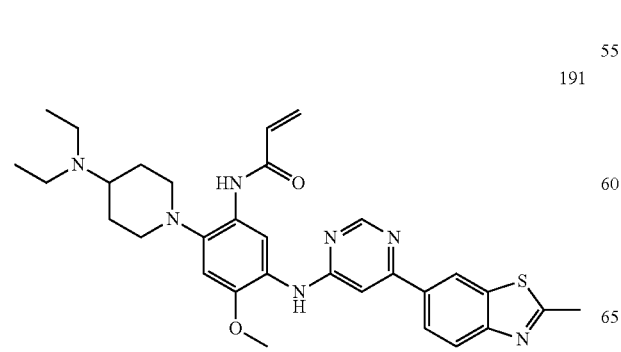
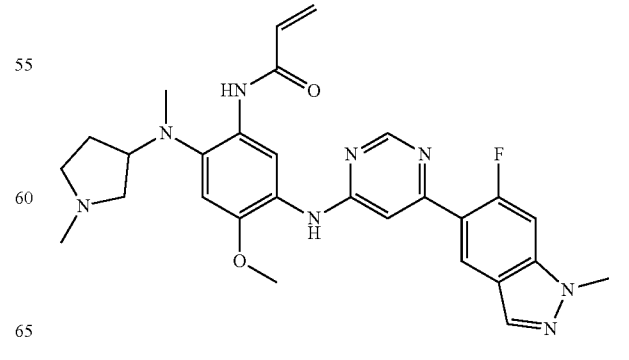

196
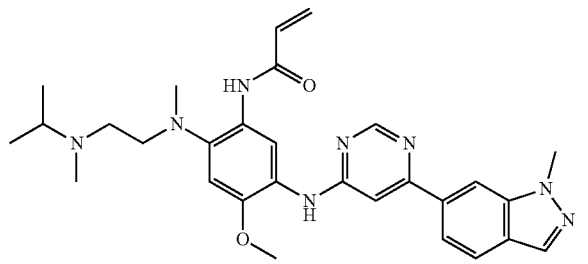
197
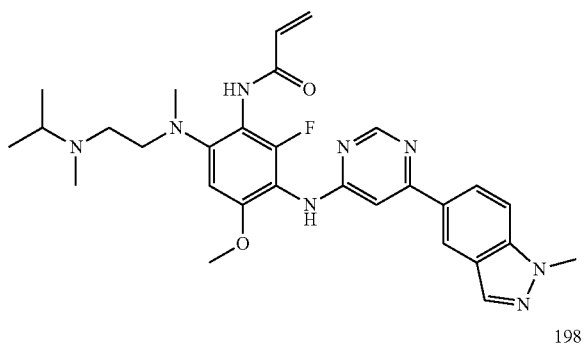
198
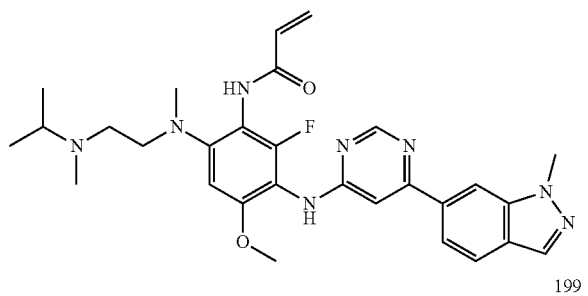
199
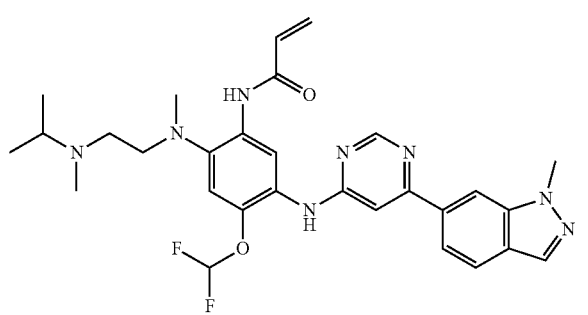
200
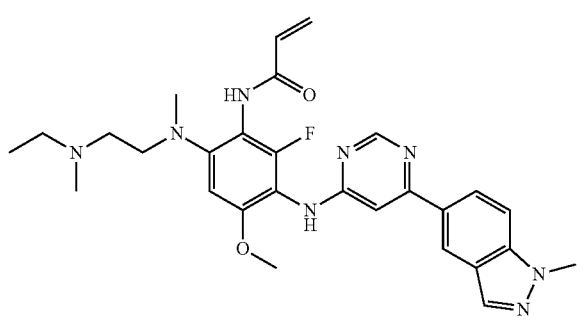
201
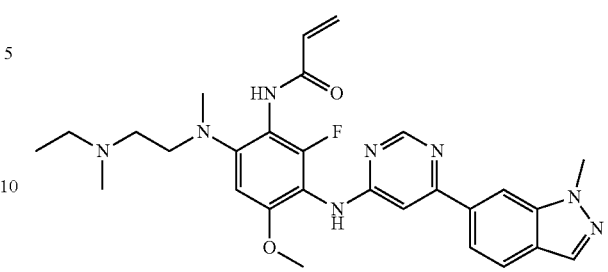
202
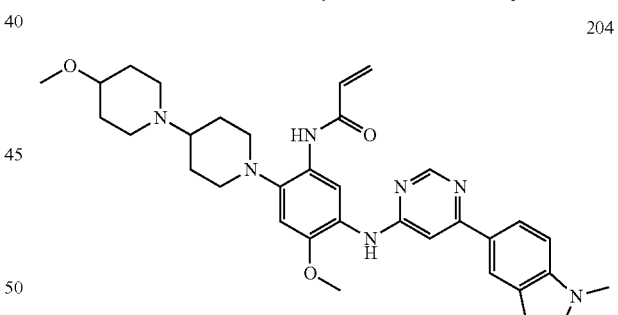
203
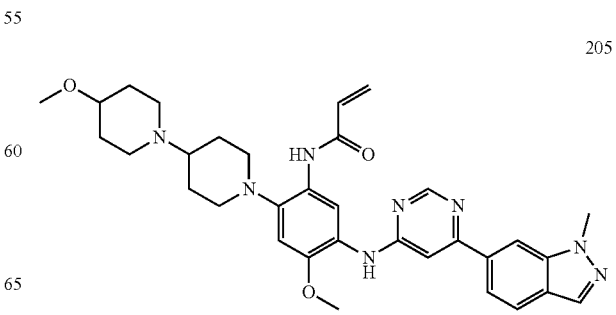
204
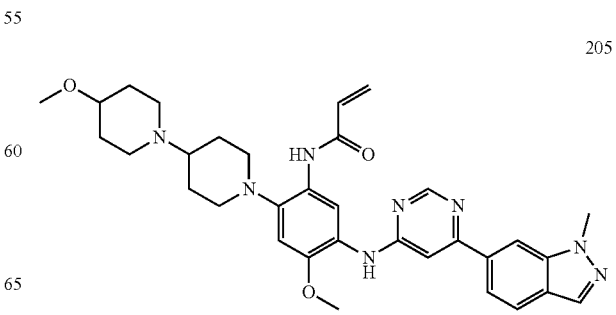
205
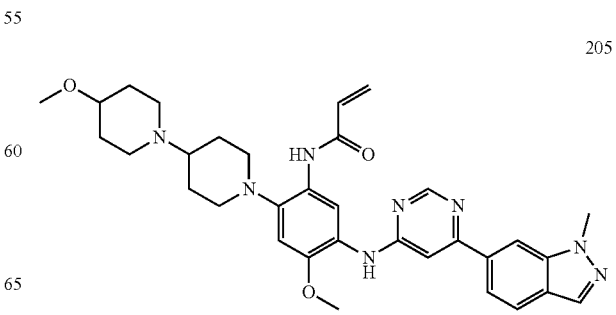

-continued
206
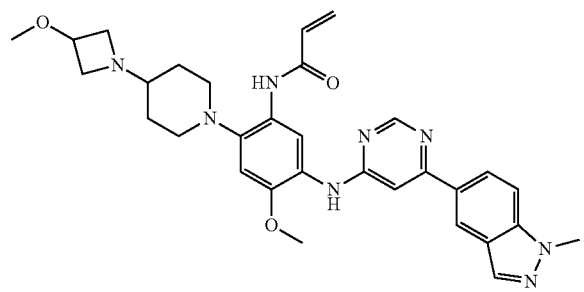
207
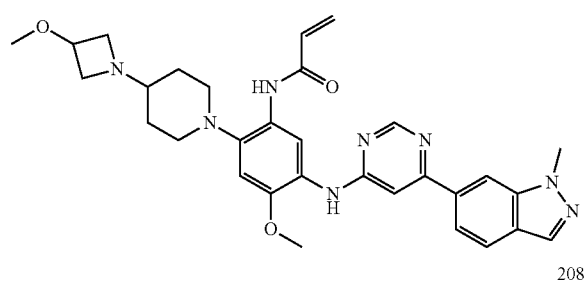
208
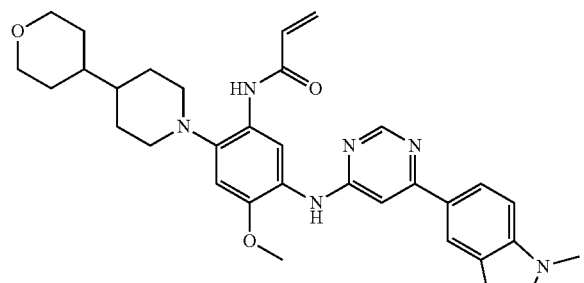
209
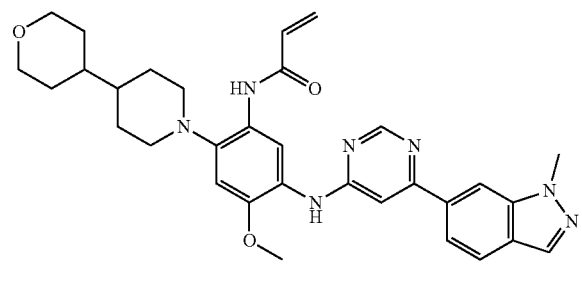
210
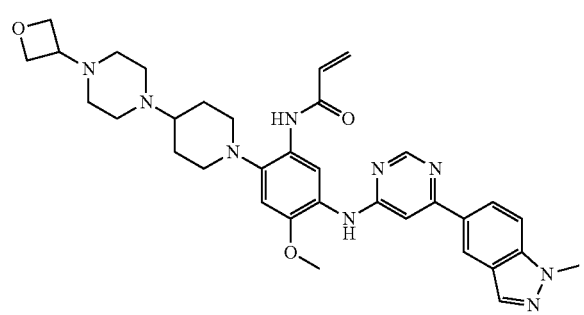
-continued
211
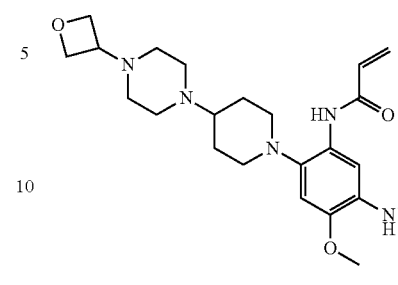
212
213
214
215
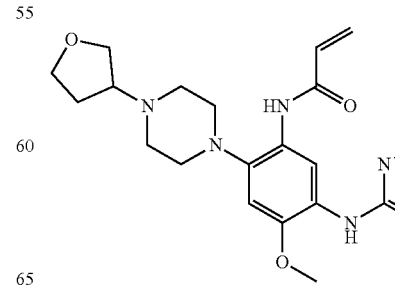

216
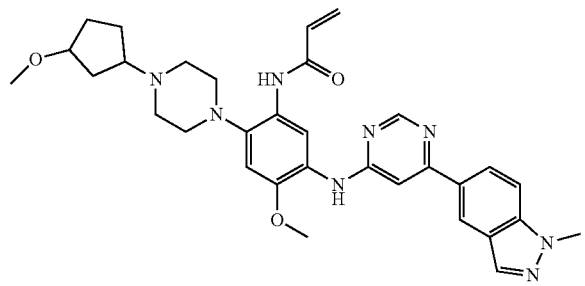
217
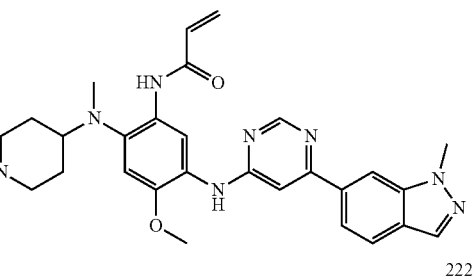
221
218
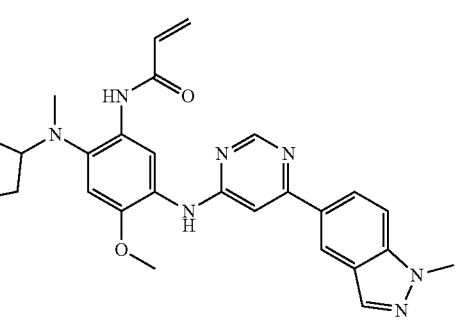
222
219
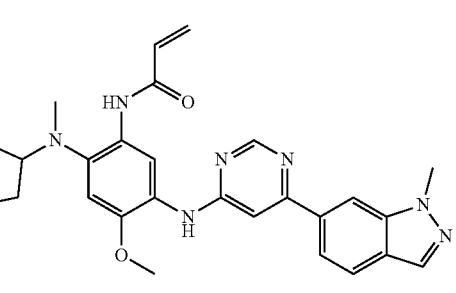
223
220
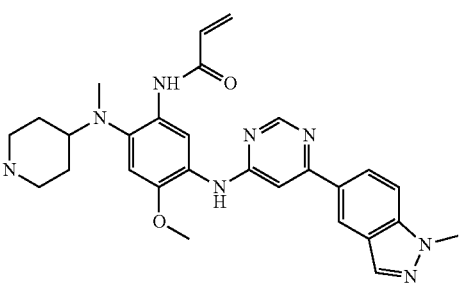
224
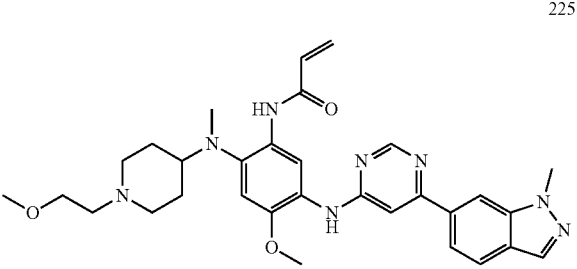
225

226 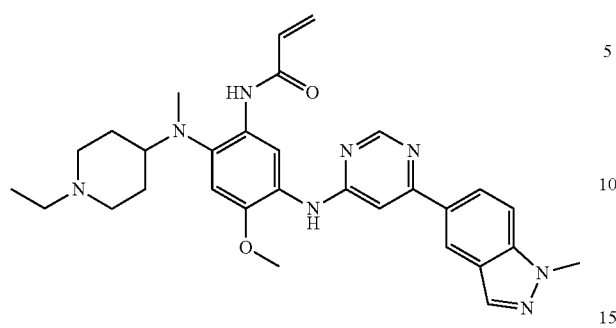
227 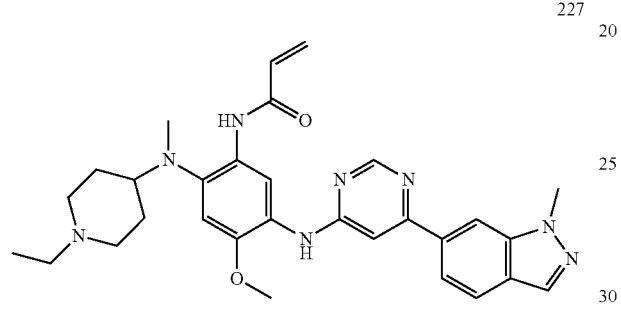
228 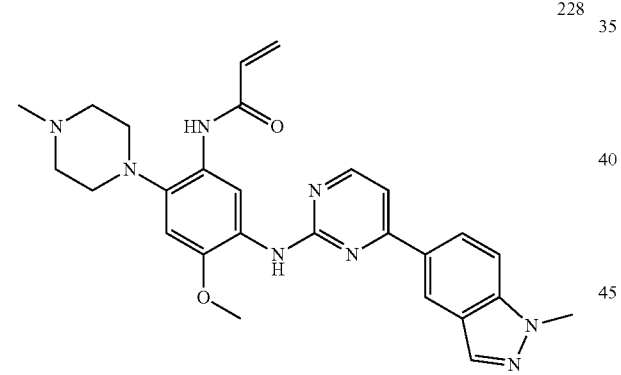
229 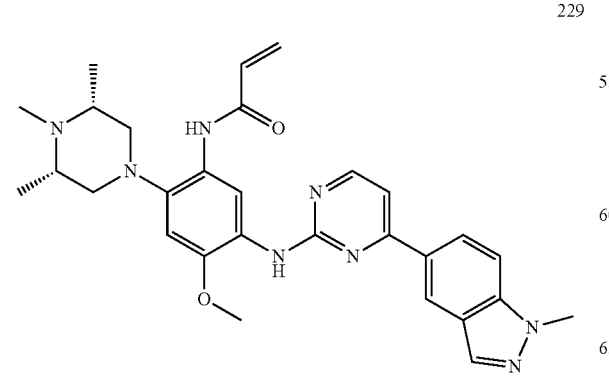
230 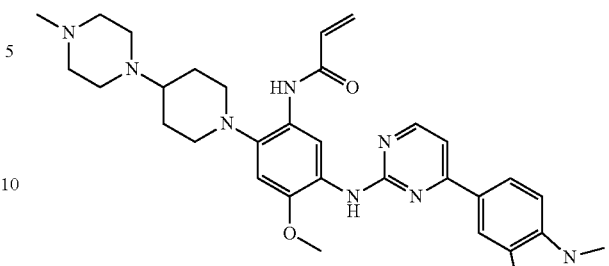
231 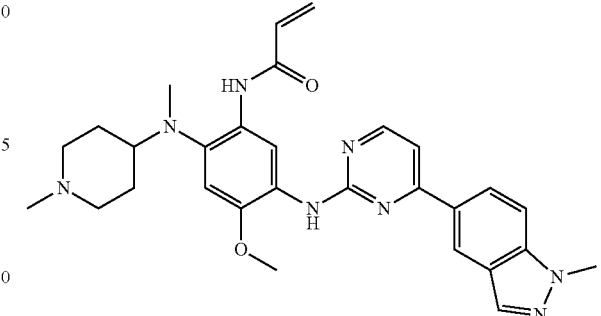
232 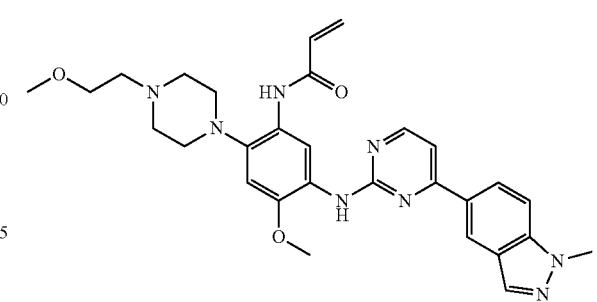
233 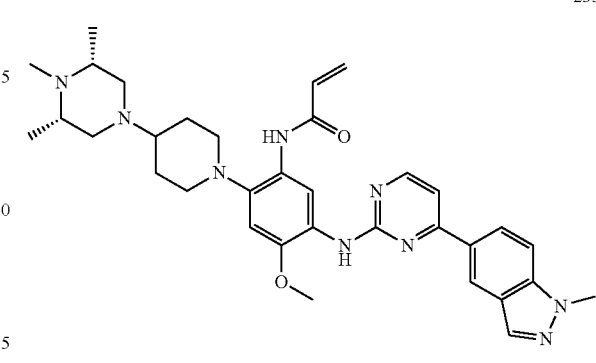

234 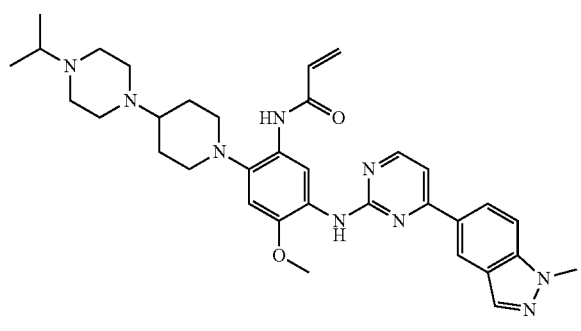
238 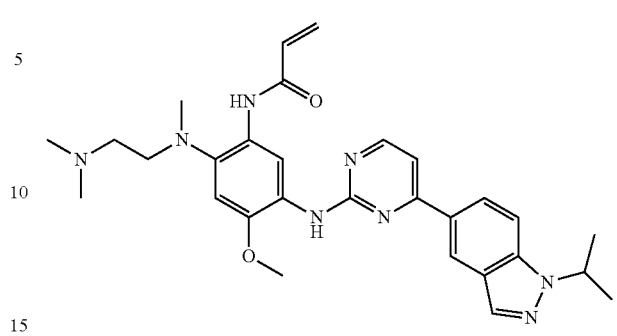
235 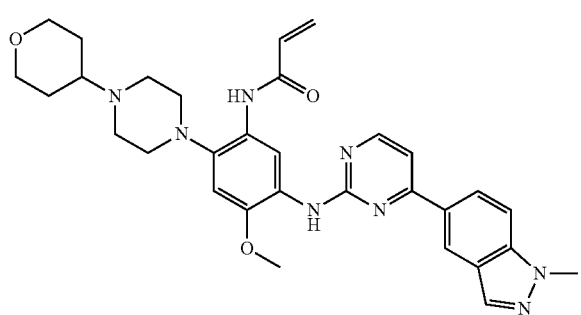
239 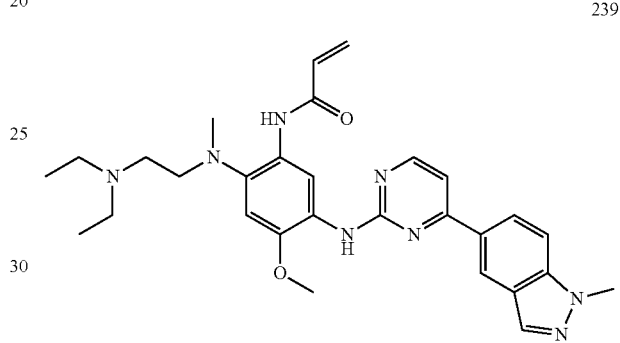
236 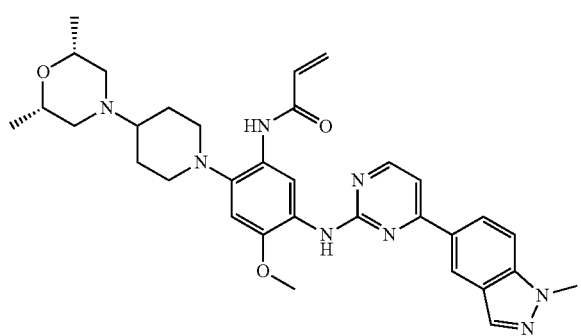
240 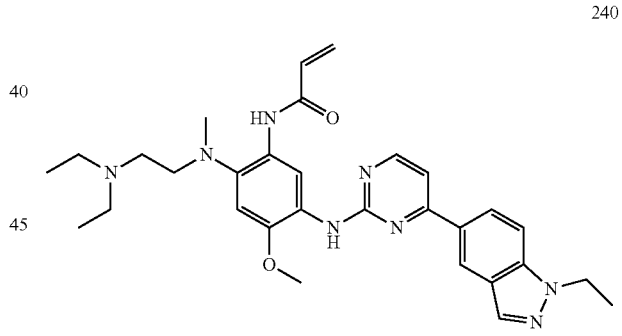
237 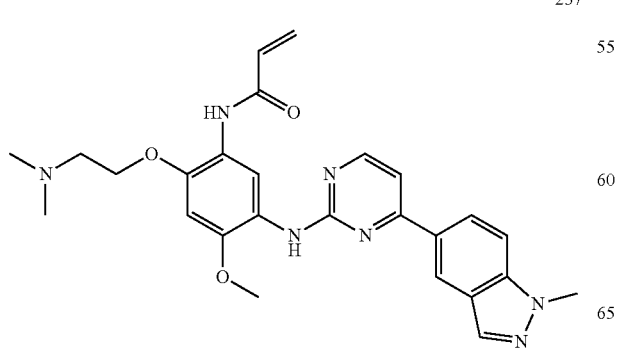
241 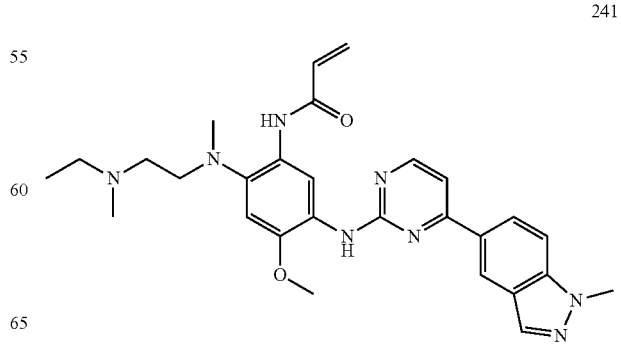

242
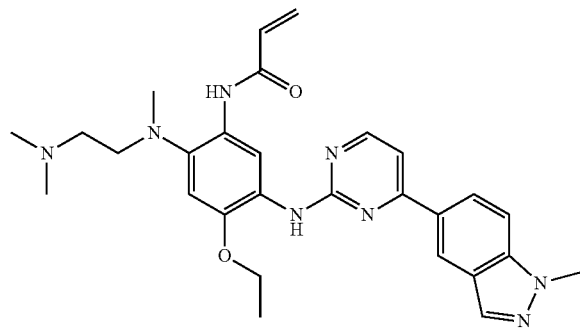
243
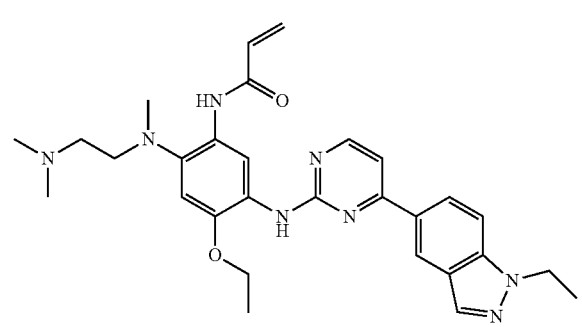
244
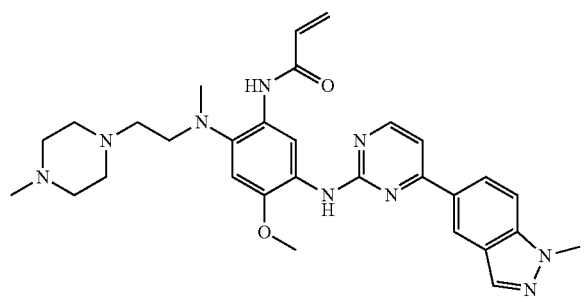
245
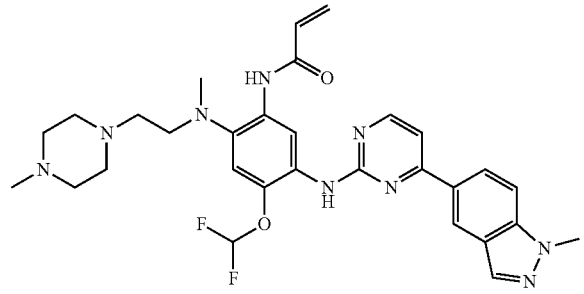
246
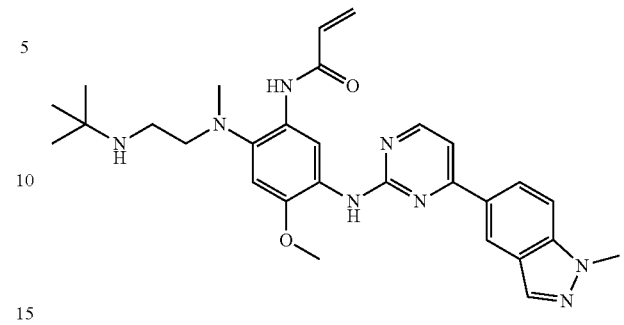
247
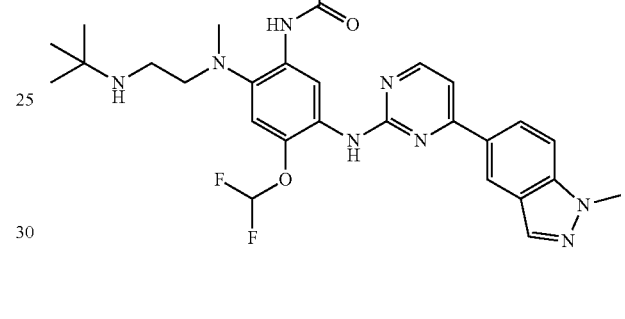
248
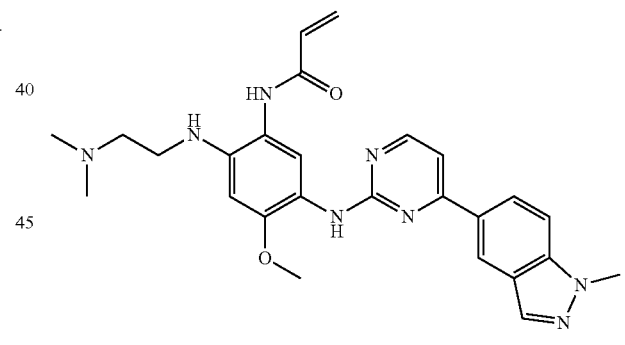
249
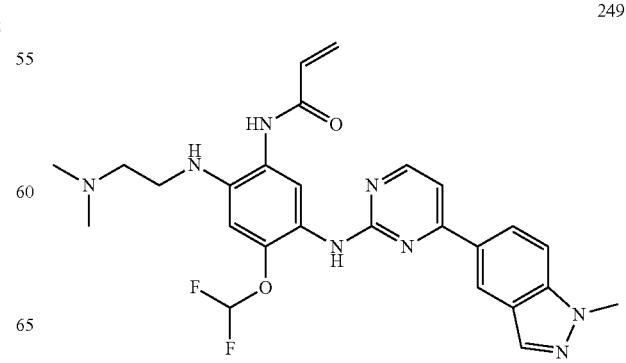

250
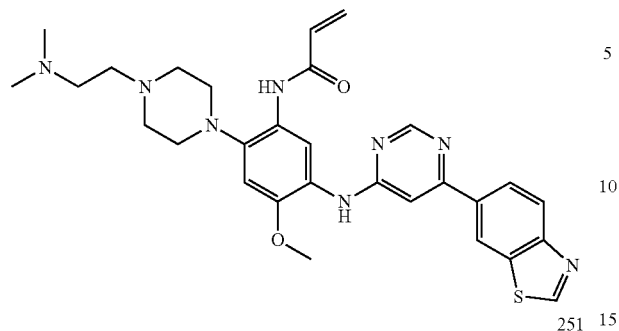
251
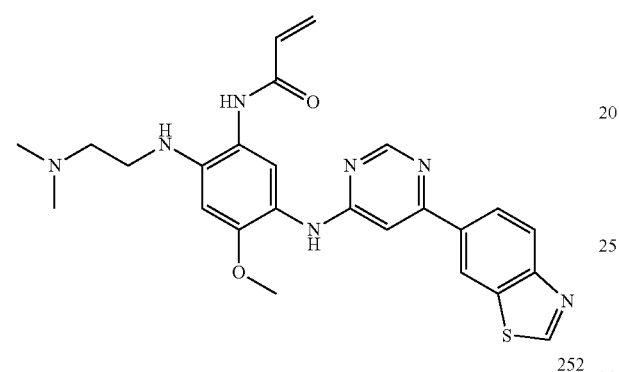
252
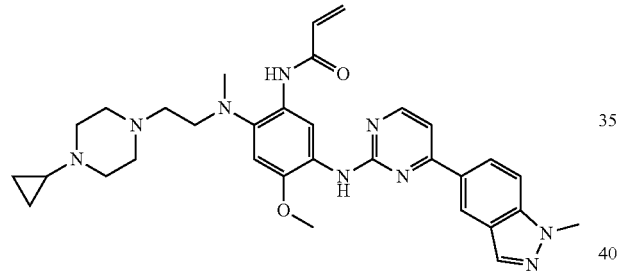
253
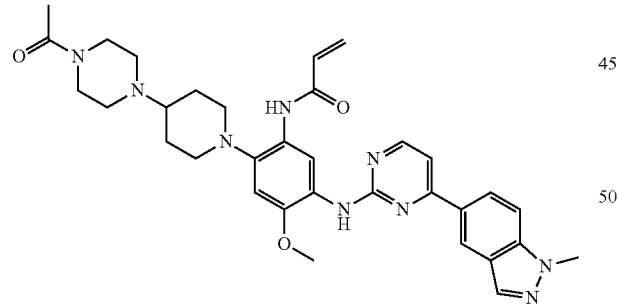
254
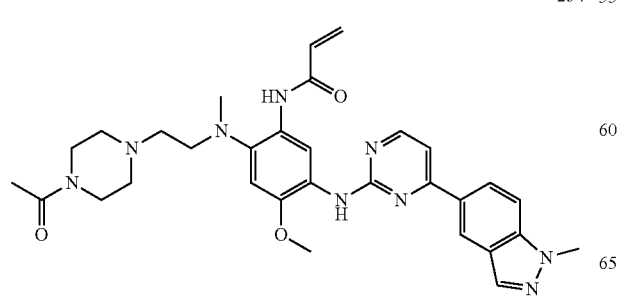
255
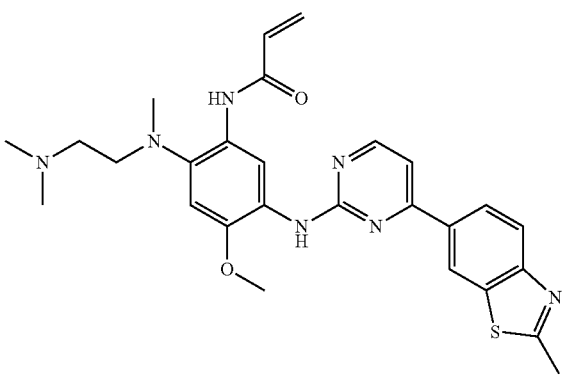
256
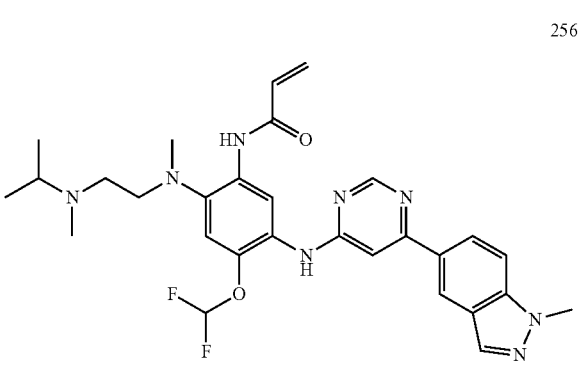
257
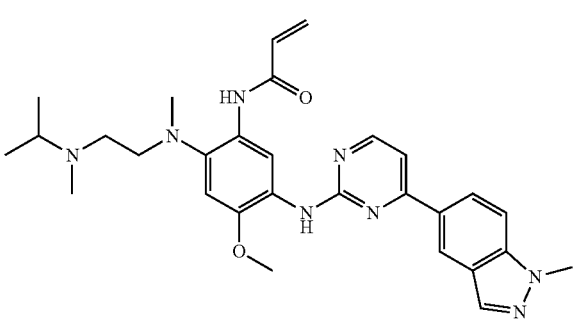
258
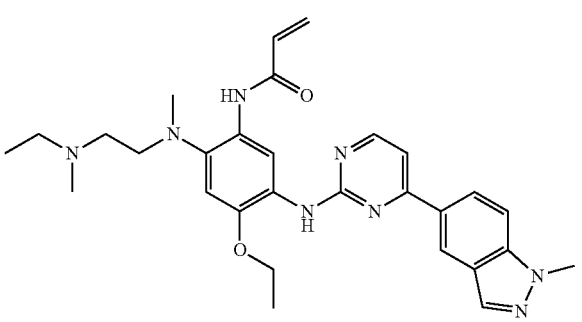

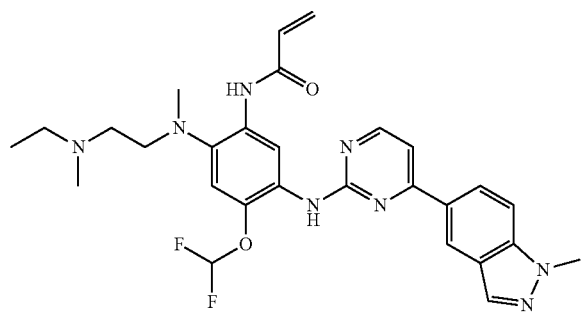
259
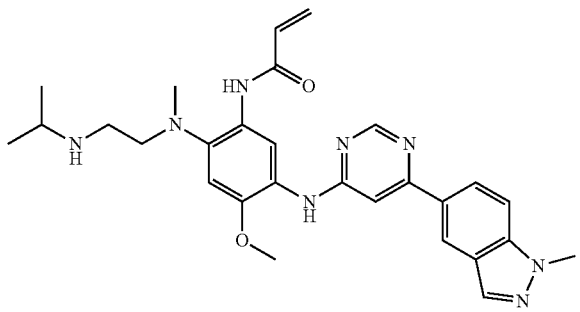
263
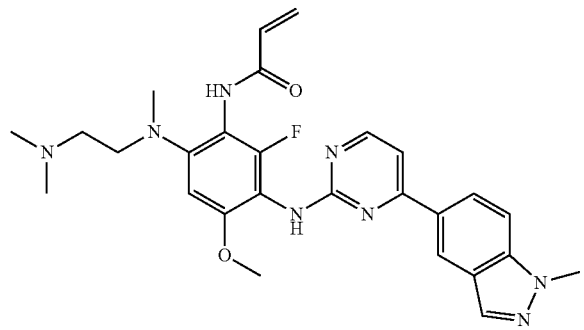
260
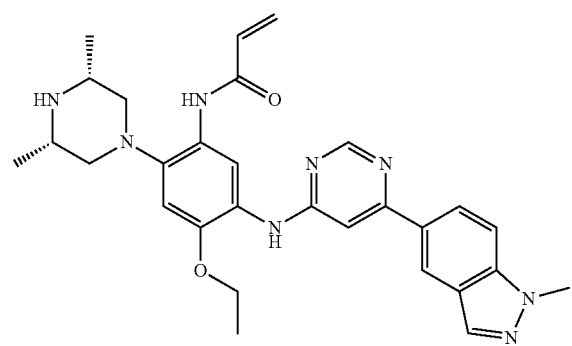
264
261
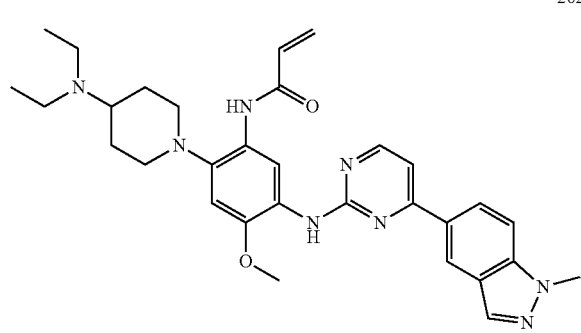
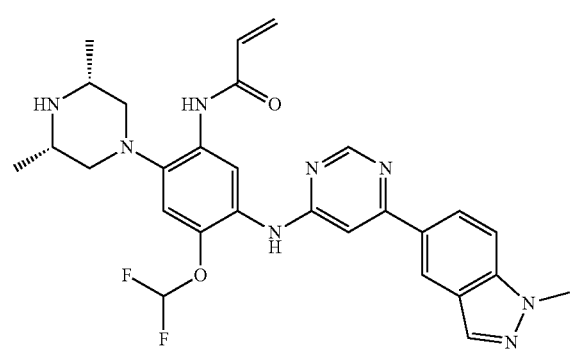
265
262
266

267
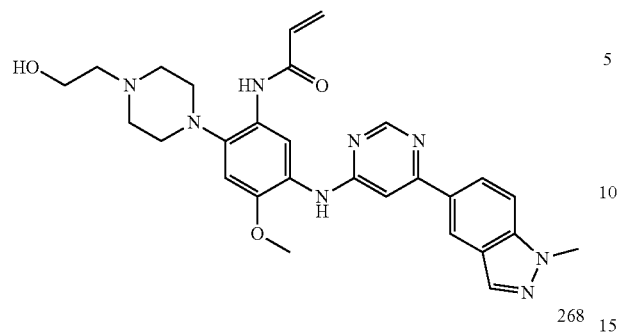
268
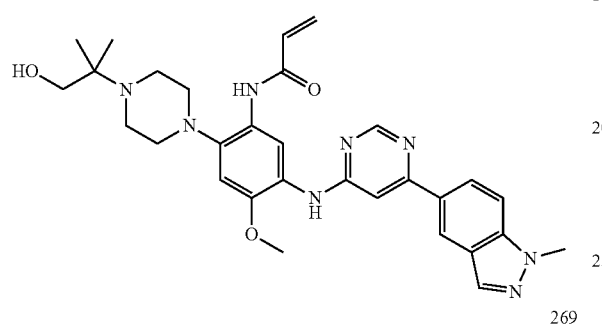
269
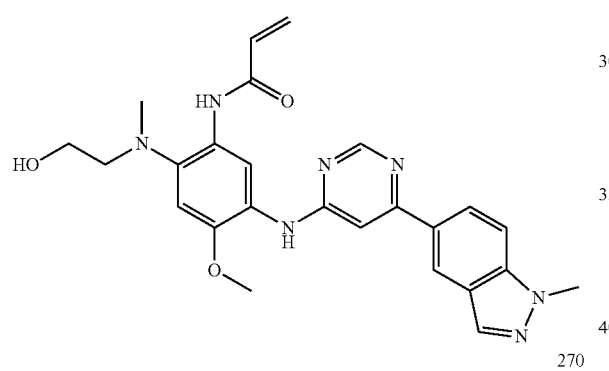
270
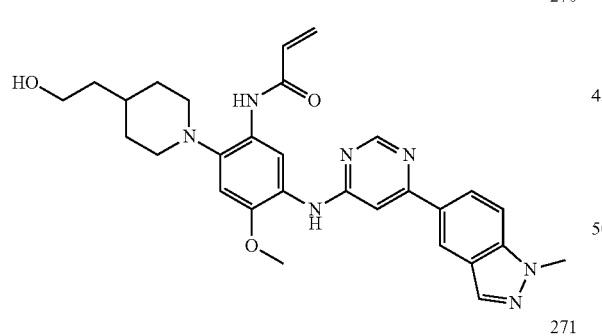
271
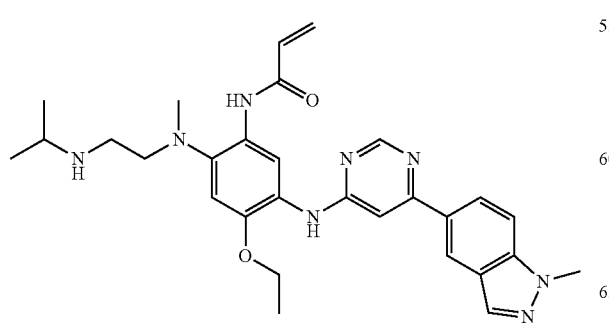
272
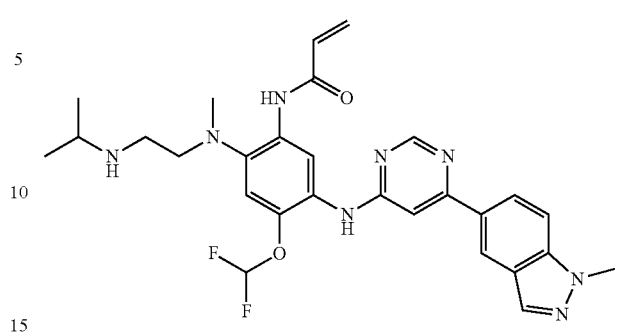
273
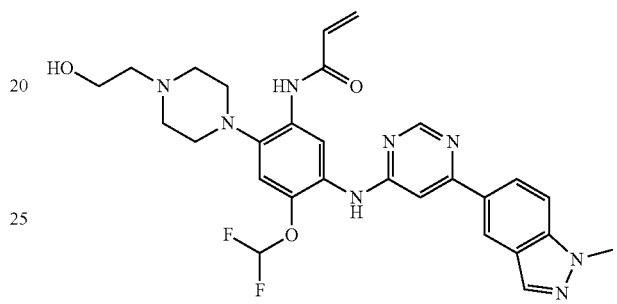
274
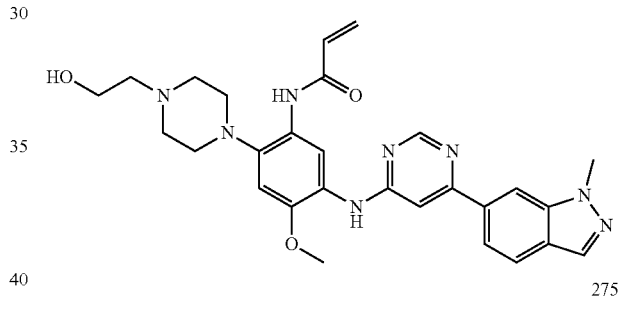
275
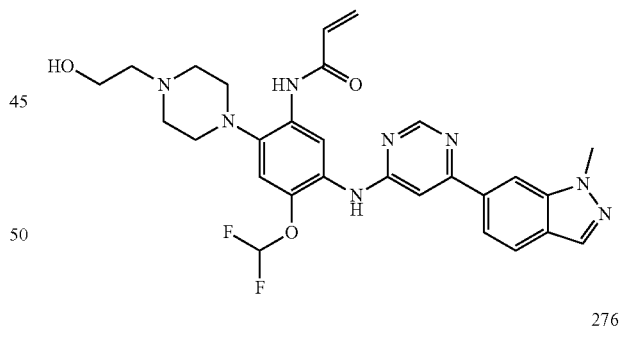
276
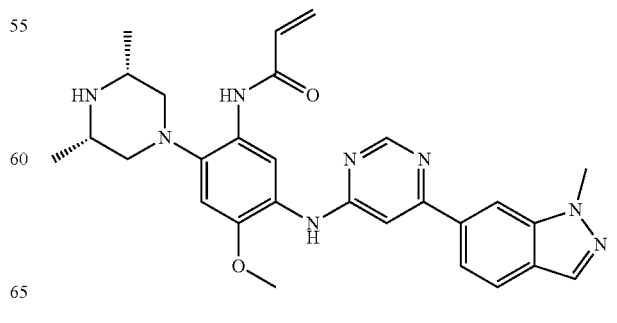

277
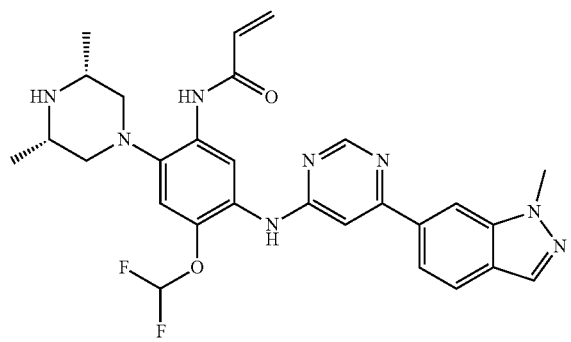
278
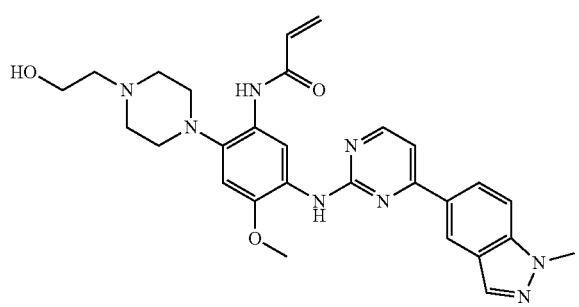
279
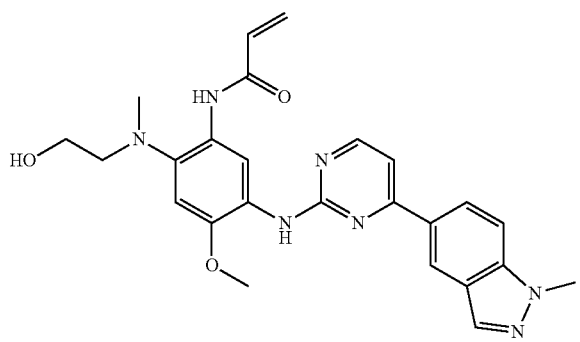
280
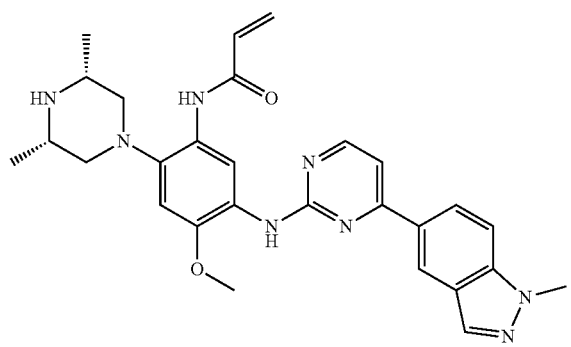
281
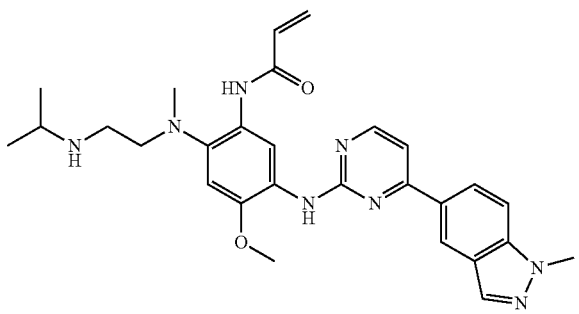
282
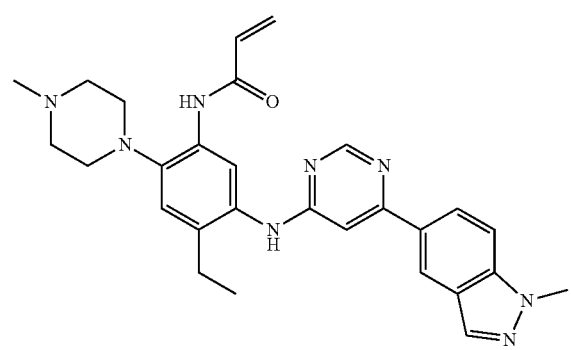
283
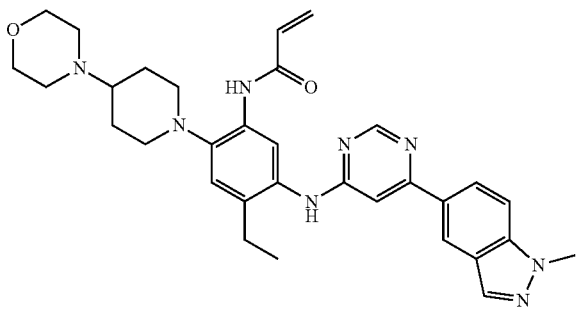
284
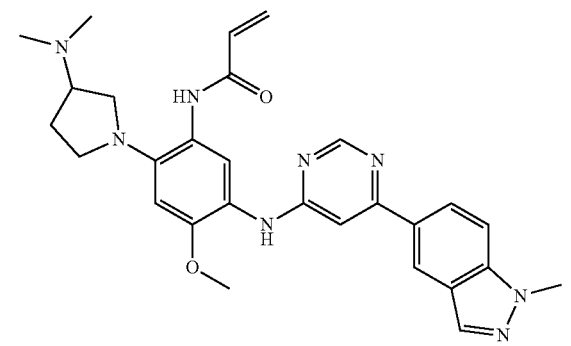

285
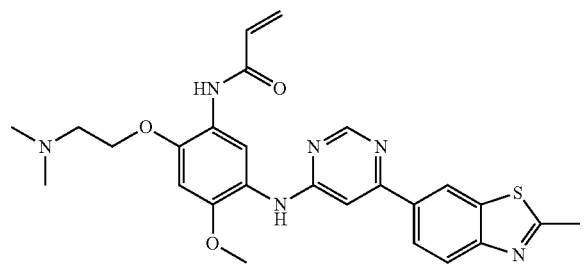
286
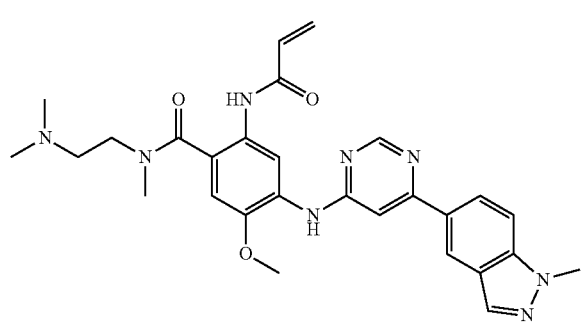
287
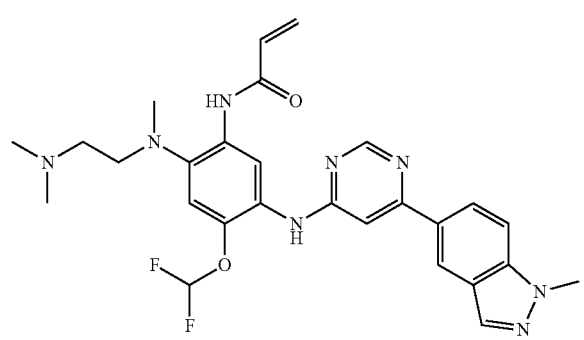
288
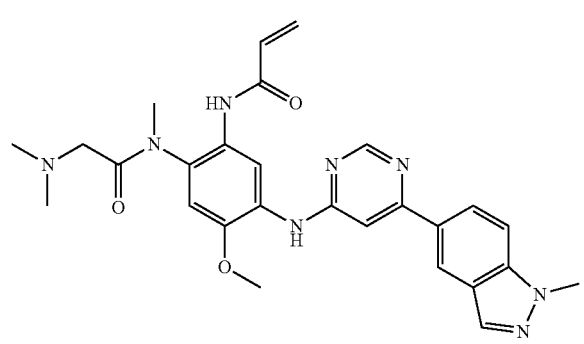
289
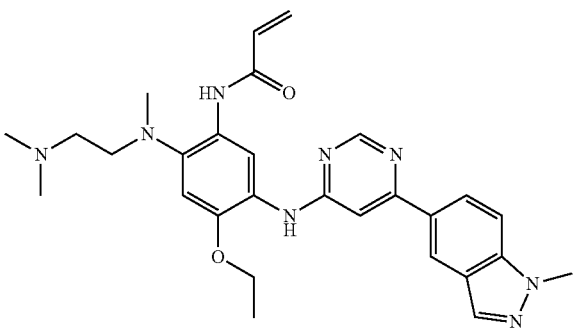
290
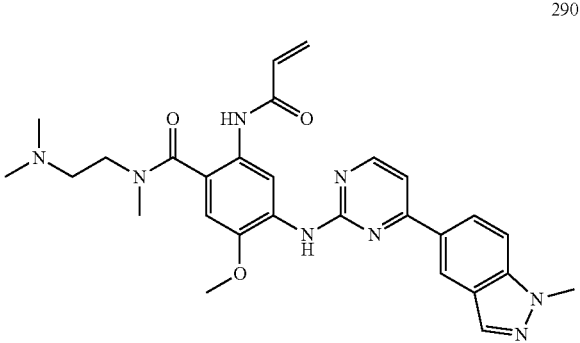
291
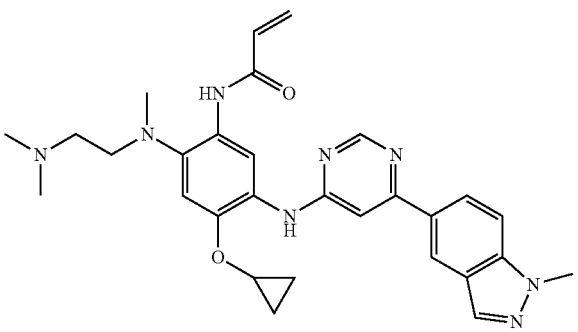
292
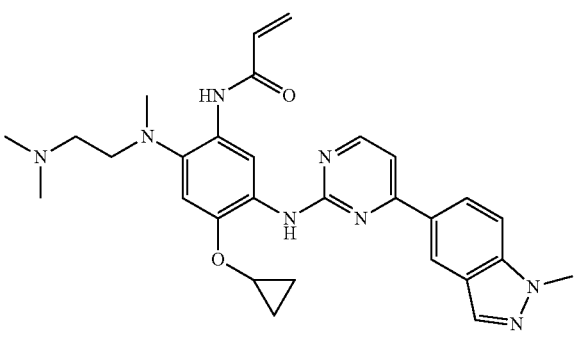

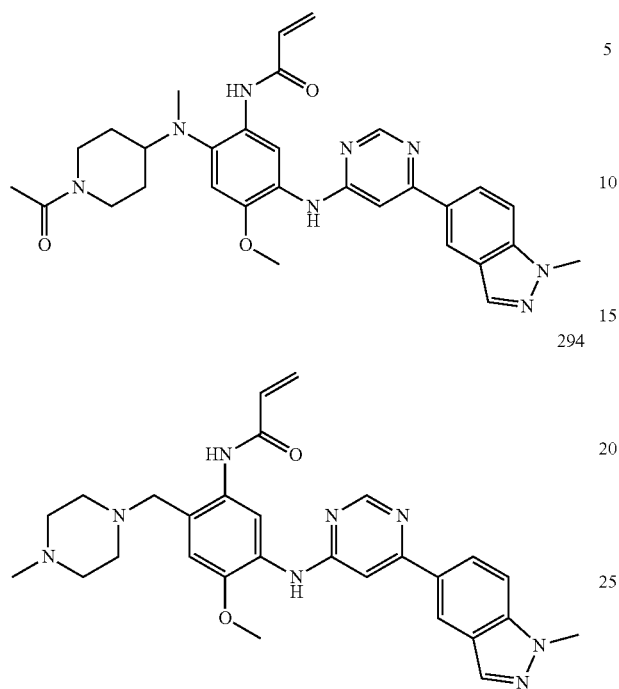
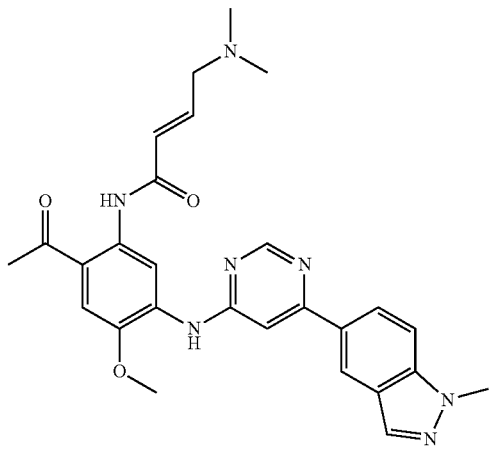
17. The pharmaceutical composition according to claim 9, wherein the pharmaceutical composition is tablet, capsule, pill, granule, powder, suppository, injection, solution, suspension, plaster, patch, lotion, drop, liniment and/or spray.
* * * * *